United States Patent
Zhang et al.

(10) Patent No.: US 11,542,266 B1
(45) Date of Patent: Jan. 3, 2023

(54) SUBSTITUTED PIPERIDINES AS BTK INHIBITORS

(71) Applicant: HAISCO PHARMACEUTICALS PTE. LTD., Singapore (SG)

(72) Inventors: Chen Zhang, Chengdu (CN); Yuting Liao, Chengdu (CN); Jianmin Wang, Chengdu (CN); Guozhi Zhu, Chengdu (CN); Fei Ye, Chengdu (CN); Pingming Tang, Chengdu (CN); Xiaogang Chen, Chengdu (CN); Zhenggang Huang, Chengdu (CN); Shoutao Wu, Chengdu (CN); Yao Li, Chengdu (CN); Pangke Yan, Chengdu (CN)

(73) Assignee: HAISCO PHARMACEUTICALS PTE. LTD., Singapore (SG)

( * ) Notice: Subject to any disclaimer, the term of this patent is extended or adjusted under 35 U.S.C. 154(b) by 0 days.

(21) Appl. No.: 17/495,088

(22) Filed: Oct. 6, 2021

Related U.S. Application Data

(63) Continuation of application No. PCT/CN2020/093455, filed on May 29, 2020.

(30) Foreign Application Priority Data

| May 31, 2019 | (CN) | 201910454977.3 |
| Aug. 2, 2019 | (CN) | 201910706239.3 |
| Oct. 25, 2019 | (CN) | 201910997078.8 |
| Dec. 16, 2019 | (CN) | 201911291561.0 |

(51) Int. Cl.
| *A61K 31/45* | (2006.01) |
| *C07D 211/40* | (2006.01) |
| *C07D 487/04* | (2006.01) |
| *A61P 35/00* | (2006.01) |
| *C07D 471/04* | (2006.01) |
| *C07D 519/00* | (2006.01) |

(52) U.S. Cl.
CPC .......... *C07D 487/04* (2013.01); *A61P 35/00* (2018.01); *C07D 471/04* (2013.01); *C07D 519/00* (2013.01); *C07B 2200/07* (2013.01); *C07B 2200/09* (2013.01)

(58) Field of Classification Search
CPC .............................. A61K 31/45; C07D 211/40
USPC ............................................ 514/320; 546/245
See application file for complete search history.

(56) References Cited

U.S. PATENT DOCUMENTS

| 2002/0156081 A1 | 10/2002 | Hirst et al. |
| 2013/0116213 A1 | 5/2013 | Cha et al. |
| 2016/0002225 A1 | 1/2016 | Chen et al. |
| 2016/0145237 A1 | 5/2016 | Hu et al. |
| 2018/0099940 A1 | 4/2018 | Crew et al. |
| 2018/0251464 A1 | 9/2018 | Shi |
| 2019/0076541 A1 | 3/2019 | Phillips et al. |
| 2019/0106423 A1 | 4/2019 | Hudson et al. |
| 2019/0210996 A1 | 7/2019 | Harling et al. |
| 2019/0315758 A1 | 10/2019 | Li et al. |

FOREIGN PATENT DOCUMENTS

| CN | 101679380 A | 3/2010 |
| CN | 102656173 A | 9/2012 |
| CN | 106831787 A | 6/2017 |
| CN | 108191871 A | 6/2018 |
| CN | 109071455 A | 12/2018 |
| CN | 109422696 A | 3/2019 |
| WO | 2017134685 A2 | 8/2017 |
| WO | 2017197056 A1 | 11/2017 |
| WO | 2018033853 A2 | 2/2018 |
| WO | WO-2020239103 A1 * | 12/2020 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Li et al., "Discovery of (R)-1-(3-(4-Amino-3-(4-phenoxyphenyl)-1H-pyrazolo[3,4-d]pyrimidin-1-yl)piperidin-1-yl)-2-dimethylamino)ethanone (CHMFL-FLT3-122) as a Potent and Orally Available FLT3 Kinase Inhibitor for FLT3-ITD Positive Acute Myeloid Leukemia," Journal of Medicinal Chemistry, 2015, 58, 9625-9638.
Peters et al., "Preparation and isolation of isobenzofuran," Beilstein Journal of Organic Chemistry, 2017, 13, 2659-2662.
Yamaguchi et al., "Synthesis of New Hydantoins Bearing Glutarimide or Succinimide Moiety and their Evaluation for Cell Differentiation-Inducing and Anti-Angiogenic Activities," Heterocycles, 2015, 91, 764-781.
Hansen et al., "Protein Degradation via CRL4CRBN Ubiquitin Ligase: Discovery and Structure—Activity Relationships of Novel Glutarimide Analogs That Promote Degradation of Aiolos and/or GSPT1," Journal of Medicinal Chemistry, 2018, 61, 492-503.
Sun et al., "PROTAC-induced BTK degradation as a novel therapy for mutated BTK C481S induced ibrutinib-resistant 3-cell malignancies," Cell Research, 2018, 28, 779-781.

(Continued)

*Primary Examiner* — Douglas M Willis
(74) *Attorney, Agent, or Firm* — Hoffman Warnick LLC

(57) ABSTRACT

Substituted piperidines as BTK inhibitors, a preparation method thereof and a pharmaceutical application thereof. The substituted piperidines is a compound represented by a general formula (I) or a stereoisomer or a pharmaceutically acceptable salt thereof, and the substituted piperidines is used to treat BTK-related diseases such as tumors or autoimmune system diseases.

B-L-K          formula (I)

19 Claims, No Drawings

(56) References Cited

OTHER PUBLICATIONS

Search report dated Nov. 8, 2021 for counterpart Taiwan patent application No. 109118113, 2 pages.
Office Action dated Mar. 1, 2022 in counterpart Eurasian Patent Application No. 202192516, with English translation, 2 pages.
PCT International Search Report for International Application No. PCT/CN2020/093455, dated Aug. 27, 2020, 12 pages.
Extended European Search Report dated Jul. 20, 2022 for counterpart European patent application No. 20812992.4.
Christopher P. Tinworth et al., "PROTAC-Mediated Degradation of Bruton's Tyrosine Kinase Is Inhibited by Covalent Binding," ACS Chemical Biology vol. 14 No.3 (2019).

* cited by examiner

SUBSTITUTED PIPERIDINES AS BTK INHIBITORS

TECHNICAL FIELD

The present disclosure relates to a compound represented by general formula (I) or a stereoisomer, a solvate, a prodrug, a metabolite, a pharmaceutically acceptable salt or a co-crystal thereof, and intermediates thereof and preparation methods therefor, as well as the use thereof in BTK-related diseases such as tumors or autoimmune system diseases.

BACKGROUND ART

Bruton's tyrosine kinase (BTK), a member of the Tec family of non-receptor protein tyrosine kinases, is a key regulator in the B cell antigen receptor (BCR) signaling pathway, and is distributed in the lymphatic system, hematopoietic and blood system. BTK mutations may activate downstream signaling pathways in tumor cell proliferation, differentiation, and angiogenesis, etc., which may lead to X-linked agammaglobulinemia, non-Hodgkin's lymphoma (NHL) and many B-cell malignancies, including chronic lymphocytic leukemia (CLL), mantle cell lymphoma, and diffuse large B-cell lymphoma. As mainly expressed in B cells and myeloid cells, BTK is a target with relatively high targeting ability and safety.

PROTAC (proteolysis targeting chimera) molecules are a class of dual function compounds which are capable of binding to both targeted proteins and E3 ubiquitin ligases. This class of compounds can induce recognition of targeted proteins by proteasomes in a cell to cause the degradation of the targeted protein, which can effectively reduce the contents of the targeted proteins in the cell. By introducing a ligand capable of binding to various targeted proteins into the PROTAC molecules, it is possible to apply the PROTAC technology to the treatment of various diseases, and this technology has attracted extensive attention in recent years.

SUMMARY OF THE DISCLOSURE

The present disclosure develops a BTK inhibitor with a novel structure, good efficacy, high bioavailability and higher safety, for use in the treatment of BTK-related diseases such as tumors or autoimmune system diseases.

The present disclosure develops a PROTAC compound of BTK inhibitors and E3 ubiquitin ligases which has a novel structure, good efficacy, high bioavailability, higher safety, and can inhibit or degrade BTKs, for use in the treatment of BTK-related diseases such as tumors or autoimmune system diseases.

The present disclosure relates to a compound represented by general formula (I) or a stereoisomer, a solvate, a prodrug, a metabolite, a pharmaceutically acceptable salt or a co-crystal thereof, wherein $$B-L-K \qquad (I);$$

L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond;

Cy1, Cy2, Cy3 and Cy4 are each independently selected from 3- to 12-membered heterocyclic ring, 3- to 12-membered cycloalkyl, 6- to 10-membered aryl or a bond, wherein the heterocyclic ring, cycloalkyl or aryl is optionally further substituted with 0 to 4 substituents selected from H, F, Cl, Br, I, OH, $NH_2$, oxo (=O), $C_{1-4}$ alkyl or $C_{1-4}$ alkoxy, and the heterocyclic ring contains 1 to 4 heteroatoms selected from O, S or N;

Cy1, Cy2, Cy3 and Cy4 cannot all be a bond;

when Ak1, Ak2, Ak3, Ak4 or Ak5 is O, they cannot be directly connected to B;

when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from $CH_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidine, piperazine, pyrimidine or pyridine;

B is selected from B1-W1-B2-B3-B4-;

B1 is selected from 6-membered heteroaryl ring or phenyl, wherein the heteroaryl ring or phenyl is optionally further substituted with 0 to 4 $R^{b1}$, and the heteroaryl ring contains 1 to 4 heteroatoms selected from O, S or N;

W1 is selected from —O—, —S—, —NH—, —NHCO— or —CONH—;

B2 is selected from 6-membered heteroaryl ring or phenyl, wherein the heteroaryl ring or phenyl is optionally further substituted with 0 to 4 $R^{b2}$, and the heteroaryl ring contains 1 to 4 heteroatoms selected from O, S or N;

B3 is selected from 8- to 10-membered fused heterocyclic ring, wherein the fused heterocyclic ring is optionally further substituted with 0 to 4 $R^{b3}$, and the fused heterocyclic ring contains 1 to 4 heteroatoms selected from O, S or N;

B4 is selected from 5- to 6-membered saturated heterocyclic ring, wherein the saturated heterocyclic ring is optionally further substituted with 0 to 4 $R^{b4}$, and the saturated heterocyclic ring contains 1 to 2 heteroatoms selected from O, S or N;

$R^{b1}$, $R^{b2}$, $R^{b3}$ or $R^{b4}$ is each independently selected from H, F, Cl, Br, I, OH, $NH_2$, CN, $CONH_2$, $C_{1-4}$ alkyl or $C_{1-4}$ alkoxy, and the alkyl and alkoxy are optionally further substituted with 0 to 4 substituents selected from H, F, Cl, Br, I, OH, $NH_2$, CN, $CONH_2$, $C_{1-4}$ alkyl or $C_{1-4}$ alkoxy;

K is selected from

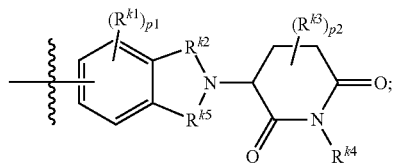

$R^{k2}$ is selected from $CH_2$, C=O, S=O, or $SO_2$;

$R^{k1}$, $R^{k3}$ or $R^{k4}$ is each independently selected from H, F, Cl, Br, I, OH, $NH_2$, CN, COOH, $C_{1-4}$ alkyl or $C_{1-4}$ alkoxy;

$R^{k5}$ is selected from C=O or

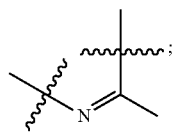 [SMILES: */N=C(\*)C]

p1 or p2 is each independently selected from 0, 1, 2, 3 or 4.

It should be understood that Ak1, Ak2, Ak3, Ak4 and Ak5, as well as Cy1, Cy2, Cy3 and Cy4, as well as B2, B3 and B4 of the present disclosure are subunits when they are each independently substituents.

Some embodiments of the present disclosure relate to a compound represented by general formula (I) or a stereoisomer, a solvate, a prodrug, a metabolite, a pharmaceutically acceptable salt or a co-crystal thereof, wherein L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond; Cy1, Cy2, Cy3 and Cy4 are each independently selected from 3-membered heterocyclic ring, 4-membered heterocyclic ring, 5-membered heterocyclic ring, 6-membered heterocyclic ring, 7-membered heterocyclic ring, 8-membered heterocyclic ring, 9-membered heterocyclic ring, 10-membered heterocyclic ring, 11-membered heterocyclic ring, 12-membered heterocyclic ring, 3-membered cycloalkyl, 4-membered cycloalkyl, 5-membered cycloalkyl, 6-membered cycloalkyl, 7-membered cycloalkyl, 8-membered cycloalkyl, 9-membered cycloalkyl, 10-membered cycloalkyl, 11-membered cycloalkyl, 12-membered cycloalkyl, 6- to 10-membered aryl or a bond, preferably a bond, 4-membered mono-heterocyclic ring, 5-membered mono-heterocyclic ring, 6-membered mono-heterocyclic ring, 7-membered mono-heterocyclic ring, 5-membered fused heterocyclic ring, 6-membered fused heterocyclic ring, 7-membered fused heterocyclic ring, 8-membered fused heterocyclic ring, 9-membered fused heterocyclic ring, 10-membered fused heterocyclic ring, 6-membered spiro-heterocyclic ring, 7-membered spiro-heterocyclic ring, 8-membered spiro-heterocyclic ring, 9-membered spiro-heterocyclic ring, 10-membered spiro-heterocyclic ring, 11-membered spiro-heterocyclic ring, 12-membered spiro-heterocyclic ring, 7-membered bridged-heterocyclic ring, 8-membered bridged-heterocyclic ring, 9-membered bridged-heterocyclic ring, 10-membered bridged-heterocyclic ring, 4-membered monocycloalkyl, 5-membered monocycloalkyl, 6-membered monocycloalkyl, 7-membered monocycloalkyl, 5-membered fused cycloalkyl, 6-membered fused cycloalkyl, 7-membered fused cycloalkyl, 8-membered fused cycloalkyl, 9-membered fused cycloalkyl, 10-membered fused cycloalkyl, 6-membered spiro cycloalkyl, 7-membered spiro cycloalkyl, 8-membered spiro cycloalkyl, 9-membered spiro cycloalkyl, 10-membered spiro cycloalkyl, 11-membered spiro cycloalkyl, 12-membered spiro cycloalkyl, 7-membered bridged cycloalkyl, 8-membered bridged cycloalkyl, 9-membered bridged cycloalkyl, 10-membered bridged cycloalkyl or 6-10-membered aryl, wherein the aryl, cycloalkyl, mono-heterocyclic ring, fused heterocyclic ring, spiro-heterocyclic ring or bridged-heterocyclic ring is optionally further substituted with 0, 1, 2, 3 or 4 substituents selected from H, F, Cl, Br, I, OH, $NH_2$, oxo, $C_{1-4}$ alkyl or $C_{1-4}$ alkoxy, and the mono-heterocyclic ring, fused heterocyclic ring, spiro-heterocyclic ring or bridged-heterocyclic ring contains 1, 2, 3 or 4 heteroatoms selected from O, S or N;

Cy1, Cy2, Cy3 and Cy4 cannot all be a bond;

when Ak1, Ak2, Ak3, Ak4 or Ak5 is O, they cannot be directly connected to B;

when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from $CH_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidine, piperazine, pyrimidine or pyridine;

B is selected from B1-W1-B2-B3-B4-;

B1 is selected from 6-membered heteroaryl ring or phenyl, preferably phenyl or pyridyl, wherein the heteroaryl ring, phenyl or pyridyl is optionally further substituted with 0, 1, 2, 3 or 4 $R^{b1}$, and the heteroaryl ring contains 1, 2, 3 or 4 heteroatoms selected from O, S or N;

W1 is selected from —O—, —NHCO— or —CONH—;

B2 is selected from 6-membered heteroaryl ring or phenyl, preferably phenyl or pyridyl, wherein the heteroaryl ring, phenyl or pyridyl is optionally further substituted with 0, 1, 2, 3 or 4 $R^{b2}$, and the heteroaryl ring contains 1, 2, 3 or 4 heteroatoms selected from O, S or N;

B3 is selected from 8-membered fused heterocyclic ring, 9-membered fused heterocyclic ring or 10-membered fused heterocyclic ring, preferably substituted or unsubstituted imidazopyrimidine, pyrazolopyrimidine, imidazopyrazine, pyrazolopyrazine, imidazotetrahydropyrimidine, or pyrazolotetrahydropyrimidine, when substituted, wherein the fused heterocyclic ring, imidazopyrimidine, pyrazolopyrimidine, imidazopyrazine, pyrazolopyrazine, imidazotetrahydropyrimidine, or pyrazolotetrahydropyrimidine is optionally further substituted with 0, 1, 2, 3 or 4 $R^{b3}$, and the fused heterocyclic ring contains 1, 2, 3 or 4 heteroatoms selected from O, S or N;

B4 is selected from 5-membered saturated heterocyclic ring or 6-membered saturated heterocyclic ring, preferably substituted or unsubstituted azacyclopentyl, piperidine or piperazine, wherein the heterocyclic ring, azacyclopentyl, piperidine or piperazine is optionally further substituted with 0, 1, 2, 3 or 4 $R^{b4}$, and the saturated heterocyclic ring contains 1 to 2 heteroatoms selected from O, S or N;

K is selected from

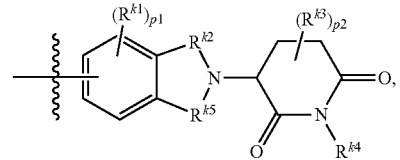

or K can be selected from

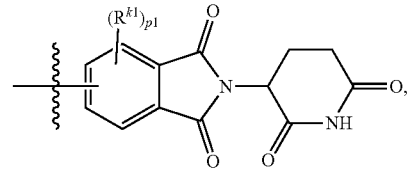

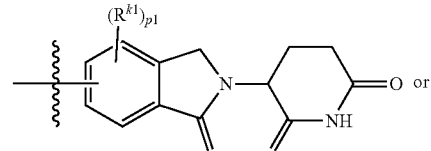

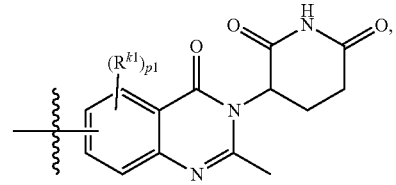

or K can be selected from
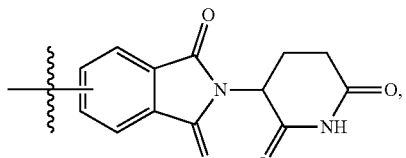
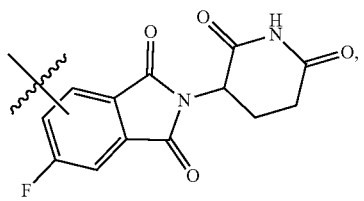
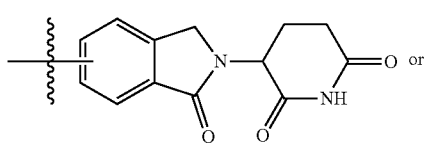 or
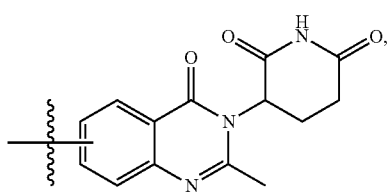
or K can be selected from
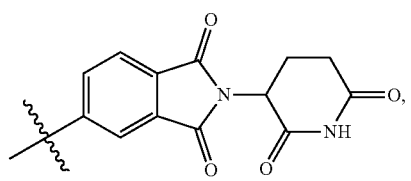
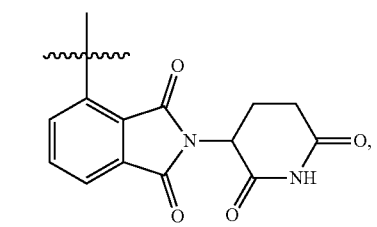
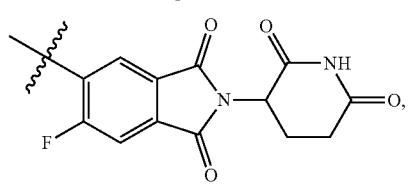
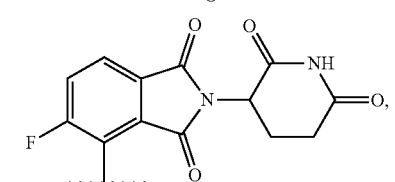
-continued
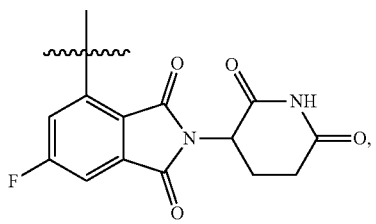
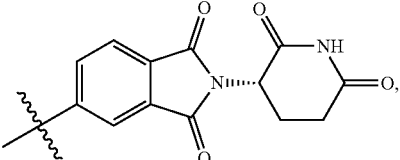
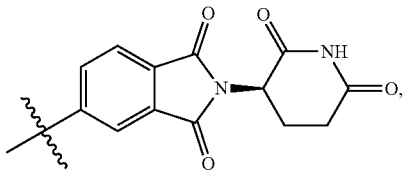
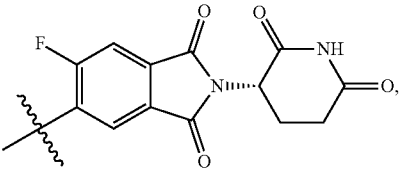
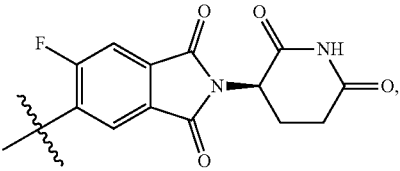
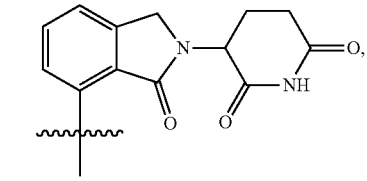
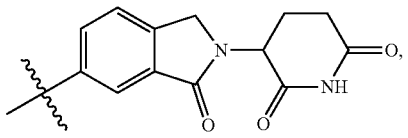
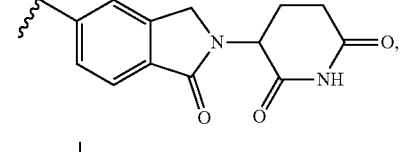
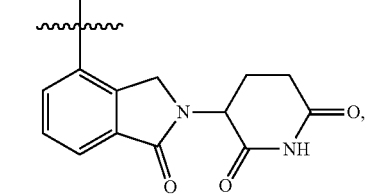

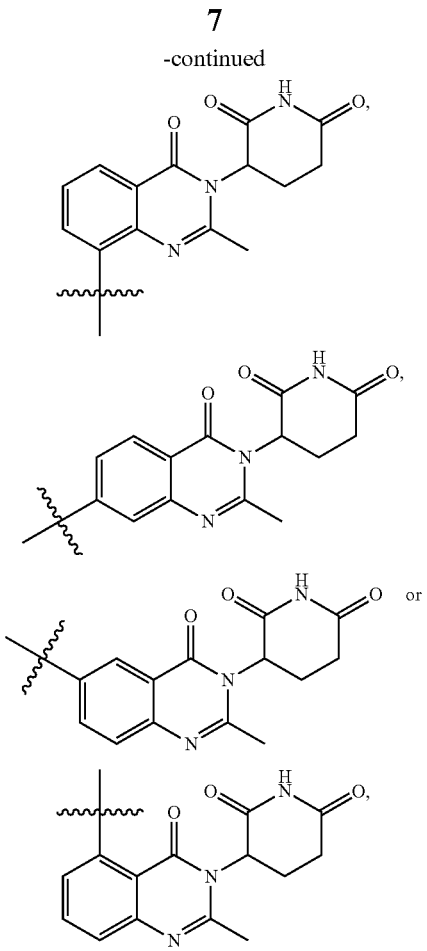

or K can be selected from

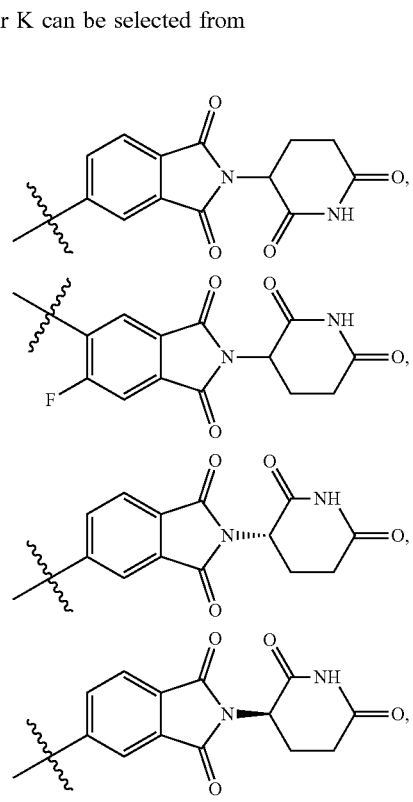

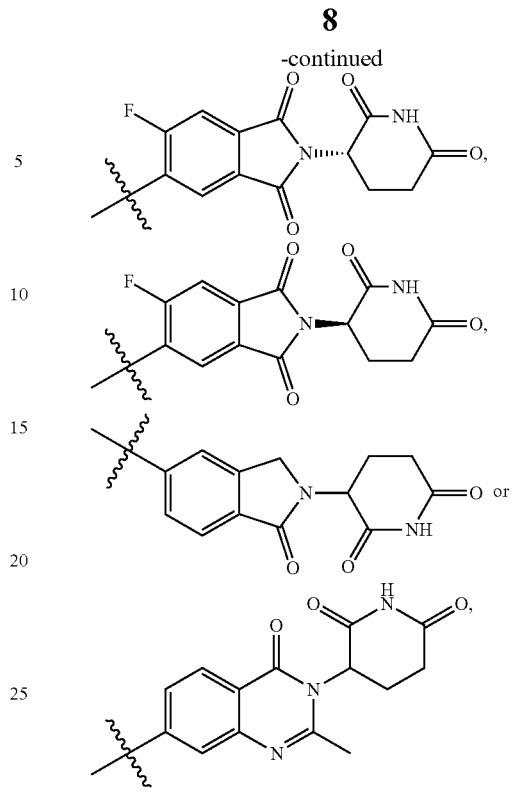

$R^{k2}$ is selected from $CH_2$, C=O, S=O, or $SO_2$;

$R^{k1}$, $R^{k3}$ or $R^{k4}$ is each independently selected from H, F, Cl, Br, I, OH, $NH_2$, CN, COOH, $C_{1-4}$ alkyl or $C_{1-4}$ alkoxy;

$R^{k5}$ is selected from C=O or

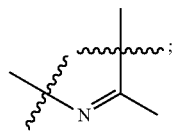 [SMILES: */N=C(\*)C]

p1 or p2 is each independently selected from 0, 1, 2, 3 or 4.

According to some embodiments of the present disclosure, wherein

L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond;

Cy1, Cy2, Cy3 and Cy4 are each independently selected from 3- to 12-membered heterocyclic ring, 3- to 12-membered cycloalkyl, 6- to 10-membered aryl or a bond, wherein the heterocyclic ring, cycloalkyl or aryl is optionally further substituted with 0 to 4 substituents selected from H, F, Cl, Br or I, and the heterocyclic ring contains 1 to 4 heteroatoms selected from O, S or N.

According to some embodiments of the present disclosure, wherein Ak2, Ak3 and Ak4 are bonds; Ak1 and Ak5 are each independently selected from $CH_2$, O or a bond.

Some embodiments of the present disclosure relate to a compound represented by general formula (I) or a stereoisomer, a solvate, a prodrug, a metabolite, a pharmaceutically acceptable salt or a co-crystal thereof, wherein L is selected from -Ak1-Cy1-Ak2-Cy2-Ak3-Cy3-Ak4-Cy4-Ak5-;

Ak1, Ak2, Ak3, Ak4 and Ak5 are each independently selected from CH$_2$, O or a bond;

Cy1, Cy2, Cy3 and Cy4 are each independently selected from a substituted or unsubstituted bond, phenyl, naphthyl, cyclobutyl, cyclopentyl, cyclohexyl, cyclobutyl-fused-cyclobutyl, cyclobutyl-fused-cyclopentyl, cyclobutyl-fused-cyclohexyl, cyclopentyl-fused-cyclopentyl, cyclopentyl-fused-cyclohexyl, cyclohexyl-fused-cyclohexyl, cyclopropyl-fused-cyclobutyl, cyclopropyl-fused-cyclopentyl, cyclopropyl-fused-cyclohexyl, cyclobutyl-spiro-cyclobutyl, cyclobutyl-spiro-cyclopentyl, cyclobutyl-spiro-cyclohexyl, cyclopentyl-spiro-cyclopentyl, cyclopentyl-spiro-cyclohexyl, cyclohexyl-spiro-cyclohexyl, cyclopropyl-spiro-cyclobutyl, cyclopropyl-spiro-cyclopentyl, cyclopropyl-spiro-cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, cyclopropyl-fused-azetidinyl, cyclopropyl-fused-azacyclopentyl, cyclopropyl-fused-azacyclohexyl, cyclopropyl-fused-piperidyl, cyclobutyl-fused-azetidinyl, cyclobutyl-fused-azacyclopentyl, cyclobutyl-fused-azacyclohexyl, cyclobutyl-fused-piperidyl, cyclopentyl-fused-azetidinyl, cyclopentyl-fused-azacyclopentyl, cyclopentyl-fused-azacyclohexyl, cyclopentyl-fused-piperidyl, cyclohexyl-fused-azetidinyl, cyclohexyl-fused-azacyclopentyl, cyclohexyl-fused-azacyclohexyl, cyclohexyl-fused-piperidyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, azacyclohexyl-fused-azetidinyl, azacyclohexyl-fused-azacyclopentyl, azacyclohexyl-fused-azacyclohexyl, azacyclohexyl-fused-piperidyl, cyclobutyl-spiro-azetidinyl, cyclobutyl-spiro-azacyclopentyl, cyclobutyl-spiro-azacyclohexyl, cyclopentyl-spiro-azetidinyl, cyclopentyl-spiro-azacyclopentyl, cyclopentyl-spiro-azacyclohexyl, cyclohexyl-spiro-azetidinyl, cyclohexyl-spiro-azacyclopentyl, cyclohexyl-spiro-azacyclohexyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, cyclobutyl-spiro-piperidyl, cyclopentyl-spiro-piperidyl, cyclohexyl-spiro-piperidyl, azetidinyl-spiro-piperidyl, azacyclopentyl-spiro-piperidyl, azacyclohexyl-spiro-piperidyl,

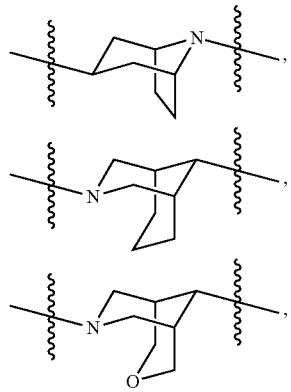

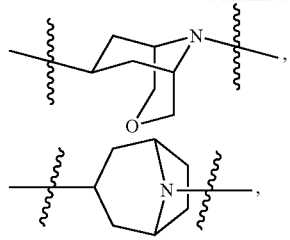

preferably a substituted or unsubstituted bond, phenyl, naphthyl, cyclobutyl, cyclopentyl, cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, cyclohexyl-spiro-azetidinyl, cyclobutyl-spiro-azacyclohexyl, cyclopentyl-fused-azacyclopentyl, azacyclohexyl-fused-azetidinyl, azacyclohexyl-fused-azacyclopentyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, azetidinyl-spiro-piperidyl, azacyclopentyl-spiro-piperidyl, or

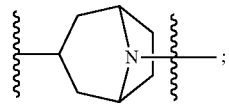 [SMILES: *C1CC2CCC(C1)N2*]

which, when substituted, are optionally further substituted with 0, 1, 2, 3 or 4 substituents selected from H, F, Cl, Br, I, OH, NH$_2$, oxo, C$_{1-4}$ alkyl or C$_{1-4}$ alkoxy, preferably substituted with 0, 1, 2, 3 or 4 substituents selected from H, F, Cl, Br, I, OH, NH$_2$, oxo, methyl, ethyl, isopropyl, methoxy, ethoxy or isopropoxy;

Cy1, Cy2, Cy3 and Cy4 cannot all be a bond;

when Ak1, Ak2, Ak3, Ak4 or Ak5 is O, they cannot be directly connected to B;

when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from CH$_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidyl, piperazinyl, pyrimidinyl or pyridyl;

B is selected from

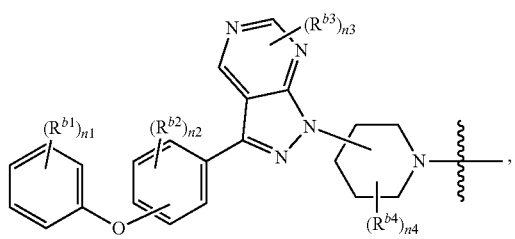

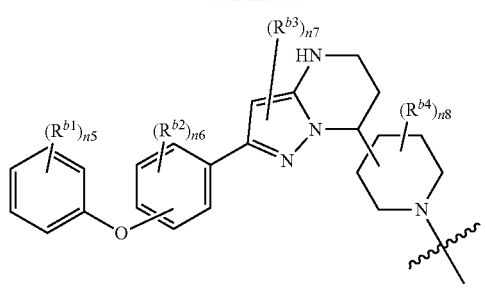
or
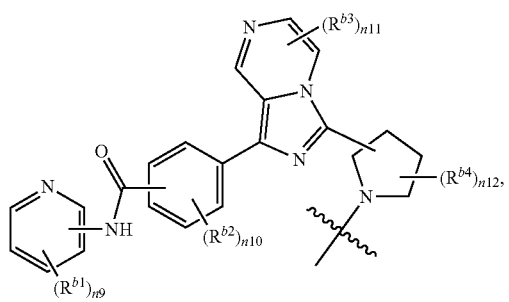
preferably,
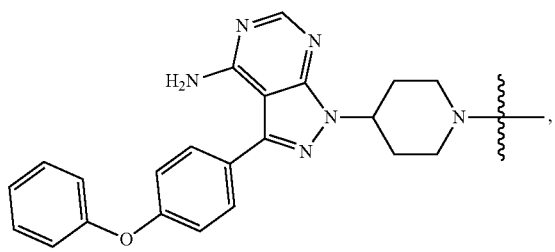
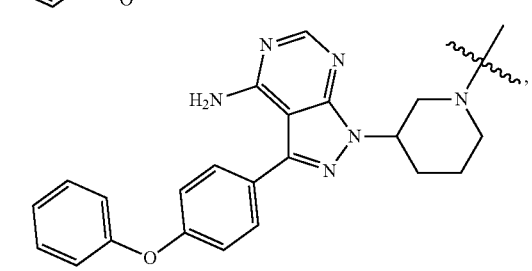
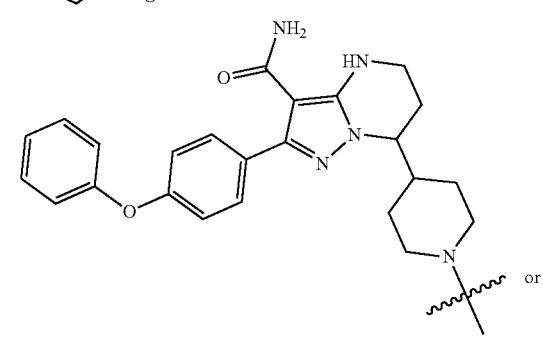
or
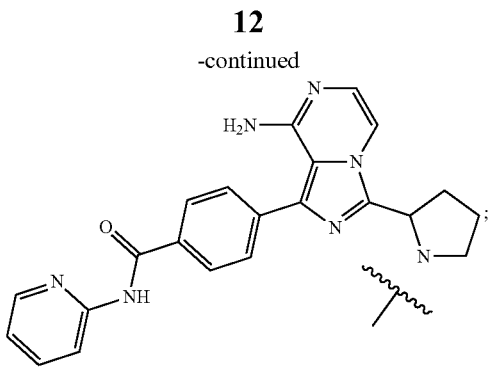
or B can be selected from
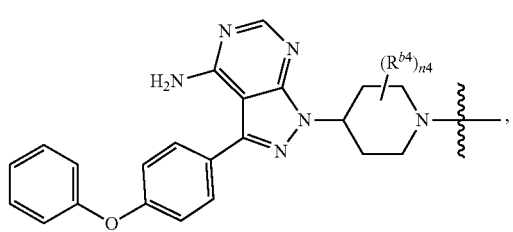
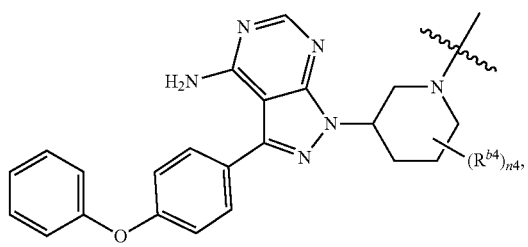
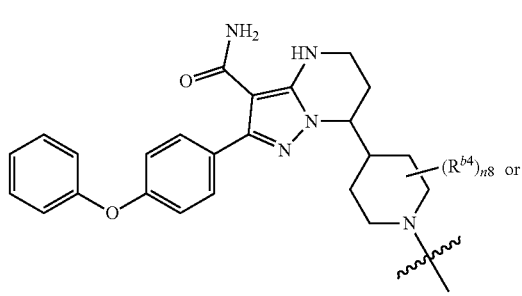
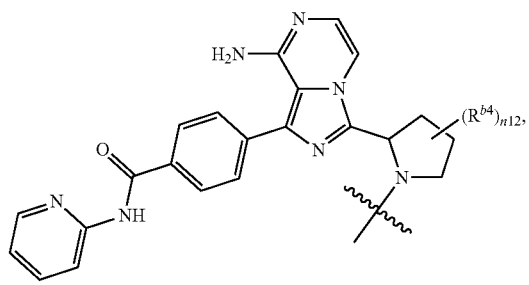

or B can be selected from
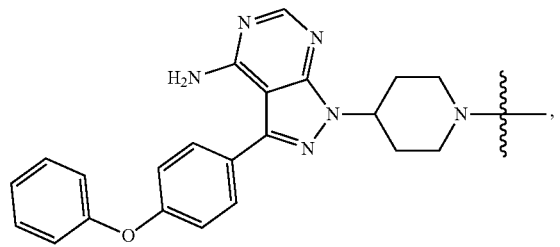
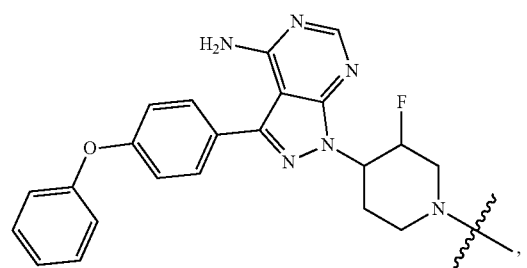
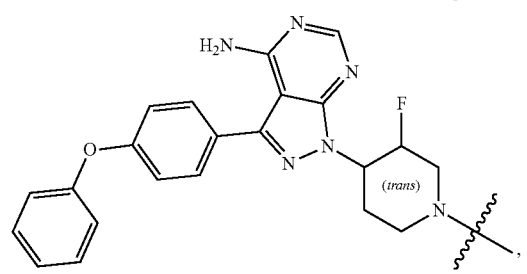
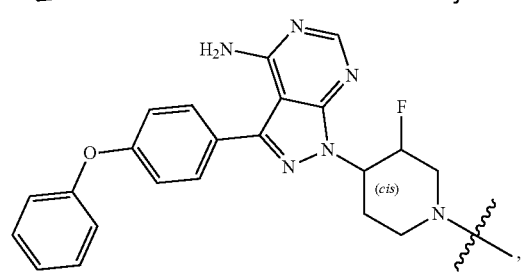
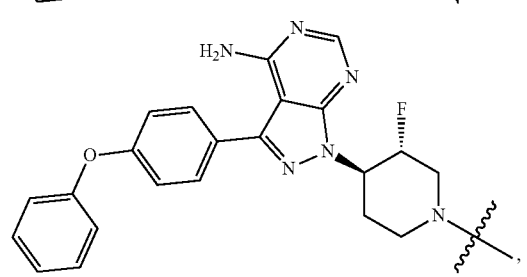
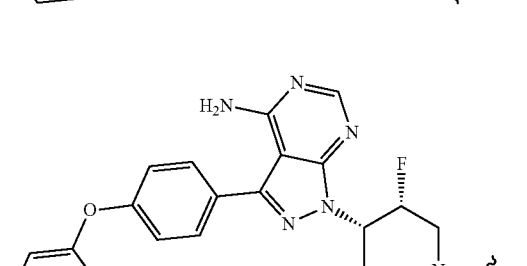
-continued
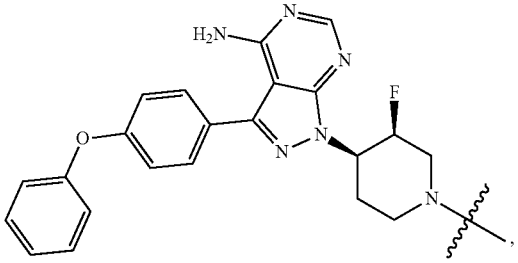
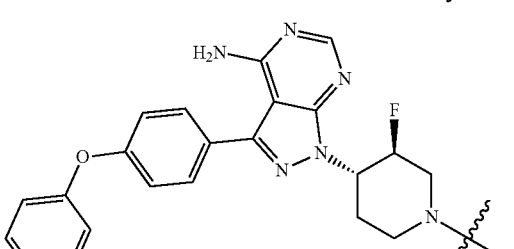
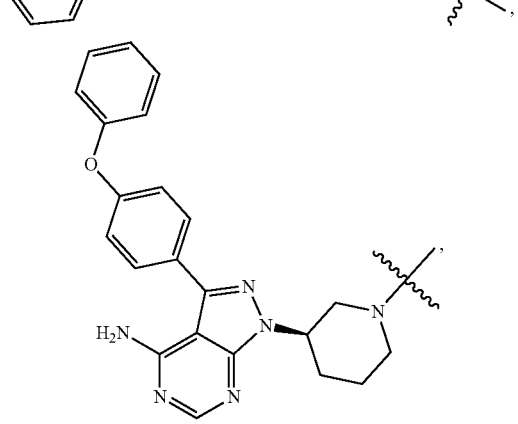
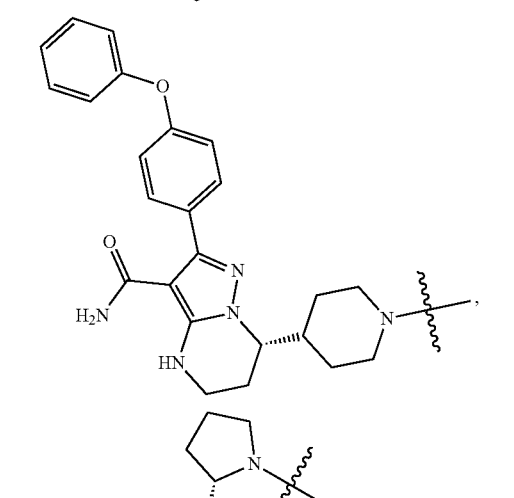
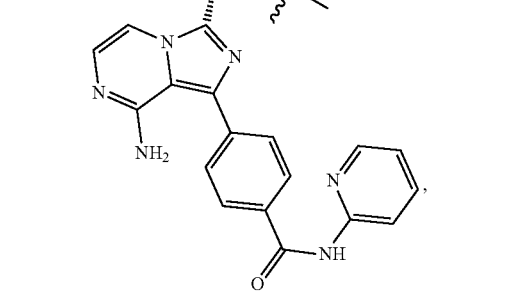

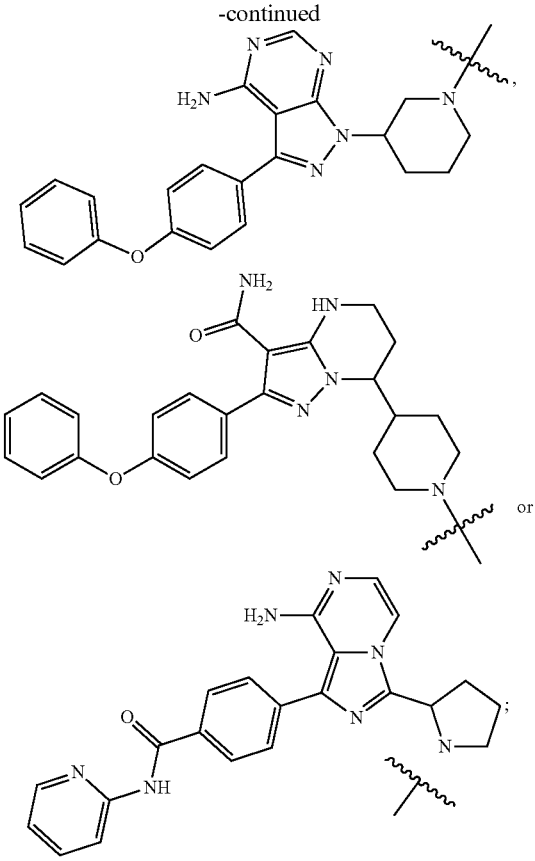

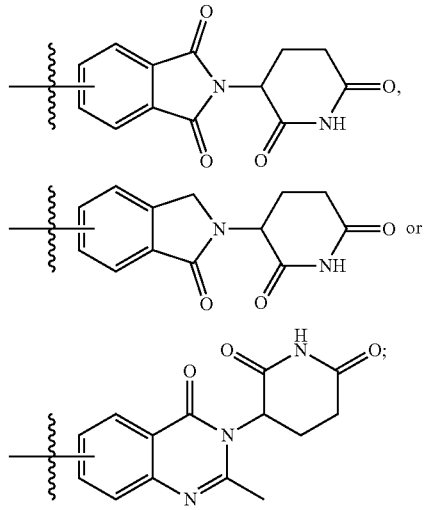

preferably or K can be selected from

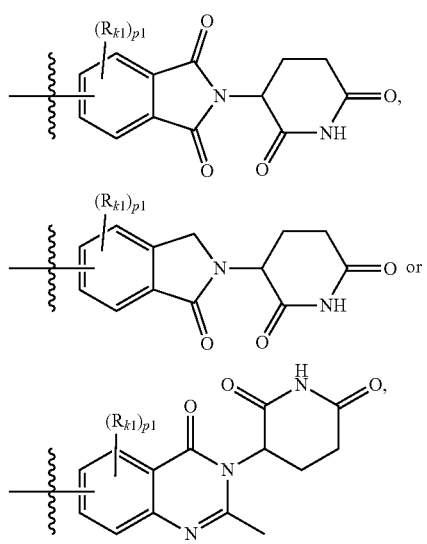

$R^{b1}$, $R^{b2}$, $R^{b3}$ or $R^{b4}$ is each independently selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n1, n2, n3, n4, n5, n6, n7, n8, n9, n10, n11, and n12 are each independently selected from 0, 1, 2, 3 or 4;

K is selected from

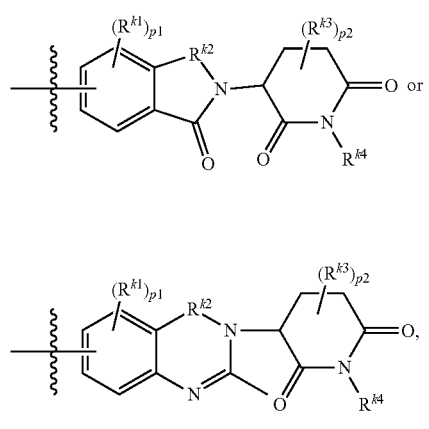

or K can be selected from

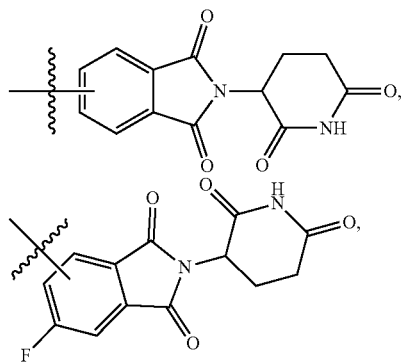

-continued
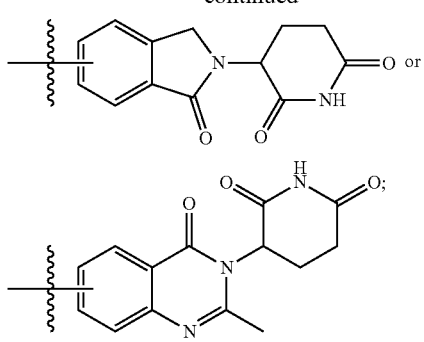
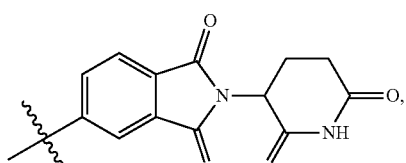
or K can be selected from
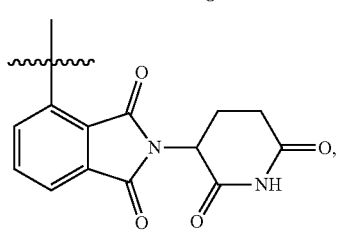
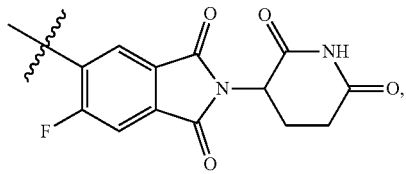
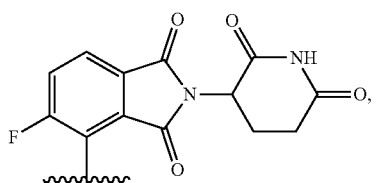
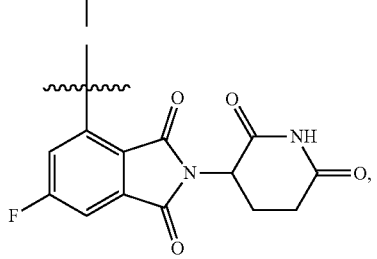
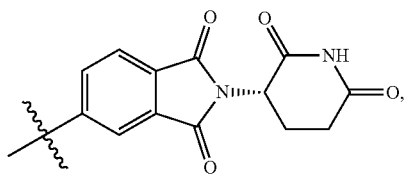
-continued
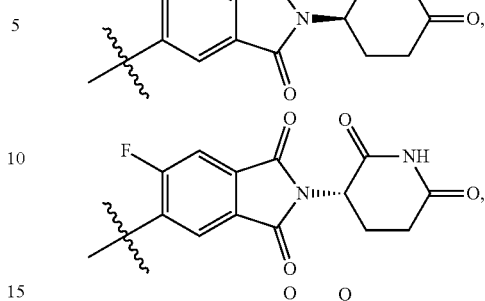
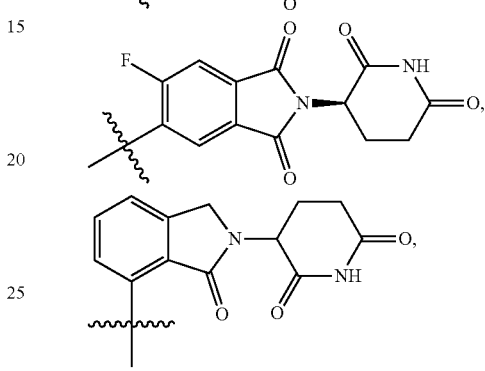
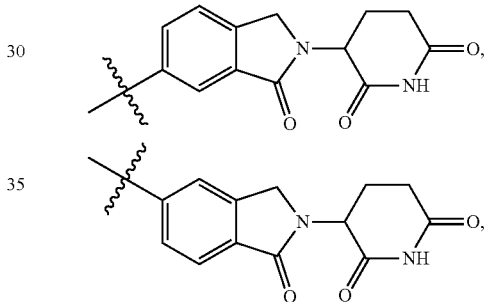
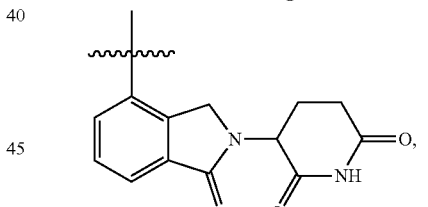
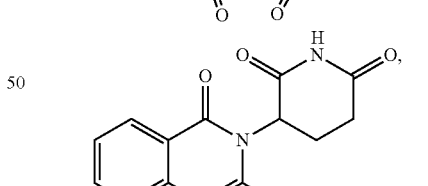
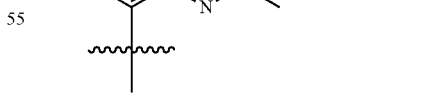

-continued

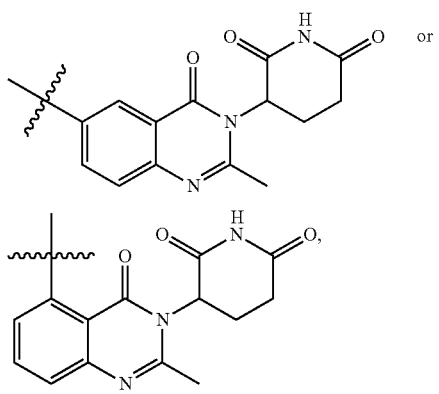

or K can be selected from

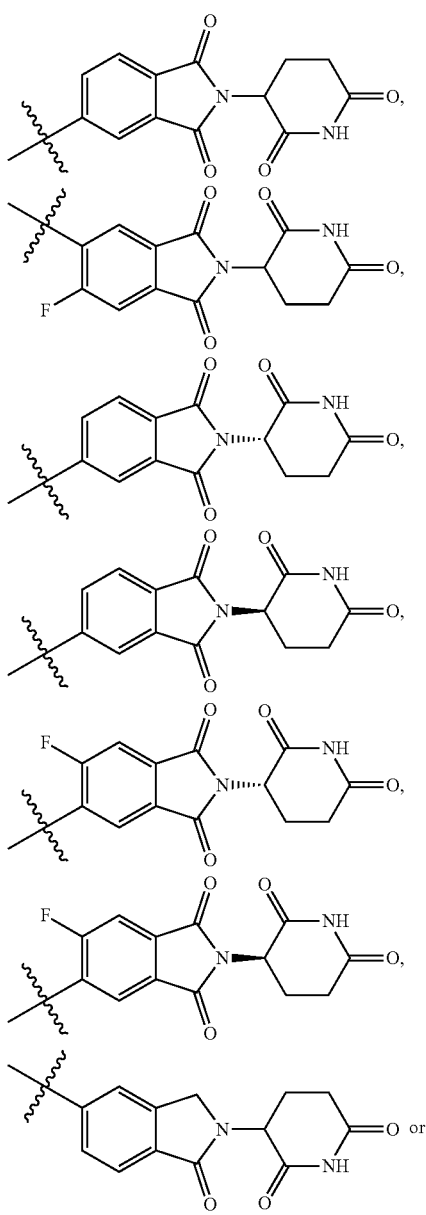

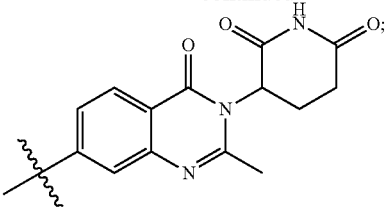

$R^{k2}$ is selected from $CH_2$ or C=O;

$R^{k1}$, $R^{k3}$ or $R^{k4}$ is each independently selected from H, F, Cl, Br, I, OH, $NH_2$, CN, COOH, $C_{1-4}$ alkyl or $C_{1-4}$ alkoxy, preferably H, F, Cl, Br, I, OH or $NH_2$;

p1 or p2 is each independently selected from 0, 1 or 2.

Some embodiments of the present disclosure relate to a compound represented by general formula (I) or a stereoisomer, a solvate, a prodrug, a metabolite, a pharmaceutically acceptable salt or a co-crystal thereof, wherein L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond;

Cy1, Cy2, Cy3 and Cy4 are each independently selected from a substituted or unsubstituted bond, phenyl, naphthyl, cyclobutyl, cyclopentyl, cyclohexyl, cyclobutyl-fused-cyclobutyl, cyclobutyl-fused-cyclopentyl, cyclobutyl-fused-cyclohexyl, cyclopentyl-fused-cyclopentyl, cyclopentyl-fused-cyclohexyl, cyclohexyl-fused-cyclohexyl, cyclopropyl-fused-cyclobutyl, cyclopropyl-fused-cyclopentyl, cyclopropyl-fused-cyclohexyl, cyclobutyl-spiro-cyclobutyl, cyclobutyl-spiro-cyclopentyl, cyclobutyl-spiro-cyclohexyl, cyclopentyl-spiro-cyclopentyl, cyclopentyl-spiro-cyclohexyl, cyclohexyl-spiro-cyclohexyl, cyclopropyl-spiro-cyclobutyl, cyclopropyl-spiro-cyclopentyl, cyclopropyl-spiro-cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, cyclopropyl-fused-azetidinyl, cyclopropyl-fused-azacyclopentyl, cyclopropyl-fused-azacyclohexyl, cyclopropyl-fused-piperidyl, cyclobutyl-fused-azetidinyl, cyclobutyl-fused-azacyclopentyl, cyclobutyl-fused-azacyclohexyl, cyclobutyl-fused-piperidyl, cyclopentyl-fused-azetidinyl, cyclopentyl-fused-azacyclopentyl, cyclopentyl-fused-azacyclohexyl, cyclopentyl-fused-piperidyl, cyclohexyl-fused-azetidinyl, cyclohexyl-fused-azacyclopentyl, cyclohexyl-fused-azacyclohexyl, cyclohexyl-fused-piperidyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, azacyclohexyl-fused-azetidinyl, azacyclohexyl-fused-azacyclopentyl, azacyclohexyl-fused-azacyclohexyl, azacyclohexyl-fused-piperidyl, cyclobutyl-spiro-azetidinyl, cyclobutyl-spiro-azacyclopentyl, cyclobutyl-spiro-azacyclohexyl, cyclopentyl-spiro-azetidinyl, cyclopentyl-spiro-azacyclopentyl, cyclopentyl-spiro-azacyclohexyl, cyclohexyl-spiro-azetidinyl, cyclohexyl-spiro-azacyclopentyl, cyclohexyl-spiro-azacyclohexyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, cyclobutyl-spiro-piperidyl, cyclopentyl-spiro-piperidyl, cyclohexylspiro-piperidyl, azetidinyl-spiro-piperidyl, azacyclopentyl-spiro-piperidyl, azacyclohexyl-spiro-piperidyl,

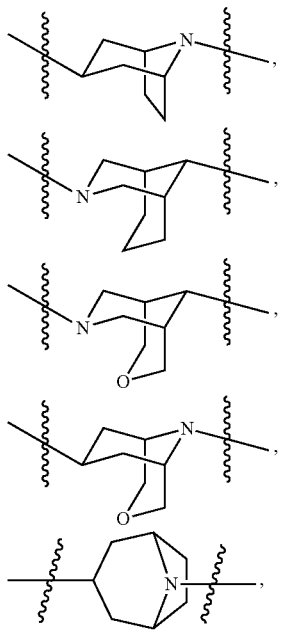

preferably a substituted or unsubstituted bond, phenyl, naphthyl, cyclobutyl, cyclopentyl, cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, cyclohexyl-spiro-azetidinyl, cyclobutyl-spiro-azacyclohexyl, cyclopentyl-fused-azacyclopentyl, azacyclohexyl-fused-azetidinyl, azacyclohexyl-fused-azacyclopentyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, azetidinyl-spiro-piperidyl, azacyclopentyl-spiro-piperidyl, or

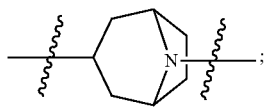 [SMILES: *C1CC2CCC(C1)N2*]

which, when substituted, are optionally further substituted with 0, 1, 2, 3 or 4 substituents selected from H, F, Cl, Br, I, OH, $NH_2$, oxo, $C_{1-4}$ alkyl or $C_{1-4}$ alkoxy, preferably substituted with 0, 1, 2, 3 or 4 substituents selected from H, F, Cl, Br, I, OH, $NH_2$, oxo, methyl, ethyl, isopropyl, methoxy, ethoxy or isopropoxy;

Cy1, Cy2, Cy3 and Cy4 cannot all be a bond;
when Ak1, Ak2, Ak3, Ak4 or Ak5 is O, they cannot be directly connected to B;
when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from $CH_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidyl, piperazinyl, pyrimidinyl or pyridyl;

B is selected from

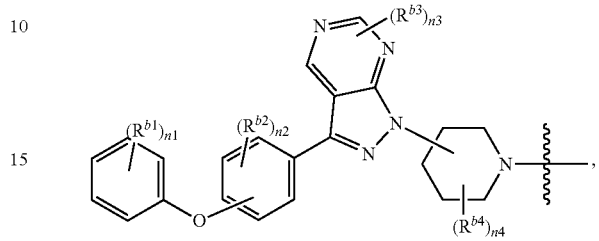

preferably

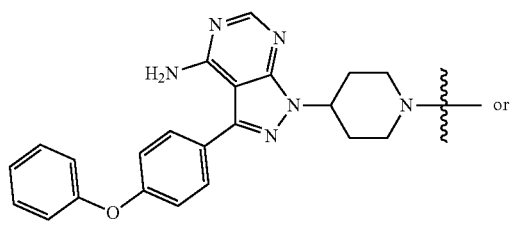

or

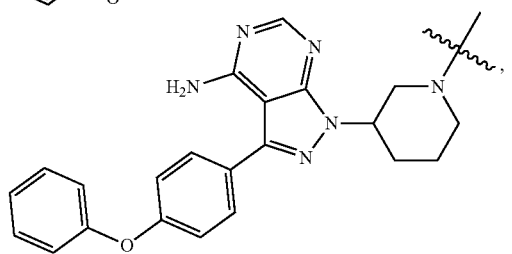

or B can be selected from

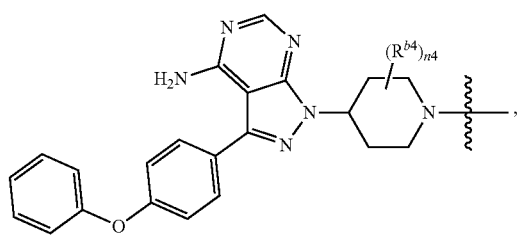

or B can be selected from

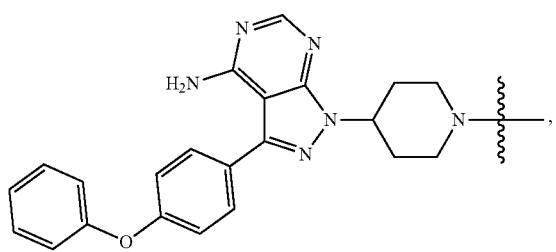

-continued

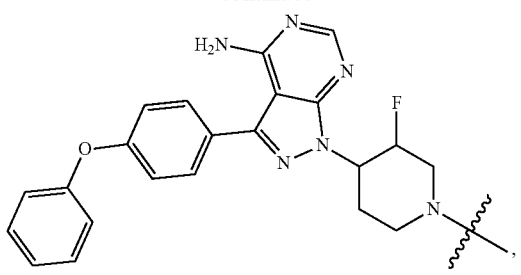

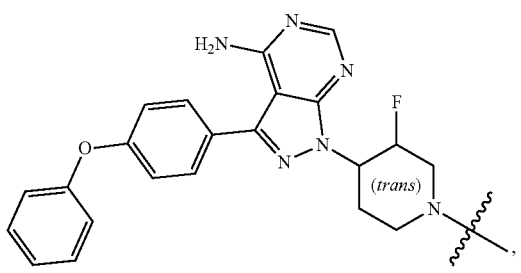

(trans)

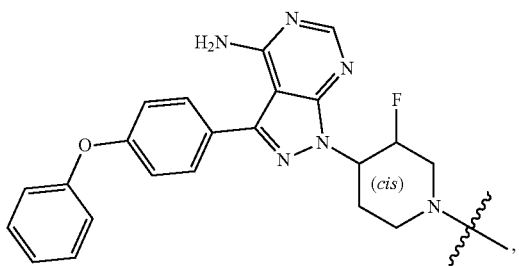

(cis)

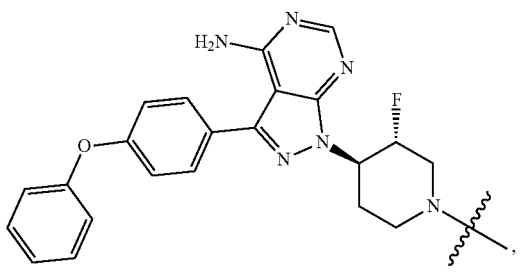

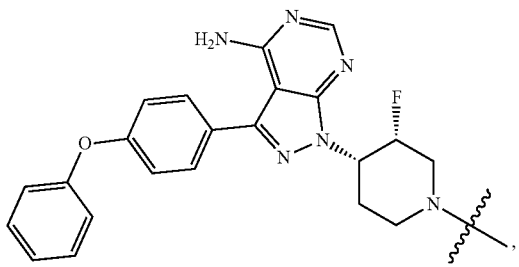

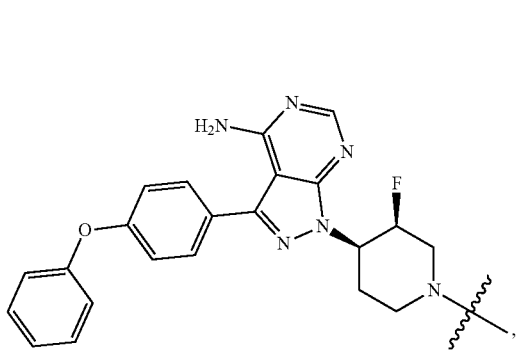

-continued

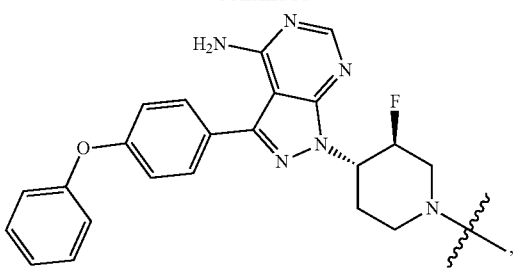

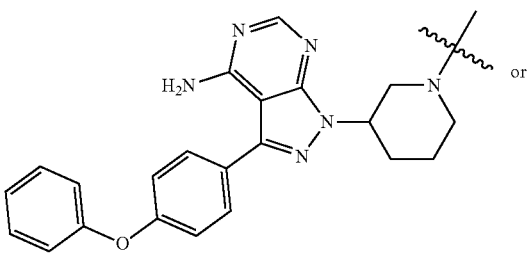

or

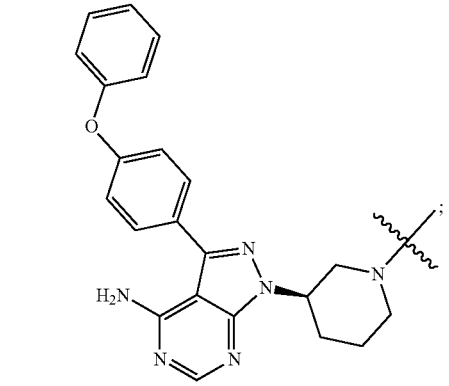

;

$R^{b1}$, $R^{b2}$, $R^{b3}$ or $R^{b4}$ is each independently selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n1, n2, n3, and n4 are each independently selected from 0, 1, 2, 3 or 4;

K is selected from

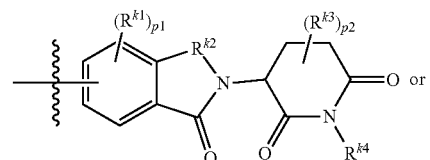 or

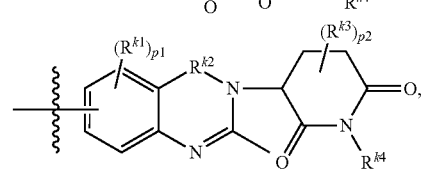

preferably
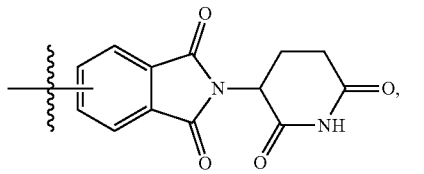
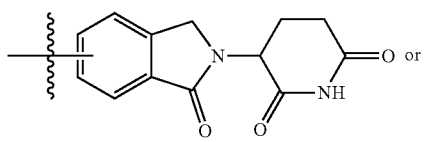
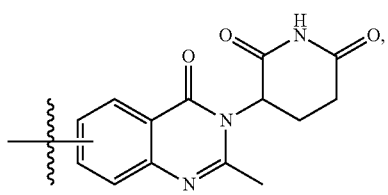
or K can be selected from
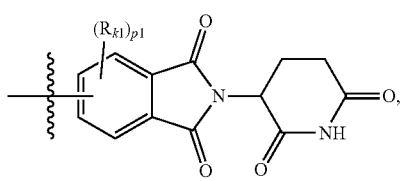
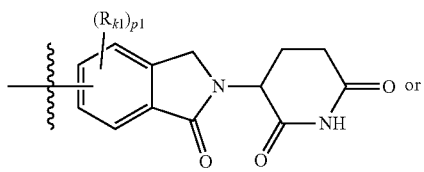
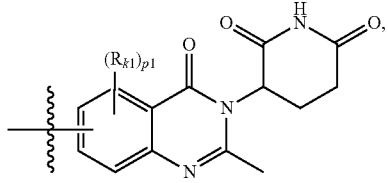
or K can be selected from
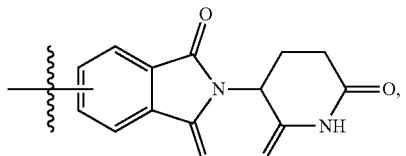
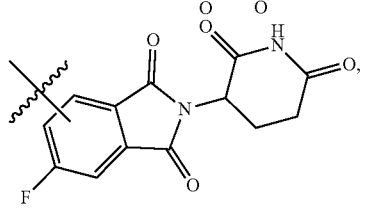
-continued
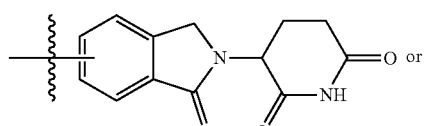
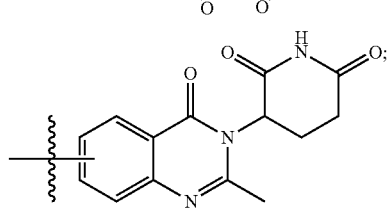
or K can be selected from
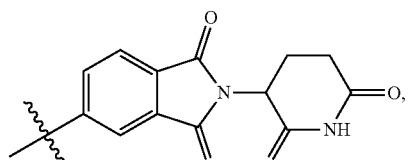
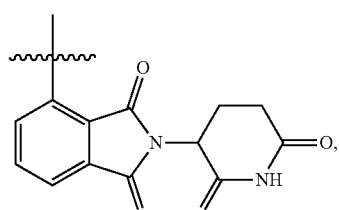
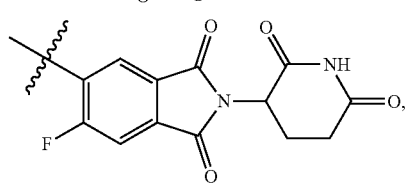
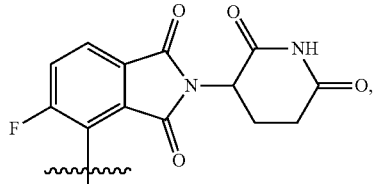
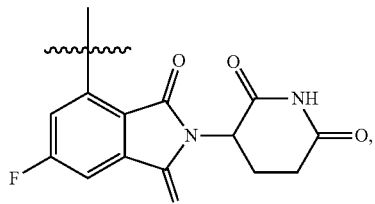
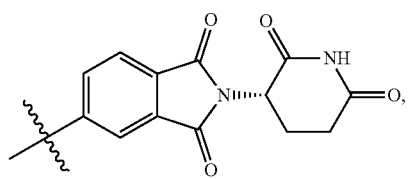

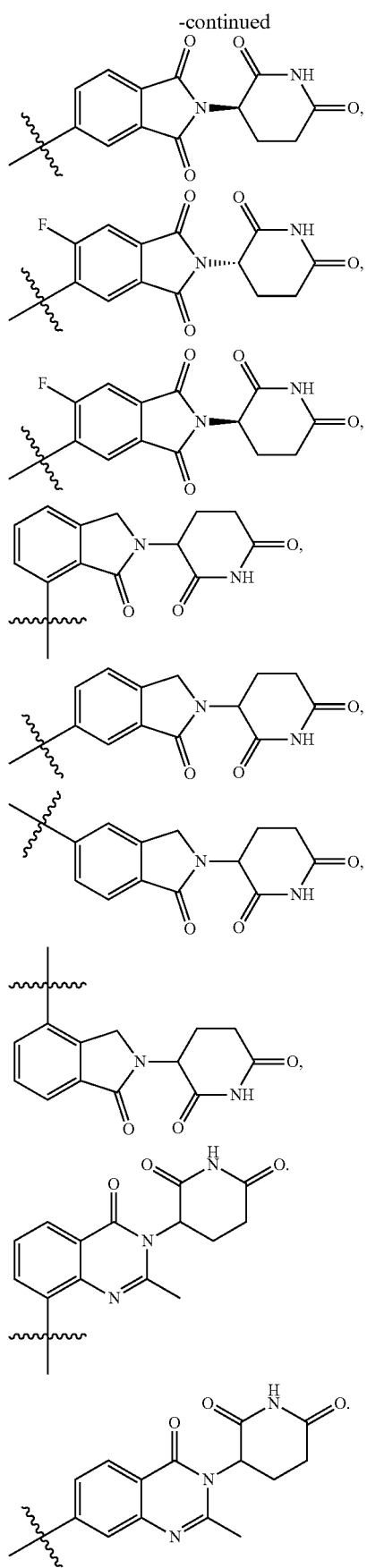
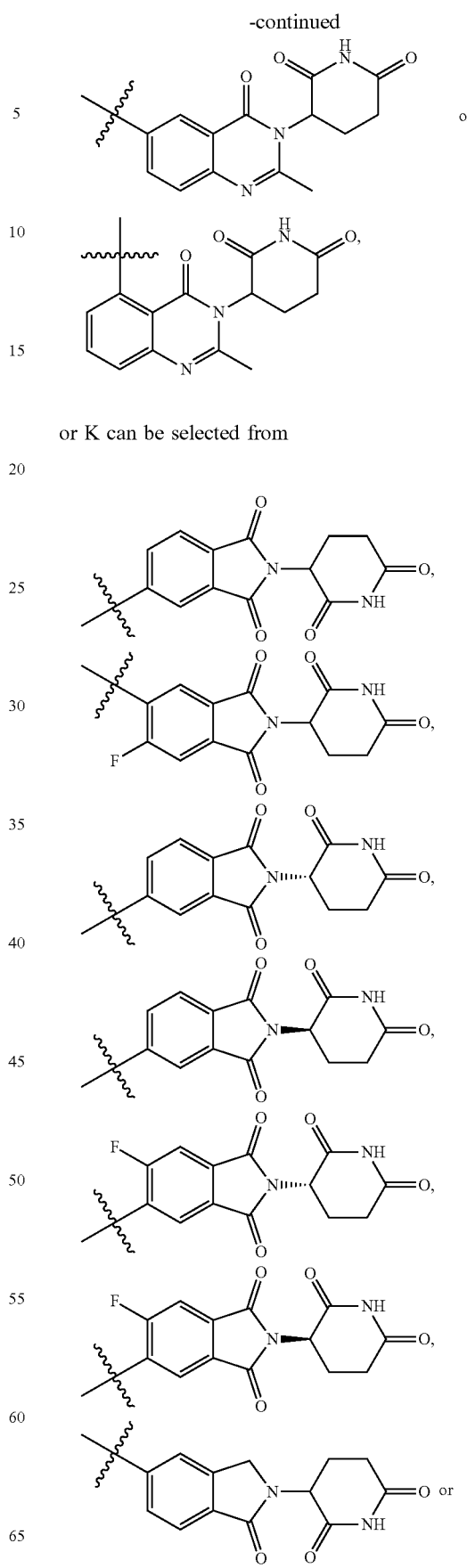
or K can be selected from

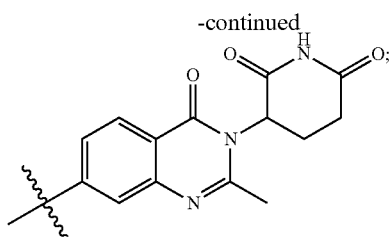

$R^{k2}$ is selected from $CH_2$ or $C=O$;

$R^{k1}$, $R^{k3}$ or $R^{k4}$ or is each independently selected from H, F, Cl, Br, I, OH, $NH_2$, CN, COOH, $C_{1-4}$ alkyl or $C_{1-4}$ alkoxy, preferably H, F, Cl, Br, I, OH or $NH_2$;

p1 or p2 is each independently selected from 0, 1 or 2.

Some embodiments of the present disclosure relate to a compound represented by general formula (I) or a stereoisomer, a solvate, a prodrug, a metabolite, a pharmaceutically acceptable salt or a co-crystal thereof, wherein L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond;

Cy1, Cy2, Cy3 and Cy4 are each independently selected from a substituted or unsubstituted bond, phenyl, naphthyl, cyclobutyl, cyclopentyl, cyclohexyl, cyclobutyl-fused-cyclobutyl, cyclobutyl-fused-cyclopentyl, cyclobutyl-fused-cyclohexyl, cyclopentyl-fused-cyclopentyl, cyclopentyl-fused-cyclohexyl, cyclohexyl-fused-cyclohexyl, cyclopropyl-fused-cyclobutyl, cyclopropyl-fused-cyclopentyl, cyclopropyl-fused-cyclohexyl, cyclobutyl-spiro-cyclobutyl, cyclobutyl-spiro-cyclopentyl, cyclobutyl-spiro-cyclohexyl, cyclopentyl-spiro-cyclopentyl, cyclopentyl-spiro-cyclohexyl, cyclohexyl-spiro-cyclohexyl, cyclopropyl-spiro-cyclobutyl, cyclopropyl-spiro-cyclopentyl, cyclopropyl-spiro-cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, cyclopropyl-fused-azetidinyl, cyclopropyl-fused-azacyclopentyl, cyclopropyl-fused-azacyclohexyl, cyclopropyl-fused-piperidyl, cyclobutyl-fused-azetidinyl, cyclobutyl-fused-azacyclopentyl, cyclobutyl-fused-azacyclohexyl, cyclobutyl-fused-piperidyl, cyclopentyl-fused-azetidinyl, cyclopentyl-fused-azacyclopentyl, cyclopentyl-fused-azacyclohexyl, cyclopentyl-fused-piperidyl, cyclohexyl-fused-azetidinyl, cyclohexyl-fused-azacyclopentyl, cyclohexyl-fused-azacyclohexyl, cyclohexyl-fused-piperidyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, azacyclohexyl-fused-azetidinyl, azacyclohexyl-fused-azacyclopentyl, azacyclohexyl-fused-azacyclohexyl, azacyclohexyl-fused-piperidyl, cyclobutyl-spiro-azetidinyl, cyclobutyl-spiro-azacyclopentyl, cyclobutyl-spiro-azacyclohexyl, cyclopentyl-spiro-azetidinyl, cyclopentyl-spiro-azacyclopentyl, cyclopentyl-spiro-azacyclohexyl, cyclohexyl-spiro-azetidinyl, cyclohexyl-spiro-azacyclopentyl, cyclohexyl-spiro-azacyclohexyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, cyclobutyl-spiro-piperidyl, cyclopentyl-spiro-piperidyl, cyclohexyl-spiro-piperidyl, azetidinyl-spiro-piperidyl, azacyclopentyl-spiro-piperidyl, azacyclohexyl-spiro-piperidyl,

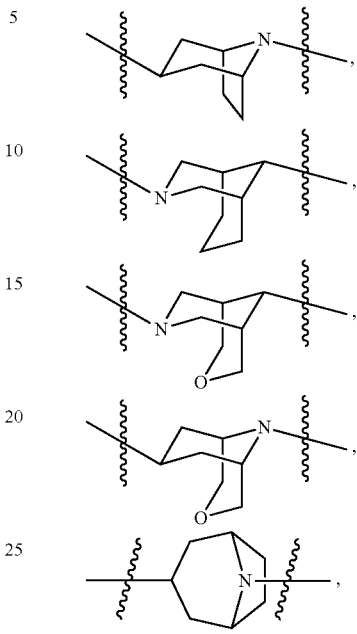

preferably a substituted or unsubstituted bond, phenyl, naphthyl, cyclobutyl, cyclopentyl, cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, cyclohexyl-spiro-azetidinyl, cyclobutyl-spiro-azacyclohexyl, cyclopentyl-fused-azacyclopentyl, azacyclohexyl-fused-azetidinyl, azacyclohexyl-fused-azacyclopentyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, azetidinyl-spiro-piperidyl, azacyclopentyl-spiro-piperidyl, or

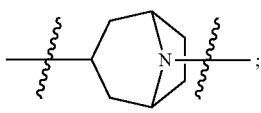

which, when substituted, are optionally further substituted with 0, 1, 2, 3 or 4 substituents selected from H, F, Cl, Br, I, OH, $NH_2$, oxo, $C_{1-4}$ alkyl or $C_{1-4}$ alkoxy, preferably substituted with 0, 1, 2, 3 or 4 substituents selected from H, F, Cl, Br, I, OH, $NH_2$, oxo, methyl, ethyl, isopropyl, methoxy, ethoxy or isopropoxy;

Cy1, Cy2, Cy3 and Cy4 cannot all be a bond;

when Ak1, Ak2, Ak3, Ak4 or Ak5 is O, they cannot be directly connected to B;

when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from CH$_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidyl, piperazinyl, pyrimidinyl or pyridyl;

B is selected from

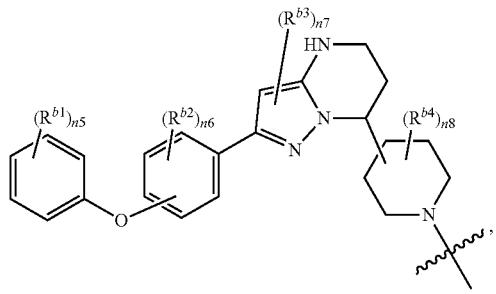

preferably

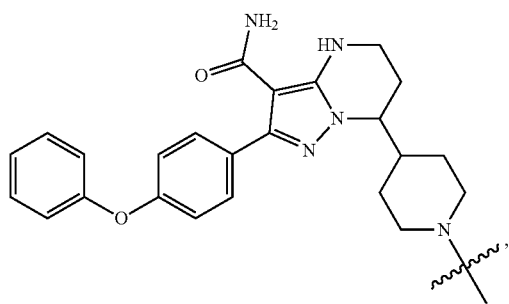 [SMILES: *N1CCC(C2CCNc3c(C(N)=O)c(-c4ccc(Oc5ccccc5)cc4)nn32)CC1]

or B can be selected from

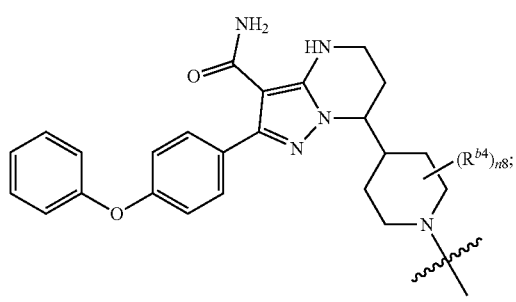

or B can be selected from

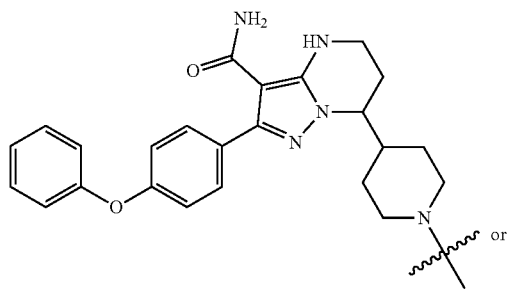

or

-continued

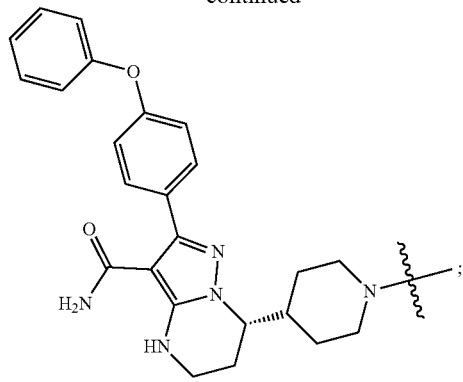

$R^{b1}$, $R^{b2}$, $R^{b3}$ r $R^{b4}$ is each independently selected from H, F, Cl, Br, I, OH, NH$_2$, CN, CONH$_2$, C$_{1-4}$ alkyl or C$_{1-4}$ alkoxy, preferably selected from H, F, Cl, Br, I, OH, NH$_2$, CN, CONH$_2$, methyl or methoxy; the methyl, methoxy, alkyl and alkoxy are optionally further substituted with 0, 1, 2, 3 or 4 substituents selected from H, F, Cl, Br, I, OH, NH$_2$, CN, CONH$_2$, C$_{1-4}$ alkyl or C$_{1-4}$ alkoxy, preferably substituted with 0, 1, 2, 3 or 4 substituents selected from H, F, Cl, Br or I;

n5, n6, n7, and n8 are each independently selected from 0, 1, 2, 3 or 4;

K is selected from

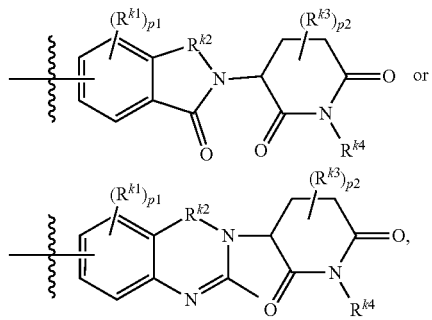

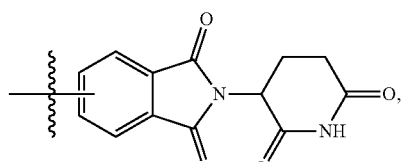

preferably

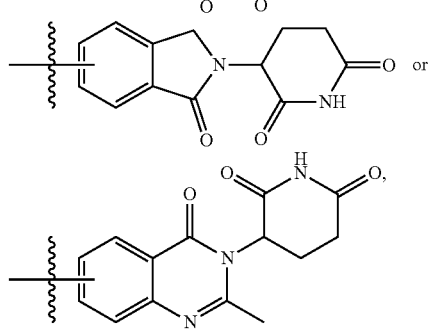

or K can be selected from
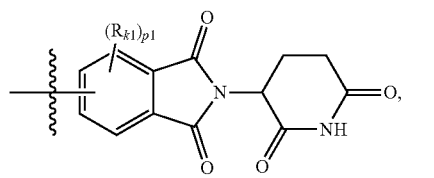
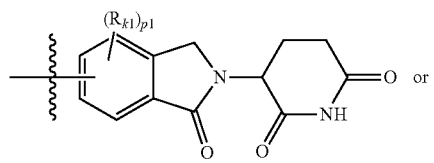
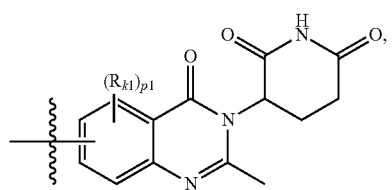
or K can be selected from
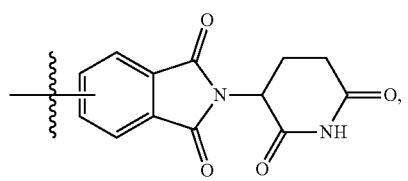
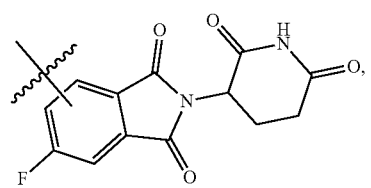
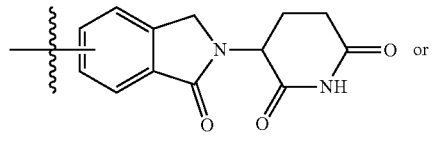
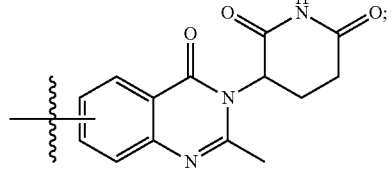
or K can be selected from
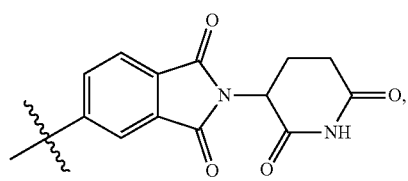
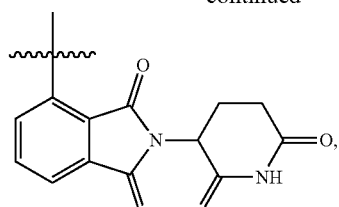
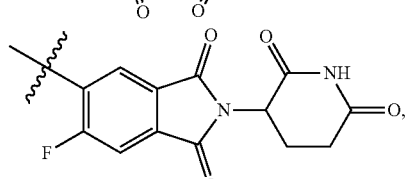
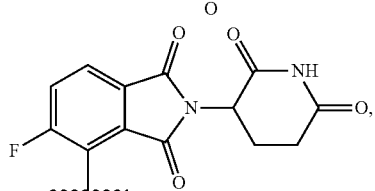

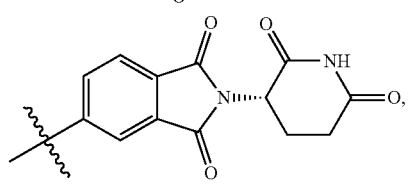
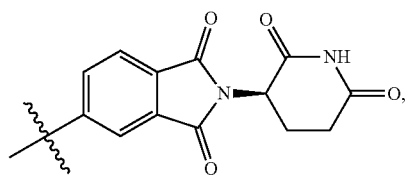
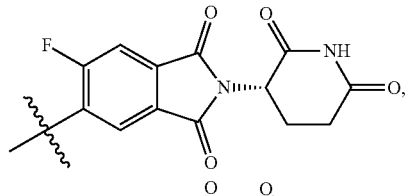
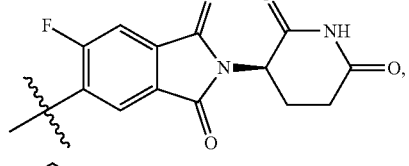
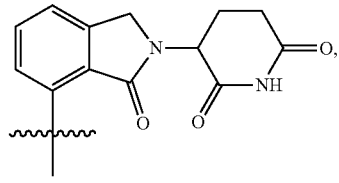

-continued

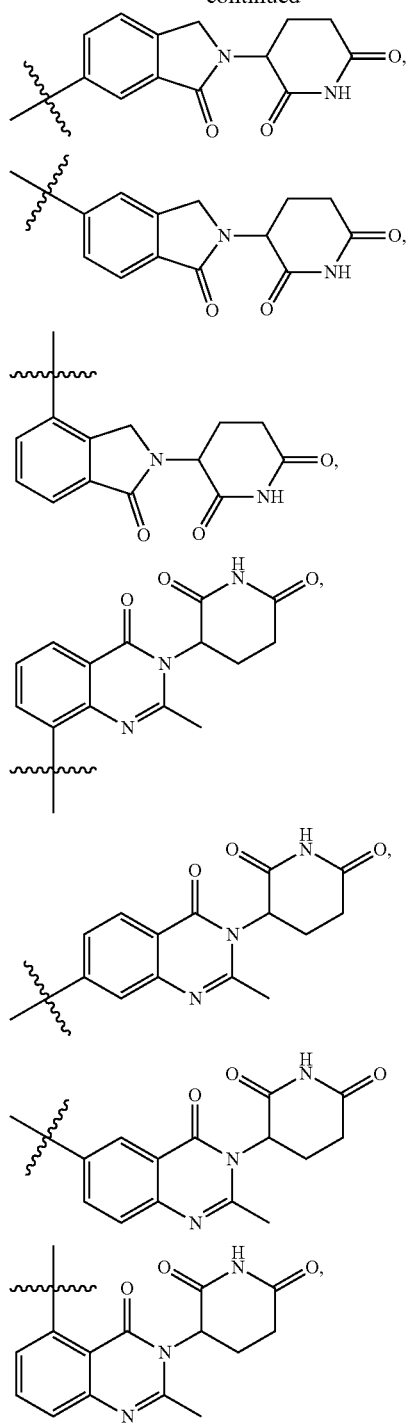

or K can be selected from

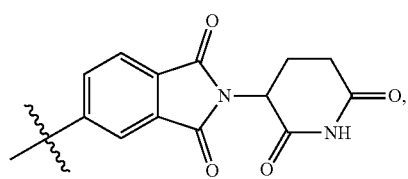

-continued

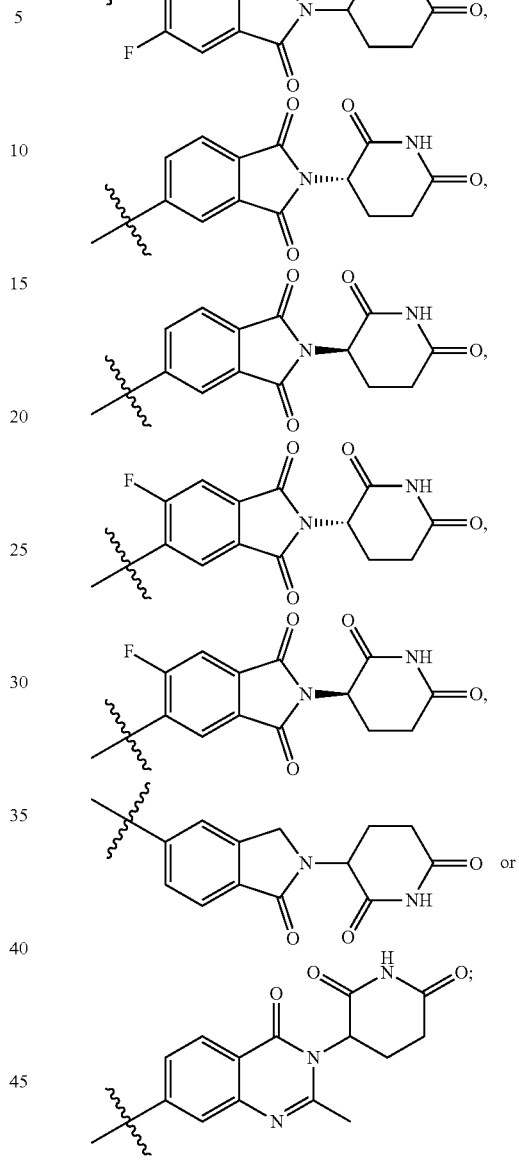

$R^{k2}$ is selected from $CH_2$ or $C=O$;
$R^{k1}$, $R^{k3}$ or $R^{k4}$ is each independently selected from H, F, Cl, Br, I, OH, $NH_2$, CN, COOH, $C_{1-4}$ alkyl or $C_{1-4}$ alkoxy, preferably H, F, Cl, Br, I, OH or $NH_2$;
p1 or p2 is each independently selected from 0, 1 or 2.

Some embodiments of the present disclosure relate to a compound represented by general formula (I) or a stereoisomer, a solvate, a prodrug, a metabolite, a pharmaceutically acceptable salt or a co-crystal thereof, wherein L is selected from -Ak1-Cy1-Ak2-Cy2-Ak3-Cy3-Ak4-Cy4-Ak5-;

Ak1, Ak2, Ak3, Ak4 and Ak5 are each independently selected from $CH_2$, O or a bond;

Cy1, Cy2, Cy3 and Cy4 are each independently selected from a substituted or unsubstituted bond, phenyl, naphthyl, cyclobutyl, cyclopentyl, cyclohexyl, cyclobutyl-fused-cyclobutyl, cyclobutyl-fused-cyclopentyl, cyclobutyl-fused-cyclohexyl, cyclopentyl-fused-cyclopentyl, cyclopentylfused-cyclohexyl, cyclohexyl-fused-cyclohexyl, cyclopropyl-fused-cyclobutyl, cyclopropyl-fused-cyclopentyl, cyclopropyl-fused-cyclohexyl, cyclobutyl-spiro-cyclobutyl, cyclobutyl-spiro-cyclopentyl, cyclobutyl-spiro-cyclohexyl, cyclopentyl-spiro-cyclopentyl, cyclopentyl-spiro-cyclohexyl, cyclohexyl-spiro-cyclohexyl, cyclopropyl-spiro-cyclobutyl, cyclopropyl-spiro-cyclopentyl, cyclopropyl-spiro-cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, cyclopropyl-fused-azetidinyl, cyclopropyl-fused-azacyclopentyl, cyclopropyl-fused-azacyclohexyl, cyclopropyl-fused-piperidyl, cyclobutyl-fused-azetidinyl, cyclobutyl-fused-azacyclopentyl, cyclobutyl-fused-azacyclohexyl, cyclobutyl-fused-piperidyl, cyclopentyl-fused-azetidinyl, cyclopentyl-fused-azacyclopentyl, cyclopentyl-fused-azacyclohexyl, cyclopentyl-fused-piperidyl, cyclohexyl-fused-azetidinyl, cyclohexyl-fused-azacyclopentyl, cyclohexyl-fused-azacyclohexyl, cyclohexyl-fused-piperidyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, azacyclohexyl-fused-azetidinyl, azacyclohexyl-fused-azacyclopentyl, azacyclohexyl-fused-azacyclohexyl, azacyclohexyl-fused-piperidyl, cyclobutyl-spiro-azetidinyl, cyclobutyl-spiro-azacyclopentyl, cyclobutyl-spiro-azacyclohexyl, cyclopentyl-spiro-azetidinyl, cyclopentyl-spiro-azacyclopentyl, cyclopentyl-spiro-azacyclohexyl, cyclohexyl-spiro-azetidinyl, cyclohexyl-spiro-azacyclopentyl, cyclohexyl-spiro-azacyclohexyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, cyclobutyl-spiro-piperidyl, cyclopentyl-spiro-piperidyl, cyclohexyl-spiro-piperidyl, azetidinyl-spiro-piperidyl, azacyclopentyl-spiro-piperidyl, azacyclohexyl-spiro-piperidyl,

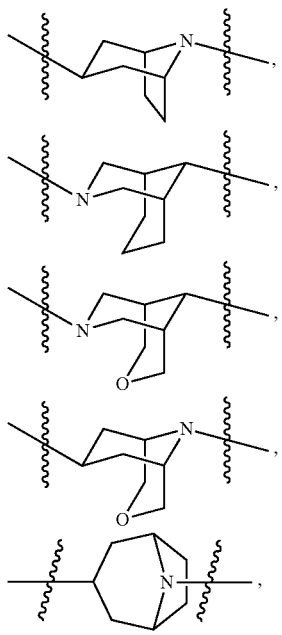

preferably a substituted or unsubstituted bond, phenyl, naphthyl, cyclobutyl, cyclopentyl, cyclohexyl, azetidinyl, azacyclopentyl, piperidyl, morpholinyl, piperazinyl, pyrrolyl, pyrazolyl, imidazolyl, thiazolyl, pyridyl, pyridazinyl, pyrimidinyl, pyrazinyl, triazolyl, tetrazolyl, azetidinyl-fused-azetidinyl, azetidinyl-fused-azacyclopentyl, azetidinyl-fused-azacyclohexyl, azetidinyl-fused-piperidyl, azacyclopentyl-fused-azetidinyl, azacyclopentyl-fused-azacyclopentyl, azacyclopentyl-fused-azacyclohexyl, azacyclopentyl-fused-piperidyl, cyclohexyl-spiro-azetidinyl, cyclobutyl-spiro-azacyclohexyl, cyclopentyl-fused-azacyclopentyl, azacyclohexyl-fused-azetidinyl, azacyclohexyl-fused-azacyclopentyl, azetidinyl-spiro-azetidinyl, azetidinyl-spiro-azacyclopentyl, azetidinyl-spiro-azacyclohexyl, azacyclopentyl-spiro-azetidinyl, azacyclopentyl-spiro-azacyclopentyl, azacyclopentyl-spiro-azacyclohexyl, azacyclohexyl-spiro-azetidinyl, azacyclohexyl-spiro-azacyclopentyl, azacyclohexyl-spiro-azacyclohexyl, azetidinyl-spiro-piperidyl, azacyclopentyl-spiro-piperidyl, or

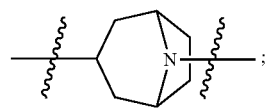 [SMILES: *C1CC2CCC(C1)N2*]

which, when substituted, are optionally further substituted with 0, 1, 2, 3 or 4 substituents selected from H, F, Cl, Br, I, OH, $NH_2$, oxo, $C_{1-4}$ alkyl or $C_{1-4}$ alkoxy, preferably substituted with 0, 1, 2, 3 or 4 substituents selected from H, F, Cl, Br, I, OH, $NH_2$, oxo, methyl, ethyl, isopropyl, methoxy, ethoxy or isopropoxy;

Cy1, Cy2, Cy3 and Cy4 cannot all be a bond;

when Ak1, Ak2, Ak3, Ak4 or Ak5 is O, they cannot be directly connected to B;

when Ak1, Ak2, Ak3, Ak4 or Ak5 is not a bond, they cannot be directly connected to one another;

when 3 of Cy1, Cy2, Cy3 and Cy4 are a bond, at least one of Ak1, Ak2, Ak3, Ak4, and Ak5 is selected from $CH_2$ and is connected to B;

when 4 or more of Ak1, Cy1, Ak2, Cy2, Ak3, Cy3, Ak4, Cy4 and Ak5 are not a bond, at least one of Cy1, Cy2, Cy3 and Cy4 is not piperidyl, piperazinyl, pyrimidinyl or pyridyl;

B is selected from

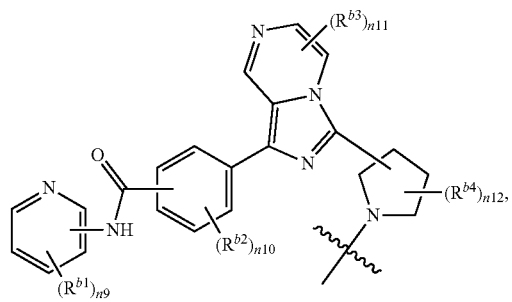

preferably

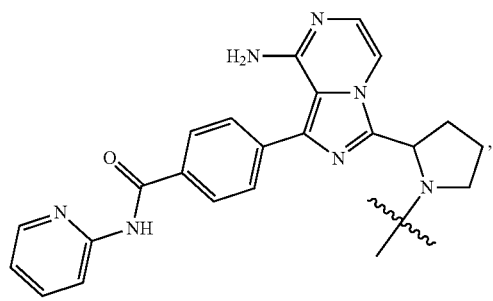 [SMILES: *N1CCCC1c1nc(-c2ccc(C(=O)Nc3ccccn3)cc2)c2c(N)nccn12]

or B can be selected from

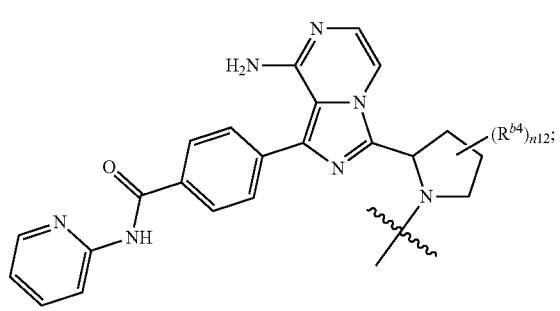

or B can be selected from

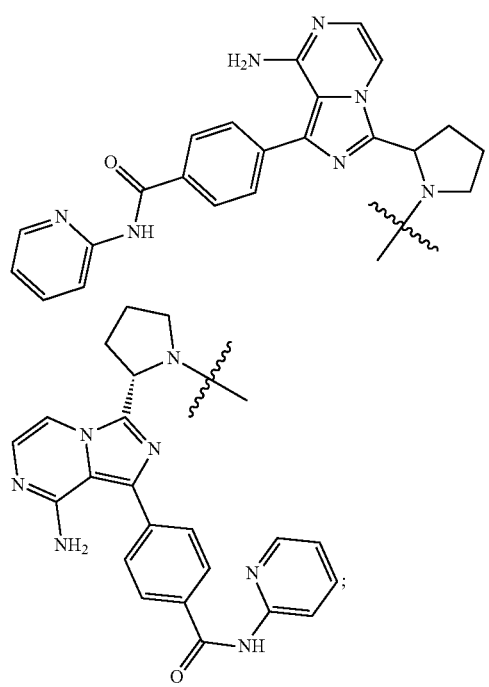

$R^{b1}$, $R^{b2}$, $R^{b3}$ or $R^{b4}$ is each independently selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n9, n10, n11, and n12 are each independently selected from 0, 1, 2, 3 or 4;

K is selected from

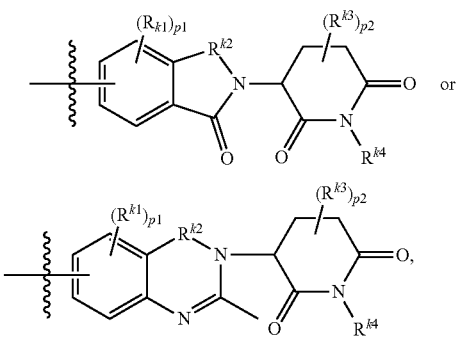

preferably

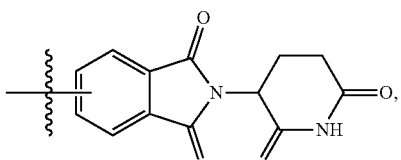

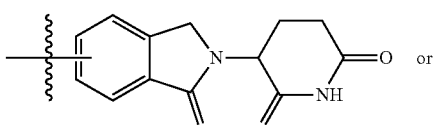

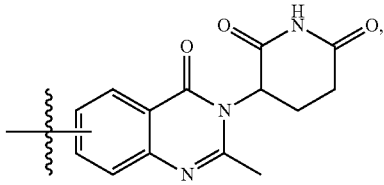

or K can be selected from

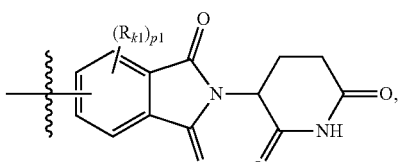

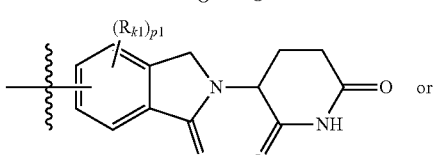

-continued
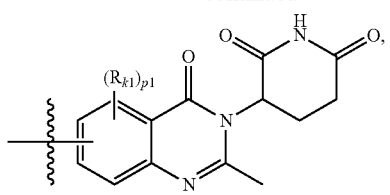
or K can be selected from
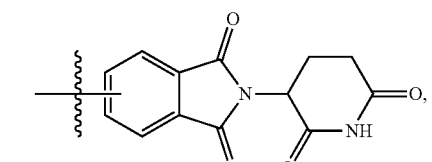
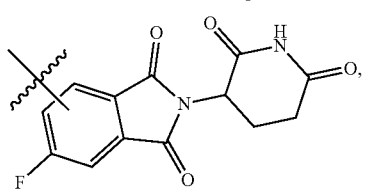
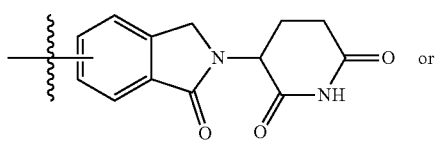 or
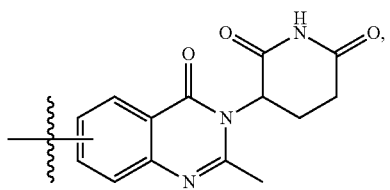
or K can be selected from
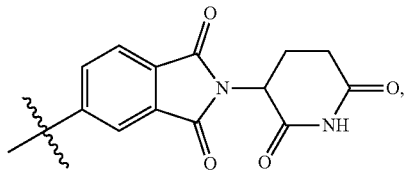
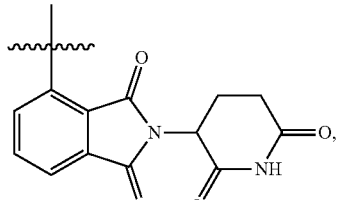
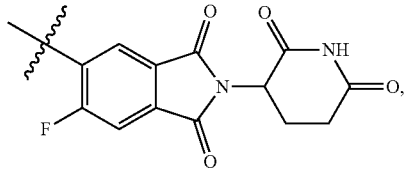
-continued
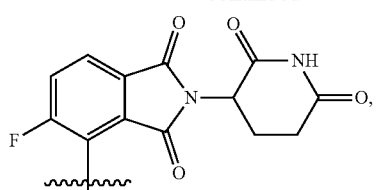
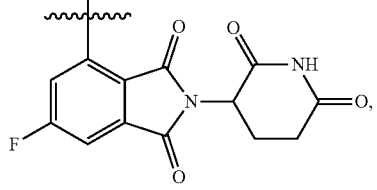
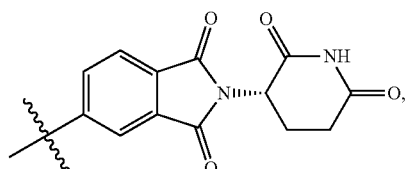
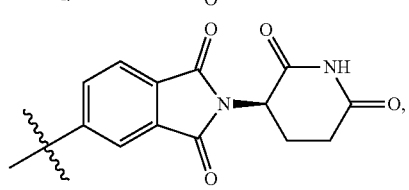
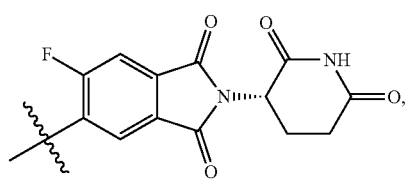
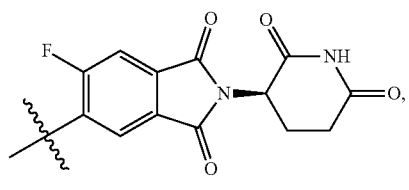
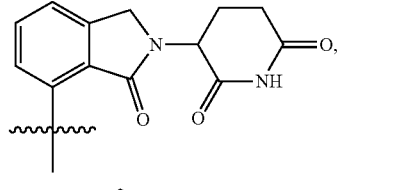
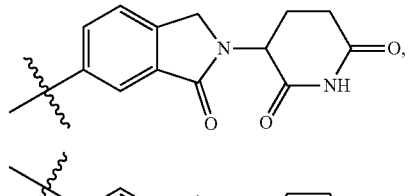
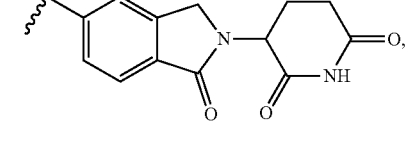

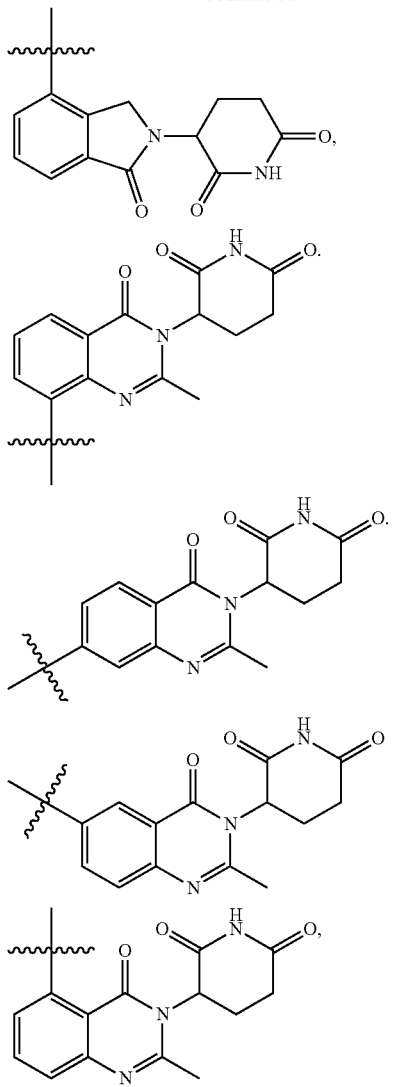

or K can be selected from

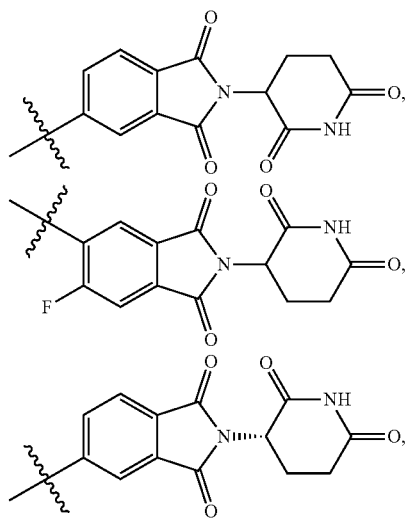

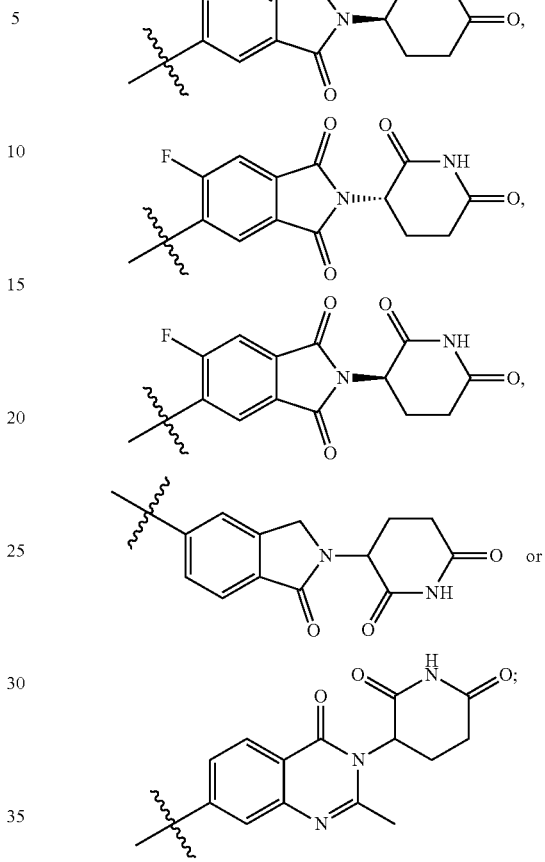

$R^{k2}$ is selected from $CH_2$ or $C=O$;

$R^{k1}$, $R^{k3}$ or $R^{k4}$ is each independently selected from H, F, Cl, Br, I, OH, $NH_2$, CN, COOH, $C_{1-4}$ alkyl or $C_{1-4}$ alkoxy, preferably H, F, Cl, Br, I, OH or $NH_2$;

p1 or p2 is each independently selected from 0, 1 or 2.

Some embodiments of the present disclosure relate to a compound represented by general formula (I) or a stereoisomer, a solvate, a prodrug, a metabolite, a pharmaceutically acceptable salt or a co-crystal thereof, wherein L is selected from

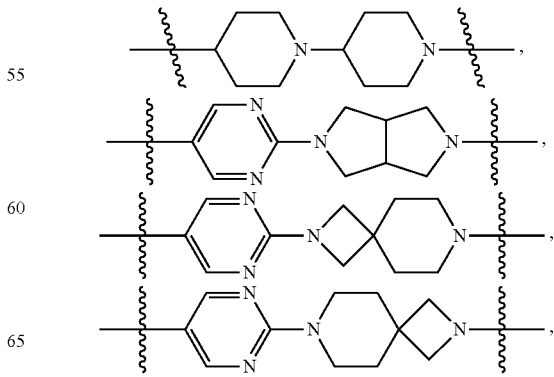

-continued
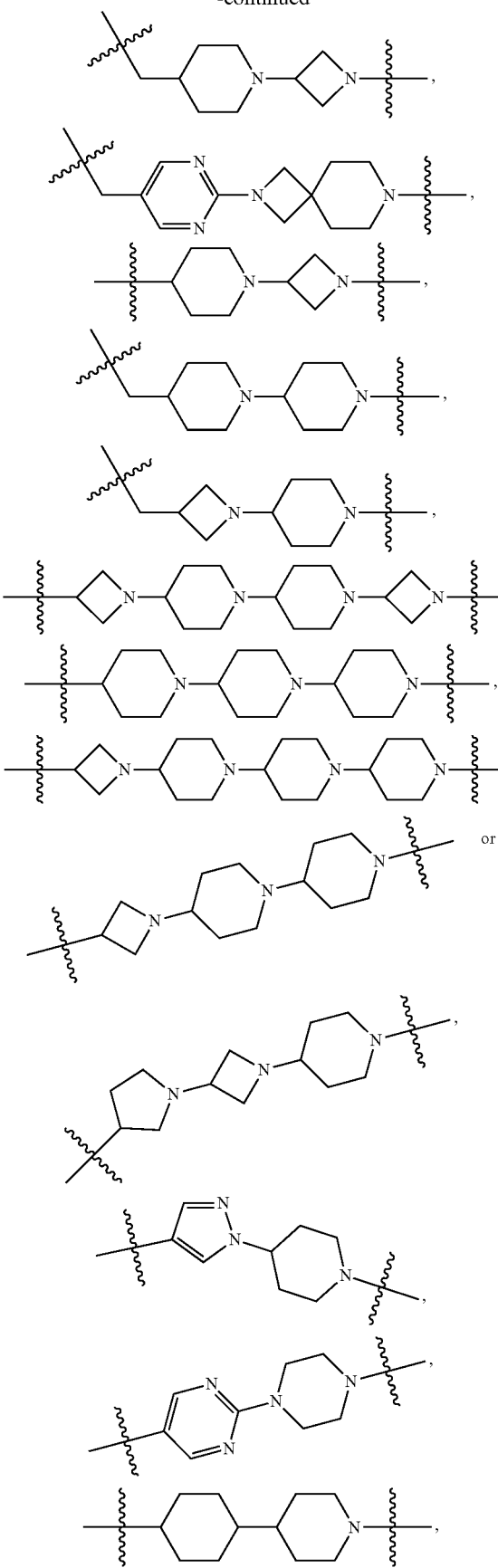
or
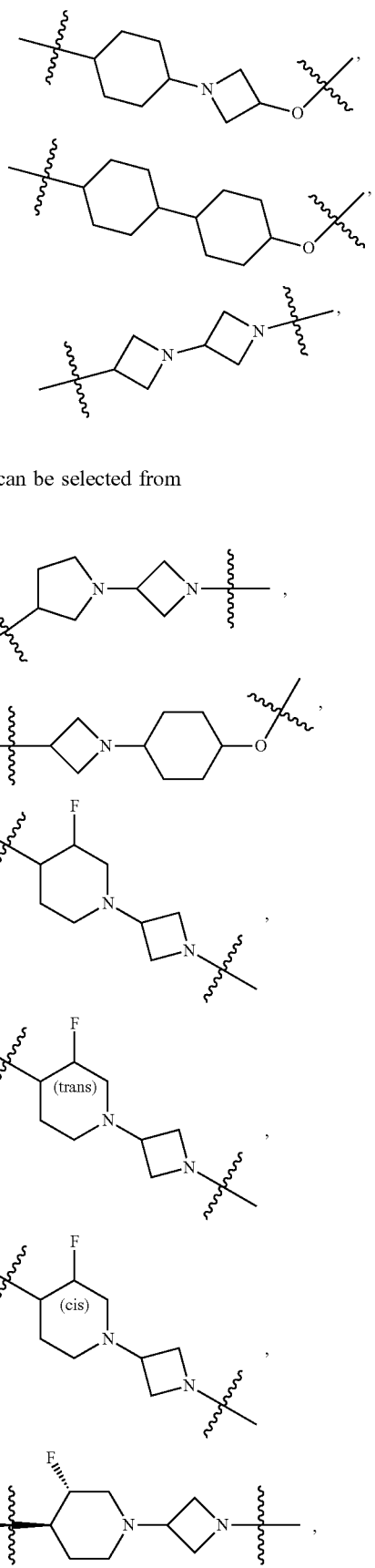
or L can be selected from

-continued
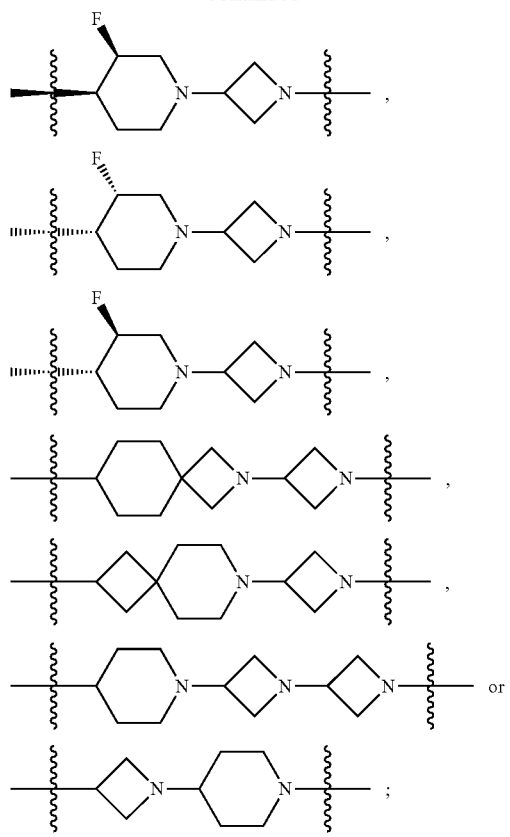
or L can be selected from
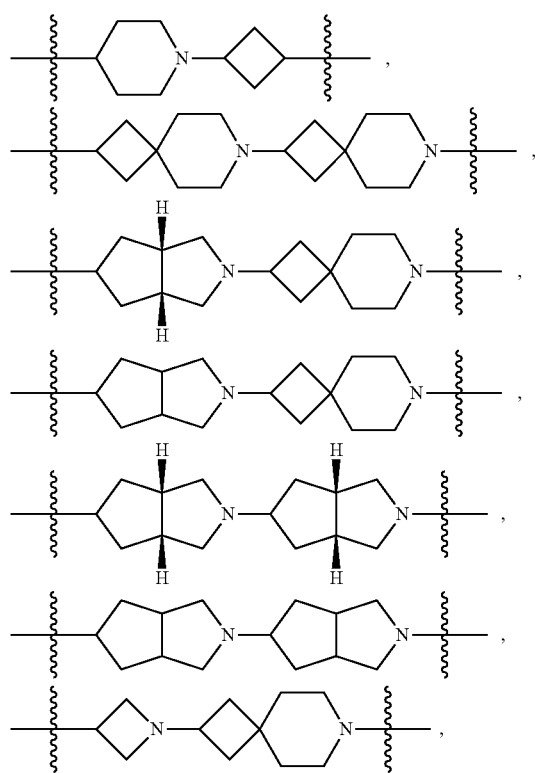
-continued
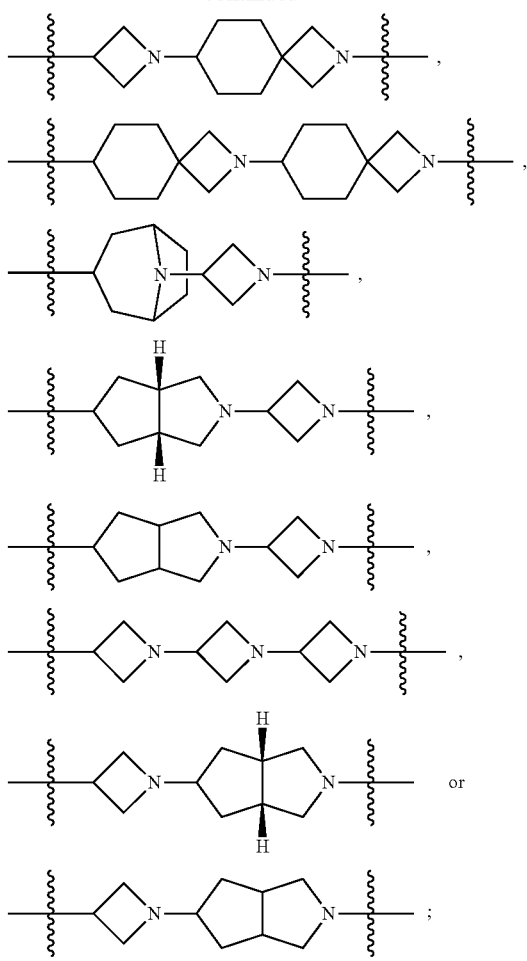
L is connected to B on the left side, and is connected to K on the right side;
B is selected from
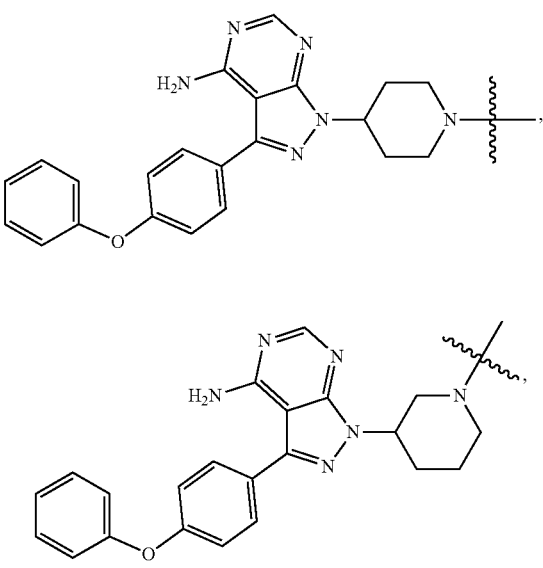

49

-continued

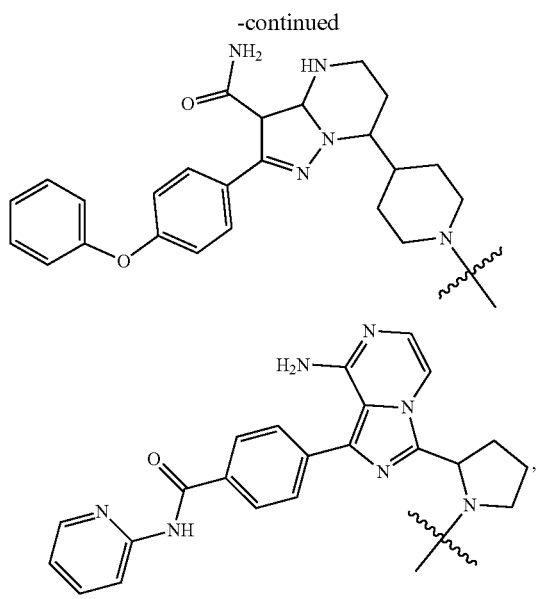

or B can be selected from

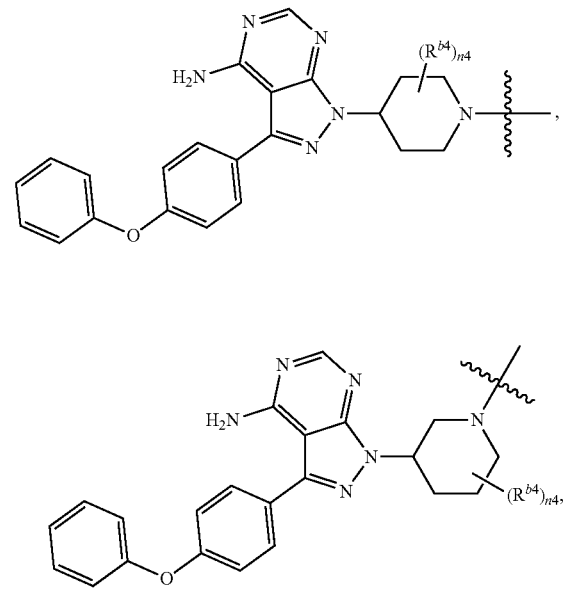

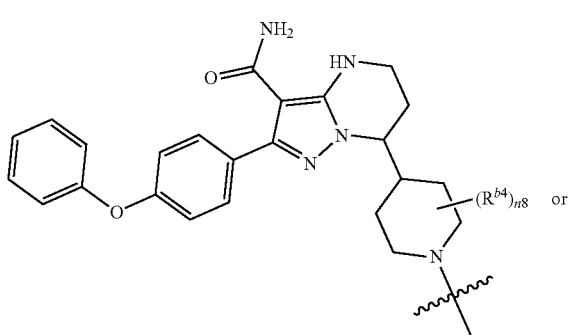 or

50

-continued

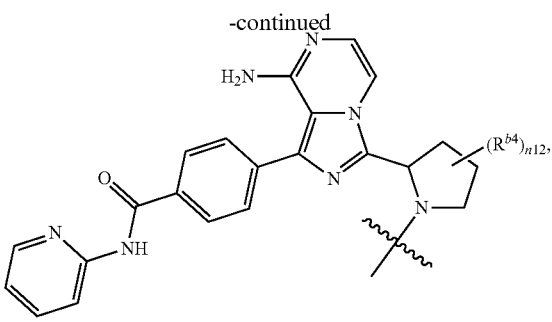

$R^{b4}$ is selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n4, n8, and n12 are each independently selected from 0, 1, 2, 3 or 4, or B can be selected from

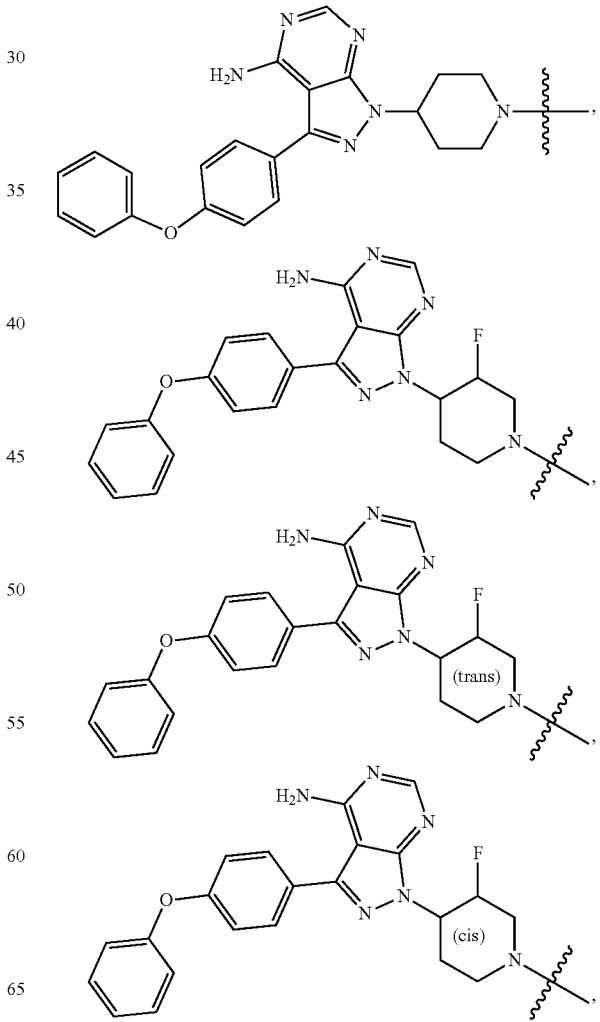

51
-continued
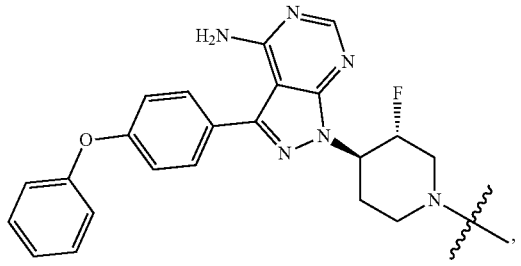
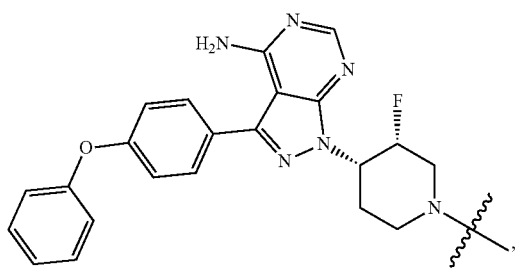
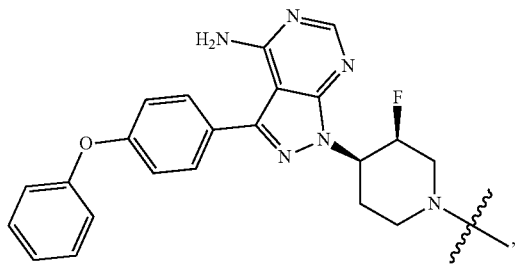
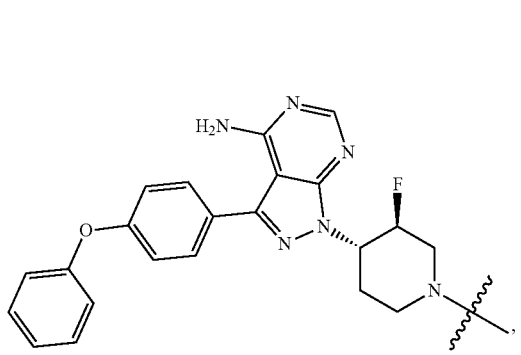
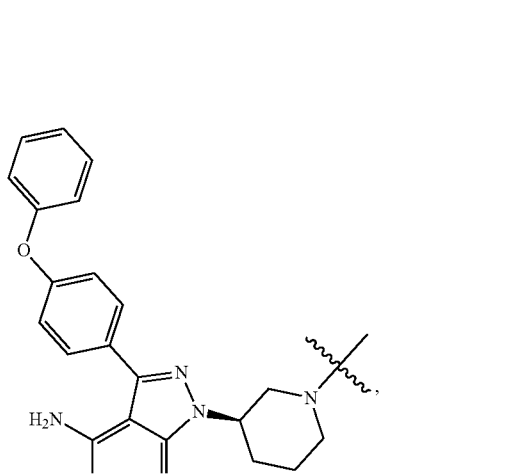
52
-continued
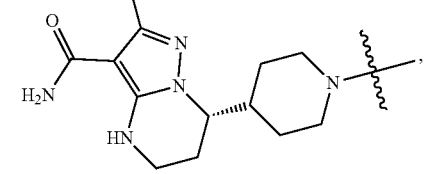
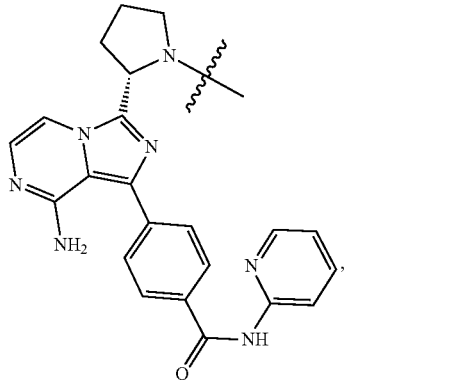
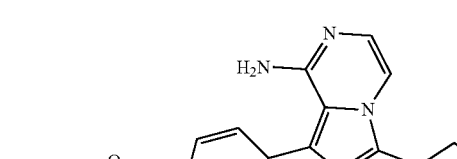
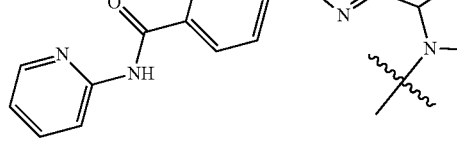
or

K is selected from
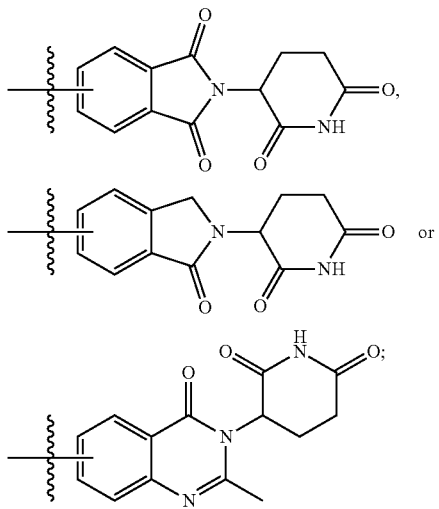
or K can be selected from
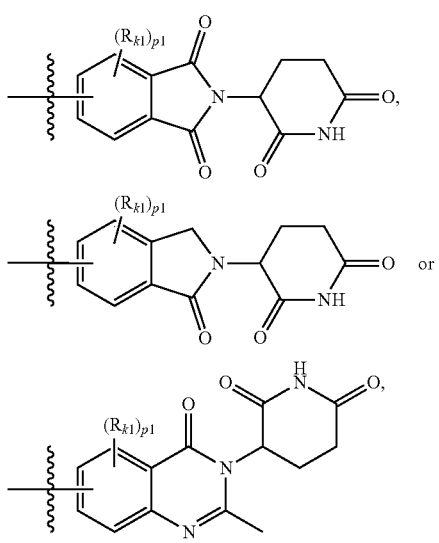
$R^{k1}$ is selected from H, F, Cl, Br, I, OH, $NH_2$, CN, COOH, $C_{1-4}$ alkyl or $C_{1-4}$ alkoxy, preferably H, F, Cl, Br, I, OH or $NH_2$,
p1 is selected from 0, 1 or 2,
or K can be selected from
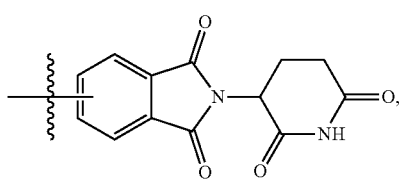
-continued
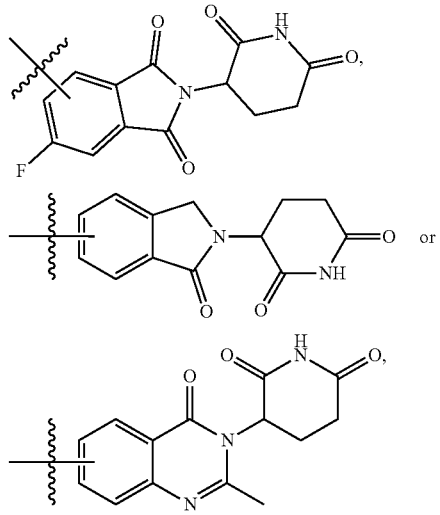
or K can be selected from
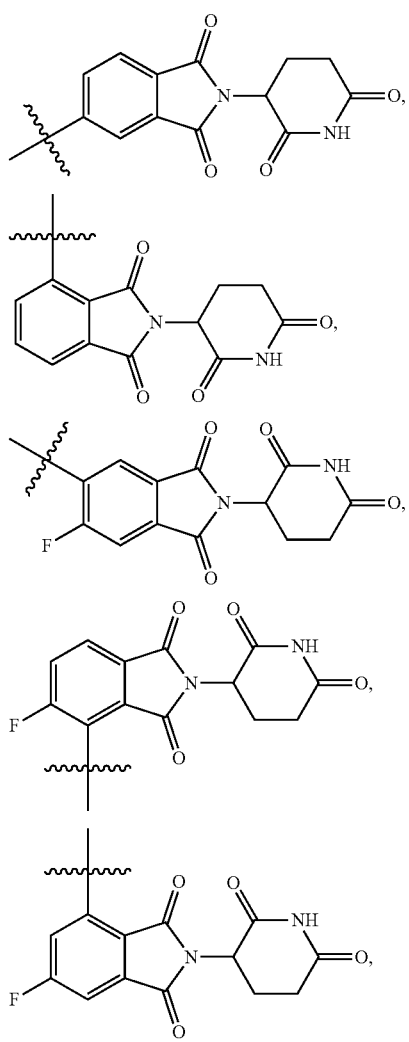

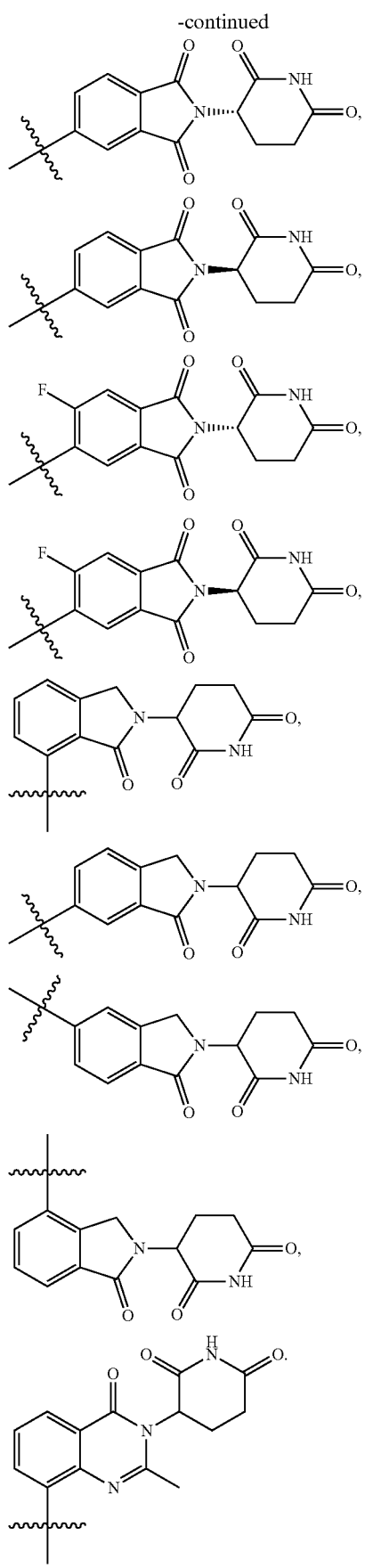
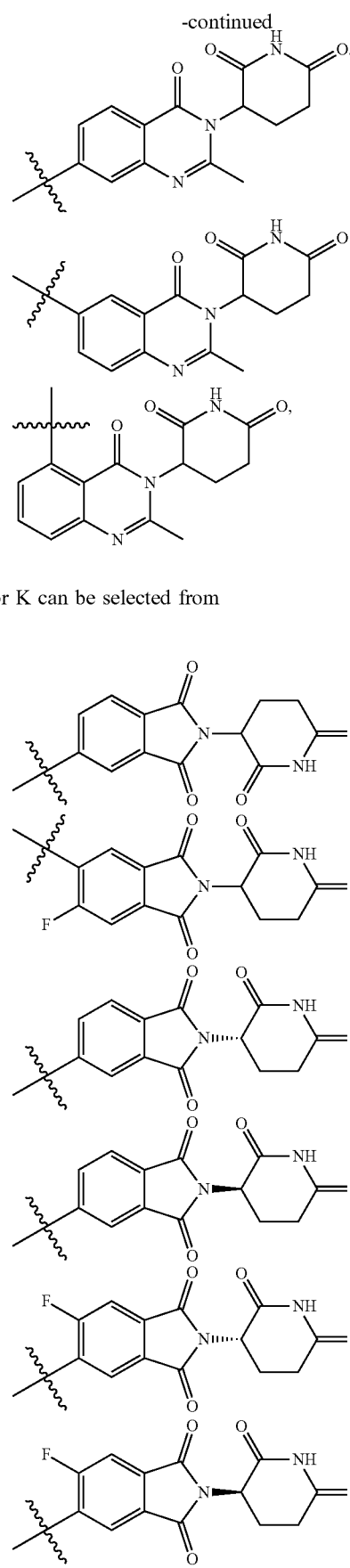
or K can be selected from
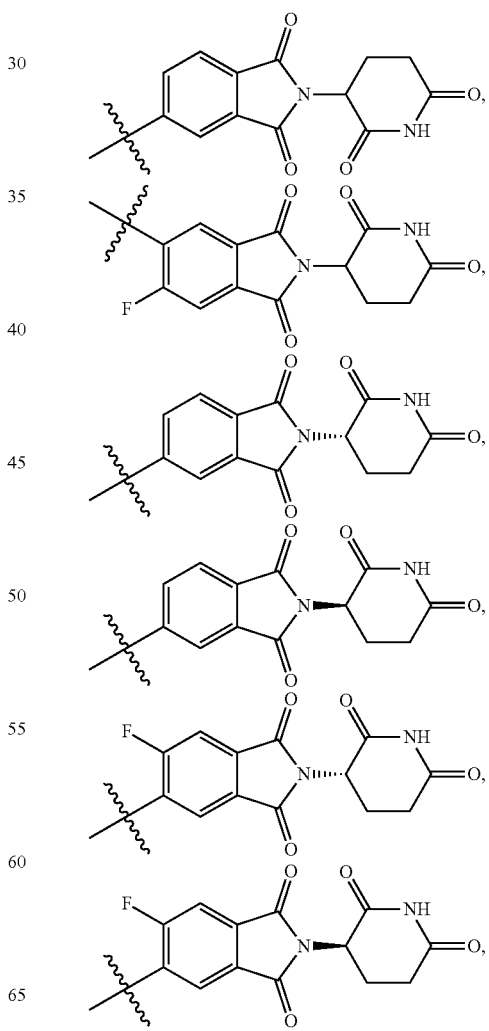

-continued
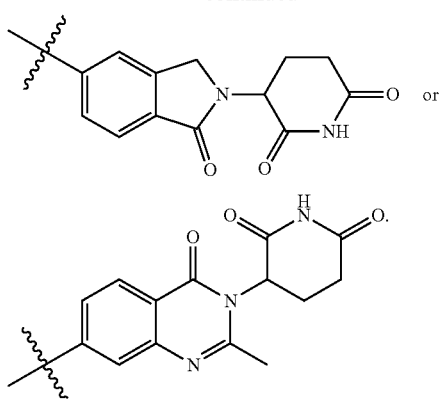 or
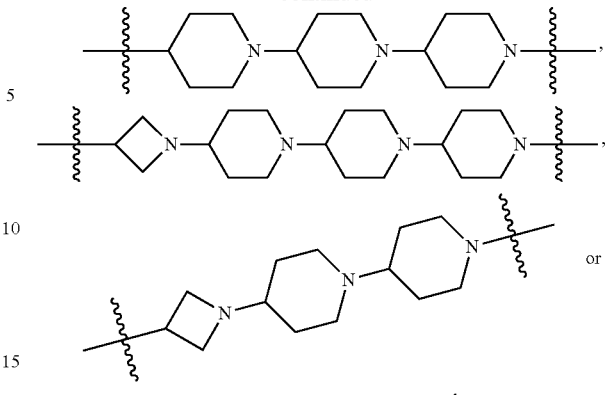
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
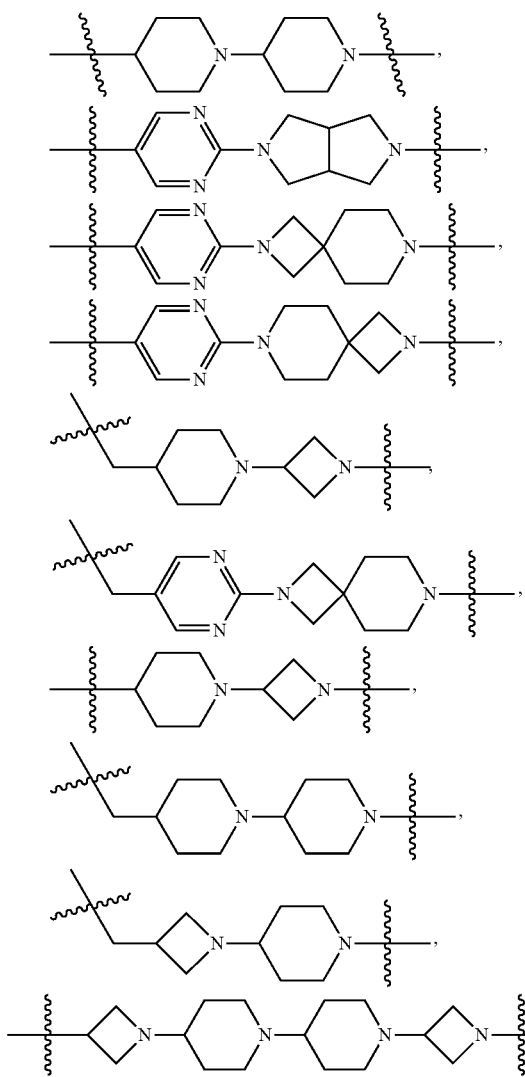
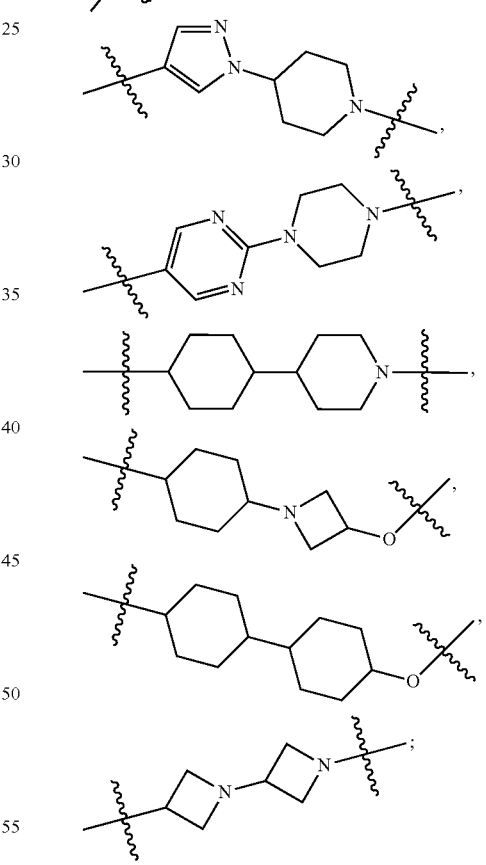
or L can be selected from
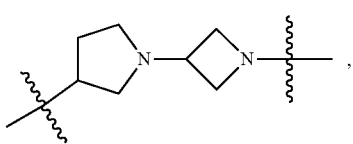

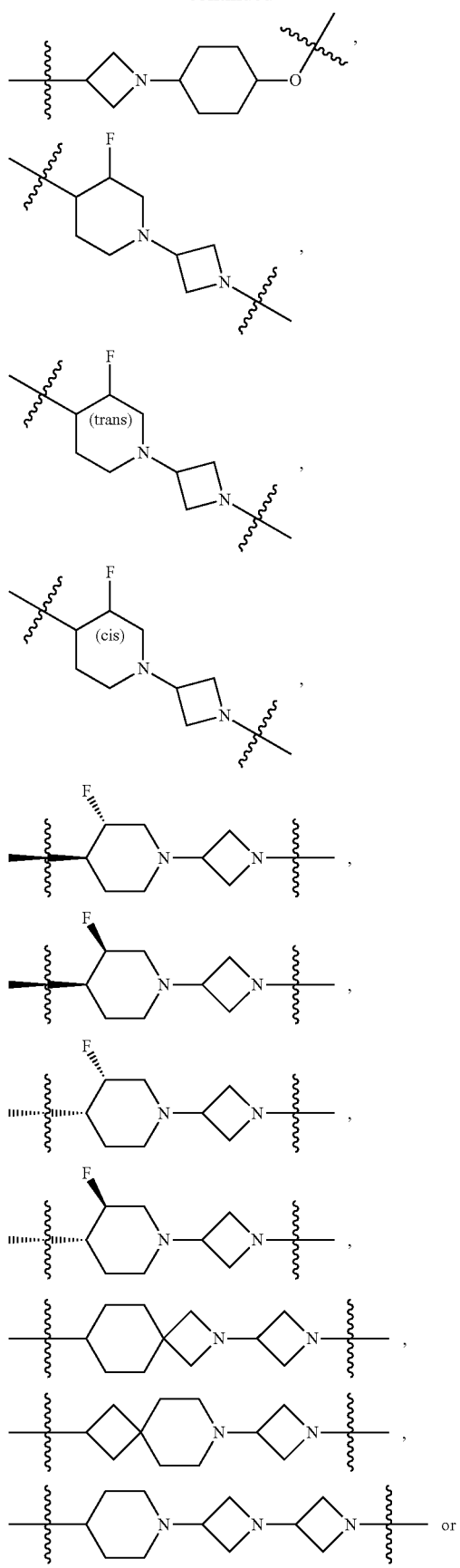
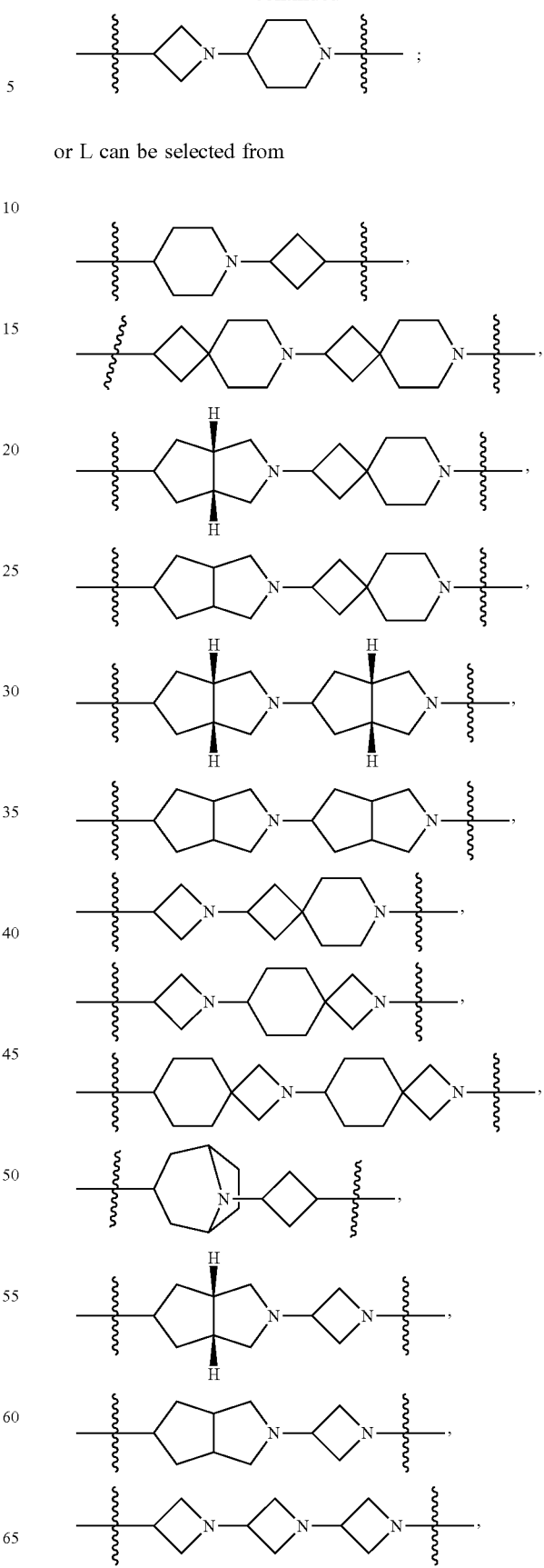
or L can be selected from

-continued

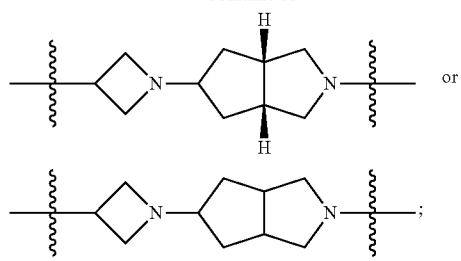

or

L is connected to B on the left side, and is connected to K on the right side;

B is selected from

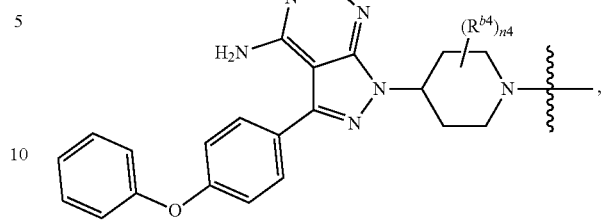

or B can be selected from

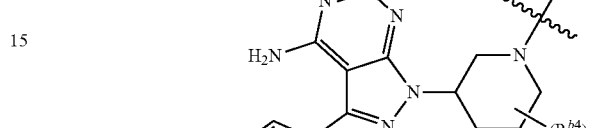

$R^{b4}$ is selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br, I, n4, n8, and n12 are each independently selected from 0, 1, 2, 3 or 4, or B can be selected from

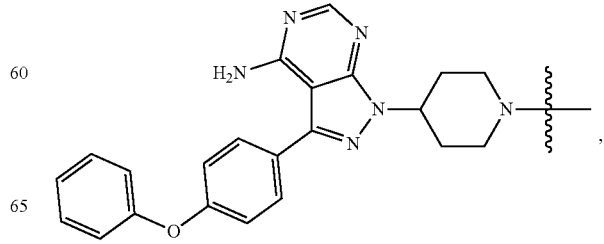

63
-continued
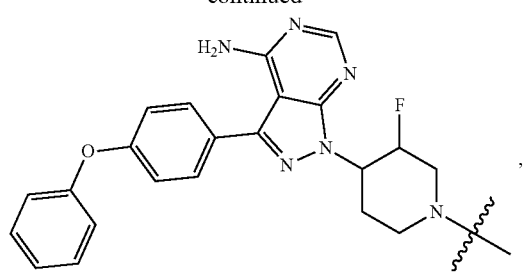
,
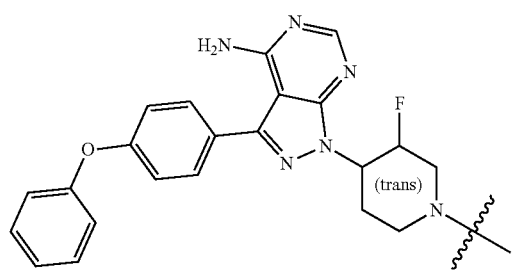
(trans),
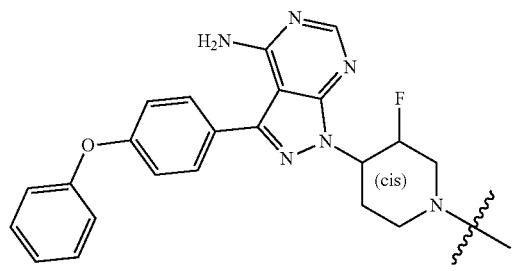
(cis),
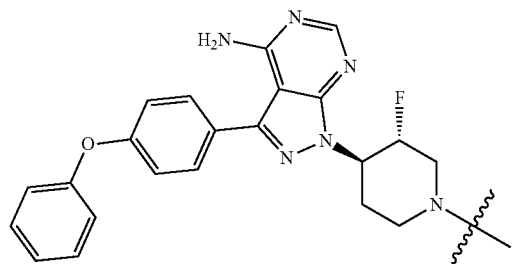
,
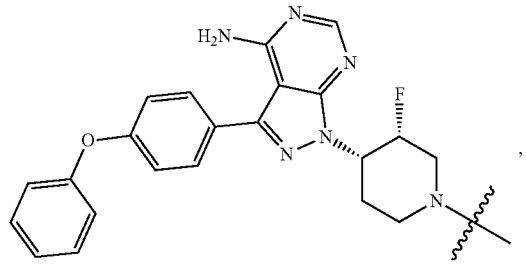
,
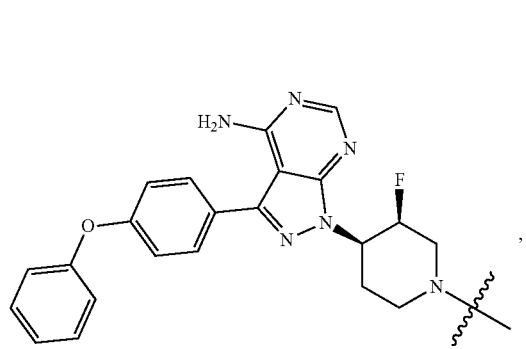
,
64
-continued
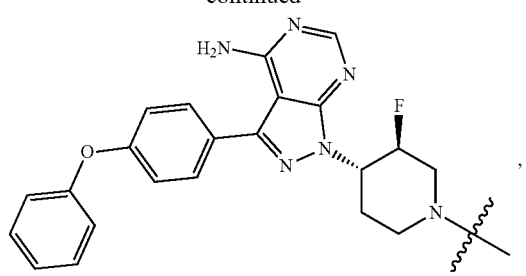
,
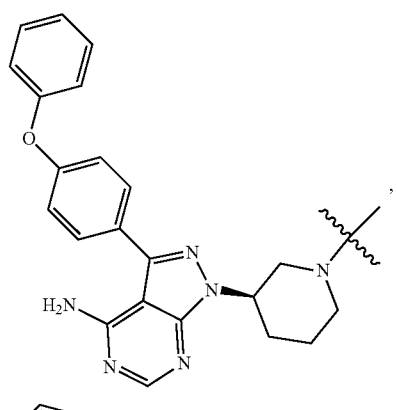
,
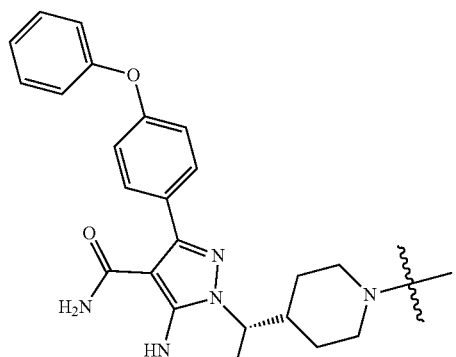
,
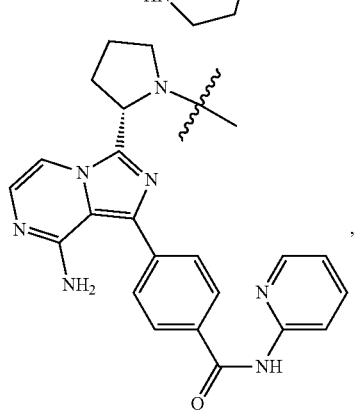
,
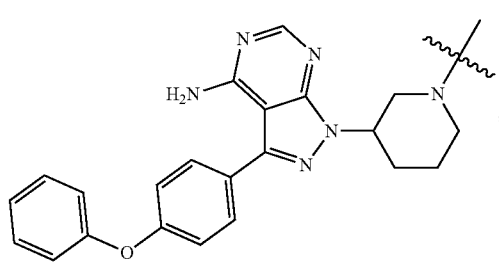
, 65
-continued
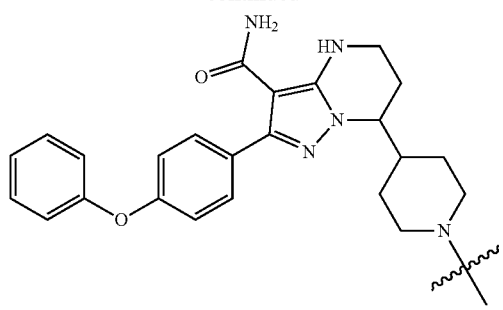
or
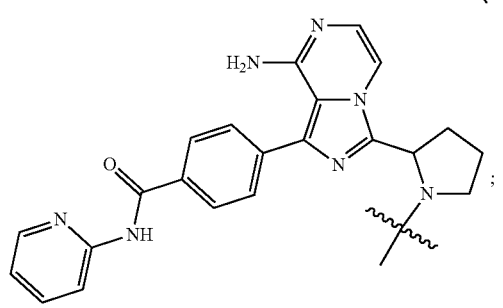
;
K can be selected from
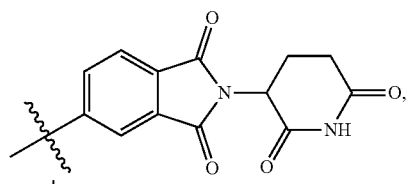
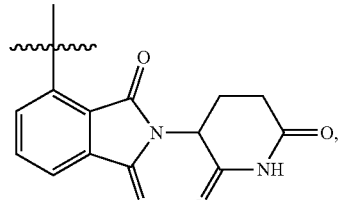
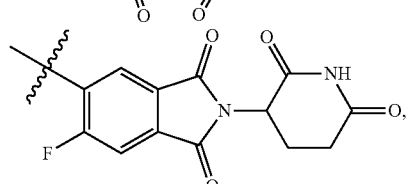
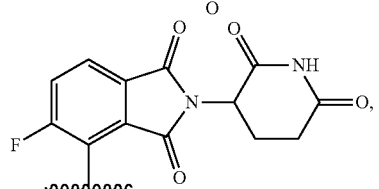
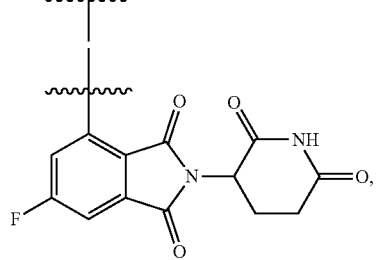
66
-continued
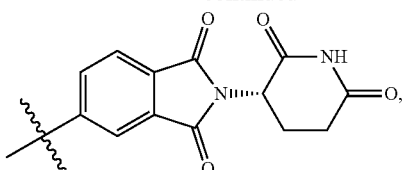
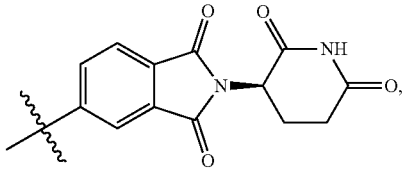
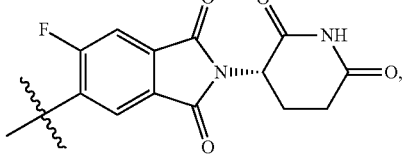
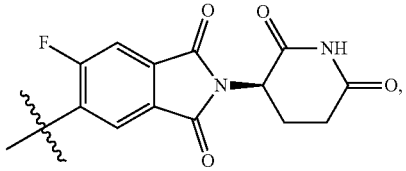
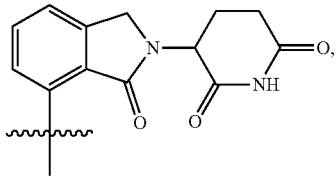
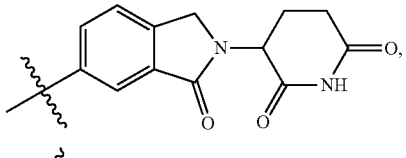
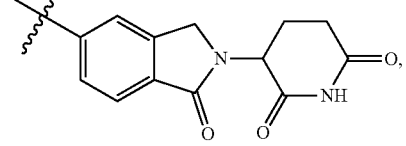
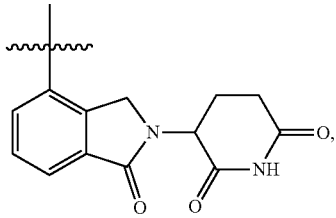
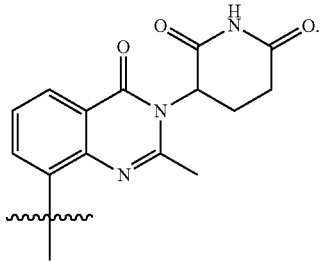

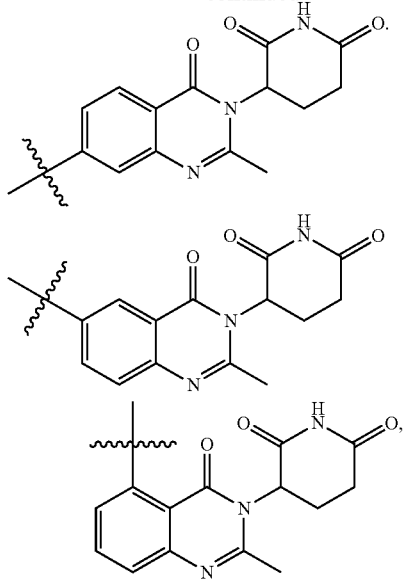
or K can be selected from
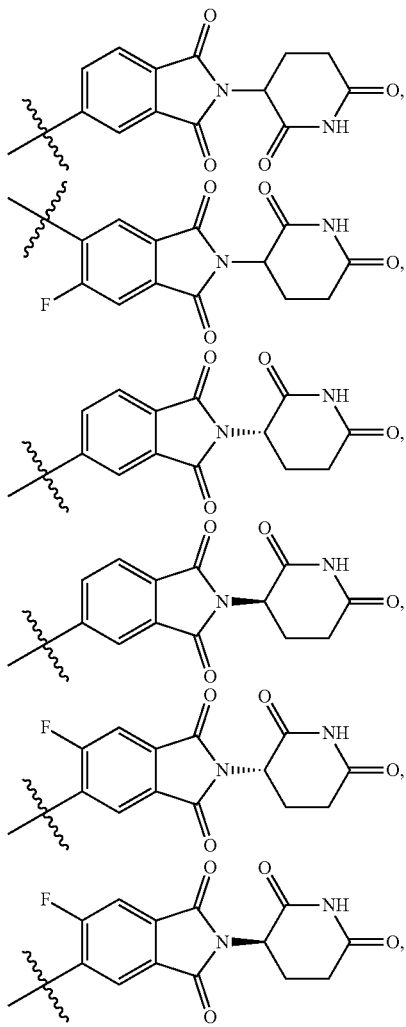
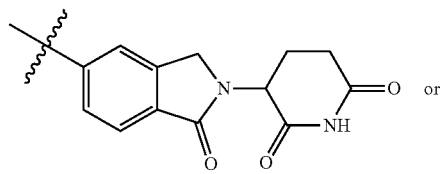
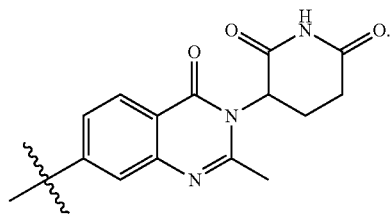
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
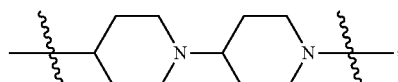
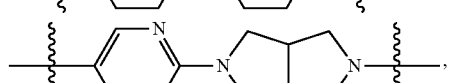
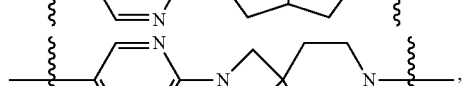
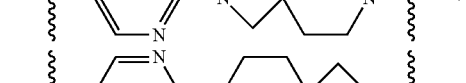
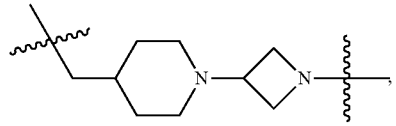
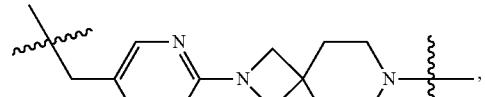
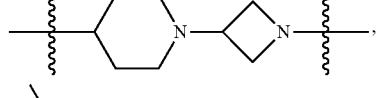
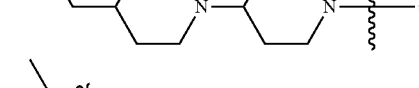
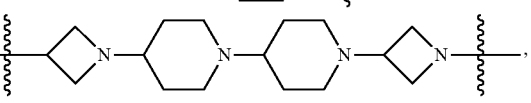

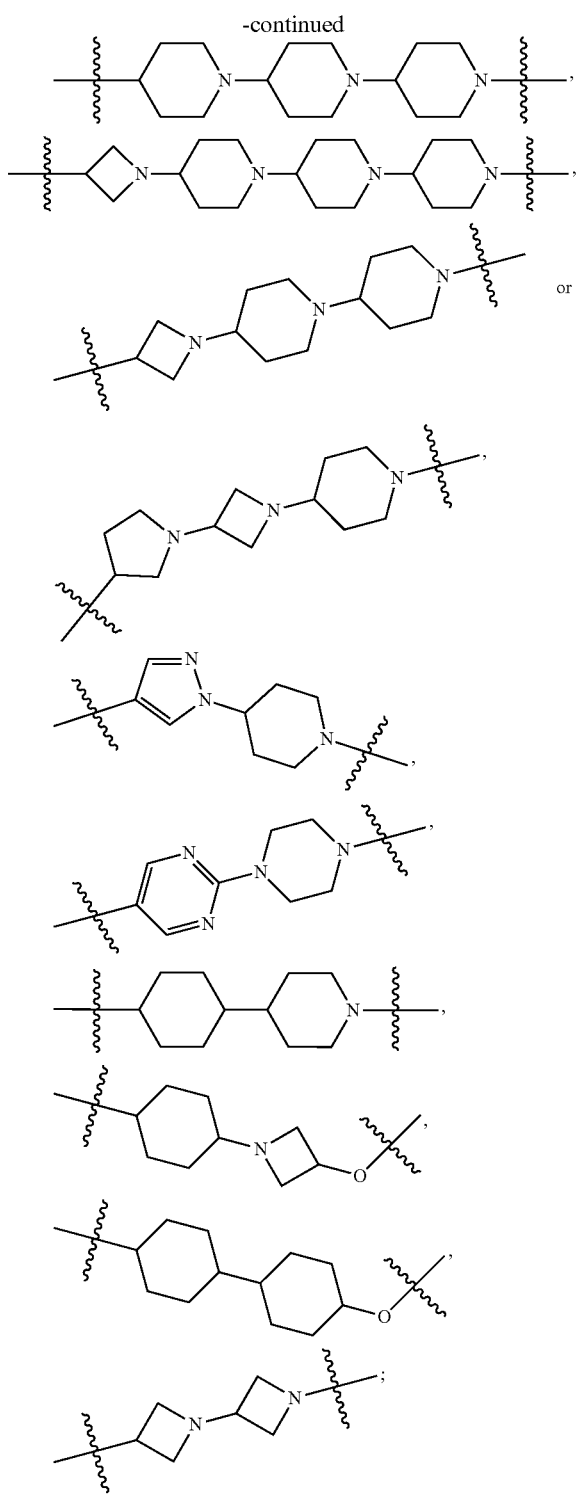
or L can be selected from
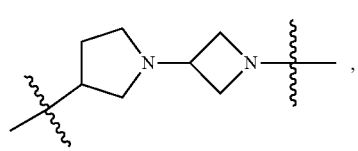
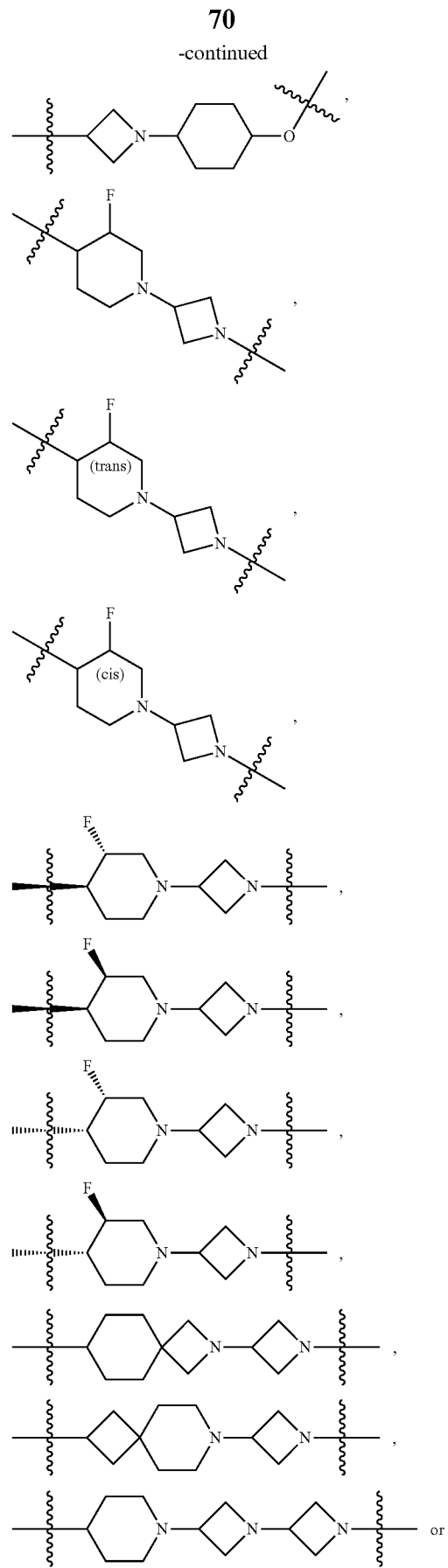

-continued
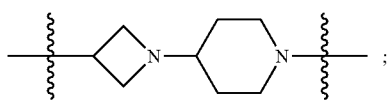
or L can be selected from
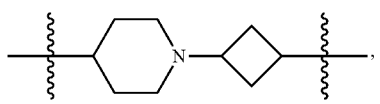
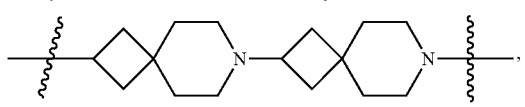
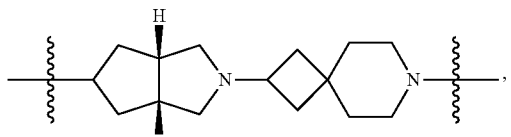
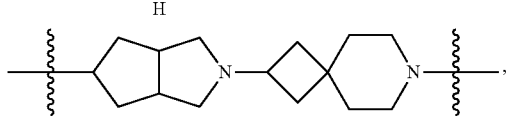
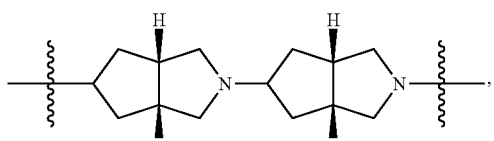
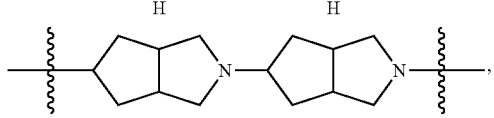
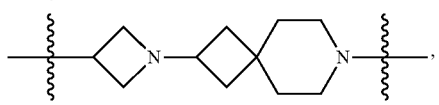
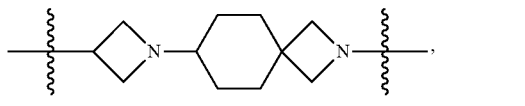
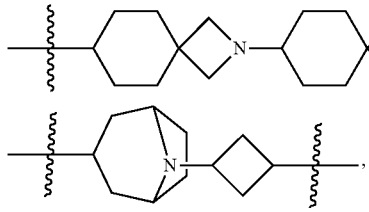
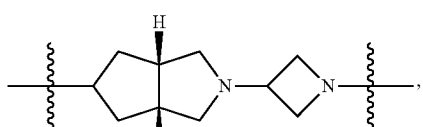
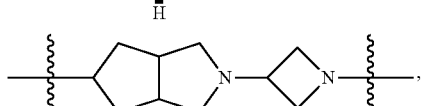
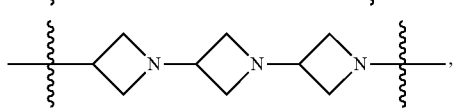
-continued
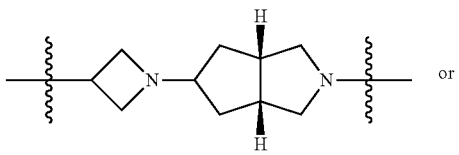 or
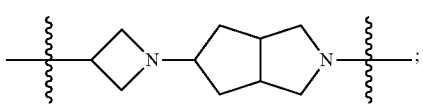;
L is connected to B on the left side, and is connected to K on the right side;
B is selected from
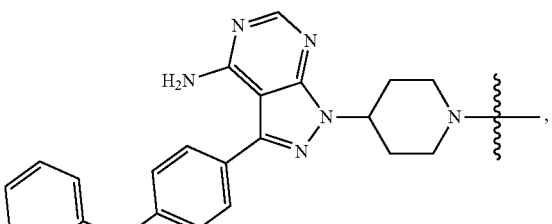
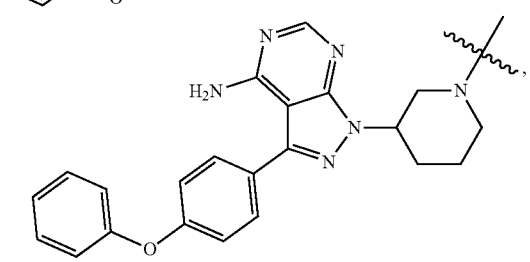
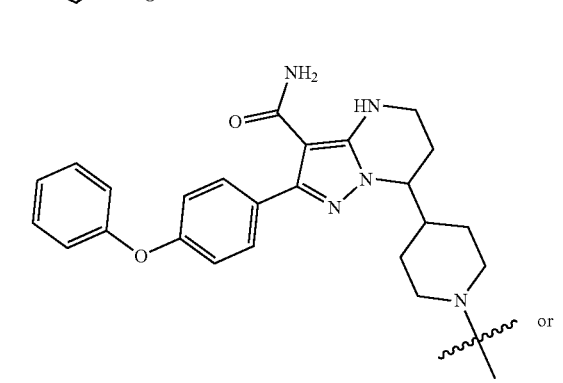 or
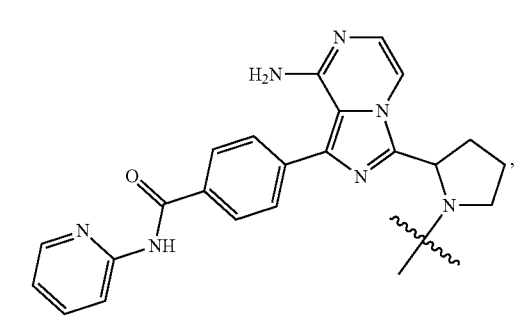

or B can be selected from

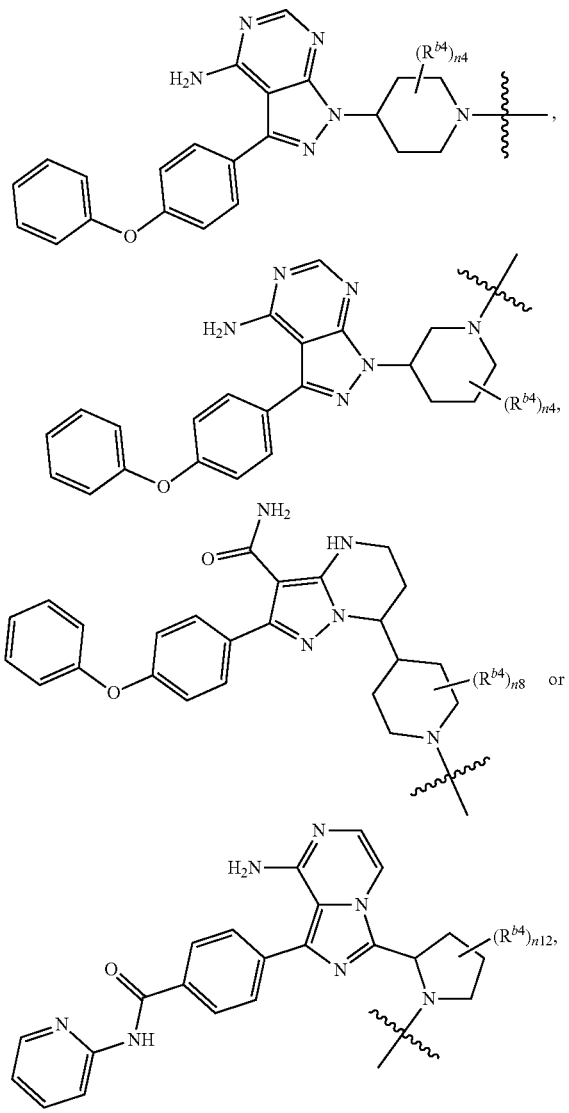

$R^{b4}$ is selected from H, F, Cl, Br, I, OH, NH$_2$, CN, CONH$_2$, C$_{1-4}$ alkyl or C$_{1-4}$ alkoxy, preferably selected from H, F, Cl, Br, I, OH, NH$_2$, CN, CONH$_2$, methyl or methoxy, wherein the methyl, methoxy, alkyl and alkoxy are optionally further substituted with 0, 1, 2, 3 or 4 substituents selected from H, F, Cl, Br, I, OH, NH$_2$, CN, CONH$_2$, C$_{1-4}$ alkyl or C$_{1-4}$ alkoxy, preferably substituted with 0, 1, 2, 3 or 4 substituents selected from H, F, Cl, Br, I, n4, n8, and n12 are each independently selected from 0, 1, 2, 3 or 4, or B can be selected from

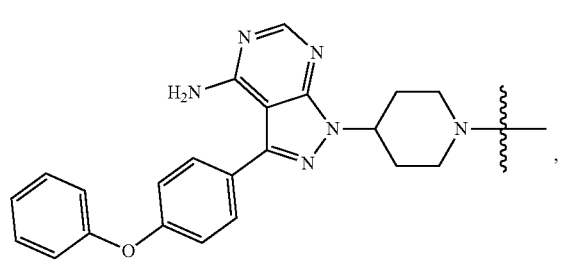

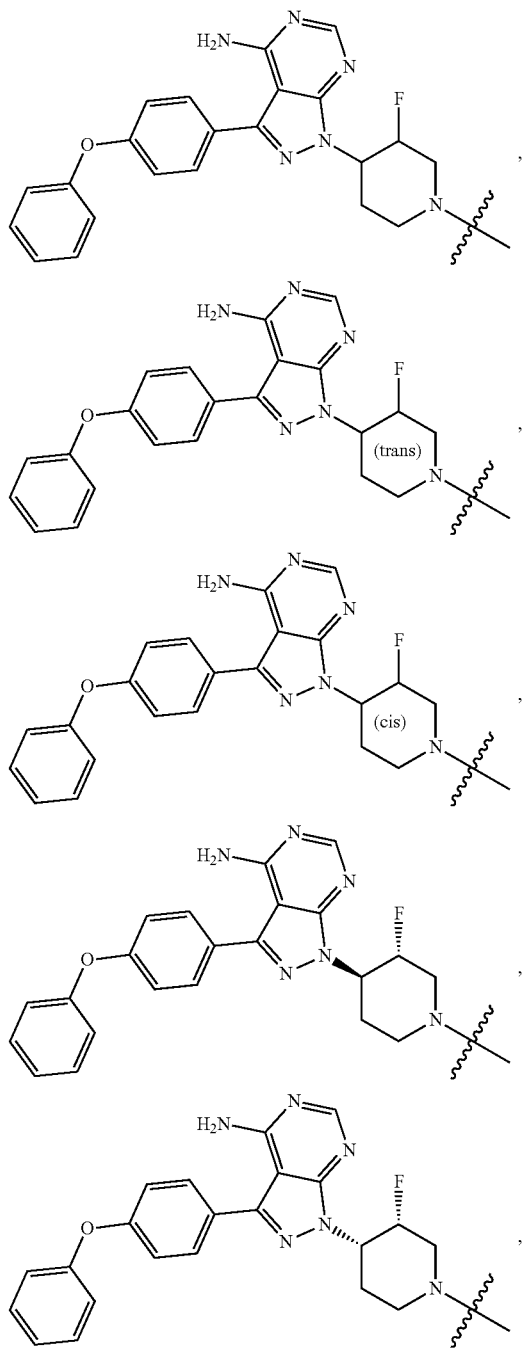

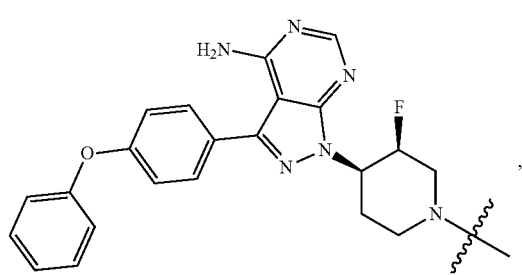

75
-continued
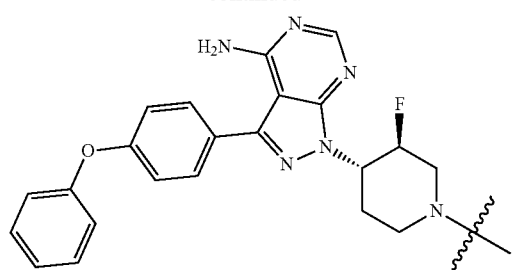
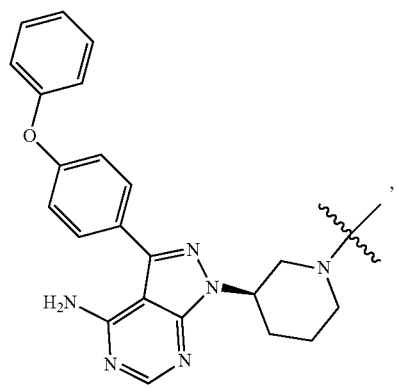
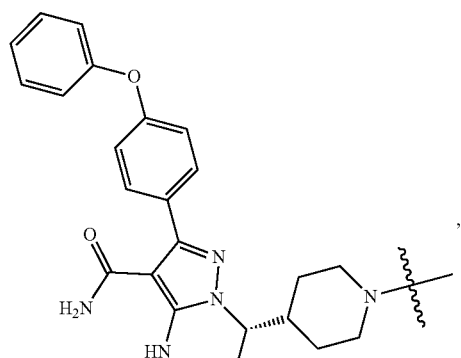
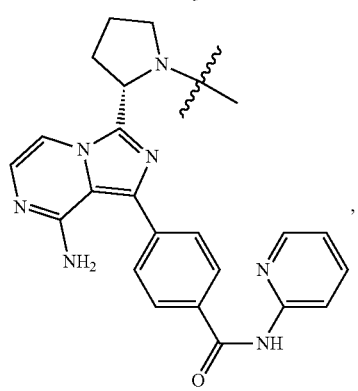
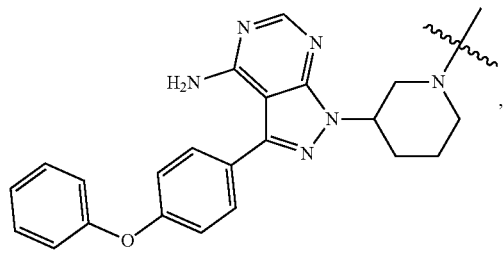
76
-continued
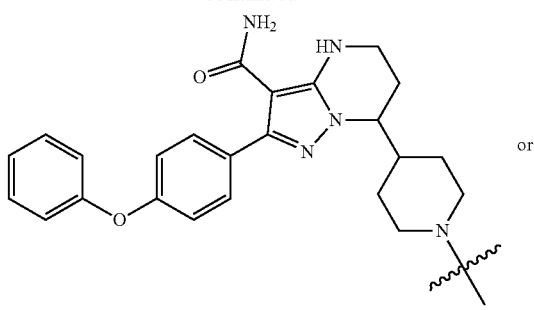 or
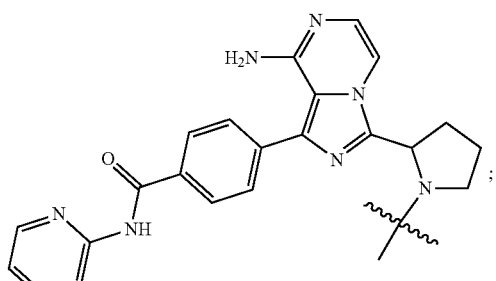;
K is selected from
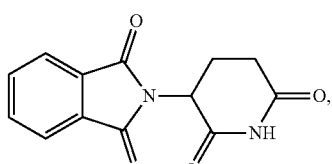
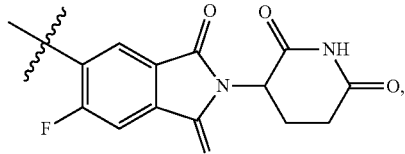
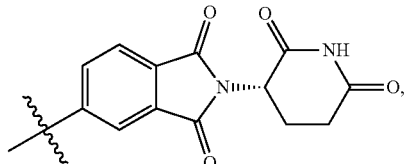
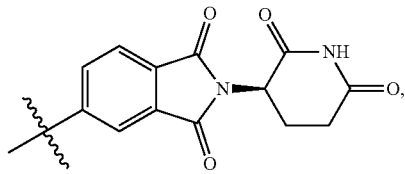
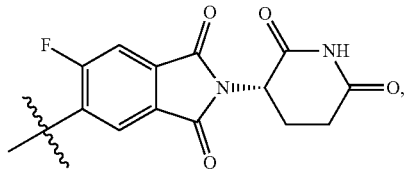

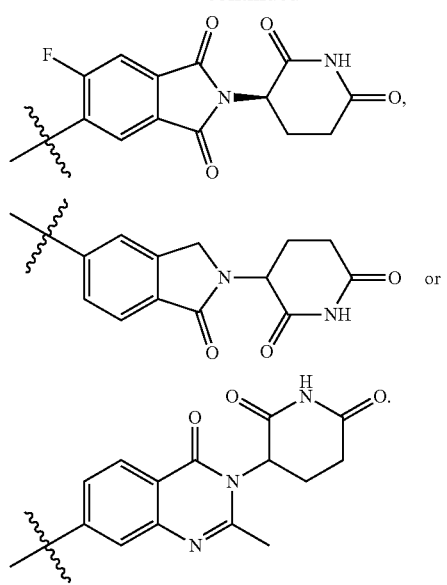
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
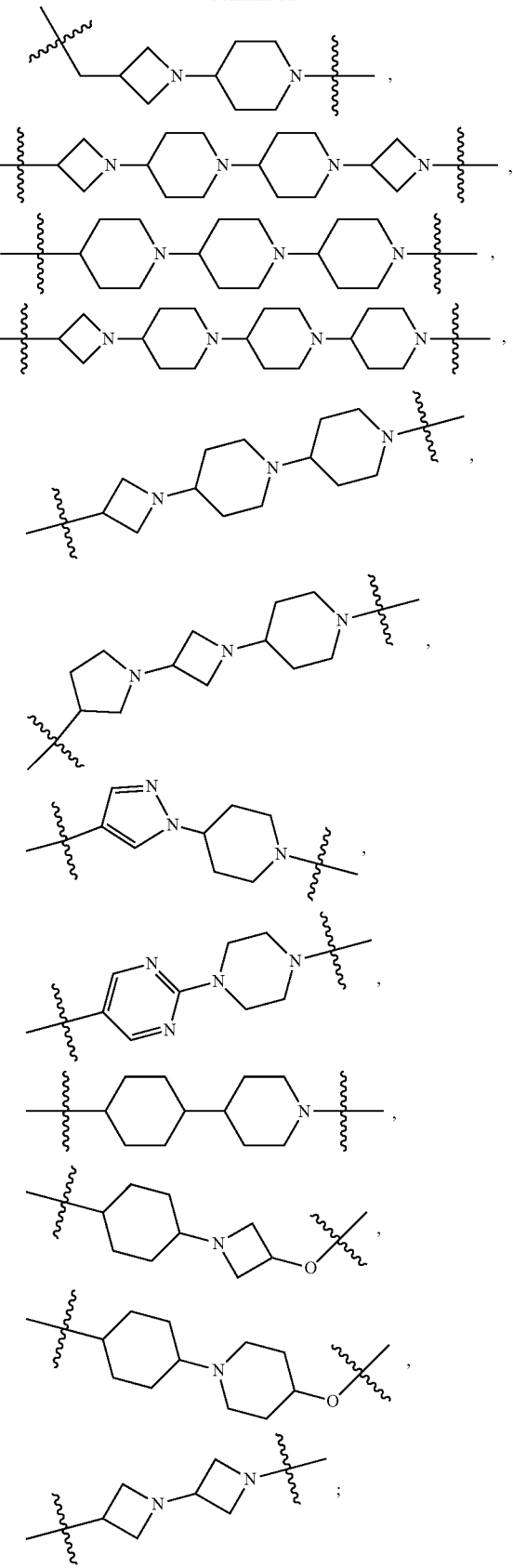

or L can be selected from
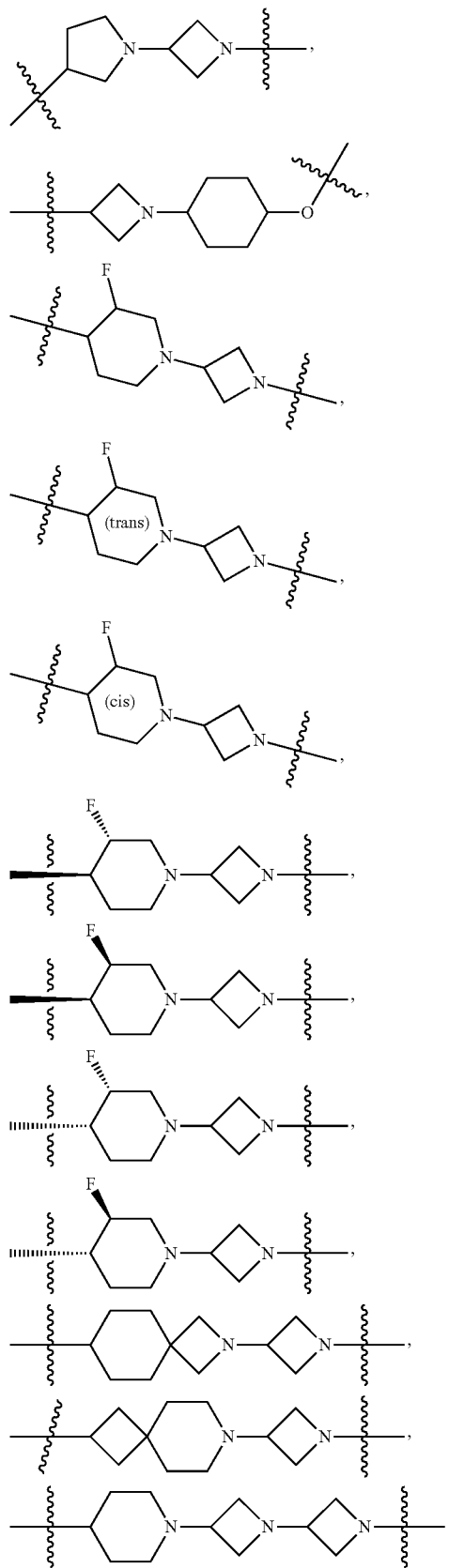
-continued
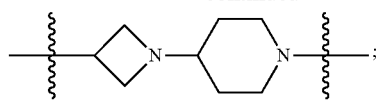
or L can be selected from
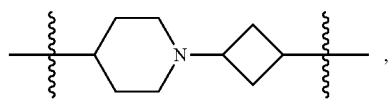
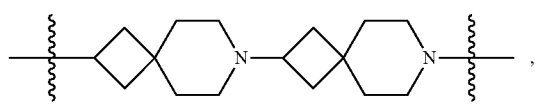
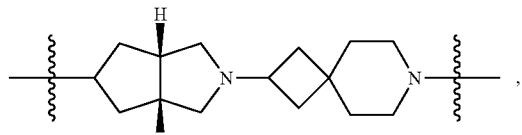
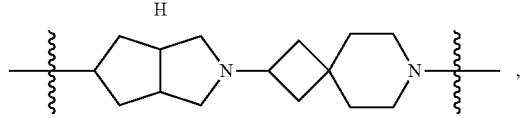
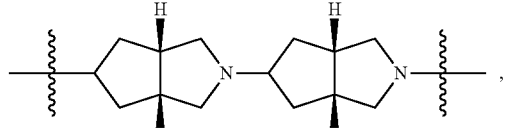
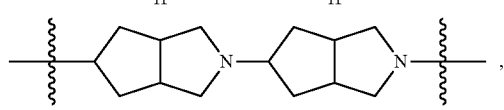
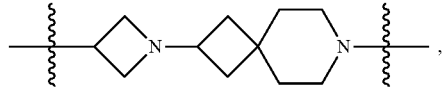
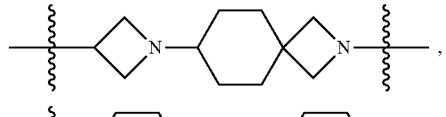
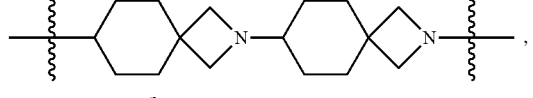
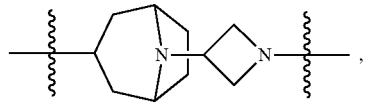
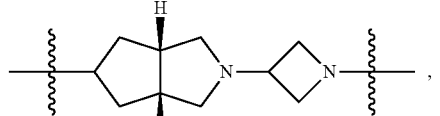
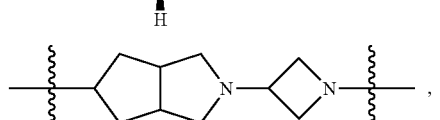
or -continued

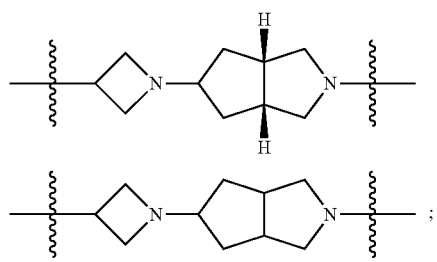

or

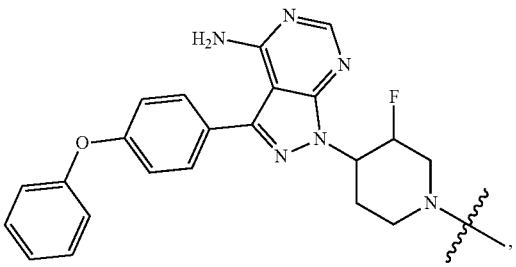

L is connected to B on the left side, and is connected to K on the right side;

B is selected from

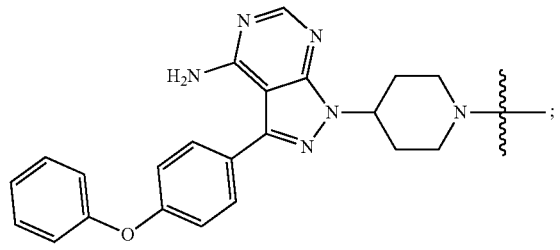 [SMILES: *N1CCC(n2nc(-c3ccc(Oc4ccccc4)cc3)c3c(N)ncnc32)CC1]

or B can be selected from

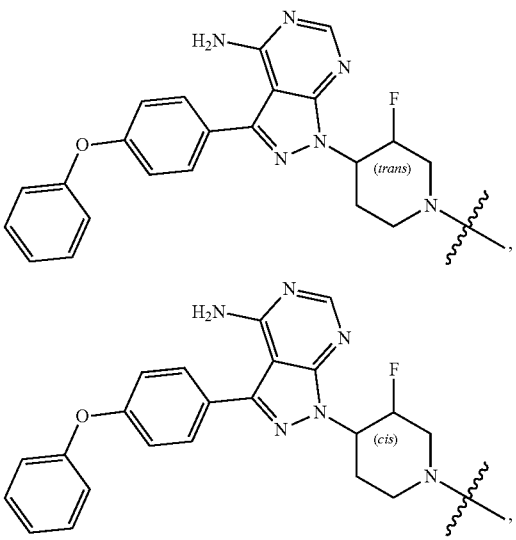

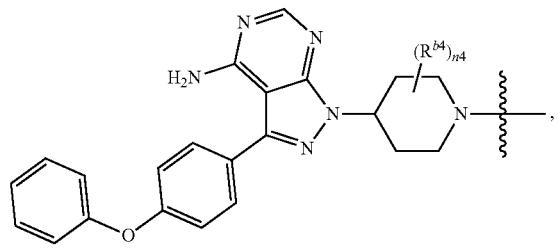

$R^{b4}$ is selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n4 is selected from 0, 1, 2, 3 or 4, or B can be selected from

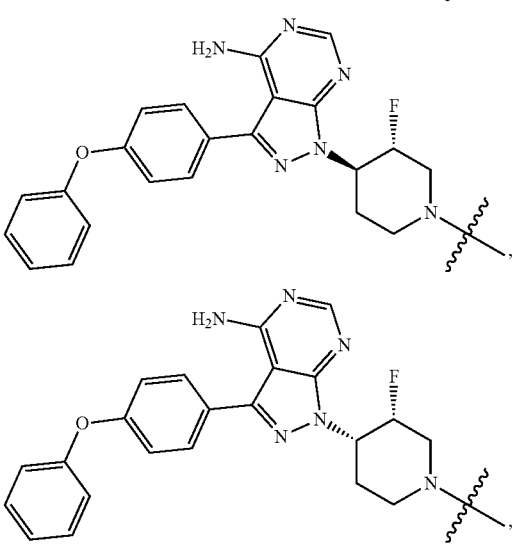

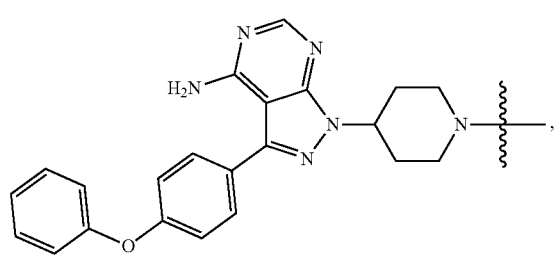

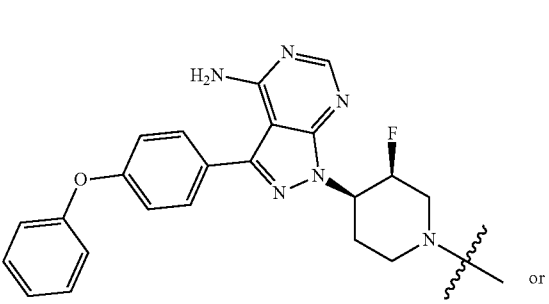

or

-continued
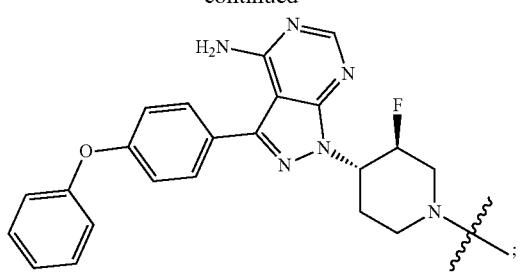
K is selected from
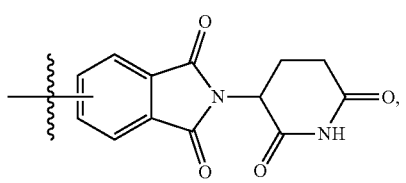
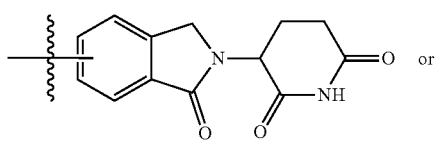
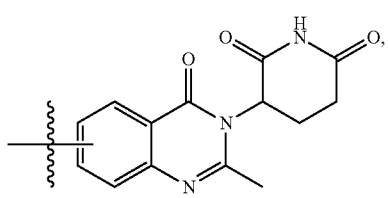
or K can be selected from
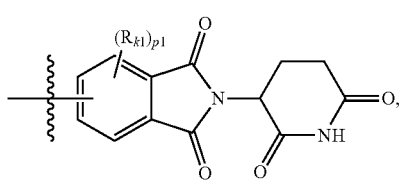
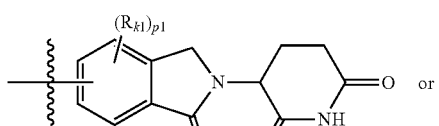
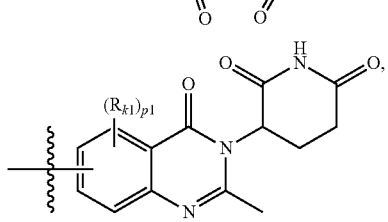
$R^{k1}$ is selected from H, F, Cl, Br, I, OH, $NH_2$, CN, COOH, $C_{1-4}$ alkyl or $C_{1-4}$ alkoxy, preferably H, F, Cl, Br, I, OH or $NH_2$,
p1 is selected from 0, 1 or 2,
or K can be selected from
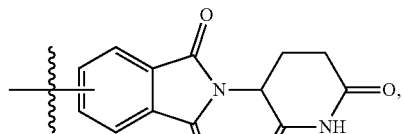
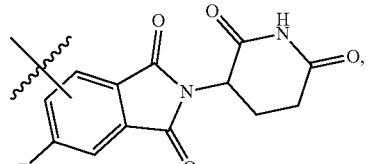
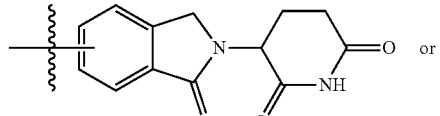
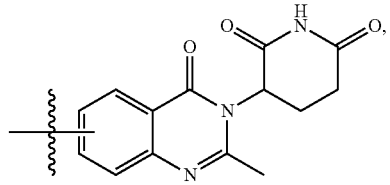
or K can be selected from
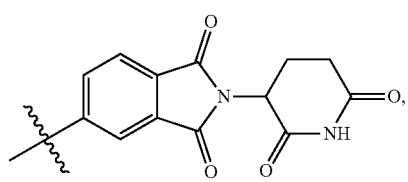
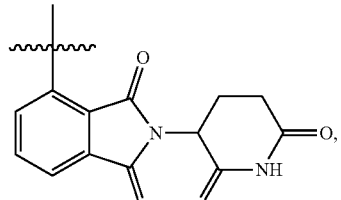
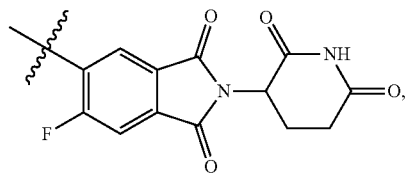
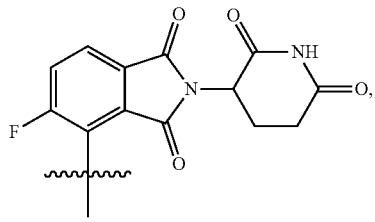

85
-continued
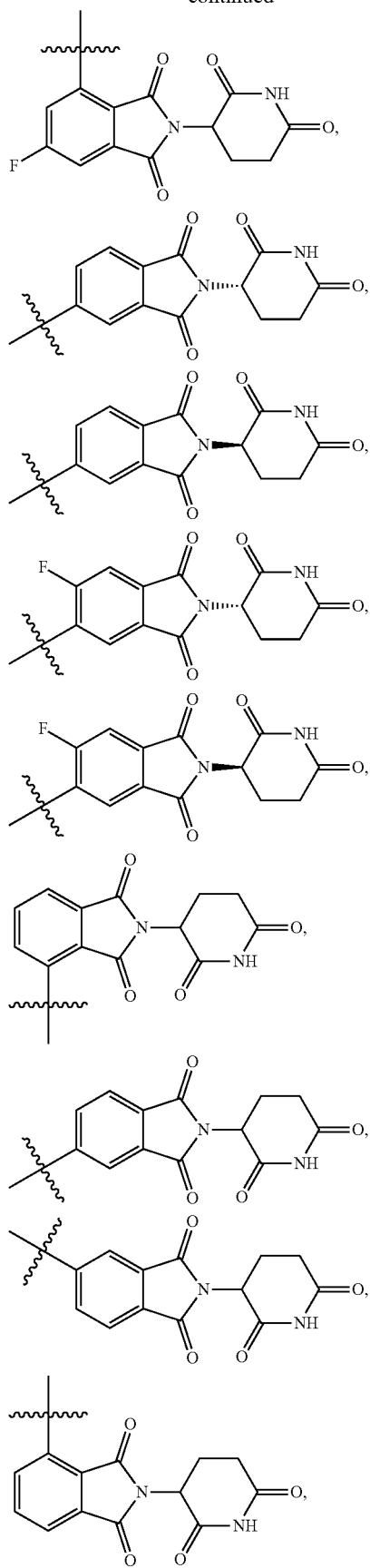
86
-continued
or K can be selected from

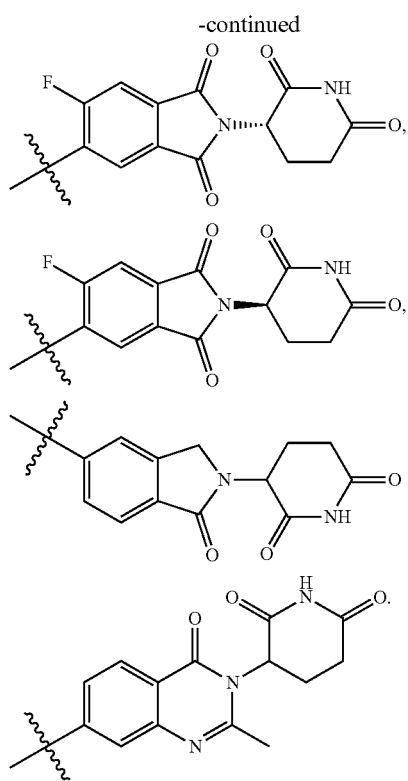
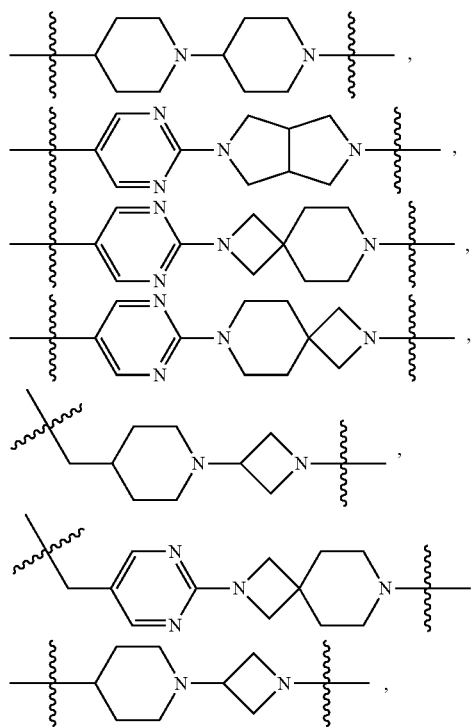
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
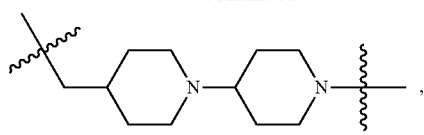
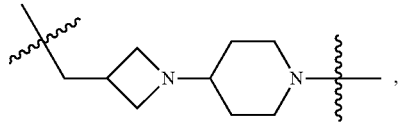
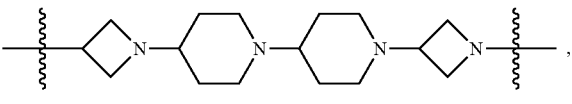
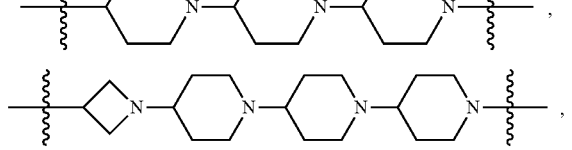
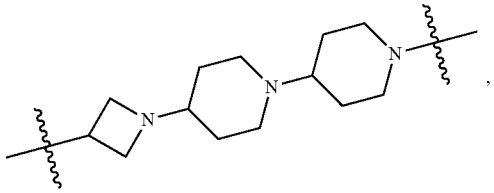
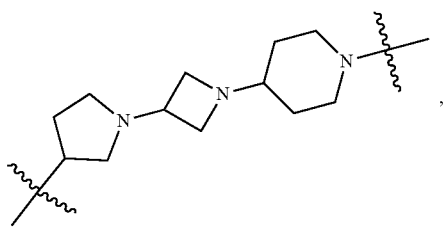
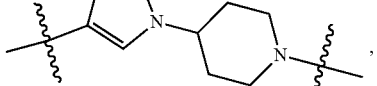
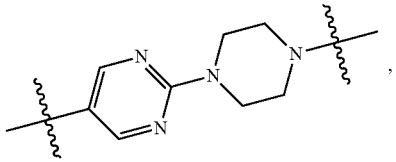
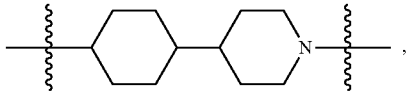
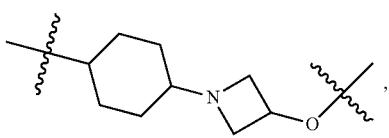
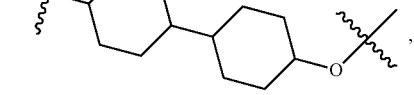

-continued
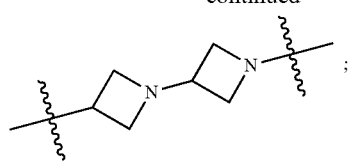
or L can be selected from
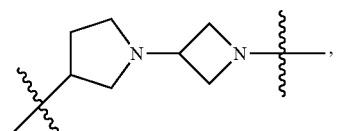
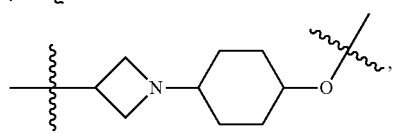
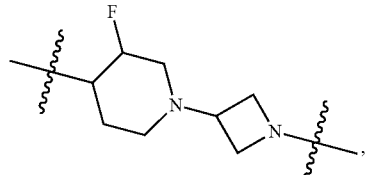
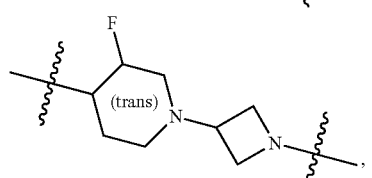
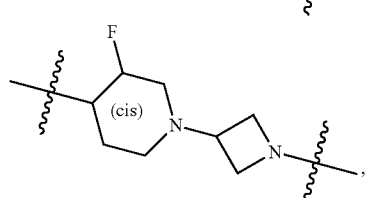
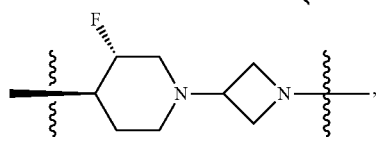
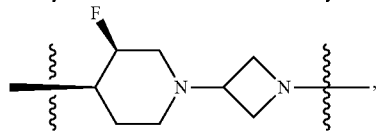
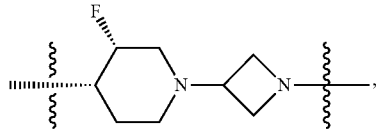
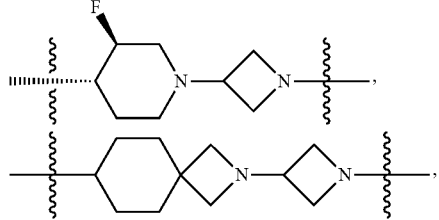
-continued
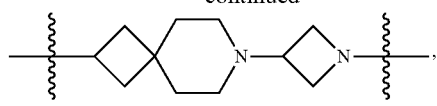
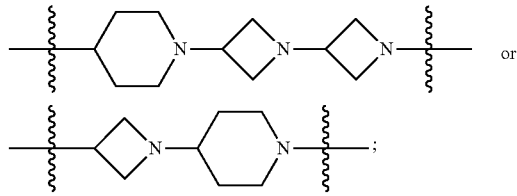 or
or L can be selected from
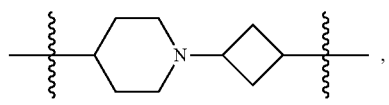
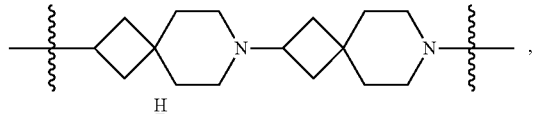
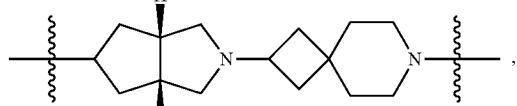
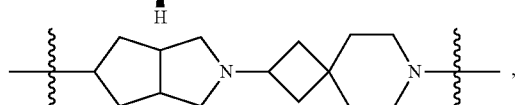
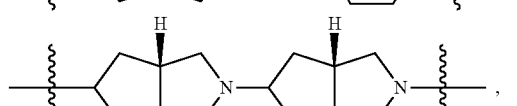
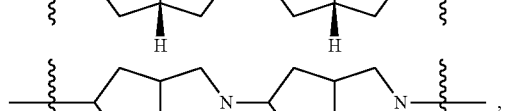
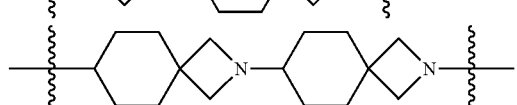
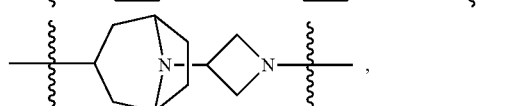
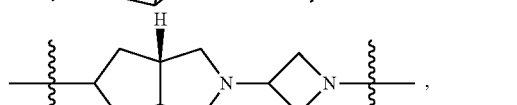
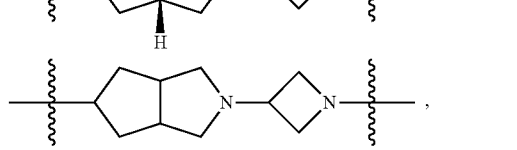

-continued

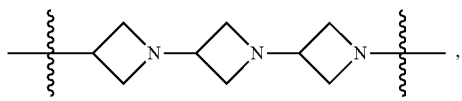

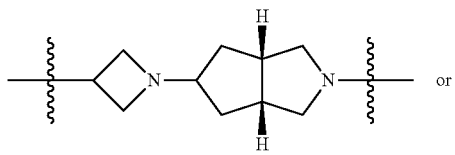

or

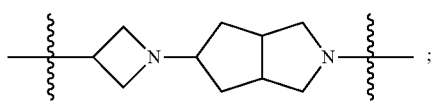

;

L is connected to B on the left side, and is connected to K on the right side;

B is selected from

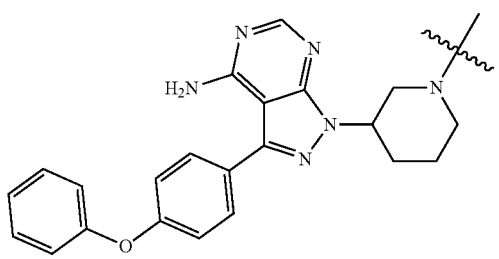

or B can be selected from

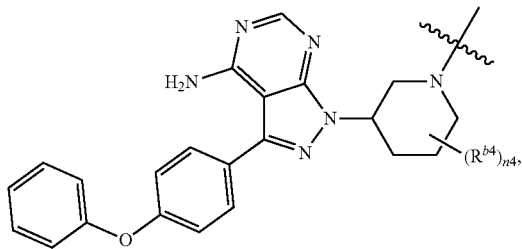

$R^{b4}$ is selected from H, F, Cl, Br, I, OH, NH$_2$, CN, CONH$_2$, C$_{1-4}$ alkyl or C$_{1-4}$ alkoxy, preferably selected from H, F, Cl, Br, I, OH, NH$_2$, CN, CONH$_2$, methyl or methoxy; the methyl, methoxy, alkyl and alkoxy are optionally further substituted with 0, 1, 2, 3 or 4 substituents selected from H, F, Cl, Br, I, OH, NH$_2$, CN, CONH$_2$, C$_{1-4}$ alkyl or C$_{1-4}$ alkoxy, preferably substituted with 0, 1, 2, 3 or 4 substituents selected from H, F, Cl, Br or I;

n4 is selected from 0, 1, 2, 3 or 4;

or B can be selected from

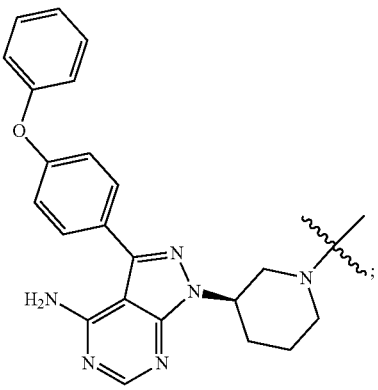

K is selected from

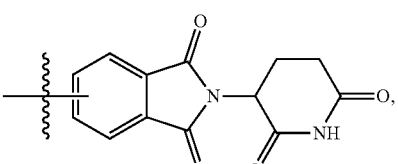

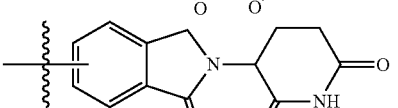

or

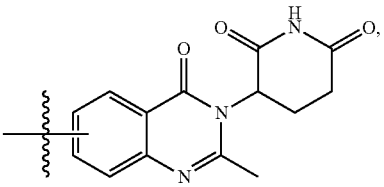

or K can be selected from

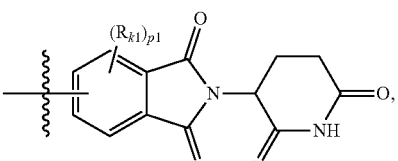

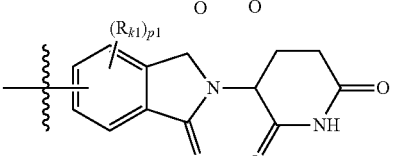

or

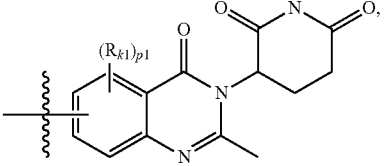

$R^{k1}$ is selected from H, F, Cl, Br, I, OH, NH$_2$, CN, COOH, C$_{1-4}$ alkyl or C$_{1-4}$ alkoxy, preferably H, F, Cl, Br, I, OH or NH$_2$, p1 is selected from 0, 1 or 2, or K can be selected from
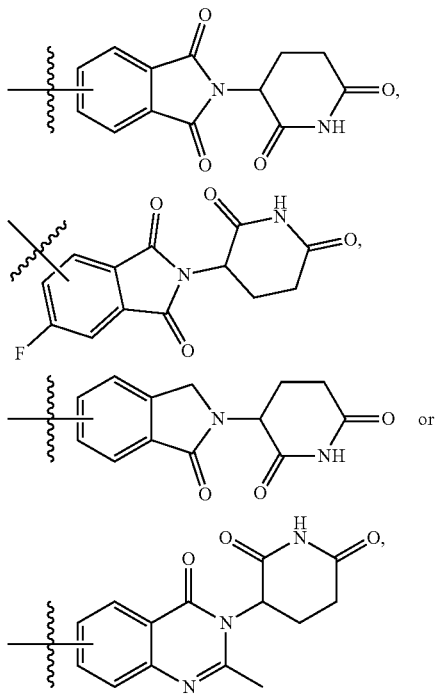
or K can be selected from
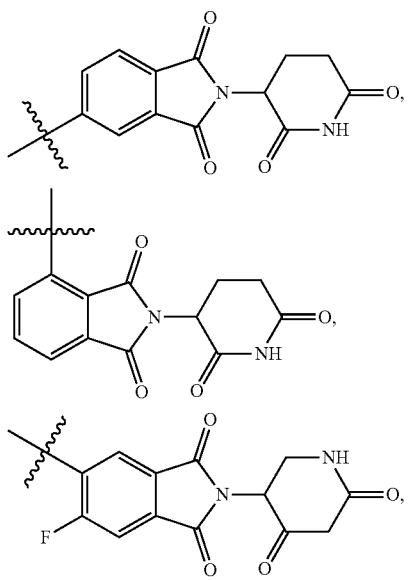
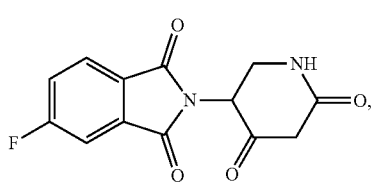
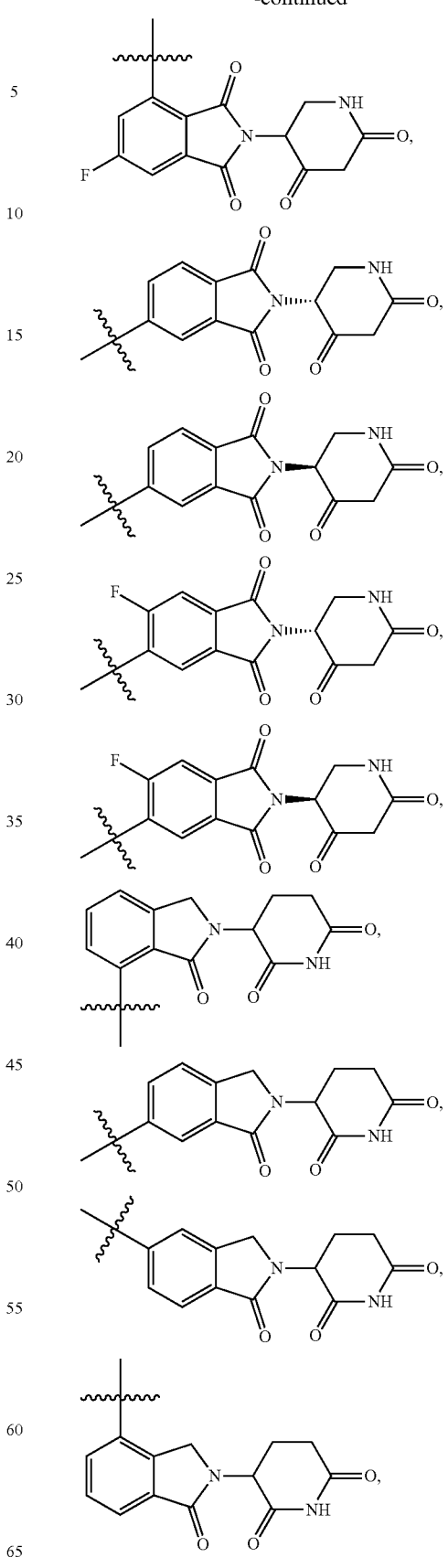

-continued
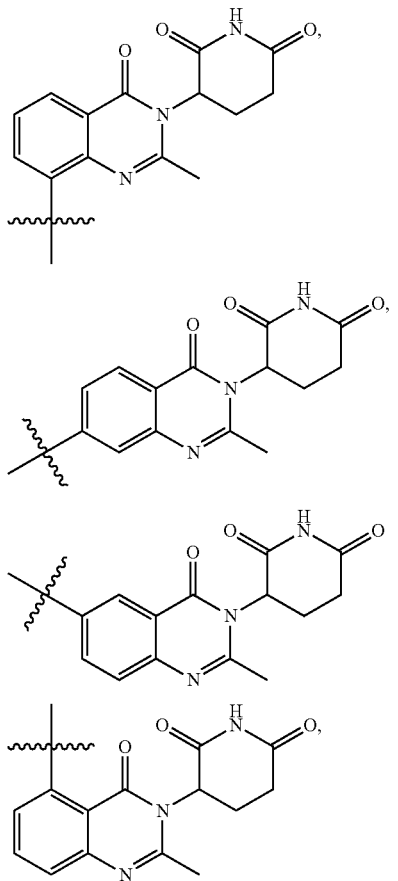
or K can be selected from
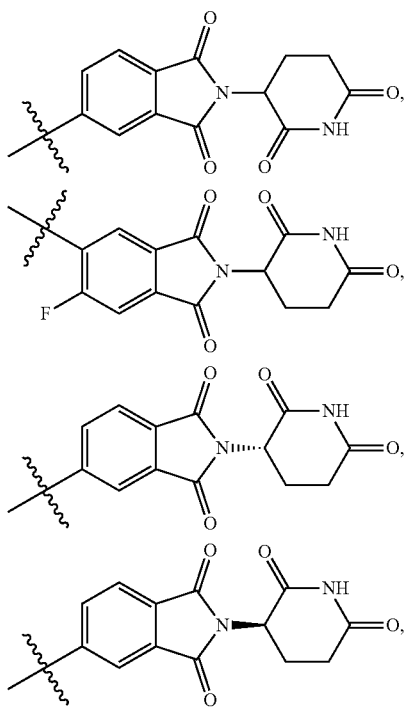
-continued
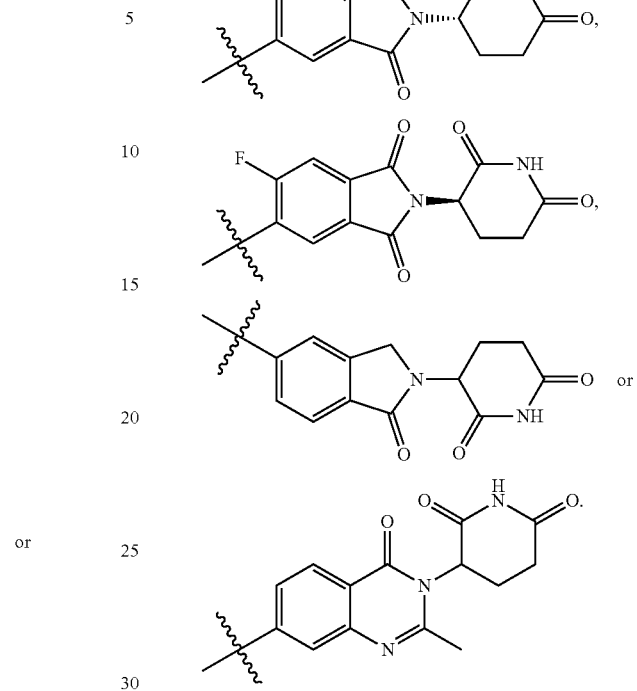
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
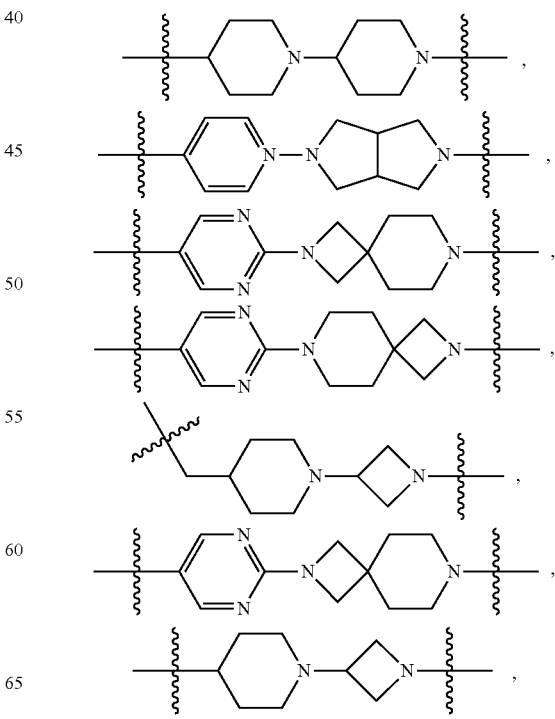

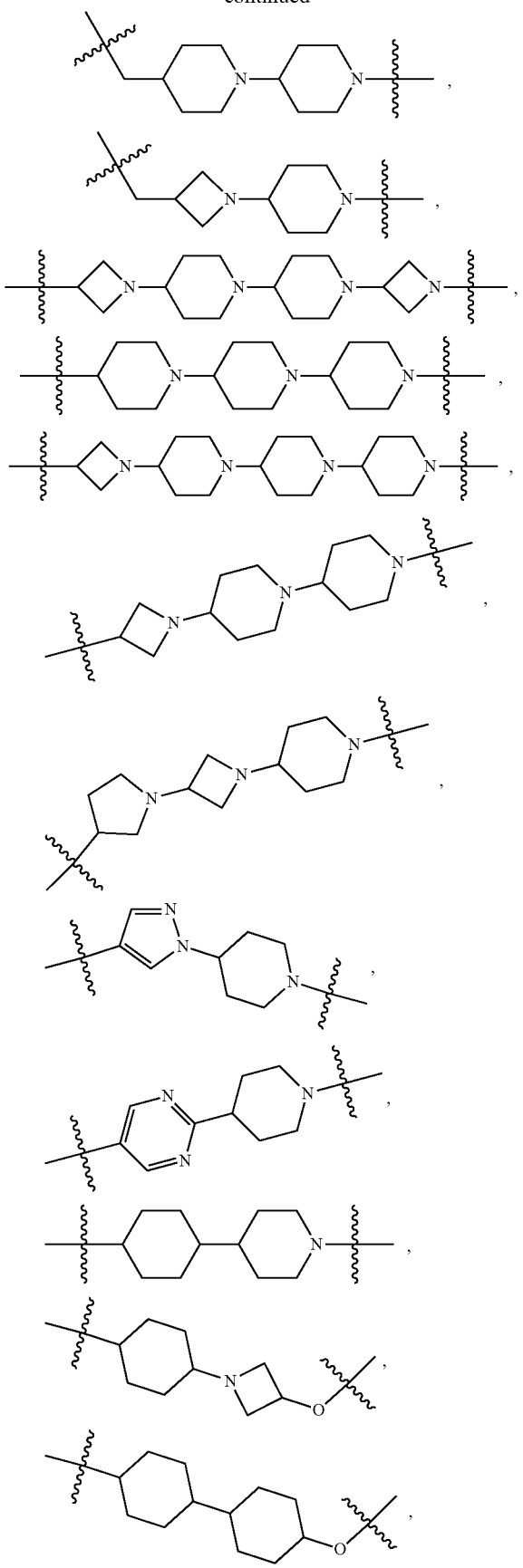
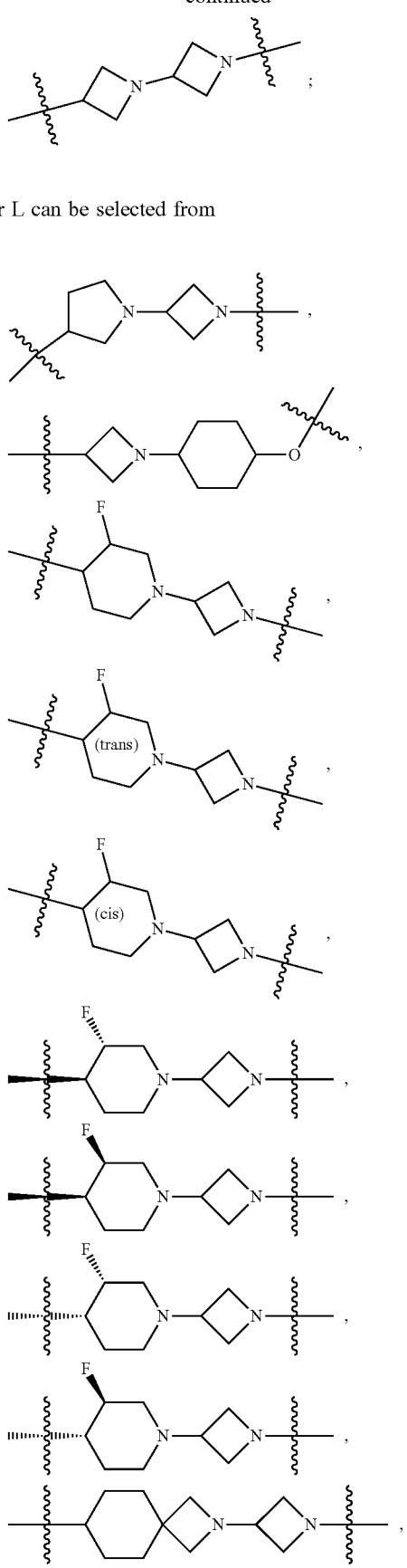
or L can be selected from

-continued

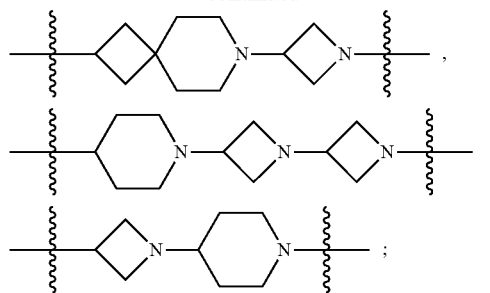

or L can be selected from

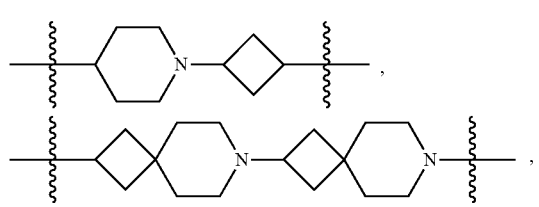
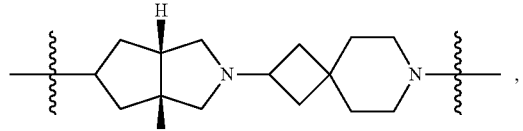
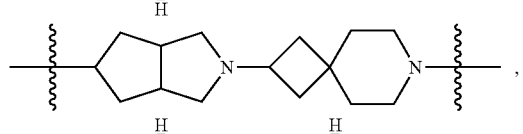
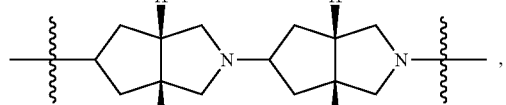
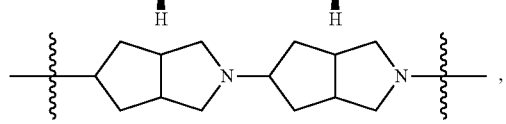
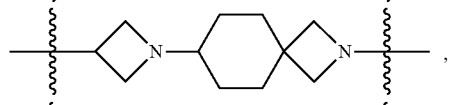
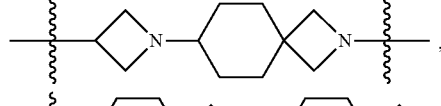
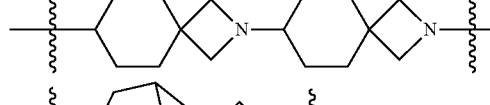
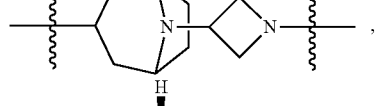
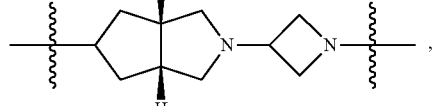

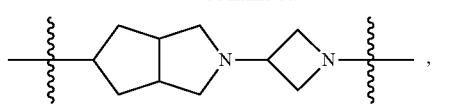
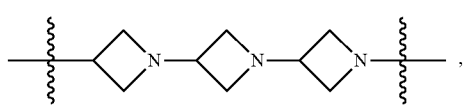
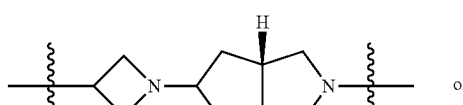
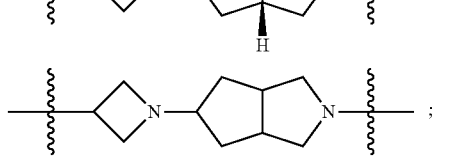

L is connected to B on the left side, and is connected to K on the right side;

B is selected from

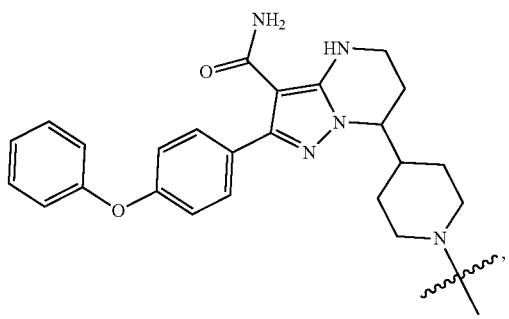

or B can be selected from

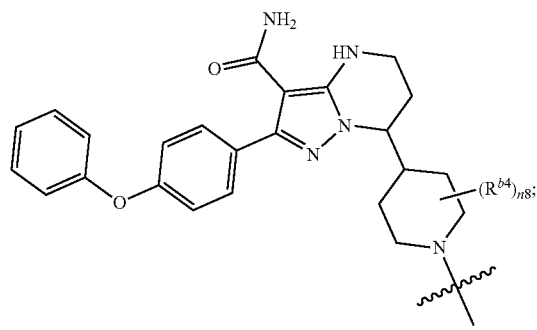

$R^{b4}$ is selected from H, F, Cl, Br, I, OH, $NH_2$, CN, $CONH_2$, $C_{1-4}$ alkyl or $C_{1-4}$ alkoxy, preferably selected from H, F, Cl, Br, I, OH, $NH_2$, CN, $CONH_2$, methyl or methoxy; the methyl, methoxy, alkyl and alkoxy are optionally further substituted with 0, 1, 2, 3 or 4 substituents selected from H, F, Cl, Br, I, OH, $NH_2$, CN, $CONH_2$, $C_{1-4}$ alkyl or $C_{1-4}$ alkoxy, preferably substituted with 0, 1, 2, 3 or 4 substituents selected from H, F, Cl, Br or I;

n8 is selected from 0, 1, 2, 3 or 4;

or B can be selected from
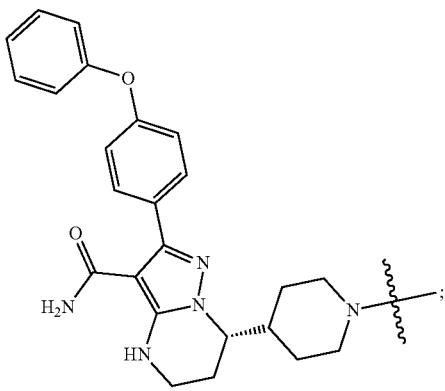 [SMILES: *N1CCC([C@@H]2CCNc3c(C(N)=O)c(-c4ccc(Oc5ccccc5)cc4)nn32)CC1]
K is selected from
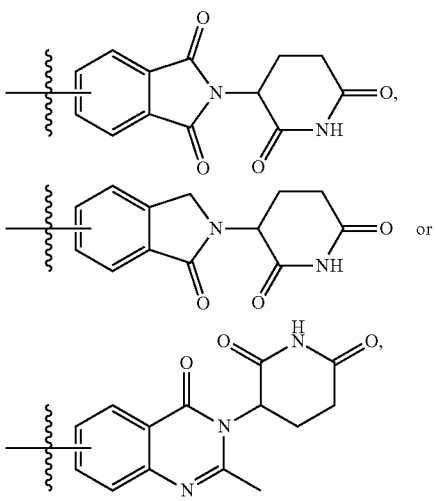
or K can be selected from
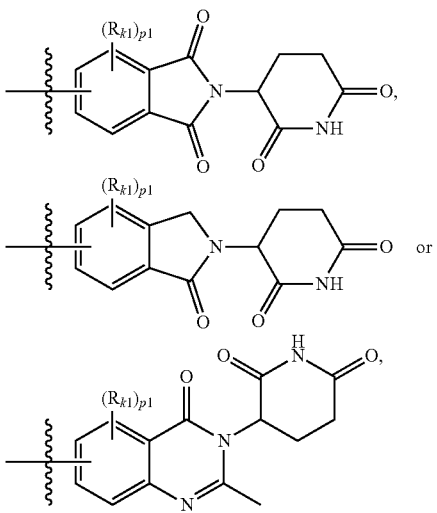
$R^{k1}$ is selected from H, F, Cl, Br, I, OH, NH$_2$, CN, COOH, C$_{1-4}$ alkyl or C$_{1-4}$ alkoxy, preferably H, F, Cl, Br, I, OH or NH$_2$,
p1 is selected from 0, 1 or 2,
or K can be selected from
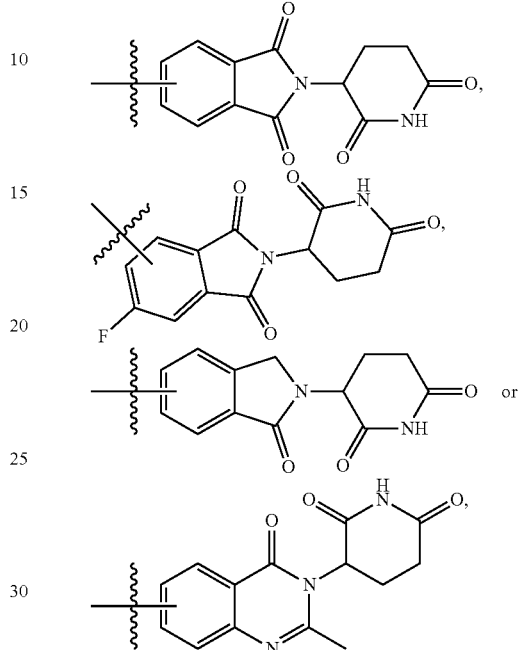
or K can be selected from
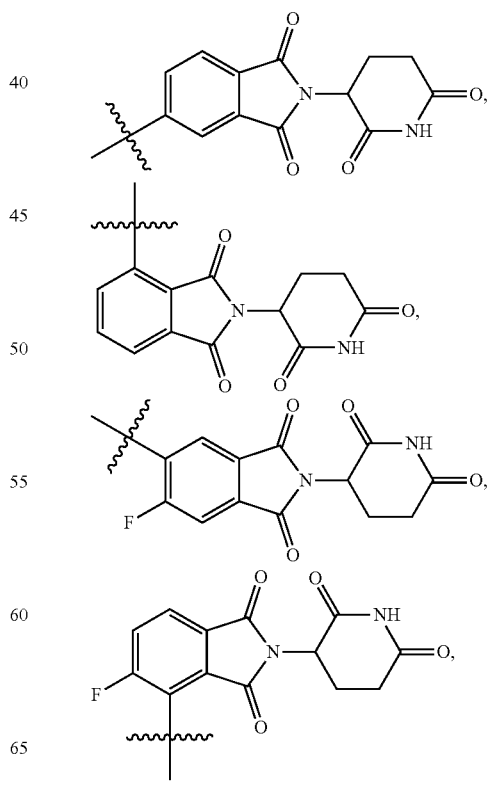

103
-continued
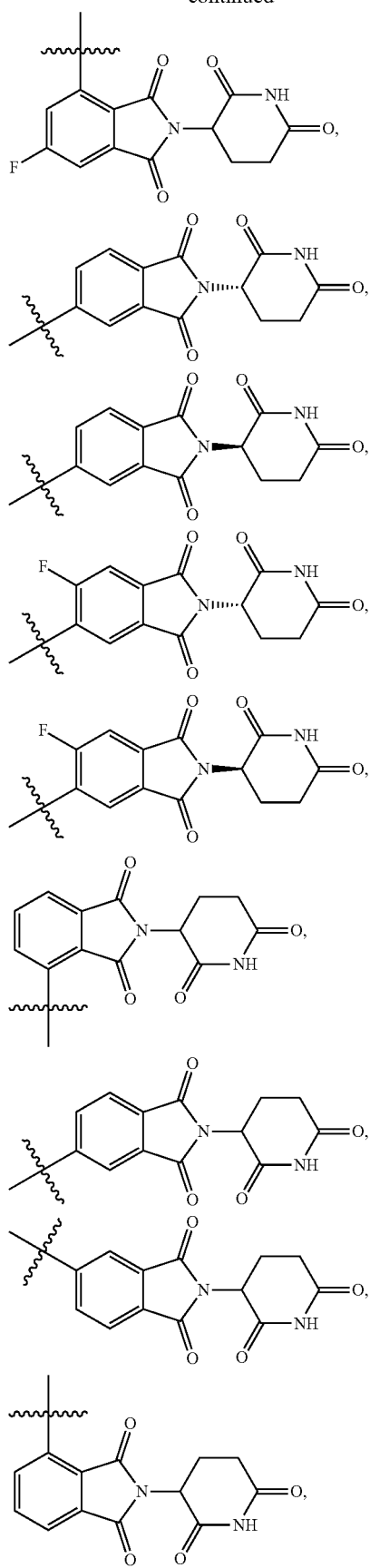
104
-continued
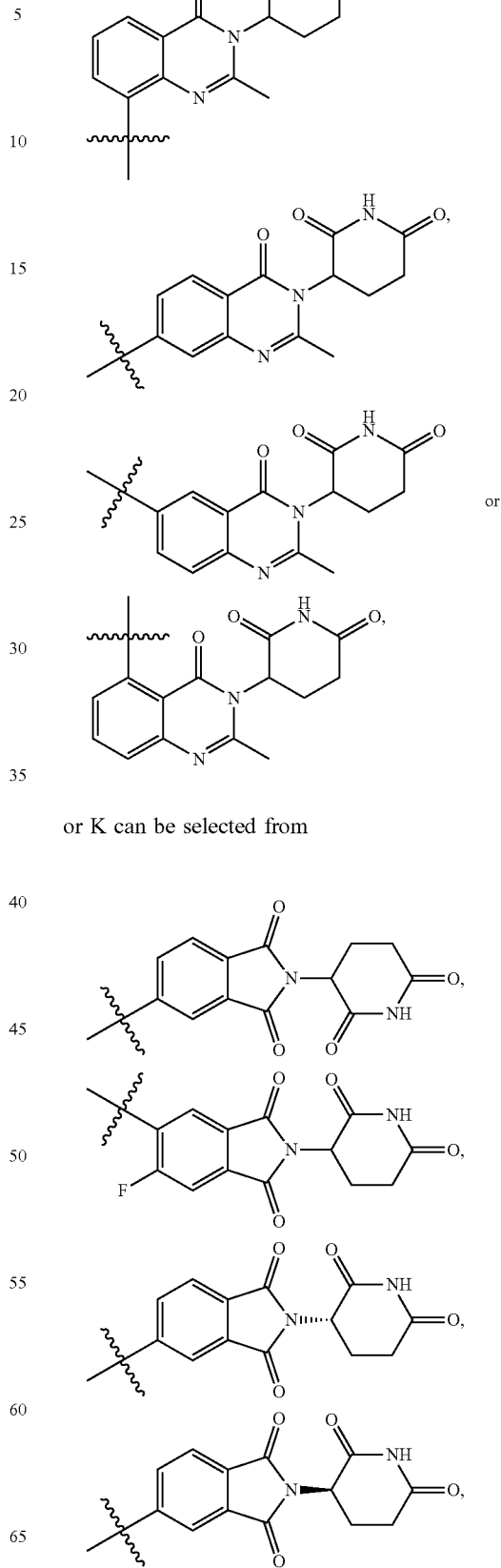
or K can be selected from

105
-continued
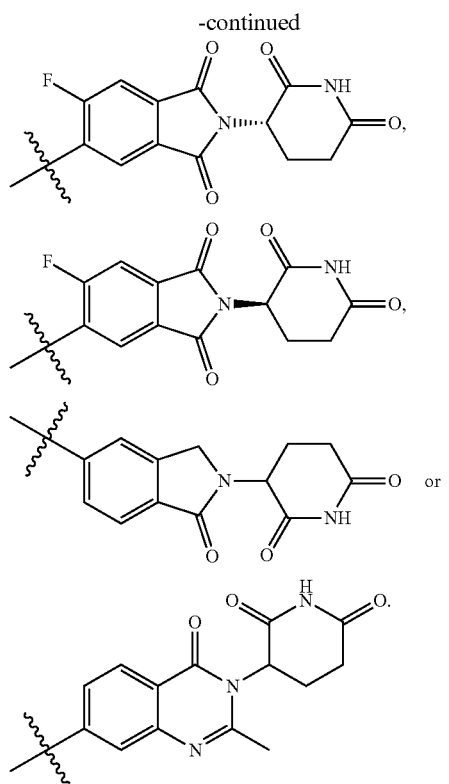
Some embodiments of the present disclosure relate to a compound represented by general formula (I) or a stereoisomer, a solvate, a prodrug, a metabolite, a pharmaceutically acceptable salt or a co-crystal thereof, wherein
L is selected from
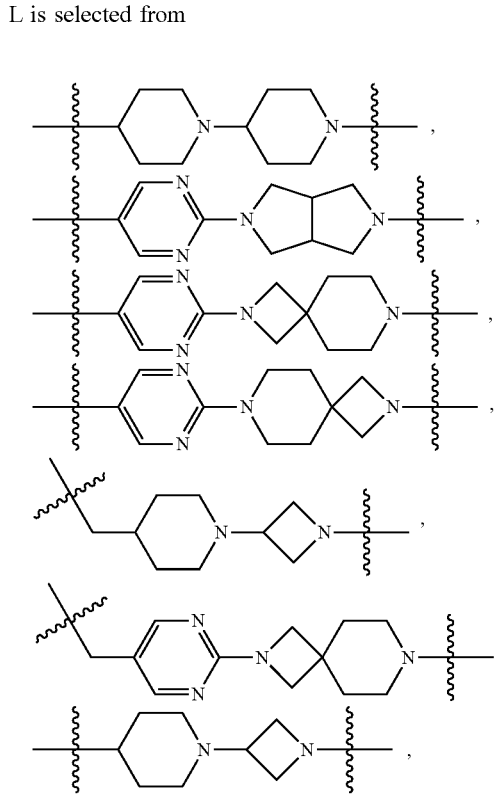
106
-continued
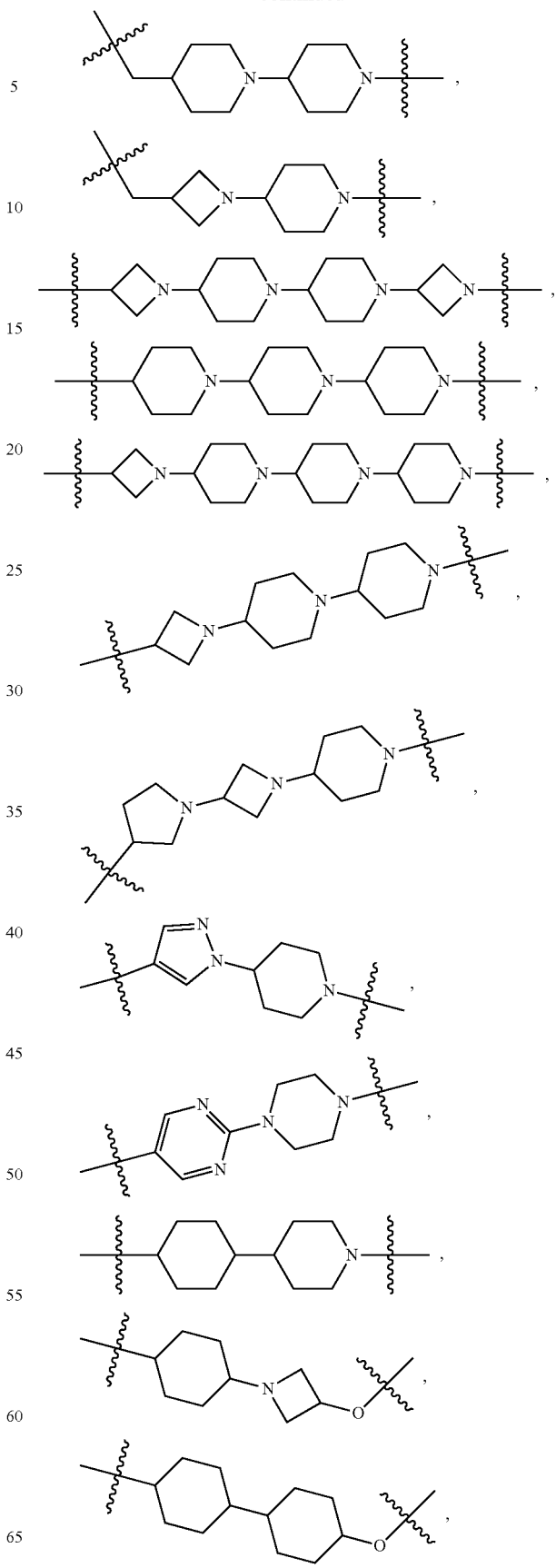

-continued
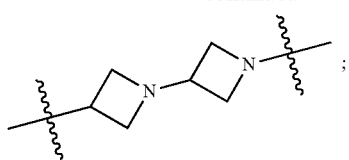
or L can be selected from
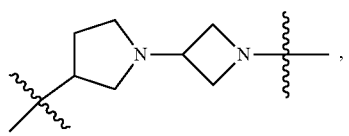
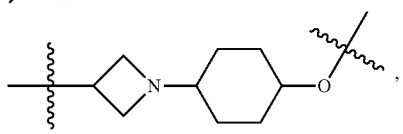
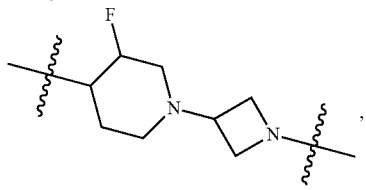
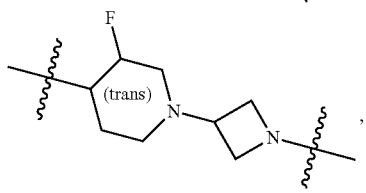
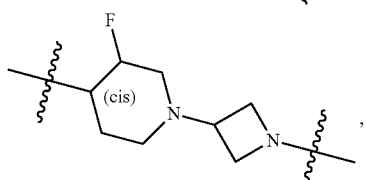
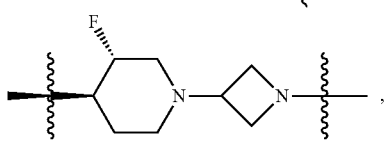
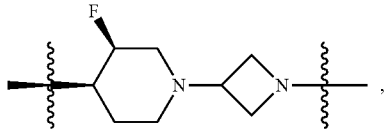
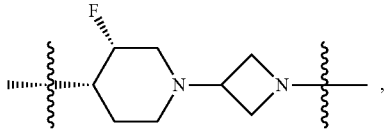
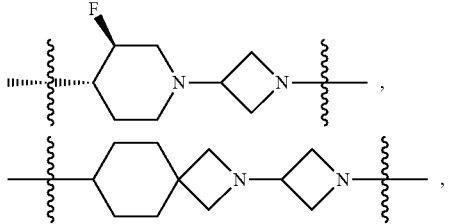
-continued

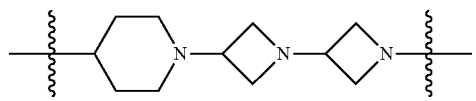 or
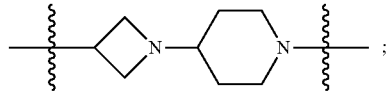
or L can be selected from
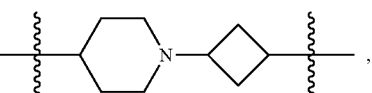
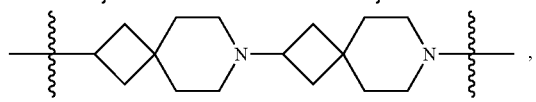
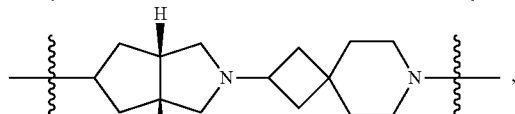
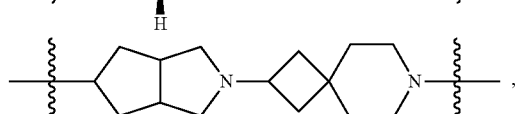
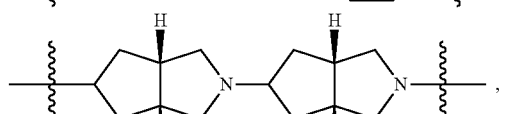
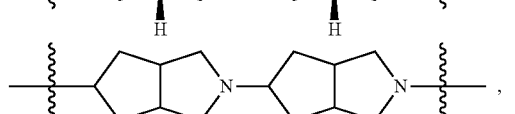
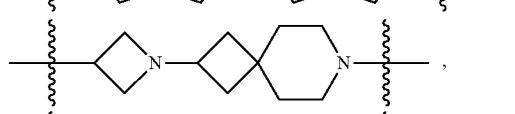
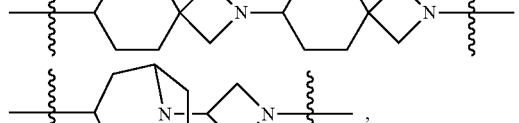
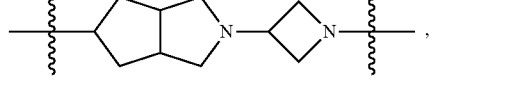

-continued

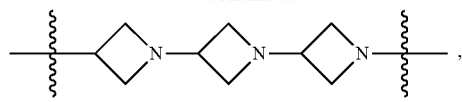

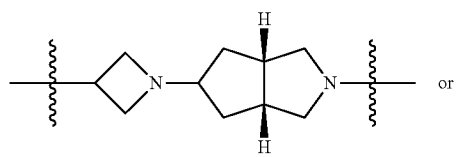 or

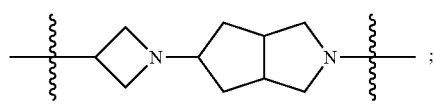 ;

L is connected to B on the left side, and is connected to K on the right side;

B is selected from

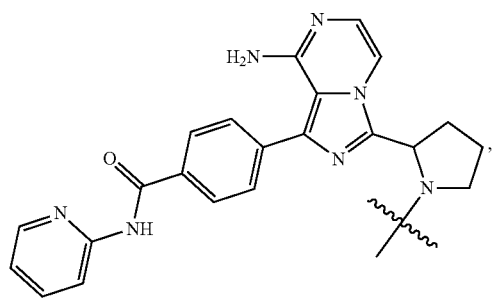 [SMILES: *N1CCCC1c1nc(-c2ccc(C(=O)Nc3ccccn3)cc2)c2c(N)nccn12]

or B can be selected from

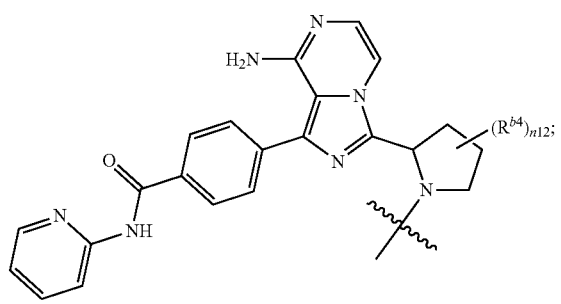

$R^{b4}$ is selected from H, F, Cl, Br, I, OH, NH$_2$, CN, CONH$_2$, C$_{1-4}$ alkyl or C$_{1-4}$ alkoxy, preferably selected from H, F, Cl, Br, I, OH, NH$_2$, CN, CONH$_2$, methyl or methoxy; the methyl, methoxy, alkyl and alkoxy are optionally further substituted with 0, 1, 2, 3 or 4 substituents selected from H, F, Cl, Br, I, OH, NH$_2$, CN, CONH$_2$, C$_{1-4}$ alkyl or C$_{1-4}$ alkoxy, preferably substituted with 0, 1, 2, 3 or 4 substituents selected from H, F, Cl, Br, I, n12 is selected from 0, 1, 2, 3 or 4;

or B can be selected from

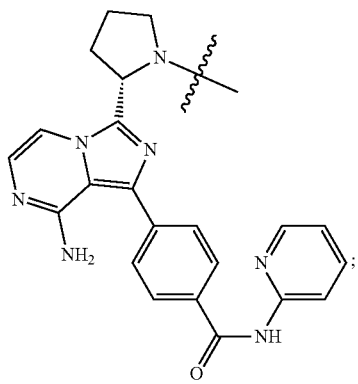

K is selected from

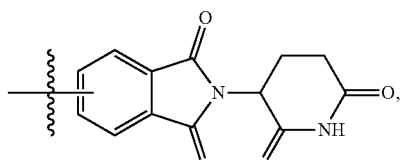

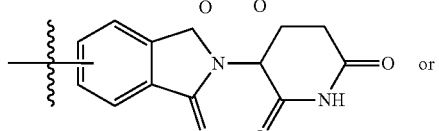 or

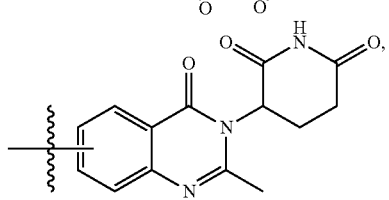

or K can be selected from

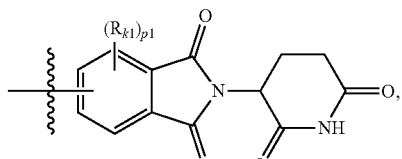

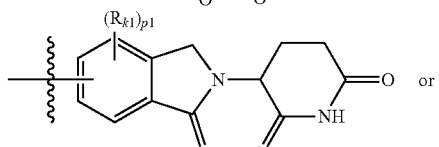 or

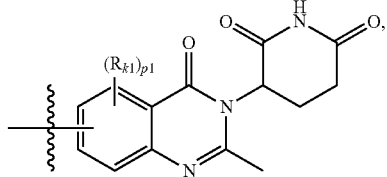

$R^{k1}$ is selected from H, F, Cl, Br, I, OH, NH$_2$, CN, COOH, C$_{1-4}$ alkyl or C$_{1-4}$ alkoxy, preferably H, F, Cl, Br, I, OH or NH$_2$, p1 is selected from 0, 1 or 2, or K can be selected from
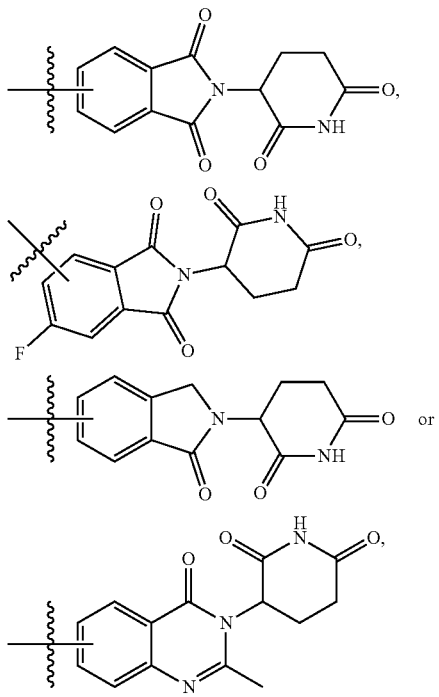
or K can be selected from
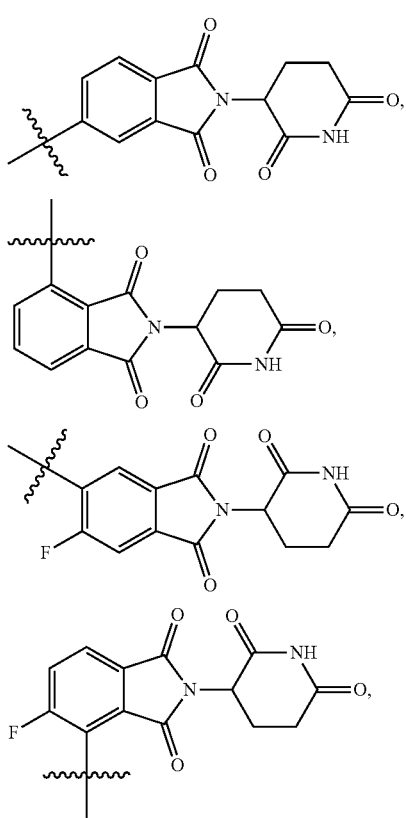
-continued
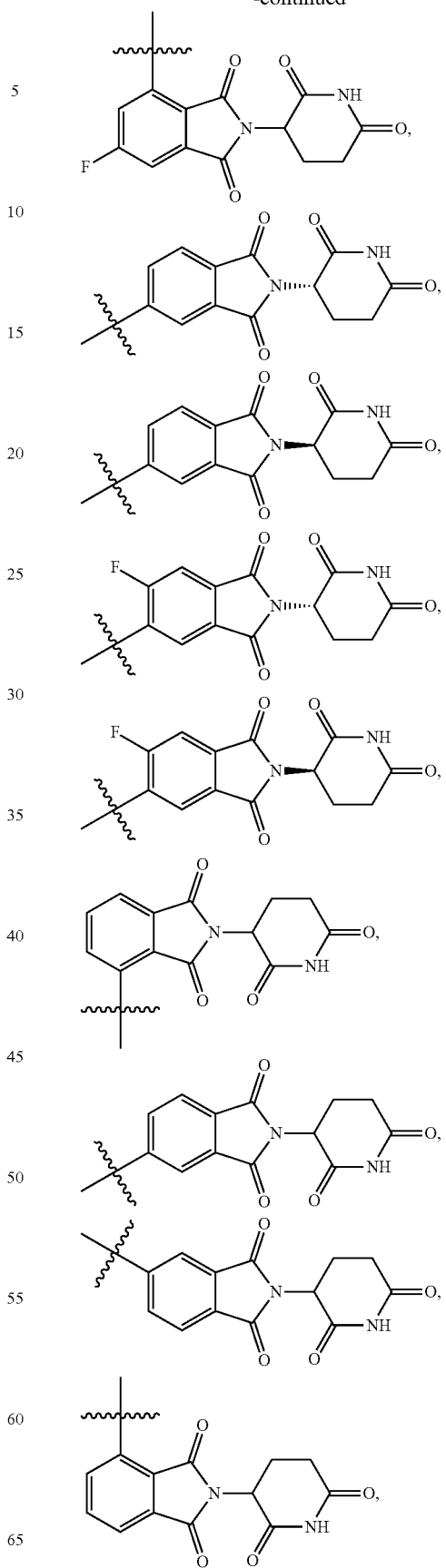

113
-continued

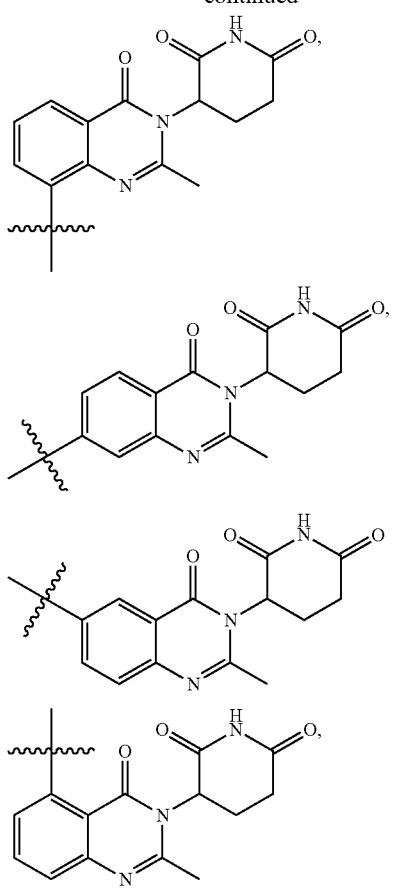

or K can be selected from

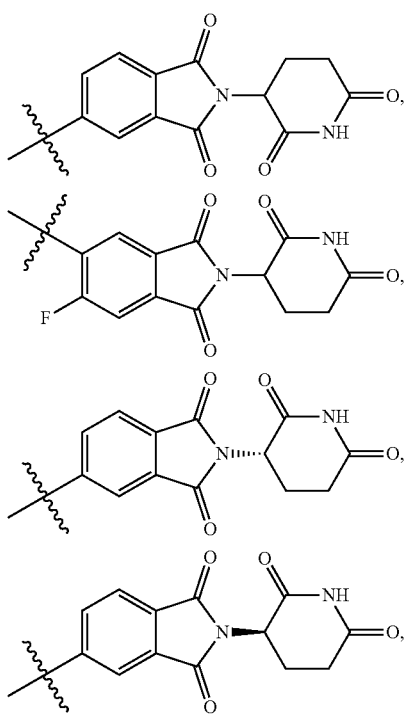

114
-continued

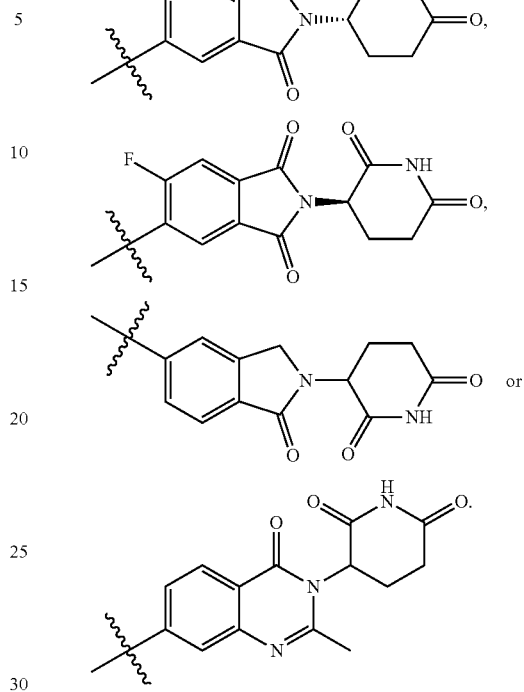

Some embodiments of the present disclosure relate to a compound represented by general formula (I) or a stereoisomer, a solvate, a prodrug, a metabolite, a pharmaceutically acceptable salt or a co-crystal thereof, wherein the compound is selected from a compound represented by general formula (Ia) or (Ib), B-Cy1-Cy2-K    (Ia)

B-Cy1-Cy2-Cy3-K    (Ib)

B is selected from

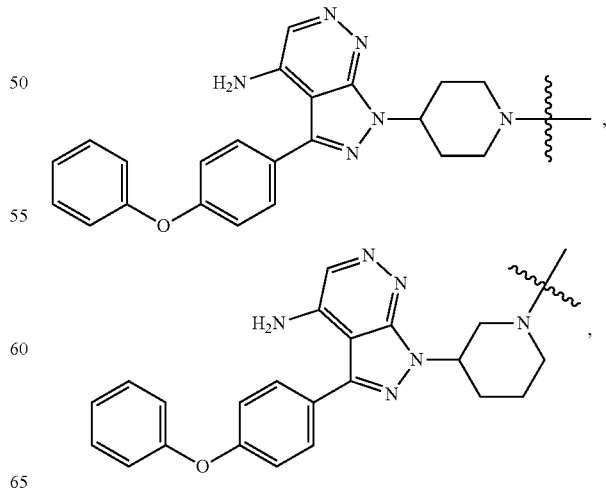

115
-continued
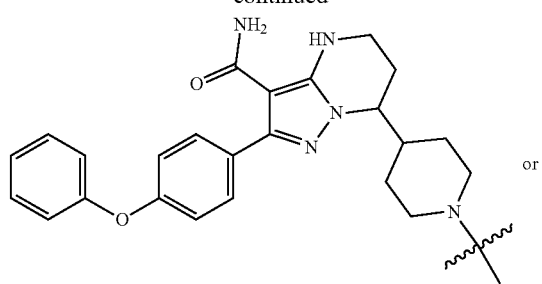
or
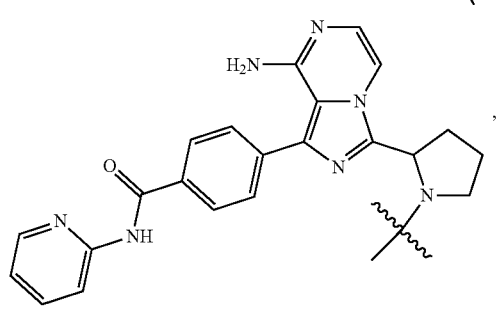
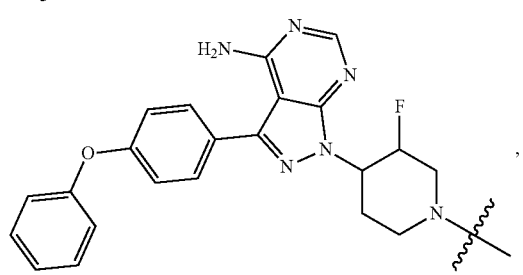
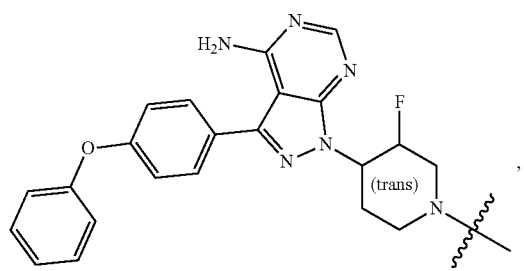
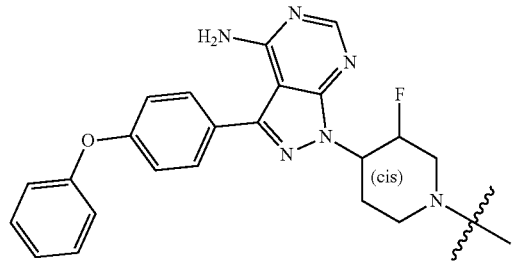
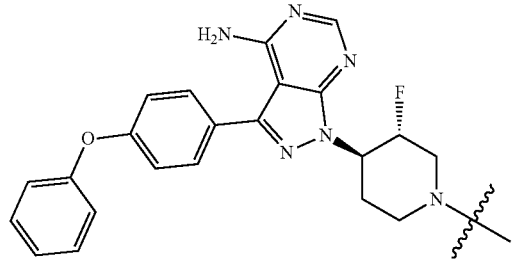
116
-continued
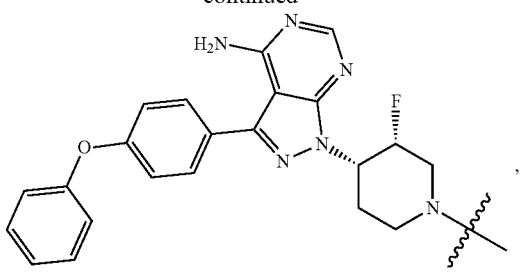
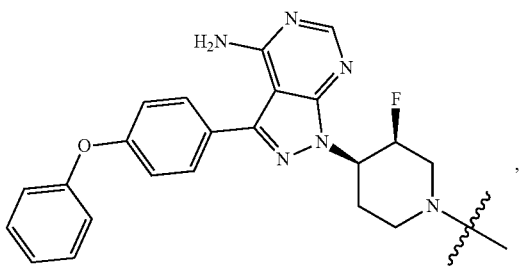
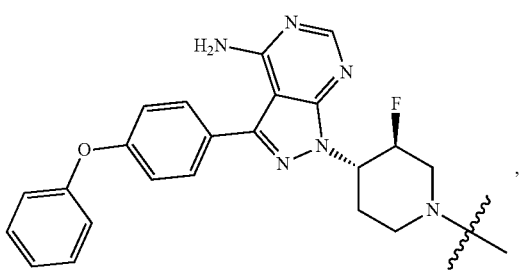
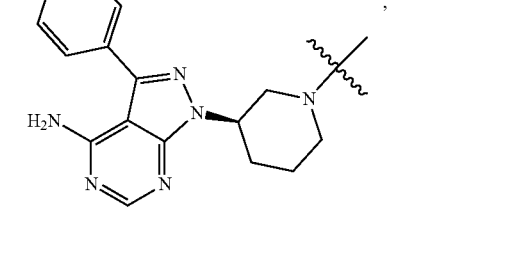
or
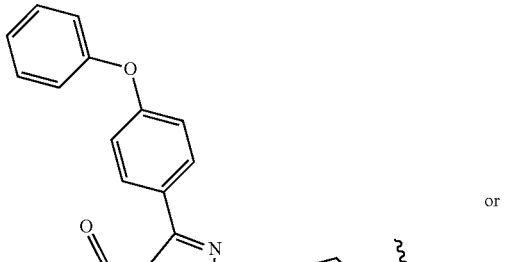

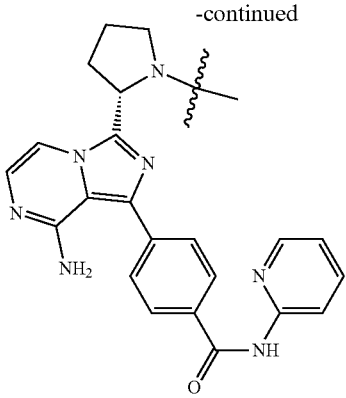

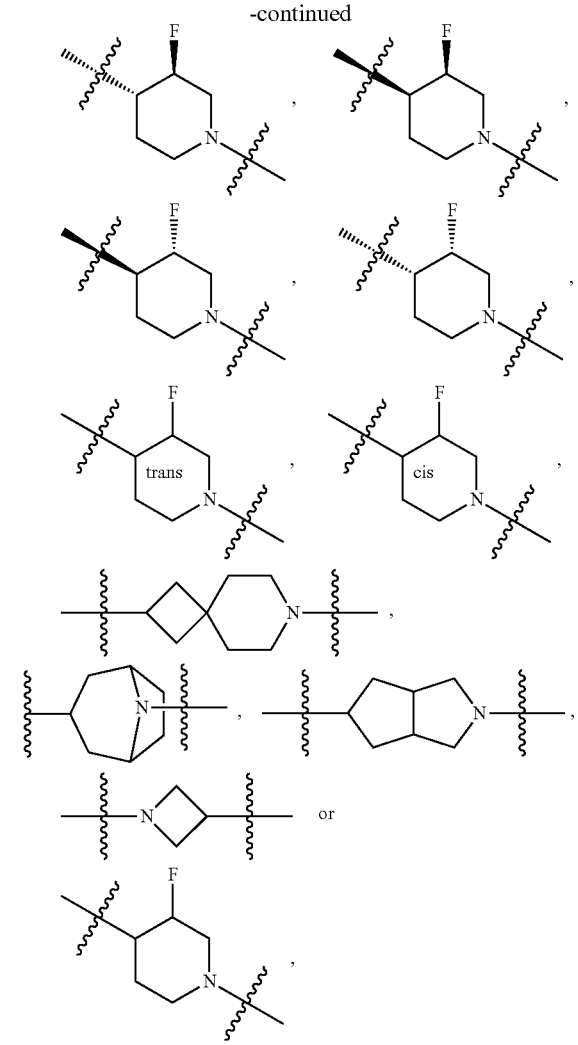

Cy1, Cy2, and Cy3 are each independently selected from one of the following substituted or unsubstituted groups: 4- to 6-membered nitrogen-containing mono-heterocyclic ring, 5- to 10-membered nitrogen-containing fused heterocyclic ring, 6- to 10-membered nitrogen-containing spiro-heterocyclic ring, 4- to 6-membered monocycloalkyl or phenyl, wherein the phenyl, cycloalkyl, mono-heterocyclic ring, fused heterocyclic ring or spiro-heterocyclic ring is optionally further substituted with 0 to 4 substituents selected from H, F, Cl, Br, I, OH, $NH_2$, oxo, $C_{1-4}$ alkyl or $C_{1-4}$ alkoxy, and the mono-heterocyclic ring, fused heterocyclic ring or spiro-heterocyclic ring contains 1 to 4 heteroatoms selected from O, S or N;

or Cy1, Cy2, and Cy3 can be each independently selected from one of the following substituted or unsubstituted groups:

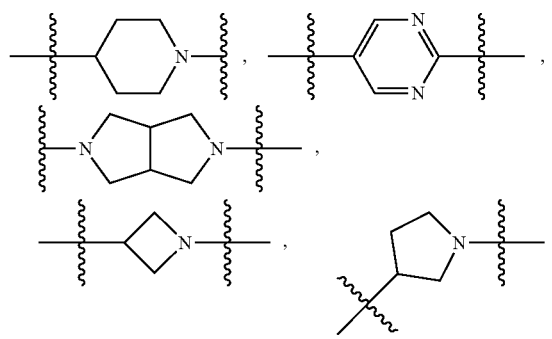

which, when substituted, are optionally further substituted with 0 to 4 substituents selected from H, F, Cl, Br, I, OH, $NH_2$, oxo, $C_{1-4}$ alkyl or $C_{1-4}$ alkoxy;

K is selected from

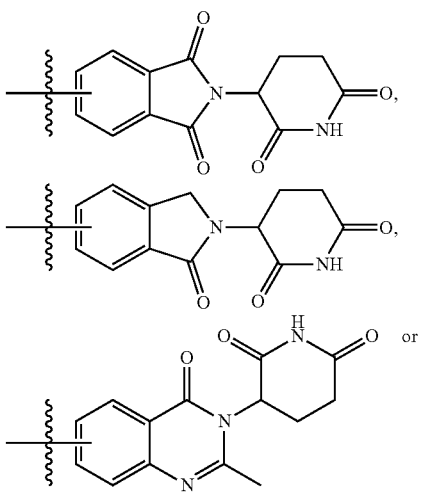

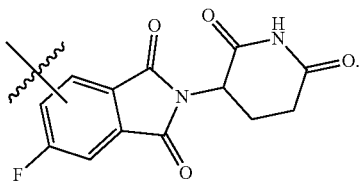
Some embodiments of the present disclosure relate to a compound represented by general formula (I) or a stereoisomer, a solvate, a prodrug, a metabolite, a pharmaceutically acceptable salt or a co-crystal thereof, wherein the compound is selected from a compound represented by general formula (Ia) or (Ib),
B is selected from
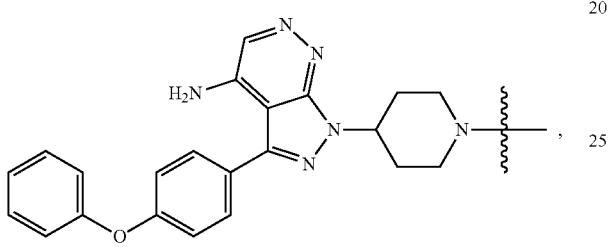
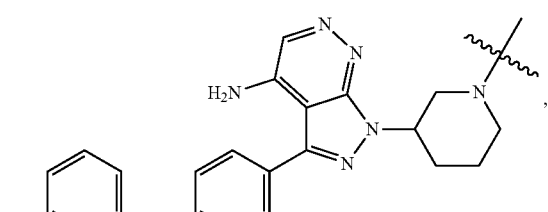
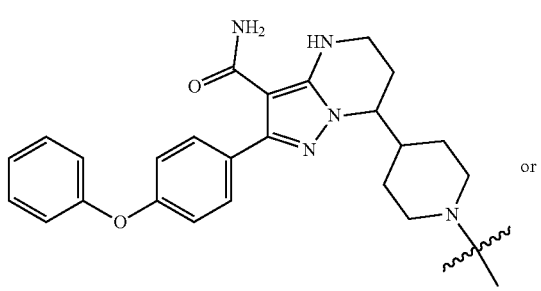
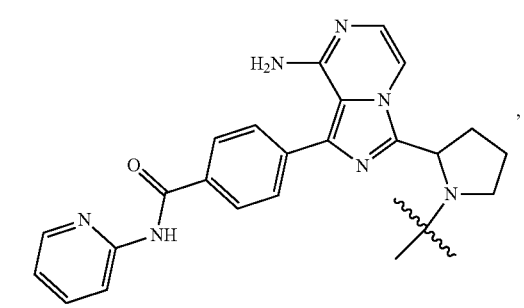
or
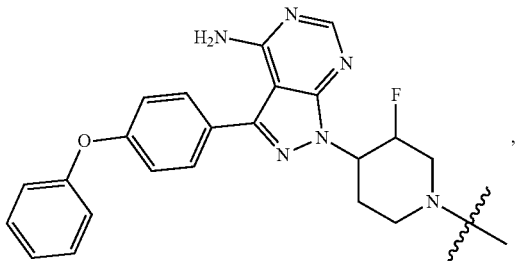
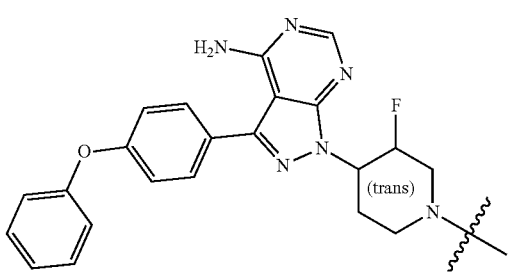
(trans)
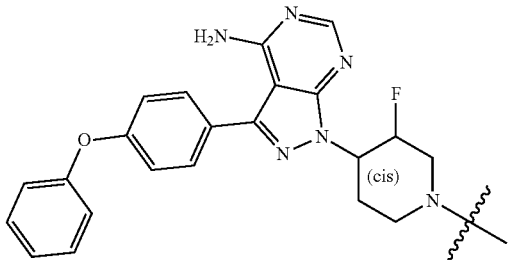
(cis)
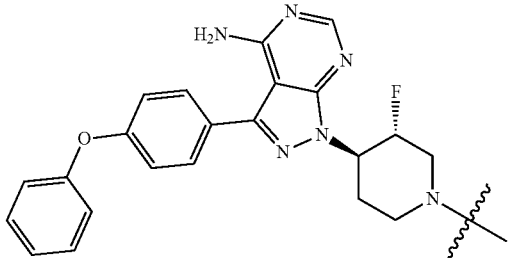
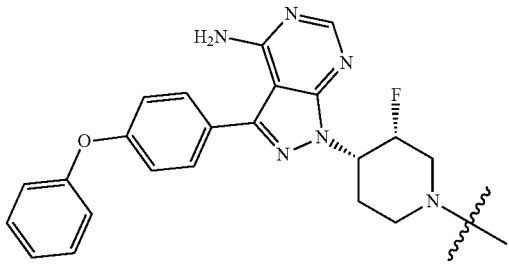
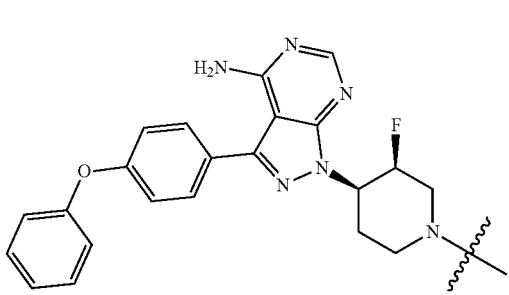

-continued
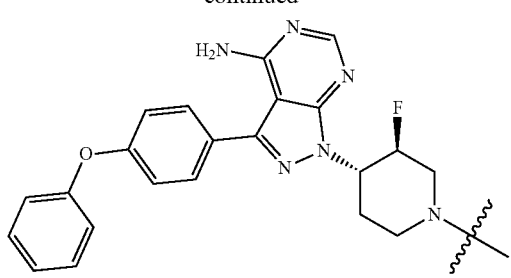
,
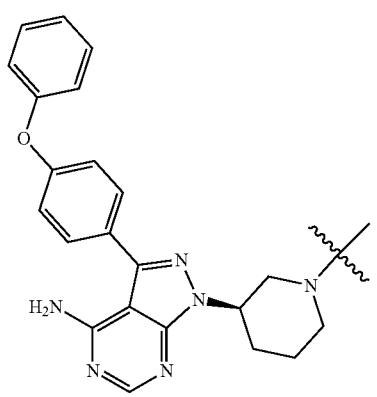
,
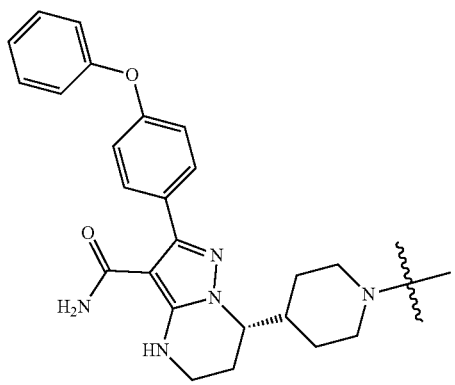
or
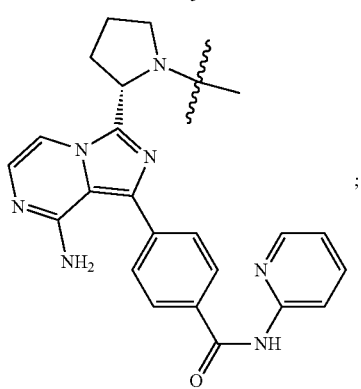
;
Cy1, Cy2, and Cy3 are each independently selected from one of the following substituted or unsubstituted groups:
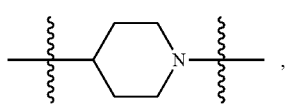
,
-continued
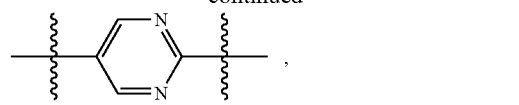
,
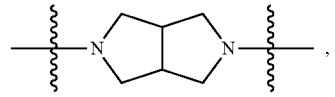 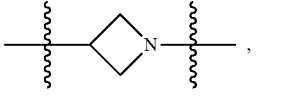 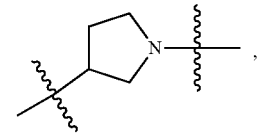
,
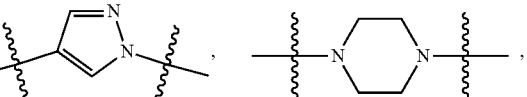
,
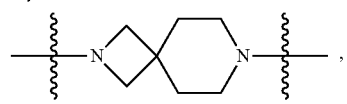
,
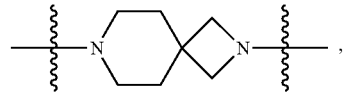
,
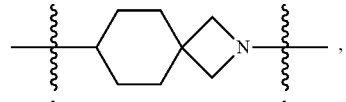
,
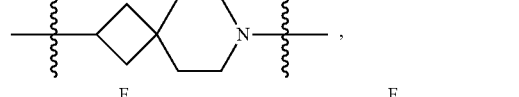
,
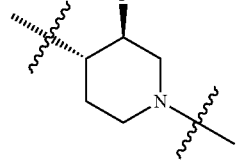 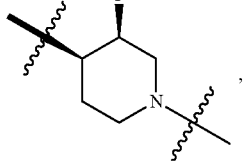
,
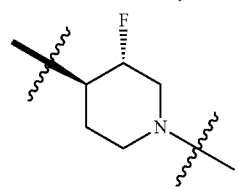 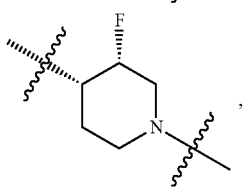
,
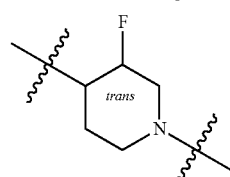 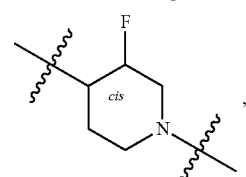
,
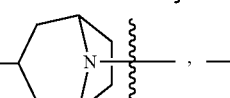 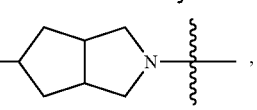
,
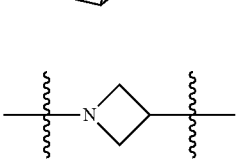 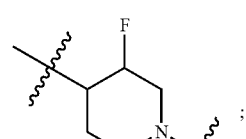
,
 or 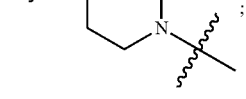
;

K is selected from
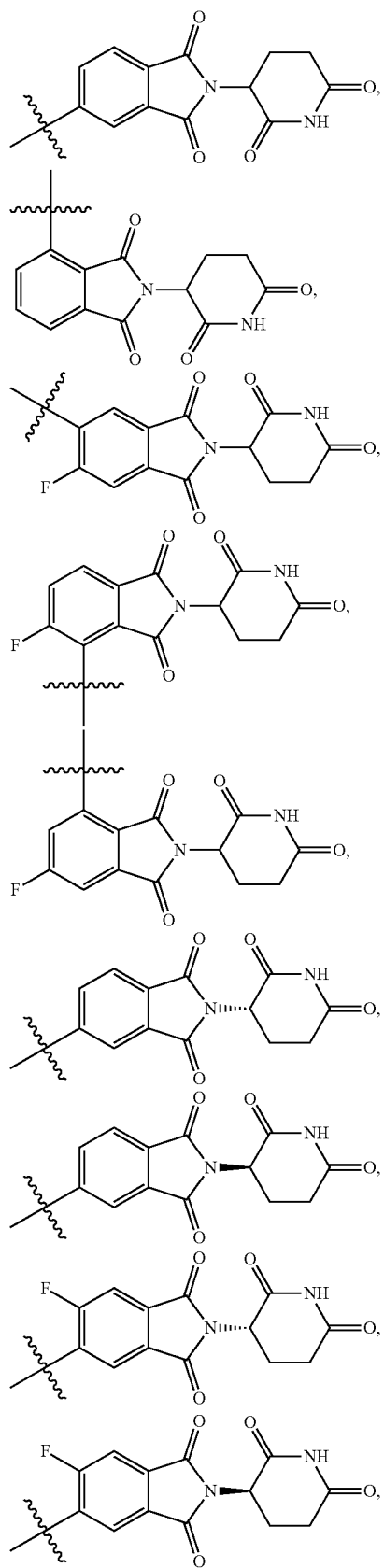
-continued
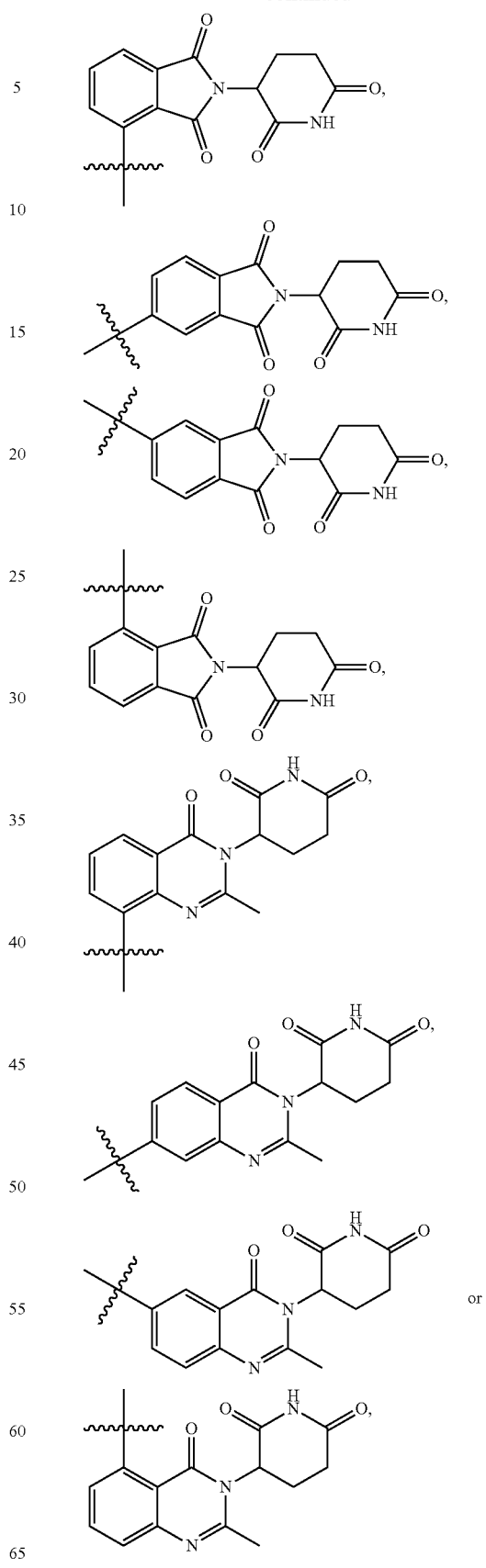
or preferably
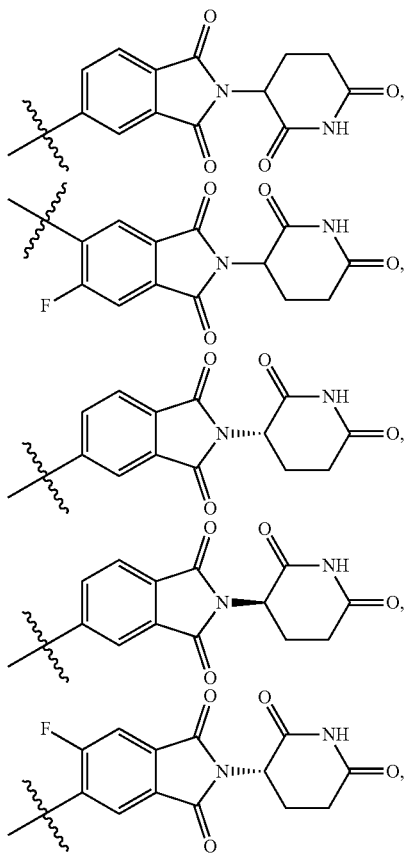
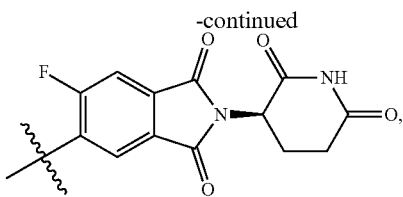
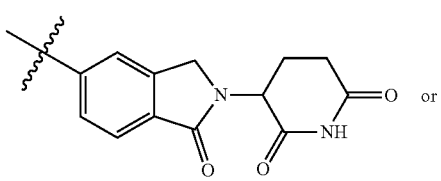
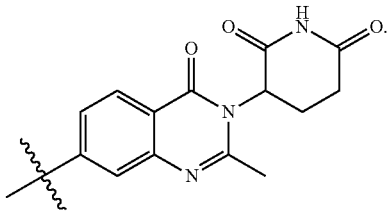
Some embodiments of the present disclosure relate to a compound represented by general formula (I) or a stereoisomer, a solvate, a prodrug, a metabolite, a pharmaceutically acceptable salt or a co-crystal thereof, wherein the compound is of the structure selected from one of:
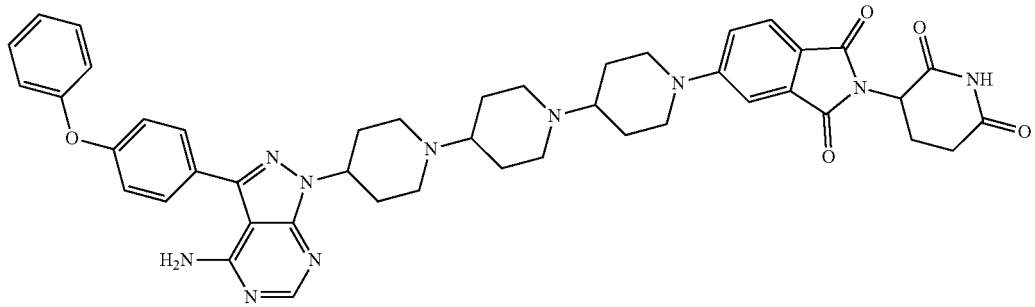
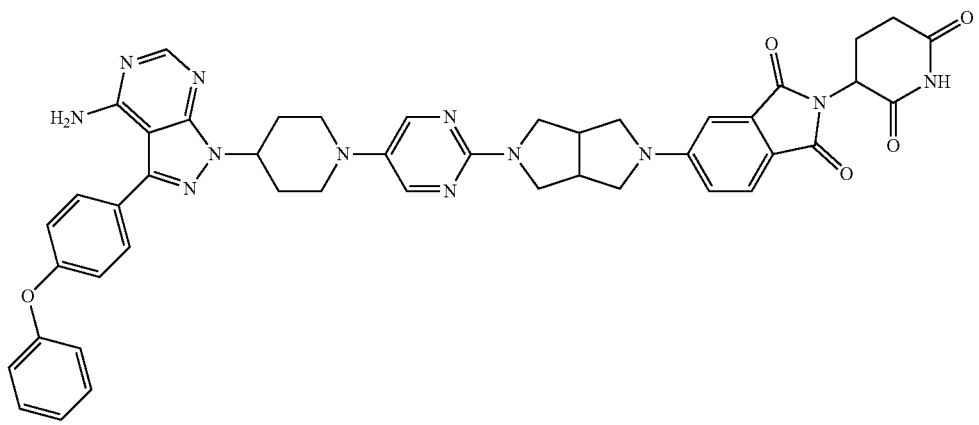

127
128
-continued
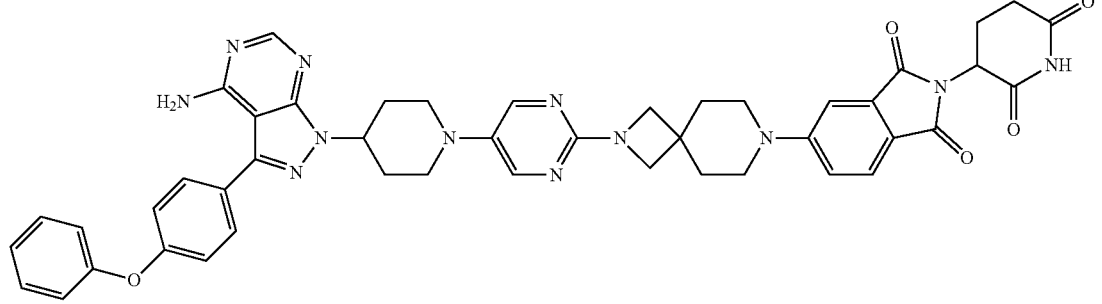
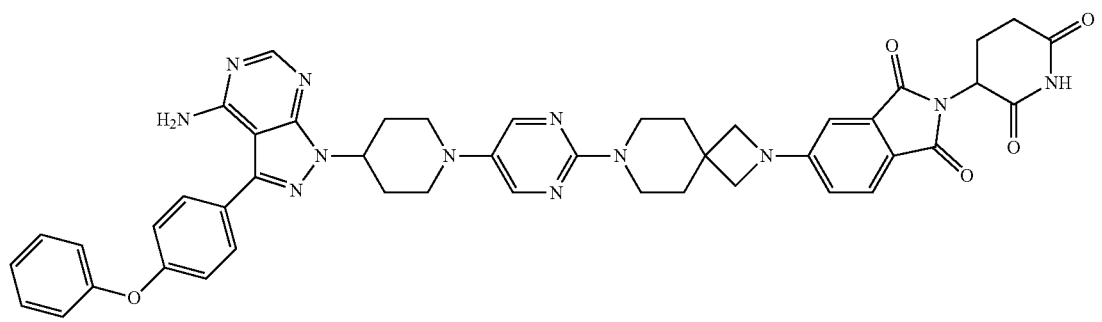
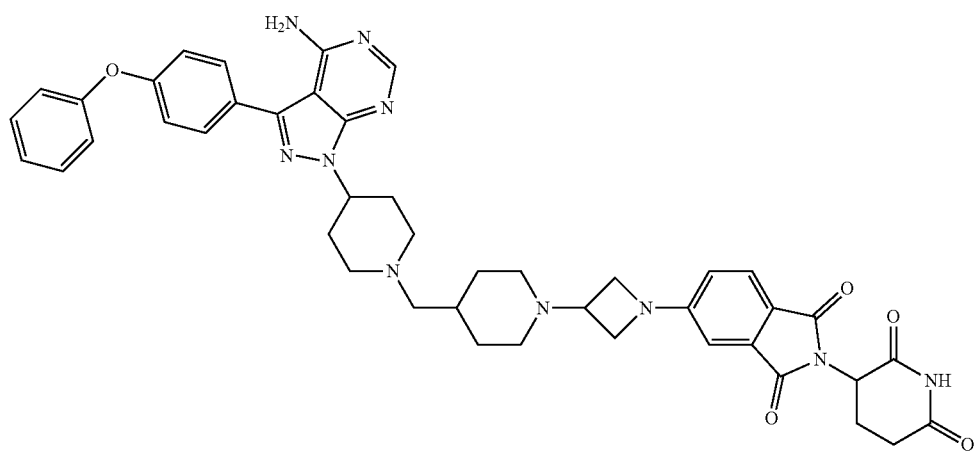
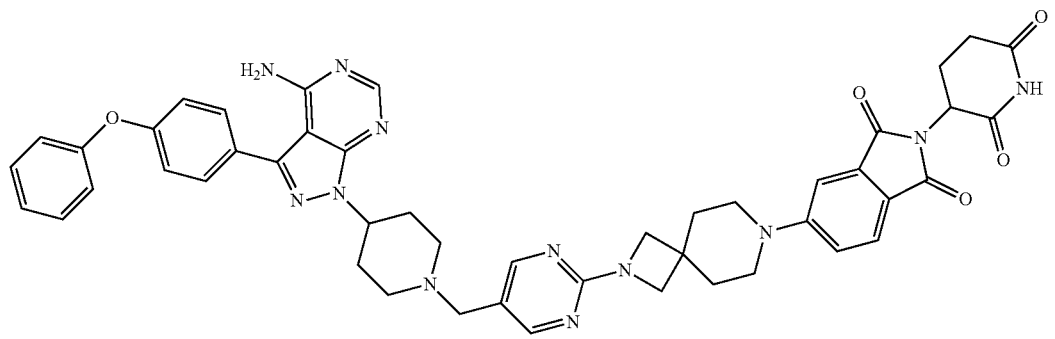

-continued
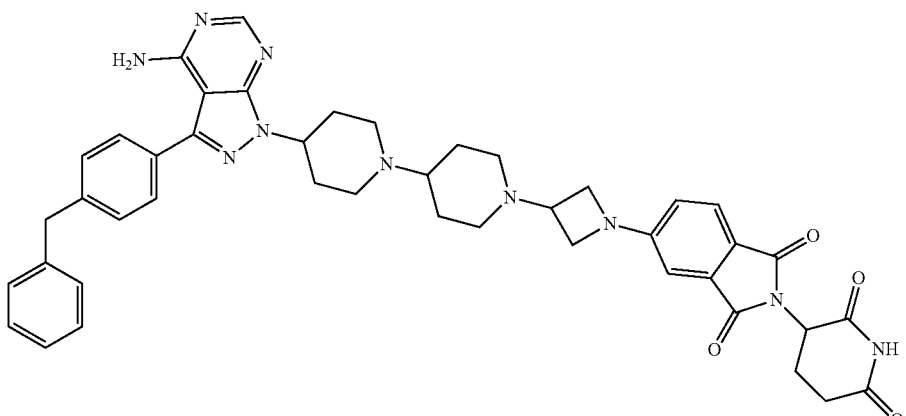
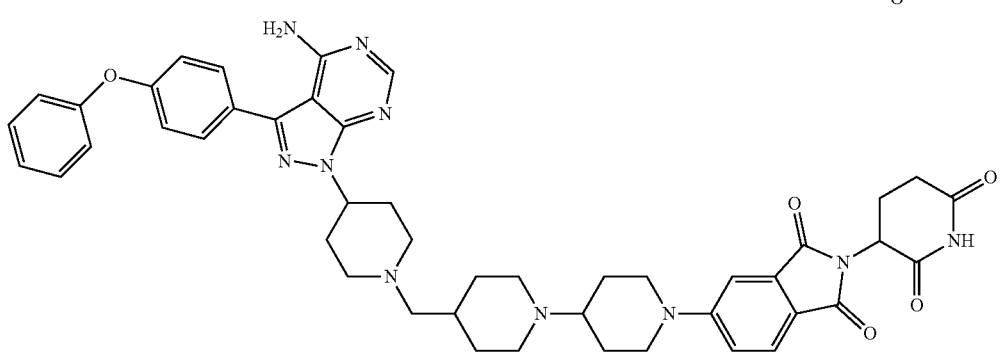
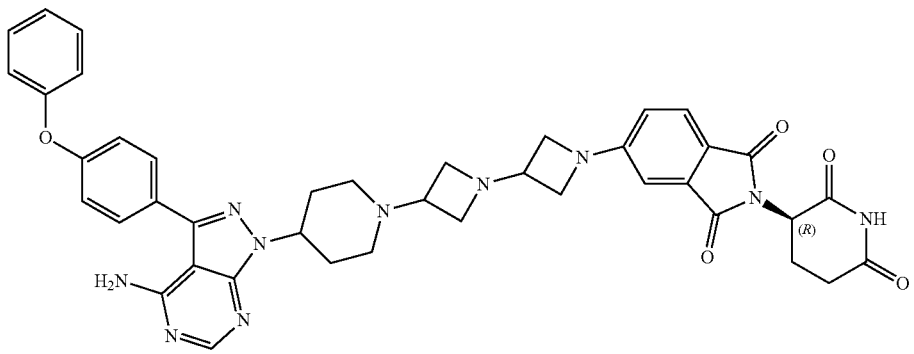
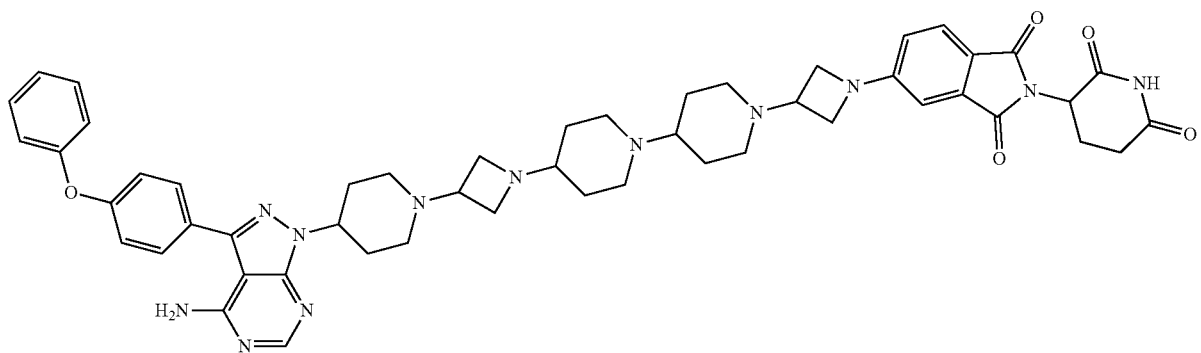

-continued
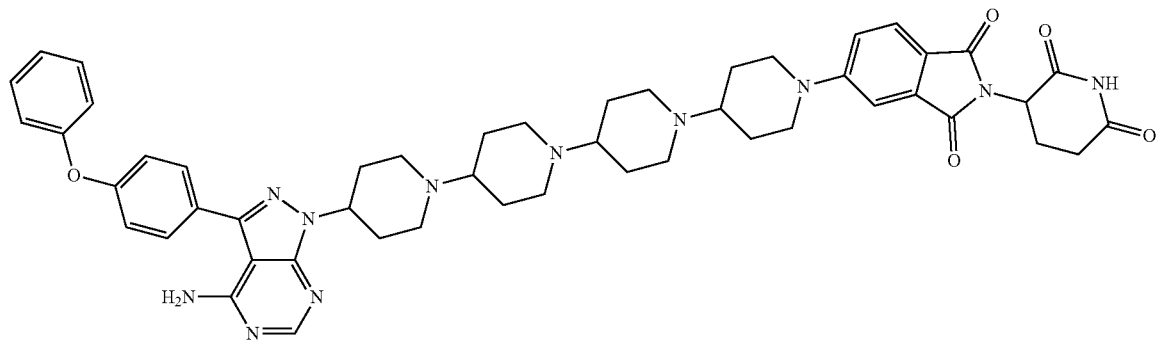
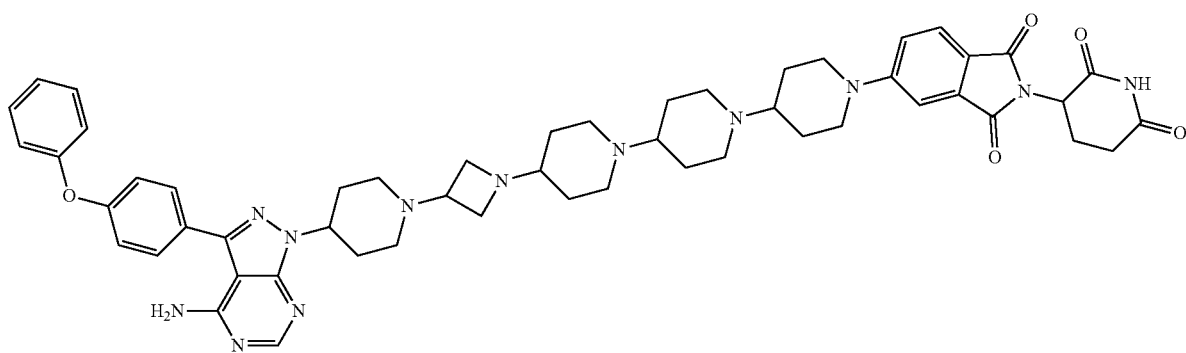
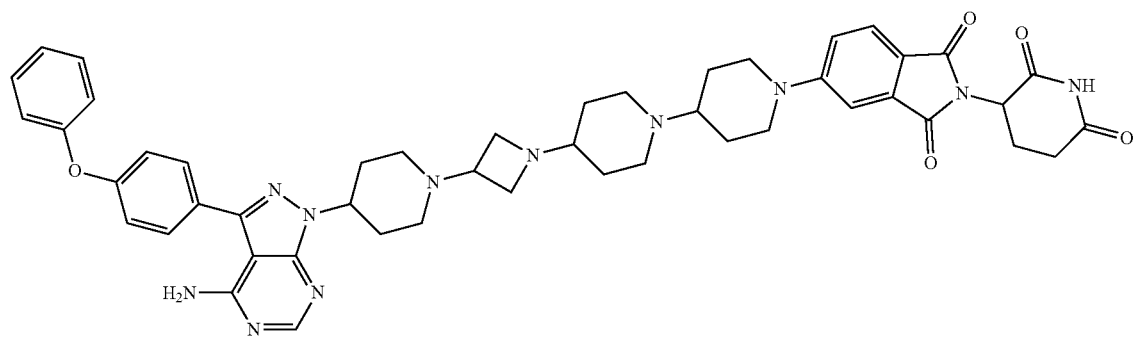
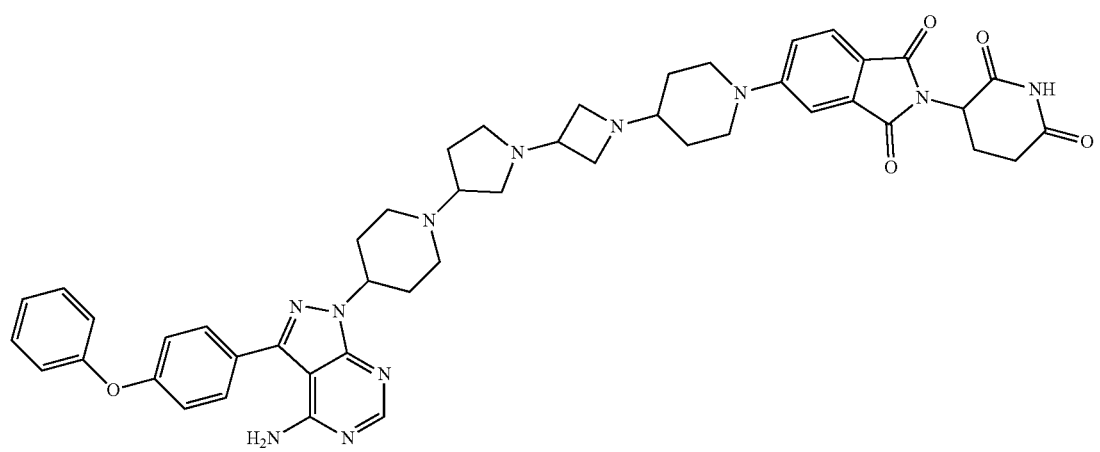

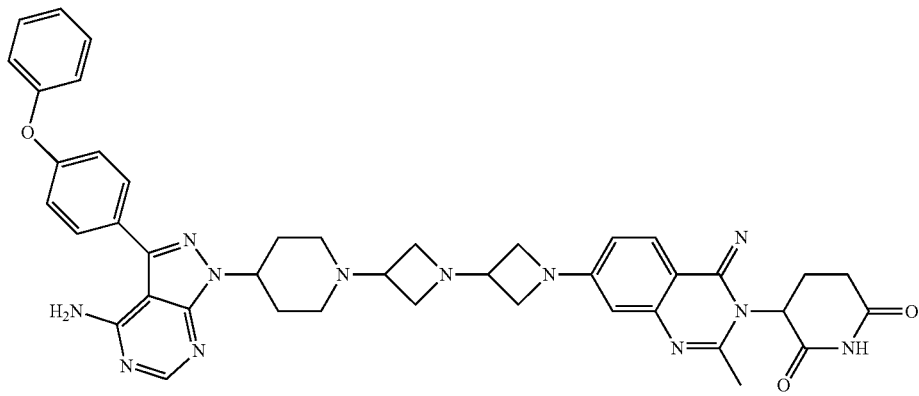
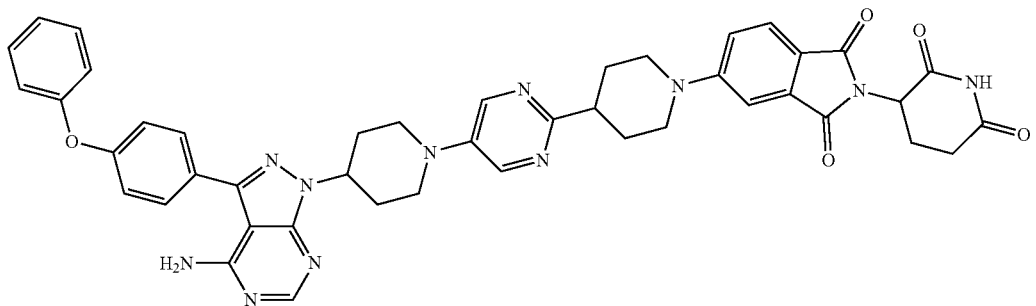
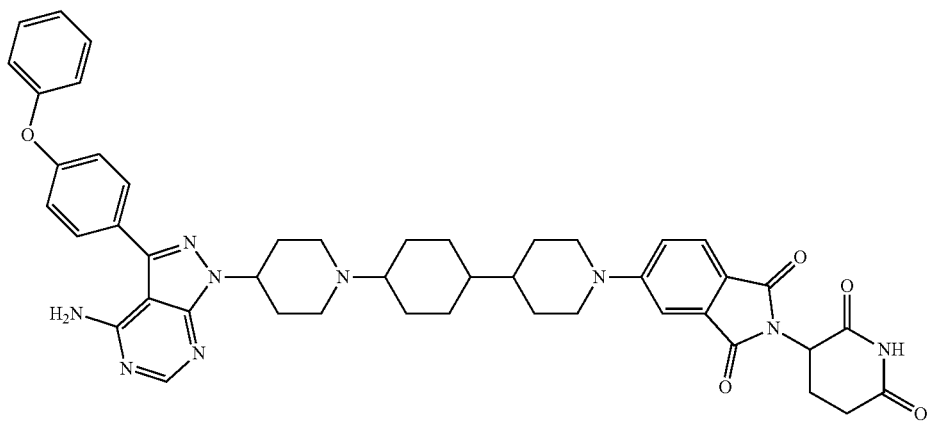
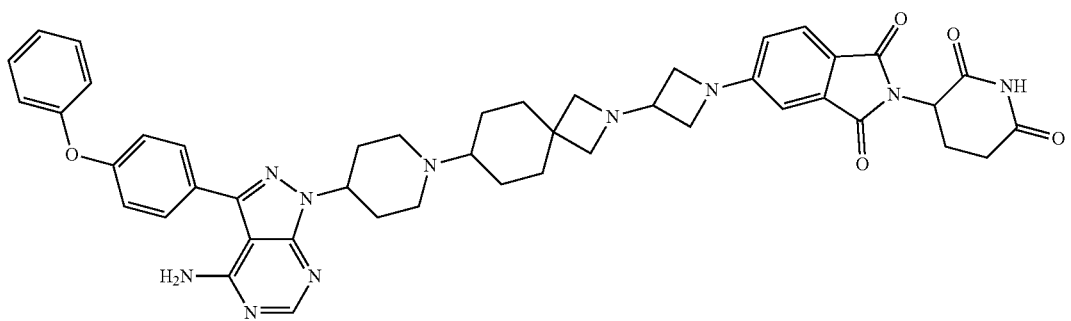

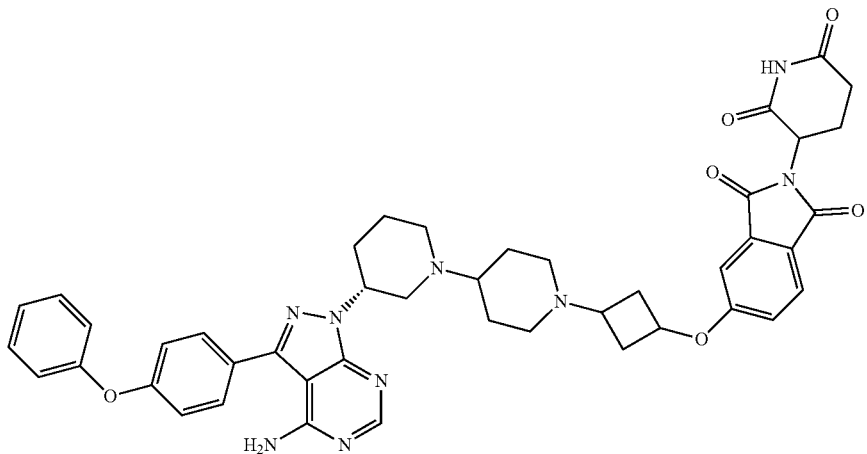
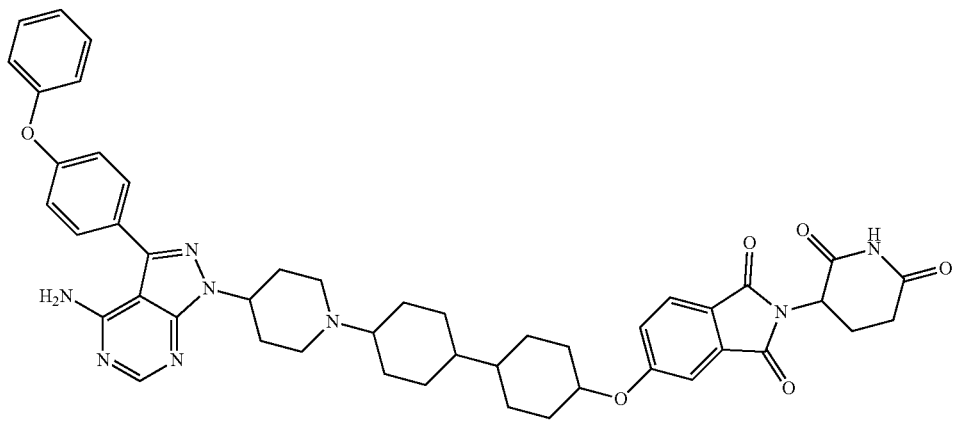
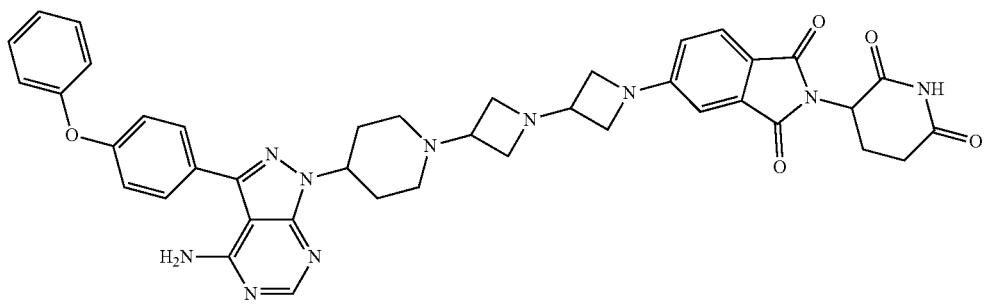
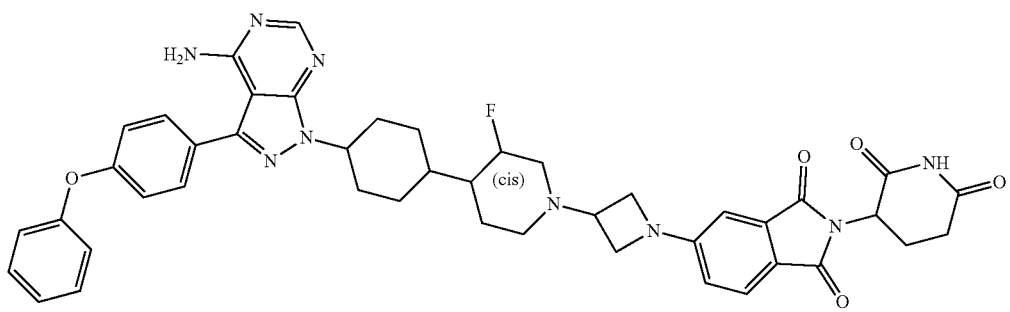

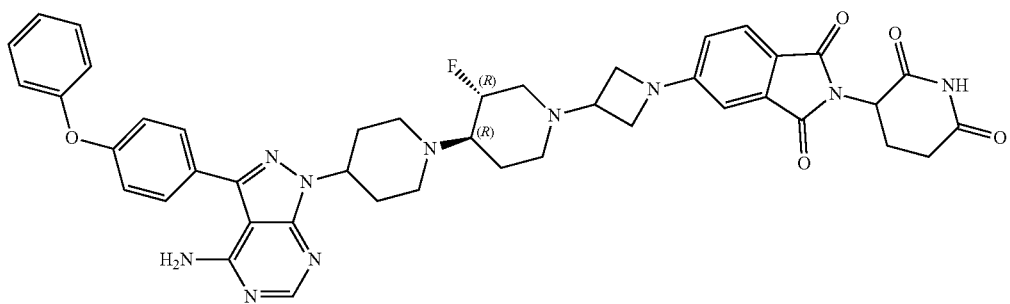
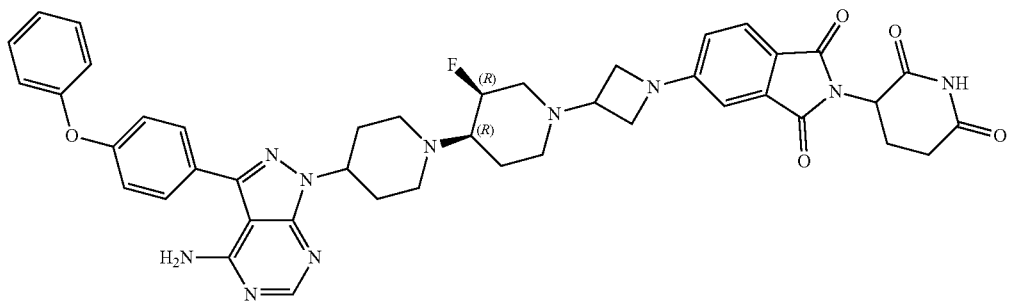
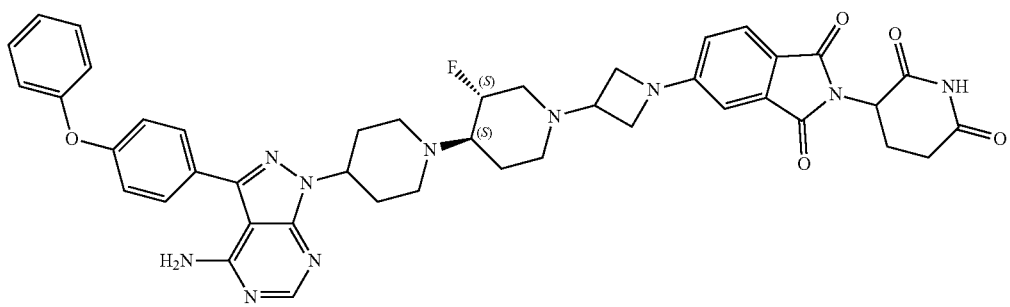
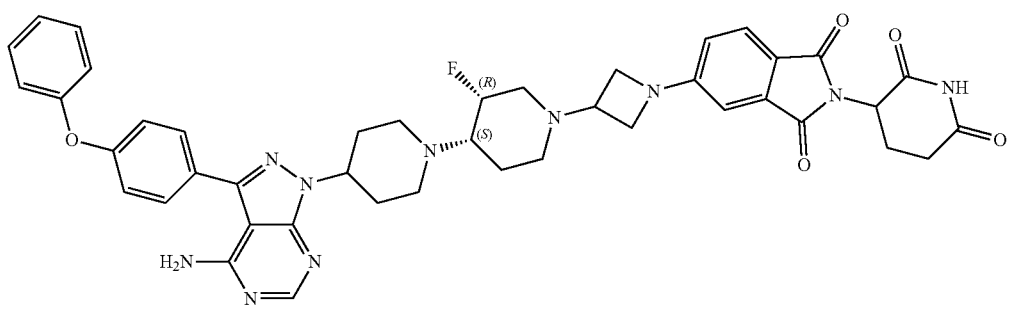
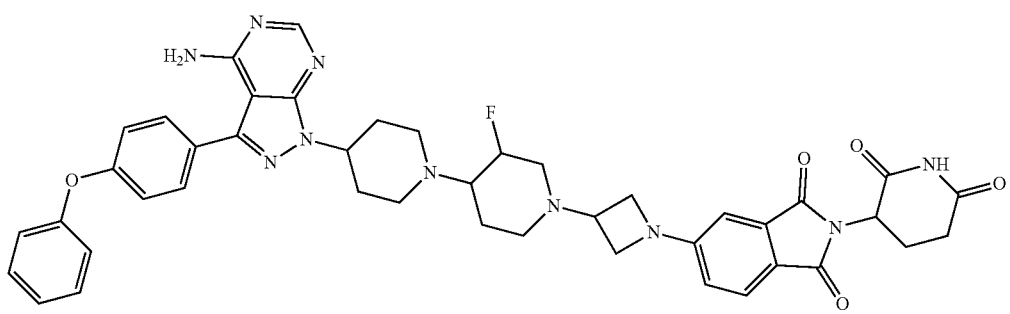

-continued
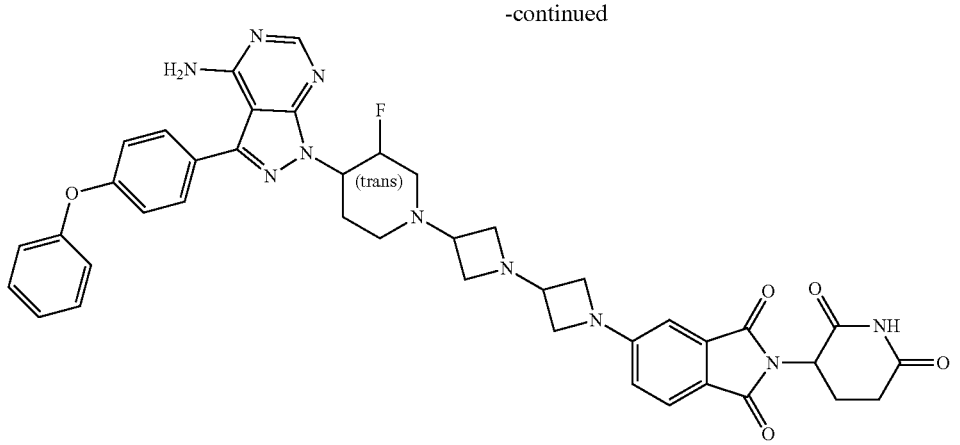
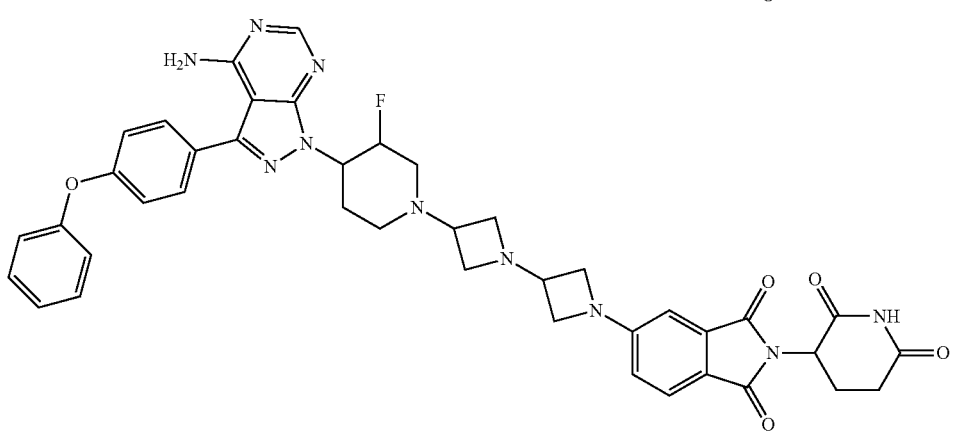
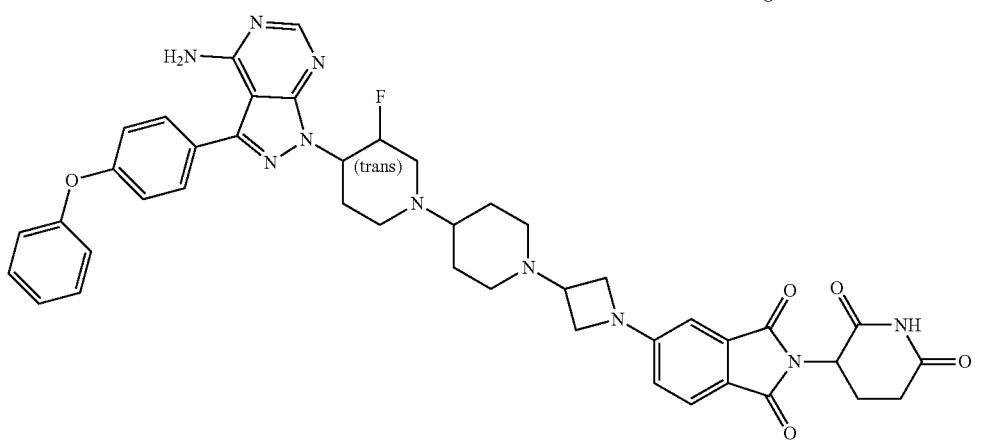
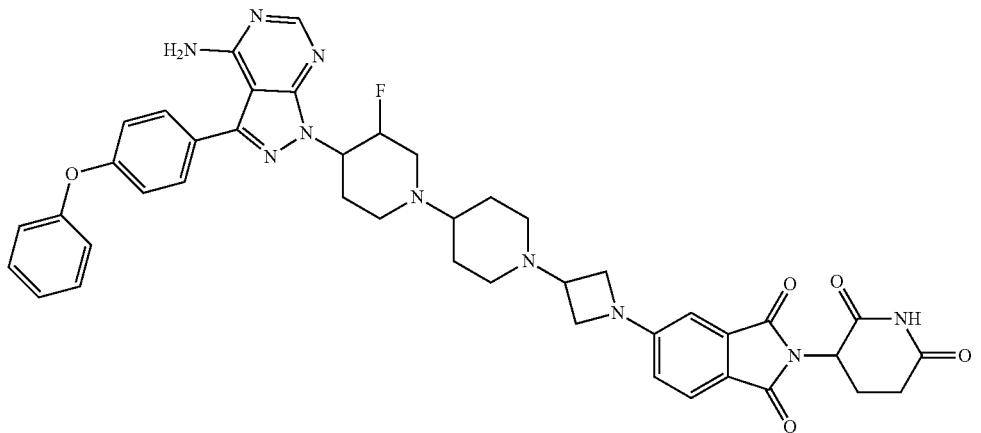

-continued
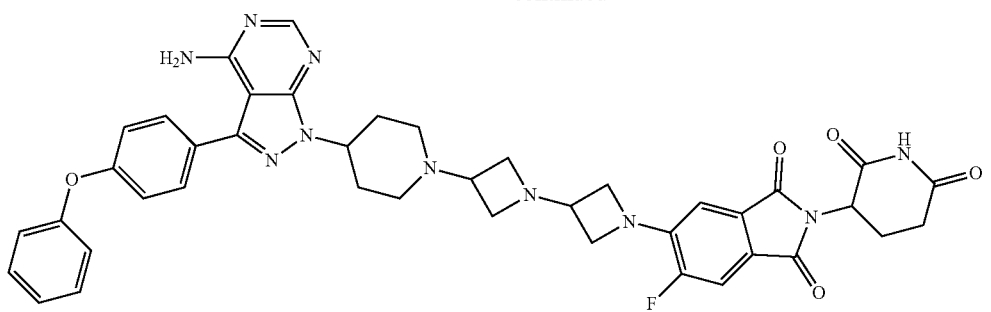
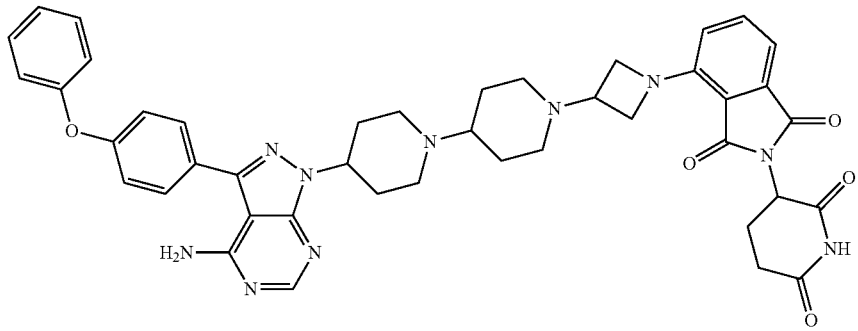
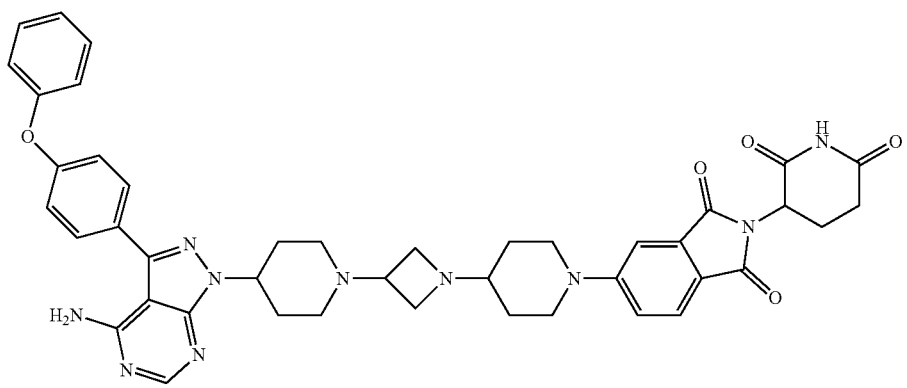
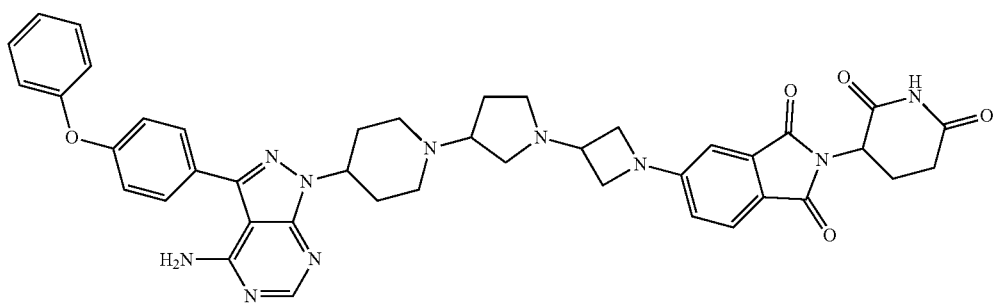
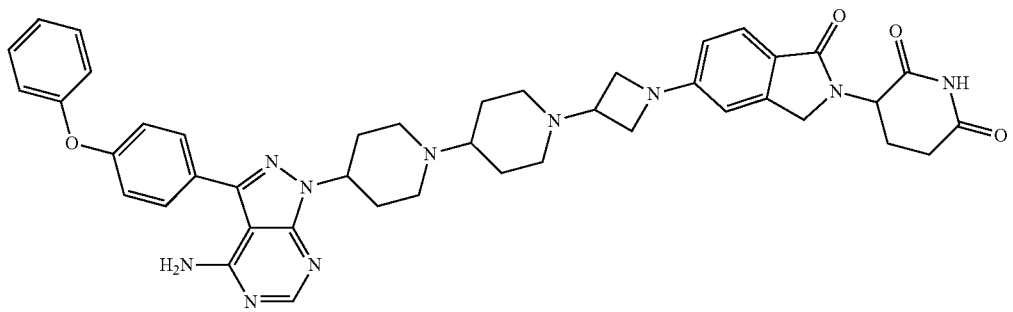

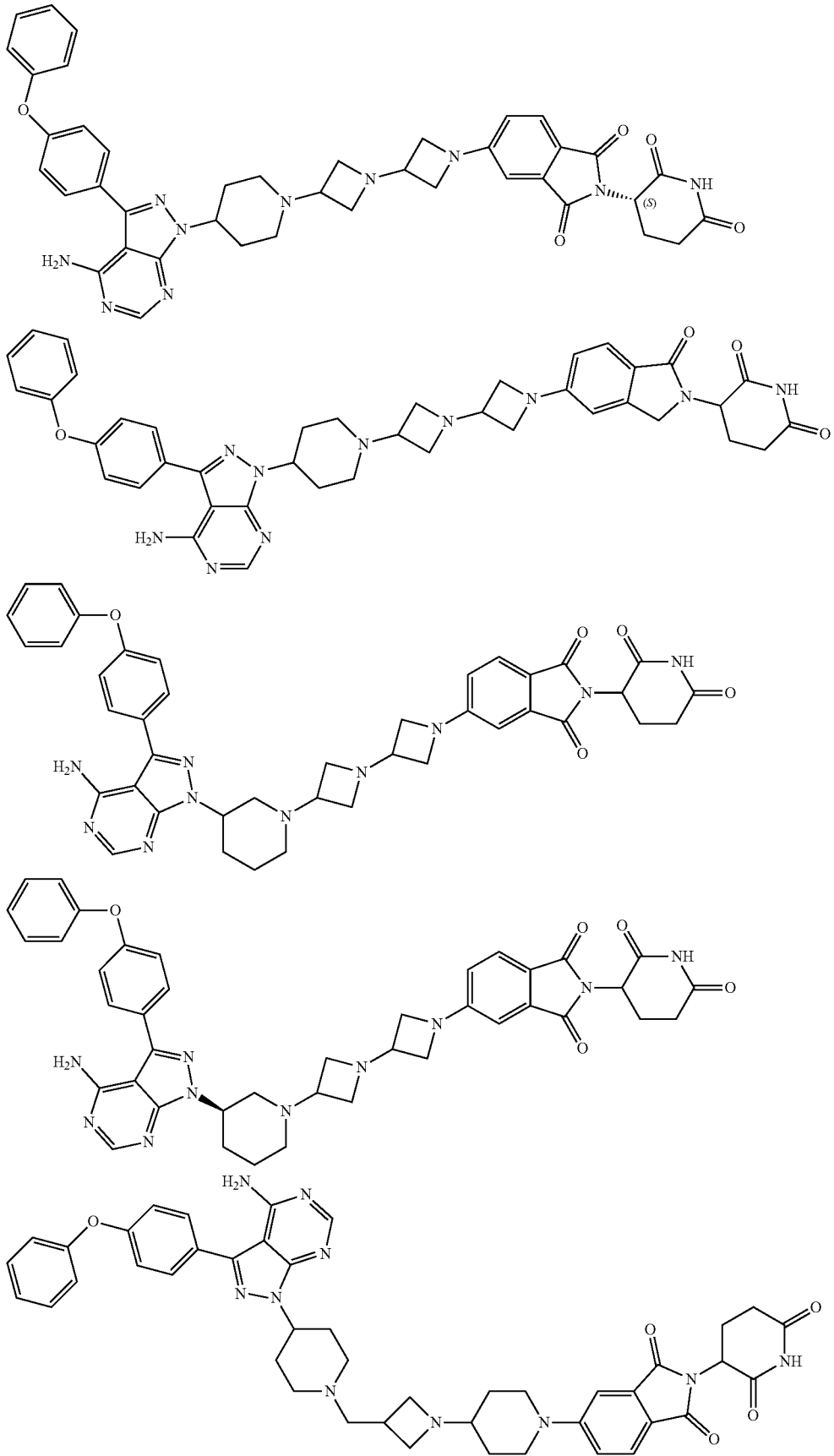

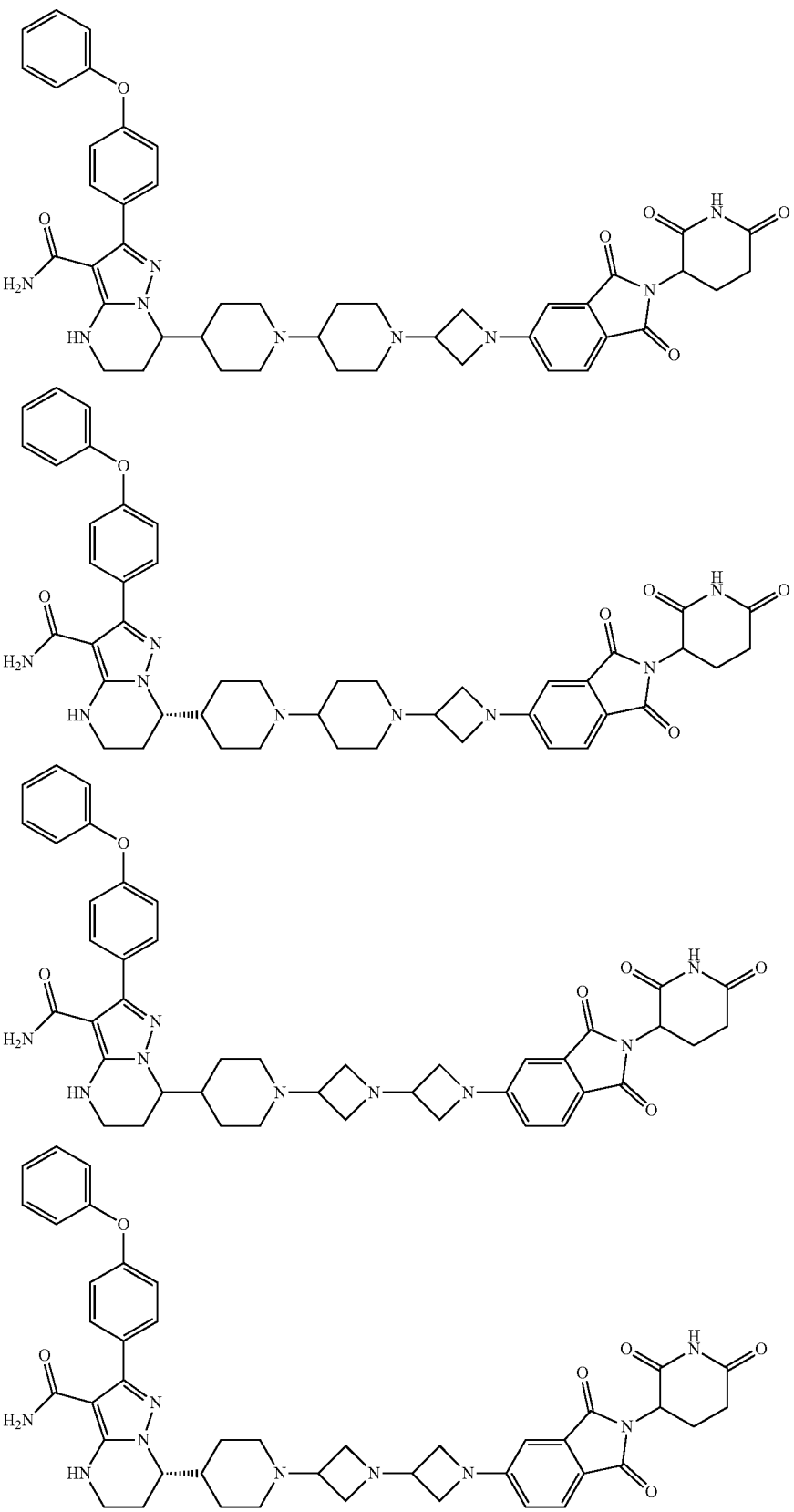

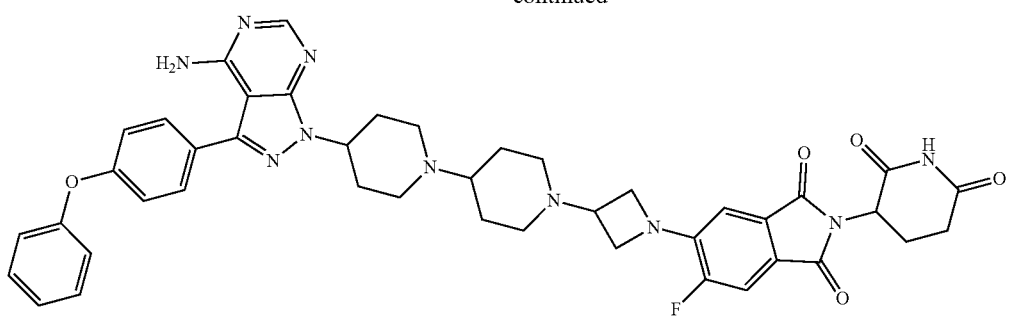
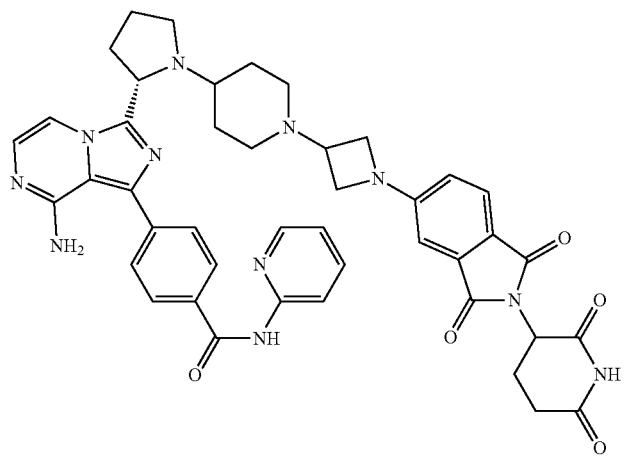
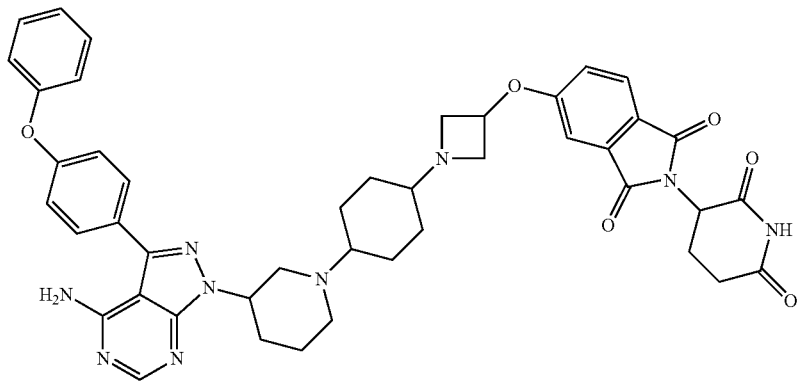
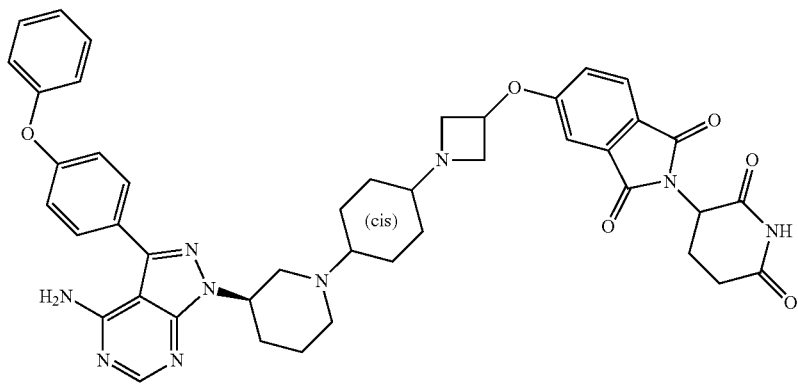

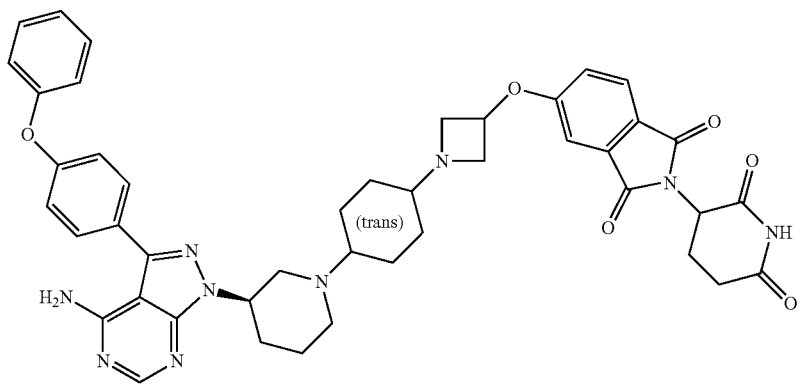
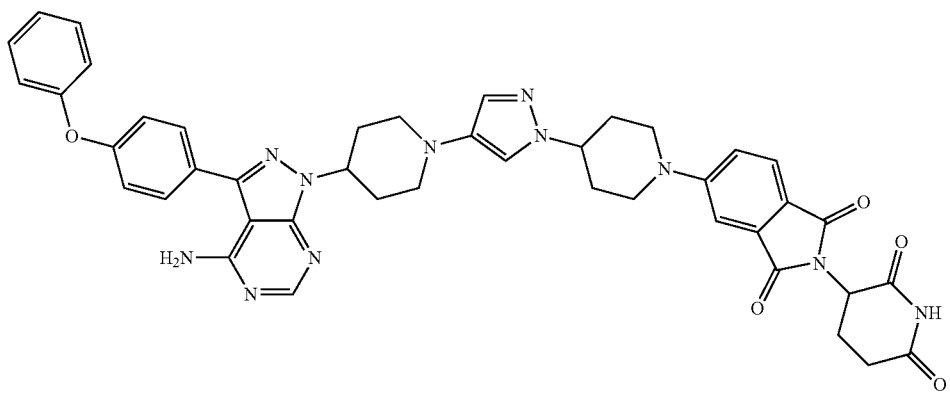
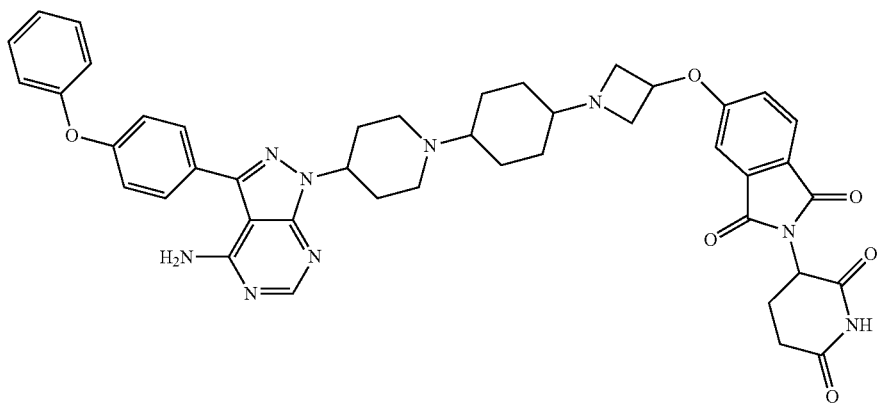
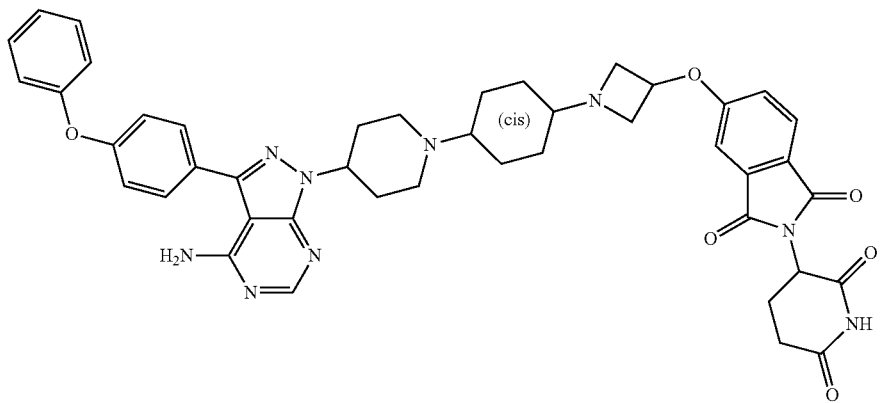

-continued
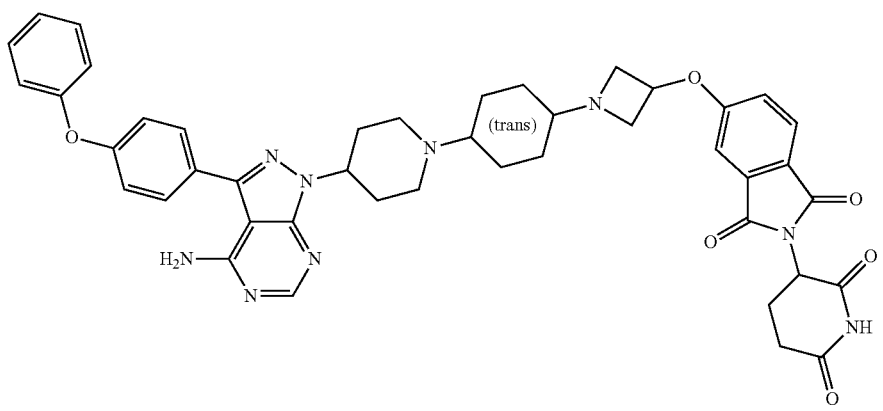
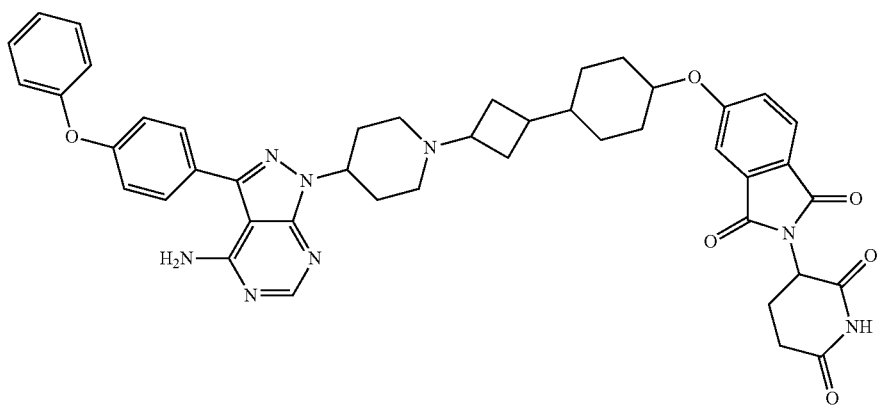
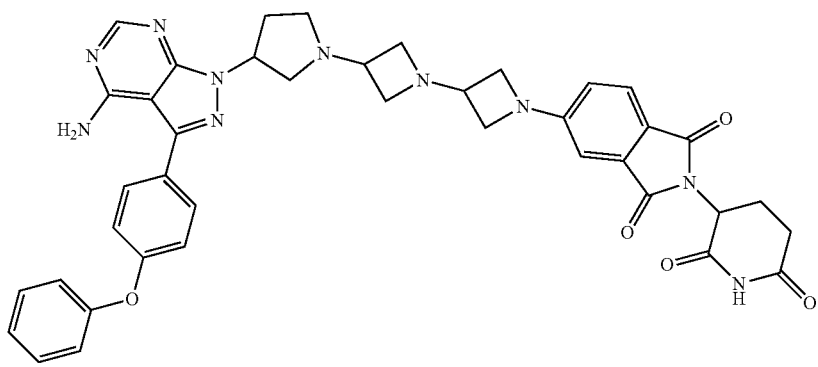
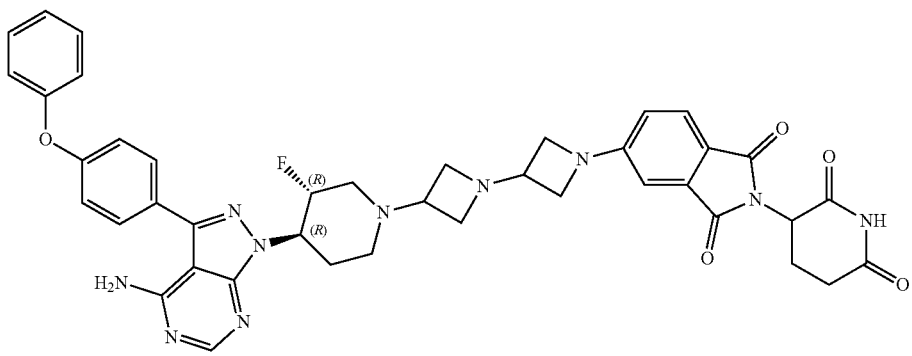

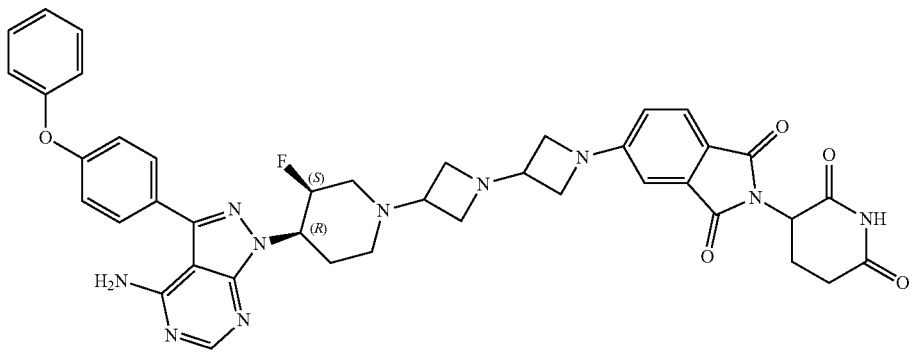
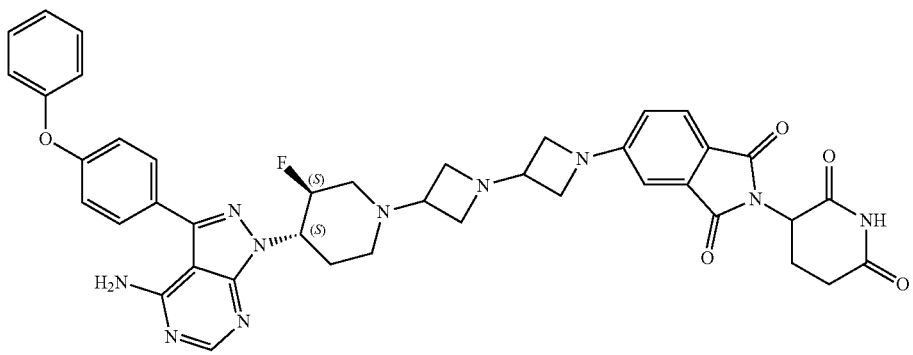
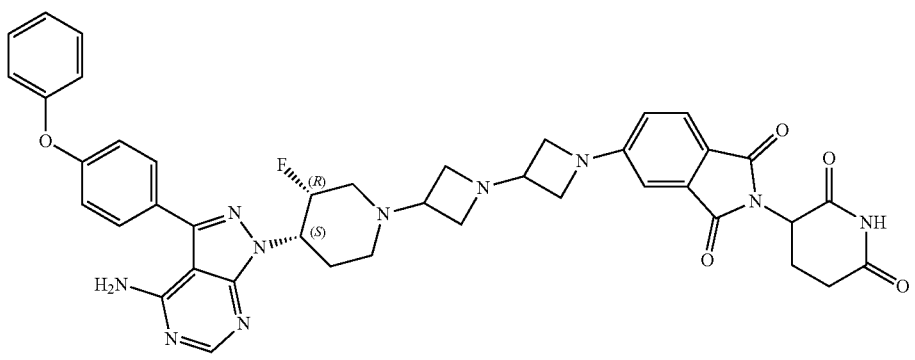
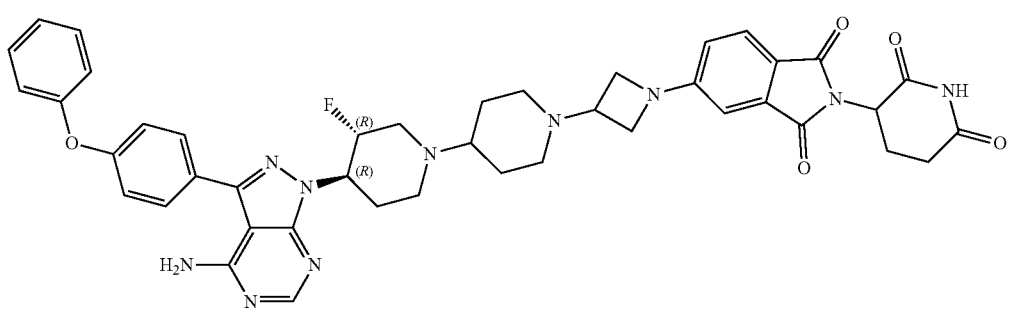
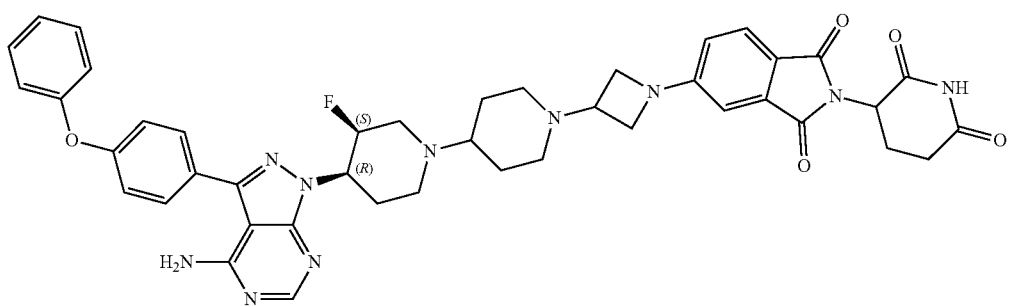

-continued
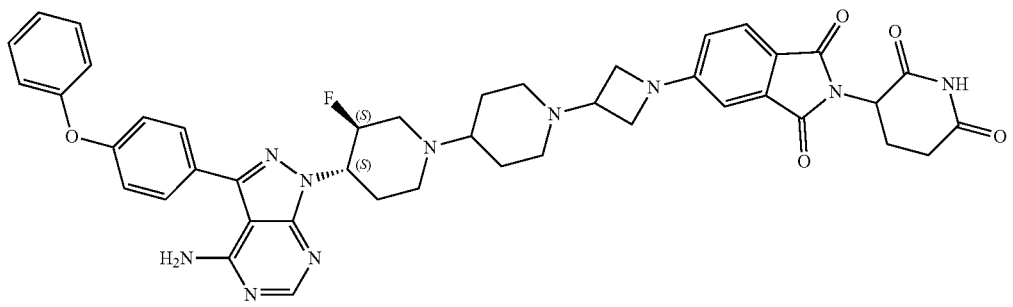
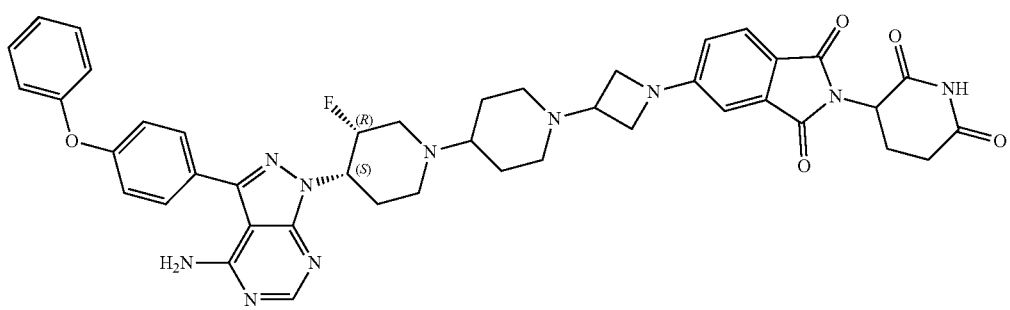
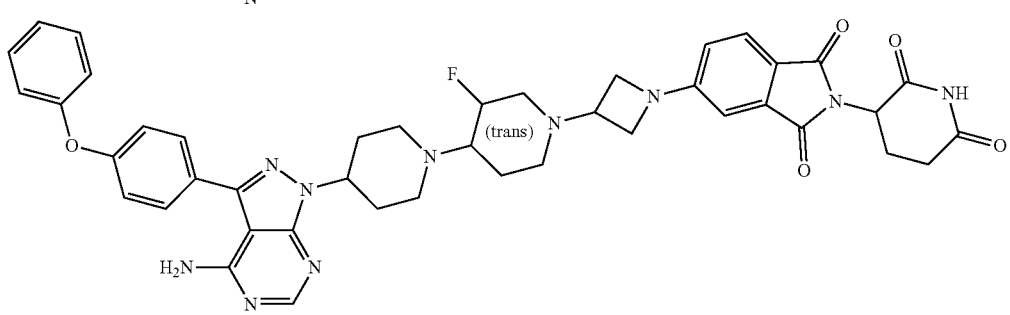
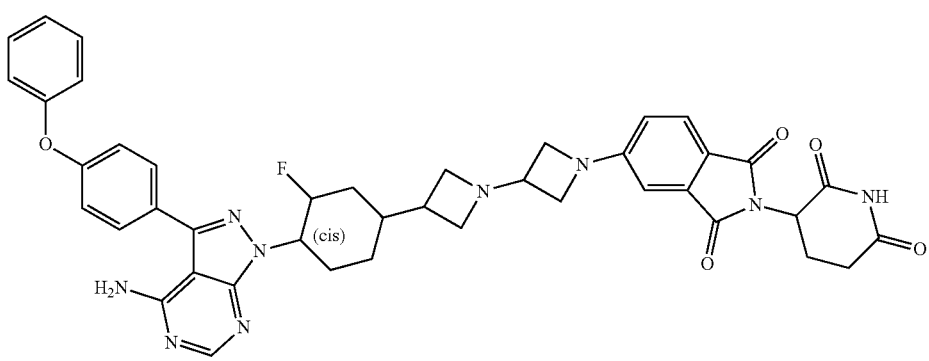
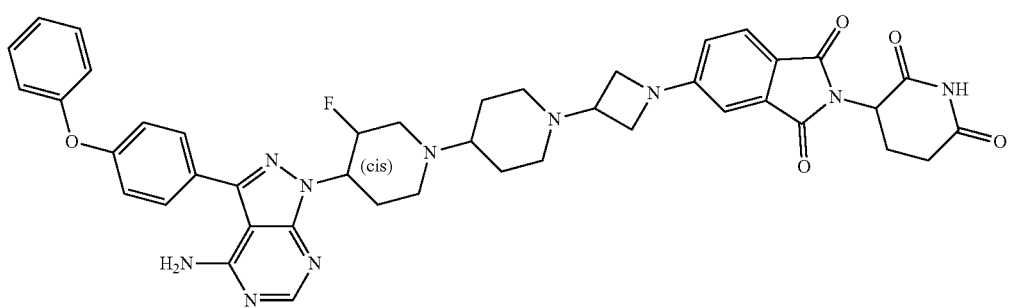

-continued
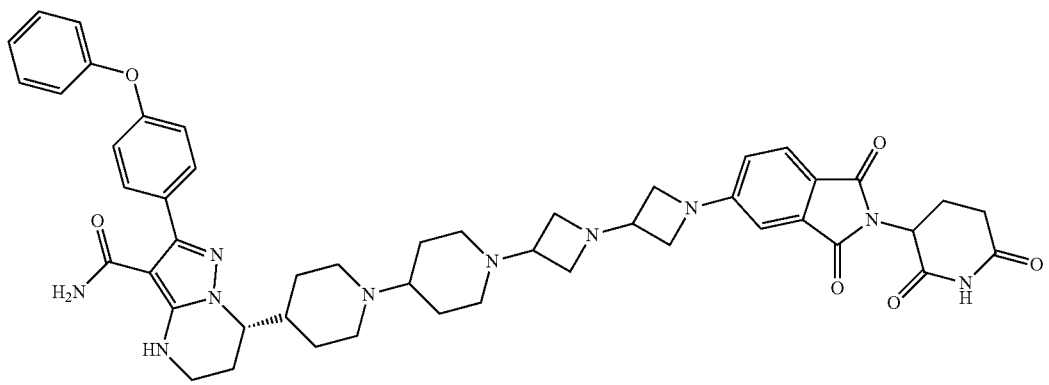
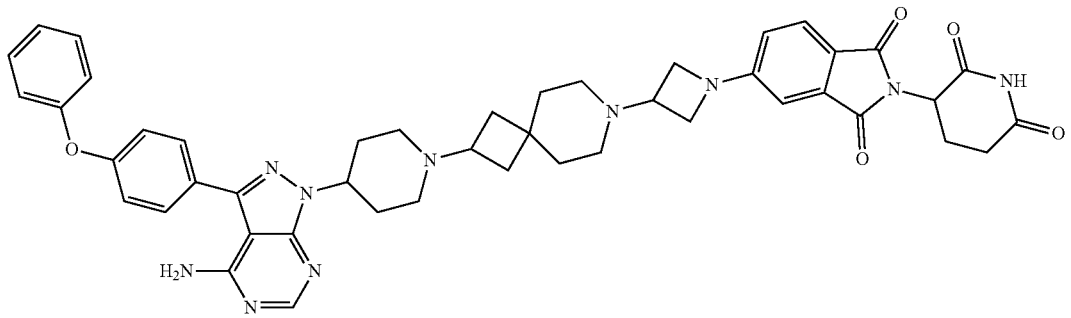
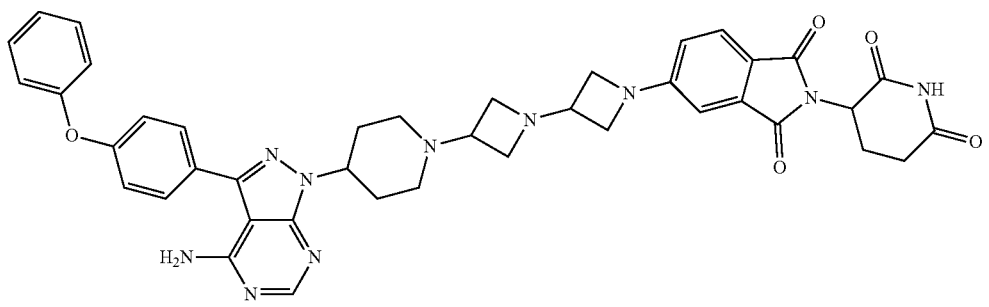
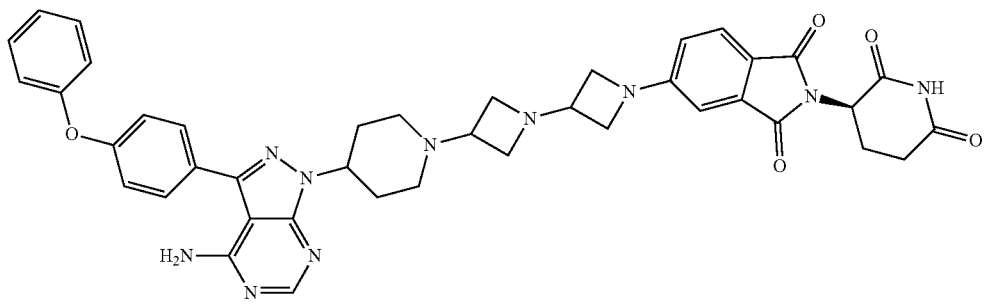
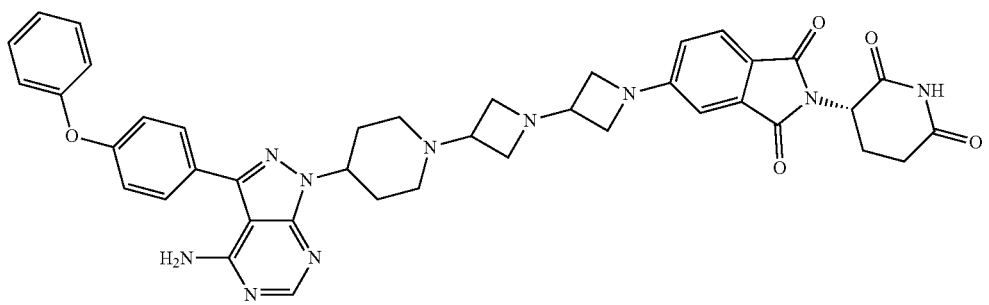

-continued
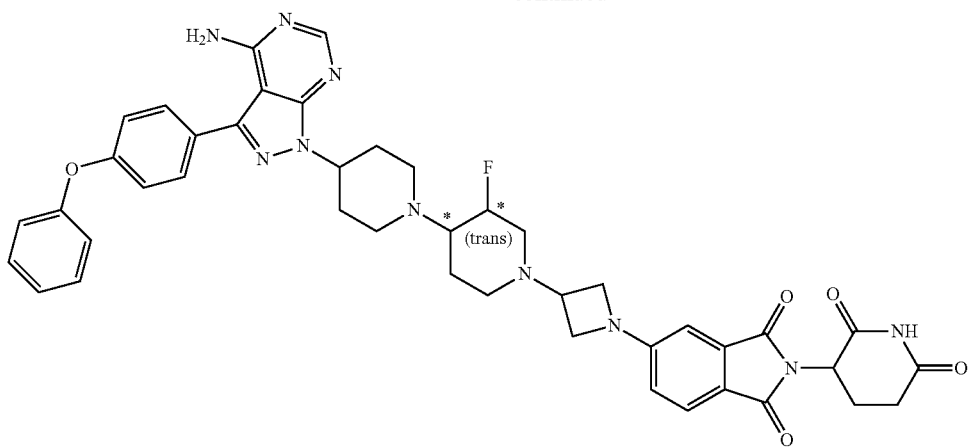
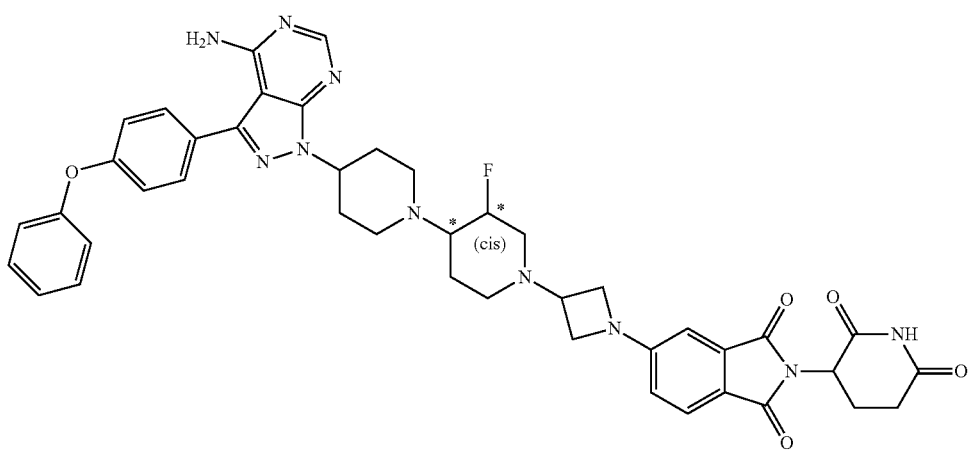
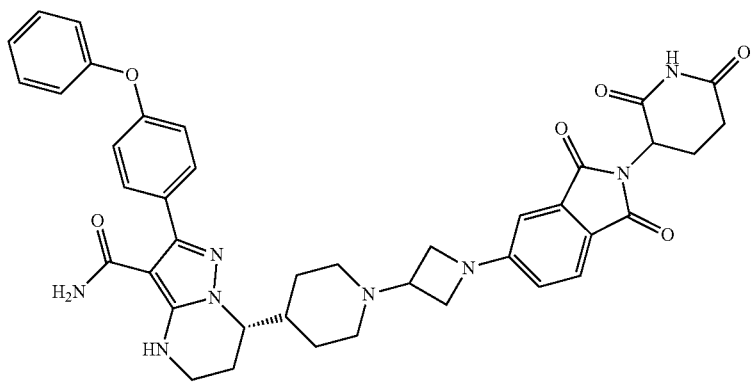
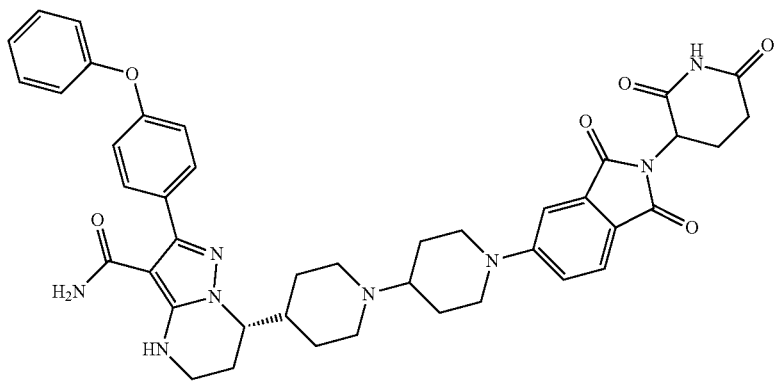

-continued
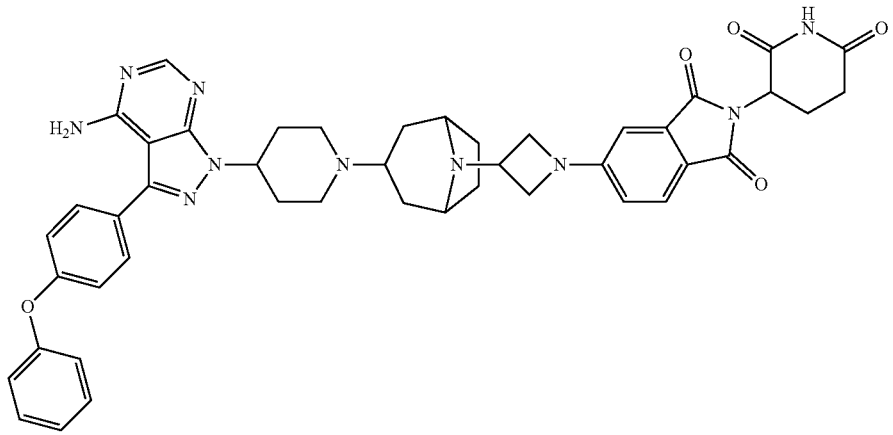
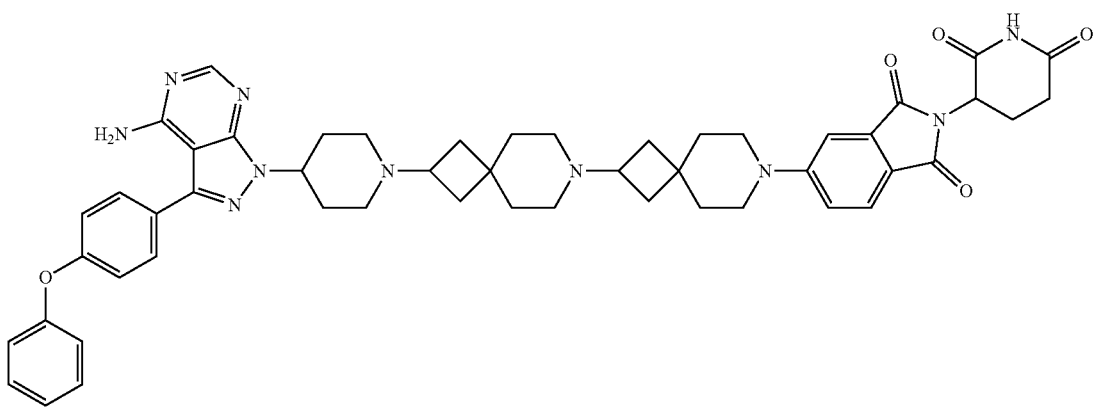
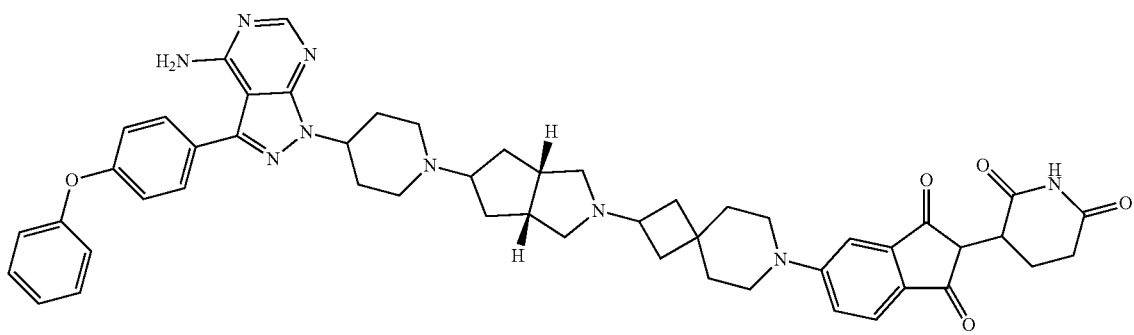
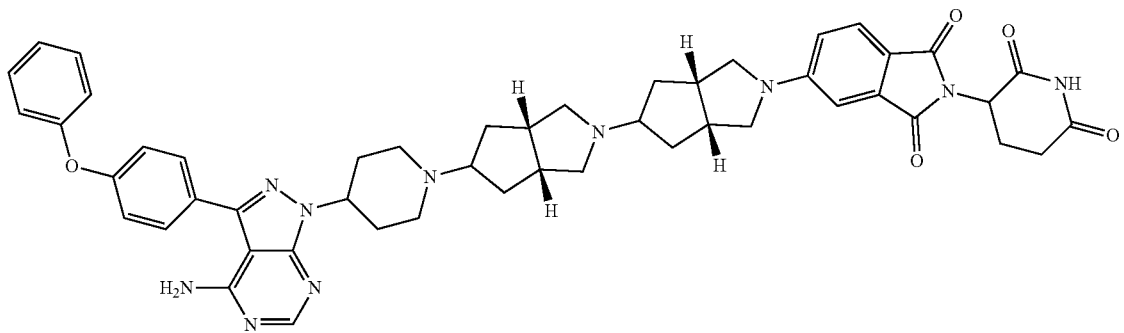

163
-continued
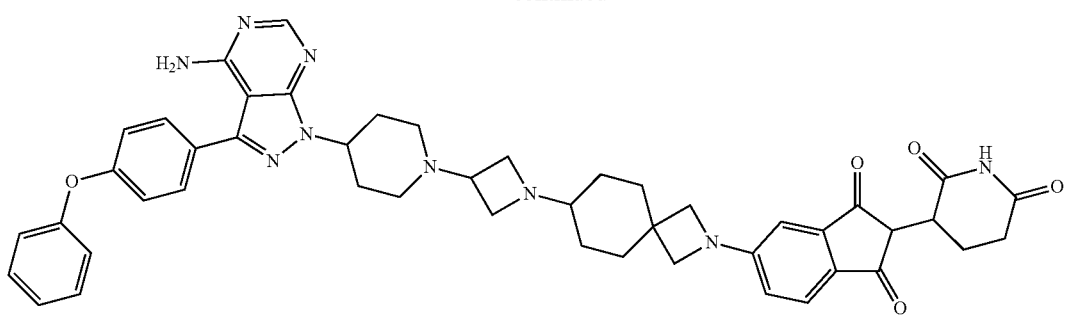
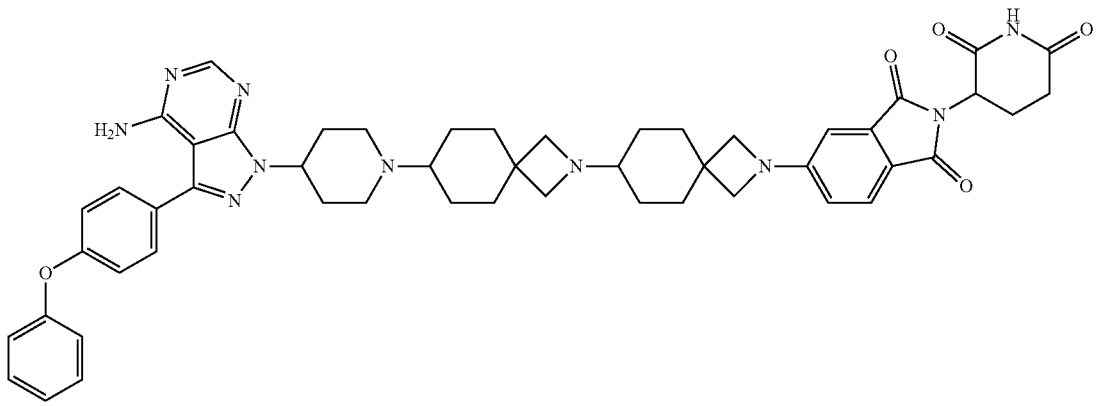
164
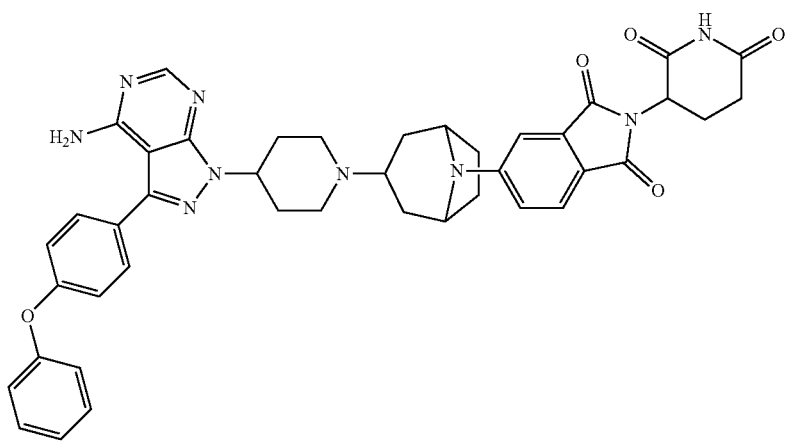
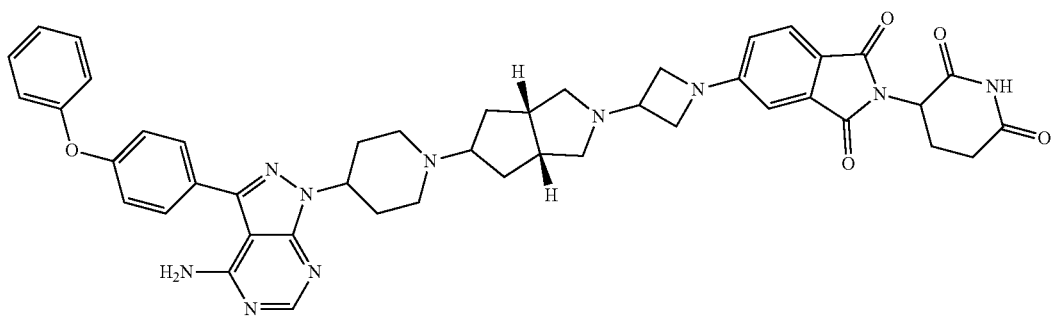

-continued
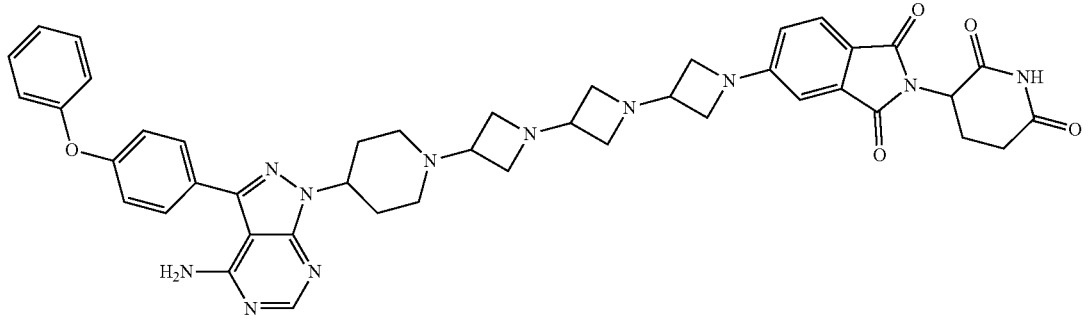
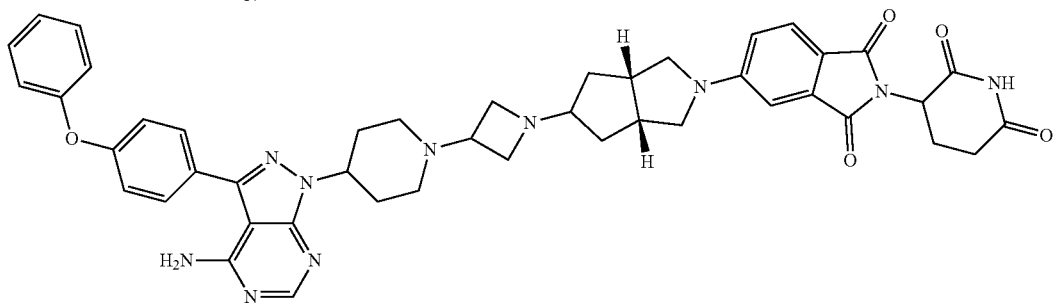
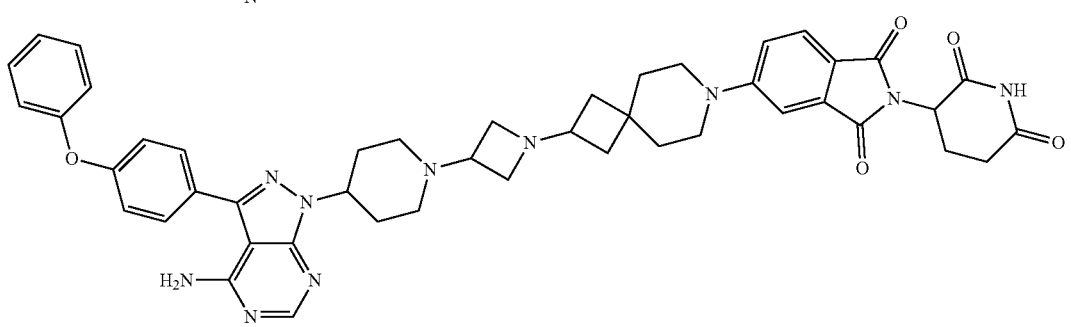
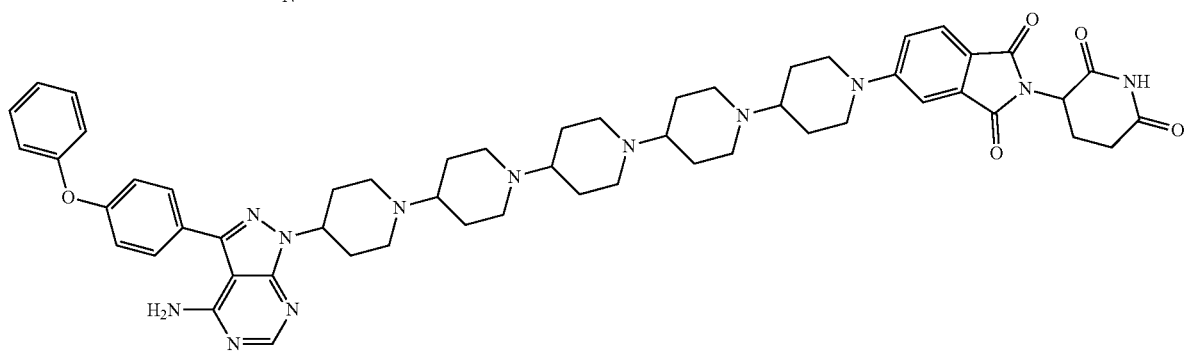
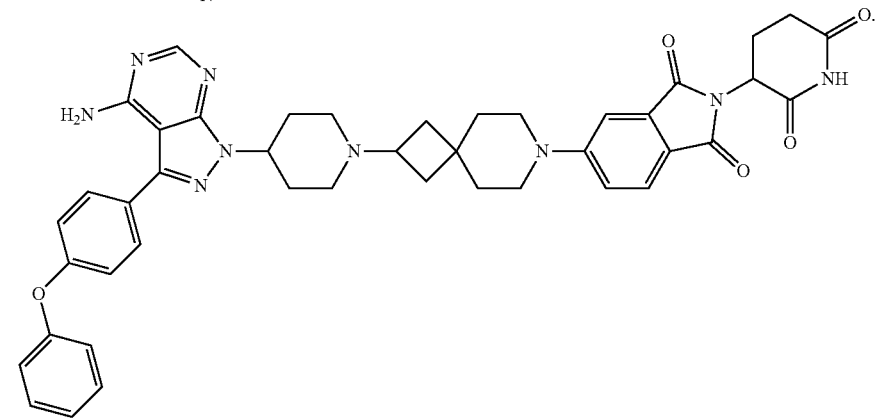

Some embodiments of the present disclosure relate to a compound represented by general formula (I) or a stereoisomer, a solvate, a prodrug, a metabolite, a pharmaceutically acceptable salt or a co-crystal thereof, wherein the salt is selected from trifluoroacetate.

The present disclosure relates to a pharmaceutical composition, comprising the compound described in the present disclosure or a stereoisomer, a solvate, a prodrug, a metabolite, a pharmaceutically acceptable salt or a co-crystal thereof, and a pharmaceutically acceptable carrier.

The present disclosure relates to the use of the compound described in the present disclosure or a stereoisomer, a solvate, a prodrug, a metabolite, a pharmaceutically acceptable salt or a co-crystal thereof in the manufacture of a medicament for treating diseases related to BTK activity or expression level.

The present disclosure relates to the use of the compound described in the present disclosure or a stereoisomer, a solvate, a prodrug, a metabolite, a pharmaceutically acceptable salt or a co-crystal thereof in the manufacture of a medicament for treating diseases related to the inhibition or degradation of BTK.

The present disclosure relates to the use of the compound described in the present disclosure or a stereoisomer, a solvate, a prodrug, a metabolite, a pharmaceutically acceptable salt or a co-crystal thereof, and the disease is selected from tumors or autoimmune diseases.

The present disclosure relates to the use of the compound described in the present disclosure or a stereoisomer, a solvate, a prodrug, a metabolite, a pharmaceutically acceptable salt or a co-crystal thereof, the tumor is selected from non-Hodgkin's lymphoma, chronic lymphocytic leukemia, mantle cell lymphoma, B cell lymphoma, and the autoimmune disease is selected from rheumatoid arthritis or psoriasis.

Synthetic Method I

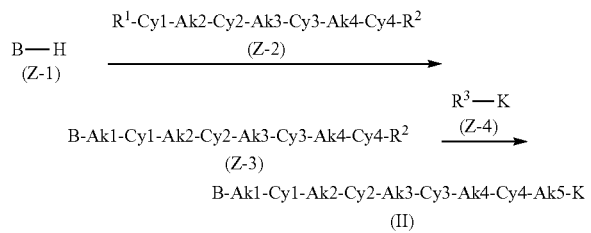

General formula (Z-1) and general formula (Z-2) are subjected to reductive amination, nucleophilic substitution reaction or coupling reaction to obtain the corresponding general formula (Z-3), and if the general formula (Z-3) has an amino protecting group at the reaction site, the amino protecting group is removed first, and then it is subjected to nucleophilic substitution reaction with general formula (Z-4) to obtain the corresponding general formula (II), namely, general formula (I), and the preparation of longer chains can be achieved by repeating the process in the first step above and removing the amino protecting group;

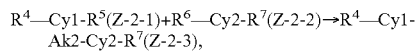

general formula (Z-2-1) and general formula (Z-2-2) can be subjected to nucleophilic substitution reaction, coupling reaction or reductive amination to obtain general formula (Z-2-3), and the preparation of longer chains can be achieved by repeating the process above;

if (Z-2-1) has an amino protecting group at the reaction site, the protecting group is removed, and then it can be subjected to nucleophilic substitution reaction or coupling reaction or reductive amination with general formula (Z-2-2) to obtain general formula (Z-2-3), and the preparation of longer chains can be achieved by repeating the process above;

or general formula (Z-1) and general formula (Z-2-1) are subjected to nucleophilic substitution reaction, coupling reaction or reductive amination reaction (the chain length can be increased by means of the preparation method for general formula (Z-2-3)) to obtain the corresponding general formula (II), namely, general formula (I), wherein the length of L chain can be prepared by means of the preparation method for general formula (Z-2-3).

Synthetic Method II

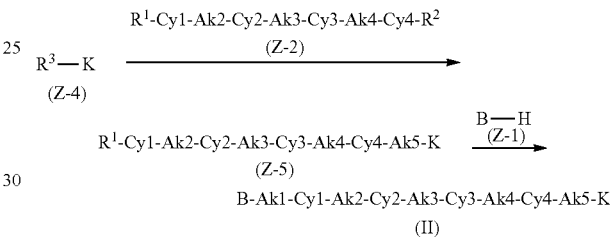

If general formula (Z-2) has an amino protecting group at the reaction site, the amino protecting group is removed first, and then it is subjected to nucleophilic substitution reaction or coupling reaction with general formula (Z-4) to obtain the corresponding general formula (Z-5), and general formula (Z-5) and general formula (Z-1) are subjected to nucleophilic substitution reaction or coupling reaction to obtain the corresponding general formula (II), namely, general formula (I).

Synthetic Method III

A part of the chain L can be subjected to nucleophilic substitution reaction or coupling reaction with general formula (Z-1) first, and then subjected to nucleophilic substitution reaction or coupling reaction with other parts of the chain L (see the preparation of general formula (Z-2-3) for the synthetic method), by such analogy, to obtain general formula (Z-3), and general formula (Z-3) and general formula (Z-4) are subjected to nucleophilic substitution reaction or coupling reaction to obtain the corresponding general formula (II), namely, general formula (I).

Synthetic Method IV

Alternatively, a part of the chain L can be subjected to nucleophilic substitution reaction or coupling reaction with general formula (Z-4) first, and then subjected to nucleophilic substitution reaction or coupling reaction with other parts of the chain L (see the preparation of general formula (Z-2-3) for the synthetic method), by such analogy, to obtain general formula (Z-5), and general formula (Z-5) and general formula (Z-1) are subjected to nucleophilic substitution reaction or coupling reaction to obtain the corresponding general formula (II), namely, general formula (I).

Synthetic Method V

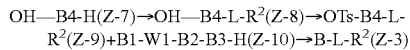

OH—B4-H(Z-7)→OH—B4-L-R²(Z-8)→OTs-B4-L-R²(Z-9)+B1-W1-B2-B3-H(Z-10)→B-L-R²(Z-3)

General formula (Z-7) and general formula (Z-2) are subjected to nucleophilic substitution reaction or coupling reaction to obtain general formula (Z-8)

or general formula (Z-7) is subjected to nucleophilic substitution reaction or coupling reaction with a part of the chain L, and then is subjected to nucleophilic substitution reaction or coupling reaction with other parts of the chain L (see the preparation of general formula (Z-2-3) for the synthetic method), to obtain general formula (Z-8), and general formula (Z-8) is reacted with p-toluenesulfonyl chloride to obtain general formula (Z-9), and general formula (Z-9) is subjected to nucleophilic substitution reaction or coupling reaction with general formula (Z-10) to obtain general formula (Z-3).

Synthetic method VI

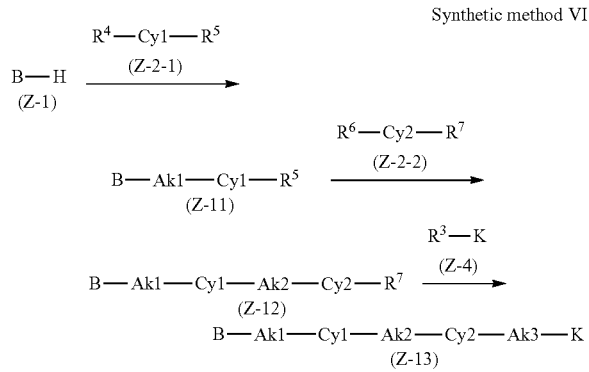

General formula (Z-1) and general formula (Z-2-1) are subjected to reductive amination reaction to obtain the corresponding general formula (Z-11), and if general formula (Z-11) has an amino protecting group at the reaction site, the amino protecting group is removed first, and then it is subjected to reductive amination reaction with general formula (Z-2-2) to obtain general formula (Z-12), and if general formula (Z-12) has an amino protecting group at the reaction site, the amino protecting group is removed first, and then it is subjected to nucleophilic substitution reaction with general formula (Z-4) to obtain general formula (Z-13), namely, general formula (I).

Synthetic medthod VII

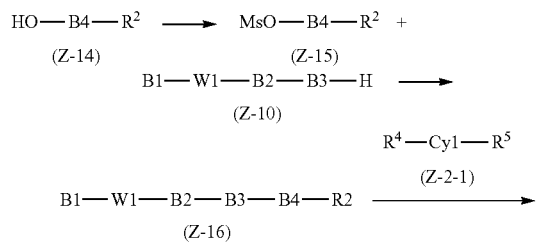

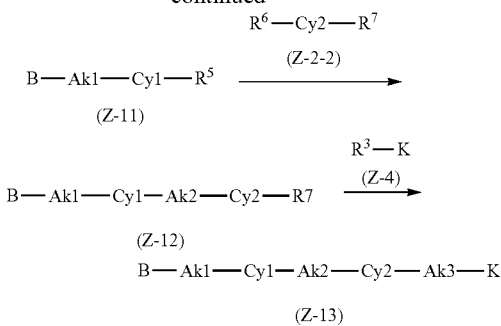

General formula (Z-14) is reacted with methanesulfonyl chloride to obtain general formula (Z-15), and general formula (Z-15) and general formula (Z-10) are subjected to nucleophilic substitution reaction to obtain general formula (Z-16), and if general formula (Z-16) has an amino protecting group at the reaction site, the amino protecting group is removed first, and then it is subjected to reductive amination with general formula (Z-2-1) to obtain the corresponding general formula (Z-11), and if general formula (Z-11) has an amino protecting group at the reaction site, the amino protecting group is removed first, and then it is subjected to reductive amination reaction with general formula (Z-2-2) to obtain general formula (Z-12), and if general formula (Z-12) has an amino protecting group at the reaction site, the amino protecting group is removed first, and then it is subjected to nucleophilic substitution reaction with general formula (Z-4) to obtain general formula (Z-13), namely, general formula (I).

See *J. Med. Chem.* 2015, 58, 9625-9638 for the synthetic method of general formula (Z-1); and see WO 2017197056 for the synthetic method of general formula (Z-4);

$R^1$ is selected from (=O), —CHO, F, Cl, Br, I, or OTf;

$R^2$ is selected from H, (=O), —CHO, F, Cl, Br, I or an amino protecting group, preferably Boc;

$R^3$ is selected from $NH_2$, F, Cl, Br, I, OTf, or OH;

$R^4$, $R^5$, $R^6$ and $R^7$ are each independently selected from H, (=O), —CHO, H, F, Cl, Br, I, OTf or an amino protecting group.

The present disclosure also provides the compounds shown below,

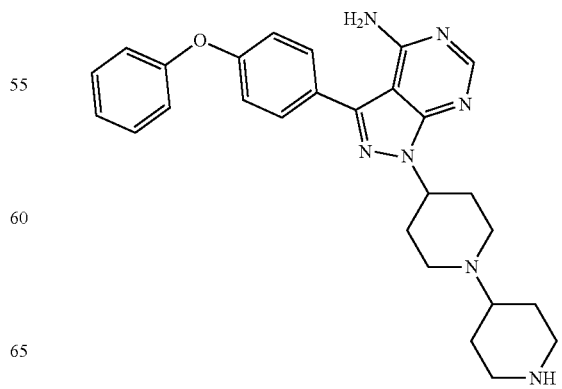

-continued

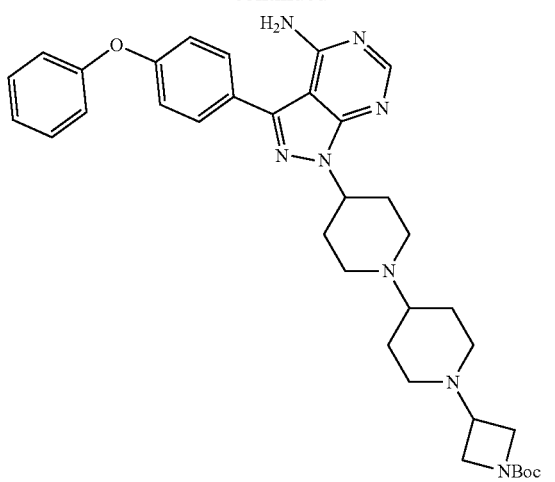

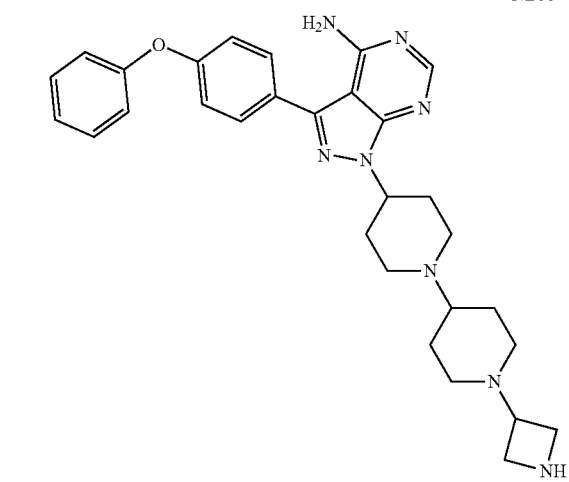

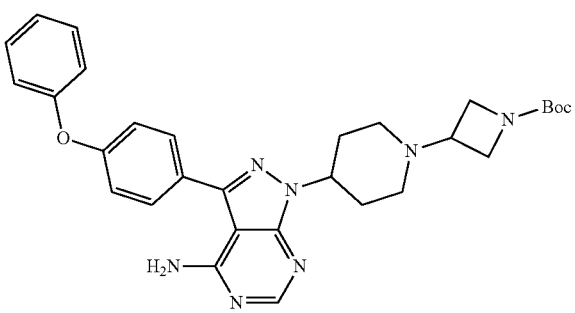

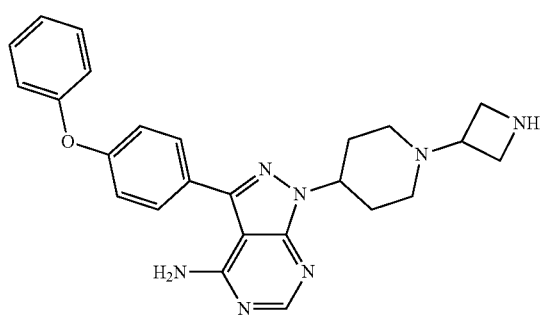

-continued

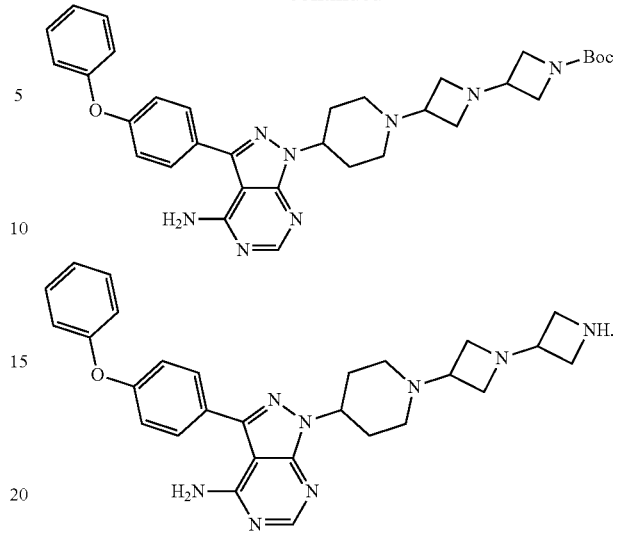

Unless stated to the contrary, the terms used in both the description and the claims have the following meanings:

The carbon, hydrogen, oxygen, sulfur, nitrogen or F, Cl, Br, I involved in the groups and compounds of the present disclosure all comprises their isotopes, and the carbon, hydrogen, oxygen, sulfur or nitrogen involved in the groups and compounds of the present disclosure is optionally further substituted by one or more of their corresponding isotopes, wherein the isotopes of carbon comprise $^{12}C$, $^{13}C$ and $^{14}C$, the isotopes of hydrogen comprise protium (H), deuterium (D, also known as heavy hydrogen), tritium (T, also known as superheavy hydrogen), the isotopes of oxygen comprise $^{16}O$, $^{17}O$ and $^{18}O$, the isotopes of sulfur comprise $^{32}S$, $^{33}S$, $^{34}S$ and $^{36}S$, the isotopes of nitrogen comprise $^{14}N$ and $^{15}N$, the isotopes of fluorine comprise $^{17}F$ and $^{19}F$, the isotopes of chlorine comprise $^{35}Cl$ and $^{37}Cl$, and the isotopes of bromine comprise $^{79}Br$ and $^{81}Br$.

"Alkyl" refers to a straight or branched saturated aliphatic hydrocarbon group containing 1 to 20 carbon atoms, preferably alkyl containing 1 to 8 carbon atoms, more preferably alkyl containing 1 to 6 carbon atoms, further preferably alkyl containing 1 to 4 carbon atoms. Non-limiting examples include methyl, ethyl, n-propyl, isopropyl, n-butyl, sec-butyl, isobutyl, tert-butyl, n-pentyl, isoamyl, neopentyl, n-hexyl and various branched isomers thereof; the alkyl can be optionally further substituted with 0 to 6 substituents selected from F, Cl, Br, I, hydroxyl, sulfhydryl, nitro, cyano, amino, alkylamino, amido, alkenyl, alkynyl, $C_{1-6}$ alkyl, $C_{1-6}$ hydroxyalkyl, $C_{1-6}$ alkoxy, 3- to 8-membered carbocyclyl, 3- to 8-membered heterocyclic group, 3- to 8-membered carbocyclyloxy, 3- to 8-membered heterocyclyloxy, carboxyl or a carboxylate group, and the definition of the alkyl described herein is consistent with this definition.

"Alkoxy" refers to —O-alkyl. Non-limiting examples include methoxy, ethoxy, n-propoxy, isopropoxy, n-butoxy, sec-butoxy, tert-butoxy, n-pentoxy, n-hexyloxy, cyclopropoxy and cyclobutoxy. The alkyl can be optionally further substituted with 0 to 5 substituents selected from F, Cl, Br, I, hydroxyl, sulfhydryl, nitro, cyano, amino, alkylamino, alkenyl, alkynyl, alkyl, hydroxyalkyl, alkoxy, carbocyclyl, heterocyclic group, carbocyclyloxy, heterocyclyloxy, carboxyl or a carboxylate group. The definition of the alkoxy described herein is consistent with this definition.

"Heterocyclic group" or "heterocyclic ring" refers to a substituted or unsubstituted saturated or unsaturated aromatic ring or non-aromatic ring, and the aromatic ring or non-aromatic ring can be 3- to 8-membered monocyclic ring, 4- to 12-membered bicyclic ring or 10- to 15-membered tricyclic ring system, and contains 1 to 3 heteroatoms selected from N, O or S, preferably 3- to 8-membered heterocyclic group, and the optionally substituted N, S in the heterocyclic group can be oxidized into various oxidation states. Heterocyclic group can be connected to a heteroatom or carbon atom, and heterocyclic group can be connected to a bridged ring or spiro ring. Non-limiting examples include oxiranyl, azacyclopropyl, oxetanyl, azetidinyl, 1,3-dioxolane, 1,4-dioxolane, 1,3-dioxane, azacycloheptyl, pyridyl, furanyl, thienyl, pyranyl, N-alkylpyrrolyl, pyrimidinyl, pyrazinyl, pyridazinyl, imidazolyl, piperidyl, piperadinyl, morpholinyl, thiomorpholinyl, 1,3-dithianyl, dihydrofuranyl, dihydropyranyl, dithiolanyl, tetrahydrofuranyl, tetrahydropyrrolyl, tetrahydroimidazolyl, tetrahydrothiazolyl, tetrahydropyranyl, benzimidazolyl, benzopyridyl, pyrrolopyridyl, benzodihydrofuranyl, azabicyclo[3.2.1]octyl, azabicyclo[5.2.0]nonyl, oxatricyclic[5.3.1.1]dodecyl, azaadamantyl and oxaspiro[3.3]heptyl. The heterocyclic group can be optionally further substituted with 0 to 5 substituents selected from F, Cl, Br, I, =O, hydroxyl, sulfhydryl, nitro, cyano, amino, alkylamino, amido, alkenyl, alkynyl, alkyl, hydroxyalkyl, alkoxy, carbocyclyl, heterocyclic group, carbocyclyloxy, heterocyclyloxy, carboxyl or a carboxylate group. The definition of the heterocyclic group described herein is consistent with this definition.

"Spiro ring" refers to a 5- to 20-membered polycyclic group sharing one carbon atom (referred to as a spiro atom) between substituted or unsubstituted monocyclic rings, which may contain 0 to 5 double bonds, and may contain 0 to 5 heteroatoms selected from N, O or S(=O)$_n$. The spiro ring is preferably 6- to 14-membered, further preferably 6- to 12-membered, and more preferably 6- to 10-membered. Its non-limiting examples include:

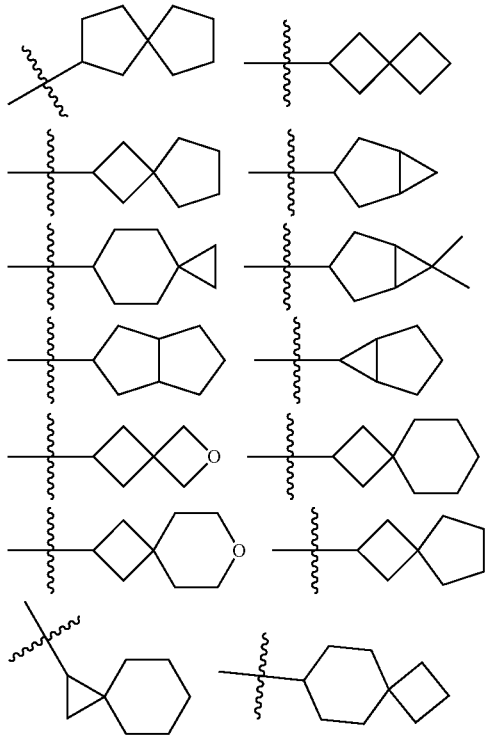

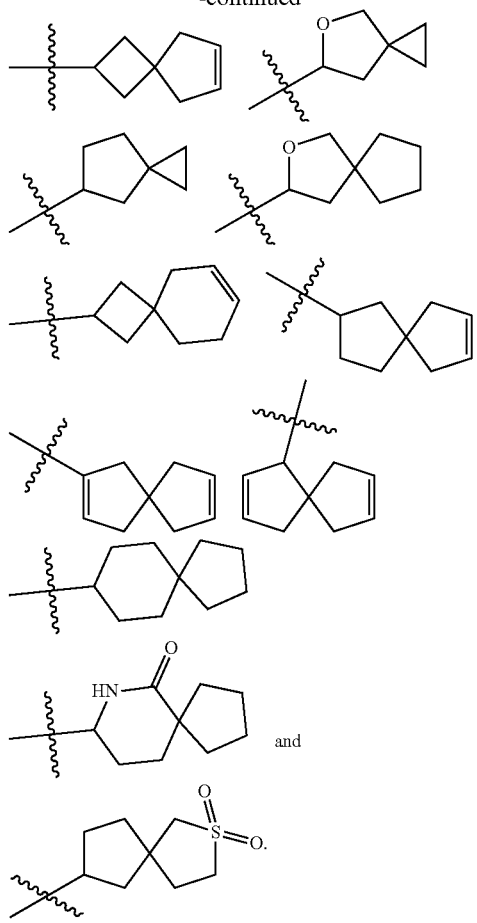

When the spiro ring is substituted, substituents can be 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclic group, bridged ring group, spiro ring group, fused ring group, hydroxyalkyl, =O, carbonyl, aldehyde, carboxylic acid, formate, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (wherein m and n are 0, 1 or 2), arylthio, thiocarbonyl, silyl or —NR$^b$R$^c$ and the like, wherein R$^b$ and R$^c$ are independently selected from H, hydroxyl, amino, carbonyl, alkyl, alkoxy, cycloalkyl, heterocyclic group, aryl, heteroaryl, sulfonyl, trifluoromethylsulfonyl. Alternatively, R$^b$ and R$^c$ may form a five- or six-membered cycloalkyl or heterocyclic group. R$^a$ and R$^d$ are each independently selected from aryl, heteroaryl, alkyl, alkoxy, cycloalkyl, heterocyclic group, carbonyl, ester group, bridged ring group, spiro ring group or fused ring group. The definition of the spiro ring described herein is consistent with this definition.

"Fused ring" refers to a polycyclic group in which each ring in the system shares an adjacent pair of carbon atoms with other rings in the system, wherein one or more of the rings may contain 0 or more double bonds, which may be substituted or unsubstituted, and each ring in the fused ring system may contain 0 to 5 heteroatoms selected from N, S(=O)$_n$ or O. The fused ring is preferably 5- to 20-membered, further preferably 5- to 14-membered, more preferably 5- to 12-membered, and still further preferably 5- to 10-membered. Non-limiting examples include:

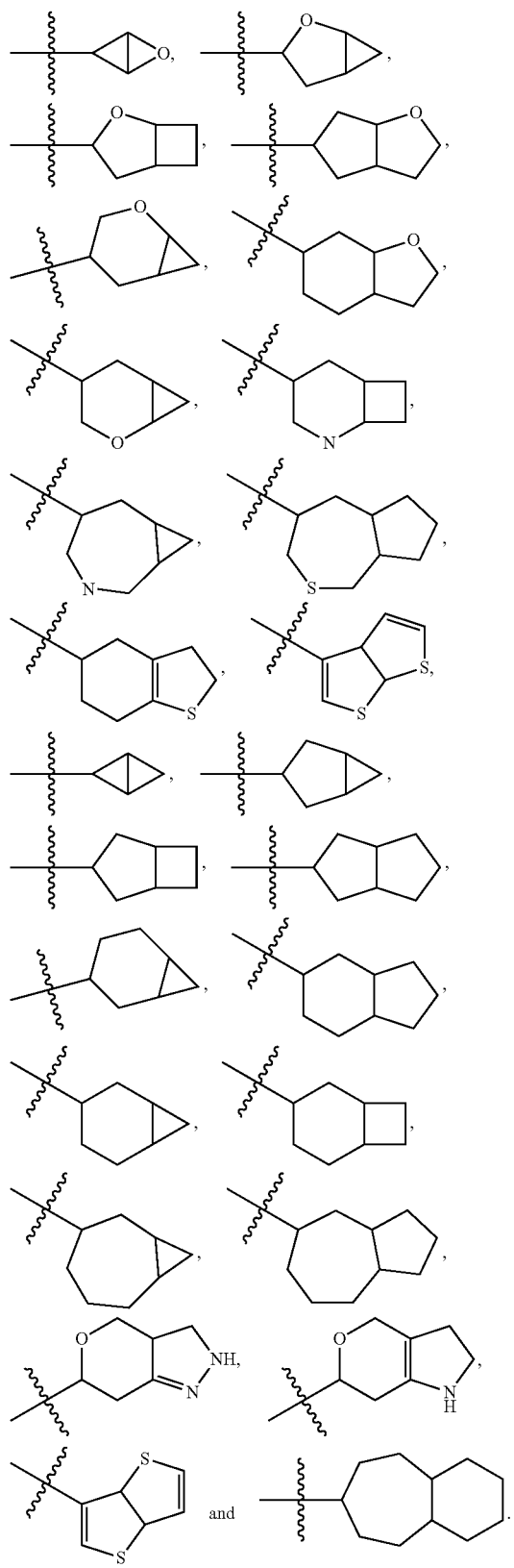

When the fused ring is substituted, substituents can be 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclic group, bridged ring group, spiro ring group, fused ring group, hydroxyalkyl, =O, carbonyl, aldehyde, carboxylic acid, formate, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)—R$^a$, OR$^d$ or —(CH$_2$)$_m$-alkynyl-R$^a$ (wherein m and n are 0, 1 or 2), arylthio, thiocarbonyl, silyl or —NR$^b$R$^c$ and the like, wherein R$^b$ and R$^c$ are independently selected from H, hydroxyl, amino, carbonyl, alkyl, alkoxy, cycloalkyl, heterocyclic group, aryl, heteroaryl, sulfonyl, trifluoromethylsulfonyl. Alternatively, R$^b$ and R$^c$ may form a five- or six-membered cycloalkyl or heterocyclic group. R$^a$ and R$^d$ are each independently selected from aryl, heteroaryl, alkyl, alkoxy, cycloalkyl, heterocyclic group, carbonyl, ester group, bridged ring group, spiro ring group or fused ring group. The definition of the fused ring described herein is consistent with this definition.

"Bridged ring" refers to a polycyclic group containing any two carbon atoms that are not directly connected, which group may contain 0 or more double bonds and can be substituted or unsubstituted, and any ring in the bridged ring system may contain 0 to 5 heteroatoms or groups selected from N, S(=O)$_n$ or O (wherein n is 0, 1, or 2). The ring atoms contain 5 to 20 atoms, preferably 5 to 14 atoms, further preferably 5 to 12 atoms, and still further preferably 5 to 10 atoms. Non-limiting examples include

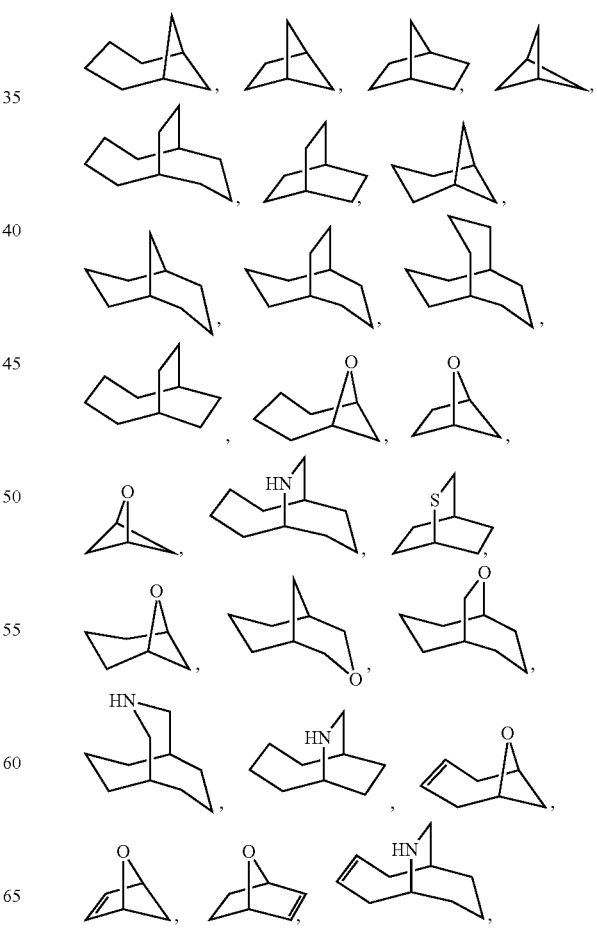

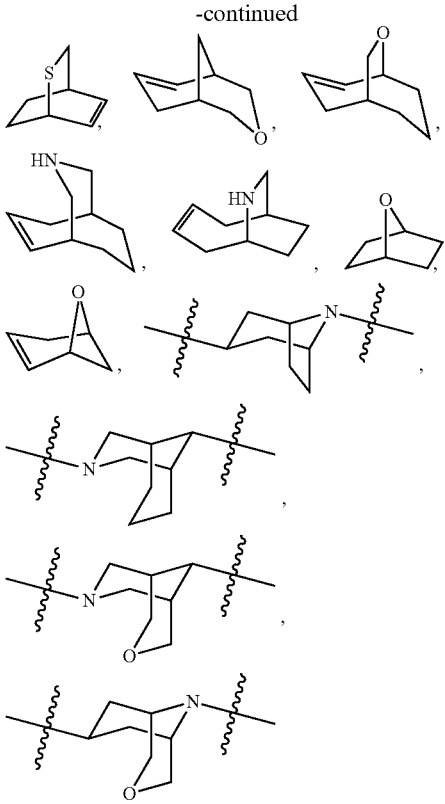

and adamantane. When the bridged ring is substituted, substituents can be 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclic group, bridged ring group, spiro ring group, fused ring group, hydroxyalkyl, =O, carbonyl, aldehyde, carboxylic acid, formate, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$—R$^a$, —(CH$_2$)$_m$-alkenyl-R$^a$, OR$^d$ or —(CH$_2$)$_m$-alkynyl-R$^a$ (wherein m and n are 0, 1 or 2), arylthio, thiocarbonyl, silyl or —NR$^b$R$^c$ and the like, wherein R$^b$ and R$^c$ are independently selected from H, hydroxyl, amino, carbonyl, alkyl, alkoxy, cycloalkyl, heterocyclic group, aryl, heteroaryl, sulfonyl, trifluoromethylsulfonyl. Alternatively, R$^b$ and R$^c$ may form a five- or six-membered cycloalkyl or heterocyclic group. R$^a$ and R$^d$ are each independently selected from aryl, heteroaryl, alkyl, alkoxy, cycloalkyl, heterocyclic group, carbonyl, ester group, bridged ring group, spiro ring group or fused ring group. The definition of the bridged ring described herein is consistent with this definition.

"Mono-heterocyclic ring" refers to "heterocyclic group" or "heterocyclic ring" in a monocyclic ring system, and the definition of the mono-heterocyclic ring described herein is consistent with this definition.

"Fused heterocyclic ring" refers to an "fused ring" containing heteroatom(s). The definition of the fused heterocyclic ring described herein is consistent with this definition.

"Spiro-heterocyclic ring" refers to a "spiro ring" containing heteroatom(s). The definition of the spiro-heterocyclic ring described herein is consistent with this definition.

"Bridged-heterocyclic ring" refers to a "bridged ring" containing heteroatom(s). The definition of the bridged-heterocyclic ring described herein is consistent with this definition.

"Heteroaryl" or "heteroaryl ring" refers to a substituted or unsubstituted 5- to 14-membered aromatic ring, and contains 1 to 5 heteroatoms or groups selected from N, O or S(=O)$_n$, preferably 5- to 10-membered aromatic ring, further preferably 5- to 6-membered. Non-limiting examples of heteroaryl include, but are not limited to pyridyl, furanyl, thienyl, pyridyl, pyranyl, N-alkylpyrrolyl, pyrimidinyl, pyrazinyl, pyridazinyl, imidazolyl, piperidyl, morpholinyl, thiomorpholinyl, 1,3-dithianyl, benzimidazolyl, benzimidazole, benzopyridine, pyrrolopyridine and the like. The heteroaryl ring can be fused to an aryl, heterocyclic group or cycloalkyl ring, wherein the ring connected to the parent structure is a heteroaryl ring, and non-limiting examples include

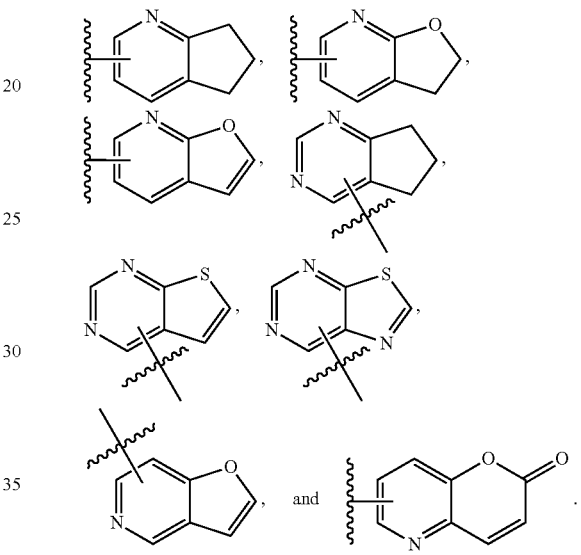

When the heteroaryl ring is substituted, substituents can be 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclic group, bridged ring group, Spiro ring group, fused ring group, hydroxyalkyl, =O, carbonyl, aldehyde, carboxylic acid, formate, —(CH$_2$)$_m$—C(=O)—R$^a$, —O—(CH$_2$)$_m$—C(=O)—R$^a$, —(CH$_2$)$_m$—C(=O)—NR$^b$R$^c$, —(CH$_2$)$_m$S(=O)$_n$R$^a$, —(CH$_2$)$_m$-alkenyl-R$^a$, OR$^d$ or —(CH$_2$)$_m$-alkynyl-R$^a$ (wherein m and n are 0, 1 or 2), arylthio, thiocarbonyl, silyl or —NR$^b$R$^c$ and the like, wherein R$^b$ and R$^c$ are independently selected from H, hydroxyl, amino, carbonyl, alkyl, alkoxy, cycloalkyl, heterocyclic group, aryl, heteroaryl, sulfonyl, trifluoromethylsulfonyl. Alternatively, R$^b$ and R$^c$ may form a five- or six-membered cycloalkyl or heterocyclic group. R$^a$ and R$^d$ are each independently selected from aryl, heteroaryl, alkyl, alkoxy, cycloalkyl, heterocyclic group, carbonyl, ester group, bridged ring group, spiro ring group or fused ring group. The definition of the heteroaryl or heteroaryl ring described herein is consistent with this definition.

"Optional" or "optionally" refers to that the event or circumstance subsequently described may but not necessarily occur, and the description includes the occasions where the events or circumstances occur or do not occur. for example, "Alkyl optionally substituted with F" means that an alkyl may but not necessarily be substituted by F, and the description includes the case where the alkyl is substituted with F and the case where the alkyl is not substituted with F.

"Pharmaceutically acceptable salt" or "pharmaceutically acceptable salt thereof" refers to a salt of the compound of the present disclosure maintaining the biological effectiveness and characteristics of the free acid or free base, and obtained by reacting the free acid with a non-toxic inorganic base or organic base, reacting the free base with a non-toxic inorganic acid or organic acid.

"Pharmaceutical composition" refers to a mixture of one or more of the compounds of the present disclosure, a pharmaceutically acceptable salt or a prodrug thereof, and other chemical components, wherein "other chemical components" refer to pharmaceutically acceptable carriers, excipients and/or one or more other therapeutic agents.

"Carrier" refers to a material that does not cause significant irritation to the organism and does not eliminate the biological activity and characteristics of the administered compound.

"Excipient" refers to an inert substance added to a pharmaceutical composition to facilitate the administration of a compound. Non-limiting examples include calcium carbonate, calcium phosphate, sugar, starch, cellulose derivatives (including microcrystalline cellulose), gelatin, vegetable oils, polyethylene glycols, diluents, granulating agents, lubricants, adhesives and disintegrants.

"Prodrug" refers to a compound that can be converted into a compound of the present disclosure with biological activity through metabolism in vivo. The prodrug of the present disclosure is prepared by modifying the amino or carboxyl group in the compound of the present disclosure, and the modification can be removed by conventional operations or in vivo to obtain the parent compound. When the prodrug of the present disclosure is administered to a mammalian individual, the prodrug is split to form free amino or carboxyl group.

"Co-crystal" refers to a crystal formed by the combination of active pharmaceutical ingredient (API) and co-crystal former (CCF) under the action of hydrogen bonds or other non-covalent bonds. The pure state of API and CCF are both solid at room temperature, and there is a fixed stoichiometric ratio between various components. The co-crystal is a multi-component crystal, which includes both a binary co-crystal formed between two neutral solids and a multi-element co-crystal formed between a neutral solid and a salt or solvate.

"Animal" is meant to include mammals, such as humans, companion animals, zoo animals, and domestic animals, preferably humans, horses, or dogs.

"Stereoisomer" refers to an isomer produced by different arrangements of atoms in a molecule in space, including cis-trans isomers, enantiomers and conformational isomers.

"Optional" or "optionally" or "selective" or "selectively" refers to that the events or conditions subsequently described may but not necessarily occur, and the description includes the case where the events or conditions occur and do not occur. For example, "heterocyclic group optionally substituted with alkyl" refers to that the alkyl may but not necessarily exist, and the description includes the case where the heterocyclic group is substituted by an alkyl group and the case where the heterocyclic group is not substituted with alkyl.

"DC50" refers to the dose at which 50% of the protein is degraded.

DETAILED DESCRIPTION OF EMBODIMENTS

The technical solutions of the present disclosure will be described in detail below in conjunction with examples, but the protection scope of the present disclosure includes but is not limited thereto.

The structures of the compounds are determined by nuclear magnetic resonance (NMR) or (and) mass spectrometry (MS). The NMR shift (δ) is given in the unit of $10^{-6}$ (ppm). NMR is measured with (Bruker Avance III 400 and Bruker Avance 300) NMR instrument, and the solvent for determination is deuterated dimethyl sulfoxide (DMSO-$d_6$), deuterated chloroform (CDCl$_3$), deuterated methanol (CD$_3$OD), and the internal standard is tetramethylsilane (TMS);

MS is measured with (Agilent 6120B (ESI) and Agilent 6120B (APCI));

HPLC is measured with Agilent 1260DAD high pressure liquid chromatography (Zorbax SB-C18 100×4.6 mm, 3.5 µM);

Yantai Huanghai HSGF254 or Qingdao GF254 silica gel plate is used for thin layer chromatography silica plate, and the silica gel plate for the thin layer chromatography (TLC) is of the specification of 0.15 mm-0.20 mm, and the specification when separating and purifying a product by thin layer chromatography is 0.4 mm-0.5 mm.

For the column chromatography, Yantai Huanghai silica gel of 200-300 mesh silica gel is generally used as a carrier;

the known starting materials of the present disclosure can be synthesized by or according to methods known in the art, or can be purchased from Titan Technology Co., Ltd., Energy Chemical Co., Ltd., Shanghai Demo Co., Ltd., Chengdu Kelong Chemical Co., Ltd., Accela ChemBio Co., Ltd., J&K Scientific Co., Ltd. and other companies;

P13I:

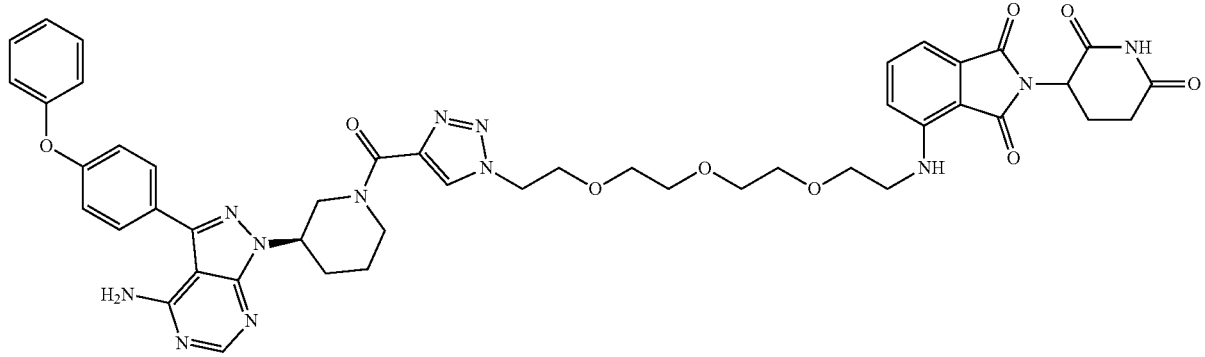 [SMILES: Nc1ncnc2c1c(-c1ccc(Oc3ccccc3)cc1)nn2[C@@H]1CCCN(C(=O)c2cn(CCOCCOCCOCCNc3cccc4c3C(=O)N(C3CCC(=O)NC3=O)C4=O)nn2)C1]

(References for synthesis: Y. Sun, X. Zhao, N. Ding, H. Gao, Y. Wu, Y. Yang, M. Zhao, J. Hwang, Y. Song, W. Liu, Y. Rao, *Cell Res*. 2018, 28, 779-781);

Tf: Trifluoromethylsulfonyl;
Boc: Tert-butoxycarbonyl;
Ts: P-toluenesulfonyl;
Cbz: Benzyloxycarbonyl;
Ms: Methylsulphonyl;
TMS: Trimethylsilane; DMSO: Dimethyl sulfoxide; DMF N,N'-dimethylformamide; DME: Ethylene glycol dimethyl ether; DCM:
Dichloromethane; DIPEA: N,N'-diisopropylethylamine; DCE: 1,2-dichloroethane; Pd₂dba₃: Tris(dibenzylidene acetone)dipalladium; JohnPhos: (2-biphenyl)di-tert-butylphosphine; THF: Tetrahydrofuran; DIAD: Diisopropyl azodicarboxylate; CDI: N,N'-carbonyl diimidazole; MsCl: Methanesulfonyl chloride; TFA: Trifluoroacetic acid.

Example 1

5-[2-[4-[4-amino-3-(4-phenoxyphenyl)pyrazolo[3,4-d]pyrimidin-1-yl]-1-piperidyl]-7-azaspiro[3.5]nonan-7-yl]-2-(2,6-dioxo-3-piperidyl)isoindoline-1,3-dione (Compound 1)

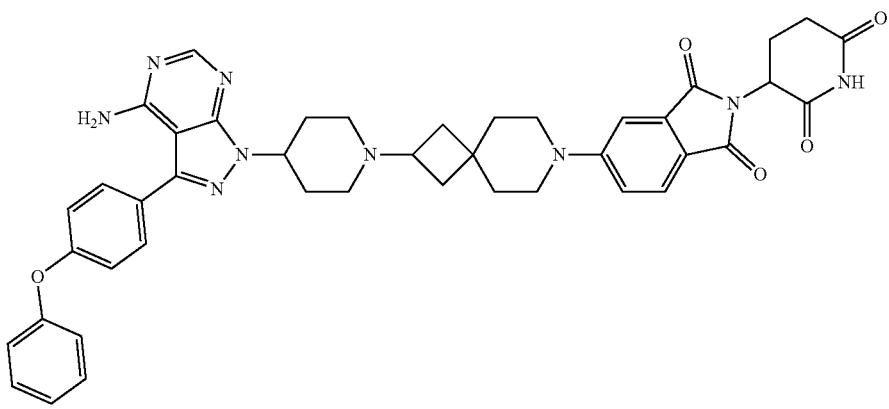

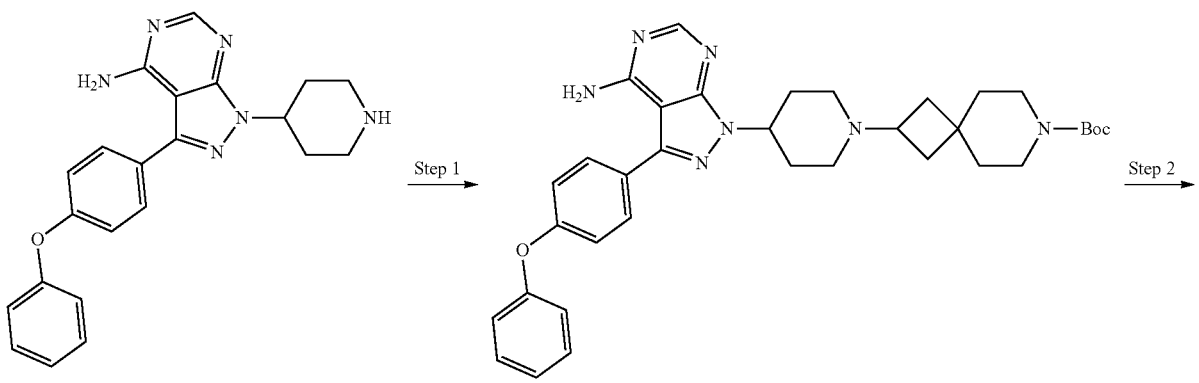

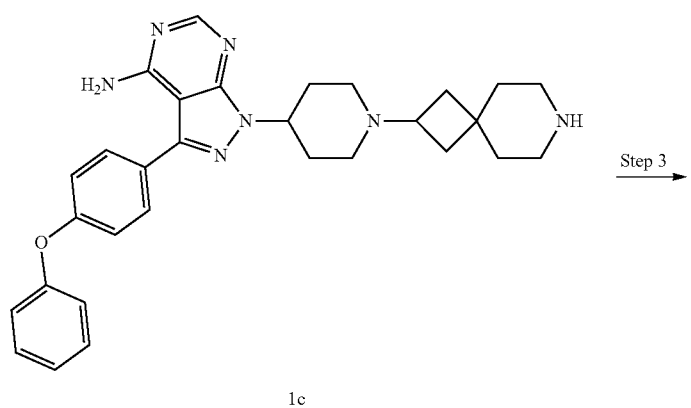

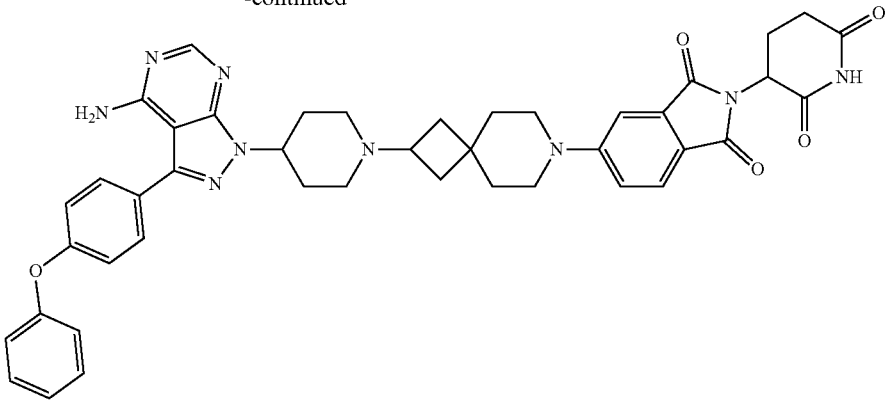

Compound 1

Step 1

Tert-butyl 2-[4-[4-amino-3-(4-phenoxyphenyl)pyrazolo[3,4-d]pyrimidin-1-yl]-1-piperidyl]-7-a zaspiro[3.5]nonane-7-carboxylate (1b)

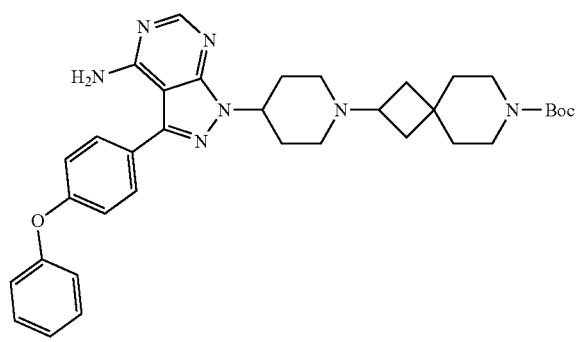 [SMILES: CC(C)(C)OC(=O)N1CCC2(CC1)CC(N1CCC(n3nc(-c4ccc(Oc5ccccc5)cc4)c4c(N)ncnc43)CC1)C2]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.200 g, 0.473 mmol) was dissolved in 5 mL of 1,2-dichloroethane, tert-butyl 2-oxo-7-azaspiro[3.5]nonane-7-carboxylate (0.100 g, 0.418 mmol) and glacial acetic acid (0.0567 g, 0.946 mmol) were added, and the mixture was stirred at room temperature for 1 h, and then sodium triacetoxyborohydride (0.177 g, 0.836 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-9:1), to obtain tert-butyl 2-[4-[4-amino-3-(4-phenoxyphenyl)pyrazolo[3,4-d]pyrimidin-1-yl]-1-piperidyl]-7-a zaspiro[3.5]nonane-7-carboxylate (1b) (0.152 g, yield: 60%).

$^1$H NMR (400 MHz, DMSO-$d_6$) δ 8.23 (s, 1H), 7.66 (d, 2H), 7.44 (t, 2H), 7.24-7.05 (m, 5H), 4.70-4.60 (m, 1H), 3.35-3.25 (m, 4H), 3.22-3.16 (m, 2H), 2.97-2.87 (m, 2H), 2.78-2.65 (m, 1H), 2.24-2.11 (m, 2H), 2.03-1.94 (m, 2H), 1.94-1.84 (m, 4H), 1.60-1.51 (m, 2H), 1.48 (t, 2H), 1.38 (s, 9H).

LCMS m/z=610.3 [M+1]$^+$.

Step 2

1-[1-(7-Azaspiro[3.5]nonan-2-yl)-4-piperidyl]-3-(4-phenoxyphenyl)pyrazolo[3,4-d]pyrimidin-4-amine (1c)

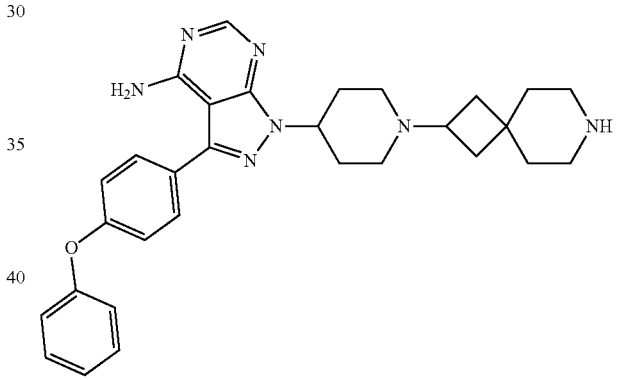

Tert-butyl 2-[4-[4-amino-3-(4-phenoxyphenyl)pyrazolo[3,4-d]pyrimidin-1-yl]-1-piperidyl]-7-a zaspiro[3.5]nonane-7-carboxylate (1b) (0.150 g, 0.246 mmol) was dissolved in 2 mL of dichloromethane, 5 mL of 4N ethyl acetate hydrochloride solution was added, and the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 1-[1-(7-azaspiro[3.5]nonan-2-yl)-4-piperidyl]-3-(4-phenoxyphenyl)pyrazolo[3,4-d]pyrimidin-4-amine (1c) (0.090 g, yield: 72%).

LCMS m/z=510.3 [M+1]$^+$.

Step 3

5-[2-[4-[4-Amino-3-(4-phenoxyphenyl)pyrazolo[3,4-d]pyrimidin-1-yl]-1-piperidyl]-7-azaspiro[3.5]nonan-7-yl]-2-(2,6-dioxo-3-piperidyl)isoindoline-1,3-dione (Compound 1)

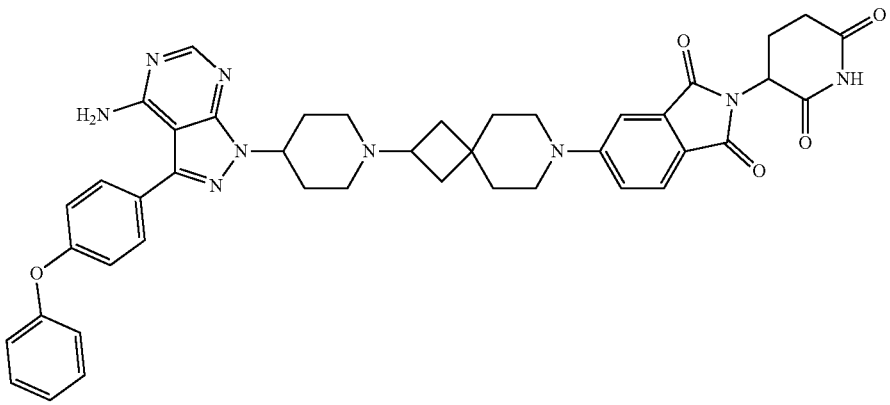 [SMILES: Nc1ncnc2c1c(-c1ccc(Oc3ccccc3)cc1)nn2C1CCN(C2CC3(CCN(c4ccc5c(c4)C(=O)N(C4CCC(=O)NC4=O)C5=O)CC3)C2)CC1]

1-[1-(7-azaspiro[3.5]nonan-2-yl)-4-piperidyl]-3-(4-phenoxyphenyl)pyrazolo[3,4-d]pyrimidin-4-amine (1c) (0.090 g, 0.18 mmol) was dissolved in 2 mL of dimethyl sulfoxide, 2-(2,6-dioxopiperidin-3-yl)-5-fluoroisoindoline-1,3-dione (see WO 2017197056 for the synthetic method) (0.049 g, 0.18 mmol) and diisopropylethylamine (0.11 g, 0.88 mmol) were added. Upon completion of the addition, the reaction was carried out at 90° C. for 2 h. The reaction solution was cooled to room temperature, to which 10 mL of water was slowly added dropwise, and filtered. The filter cake was dissolved with 20 mL of dichloromethane, and then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-9:1), to obtain 5-[2-[4-[4-amino-3-(4-phenoxyphenyl)pyrazolo[3,4-d]pyrimidin-1-yl]-1-piperidyl]-7-azaspiro[3.5]nonan-7-yl]-2-(2,6-dioxo-3-piperidyl)isoindoline-1,3-dione (Compound 1) (0.092 g, Yield: 68%).

$^1$H NMR (400 MHz, CDCl$_3$) δ 8.61 (s, 1H), 8.39 (s, 1H), 7.68-7.60 (m, 3H), 7.39 (t, 2H), 7.27 (d, 1H), 7.20-7.06 (m, 3H), 7.09 (d, 2H), 7.04 (dd, 1H), 5.56 (br, 2H), 4.97-4.90 (m, 1H), 4.80 (s, 1H), 3.38 (dd, 4H), 3.06 (s, 2H), 2.95-2.66 (m, 5H), 2.44 (s, 2H), 2.12 (dd, 6H), 1.69 (d, 6H).

LCMS m/z=383.8 [M/2+1]$^+$.

Example 2

5-[4-[4-[4-[4-amino-3-(4-phenoxyphenyl)pyrazolo[3,4-d]pyrimidin-1-yl]-1-piperidyl]-1-piperidyl]-1-piperidyl]-2-(2,6-dioxo-3-piperidyl)isoindoline-1,3-dione (Compound 2)

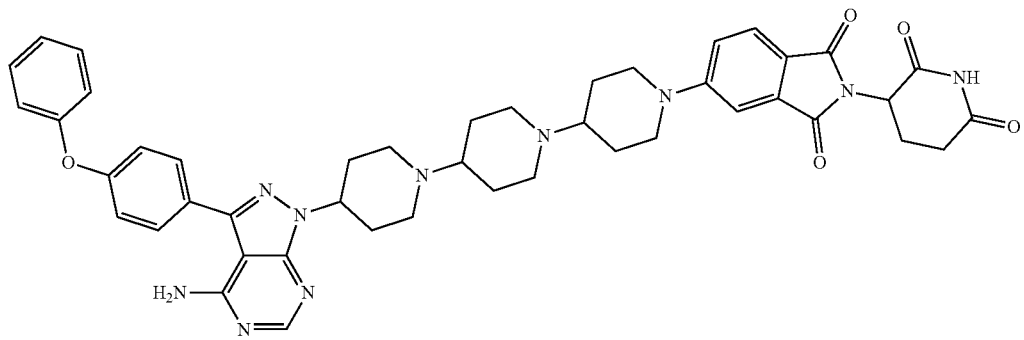

-continued
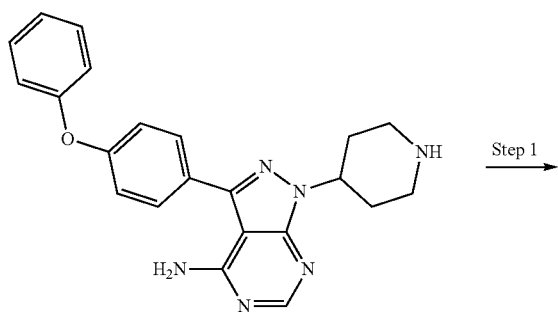
1a
Step 1 →
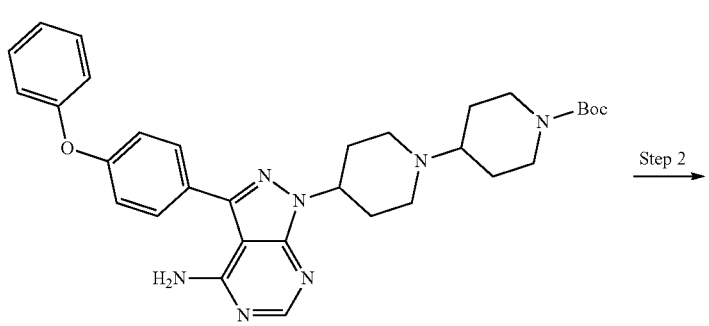
2a
Step 2 →
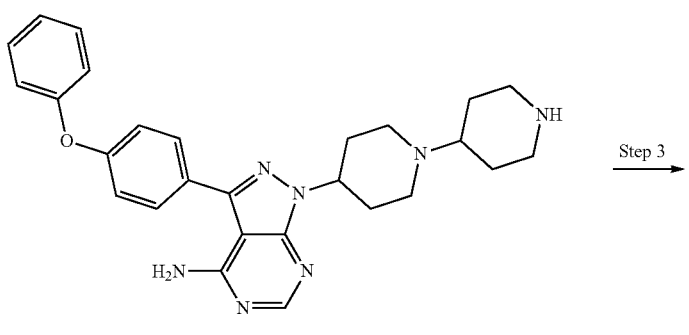
2b
Step 3 →
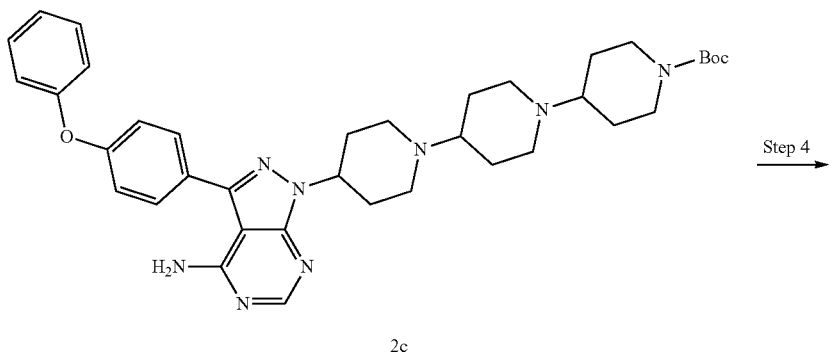
2c
Step 4 →

-continued

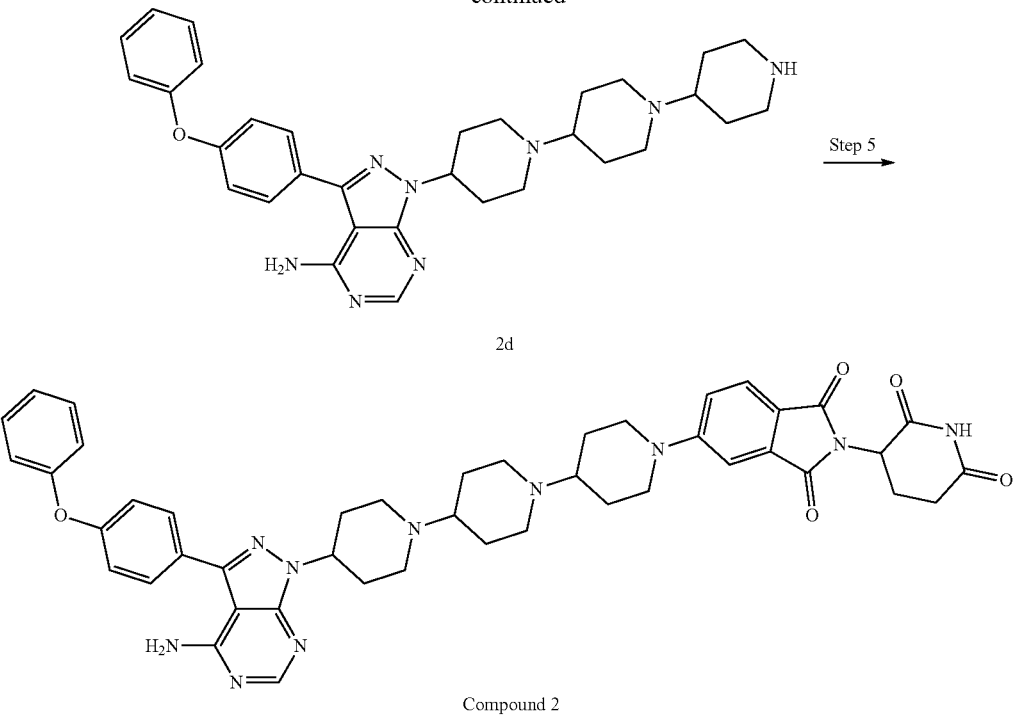

2d

Compound 2

Step 1

Tert-butyl 4-[4-[4-amino-3-(4-phenoxyphenyl)pyrazolo[3,4-d]pyrimidin-1-yl]-1-piperidyl]pipe ridine-1-carboxylate (2a)

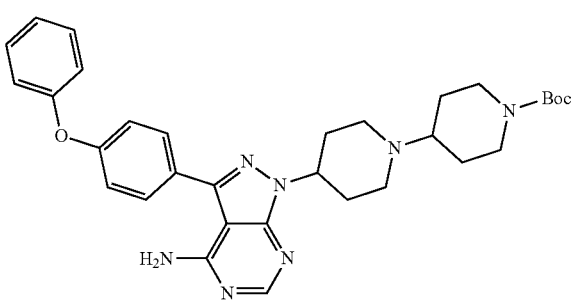 [SMILES: CC(C)(C)OC(=O)N1CCC(N2CCC(n3nc(-c4ccc(Oc5ccccc5)cc4)c4c(N)ncnc43)CC2)CC1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.500 g, 1.29 mmol) was dissolved in 5 mL of 1,2-dichloroethane, to which was added tert-butyl 4-oxopiperidine-1-carboxylate (0.309 g, 1.55 mmol) and glacial acetic acid (0.412 g, 6.86 mmol). Upon completion of the addition, the reaction was stirred at 65° C. for 3 h, then the reaction system was cooled to room temperature, and sodium triacetoxyborohydride (0.548 g, 2.59 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-19:1), to obtain tert-butyl 4-[4-[4-amino-3-(4-phenoxyphenyl)pyrazolo[3,4-d]pyrimidin-1-yl]-1-piperidyl]pipe ridine-1-carboxylate (2a) (0.310 g, yield: 42%).

$^1$H NMR (400 MHz, CDCl$_3$) δ 8.34 (s, 1H), 7.64 (d, 2H), 7.39 (t, 2H), 7.19-7.13 (m, 3H), 7.08 (d, 2H), 5.73 (br, 2H), 4.82-4.72 (m, 1H), 4.25-4.10 (m, 2H), 3.17-3.05 (m, 2H), 2.73 (t, 2H), 2.60-2.35 (m, 5H), 2.08-1.99 (m, 2H), 1.90-1.76 (m, 2H), 1.55-1.45 (m, 11H).

Step 2

3-(4-phenoxyphenyl)-1-[1-(4-piperidyl)-4-piperidyl]pyrazolo[3,4-d]pyrimidin-4-amine (2b)

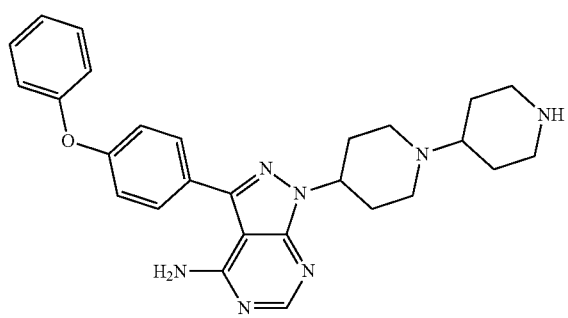 [SMILES: Nc1ncnc2c1c(-c1ccc(Oc3ccccc3)cc1)nn2C1CCN(C2CCNCC2)CC1]

Tert-butyl 4-[4-[4-amino-3-(4-phenoxyphenyl)pyrazolo[3,4-d]pyrimidin-1-yl]-1-piperidyl]pipe ridine-1-carboxylate (2a) (0.310 g, 0.544 mmol) was dissolved in 2 mL of dichloromethane, 5 mL of 4N ethyl acetate hydrochloride solution was added, and the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 3-(4-phenoxyphenyl)-1-[1-(4-piperidyl)-4-piperidyl]pyrazolo[3,4-d]pyrimidin-4-am ine (2b) (0.256 g, yield: >99%).

LCMS m/z=235.8 [M/2+1]⁺.

Step 3

Tert-butyl 4-[4-[4-[4-amino-3-(4-phenoxyphenyl)pyrazolo[3,4-d]pyrimidin-1-yl]-1-piperidyl]-1-piperidyl]piperidine-1-carboxylate (2c)

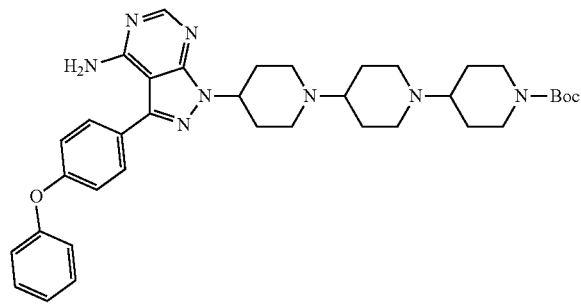 [SMILES: CC(C)(C)OC(=O)N1CCC(N2CCC(N3CCC(n4nc(-c5ccc(Oc6ccccc6)cc5)c5c(N)ncnc54)CC3)CC2)CC1]

3-(4-phenoxyphenyl)-1-[1-(4-piperidyl)-4-piperidyl]pyrazolo[3,4-d]pyrimidin-4-amine (2b) (0.256 g, 0.545 mmol) was dissolved in 3 mL of 1,2-dichloroethane, tert-butyl 4-oxopiperidine-1-carboxylate (0.130 g, 0.654 mmol) and glacial acetic acid (0.174 g, 2.89 mmol) were added. Upon completion of the addition, the reaction was stirred at 65° C. for 3 h, and then cooled to room temperature. Sodium triacetoxyborohydride (0.231 g, 1.09 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-19:1), to obtain tert-butyl 4-[4-[4-[4-amino-3-(4-phenoxyphenyl)pyrazolo[3,4-d]pyrimidin-1-yl]-1-piperidyl]-1-piperidyl]piperidine-1-tert-butyl carboxylate (2c) (0.230 g, yield: 65%).

Step 4

3-(4-phenoxyphenyl)-1-[1-[1-(4-piperidyl)-4-piperidyl]-4-piperidyl]pyrazolo[3,4-d]pyrimidin-4-amine (2d)

Tert-butyl 4-[4-[4-[4-amino-3-(4-phenoxyphenyl)pyrazolo[3,4-d]pyrimidin-1-yl]-1-piperidyl]-1-piperidyl]piperidine-1-carboxylate (2c) (0.230 g, 0.352 mmol) was dissolved in 2 mL of dichloromethane, 5 mL of 4N ethyl acetate hydrochloride solution was added, and the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 3-(4-phenoxyphenyl)-1-[1-[1-(4-piperidyl)-4-piperidyl]-4-piperidyl]pyrazolo[3,4-d]pyrimidin-4-amine (2d) (0.195 g, yield: >99%).

LCMS m/z=277.3 [M/2+1]⁺.

Step 5

5-[4-[4-[4-[4-amino-3-(4-phenoxyphenyl)pyrazolo[3,4-d]pyrimidin-1-yl]-1-piperidyl]-1-piperidyl]-1-piperidyl]-2-(2,6-dioxo-3-piperidyl)isoindoline-1,3-dione (Compound 2)

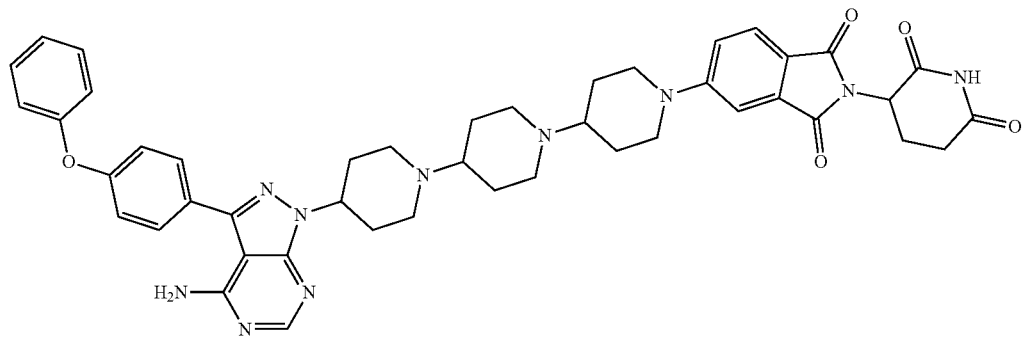 [SMILES: Nc1ncnc2c1c(-c1ccc(Oc3ccccc3)cc1)nn2C1CCN(C2CCN(C3CCN(c4ccc5c(c4)C(=O)N(C4CCC(=O)NC4=O)C5=O)CC3)CC2)CC1]

3-(4-phenoxyphenyl)-1-[1-[1-(4-piperidyl)-4-piperidyl]-4-piperidyl]pyrazolo[3,4-d]pyrimidin-4-amine (2d) (0.165 g, 0.299 mmol) was dissolved in 2 mL of dimethyl sulfoxide, 2-(2,6-dioxopiperidin-3-yl)-5-fluoroisoindoline-1,3-dione (see WO 2017197056 for the synthetic method) (0.0907 g, 0.328 mmol) and diisopropylethylamine (0.193 g, 1.49 mmol) were added. Upon completion of the addition, the reaction was stirred at 90° C. for 2 h. The reaction solution was cooled to room temperature, to which 10 mL of water was slowly added dropwise, and filtered. The filter cake was dissolved with 20 mL of dichloromethane, and then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-92:8), to obtain 5-[4-[4-[4-[4-amino-3-(4-phenoxyphenyl)pyrazolo[3,4-d]pyrimidin-1-yl]-1-piperidyl]-1-piperidyl]-1-piperidyl]-2-(2,6-dioxo-3-piperidyl)isoindoline-1,3-dione (Compound 2) (0.157 g, yield: 65%).

$^1$H NMR (400 MHz, DMSO-$d_6$) δ 11.06 (s, 1H), 8.23 (s, 1H), 7.67-7.64 (m, 3H), 7.46-7.40 (m, 2H), 7.31 (s, 1H), 7.25-7.23 (m, 1H), 7.22-7.10 (m, 5H), 5.06 (dd, 1H), 4.67-4.57 (m, 1H), 4.10-4.02 (m, 2H), 3.06-2.82 (m, 7H), 2.62-2.47 (m, 3H), 2.35-2.07 (m, 7H), 2.06-1.97 (m, 1H), 1.94-1.86 (m, 2H), 1.85-1.77 (m, 2H), 1.77-1.70 (m, 2H), 1.54-1.36 (m, 4H).

LCMS m/z=405.3 [M/2+1]$^+$.

Example 3

5-[5-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrol-2-yl]-2-(2,6-dioxo-3-piperidyl)isoindoline-1,3-dione tetratrifluoroacetate (Compound 3)

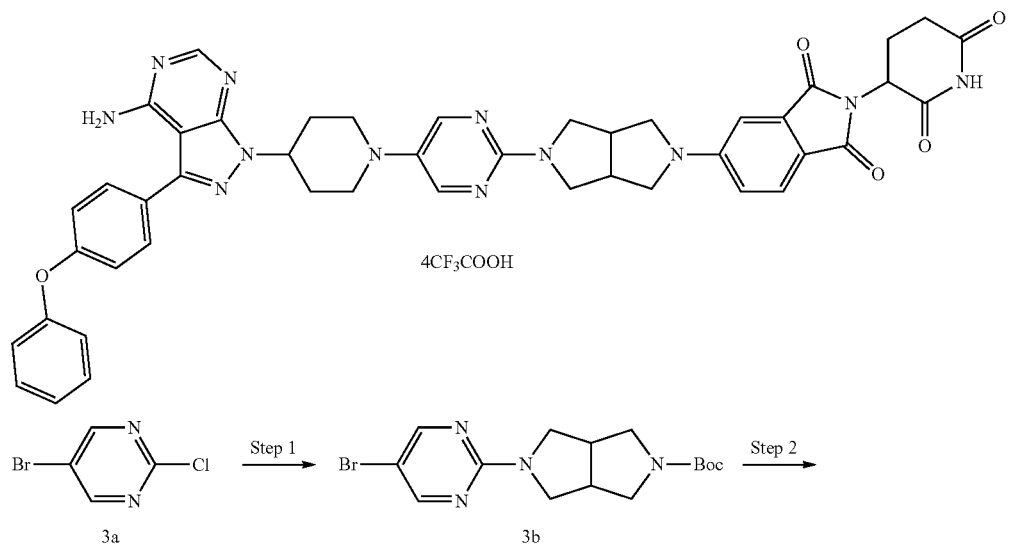

-continued
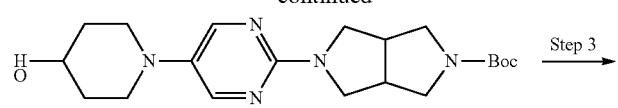
3c
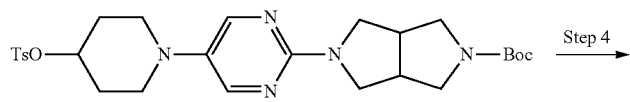
3d
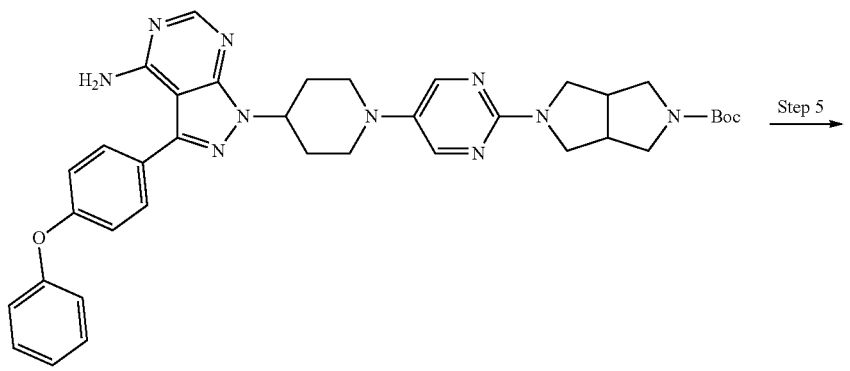
3e
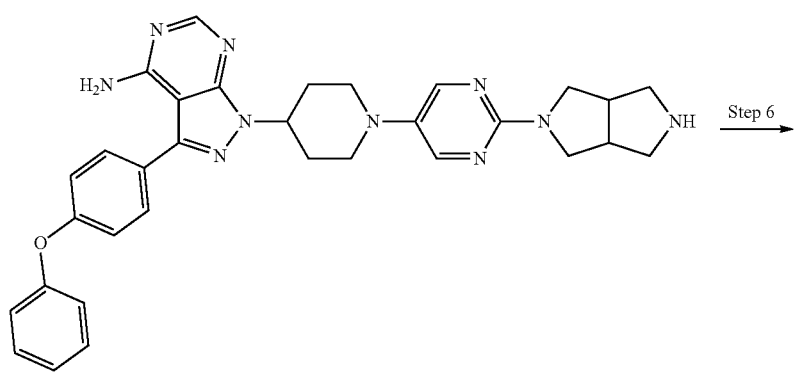
3f
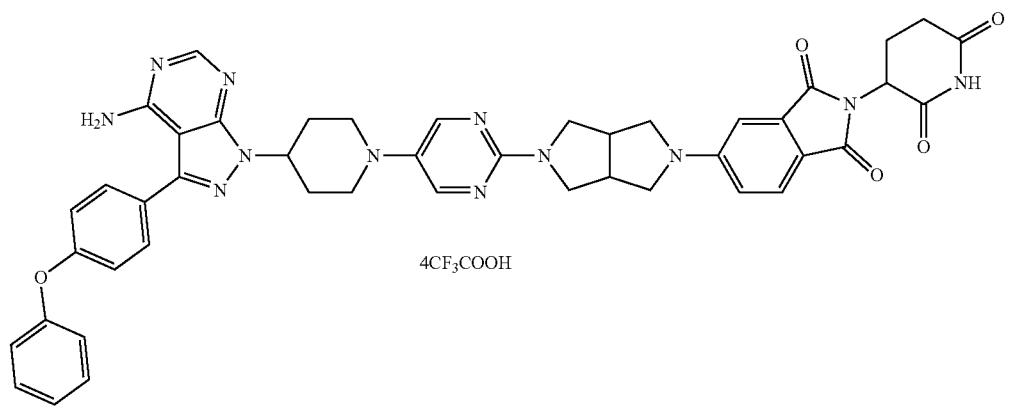
4CF₃COOH

Step 1

Tert-butyl 2-(5-bromopyrimidin-2-yl)-1,3,3a,4,6,6a-hexahydropyrrolo[3,4-c]pyrrole-5-carboxylate (3b)

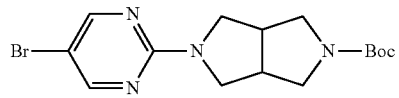

5-bromo-2-chloro-pyrimidine (1.0 g, 5.17 mmol) was dissolved in 10 mL of anhydrous ethanol, 2-Boc-hexahydropyrrolo[3,4-c]pyrrole (1.32 g, 6.20 mmol) was added, and then triethylamine (1.31 g, 12.9 mmol) was added. Upon completion of the addition, the reaction was stirred at 60° C. for 2 h. The reaction solution was cooled to room temperature, and 20 mL of water and 50 mL of ethyl acetate were added. The liquid separation was conducted, and the organic layer was washed with 20 mL of saturated sodium chloride solution, dried over anhydrous sodium sulfate, and concentrated under reduced pressure, then the crude product was separated and purified by silica gel column chromatography (petroleum ether/ethyl acetate (v/v)=9:1-4:1), to obtain tert-butyl 2-(5-bromopyrimidin-2-yl)-1,3,3a,4,6,6a-hexahydropyrrolo[3,4-c]pyrrole-5-carboxylate (3b) (1.80 g, yield: 94%).

Step 2

Tert-butyl 2-[5-(4-hydroxy-1-piperidyl)pyrimidin-2-yl]-1,3,3a,4,6,6a-hexahydropyrrolo[3,4-c]pyrrole-5-carboxylate (3c)

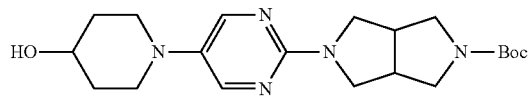

Tert-butyl 2-(5-bromopyrimidin-2-yl)-1,3,3a,4,6,6a-hexahydropyrrolo[3,4-c]pyrrole-5-carboxylate (3b) (1.0 g, 2.71 mmol) was dissolved in 10 mL of dried toluene, 4-hydroxypiperidine (0.548 g, 5.42 mmol), JohnPhos (2-(di-tert-butylphosphine)biphenyl) (0.0808 g, 0.271 mmol, CAS:224311-51-7) and tert-butoxysodium (0.520 g, 5.42 mmol) were successively added. Nitrogen replacement was carried out three times, then Pd$_2$(dba)$_3$ (0.060 g, 0.135 mmol, CAS:51364-51-3) was added. Upon completion of the addition, the reaction was stirred at 100° C. for 2 h. The reaction solution was cooled to room temperature, and 20 mL of dichloromethane and 20 mL of water were added. The liquid separation was conducted, and the organic layer was washed with 10 mL of saturated sodium chloride solution, dried over anhydrous sodium sulfate, and concentrated under reduced pressure, then the crude product was separated and purified by silica gel column chromatography (petroleum ether/ethyl acetate (v/v)=4:1-0:100), to obtain tert-butyl 2-[5-(4-hydroxy-1-piperidyl)pyrimidin-2-yl]-1,3,3a,4,6,6a-hexahydropyrrolo[3,4-c]pyrrole-5-carboxylate (3c) (0.300 g, yield: 28%).

LCMS m/z=390.3 [M+1]$^+$.

Step 3

Tert-butyl 2-[5-[4-(p-tosyloxy)-1-piperidyl]pyrimidin-2-yl]-1,3,3a,4,6,6a-hexahydropyrrolo[3,4-c]pyrrole-5-carboxylate (3d)

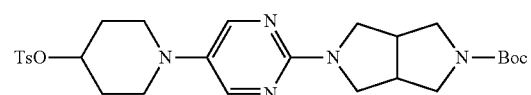

Tert-butyl

2-[5-(4-hydroxy-1-piperidyl)pyrimidin-2-yl]-1,3,3a,4,6,6a-hexahydropyrrolo[3,4-c]pyrrole-5-carboxylate (3c) (0.300 g, 0.770 mmol) was dissolved in 10 mL of dichloromethane, 4-dimethylaminopyridine (0.113 g, 0.924 mmol) was added, then p-toluenesulfonyl chloride (0.176 g, 0.924 mmol) was added. Upon completion of the addition, the reaction was carried out at room temperature for 2 h. 20 mL of saturated sodium bicarbonate solution and 20 mL of dichloromethane were added. The liquid separation was conducted, and the organic layer was dried over anhydrous sodium sulfate, and concentrated under reduced pressure, then the crude product was separated and purified by silica gel column chromatography (petroleum ether/ethyl acetate (v/v)=2:3-1:4), to obtain tert-butyl 2-[5-[4-(p-tolylsulfonyloxy)-1-piperidyl]pyrimidin-2-yl]-1,3,3a,4,6,6a-hexahydropyrrolo[3,4-c]pyrrole-5-carboxylate (3d) (0.420 g, yield: >99%).

LCMS m/z=544.3 [M+1]$^+$.

Step 4

Tert-butyl 2-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrole-5-carboxylate (3e)

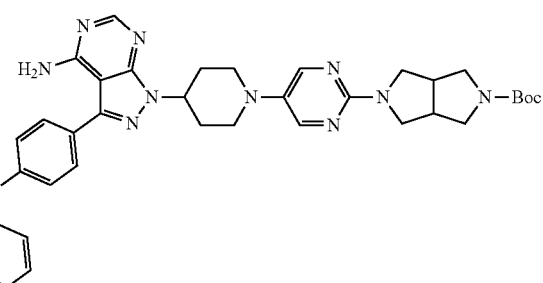

Tert-butyl

2-[5-[4-(p-tosyloxy)-1-piperidyl]pyrimidin-2-yl]-1,3,3a,4,6,6a-hexahydropyrrolo[3,4-c]pyrrole-5-carboxylate (3d) (0.400 g, 0.736 mmol) was dissolved in 5 mL of N,N'-dimethylformamide, and 3-(4-phenoxyphenyl)-1-(piperidin-4-yl)-1H-pyrazolo[3,4-d]pyrimidin-4-amine (1a) (see J. Med. Chem. 2015, 58, 9625-9638 for the synthetic method) (0.268 g, 0.883 mmol) was added, and then cesium carbonate (0.479 g, 1.47 mmol) was added. Upon completion of the addition, the reaction was stirred at 80° C. for 2 h. The reaction solution was cooled to room temperature, and 10 mL of water and 30 mL of ethyl acetate were added. The liquid separation was conducted, and the organic layer was with washed 10 mL of saturated sodium chloride solution, dried over anhydrous sodium sulfate, and concentrated under reduced pressure, then the crude product was separated and purified by silica gel column chromatography (petroleum ether/ethyl acetate (v/v)=2:3-1:4) to (dichloromethane/methanol (v/v)=25:2), to obtain tert-butyl 2-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrole-5-carboxylate (3e) (0.200 g, yield: 40%).

$^1$H NMR (400 MHz, CDCl$_3$) δ 8.37 (s, 1H), 8.19 (s, 2H), 7.70-7.62 (m, 2H), 7.44-7.34 (m, 2H), 7.21-7.13 (m, 3H), 7.13-7.05 (m, 2H), 5.80 (br, 2H), 4.94-4.85 (m, 1H), 3.85-3.75 (m, 2H), 3.72-3.58 (m, 2H), 3.54-3.46 (m, 4H), 3.38-3.24 (m, 2H), 3.02-2.90 (m, 4H), 2.64-2.52 (m, 2H), 2.16-2.12 (m, 2H), 1.45 (s, 9H).

LCMS m/z=675.3 [M+1]$^+$.

Step 5

1-[1-[2-(2,3,3a,4,6,6a-hexahydro-1H-pyrrolo[3,4-c]pyrrol-5-yl)pyrimidin-5-yl]-4-piperidyl]-3-(4-phenoxyphenyl)pyrazolo[3,4-d]pyrimidin-4-amine (3f)

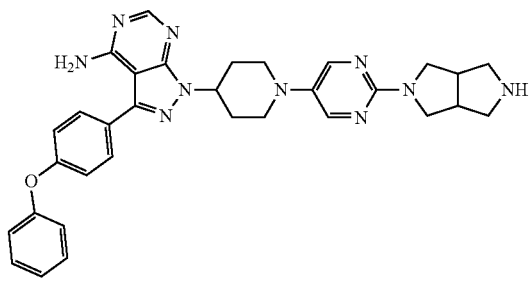 [SMILES: Nc1ncnc2c1c(-c1ccc(Oc3ccccc3)cc1)nn2C1CCN(c2cnc(N3CC4CNCC4C3)nc2)CC1]

Tert-butyl

2-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrole-5-carboxylate (3e) (0.200 g, 0.296 mmol) was dissolved in 2 mL of dichloromethane, 10 mL of 4N ethyl acetate hydrochloride solution was added, and the mixture was stirred at room temperature for 1 h. The reaction solution was concentrated, and then to the crude product was added 30 mL of dichloromethane. The pH was adjusted to 9-10 with saturated sodium bicarbonate solution. The liquid separation was conducted, and the aqueous layer was further extracted with 20 mL of dichloromethane once, the organic layers were combined, dried over anhydrous sodium sulfate, and concentrated under reduced pressure to obtain 1-[1-[2-(2,3,3a,4,6,6a-hexahydro-1H-pyrrolo[3,4-c]pyrrol-5-yl)pyrimidin-5-yl]-4-piperidyl]-3-(4-phenoxyphenyl)pyrazolo[3,4-d]pyrimidin-4-amine (30 (0.170 g, yield: >99%).

LCMS m/z=288.2 [M/2+1]$^+$.

Step 6

5-[5-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrol-2-yl]-2-(2,6-dio xo-3-piperidyl)isoindoline-1,3-dione tetratrifluoroacetate (Compound 3)

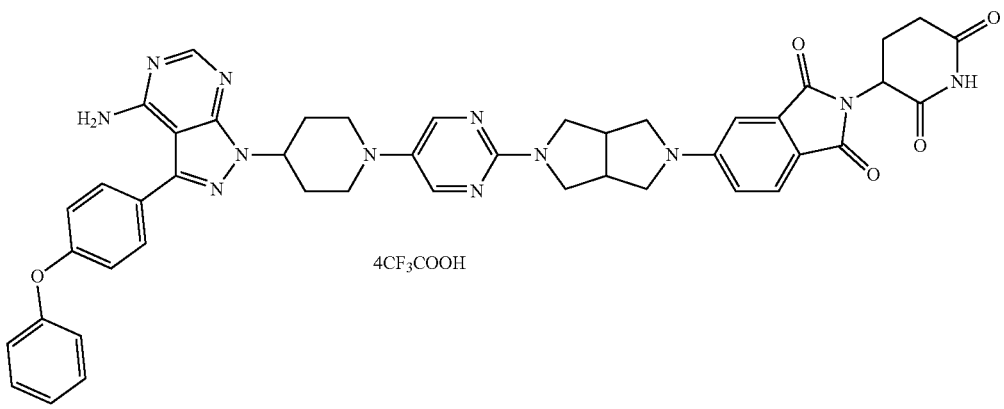 [SMILES: Nc1ncnc2c1c(-c1ccc(Oc3ccccc3)cc1)nn2C1CCN(c2cnc(N3CC4CN(c5ccc6c(c5)C(=O)N(C5CCC(=O)NC5=O)C6=O)CC4C3)nc2)CC1]

1-[1-[2-(2,3,3a,4,6,6a-hexahydro-1H-pyrrolo[3,4-c]pyrrol-5-yl)pyrimidin-5-yl]-4-piperidyl]-3-(4-phenoxyphenyl)pyrazolo[3,4-d]pyrimidin-4-amine (30 (0.170 g, 0.296 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.090 g, 0.325 mmol) and diisopropylethylamine (0.191 g, 1.48 mmol) were added. Upon completion of the addition, the reaction was stirred at 90° C. for 2 h. The reaction solution was cooled to room temperature, to which 10 mL of water was slowly added dropwise, and filtered. The filter cake was dissolved with 20 mL of dichloromethane, then washed with 5 mL of saturated sodium chloride solution. The liquid separation was conducted, and the organic layer was dried over anhydrous sodium sulfate, and concentrated under reduced pressure, then the crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-[5-[5-[4-[4-amino-3-(4-phenoxyphenyl)pyrazolo[3,4-d]pyrimidin-1-yl]-1-piperidyl]pyrimidin-2-yl]-1,3,3a,4,6,6a-hexahydropyrrolo[3,4-c]pyrrol-2-yl]-2-(2,6-dioxo-3-piperidyl)isoindoline-1,3-dione tetratrifluoroacetate (Compound 3) (0.082 g, yield: 22%).

$^1$H NMR (400 MHz, CDCl$_3$) δ 8.39 (s, 1H), 8.36 (s, 1H), 8.19 (s, 2H), 7.69-7.59 (m, 3H), 7.40 (t, 2H), 7.20-7.12 (m, 3H), 7.11-7.06 (m, 2H), 6.96 (d, 1H), 6.70 (dd, 1H), 6.30 (br, 2H), 4.95-4.88 (m, 2H), 3.94-3.86 (m, 2H), 3.86-3.70 (m, 2H), 3.60 (dd, 2H), 3.57-3.48 (m, 2H), 3.41 (dd, 2H), 3.27-3.12 (m, 2H), 3.04-2.65 (m, 6H), 2.64-2.51 (m, 2H), 2.19-2.10 (m, 2H).

LCMS m/z=416.3 [M/2+1]$^+$.

Example 4

5-[2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-7-yl]-2-(2,6-dioxo-3-piperidyl)isoindoline-1,3-dione (Compound 4)

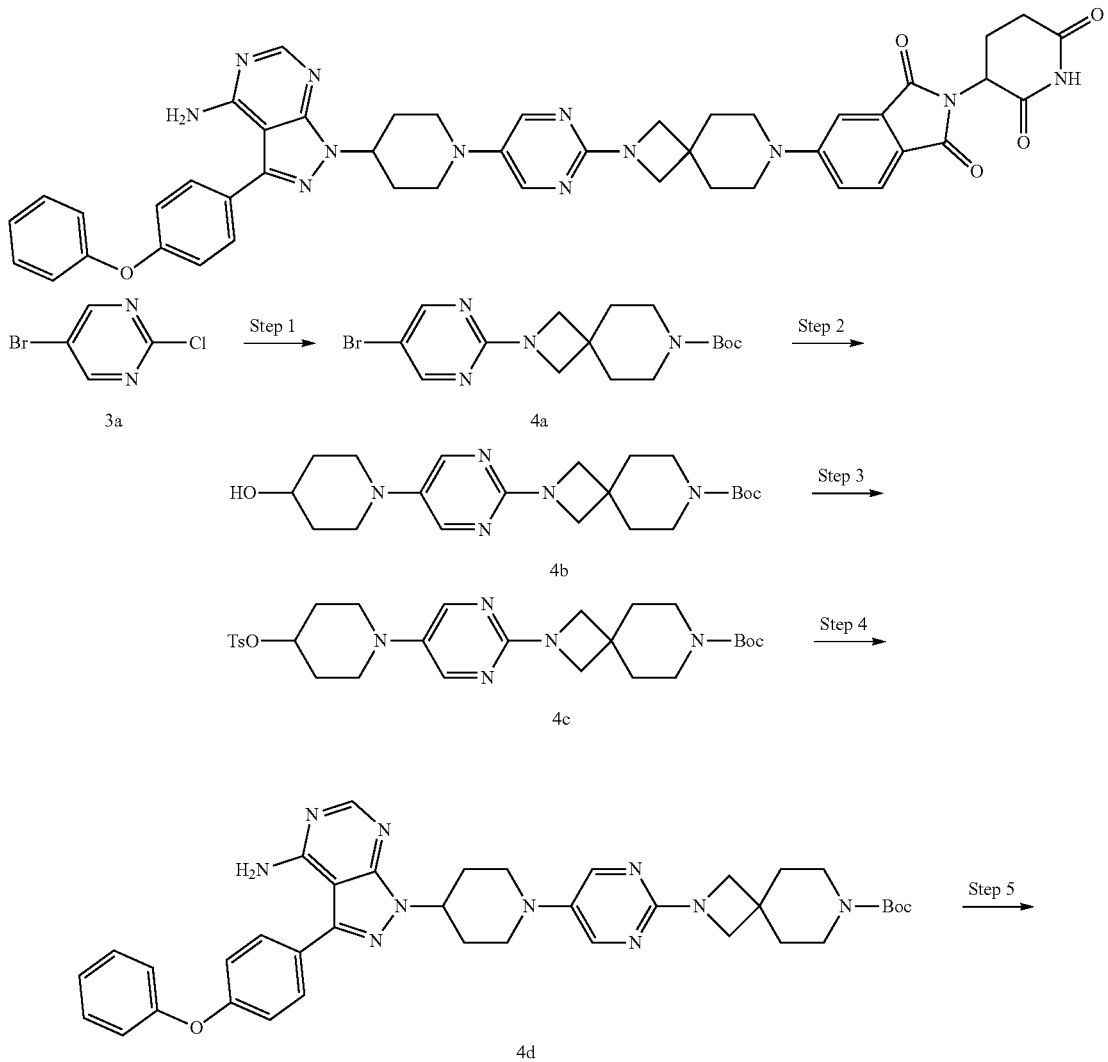

-continued

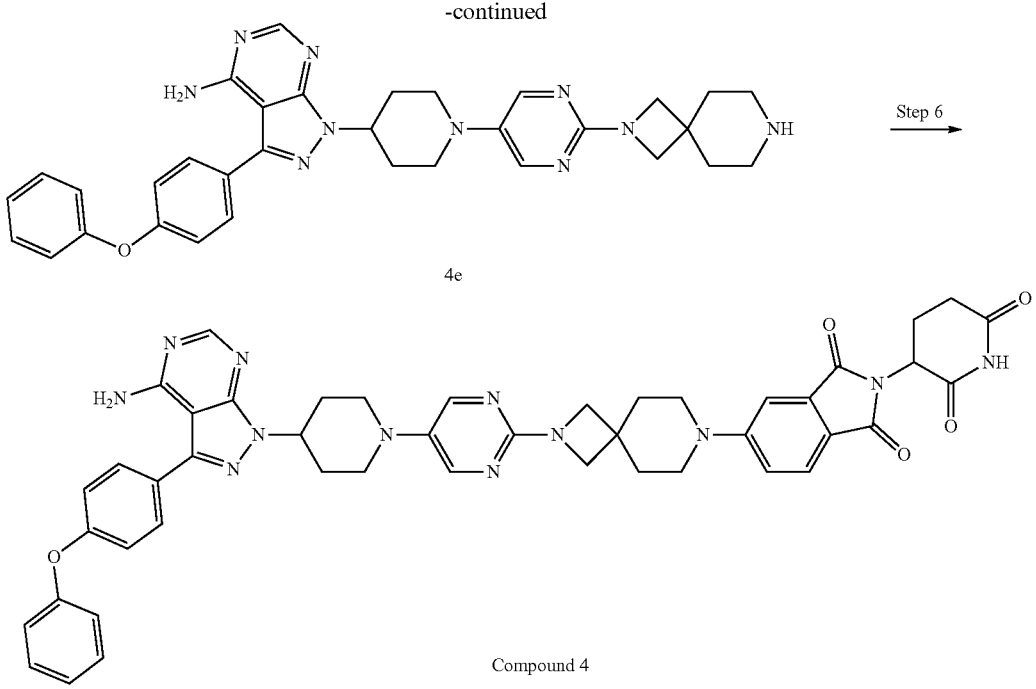

4e

Compound 4

Step 1

Tert-butyl 2-(5-bromopyrimidin-2-yl)-2,7-diazaspiro[3.5]nonane-7-carboxylate (4a)

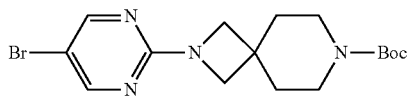

Tert-butyl 5-bromo-2-chloro-pyrimidine (3a) (1.0 g, 5.17 mmol) was dissolved in 10 mL of anhydrous ethanol, and 2,7-diazaspiro[3.5]nonane-7-carboxylate hydrochloride (1.60 g, 6.20 mmol) was added, and then triethylamine (1.31 g, 12.9 mmol) was added. Upon completion of the addition, the reaction was stirred at 60° C. for 2 h. The reaction solution was cooled to room temperature, and 20 mL of water and 50 mL of ethyl acetate were added. The liquid separation was conducted, and the organic layer was washed with 30 mL of saturated sodium chloride solution, dried over anhydrous sodium sulfate, and concentrated under reduced pressure, then the crude product was separated and purified by silica gel column chromatography (petroleum ether/ethyl acetate (v/v)=4:1), to obtain tert-butyl 2-(5-bromopyrimidin-2-yl)-2,7-diazaspiro[3.5]nonane-7-carboxylate (4a) (1.60 g, yield: 81%).

LCMS m/z=383.1 [M+1]$^+$.

Step 2

Tert-butyl 2-[5-(4-hydroxy-1-piperidyl)pyrimidin-2-yl]-2,7-diazaspiro[3.5]nonane-7-carboxylate (4b)

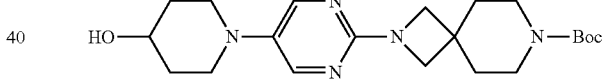

Tert-butyl 2-(5-bromopyrimidin-2-yl)-2,7-diazaspiro[3.5]nonane-7-carboxylate (4a) (1.00 g, 2.61 mmol) was dissolved in 10 mL of dried toluene, and 4-hydroxypiperidine (0.264 g, 2.61 mmol), JohnPhos (0.0389 g, 0.130 mmol) and tert-butoxysodium (0.251 g, 2.61 mmol) were added. Nitrogen replacement was carried out three times, then Pd$_2$(dba)$_3$ (0.060 g, 0.13 mmol) was added. Upon completion of the addition, the reaction was stirred at 100° C. for 2 h. The reaction solution was cooled to room temperature, and 20 mL of dichloromethane and 20 mL of water were added. The liquid separation was conducted, and the organic layer was washed with 10 mL of saturated sodium chloride solution, dried over anhydrous sodium sulfate, and concentrated under reduced pressure, then the crude product was separated and purified by silica gel column chromatography (petroleum ether/ethyl acetate (v/v)=4:1-0:100), to obtain tert-butyl 2-[5-(4-hydroxy-1-piperidyl)pyrimidin-2-yl]-2,7-diazaspiro[3.5]nonane-7-carboxylate (4b) (0.530 g, yield: 50%).

$^1$H NMR (400 MHz, DMSO-d$_6$) δ 8.14 (s, 2H), 4.64 (s, 1H), 3.68 (s, 4H), 3.61-3.53 (m, 1H), 3.31-3.23 (m, 6H), 2.76-2.65 (m, 2H), 1.87-1.75 (m, 2H), 1.71-1.59 (m, 4H), 1.58-1.44 (m, 2H), 1.39 (s, 9H).

LCMS m/z=404.3 [M+1]$^+$.

Step 3

Tert-butyl

2-[5-[4-(p-tosyloxy)-1-piperidyl]pyrimidin-2-yl]-2,7-diazaspiro[3.5]nonane-7-carboxylate (4c)

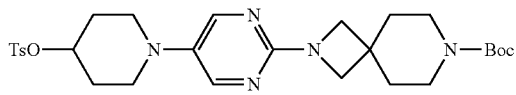

Tert-butyl

2-[5-(4-hydroxy-1-piperidyl)pyrimidin-2-yl]-2,7-diazaspiro[3.5]nonane-7-carboxylate (4b) (0.530 g, 1.31 mmol) was dissolved in 10 mL of dichloromethane, and 4-dimethylaminopyridine (0.321 g, 2.63 mmol) was added, then p-toluenesulfonyl chloride (0.501 g, 2.63 mmol) was added. Upon completion of the addition, the reaction was carried out at room temperature for 2 h. 20 mL of saturated sodium bicarbonate solution and 20 mL of dichloromethane were added. The liquid separation was conducted, and the organic layer was dried over anhydrous sodium sulfate, and concentrated under reduced pressure, then the crude product was separated and purified by silica gel column chromatography (petroleum ether/ethyl acetate (v/v)=2:3-1:4), to obtain tert-butyl 2-[5-[4-(p-tosyloxy)-1-piperidyl]pyrimidin-2-yl]-2,7-diazaspiro[3.5]nonane-7-carboxylate (4c) (0.550 g, yield: 75%).

LCMS m/z=558.3 [M+1]$^+$.

Step 4

Tert-butyl

2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-7-carboxylate (4d)

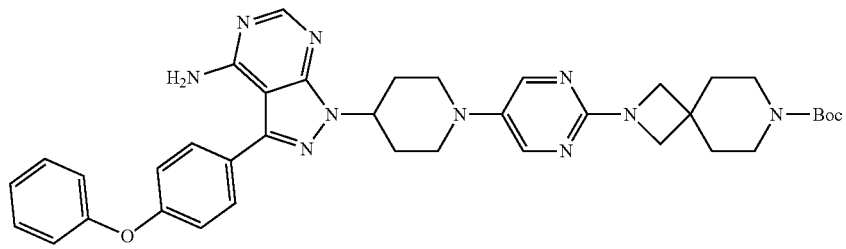 [SMILES: CC(C)(C)OC(=O)N1CCC2(CC1)CN(c1ncc(N3CCC(n4nc(-c5ccc(Oc6ccccc6)cc5)c5c(N)ncnc54)CC3)cn1)C2]

Tert-butyl

2-[5-[4-(p-tosyloxy)-1-piperidyl]pyrimidin-2-yl]-2,7-diazaspiro[3.5]nonane-7-carboxylate (4c) (0.500 g, 0.897 mmol) was dissolved in 5 mL of N,N'-dimethylformamide, and 3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.326 g, 1.08 mmol) was added, and then cesium carbonate (0.584 g, 1.79 mmol) was added. Upon completion of the addition, the reaction was stirred at 80° C. for 2 h. The reaction solution was cooled to room temperature, and 10 mL of water and 30 mL of ethyl acetate were added. The liquid separation was conducted, and the organic layer was with washed 10 mL of saturated sodium chloride solution, dried over anhydrous sodium sulfate, and concentrated under reduced pressure, then the crude product was separated and purified by silica gel column chromatography (petroleum ether/ethyl acetate (v/v)=2:3-1:4) to (dichloromethane/methanol (v/v)=25:2), to obtain tert-butyl 2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-7-carboxylate (4d) (0.230 g, yield: 37%).

LCMS m/z=345.3 [M/2+1]$^+$.

Step 5

1-[1-[2-(2,7-diazaspiro[3.5]nonan-2-yl)pyrimidin-5-yl]-4-piperidyl]-3-(4-phenoxyphenyl)pyrazolo[3,4-d]pyrimidin-4-amine (4e)

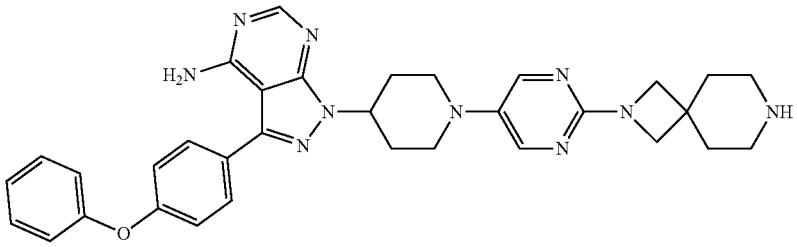 [SMILES: Nc1ncnc2c1c(-c1ccc(Oc3ccccc3)cc1)nn2C1CCN(c2cnc(N3CC4(CCNCC4)C3)nc2)CC1]

Tert-butyl 2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-7-carboxylate (4d) (0.230 g, 0.334 mmol) was dissolved in 2 mL of dichloromethane, and 10 mL of 4N ethyl acetate hydrochloride solution was added, and the mixture was stirred at room temperature for 1 h. The reaction solution was concentrated, and then to the crude product was added 30 mL of dichloromethane. The pH was adjusted to 9-10 with saturated sodium bicarbonate solution. The liquid separation was conducted, and the aqueous layer was further extracted with 20 mL of dichloromethane once, the organic layers were combined, dried over anhydrous sodium sulfate, and concentrated under reduced pressure to obtain 1-[1-[2-(2,7-diazaspiro[3.5]nonan-2-yl)pyrimidin-5-yl]-4-piperidyl]-3-(4-phenoxyphenyl)pyrazolo[3,4-d]pyrimidin-4-amine (4e) (0.197 g, yield: >99%).

LCMS m/z=589.3 [M+1]$^+$.

Step 6

5-[2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-7-yl]-2-(2,6-dioxo-3-piperidyl)isoindoline-1,3-dione (Compound 4)

1-[1-[2-(2,7-diazaspiro[3.5]nonan-2-yl)pyrimidin-5-yl]-4-piperidyl]-3-(4-phenoxyphenyl)pyrazolo[3,4-d]pyrimidin-4-amine (4e) (0.170 g, 0.289 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.0877 g, 0.318 mmol) and diisopropylethylamine (0.187 g, 1.44 mmol) were added. Upon completion of the addition, the reaction was stirred at 90° C. for 2 h. The reaction solution was cooled to room temperature, to which 10 mL of water was slowly added dropwise, and filtered. The filter cake was dissolved with 20 mL of dichloromethane, and then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-92:8), to obtain 5-[2-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-7-yl]-2-(2,6-dioxo-3-piperidyl)isoindoline-1,3-dione (Compound 4) (0.030 g, yield: 11%).

$^1$H NMR (400 MHz, DMSO-d$_6$) δ 11.06 (s, 1H), 8.28 (s, 1H), 8.25 (s, 2H), 7.68-7.65 (m, 3H), 7.44 (t, 2H), 7.35 (s, 1H), 7.28 (d, 1H), 7.22-7.09 (m, 5H), 5.06 (dd, 1H), 4.90-4.80 (m, 1H), 3.77 (s, 4H), 3.63-3.58 (m, 2H), 3.55-3.47 (m, 4H), 2.95-2.85 (m, 3H), 2.63-2.51 (m, 2H), 2.40-2.27 (m, 2H), 2.05-1.97 (m, 3H), 1.83 (s, 4H).

LCMS m/z=423.3 [M/2+1]$^+$.

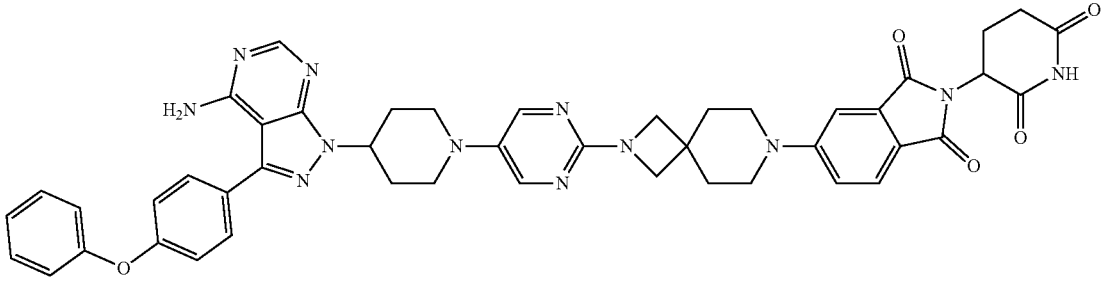 [SMILES: Nc1ncnc2c1c(-c1ccc(Oc3ccccc3)cc1)nn2C1CCN(c2cnc(N3CC4(CCN(c5ccc6c(c5)C(=O)N(C5CCC(=O)NC5=O)C6=O)CC4)C3)nc2)CC1]

Example 5
5-[7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-2-yl]-2-(2,6-dioxo-3-piperidyl)isoindoline-1,3-dione (Compound 5)
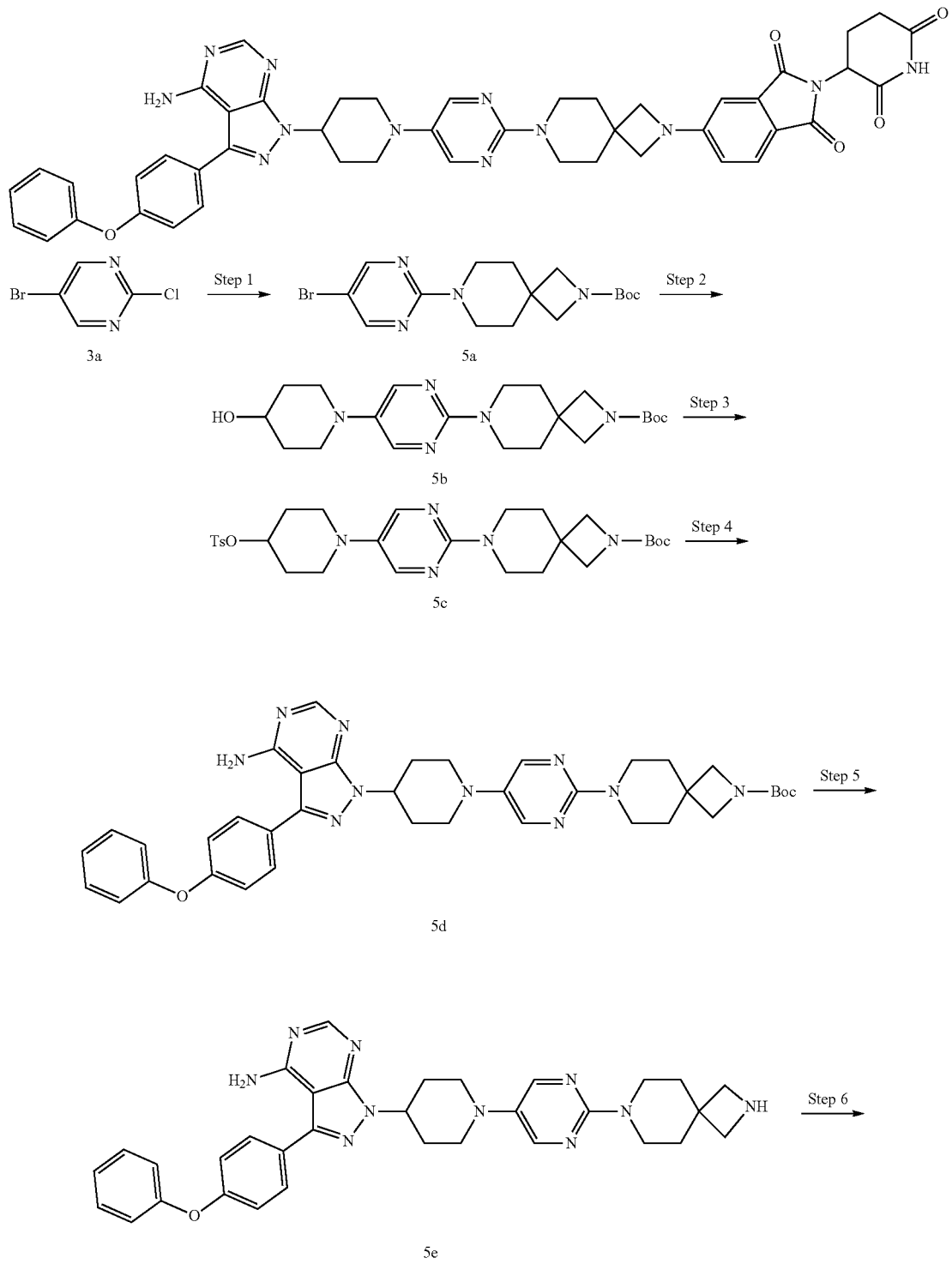

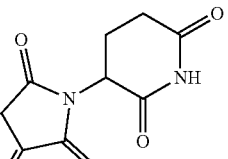

Compound 5

Step 1

Tert-butyl 7-(5-bromopyrimidin-2-yl)-2,7-diazaspiro[3.5]nonane-2-carboxylate (5a)

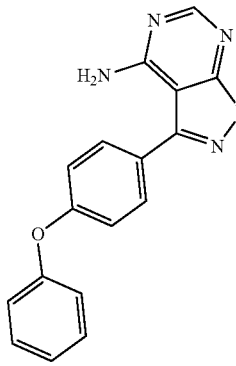

Tert-butyl 5-bromo-2-chloro-pyrimidine (3a) (1.0 g, 5.17 mmol) was dissolved in 10 mL of anhydrous ethanol, and 2,7-diazaspiro[3.5]nonane-2-carboxylate hydrochloride (1.60 g, 6.20 mmol) was added, then triethylamine (1.31 g, 12.9 mmol) was added. Upon completion of the addition, the reaction was stirred at 60° C. for 2 h. The reaction solution was cooled to room temperature, and 20 mL of water and 50 mL of ethyl acetate were added. The liquid separation was conducted, and the organic layer was washed with 20 mL of saturated sodium chloride solution, dried over anhydrous sodium sulfate, and concentrated under reduced pressure, then the crude product was separated and purified by silica gel column chromatography (petroleum ether/ethyl acetate (v/v)=4:1), to obtain tert-butyl 7-(5-bromopyrimidin-2-yl)-2,7-diazaspiro[3.5]nonane-2-carboxylate (5a) (1.60 g, yield: 81%).

Step 2

Tert-butyl 7-[5-(4-hydroxy-1-piperidyl)pyrimidin-2-yl]-2,7-diazaspiro[3.5]nonane-2-carboxylate (5b)

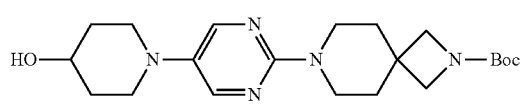 [SMILES: CC(C)(C)OC(=O)N1CC2(CCN(c3ncc(N4CCC(O)CC4)cn3)CC2)C1]

Tert-butyl 7-(5-bromopyrimidin-2-yl)-2,7-diazaspiro[3.5]nonane-2-carboxylate (5a) (0.500 g, 1.30 mmol) was dissolved in 10 mL of dried toluene, and 4-hydroxypiperidine (0.264 g, 2.61 mmol), JohnPhos (0.0389 g, 0.130 mmol) and tert-butoxysodium (0.251 g, 2.61 mmol) were added. Nitrogen replacement was carried out three times, and then Pd$_2$(dba)$_3$ (0.060 g, 0.065 mmol) was added. Upon completion of the addition, the reaction was stirred at 100° C. for 2 h. The reaction solution was cooled to room temperature, and 20 mL of dichloromethane and 20 mL of water were added. The liquid separation was conducted, and the organic layer was washed with 10 mL of saturated sodium chloride solution, dried over anhydrous sodium sulfate, and concentrated under reduced pressure, then the crude product was separated and purified by silica gel column chromatography (petroleum ether/ethyl acetate (v/v)=4:1-0:100), to obtain tert-butyl 7-[5-(4-hydroxy-1-piperidyl)pyrimidin-2-yl]-2,7-diazaspiro[3.5]nonane-2-carboxylate (5b) (0.200 g, yield: 38%).

LCMS m/z=404.3 [M+1]$^+$.

Step 3

Tert-butyl 7-[5-[4-(p-tosyloxy)-1-piperidyl]pyrimidin-2-yl]-2,7-diazaspiro[3.5]nonane-2-carboxylate (5c)

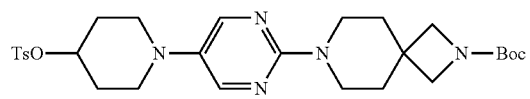 [SMILES: Cc1ccc(S(=O)(=O)OC2CCN(c3cnc(N4CCC5(CC4)CN(C(=O)OC(C)(C)C)C5)nc3)CC2)cc1]

Tert-butyl 7-[5-(4-hydroxy-1-piperidyl)pyrimidin-2-yl]-2,7-diazaspiro[3.5]nonane-2-carboxylate (5b) (0.380 g, 0.942 mmol) was dissolved in 10 mL of dichloromethane, and 4-dimethylaminopyridine (0.230 g, 1.88 mmol) was added, then p-toluenesulfonyl chloride (0.359 g, 1.88 mmol) was added. Upon completion of the addition, the reaction was carried out at room temperature for 2 h. 20 mL of saturated sodium bicarbonate solution and 20 mL of dichloromethane were added. The liquid separation was conducted, and the organic layer was dried over anhydrous sodium sulfate, and concentrated under reduced pressure, then the crude product was separated and purified by silica gel column chromatography (petroleum ether/ethyl acetate (v/v)=2:3-1:4), to obtain tert-butyl 7-[5-[4-(p-tosyloxy)-1-piperidyl]pyrimidin-2-yl]-2,7-diazaspiro[3.5]nonane-2-carboxylate (5c) (0.440 g, yield: 84%).

LCMS m/z=558.3 [M+1]$^+$.

Step 4

Tert-butyl 7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-2-carboxylate (5d)

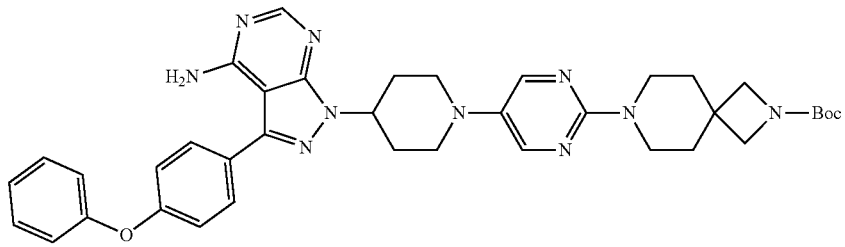 [SMILES: CC(C)(C)OC(=O)N1CC2(CCN(c3ncc(N4CCC(n5nc(-c6ccc(Oc7ccccc7)cc6)c6c(N)ncnc65)CC4)cn3)CC2)C1]

Tert-butyl 7-[5-[4-(p-tosyloxy)-1-piperidyl]pyrimidin-2-yl]-2,7-diazaspiro[3.5]nonane-2-carboxylate (5c) (0.440 g, 0.789 mmol) was dissolved in 5 mL of N,N'-dimethylformamide, and 3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.287 g, 0.947 mmol) was added, then cesium carbonate (0.514 g, 1.58 mmol) was added. Upon completion of the addition, the reaction was stirred at 80° C. for 2 h. The reaction solution was cooled to room temperature, and 10 mL of water and 30 mL of ethyl acetate were added. The liquid separation was conducted, and the organic layer was with washed 10 mL of saturated sodium chloride solution, dried over anhydrous sodium sulfate, and concentrated under reduced pressure, then the crude product was separated and purified by silica gel column chromatography (petroleum ether/ethyl acetate (v/v)=2:3-1:4) to (dichloromethane/methanol (v/v)=25:2), to obtain tert-butyl 7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-2-carboxylate (5d) (0.230 g, yield: 42%).

LCMS m/z=689.3 [M+1]$^+$.

Step 5

1-[1-[2-(2,7-diazaspiro[3.5]nonan-7-yl)pyrimidin-5-yl]-4-piperidyl]-3-(4-phenoxyphenyl)pyrazolo[3,4-d]pyrimidin-4-amine (5e)

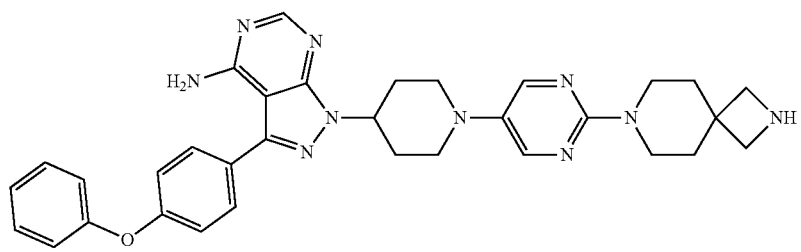 [SMILES: Nc1ncnc2c1c(-c1ccc(Oc3ccccc3)cc1)nn2C1CCN(c2cnc(N3CCC4(CC3)CNC4)nc2)CC1]

Tert-butyl 7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonane-2-carboxylate (5d) (0.230 g, 0.334 mmol) was dissolved in 2 mL of dichloromethane, and 10 mL of 4N ethyl acetate hydrochloride solution was added, and the mixture was stirred at room temperature for 1 h. The reaction solution was concentrated, and then to the crude product was added 30 mL of dichloromethane. The pH was adjusted to 9-10 with saturated sodium bicarbonate solution. The liquid separation was conducted, and the aqueous layer was further extracted with 20 mL of dichloromethane once, the organic layers were combined, dried over anhydrous sodium sulfate, and concentrated under reduced pressure to obtain 1-[1-[2-(2,7-diazaspiro[3.5]nonan-7-yl)pyrimidin-5-yl]-4-piperidyl]-3-(4-phenoxyphenyl)pyrazolo[3,4-d]pyrimidin-4-amine (5e) (0.197 g, yield: >99%).

LCMS m/z=589.3 [M+1]$^+$.

Step 6

5-[7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-2-yl]-2-(2,6-dioxo-3-piperidyl)isoindoline-1,3-dione (Compound 5)

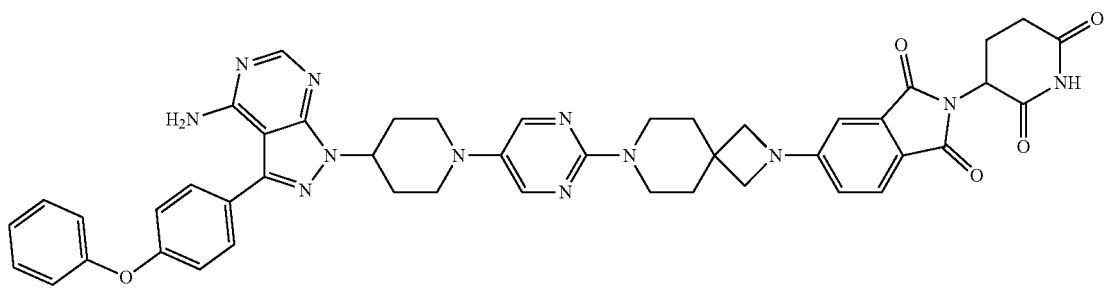 [SMILES: Nc1ncnc2c1c(-c1ccc(Oc3ccccc3)cc1)nn2C1CCN(c2cnc(N3CCC4(CC3)CN(c3ccc5c(c3)C(=O)N(C3CCC(=O)NC3=O)C5=O)C4)nc2)CC1]

1-[1-[2-(2,7-diazaspiro[3.5]nonan-7-yl)pyrimidin-5-yl]-4-piperidyl]-3-(4-phenoxyphenyl)pyrazolo[3,4-d]pyrimidin-4-amine (5e) (0.170 g, 0.289 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.0877 g, 0.318 mmol) and diisopropylethylamine (0.187 g, 1.44 mmol) were added. Upon completion of the addition, the reaction was stirred at 90° C. for 2 h. The reaction solution was cooled to room temperature, to which 10 mL of water was slowly added dropwise, and filtered. The filter cake was dissolved with 20 mL of dichloromethane, and then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-92:8), to obtain 5-[7-[5-[4-[4-amino-3-(4-phenoxyphenyl)pyrazolo[3,4-d]pyrimidin-1-yl]-1-piperidyl]pyrimidin-2-yl]-2,7-diazaspiro[3.5]nonan-2-yl]-2-(2,6-dioxo-3-piperidyl)isoindoli ne-1,3-dione (Compound 5) (0.040 g, yield: 16%).

$^1$H NMR (400 MHz, CDCl$_3$) δ 9.19 (s, 1H), 8.39 (s, 1H), 8.18 (s, 2H), 7.65 (d, 3H), 7.39 (t, 2H), 7.22-7.12 (m, 3H), 7.08 (d, 2H), 6.81 (s, 1H), 6.54 (d, 1H), 5.93 (br, 2H), 5.00-4.84 (m, 2H), 3.80 (d, 8H), 3.55 (d, 2H), 3.04-2.66 (m, 5H), 2.66-2.50 (m, 2H), 2.20-2.05 (m, 3H), 1.89 (s, 4H).

LCMS m/z=423.3 [M/2+1]$^+$.

Example 6
5-(3-(4-((4-(4-amino-3-(4-phenoxyphenyl)-1H-pyra-
zolo[3,4-d]pyrimidin-1-yl) piperidin-1-yl)methyl)
piperidin-1-yl)azetidin-1-yl)-2-(2,6-dioxopiperidin-
3-yl)isoindoline-1,3-dione tritrifluoroacetate
(Compound 6)
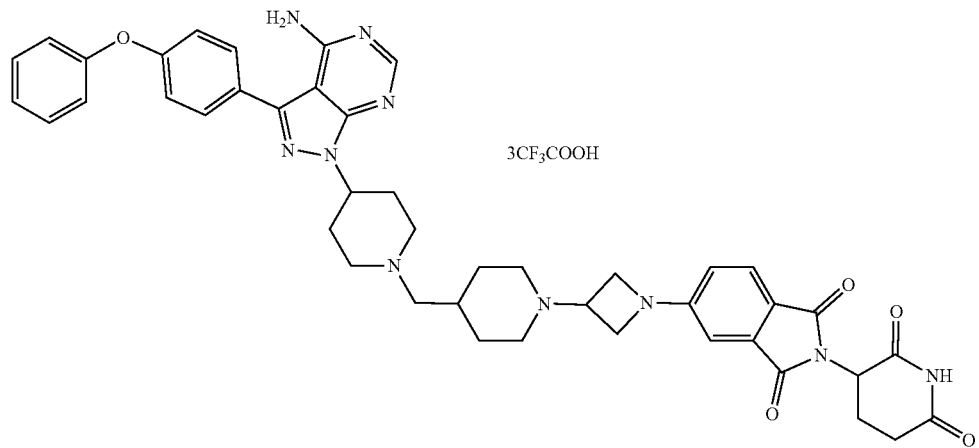
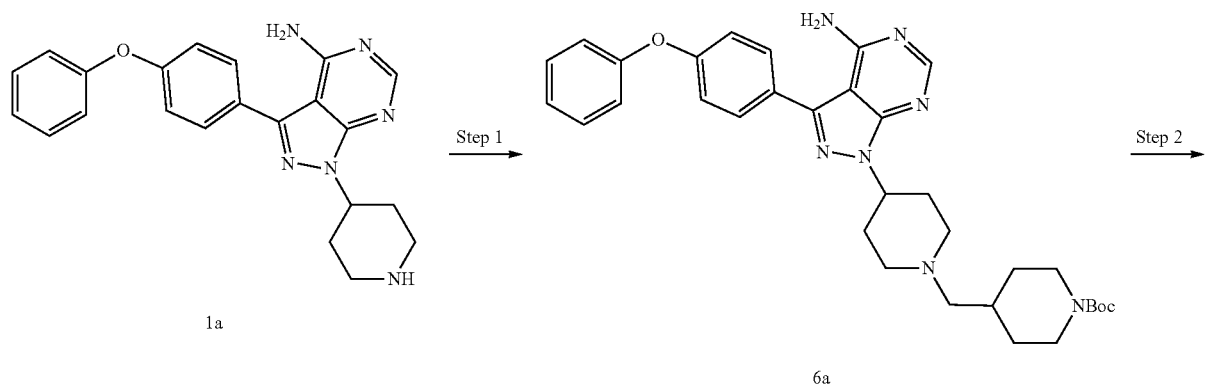
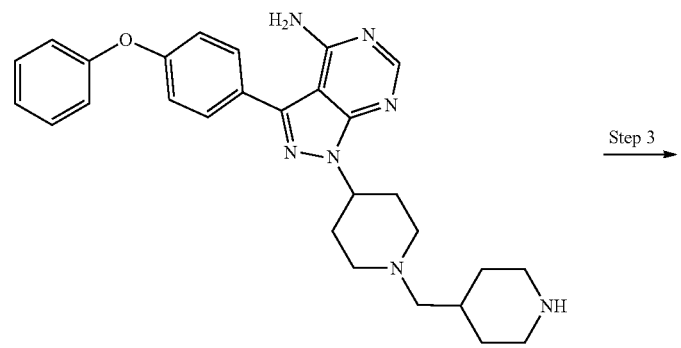

-continued
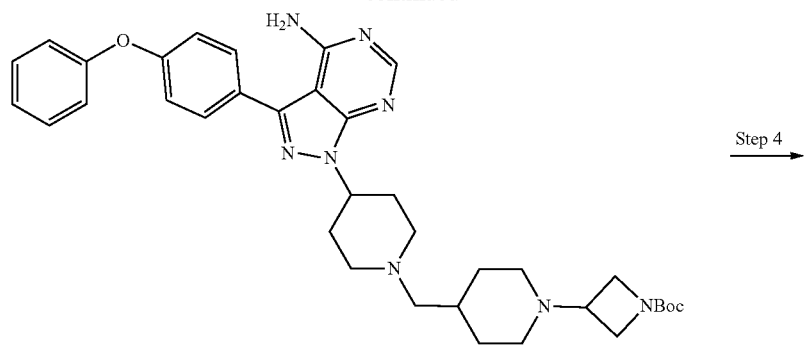
6c
Step 4
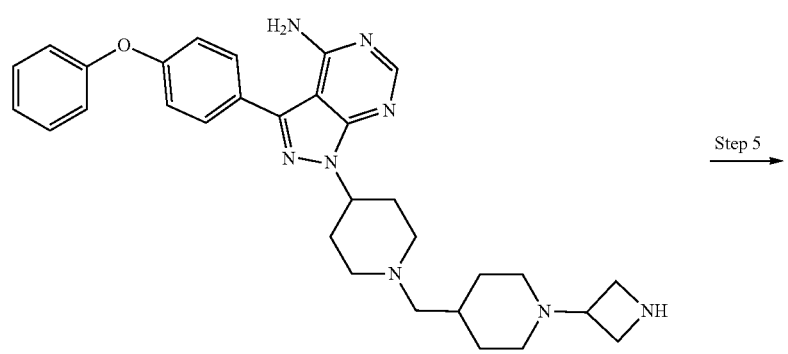
6d
Step 5
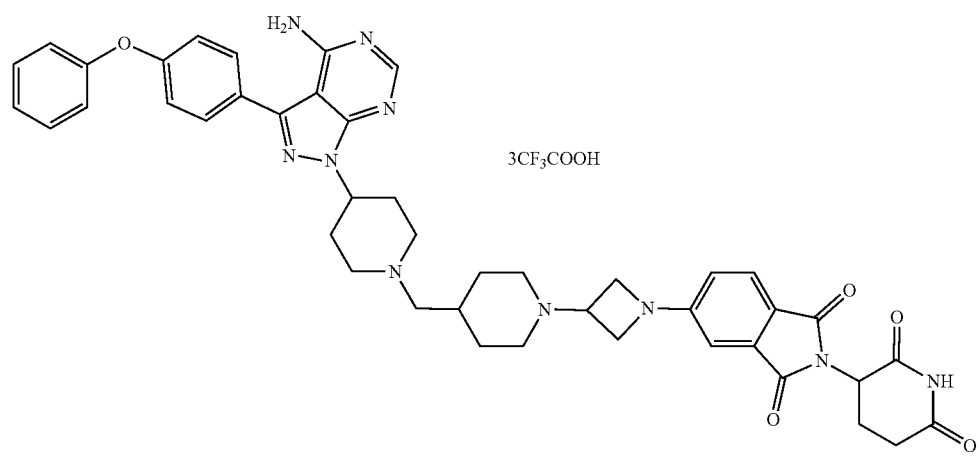
Compound 6

Step 1

Tert-butyl 4-((4-(4-amino-3-(4-phenoxyphenyl)-1H-pyrazolo[3,4-d]pyrimidin-1-yl) piperidin-1-yl)methyl)piperidine-1-carboxylate (6a)

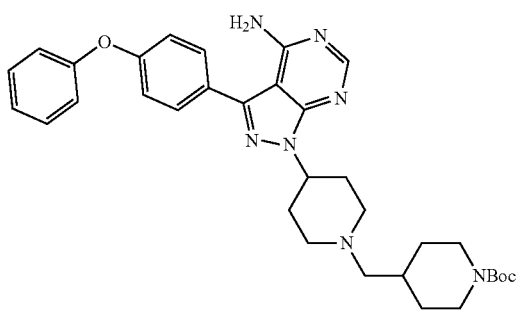 [SMILES: CC(C)(C)OC(=O)N1CCC(CN2CCC(n3nc(-c4ccc(Oc5ccccc5)cc4)c4c(N)ncnc43)CC2)CC1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.25 g, 0.59 mmol) was dissolved in 20 mL of dichloromethane, and glacial acetic acid (0.052 g, 0.89 mmol) and tert-butyl 4-formylpiperidine-1-carboxylate (0.152 g, 0.71 mmol) were successively added. The mixture was stirred under nitrogen atmosphere for 1 h, sodium triacetoxyborohydride (0.627 g, 2.96 mmol) was added, and the mixture was stirred at room temperature overnight. The reaction was quenched by adding 20 mL of saturated sodium bicarbonate solution, stirred, and allowed to stand for layer separation. The aqueous phase was extracted with dichloromethane (15 mL×2), and the organic phase was combined, washed with 30 mL of saturated saline, dried over anhydrous sodium sulfate, filtered, and concentrated under reduced pressure. The crude product was separated and purified by silica gel column chromatography (dichloromethane/methanol (v/v)=100:1-25:1), to obtain tert-butyl 4-((4-(4-amino-3-(4-phenoxyphenyl)-1H-pyrazolo[3,4-d]pyrimidin-1-yl)piperidin-1-yl)methyl)piperidine-1-carboxylate (6a) (0.284 g, yield: 82%).

Step 2

3-(4-Phenoxyphenyl)-1-(1-(piperidin-4-ylmethyl) piperidin-4-yl)-1H-pyrazolo[3,4-d]pyrimidin-4-amine (6b)

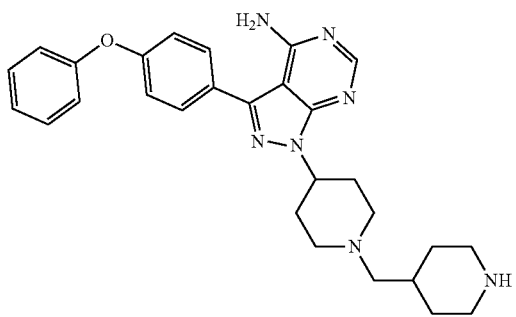 [SMILES: Nc1ncnc2c1c(-c1ccc(Oc3ccccc3)cc1)nn2C1CCN(CC2CCNCC2)CC1]

Tert-butyl 4-((4-(4-amino-3-(4-phenoxyphenyl)-1H-pyrazolo[3,4-d]pyrimidin-1-yl)piperidin-1-yl)methyl)piperidine-1-carboxylate (6a) (0.284 g, 0.487 mmol) was dissolved with 2 mL of methanol, and 10 mL of saturated ethyl acetate hydrochloride solution was added dropwise, and the mixture was reacted at room temperature overnight. The reaction solution was concentrated under reduced pressure to obtain a crude product, and the pH of the crude product was adjusted to 8-9 with saturated sodium bicarbonate solution, and the resulted solution was extracted with dichloromethane (20 mL×3). The organic phase was combined, dried over anhydrous sodium sulfate, filtered, and concentrated under reduced pressure to obtain 3-(4-phenoxyphenyl)-1-(1-(piperidin-4-ylmethyl)piperidin-4-yl)-1H-pyrazolo[3,4-d]pyrimidin-4-amine (6b) (0.22 g, yield: 94%).

Step 3

Tert-butyl 3-(4-((4-(4-amino-3-(4-phenoxyphenyl)-1H-pyrazolo[3,4-d]pyrimidin-1-yl) piperidin-1-yl)methyl) piperidin-1-yl)azetidine-1-carboxylate (6c)

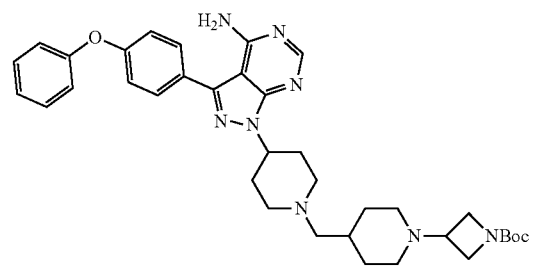 [SMILES: CC(C)(C)OC(=O)N1CC(N2CCC(CN3CCC(n4nc(-c5ccc(Oc6ccccc6)cc5)c5c(N)ncnc54)CC3)CC2)C1]

3-(4-phenoxyphenyl)-1-(1-(piperidin-4-ylmethyl)piperidin-4-yl)-1H-pyrazolo[3,4-d]pyrimidin-4-amine (6b) (0.22 g, 0.455 mmol) was dissolved in 20 mL of 1,2-dichloroethane, and glacial acetic acid (0.055 g, 0.910 mmol) and tert-butyl 3-oxoazetidine-1-carboxylate (0.094 g, 0.546 mmol) were successively added. The mixture was stirred under nitrogen atmosphere for 1 h, sodium triacetoxyborohydride (0.578 g, 2.73 mmol) was added, and the mixture was stirred at room temperature overnight. The reaction was quenched by adding 20 mL of saturated sodium bicarbonate solution, stirred, and allowed to stand for layer separation. The aqueous phase was extracted with dichloromethane (15 mL×2), and the organic phase was combined, washed with 30 mL of saturated saline, dried over anhydrous sodium sulfate, filtered, and concentrated under reduced pressure. The crude product was separated and purified by silica gel column chromatography (dichloromethane/methanol (v/v)=100:1-25:1), to obtain tert-butyl 3-(4-((4-(4-amino-3-(4-phenoxyphenyl)-1H-pyrazolo[3,4-d]pyrimidin-1-yl)piperidin-1-yl)methyl)piperidin-1-yl)azetidine-1-carboxylate (6c) (0.25 g, yield: 86%).

Step 4

1-(1-((1-(azetidin-3-yl)piperidin-4-yl)methyl)piperidin-4-yl)-3-(4-phenoxyphenyl)-1H-pyrazolo[3,4-d]pyrimidin-4-amine (6d)

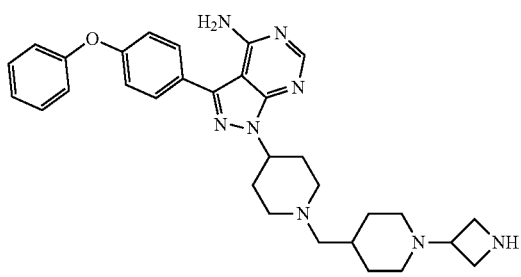 [SMILES: Nc1ncnc2c1c(-c1ccc(Oc3ccccc3)cc1)nn2C1CCN(CC2CCN(C3CNC3)CC2)CC1]

Tert-butyl 3-(4-((4-(4-amino-3-(4-phenoxyphenyl)-1H-pyrazolo[3,4-d]pyrimidin-1-yl)piperidin-1-yl)methyl)piperidin-1-yl)azetidine-1-carboxylate (6c) (0.25 g, 0.391 mmol) was dissolved with 2 mL of methanol, and 10 mL of saturated ethyl acetate hydrochloride solution was added dropwise, the mixture was reacted at room temperature overnight. The reaction solution was concentrated under reduced pressure to obtain a crude product, and the pH of the crude product was adjusted to 8-9 with saturated sodium bicarbonate solution, which was extracted with dichloromethane (20 mL×3). The organic phase was combined, dried over anhydrous sodium sulfate, filtered, and concentrated under reduced pressure to obtain 1-(1-((1-(azetidin-3-yl)piperidin-4-yl)methyl)piperidin-4-yl)-3-(4-phenoxyphenyl)-1H-pyrazolo[3,4-d]pyrimidin-4-amine (6d) (0.137 g, yield: 65%).

Step 5

5-(3-(4-((4-(4-amino-3-(4-phenoxyphenyl)-1H-pyrazolo[3,4-d]pyrimidin-1-yl) piperidin-1-yl)methyl)piperidin-1-yl)azetidin-1-yl)-2-(2,6-dioxopiperidin-3-yl)isoindoline-1,3-dione tritrifluoroacetate (Compound 6)

1-(1-((1-(azetidin-3-yl)piperidin-4-yl)methyl)piperidin-4-yl)-3-(4-phenoxyphenyl)-1H-pyrazolo[3,4-d]pyrimidin-4-amine (6d) (0.137 g, 0.254 mmol) was dissolved in 10 mL of dimethyl sulfoxide, and N,N'-diisopropylethylamine (0.330 g, 2.54 mmol) and 2-(2,6-dioxopiperidin-3-yl)-5-fluoroisoindoline-1,3-dione (see WO 2017197056 for the synthetic method) (0.1 g, 0.331 mmol) were successively added, the mixture was heated to 90° C. and reacted for 6 h under nitrogen atmosphere. To the reaction solution was added 10 mL of water, a solid was precipitated out, filtered off with suction, and the filtrate was extracted with ethyl acetate (40 mL×2). The organic phase was combined, washed with 50 mL of saturated saline, dried over anhydrous sodium sulfate, filtered, and concentrated under reduced pressure, the residue was separated and purified by silica gel column chromatography (dichloromethane/methanol (v/v) =100:1-20:1), to obtain 0.127 g of a crude product, and the crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-(3-(4-((4-(4-amino-3-(4-phenoxyphenyl)-1H-pyrazolo[3,4-d]pyrimidin-1-yl)piper idin-1-yl)methyl)piperidin-1-yl)azetidin-1-yl)-2-(2,6-dioxopiperidin-3-yl)isoindoline-1,3-dione tritrifluoroacetate (Compound 6) (78 mg, yield: 27%).

$^1$H NMR (400 MHz, DMSO-$d_6$) δ 11.07 (s, 1H), 8.34 (s, 1H), 7.77-7.62 (m, 3H), 7.50-7.41 (m, 2H), 7.24-7.10 (m, 5H), 6.90 (d, 1H), 6.76 (dd, 1H), 5.08 (dd, 2H), 4.35 (d, 6H), 4.27 (d, 6H), 3.73 (d, 2H), 3.62-3.49 (m, 2H), 2.97-2.80 (m, 3H), 2.57 (dd, 3H), 2.26-1.99 (m, 6H).

LCMS m/z=398.3 [M/2+1]$^+$.

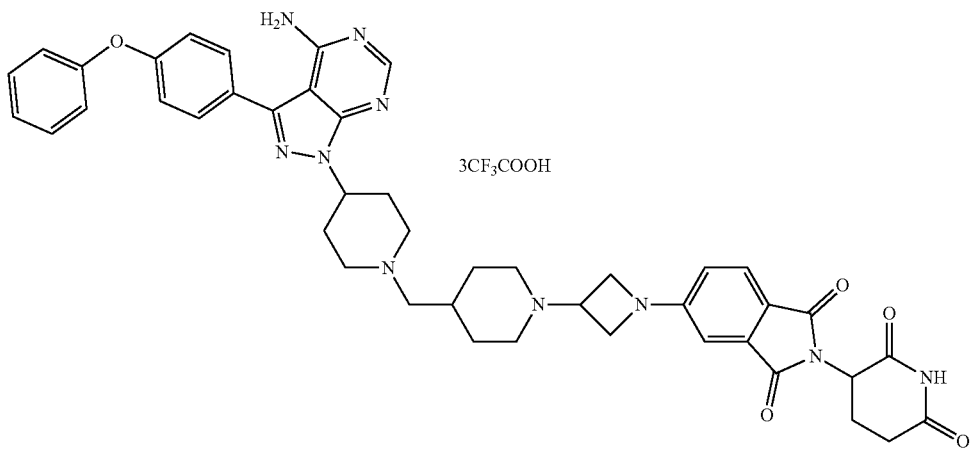 [SMILES: Nc1ncnc2c1c(-c1ccc(Oc3ccccc3)cc1)nn2C1CCN(CC2CCN(C3CN(c4ccc5c(c4)C(=O)N(C4CCC(=O)NC4=O)C5=O)C3)CC2)CC1]

Example 7
5-(2-(5-((4-(4-amino-3-(4-phenoxyphenyl)-1H-pyrazolo[3,4-d]pyrimidin-1-yl) piperidin-1-yl)methyl) pyrimidin-2-yl)-2,7-diazaspiro[3.5]nonan-7-yl)-2-(2,6-dioxopiperidin-3-yl)isoindoline-1,3-dione tritrifluoroacetate (Compound 7)
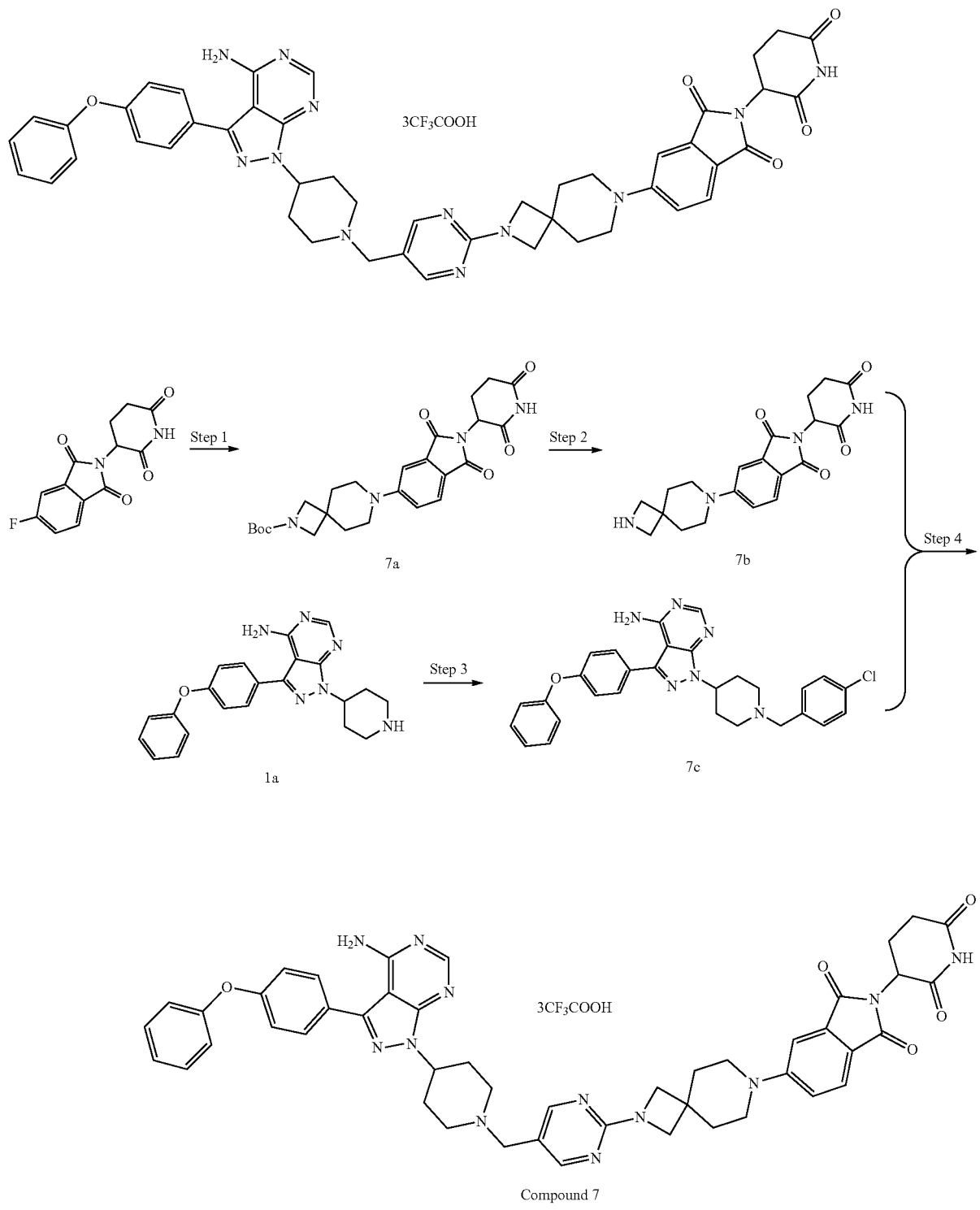
Compound 7

Step 1

Tert-butyl 7-[2-(2,6-dioxo-3-piperidyl)-1,3-dioxo-isoindolin-5-yl]-2,7-diazaspiro[3.5]nonane-2-carboxylate (7a)

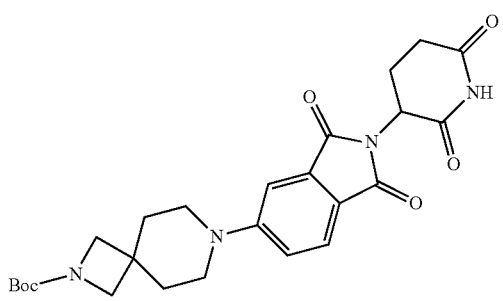 [SMILES: CC(C)(C)OC(=O)N1CC2(CCN(c3ccc4c(c3)C(=O)N(C3CCC(=O)NC3=O)C4=O)CC2)C1]

2-(2,6-dioxopiperidin-3-yl)-5-fluoroisoindoline-1,3-dione (see WO 2017197056 for the synthetic method) (1.0 g, 3.62 mmol) was dissolved in 20 mL of DMSO, and tert-butyl 2,7-diazaspiro[3.5]nonane-2-carboxylate (0.82 g, 3.62 mmol) and DIPEA (N,N-diisopropylethylamine) (2.3 g, 3.62 mmol) were added at room temperature, the reaction was stirred at 90° C. for 2 h. To the reaction solution was added 50 mL of water, the aqueous phase was extracted with ethyl acetate (50 mL×3), and the organic phase was combined, washed with water (20 mL×2), dried over anhydrous sodium sulfate, and concentrated. The crude product was separated and purified by silica gel column chromatography (dichloromethane/methanol (v/v)=100:1-20:1), to obtain tert-butyl 7-[2-(2,6-dioxo-3-piperidyl)-1,3-dioxo-isoindolin-5-yl]-2,7-diazaspiro[3.5]nonane-2-carboxylate (7a) (1.0 g, yield: 57%).

LCMS m/z=483.3 [M+1]$^+$.

Step 2

5-(2,7-diazaspiro[3.5]nonan-7-yl)-2-(2,6-dioxo-3-piperidyl)isoindoline-1,3-dione Hydrochloride (7b)

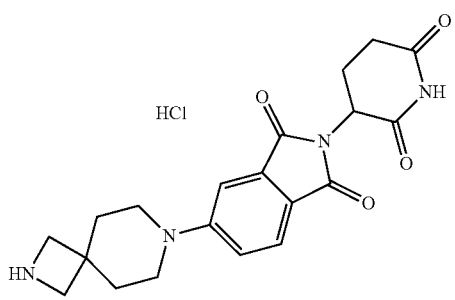 [SMILES: O=C1CCC(N2C(=O)c3ccc(N4CCC5(CC4)CNC5)cc3C2=O)C(=O)N1 ; Cl]

Tert-butyl 7-[2-(2,6-dioxo-3-piperidyl)-1,3-dioxo-isoindolin-5-yl]-2,7-diazaspiro[3.5]nonane-2-carboxylate (7a) (2.0 g, 4.14 mmol) was dissolved in 20 mL of 4N ethyl acetate hydrochloride solution, and 5 mL of methanol was added, and the reaction was carried out at room temperature for 2 h. The reaction solution was directly concentrated, to obtain 5-(2,7-diazaspiro[3.5]nonan-7-yl)-2-(2,6-dioxo-3-piperidyl)isoindoline-1,3-dione hydrochloride (7b) (1.5 g, yield: 86%).

LCMS m/z=383.2 [M+1]$^+$.

Step 3

1-[1-[(2-chloropyrimidin-5-yl)methyl]-4-piperidyl]-3-(4-phenoxyphenyl)pyrazolo[3,4-d]pyrimidin-4-amine (7c)

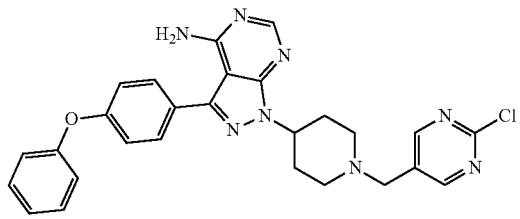 [SMILES: Nc1ncnc2c1c(-c1ccc(Oc3ccccc3)cc1)nn2C1CCN(Cc2cnc(Cl)nc2)CC1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (2.97 g, 7.0 mmol) was dissolved in 20 mL of 1,2-dichloroethane. At room temperature, 2-chloropyrimidine-5-formaldehyde (1.0 g, 7.0 mmol) was added, then 1 mL of acetic acid was added, and the mixture was reacted at room temperature for 1 h. To the reaction solution was added sodium triacetoxyborohydride (4.5 g, 21.0 mmol), and the mixture was reacted at room temperature overnight. The reaction solution was poured into 50 mL of saturated sodium bicarbonate solution, the aqueous phase was extracted with ethyl acetate (50 mL×3), and the organic phase was combined, washed with water (50 mL×2), dried over anhydrous sodium sulfate, and concentrated, to obtain 1-[1-[(2-chloropyrimidin-5-yl) methyl]-4-piperidyl]-3-(4-phenoxyphenyl)pyrazolo[3,4-d]pyrimidin-4-amine (7c) (0.4 g, yield: 11.1%).

LCMS m/z=513.6 [M+1]$^+$.

Step 4

5-[2-[5-[[4-[4-amino-3-(4-phenoxyphenyl)pyrazolo[3,4-d]pyrimidin-1-yl]-1-piperidyl]methyl]pyrimidin-2-yl]-2,7-diazaspiro[3.5]nonan-7-yl]-2-(2,6-dioxo-3-piper idyl)isoindoline-1,3-dione tritrifluoroacetate (Compound 7)

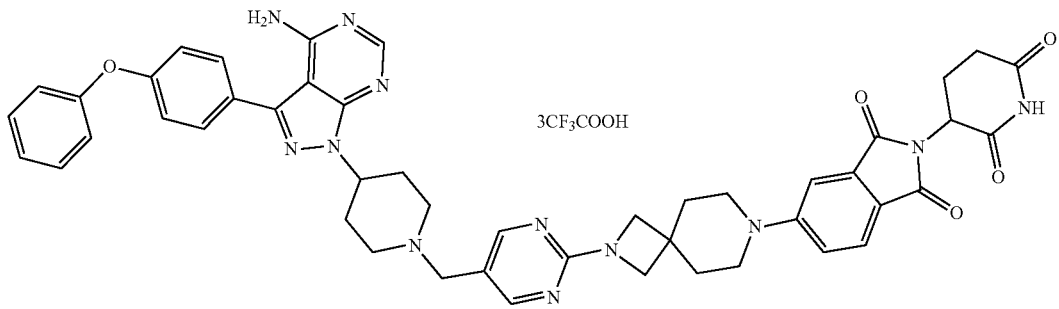 [SMILES: Nc1ncnc2c1c(-c1ccc(Oc3ccccc3)cc1)nn2C1CCN(Cc2cnc(N3CC4(CCN(c5ccc6c(c5)C(=O)N(C5CCC(=O)NC5=O)C6=O)CC4)C3)nc2)CC1]

1-[1-[(2-chloropyrimidin-5-yl)methyl]-4-piperidyl]-3-(4-phenoxyphenyl)pyrazolo[3,4-d]pyrimidin-4-amine (7c) (0.2 g, 0.39 mmol) was dissolved in 2 mL of DMF. At room temperature, 5-(2,7-diazaspiro[3.5]nonan-7-yl)-2-(2,6-dioxo-3-piperidyl)isoindoline-1,3-dione hydrochloride (7b) (0.32 g, 0.78 mmol) and triethylamine (0.15 g, 1.55 mmol) were added, and the mixture was warmed to 80° C. and reacted for 5 h. The reaction solution was poured into 50 mL of water, the aqueous phase was extracted with dichloromethane/methanol (v/v)=10:1 (50 mL×3), and the organic phase was combined, washed with 50 mL of water, dried over anhydrous sodium sulfate, and concentrated. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-[2-[5-[[4-[4-amino-3-(4-phenoxyphenyl)pyrazolo[3,4-d]pyrimidin-1-yl]-1-piperid yl]methyl]pyrimidin-2-yl]-2,7-diazaspiro[3.5]nonan-7-yl]-2-(2,6-dioxo-3-piperidyl) isoindoline-1,3-dione tritrifluoroacetate (Compound 7) (0.08 g, yield: 20%).

$^1$H NMR (400 MHz, CD$_3$OD) δ 8.48 (s, 2H), 8.42 (s, 1H), 7.65 (t, 3H), 7.45-7.37 (m, 2H), 7.33 (d, 1H), 7.27-7.13 (m, 4H), 7.13-7.05 (m, 2H), 5.31-5.17 (m, 1H), 5.05 (dd, 1H), 4.31 (s, 2H), 3.96 (s, 4H), 3.73 (d, 2H), 3.54-3.43 (m, 4H), 3.43-3.31 (m, 2H), 2.90-2.54 (m, 5H), 2.41 (s, 2H), 2.16-2.02 (m, 1H), 1.99-1.88 (m, 4H).

LCMS m/z=859.3 [M+1]$^+$.

Example 8

5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)isoindoline-1,3-dione tritrifluoroacetate (Compound 8)

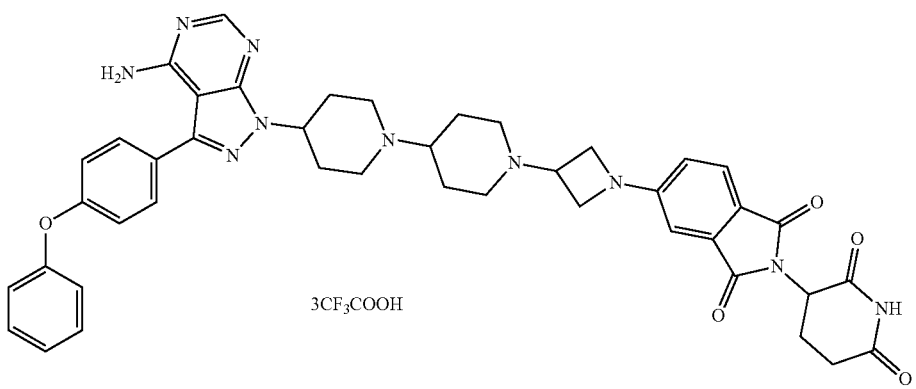

-continued
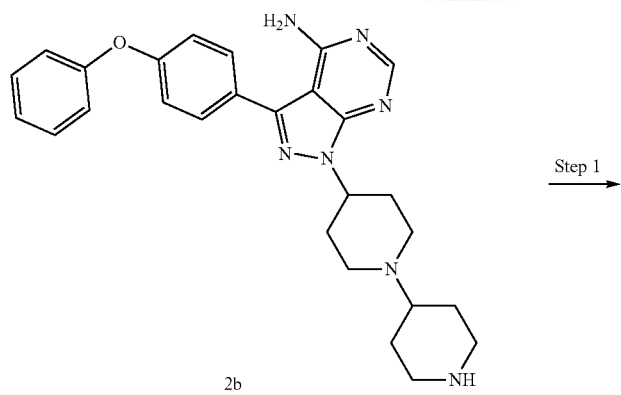
2b
Step 1
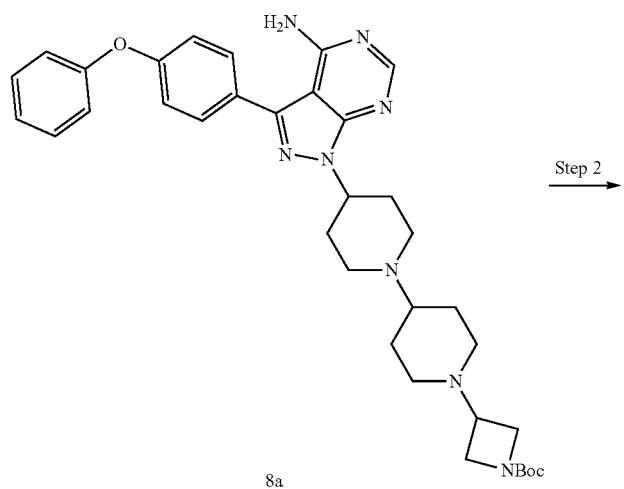
8a
Step 2
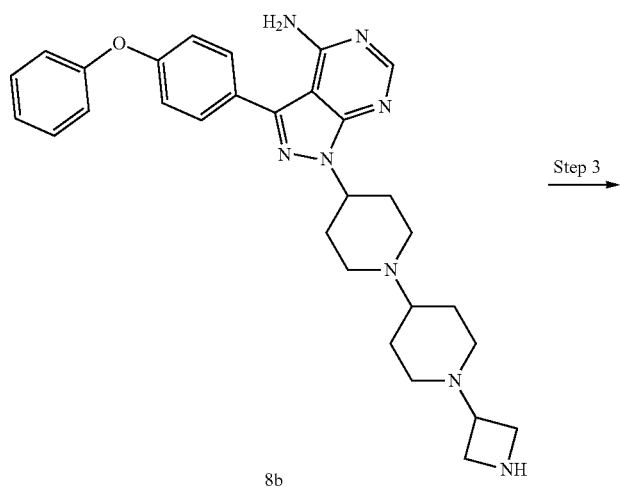
8b
Step 3

-continued

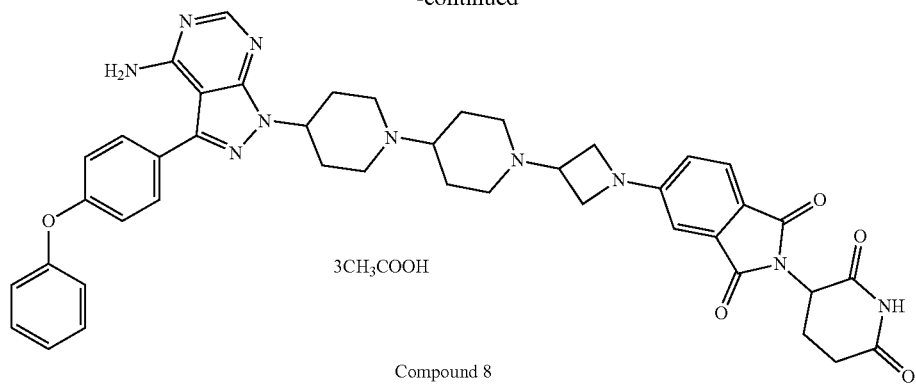

3CH₃COOH

Compound 8

Step 1

Tert-butyl 3-(4-(4-amino-3-(4-phenoxyphenyl)-1H-pyrazolo[3,4-d]pyrimidin-1-yl)-[1,4'-bipiperidin]-1'-yl)azetidine-1-carboxylate (8a)

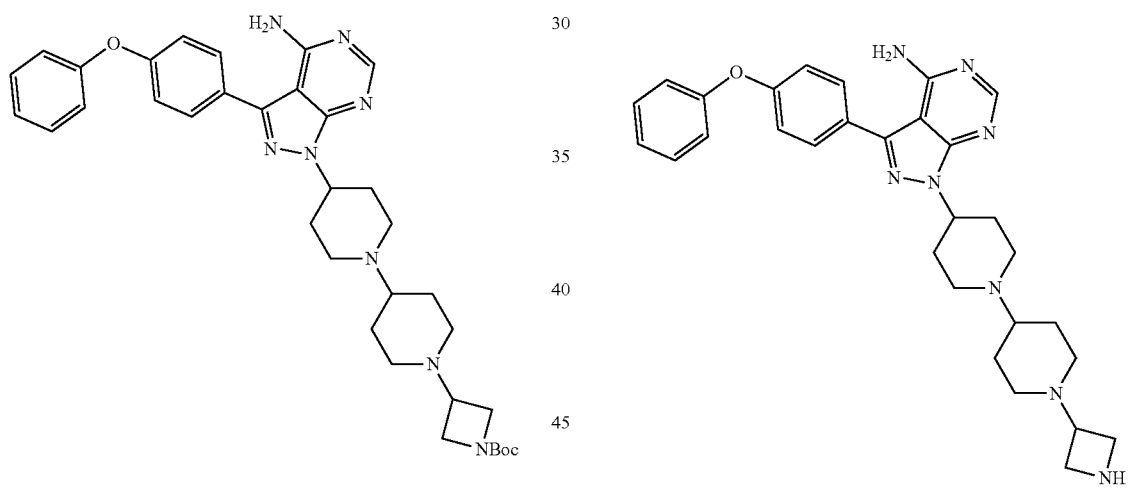

Tert-butyl 3-(4-(4-amino-3-(4-phenoxyphenyl)-1H-pyrazolo[3,4-d]pyrimidin-1-yl)-[1,4'-bipiperidin]-1'-yl)azetidine-1-carboxylate (8a)

3-(4-phenoxyphenyl)-1-[1-(4-piperidyl)-4-piperidyl]pyrazolo[3,4-d]pyrimidin-4-amine (2b) (0.256 g, 0.545 mmol) was dissolved in 20 mL of 1,2-dichloroethane, and glacial acetic acid (0.049 g, 0.818 mmol) and tert-butyl 3-oxoazetidine-1-carboxylate (0.131 g, 0.763 mmol) were successively added. Under nitrogen atmosphere, the mixture was heated to 65° C., stirred and reacted for 3 h, then cooled to room temperature, followed by addition of sodium triacetoxyborohydride (0.693 g, 3.27 mmol), and the mixture was stirred at room temperature overnight. The reaction was quenched by adding 20 mL of saturated sodium bicarbonate solution, stirred, and allowed to stand for layer separation. The aqueous phase was extracted with dichloromethane (15 mL×2), and the organic phase was combined, washed with 30 mL of saturated saline, dried over anhydrous sodium sulfate, filtered, and concentrated under reduced pressure. The crude product was separated and purified by silica gel column chromatography (dichloromethane/methanol (v/v) =100/1-15/1), to obtain tert-butyl 3-(4-(4-amino-3-(4-phenoxyphenyl)-1H-pyrazolo[3,4-d]pyrimidin-1-yl)-[1,4'-bipiperidin]-1'-yl)azetidine-1-carboxylate (8a) (0.301 g, yield: 88%).

Step 2

1-(1'-(azetidin-3-yl)-[1,4'-bipiperidin]-4-yl)-3-(4-phenoxyphenyl)-1H-pyrazolo[3,4-d]pyrimidin-4-amine (8b)

tert-butyl 3-(4-(4-amino-3-(4-phenoxyphenyl)-1H-pyrazolo[3,4-d]pyrimidin-1-yl)-[1,4'-bipiperidin]-1'-yl)azetidine-1-carboxylate (8a) (0.301 g, 0.482 mmol) was dissolved with 2 mL of methanol, and 10 mL of 4N ethyl acetate hydrochloride solution was added dropwise, the mixture was reacted at room temperature overnight. The reaction solution was concentrated under reduced pressure to obtain a crude product, and the pH of the crude product was adjusted to 9-10 with saturated sodium bicarbonate solution, which was extracted with dichloromethane (20 mL×3). The organic phase was combined, dried over anhydrous sodium sulfate, filtered, and concentrated under reduced pressure to obtain 1-(1'-(azetidin-3-yl)-[1,4'-bipiperidin]-4-yl)-3-(4-phenoxyphenyl)-1H-pyrazolo[3,4-d]pyrimidin-4-amine (8b) (0.239 g, yield: 70%).

Step 3

5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)isoindoline-1,3-dione tritrifluoroacetate (Compound 8)

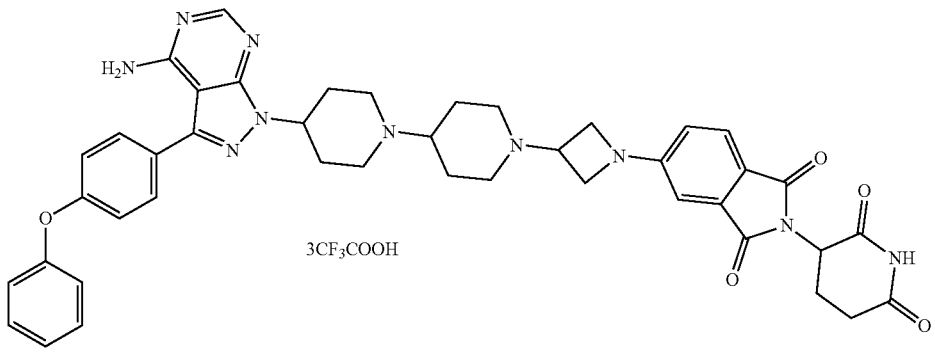 [SMILES: Nc1ncnc2c1c(-c1ccc(Oc3ccccc3)cc1)nn2C1CCN(C2CCN(C3CN(c4ccc5c(c4)C(=O)N(C4CCC(=O)NC4=O)C5=O)C3)CC2)CC1]

1-(1'-(azetidin-3-yl)-[1,4'-bipiperidin]-4-yl)-3-(4-phenoxyphenyl)-1H-pyrazolo[3,4-d]pyrimidin-4-amine (8b) (0.239 g, 0.456 mmol) was dissolved in 10 mL of dimethyl sulfoxide, and N,N'-diisopropylethylamine (0.295 g, 2.28 mmol) and 2-(2,6-dioxopiperidin-3-yl)-5-fluoroisoindoline-1,3-dione (see WO 2017197056 for the synthetic method) (0.164 g, 0.592 mmol) were successively added, and the mixture was heated to 90° C. and reacted for 6 h under nitrogen atmosphere. To the reaction solution was added 10 mL of water, a solid was precipitated out, filtered off with suction, and the filtrate was extracted with ethyl acetate (40 mL×2). The organic phase was combined, washed with 50 mL of saturated saline, dried over anhydrous sodium sulfate, filtered, and concentrated under reduced pressure, the residue was separated and purified by silica gel column chromatography (dichloromethane/methanol (v/v)=100/1-20/1), to obtain a crude product. The crude product was passed through Pre-HPLC (instrument and preparative column: using Glison GX-281 to prepare the liquid phase, preparative column model: Sunfire C18, 5 μm, inner diameter× length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)isoindoline-1,3-dione tritrifluoroacetate (Compound 8) (0.207 g, yield: 40%).

$^1$H NMR (400 MHz, DMSO-d$_6$) δ 11.07 (s, 1H), 8.34 (s, 1H), 7.72 (d, 1H), 7.66 (d, 2H), 7.45 (t, 2H), 7.23-7.09 (m, 5H), 6.89 (s, 1H), 6.75 (d, 1H), 5.19-5.04 (m, 2H), 4.40-4.05 (m, 7H), 3.76-3.27 (m, 7H), 2.97-2.75 (m, 2H), 2.64-2.52 (m, 3H), 2.40-2.19 (m, 4H), 2.08-1.79 (m, 3H).

LCMS m/z=781.3 [M+1]$^+$.

Example 8-1

5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)isoindoline-1,3-dione (Compound 8-1)

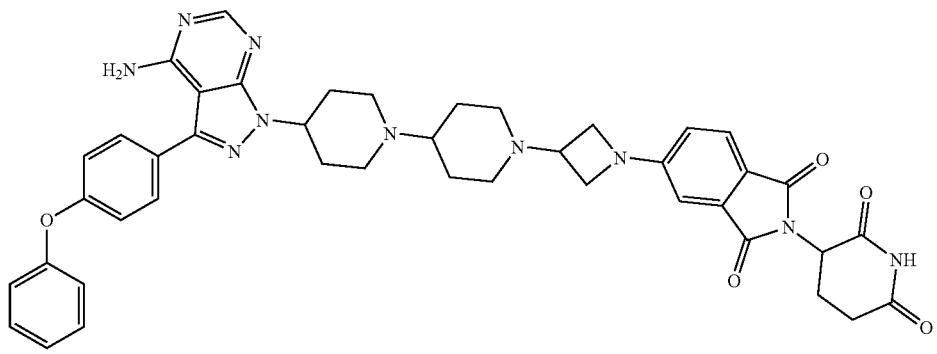 [SMILES: Nc1ncnc2c1c(-c1ccc(Oc3ccccc3)cc1)nn2C1CCN(C2CCN(C3CN(c4ccc5c(c4)C(=O)N(C4CCC(=O)NC4=O)C5=O)C3)CC2)CC1]

The compound 8 (2 g) was dissolved in 50 mL of dichloromethane, and the mixed solution was washed with concentrated ammonia water with a mass fraction of 28% (50 mL×5). The organic layer was dried over anhydrous sodium sulfate, and concentrated under reduced pressure. To the residue was added 20 mL of ethyl acetate, stirred for 3 h, and filtered, and the filter cake was vacuum-dried, to obtain the free base 5-(3-(4-(4-amino-3-(4-phenoxyphenyl)-

1H-pyrazolo[3,4-d]pyrimidin-1-yl)-[1,4'-bipiperidin]-1'-yl) azetidin-1-yl)-2-(2,6-dioxopiperidin-3-yl)isoindoline-1,3-dione (Compound 8-1) (1.3 g).

$^1$H NMR (400 MHz, CDCl$_3$) δ 10.22 (brs, 1H), 8.39 (s, 1H), 7.67-7.60 (m, 3H), 7.42-7.34 (m, 2H), 7.19-7.10 (m, 3H), 7.10-7.04 (m, 2H), 6.78 (d, 1H), 6.51 (dd, 1H), 5.89 (brs, 2H), 4.96-4.88 (m, 1H), 4.83-4.70 (m, 1H), 4.14-4.04 (m, 2H), 3.92-3.84 (m, 2H), 3.39-3.30 (m, 1H), 3.18-3.04 (m, 2H), 3.00-2.91 (m, 2H), 2.90-2.65 (m, 3H), 2.56-2.32 (m, 5H), 2.16-2.01 (m, 3H), 2.01-1.84 (m, 4H), 1.73-1.59 (m, 2H).

LC-MS m/z=781.4 [M+1]$^+$.

Example 9

5-(4-((4-(4-amino-3-(4-phenoxyphenyl)-1H-pyrazolo[3,4-d]pyrimidin-1-yl)piperidin-1-yl)methyl)-[1,4'-bipiperidin]-1'-yl)-2-(2,6-dioxopiperidin-3-yl) isoindoline-1,3-dione tetratrifluoroacetate (Compound 9)

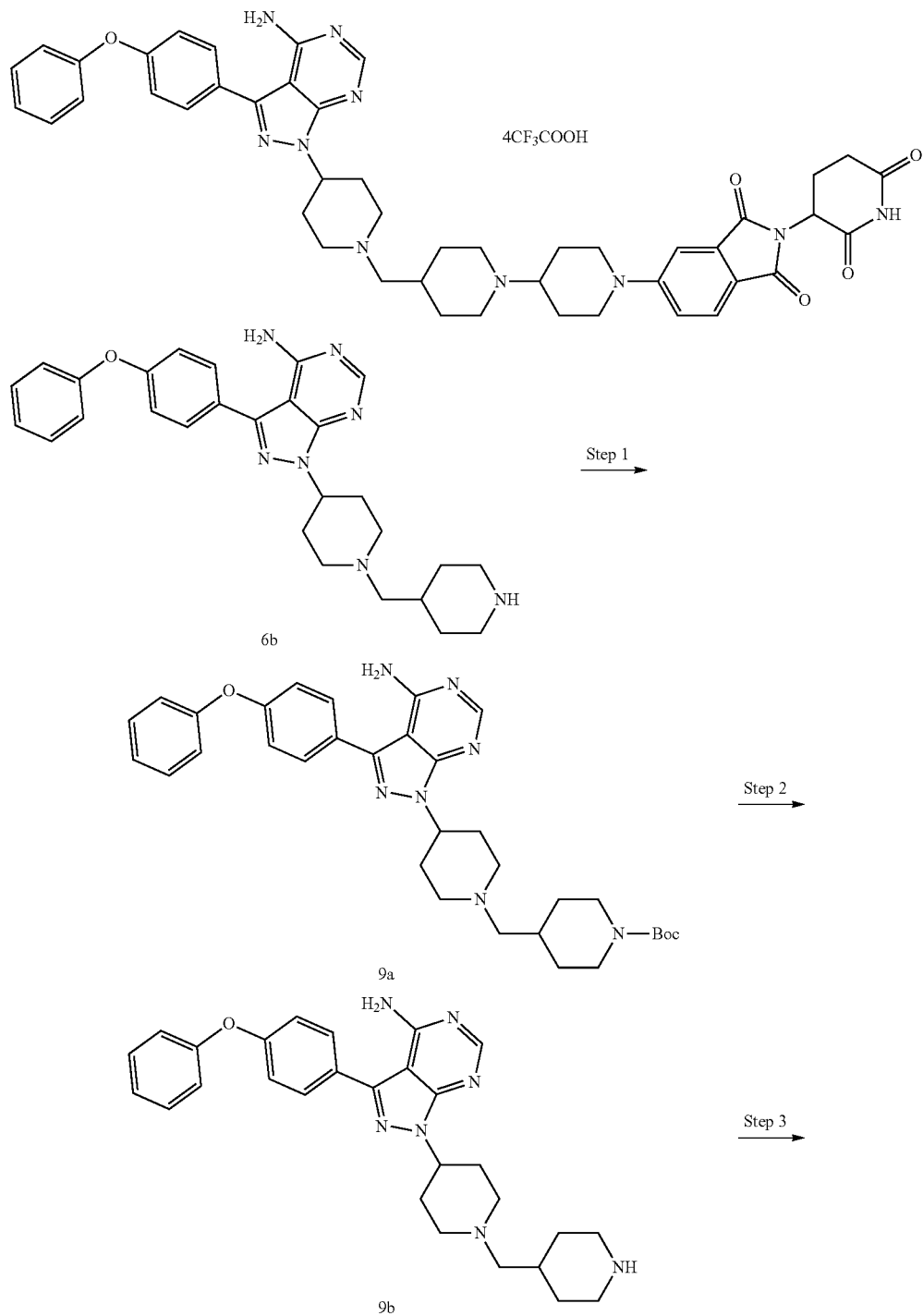

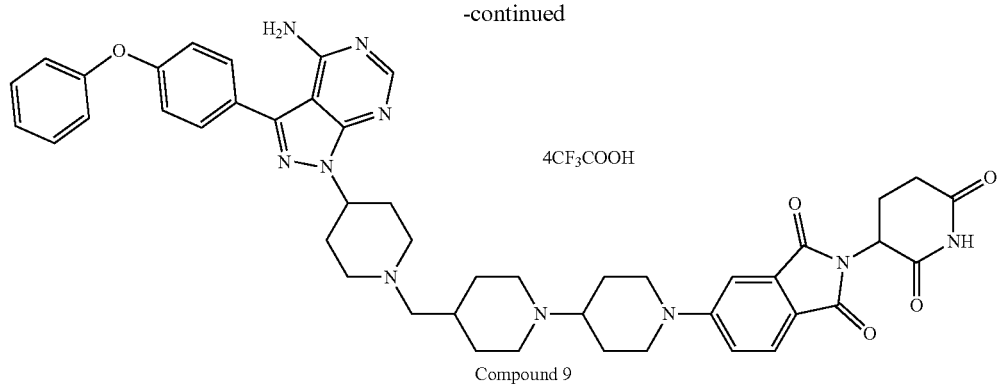

Compound 9

Step 1

Tert-butyl 4-((4-(4-amino-3-(4-phenoxyphenyl)-1H-pyrazolo[3,4-d]pyrimidin-1-yl)piperidin-1-yl)methyl)[1,4'-bipiperidine]-1'-carboxylate (9a)

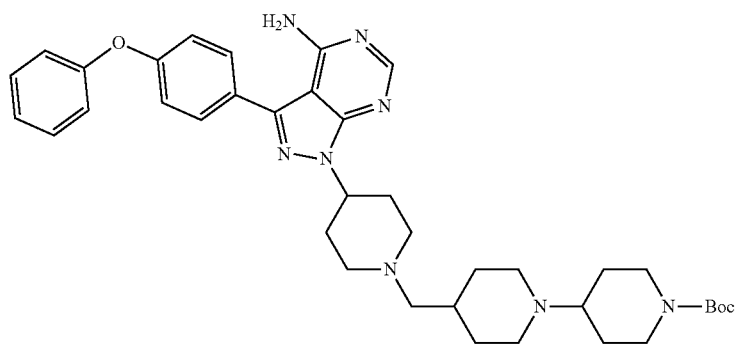 [SMILES: CC(C)(C)OC(=O)N1CCC(N2CCC(CN3CCC(n4nc(-c5ccc(Oc6ccccc6)cc5)c5c(N)ncnc54)CC3)CC2)CC1]

3-(4-phenoxyphenyl)-1-(1-(piperidin-4-ylmethyl)piperidin-4-yl)-1H-pyrazolo[3,4-d]pyrimidin-4-amine (6b) (0.44 g, 0.91 mmol) was dissolved in 10 mL of 1,2-dichloroethane, and tert-butyl 4-oxopiperidine-1-carboxylate (0.24 g, 1.18 mmol) was added at room temperature, the mixture was heated to 50° C., stirred for 1 h, and then cooled to room temperature. To the reaction solution was added sodium triacetoxyborohydride (0.48 g, 2.28 mmol), and the mixture was reacted at room temperature overnight. The reaction solution was poured into 50 mL of saturated sodium bicarbonate solution, the aqueous phase was extracted with ethyl acetate (50 mL×3), and the organic phase was combined, washed with water (50 mL×2), dried over anhydrous sodium sulfate, and concentrated, to obtain tert-butyl 4-((4-(4-amino-3-(4-phenoxyphenyl)-1H-pyrazolo[3,4-d]pyrimidin-1-yl)piperidin-1-yl)methyl)[1,4'-bipiperidine]-1'-carboxylate (9a) (0.31 g, yield: 51%).

LCMS m/z=667.4 [M+1]$^+$.

Step 2

1-(1-([1,4'-bipiperidin]-4-ylmethyl)piperidin-4-yl)-3-(4-phenoxyphenyl)-1H-pyrazolo[3,4-d]pyrimidin-4-amine (9b)

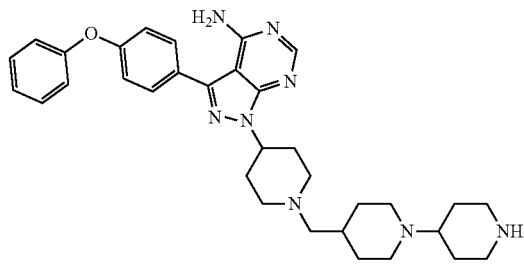 [SMILES: Nc1ncnc2c1c(-c1ccc(Oc3ccccc3)cc1)nn2C1CCN(CC2CCN(C3CCNCC3)CC2)CC1]

Tert-butyl 4-((4-(4-amino-3-(4-phenoxyphenyl)-1H-pyrazolo[3,4-d]pyrimidin-1-yl)piperidin-1-yl)methyl)[1,4'-bipiperidine]-1'-carboxylate (9a) (0.31 g, 0.46 mmol) was dissolved in 6 mL of dichloromethane, and 2 mL of trifluoroacetic acid was added, and the reaction was carried out at room temperature for 2 h. The pH was adjusted to 9-10 with 20 mL of 2N sodium hydroxide aqueous solution, the aqueous phase was extracted with dichloromethane (10 mL×3), and the organic phase was dried over anhydrous sodium sulfate, and concentrated, to obtain 1-(1-([1,4'-bipiperidin]-4-ylmethyl)piperidin-4-yl)-3-(4-phenoxyphenyl)-1H-pyrazolo[3,4-d]pyrimidin-4-amine (9b) (0.17 g, yield: 65%).

LCMS m/z=567.4 [M+1]$^+$.

Step 3

5-(4-((4-(4-amino-3-(4-phenoxyphenyl)-1H-pyrazolo[3,4-d]pyrimidin-1-yl)piperidin-1-yl)methyl)-[1,4'-bipiperidin]-1'-yl)-2-(2,6-dioxopiperidin-3-yl)isoindoline-1,3-dione tetratrifluoroacetate
(Compound 9)

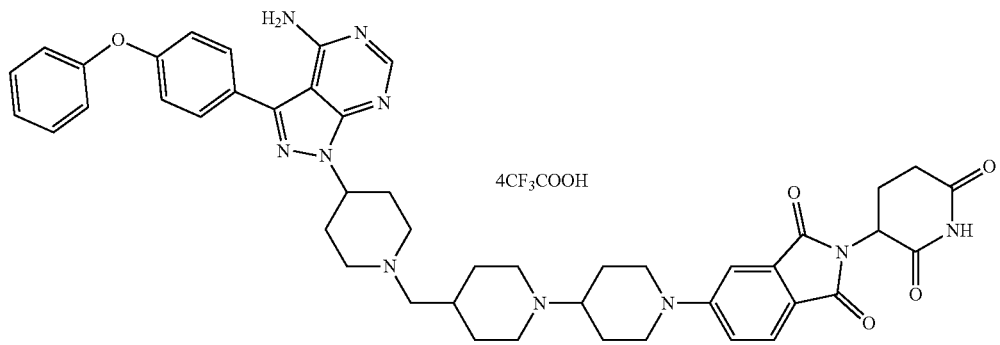 [SMILES: Nc1ncnc2c1c(-c1ccc(Oc3ccccc3)cc1)nn2C1CCN(CC2CCN(C3CCN(c4ccc5c(c4)C(=O)N(C4CCC(=O)NC4=O)C5=O)CC3)CC2)CC1]

1-(1-([1,4'-bipiperidin]-4-ylmethyl)piperidin-4-yl)-3-(4-phenoxyphenyl)-1H-pyrazolo[3,4-d]pyrimidin-4-amine (9b) (0.17 g, 0.3 mmol) was dissolved in 5 mL of DMSO, and 2-(2,6-dioxopiperidin-3-yl)-5-fluoroisoindoline-1,3-dione (see WO 2017197056 for the synthetic method) (0.1 g, 0.36 mmol) and N,N'-diisopropylethylamine (0.3 g, 2.3 mmol) were added at room temperature, and the mixture was warmed to 80° C. and reacted for 3 h. The reaction solution was poured into 20 mL of water, the aqueous phase was extracted with dichloromethane/methanol (v/v)=10:1 (30 mL×3), and the organic phase was combined, washed with 50 mL of water, dried over anhydrous sodium sulfate, and concentrated. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-(4-((4-(4-amino-3-(4-phenoxyphenyl)-1H-pyrazolo[3,4-d]pyrimidin-1-yl)piperidin-1-yl)methyl)-[1,4'-bipiperidin]-1'-yl)-2-(2,6-dioxopiperidin-3-yl)isoindoline-1,3-dione tetratrifluoroacetate (Compound 9) (0.11 g, yield: 45%).

$^1$H NMR (400 MHz, DMSO-d$_6$) δ 11.06 (s, 1H), 9.46 (d, 2H), 8.32 (s, 1H), 7.72-7.55 (m, 3H), 7.47-7.41 (m, 3H), 7.35-7.29 (m, 1H), 7.22-7.12 (m, 5H), 5.10-5.05 (m, 2H), 4.26 (d, 2H), 3.71 (d, 2H), 3.63-3.39 (m, 4H), 3.32-3.17 (m, 2H), 3.07-2.85 (m, 6H), 2.65-2.51 (m, 4H), 2.32-1.94 (m, 8H), 1.72-1.69 (m, 2H), 1.48-1.45 (m, 2H).

LCMS m/z=412.3 [M/2+1]$^+$.

Example 10
5-(4-(3-((4-(4-amino-3-(4-phenoxyphenyl)-1H-pyrazolo[3,4-d]pyrimidin-1-yl) piperidin-1-yl)methyl) azetidin-1-yl)piperidin-1-yl)-2-(2,6-dioxopiperidin-3-yl)isoindoline-1,3-dione tetratrifluoroacetate
(Compound 10)
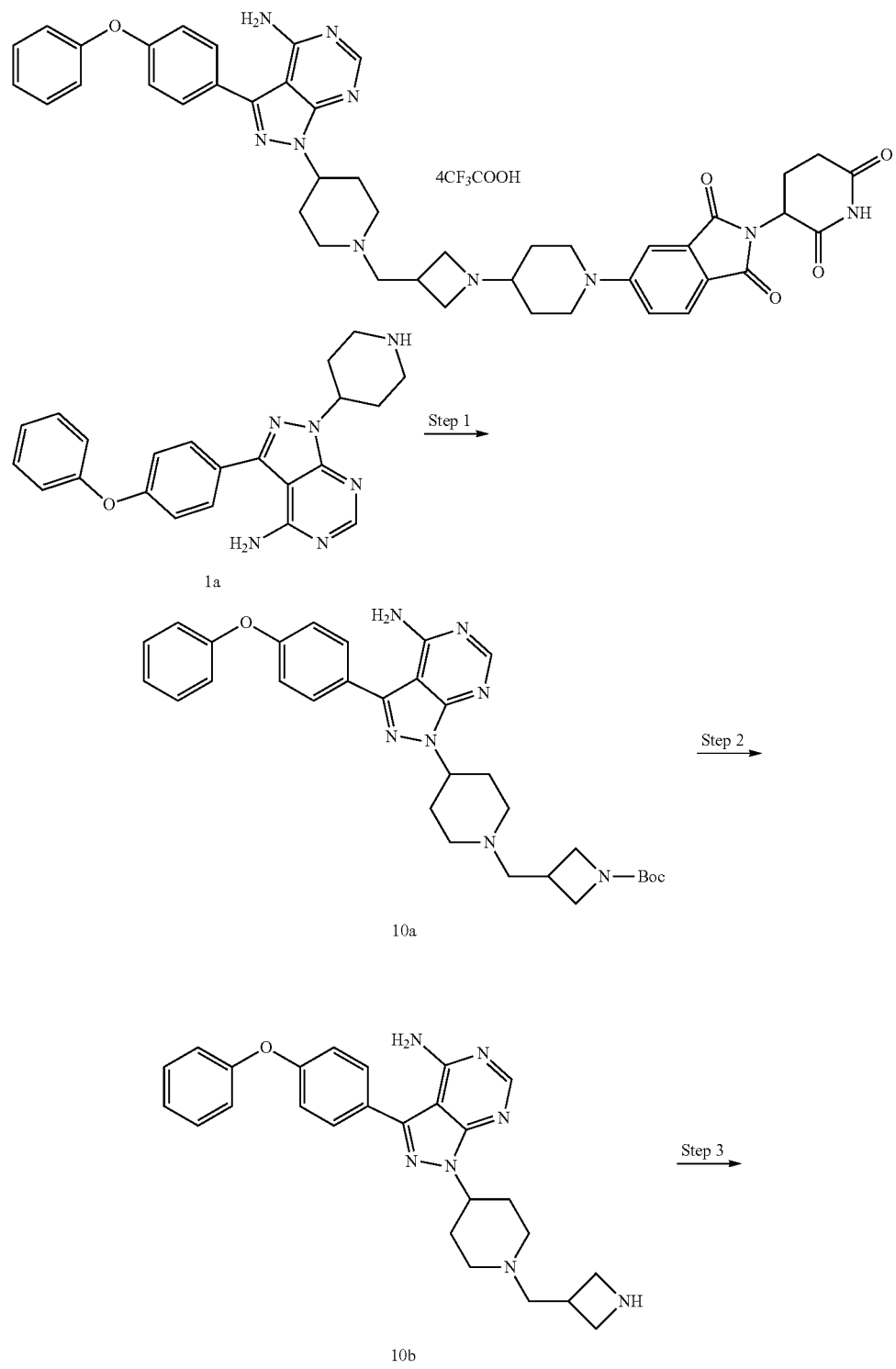

-continued
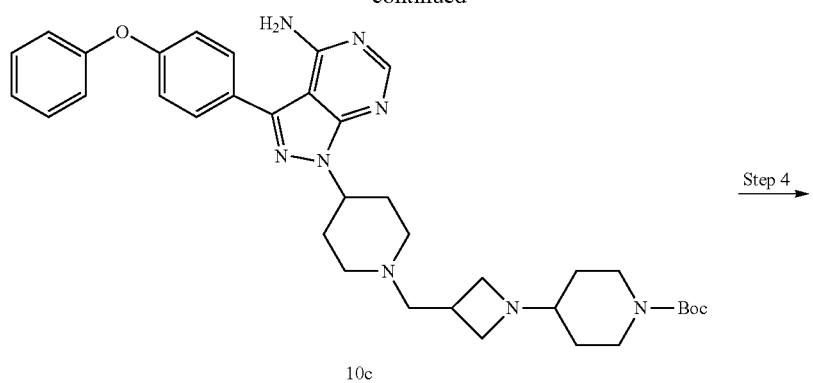
10c
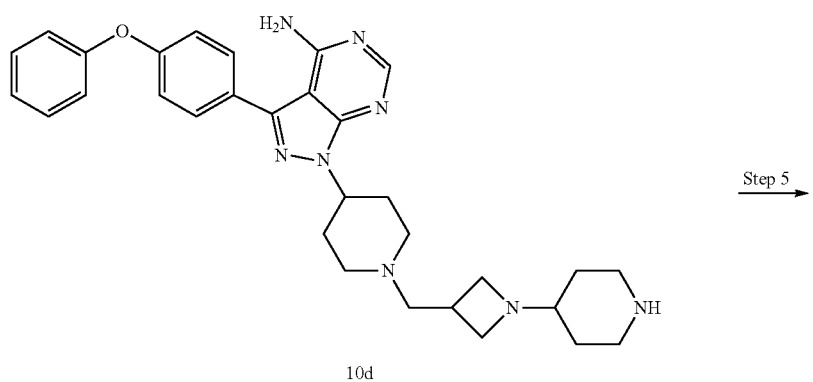
10d
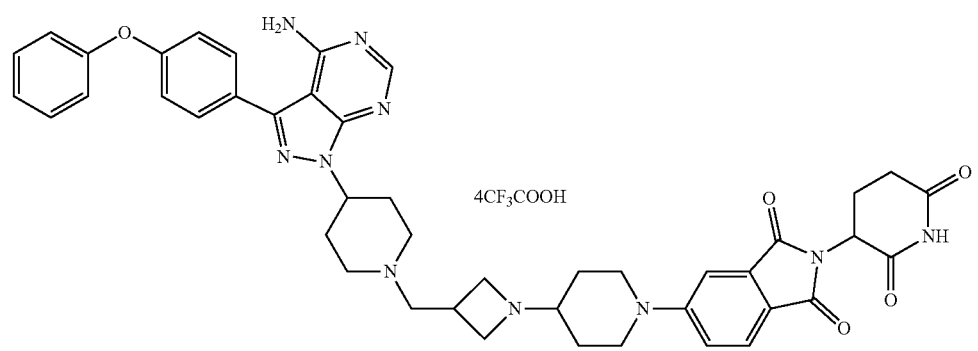
Compound 10

Step 1

Tert-butyl 3-((4-(4-amino-3-(4-phenoxyphenyl)-1H-pyrazolo[3,4-d]pyrimidin-1-yl)piperidin-1-yl)methyl)azetidine-1-carboxylate (10a)

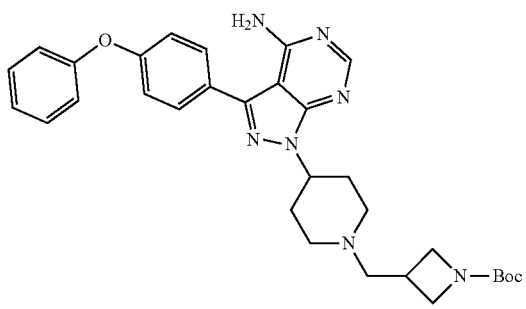 [SMILES: CC(C)(C)OC(=O)N1CC(CN2CCC(n3nc(-c4ccc(Oc5ccccc5)cc4)c4c(N)ncnc43)CC2)C1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.5 g, 1.29 mmol) was dissolved in 15 mL of DME, and tert-butyl 3-formylazetidine-1-carboxylate (0.31 g, 1.68 mmol) was added at room temperature, the reaction was stirred at room temperature for 0.5 h, and then sodium triacetoxyborohydride (0.68 g, 3.22 mmol) was added, and the mixture was stirred at room temperature overnight. To the reaction solution was added 50 mL of water, the aqueous phase was extracted with dichloromethane (30 mL×3), and the organic phase was combined, washed with water (20 mL×2), dried over anhydrous sodium sulfate, and concentrated. The crude product was separated and purified by silica gel column chromatography (dichloromethane/methanol (v/v)=100:1-20:1), to obtain tert-butyl 3-((4-(4-amino-3-(4-phenoxyphenyl)-1H-pyrazolo[3,4-d]pyrimidin-1-yl)piperidin-1-yl)methyl)azetidine-1-carboxylate (10a) (0.65 g, yield: 91%).

LCMS m/z=556.4 [M+1]$^+$.

Step 2

1-(1-(azetidin-3-ylmethyl)piperidin-4-yl)-3-(4-phenoxyphenyl)-1H-pyrazolo[3,4-d]pyrimidin-4-amine (10b)

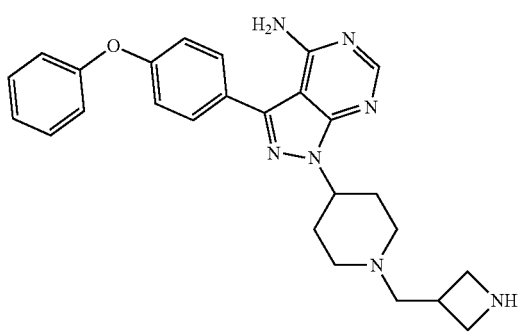 [SMILES: Nc1ncnc2c1c(-c1ccc(Oc3ccccc3)cc1)nn2C1CCN(CC2CNC2)CC1]

Tert-butyl 3-((4-(4-amino-3-(4-phenoxyphenyl)-1H-pyrazolo[3,4-d]pyrimidin-1-yl)piperidin-1-yl)methyl)azetidine-1-carboxylate (10a) (0.61 g, 1.17 mmol) was dissolved in 6 mL of dichloromethane, and 2 mL of trifluoroacetic acid was added, and the reaction was carried out at room temperature for 2 h. The pH was adjusted to 9-10 with 20 mL of 2N sodium hydroxide aqueous solution, the aqueous phase was extracted with dichloromethane (10 mL×3), and the organic phase was dried over anhydrous sodium sulfate, and concentrated, to obtain 1-(1-(azetidin-3-ylmethyl)piperidin-4-yl)-3-(4-phenoxyphenyl)-1H-pyrazolo[3,4-d]pyrimidin-4-amine (10b) (0.47 g, yield: 89%).

LCMS m/z=456.3 [M+1]$^+$.

Step 3

Tert-butyl 4-(3-((4-(4-amino-3-(4-phenoxyphenyl)-1H-pyrazolo[3,4-d]pyrimidin-1-yl)piperidin-1-yl)methyl)azetidin-1-yl)piperidine-1-carboxylate (10c)

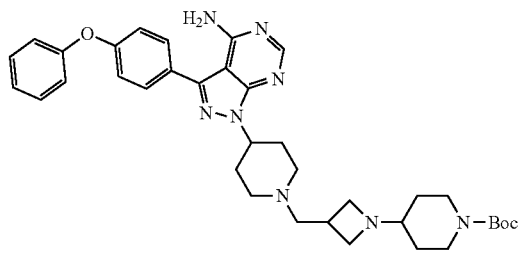 [SMILES: CC(C)(C)OC(=O)N1CCC(N2CC(CN3CCC(n4nc(-c5ccc(Oc6ccccc6)cc5)c5c(N)ncnc54)CC3)C2)CC1]

1-(1-(azetidin-3-ylmethyl)piperidin-4-yl)-3-(4-phenoxyphenyl)-1H-pyrazolo[3,4-d]pyrimidin-4-amine (10b) (0.47 g, 1.03 mmol) was dissolved in 10 mL of 1,2-dichloroethane, and tert-butyl 4-oxopiperidine-1-carboxylate (0.27 g, 1.34 mmol) was added at room temperature, and the mixture was heated to 50° C., stirred for 1 h, and then cooled to room temperature. To the reaction solution was added sodium triacetoxyborohydride (0.55 g, 2.58 mmol), and the mixture was reacted at room temperature overnight. The reaction solution was poured into 50 mL of saturated sodium bicarbonate solution, the aqueous phase was extracted with ethyl acetate (50 mL×3), and the organic phase was combined, washed with water (50 mL×2), dried over anhydrous sodium sulfate, and concentrated, to obtain tert-butyl 4-(3-((4-(4-amino-3-(4-phenoxyphenyl)-1H-pyrazolo[3,4-d]pyrimidin-1-yl)piperidin-1-yl)methyl)azetidin-1-yl)piperidine-1-carboxylate (10c) (0.31 g, yield: 48%).

LCMS m/z=639.8 [M+1]$^+$.

Step 4

3-(4-phenoxyphenyl)-1-(1-((1-(piperidin-4-yl)azetidin-3-yl)methyl)piperidin-4-yl)-1H-pyrazolo[3,4-d]pyrimidin-4-amine (10d)

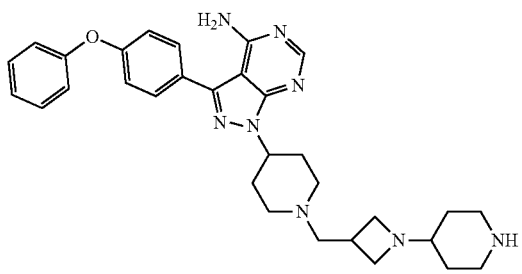 [SMILES: Nc1ncnc2c1c(-c1ccc(Oc3ccccc3)cc1)nn2C1CCN(CC2CN(C3CCNCC3)C2)CC1]

Tert-butyl 4-(3-((4-(4-amino-3-(4-phenoxyphenyl)-1H-pyrazolo[3,4-d]pyrimidin-1-yl)piperidin-1-yl)methyl)azetidin-1-yl)piperidine-1-carboxylate (10c) (0.31 g, 0.49 mmol) was dissolved in 6 mL of dichloromethane, and 2 mL of trifluoroacetic acid was added, and the reaction was carried out at room temperature for 2 h. The pH was adjusted to 9-10 with 20 mL of 2N sodium hydroxide aqueous solution, the aqueous phase was extracted with dichloromethane (10 mL×3), and the organic phase was dried over anhydrous sodium sulfate, and concentrated, to obtain 3-(4-phenoxyphenyl)-1-(1-((1-(piperidin-4-yl)azetidin-3-yl)methyl)piperidin-4-yl)-1H-pyrazolo[3,4-d]pyrimidin-4-amine (10d) (0.18 g, yield: 65%).

LCMS m/z=539.7 [M+1]+.

Step 5

5-(4-(3-((4-(4-amino-3-(4-phenoxyphenyl)-1H-pyrazolo[3,4-d]pyrimidin-1-yl) piperidin-1-yl)methyl)azetidin-1-yl)piperidin-1-yl)-2-(2,6-dioxopiperidin-3-yl)isoindoline-1,3-dione Tetratrifluoroacetate (Compound 10)

3-(4-phenoxyphenyl)-1-(1-((1-(piperidin-4-yl)azetidin-3-yl)methyl)piperidin-4-yl)-1H-pyrazolo[3,4-d]pyrimidin-4-amine (10d) (0.18 g, 0.34 mmol) was dissolved in 5 mL of DMSO, and 2-(2,6-dioxopiperidin-3-yl)-5-fluoroisoindoline-1,3-dione (see WO 2017197056 for the synthetic method) (0.12 g, 0.37 mmol) and N,N'-diisopropylethylamine (0.3 g, 2.3 mmol) were added at room temperature, the mixture was warmed to 80° C. and reacted for 3 h. The reaction solution was poured into 20 mL of water, the aqueous phase was extracted with dichloromethane/methanol (v/v)=10:1 (30 mL×3), and the organic phase was combined, washed with 50 mL of water, dried over anhydrous sodium sulfate, and concentrated. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-(4-(3-((4-(4-amino-3-(4-phenoxyphenyl)-1H-pyrazolo[3,4-d]pyrimidin-1-yl)piperidin-1-yl)methyl)azetidin-1-yl)piperidin-1-yl)-2-(2,6-dioxopiperidin-3-yl)isoindoline-1,3-dione tetratrifluoroacetate (Compound 10) (0.13 g, yield: 48%).

$^1$H NMR (400 MHz, DMSO-$d_6$) δ 11.06 (s, 1H), 8.31 (s, 1H), 7.72-7.54 (m, 3H), 7.48-7.39 (m, 3H), 7.33-7.31 (m, 1H), 7.24-7.09 (m, 5H), 5.10-5.05 (m, 3H), 4.25-4.08 (m, 7H), 3.70-3.38 (m, 6H), 3.01-2.89 (m, 3H), 2.69-2.39 (m, 4H), 2.22-2.19 (m, 2H), 2.10-1.89 (m, 3H), 1.41-1.39 (m, 2H).

LCMS m/z=398.3 [M/2+1]+.

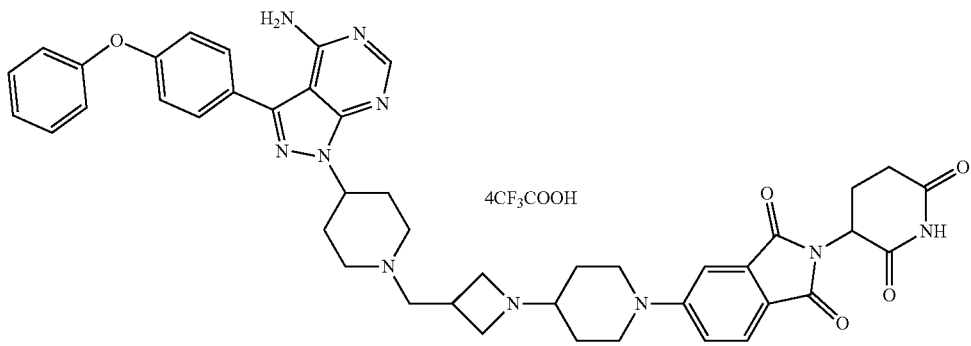 [SMILES: Nc1ncnc2c1c(-c1ccc(Oc3ccccc3)cc1)nn2C1CCN(CC2CN(C3CCN(c4ccc5c(c4)C(=O)N(C4CCC(=O)NC4=O)C5=O)CC3)C2)CC1]

Example 11
5-[4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-1-piperidyl]-2-(2,6-dioxo-3-piperidyl)isoindoline-1,3-dione Hexatrifluoroacetate (Compound 11)
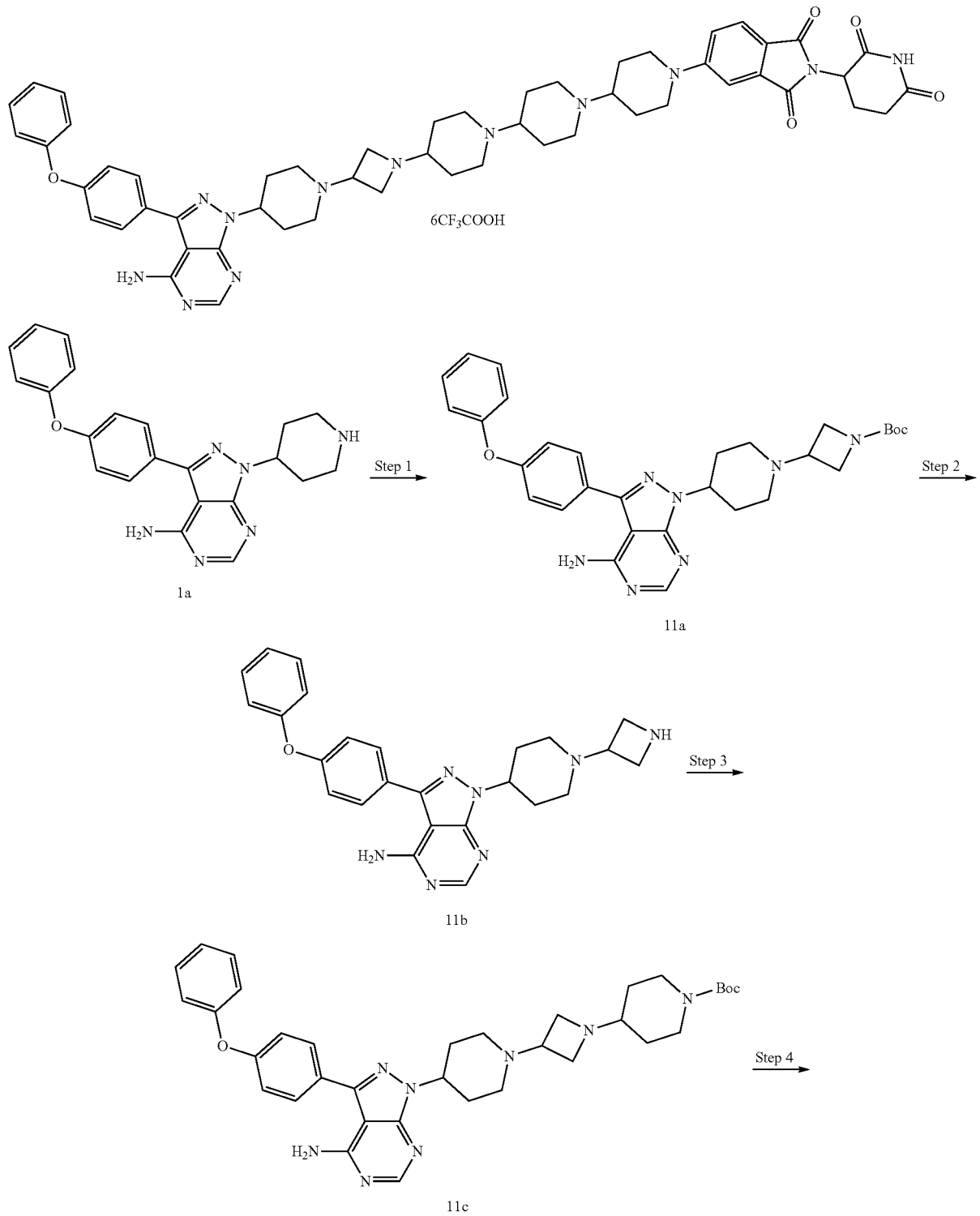

-continued
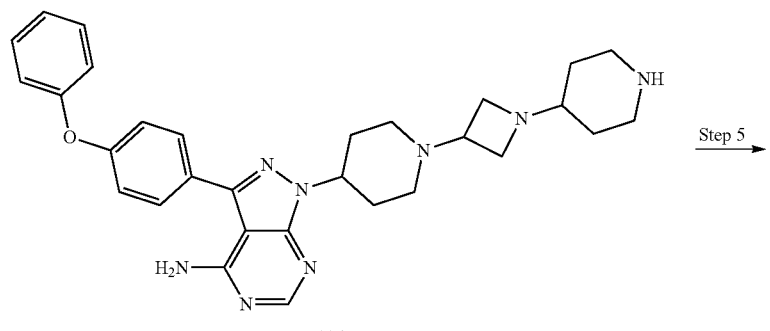
11d
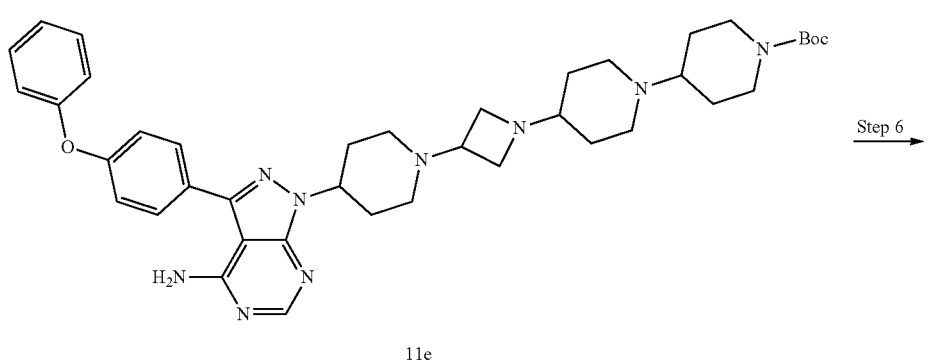
11e
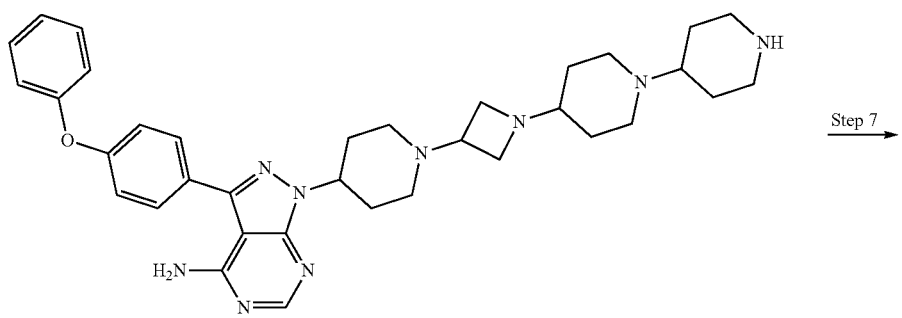
11f
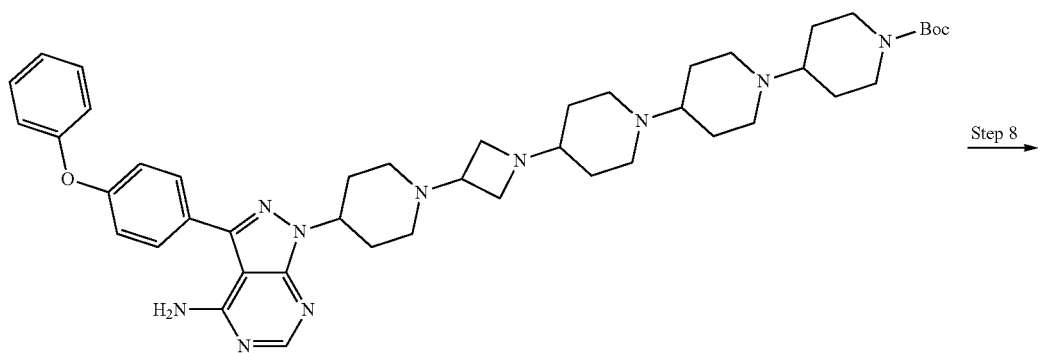
11g

-continued

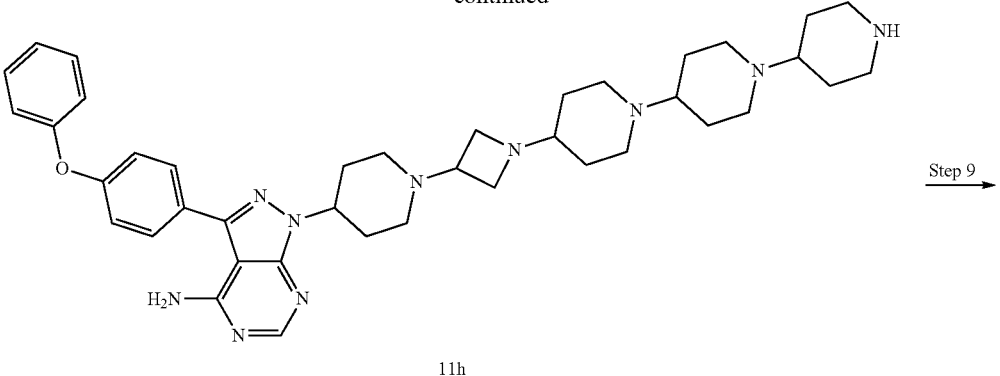

11h

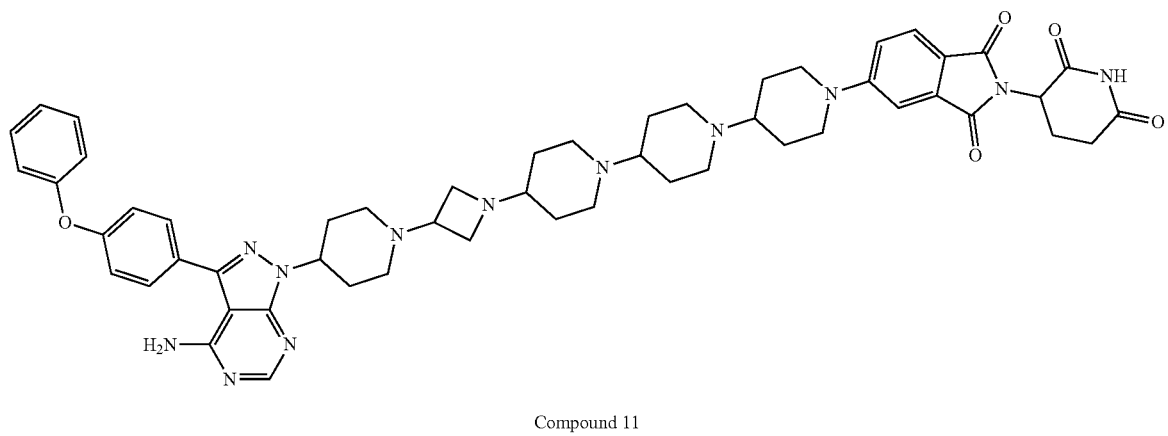 [SMILES: Nc1ncnc2c1c(-c1ccc(Oc3ccccc3)cc1)nn2C1CCN(C2CN(C3CCN(C4CCN(C5CCN(c6ccc7c(c6)C(=O)N(C6CCC(=O)NC6=O)C7=O)CC5)CC4)CC3)C2)CC1]

Compound 11

Step 1

Tert-butyl 3-[4-[4-amino-3-(4-phenoxyphenyl)pyrazolo[3,4-d]pyrimidin-1-yl]-1-piperidyl]azetidine-1-carboxylate (11a)

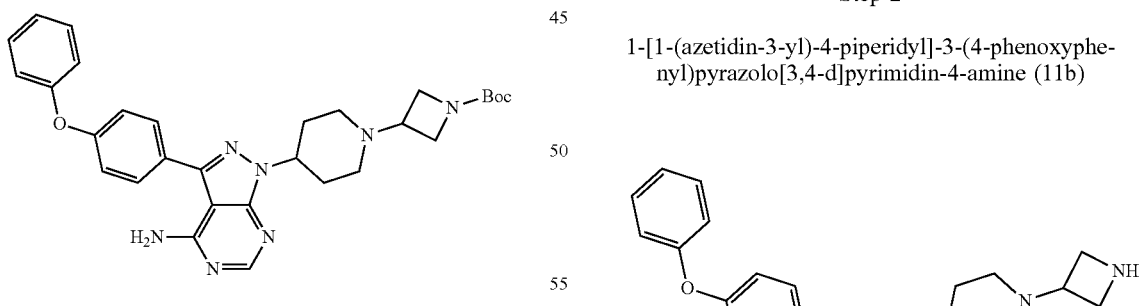

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.500 g, 1.29 mmol) was dissolved in 5 mL of 1,2-dichloroethane, and tert-butyl 3-oxoazetidine-1-carboxylate (0.266 g, 1.55 mmol) and glacial acetic acid (0.412 g, 6.86 mmol) were added. Upon completion of the addition, the reaction was stirred at 65° C. for 3 h, then cooled to room temperature, and sodium triacetoxyborohydride (0.548 g, 2.59 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-19:1), to obtain tert-butyl 3-[4-[4-amino-3-(4-phenoxyphenyl)pyrazolo[3,4-d]pyrimidin-1-yl]-1-piperidyl]azetidine-1-carboxylate (11a) (0.700 g, yield: >99%).

LCMS m/z=542.3 [M+1]$^+$.

Step 2

1-[1-(azetidin-3-yl)-4-piperidyl]-3-(4-phenoxyphenyl)pyrazolo[3,4-d]pyrimidin-4-amine (11b)

Tert-butyl 3-[4-[4-amino-3-(4-phenoxyphenyl)pyrazolo[3,4-d]pyrimidin-1-yl]-1-piperidyl]azetidine-1-carboxylate (11a)

(0.700 g, 1.29 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 1-[1-(azetidin-3-yl)-4-piperidyl]-3-(4-phenoxyphenyl)pyrazolo[3,4-d]pyrimidin-4-a mine (11b) (0.410 g, yield: 72%).

LCMS m/z=442.2 [M+1]⁺.

Step 3

Tert-butyl 4-[3-[4-[4-amino-3-(4-phenoxyphenyl)pyrazolo[3,4-d]pyrimidin-1-yl]-1-piperidyl]azetidin-1-yl]piperidine-1-carboxylate (11c)

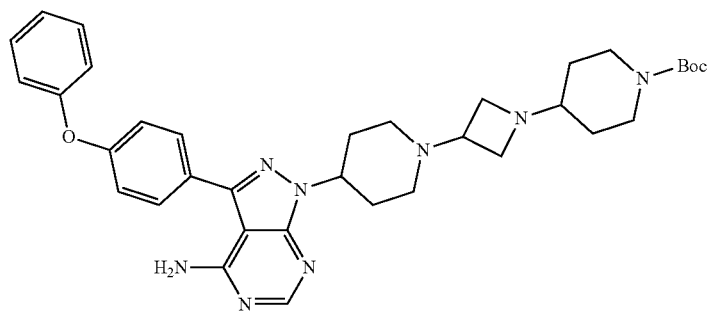 [SMILES: CC(C)(C)OC(=O)N1CCC(N2CC(N3CCC(n4nc(-c5ccc(Oc6ccccc6)cc5)c5c(N)ncnc54)CC3)C2)CC1]

1-[1-(azetidin-3-yl)-4-piperidyl]-3-(4-phenoxyphenyl)pyrazolo[3,4-d]pyrimidin-4-amine (11b) (0.410 g, 0.929 mmol) was dissolved in 5 mL of 1,2-dichloroethane, and tert-butyl 4-oxopiperidine-1-carboxylate (0.222 g, 1.11 mmol) and glacial acetic acid (0.296 g, 4.92 mmol) were added. Upon completion of the addition, the reaction was stirred at 65° C. for 3 h, then cooled to room temperature, and sodium triacetoxyborohydride (0.394 g, 1.86 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-19:1), to obtain tert-butyl 4-[3-[4-[4-amino-3-(4-phenoxyphenyl)pyrazolo[3,4-d]pyrimidin-1-yl]-1-piperidyl]a zetidin-1-yl]piperidine-1-carboxylate (11c) (0.380 g, yield: 66%).

¹H NMR (400 MHz, CDCl₃) δ 8.35 (s, 1H), 7.67-7.61 (m, 2H), 7.43-7.35 (m, 2H), 7.21-7.12 (m, 3H), 7.11-7.05 (m, 2H), 5.56 (br, 2H), 4.82-4.72 (m, 1H), 4.07-3.93 (m, 2H), 3.72-3.55 (m, 2H), 3.15-2.87 (m, 5H), 2.81 (t, 2H), 2.49-2.35 (m, 2H), 2.17-1.97 (m, 5H), 1.75-1.67 (m, 2H), 1.45 (s, 9H), 1.35-1.25 (m, 2H).

Step 4

3-(4-phenoxyphenyl)-1-[1-[1-(4-piperidyl)azetidin-3-yl]-4-piperidyl]pyrazolo[3,4-d]pyrimidin-4-amine (11d)

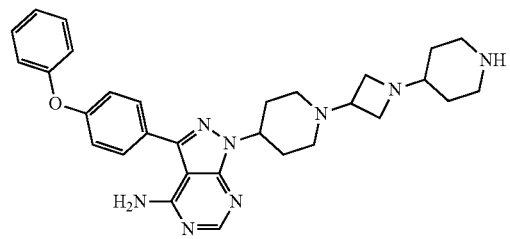 [SMILES: Nc1ncnc2c1c(-c1ccc(Oc3ccccc3)cc1)nn2C1CCN(C2CN(C3CCNCC3)C2)CC1]

Tert-butyl 4-[3-[4-[4-amino-3-(4-phenoxyphenyl)pyrazolo[3,4-d]pyrimidin-1-yl]-1-piperidyl]a zetidin-1-yl]piperidine-1-carboxylate (11c) (0.380 g, 0.608 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 3-(4-phenoxyphenyl)-1-[1-[1-(4-piperidyl)azetidin-3-yl]-4-piperidyl]pyrazolo[3,4-d]pyrimidin-4-amine (11d) (0.256 g, yield: 80%).

LCMS m/z=263.3 [M/2+1]⁺.

Step 5

Tert-butyl 4-[4-[3-[4-[4-amino-3-(4-phenoxyphenyl)pyrazolo[3,4-d]pyrimidin-1-yl]-1-piperidyl]azetidin-1-yl]-1-piperidyl]piperidine-1-carboxylate (11e)

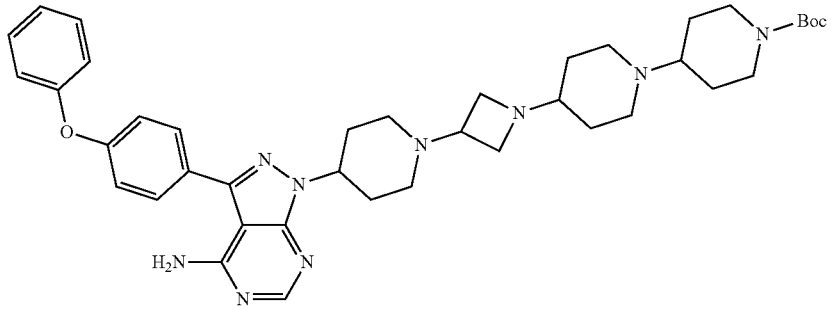 [SMILES: CC(C)(C)OC(=O)N1CCC(N2CCC(N3CC(N4CCC(n5nc(-c6ccc(Oc7ccccc7)cc6)c6c(N)ncnc65)CC4)C3)CC2)CC1]

3-(4-phenoxyphenyl)-1-[1-[1-(4-piperidyl)azetidin-3-yl]-4-piperidyl]pyrazolo[3,4-d]pyrimidin-4-amine (11d) (0.256 g, 0.488 mmol) was dissolved in 3 mL of 1,2-dichloroethane, and tert-butyl 4-oxopiperidine-1-carboxylate (0.117 g, 0.585 mmol) and glacial acetic acid (0.155 g, 2.59 mmol) were added. Upon completion of the addition, the reaction was stirred at 65° C. for 3 h, then cooled to room temperature, and sodium triacetoxyborohydride (0.207 g, 0.976 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-19:1), to obtain tert-butyl 4-[4-[3-[4-[4-amino-3-(4-phenoxyphenyl)pyrazolo[3,4-d]pyrimidin-1-yl]-1-piperidyl]azetidin-1-yl]-1-piperidyl]piperidine-1-carboxylate (11e) (0.244 g, yield: 71%).

LCMS m/z=708.5 [M+1]$^+$.

Step 6

3-(4-phenoxyphenyl)-1-[1-[1-[1-(4-piperidyl)-4-piperidyl]azetidin-3-yl]-4-piperidyl]pyrazolo[3,4-d]pyrimidin-4-amine (11f)

Tert-butyl 4-[4-[3-[4-[4-amino-3-(4-phenoxyphenyl)pyrazolo[3,4-d]pyrimidin-1-yl]-1-piperidyl]azetidin-1-yl]-1-piperidyl]piperidine-1-carboxylate (11e) (0.244 g, 0.345 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, the aqueous layer was extracted with 100 mL of dichloromethane/methanol (v/v) =10:1, and the organic layers were combined, dried over anhydrous sodium sulfate, and concentrated under reduced pressure to obtain 3-(4-phenoxyphenyl)-1-[1-[1-[1-(4-piperidyl)-4-piperidyl]azetidin-3-yl]-4-piperidyl]pyrazolo[3,4-d]pyrimidin-4-amine (11f)(0.209 g, yield: >99%).

LCMS m/z=304.8 [M/2+1]$^+$.

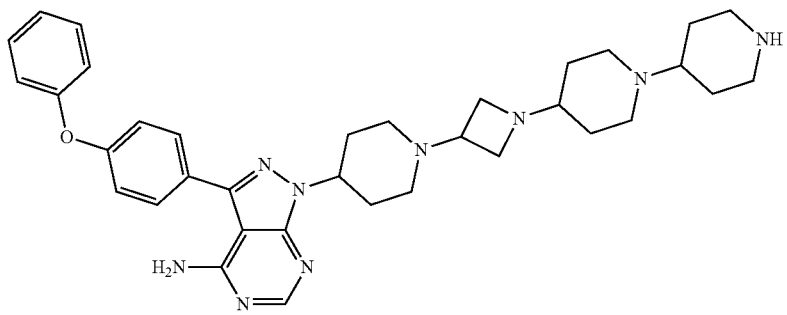 [SMILES: Nc1ncnc2c1c(-c1ccc(Oc3ccccc3)cc1)nn2C1CCN(C2CN(C3CCN(C4CCNCC4)CC3)C2)CC1]

Step 7

Tert-butyl 4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]piperidine-1-carboxylate (11g)

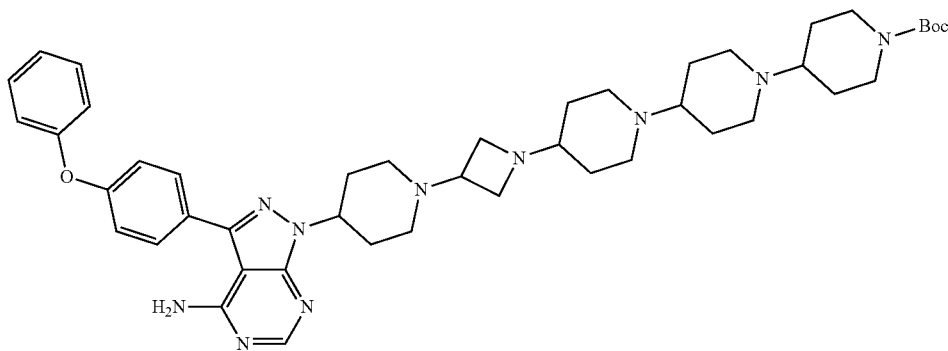 [SMILES: CC(C)(C)OC(=O)N1CCC(N2CCC(N3CCC(N4CC(N5CCC(n6nc(-c7ccc(Oc8ccccc8)cc7)c7c(N)ncnc76)CC5)C4)CC3)CC2)CC1]

3-(4-phenoxyphenyl)-1-[1-[1-[1-(4-piperidyl)-4-piperidyl]azetidin-3-yl]-4-piperidyl]pyrazolo[3,4-d]pyrimidin-4-amine (110 (0.208 g, 0.342 mmol) was dissolved in 3 mL of 1,2-dichloroethane, and tert-butyl 4-oxopiperidine-1-carboxylate (0.102 g, 0.513 mmol) and glacial acetic acid (0.109 g, 1.81 mmol) were added. Upon completion of the addition, the reaction was stirred at 65° C. for 3 h, then cooled to room temperature, and sodium triacetoxyborohydride (0.145 g, 0.684 mmol) was added. Upon completion of the addition, the reaction was carried out at room temperature overnight. The pH was adjusted to 9-10 by adding dropwise saturated sodium bicarbonate solution. The reaction solution was concentrated under reduced pressure, and then the crude product was separated and purified by silica gel column chromatography (dichloromethane/methanol (v/v)=100:0-7:3), to obtain tert-butyl 4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]piperidine-1-carboxylate (11g) (0.152 g, yield: 56%).

LCMS m/z=396.3 [M/2+1]$^+$.

Step 8

3-(4-phenoxyphenyl)-1-[1-[1-[1-[1-(4-piperidyl)-4-piperidyl]-4-piperidyl]azetidin-3-yl]-4-piperidyl]pyrazolo[3,4-d]pyrimidin-4-amine (11h)

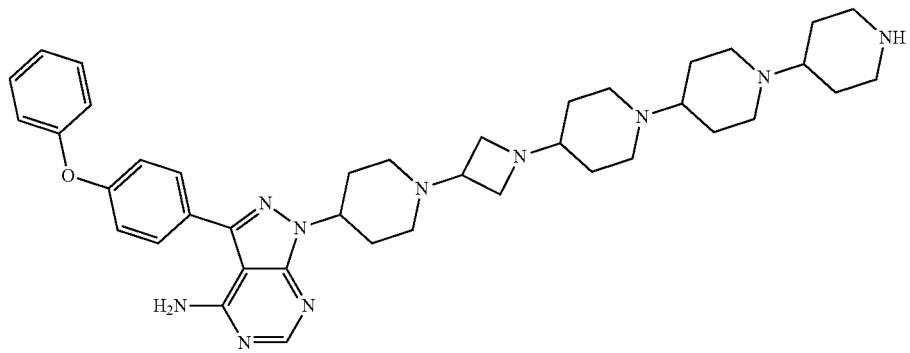 [SMILES: Nc1ncnc2c1c(-c1ccc(Oc3ccccc3)cc1)nn2C1CCN(C2CN(C3CCN(C4CCN(C5CCNCC5)CC4)CC3)C2)CC1]

Tert-butyl
4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]piperidine-1-carboxylate (11g) (0.152 g, 0.192 mmol) was dissolved in 2 mL of dichloromethane, and 5 mL of 4N ethyl acetate hydrochloride solution was added, and the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, the aqueous layer was extracted with 100 mL of dichloromethane/methanol (v/v)=10:1, and the organic layers were combined, dried over anhydrous sodium sulfate, and concentrated under reduced pressure to obtain 3-(4-phenoxyphenyl)-1-[1-[1-[1-[1-(4-piperidyl)-4-piperidyl]-4-piperidyl]azetidin-3-yl]-4-piperidyl]pyrazolo[3,4-d]pyrimidin-4-amine (11h) (0.133 g, yield: >99%).

LCMS m/z=346.4 [M/2+1]⁺.

Step 9

5-[4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-1-piperidyl]-2-(2,6-dioxo-3-piperidyl)isoindoline-1,3-dione Hexatrifluoroacetate (Compound 11)

3-(4-phenoxyphenyl)-1-[1-[1-[1-[1-(4-piperidyl)-4-piperidyl]-4-piperidyl]azetidin-3-yl]-4-piperidyl]pyrazolo[3,4-d]pyrimidin-4-amine (11h) (0.130 g, 0.188 mmol) was dissolved in 2 mL of dimethyl sulfoxide, 2-(2,6-dioxopiperidin-3-yl)-5-fluoroisoindoline-1,3-dione (see WO 2017197056 for the synthetic method) (0.0676 g, 0.245 mmol) and diisopropylethylamine (0.122 g, 0.941 mmol) were added. Upon completion of the addition, the reaction was stirred at 90° C. for 2 h. The reaction solution was cooled to room temperature, to which 10 mL of water was slowly added dropwise, and filtered. The filter cake was dissolved with 20 mL of dichloromethane, then washed with 5 mL of saturated sodium chloride solution. The liquid separation was conducted, and the organic layer was dried over anhydrous sodium sulfate, and concentrated under reduced pressure, then the crude product was passed through Pre-HPLC (instrument and preparative column: using Glison GX-281 to prepare the liquid phase, preparative column model: Sunfire C18, 5 μm, inner diameter×length=30 mm× 150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-[4-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-1-piperidyl]-2-(2,6-dioxo-3-piperidy 1)isoindoline-1,3-dione hexatrifluoroacetate (Compound 11) (0.013 g, yield: 4%).

¹H NMR (400 MHz, DMSO-d₆) δ 11.06 (s, 1H), 8.28 (s, 1H), 7.78-7.62 (m, 4H), 7.47-7.40 (m, 2H), 7.36-7.28 (m, 1H), 7.26-7.06 (m, 5H), 5.08 (dd, 1H), 4.89-4.78 (m, 1H), 4.31-4.10 (m, 5H), 4.04-3.88 (m, 4H), 3.68-3.45 (m, 6H), 3.07-2.81 (m, 6H), 2.65-2.53 (m, 2H), 2.41-1.82 (m, 12H), 1.76-1.48 (m, 5H), 1.32-1.21 (m, 4H).

LCMS m/z=474.4 [M/2+1]⁺.

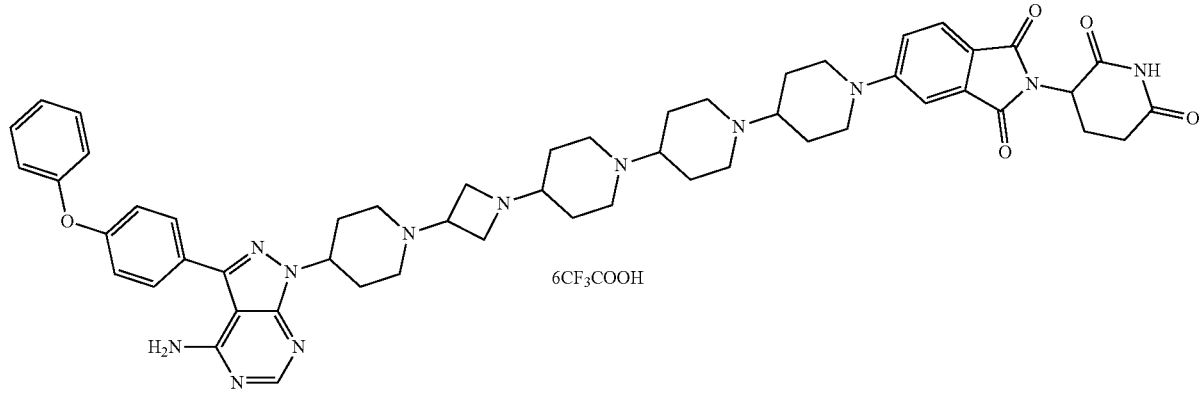 [SMILES: Nc1ncnc2c1c(-c1ccc(Oc3ccccc3)cc1)nn2C1CCN(C2CN(C3CCN(C4CCN(C5CCN(c6ccc7c(c6)C(=O)N(C6CCC(=O)NC6=O)C7=O)CC5)CC4)CC3)C2)CC1]

Example 12
5-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-2-(2,6-dioxo-3-piperidyl)isoindoline-1,3-dione Pentatrifluoroacetate (Compound 12)
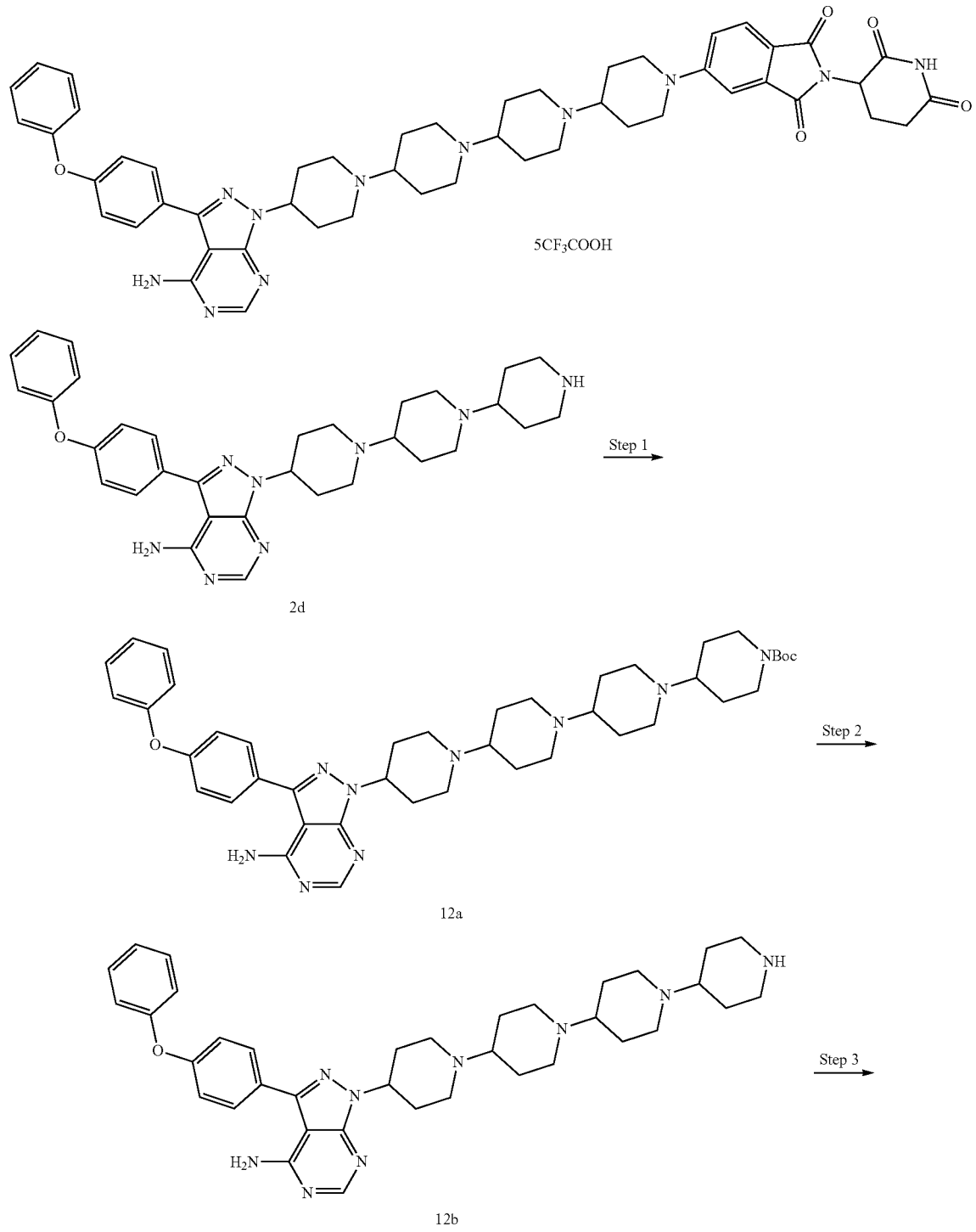

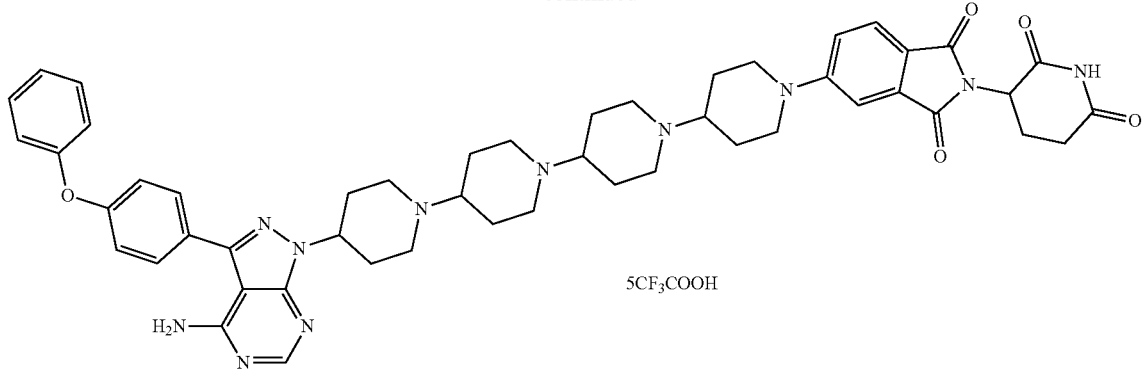

Compound 12

Step 1

Tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]piperidine-1-carboxylate (12a)

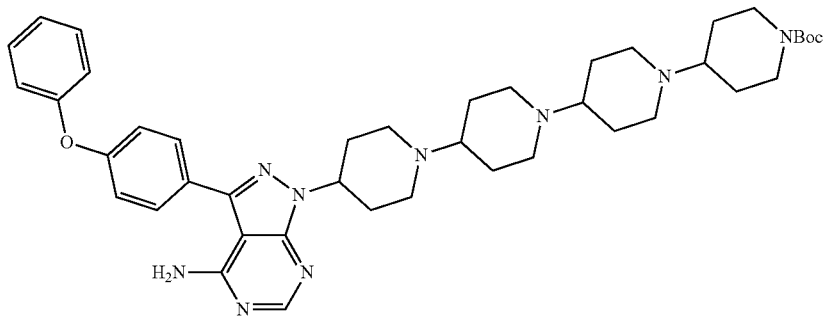 [SMILES: CC(C)(C)OC(=O)N1CCC(N2CCC(N3CCC(N4CCC(n5nc(-c6ccc(Oc7ccccc7)cc6)c6c(N)ncnc65)CC4)CC3)CC2)CC1]

3-(4-phenoxyphenyl)-1-[1-[1-(4-piperidyl)-4-piperidyl]-4-piperidyl]pyrazolo[3,4-d]pyrimidin-4-amine (2d) (0.8 g, 1.45 mmol) was dissolved in 20 mL of 1,2-dichloroethane, and N-tert-butoxycarbonyl-4-piperidone (0.9 g, 4.51 mmol) was added, then acetic acid (0.4 g, 6.67 mmol) and anhydrous sodium sulfate (1 g) were added. Upon completion of the addition, the reaction was carried out at 85° C. for 3 h, and cooled to room temperature, sodium triacetoxyborohydride (2 g, 9.43 mmol) was added, and the mixture was reacted at room temperature overnight. The pH was adjusted to 9-10 by adding dropwise saturated sodium bicarbonate solution, and the organic layer was dried over anhydrous sodium sulfate, then concentrated under reduced pressure. The residue was separated and purified by silica gel column chromatography (DCM/MeOH (v/v)=50/1-5/1), to obtain tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]piperidine-1-carboxylate (12a) (0.7 g, yield: 70%). LCMS m/z=736.5 [M+1]$^+$.

Step 2

3-(4-phenoxyphenyl)-1-[1-[1-[1-[1-(4-piperidyl]-4-piperidyl]-4-piperidyl]-4-piperidyl]pyrazolo[3,4-d]pyrimidin-4-amine (12b)

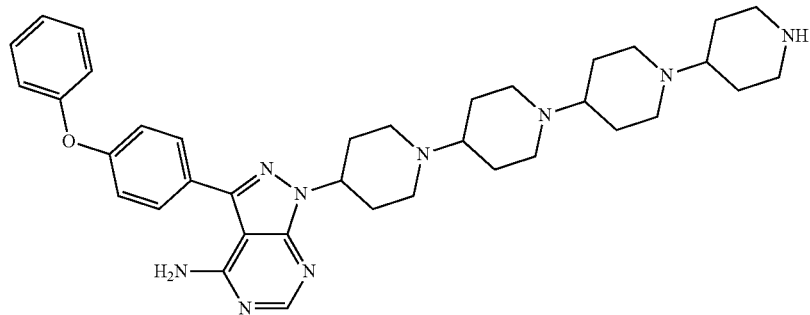 [SMILES: Nc1ncnc2c1c(-c1ccc(Oc3ccccc3)cc1)nn2C1CCN(C2CCN(C3CCN(C4CCNCC4)CC3)CC2)CC1]

Tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]piperidine-1-carboxylate (12a) (0.7 g, 0.95 mmol) was dissolved in 5 mL of dichloromethane, and 5 mL of trifluoroacetic acid was added, the mixture was stirred at room temperature overnight. The solvent was removed under reduced pressure, and 20 mL of dichloromethane and 2 mL of ethanol were added, and the resulting solution was washed with saturated sodium bicarbonate solution, the aqueous phase was further extracted with 20 mL of dichloromethane and 2 mL of ethanol, and the organic layers were combined, dried over anhydrous sodium sulfate, and concentrated under reduced pressure to obtain 3-(4-phenoxyphenyl)-1-[1-[1-[1-(4-piperidyl)-4-piperidyl]-4-piperidyl]-4-piperidyl]pyrazolo[3,4-d]pyrimidin-4-amine (12b) (0.60 g, yield: 99%).

LCMS m/z=636.3 [M+1]$^+$.

Step 3

5-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-2-(2,6-dioxo-3-piperidyl)isoindoline-1,3-dione pentatrifluoroacetate (Compound 12)

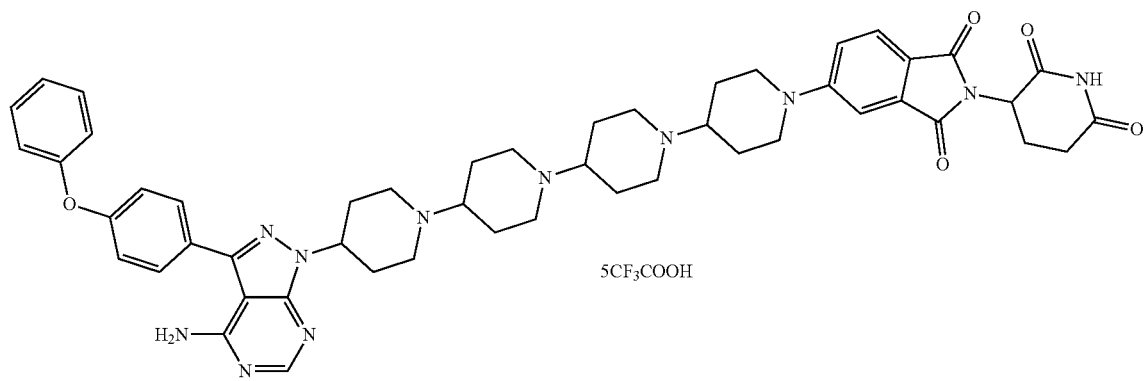 [SMILES: Nc1ncnc2c1c(-c1ccc(Oc3ccccc3)cc1)nn2C1CCN(C2CCN(C3CCN(C4CCN(c5ccc6c(c5)C(=O)N(C5CCC(=O)NC5=O)C6=O)CC4)CC3)CC2)CC1]

3-(4-phenoxyphenyl)-1-[1-[1-[1-[1-(4-piperidyl]-4-piperidyl]-4-piperidyl]-4-piperidyl]pyrazolo[3,4-d]pyrimidin-4-amine (12b) (0.25 g, 0.39 mmol), 2-(2,6-dioxopiperidin-3-yl)-5-fluoroisoindoline-1,3-dione (see WO 2017197056 for the synthetic method) (0.11 g, 0.39 mmol) and triethylamine (0.12 g, 1.2 mmol) were dissolved in 3 mL of DMSO, and the mixed solution was warmed to 90° C. and stirred for 12 h. The reaction solution was cooled to room temperature, added 10 mL of water, and filtered. The filter cake was passed through Pre-HPLC (instrument and preparative column: using Glison GX-281 to prepare the liquid phase, preparative column model: Sunfire C18, 5 μm, inner diameter×length=30 mm× 150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain 5-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-2-(2,6-dioxo-3-piperidyl)isoindoline-1,3-dione pentatrifluoroacetate (Compound 12) (0.15 g, yield: 28%).

$^1$H NMR (400 MHz, DMSO-$d_6$) δ 11.07 (s, 1H), 10.05 (br, 2H), 8.33 (s, 1H), 7.75-7.62 (m, 3H), 7.48-7.39 (m, 3H), 7.35-7.29 (m, 1H), 7.24-7.10 (m, 5H), 5.27-5.04 (m, 3H), 5.04-4.35 (br, 5H), 4.30-4.20 (m, 2H), 3.73-3.43 (m, 8H), 3.13-2.84 (m, 6H), 2.64-2.54 (m, 2H), 2.40-2.17 (m, 6H), 2.15-1.87 (m, 7H), 1.77-1.60 (m, 2H).

LCMS m/z=892.4 [M+1]$^+$.

Example 13

5-[3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidin-1-yl]-2-(2,6-dioxo-3-piperidyl)isoindoline-1,3-dione (Compound 13)

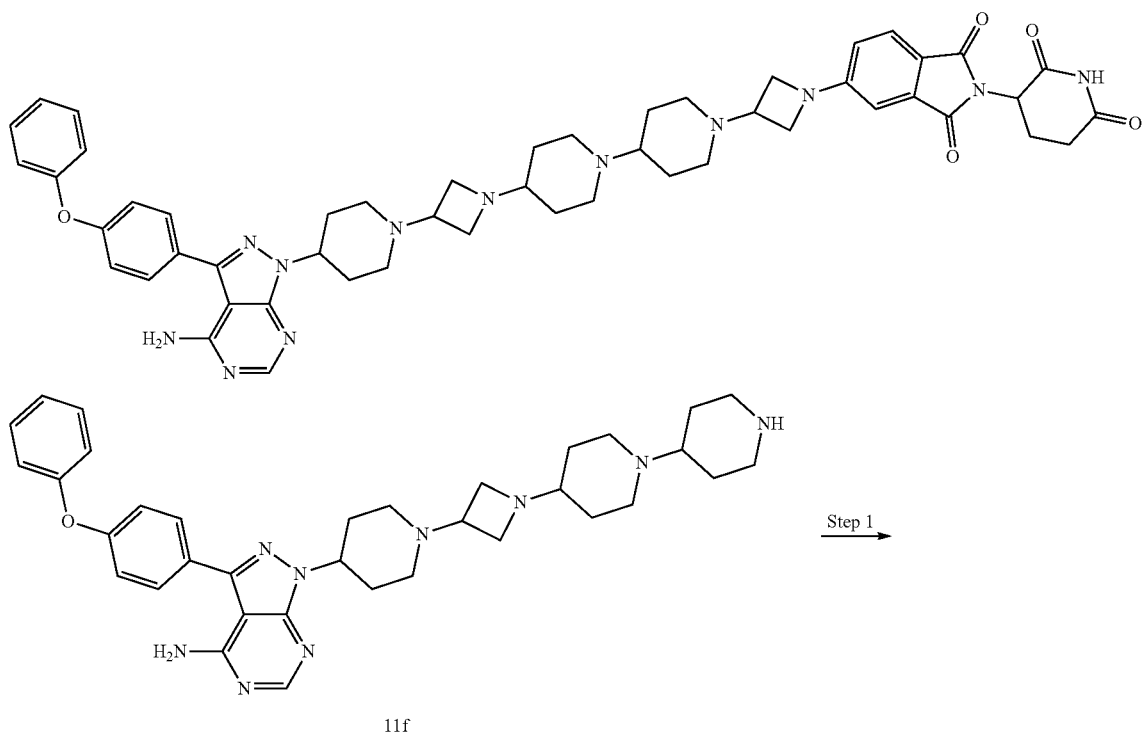

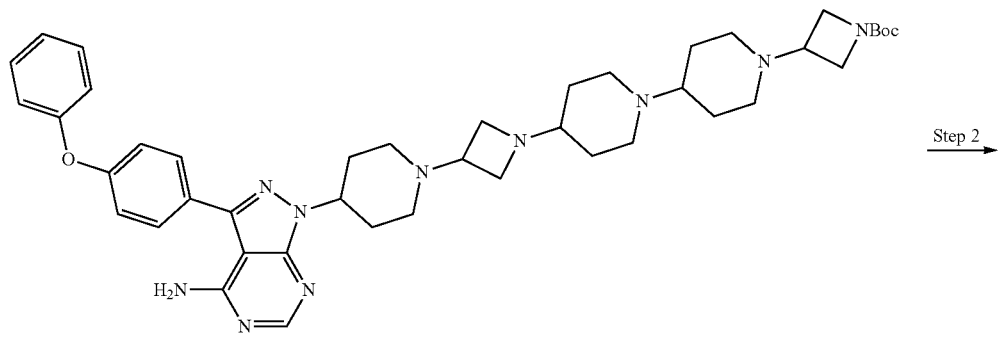

-continued

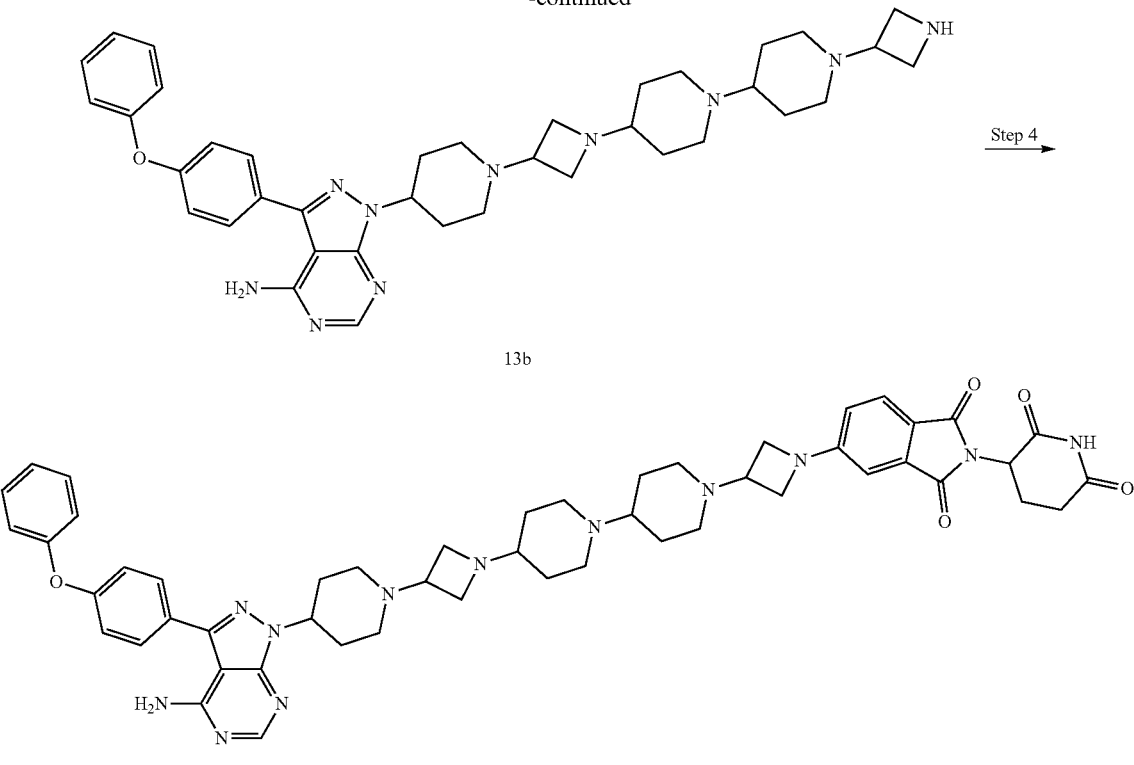

13b

Compound 13

Step 1

Tert-butyl 3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidine-1-carboxylate (13a)

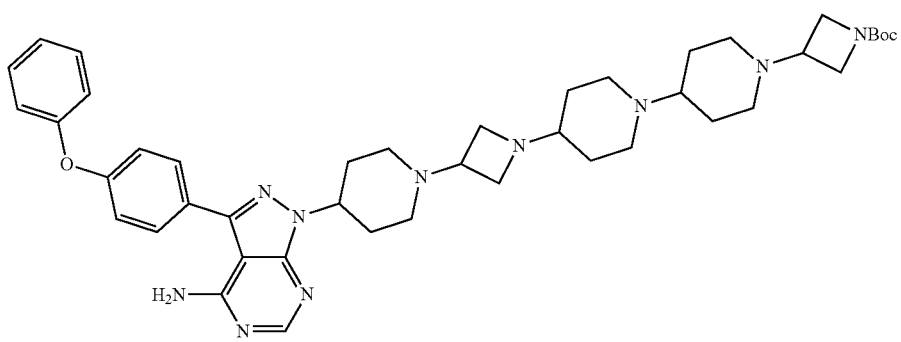 [SMILES: CC(C)(C)OC(=O)N1CC(N2CCC(N3CCC(N4CC(N5CCC(n6nc(-c7ccc(Oc8ccccc8)cc7)c7c(N)ncnc76)CC5)C4)CC3)CC2)C1]

To a 50 mL reaction flask was successively added 3-(4-phenoxyphenyl)-1-[1-[1-[1-(4-piperidyl)-4-piperidyl]azetidin-3-yl]-4-piperidyl]pyrazolo[3,4-d]pyrimidin-4-amine (110 (420 mg, 0.69 mmol), acetic acid (41.4 mg, 0.69 mmol), tert-butyl 3-oxo azetidine-1-carboxylate (118 mg, 0.69 mmol), sodium triacetoxyborohydride (292.5 mg, 1.38 mmol) and dichloromethane (20 mL). Upon completion of the addition, the reaction was stirred at room temperature for 3 h. The reaction solution was filtered off with suction, and the filtrate was washed with saturated sodium bicarbonate solution (8 mL). The liquid separation was conducted, then the organic layer was dried over anhydrous sodium sulfate, filtered off with suction, and the filtrate was concentrated under reduced pressure, to obtain tert-butyl 3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidine-1-carboxylate (13a) (350 mg, yield: 67%).

Step 2

1-[1-[1-[1-[1-(azetidin-3-yl)-4-piperidyl]-4-piperidyl]azetidin-3-yl]-4-piperidyl]-3-(4-phenoxyphenyl)pyrazolo[3,4-d]pyrimidin-4-amine (13b)

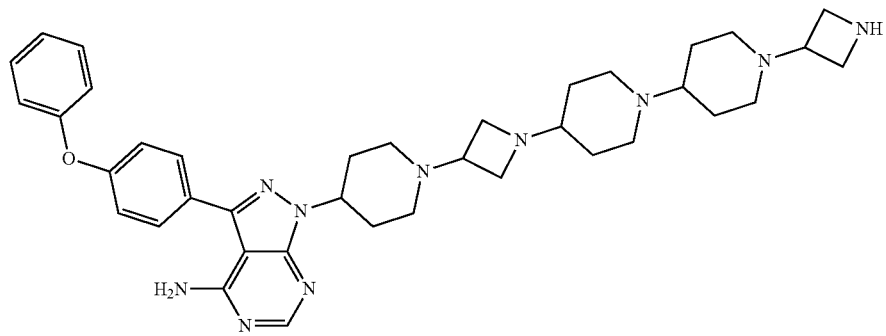 [SMILES: Nc1ncnc2c1c(-c1ccc(Oc3ccccc3)cc1)nn2C1CCN(C2CN(C3CCN(C4CCN(C5CNC5)CC4)CC3)C2)CC1]

Tert-butyl 3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidine-1-carboxylate (13a) (350 mg, 0.46 mmol) was dissolved in 8 mL of 4N ethyl acetate hydrochloride solution, and 5 mL of methanol was added, the reaction was carried out at room temperature for 2 h. The reaction solution was directly concentrated, then the reaction system was diluted with ethyl acetate (30 mL), quenched with saturated sodium bicarbonate solution (10 mL), and extracted with ethyl acetate (5 mL×3). The organic phase was combined, dried over anhydrous sodium sulfate, and filtered, and the filtrate was concentrated under reduced pressure, to obtain 1-[1-[1-[1-[1-(azetidin-3-yl)-4-piperidyl]-4-piperidyl]azetidin-3-yl]-4-piperidyl]-3-(4-phenoxyphenyl)pyrazolo[3,4-d]pyrimidin-4-amine (13b) (180 mg, yield: 59%).

Step 3

5-[3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidin-1-yl]-2-(2,6-dioxo-3-piperidyl)isoindoline-1,3-dione (Compound 13)

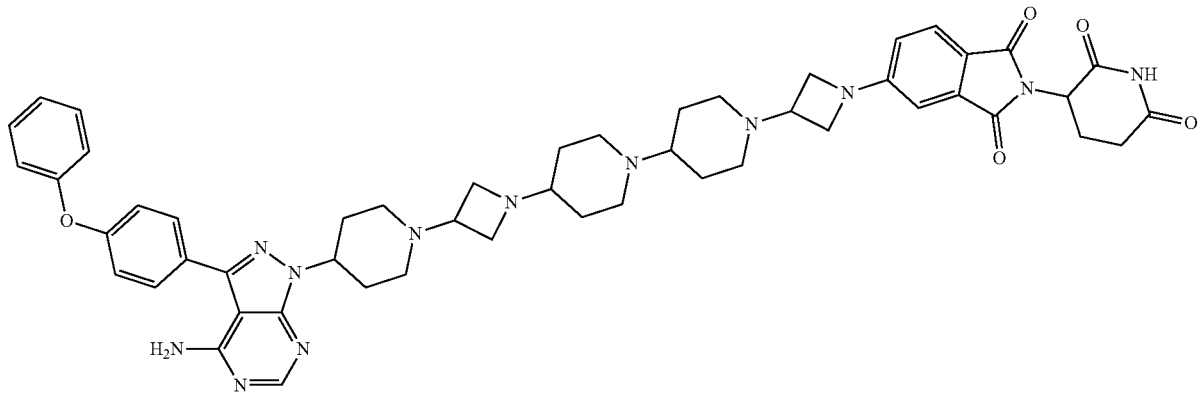 [SMILES: Nc1ncnc2c1c(-c1ccc(Oc3ccccc3)cc1)nn2C1CCN(C2CN(C3CCN(C4CCN(C5CN(c6ccc7c(c6)C(=O)N(C6CCC(=O)NC6=O)C7=O)C5)CC4)CC3)C2)CC1]

1-[1-[1-[1-[1-(azetidin-3-yl)-4-piperidyl]-4-piperidyl]azetidin-3-yl]-4-piperidyl]-3-(4-phenoxyphenyl)pyrazolo[3,4-d]pyrimidin-4-amine (13b) (180 mg, 0.27 mmol) was dissolved in DMSO (20 mL), and 2-(2,6-dioxopiperidin-3-yl)-5-fluoroisoindoline-1,3-dione (see WO 2017197056 for the synthetic method) (74.5 mg, 0.27 mmol) and DIPEA (174.4 mg, 1.35 mmol) were added at room temperature, the reaction was stirred at 90° C. for 2 h. To the reaction solution was added 50 mL of water, the aqueous phase was extracted with ethyl acetate (50 mL×3), and the organic phase was combined, washed with water (20 mL×2), dried over anhydrous sodium sulfate, and concentrated. The residue was separated and purified by silica gel column chromatography (dichloromethane/methanol (v/v)=100:1-20:1), to obtain a crude product. The crude product was passed through Pre-HPLC (instrument and preparative column: using Glison GX-281 to prepare the liquid phase, preparative column model: Sunfire C18, 5 μm, inner diameter×length=30 mm× 150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the prepared product was alkalized and concentrated to obtain 5-[3-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]azetidin-1-yl]-2-(2,6-dioxo-3-piperid yl)isoindoline-1,3-dione (Compound 13) (63 mg, yield: 25%).

$^1$H NMR (400 MHz, CDCl$_3$) δ 8.37 (s, 1H), 7.74-7.49 (m, 4H), 7.43-7.34 (m, 2H), 7.18-7.13 (m, 3H), 7.09-7.04 (m, 2H), 6.77 (d, 1H), 6.51 (dd, 1H), 5.67 (br, 2H), 5.01-4.88 (m, 2H), 4.34-4.20 (m, 1H), 4.08 (t, 2H), 3.90-3.82 (m, 2H), 3.58-3.50 (m, 2H), 3.38-3.30 (m, 1H), 3.13-3.05 (m, 1H), 3.00-2.70 (m, 11H), 2.46 (t, 2H), 2.38-2.29 (m, 2H), 2.19-2.14 (m, 2H), 1.94-1.86 (m, 6H), 1.81-1.74 (m, 2H), 1.67-1.59 (m, 2H), 1.44-1.39 (m, 2H), 0.99-0.90 (m, 2H).

LCMS m/z=460.4 [M/2+1]$^+$.

Example 14

5-[4-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-1-piperidyl]-2-(2,6-dioxo-3-piperidyl)isoindoline-1,3-dione Hexatrifluoroacetate (Compound 14)

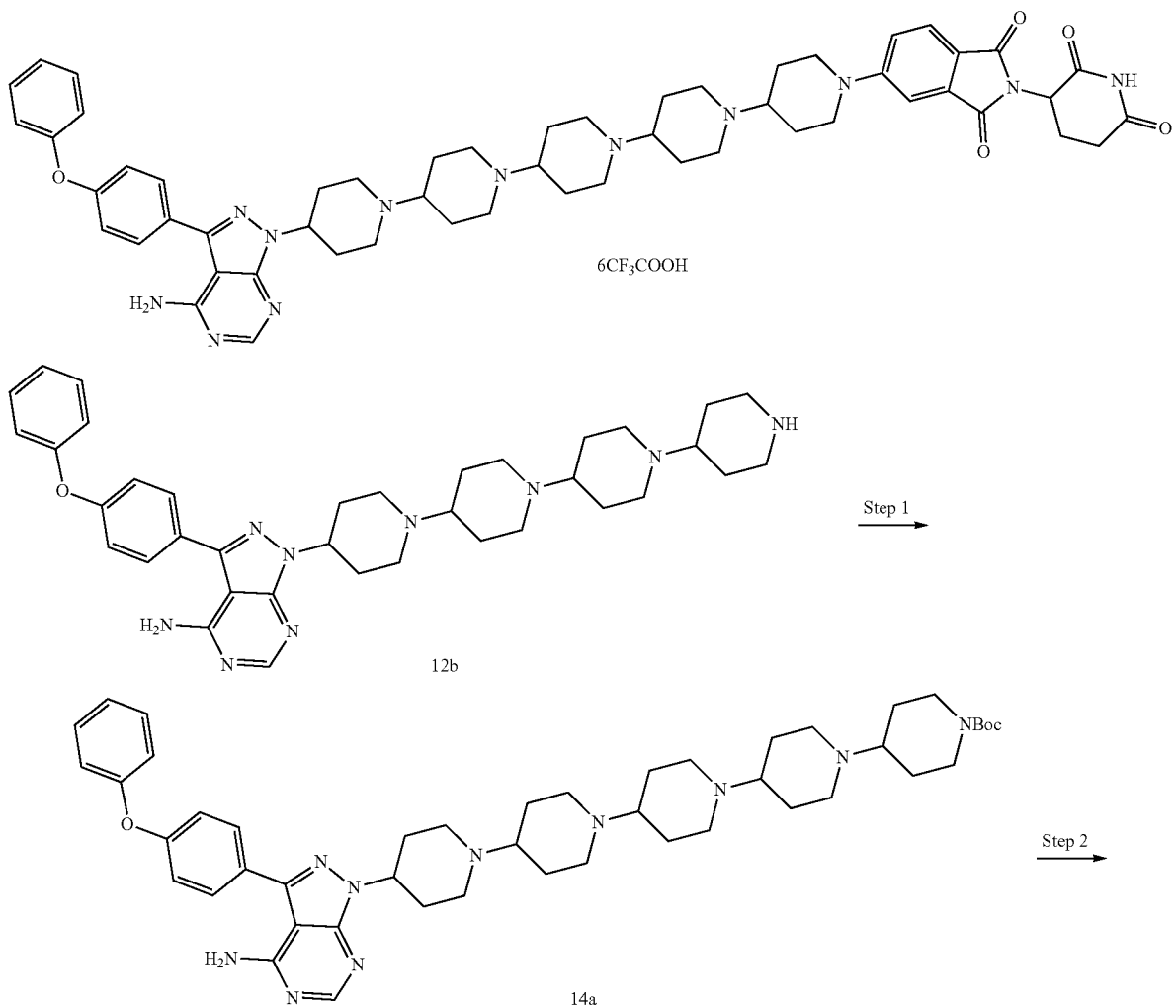

-continued

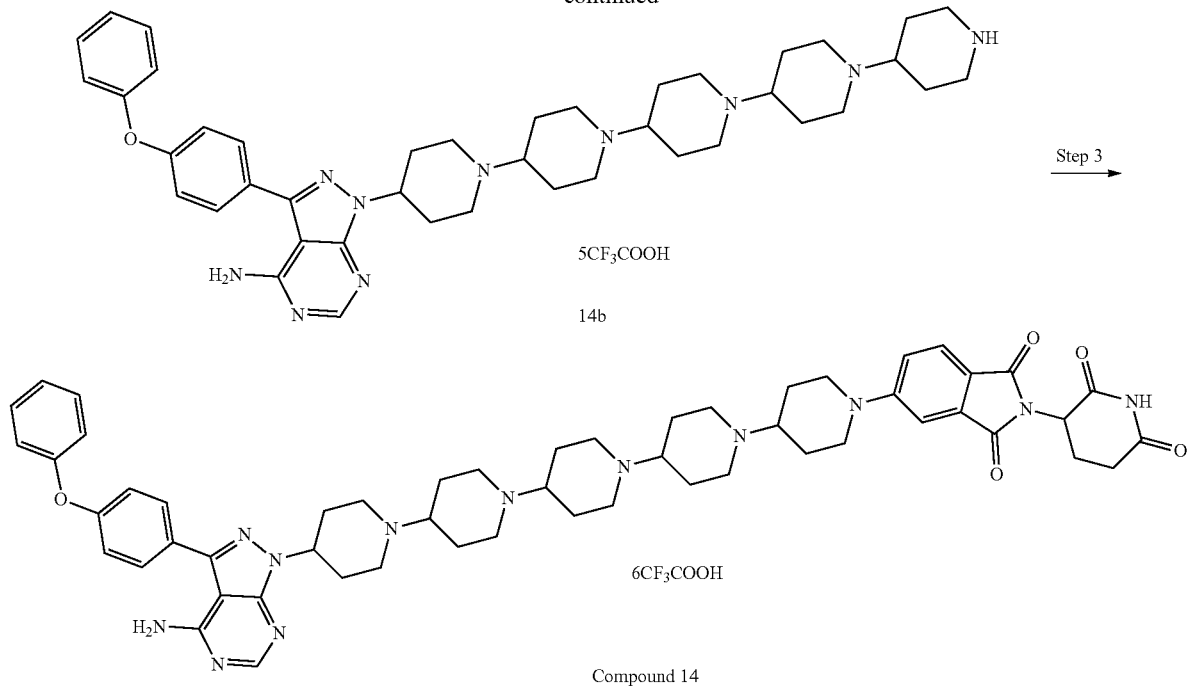

Step 1

Tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]piperidine-1-carboxylate (14a)

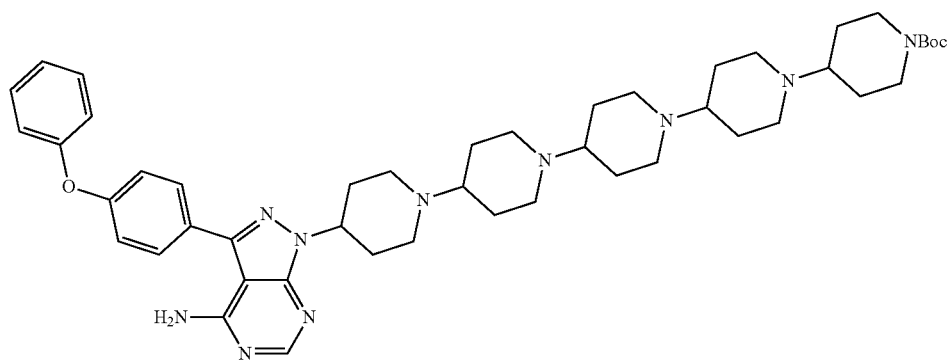 [SMILES: CC(C)(C)OC(=O)N1CCC(N2CCC(N3CCC(N4CCC(N5CCC(n6nc(-c7ccc(Oc8ccccc8)cc7)c7c(N)ncnc76)CC5)CC4)CC3)CC2)CC1]

3-(4-phenoxyphenyl)-1-[1-[1-[1-(4-piperidyl)-4-piperidyl]-4-piperidyl]-4-piperidyl]pyrazolo[3,4-d]pyrimidin-4-amine (12b) (0.3 g, 0.47 mmol) was dissolved in 20 mL of 1,2-dichloroethane, and N-tert-butoxycarbonyl-4-piperidone (0.28 g, 1.42 mmol) was added, then acetic acid (0.14 g, 2.36 mmol) and 0.5 g of anhydrous sodium sulfate were added. Upon completion of the addition, the mixture was warmed to 85° C. and reacted for 3 h, and cooled to room temperature. Sodium triacetoxyborohydride (0.5 g, 2.36 mmol) was added, and the mixture was reacted at room temperature overnight. The pH was adjusted to 9-10 by adding dropwise saturated sodium bicarbonate aqueous solution, and the organic layer was dried over anhydrous sodium sulfate, then concentrated under reduced pressure. The residue was separated and purified by silica gel column chromatography (DCM/MeOH (v/v)=50/1-5/1), to obtain tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]piperidine-1-carboxylate (14a) (0.13 g, yield: 33%).

LCMS m/z=819.5 [M+1]$^+$.

Step 2

3-(4-phenoxyphenyl)-1-[1-[1-[1-[1-(4-piperidyl)-4-piperidyl]-4-piperidyl]-4-piperidyl]-4-piperidyl] pyrazolo[3,4-d]pyrimidin-4-amine pentatrifluoroacetate (14b)

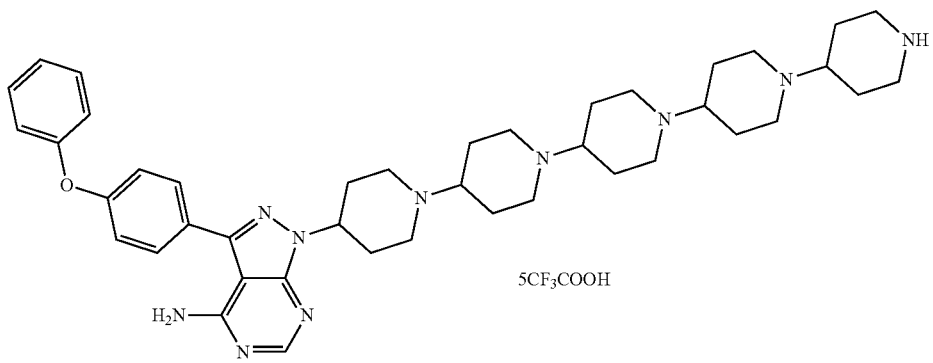 [SMILES: Nc1ncnc2c1c(-c1ccc(Oc3ccccc3)cc1)nn2C1CCN(C2CCN(C3CCN(C4CCN(C5CCNCC5)CC4)CC3)CC2)CC1]

Tert-butyl 4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]piperidine-1-carboxylate (14a) (0.13 g, 0.16 mmol) was dissolved in 2 mL of DCM, and 2 mL of trifluoroacetic acid was added. Upon completion of the addition, the mixture was stirred at room temperature overnight. The solvent was removed under reduced pressure, and the crude product was directly used in the next step.

LCMS m/z=719.5 [M+1]+.

Step 3

5-[4-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-1-piperidyl]-2-(2,6-dioxo-3-piperidyl)isoindoline-1,3-dione Hexatrifluoroacetate (Compound 14)

3-(4-phenoxyphenyl)-1-[1-[1-[1-[1-(4-piperidyl)-4-piperidyl]-4-piperidyl]-4-piperidyl]-4-piperidyl]pyrazolo[3,4-d]pyrimidin-4-amine pentatrifluoroacetate (14b) (0.20 g, 0.16 mmol), 2-(2,6-dioxopiperidin-3-yl)-5-fluoroisoindoline-1,3-dione (see WO 2017197056 for the synthetic method) (0.05 g, 0.17 mmol) and triethylamine (0.12 g, 1.2 mmol) were dissolved in 3 mL of DMSO, and the mixed solution was warmed to 120° C. and stirred for 6 h. The reaction solution was cooled to room temperature, added 10 mL of water, and filtered. The filter cake was passed through Pre-HPLC (instrument and preparative column: using Gilson GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from concentration (v/v, the same below) of 5% to concentration of 60% (elution time: min), the reaction system was lyophilized to obtain 5-[4-[4-[4-[4-[4-[4-amino-3-(4-phenoxyphenyl)pyrazolo[3,4-d]pyrimidin-1-yl]-1-piperidyl]-1-piperidyl]-1-piperidyl]-1-piperidyl]-1-piperidyl]-2-(2,6-dioxo-3-piperidyl) isoindoline-1,3-dione hexatrifluoroacetate (Compound 14) (0.06 g, yield: 25%).

1H NMR (400 MHz, DMSO-d6) δ 11.06 (s, 1H), 10.01 (br, 2H), 8.32 (s, 1H), 7.74-7.62 (m, 3H), 7.48-7.40 (m, 3H), 7.35-7.28 (m, 1H), 7.24-7.10 (m, 5H), 5.24-4.92 (m, 3H), 4.60-4.17 (m, 9H), 3.75-3.45 (m, 11H), 3.13-2.85 (m, 8H), 2.67-2.56 (m, 2H), 2.40-2.20 (m 7H), 2.14-1.88 (m, 8H), 1.77-1.57 (m, 2H).

LCMS m/z=975.5 [M+1]+.

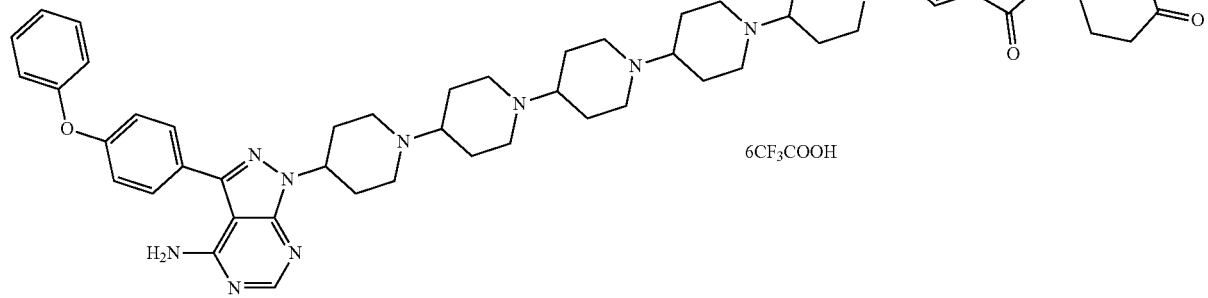

Example 15
5-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-2-(2,6-dioxo-3-piperidyl)isoindoline-1,3-dione (Compound 15)
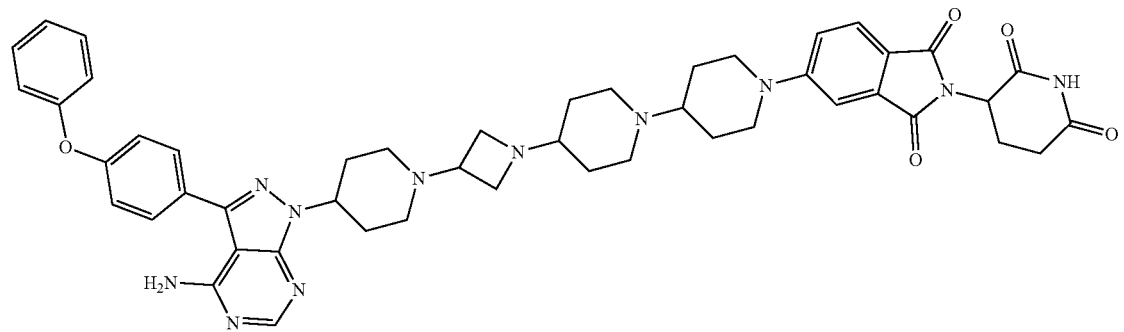
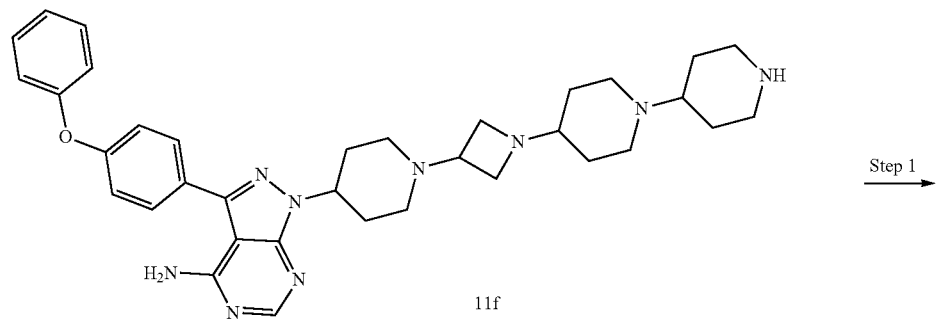
Step 1
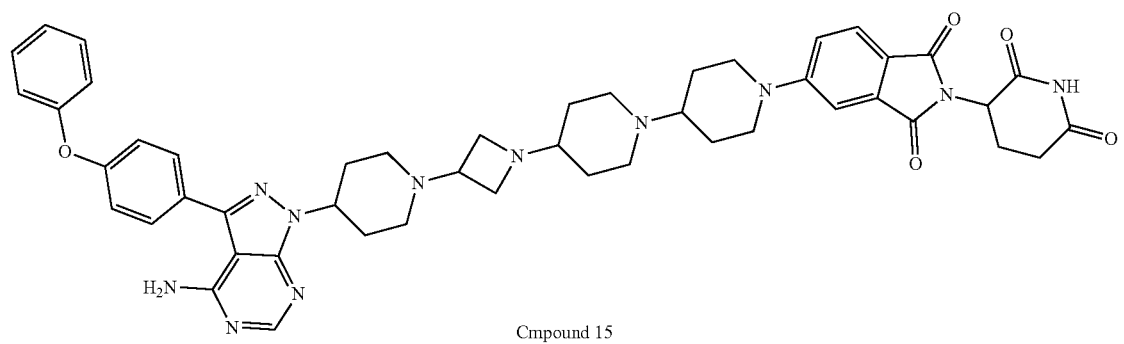
Cmpound 15

Step 1

5-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-2-(2,6-dioxo-3-piperidyl)isoindoline-1,3-dione (Compound 15)

3-(4-phenoxyphenyl)-1-[1-[1-[1-(4-piperidyl)-4-piperidyl]azetidin-3-yl]-4-piperidyl]pyrazolo[3,4-d]pyrimidin-4-amine (110 (164 mg, 0.27 mmol) was dissolved in 20 mL of DMSO, and 2-(2,6-dioxopiperidin-3-yl)-5-fluoroisoindoline-1,3-dione (see WO 2017197056 for the synthetic method) (74.5 mg, 0.27 mmol) and DIPEA (174.4 mg, 1.35 mmol) were added at room temperature, the reaction was stirred at 90° C. for 2 h. To the reaction solution was added 50 mL of water, the aqueous phase was extracted with ethyl acetate (50 mL×3), and the organic phase was combined, washed with water (20 mL×2), dried over anhydrous sodium sulfate, and concentrated. The crude product was separated and purified by silica gel column chromatography (dichloromethane/methanol (v/v)=100:1-20:1), to obtain a crude product. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from concentration of 5% to concentration of 60% (elution time: 15 min), the prepared product was alkalized and concentrated to obtain 5-[4-[4-[3-[4-[4-amino-3-(4-phenoxyphenyl)pyrazolo[3,4-d]pyrimidin-1-yl]-1-piperidyl]azetidin-1-yl]-1-piperidyl]-1-piperidyl]-2-(2,6-dioxo-3-piperidyl)isoindoline-1,3-dione (Compound 15) (58 mg, yield: 25%).

$^1$H NMR (400 MHz, CDCl$_3$) δ 8.38 (s, 1H), 7.75-7.58 (m, 4H), 7.54-7.51 (m, 1H), 7.40-7.36 (m, 2H), 7.17-7.13 (m, 3H), 7.08-7.02 (m, 3H), 5.65 (s, 2H), 4.95-4.91 (m, 2H), 4.32-4.20 (m, 1H), 3.97 (d, 2H), 3.61 (s, 1H), 3.53 (s, 1H), 3.11-3.10 (m, 1H), 2.99-2.90 (m, 7H), 2.86-2.85 (m, 1H), 2.80-2.69 (m, 3H), 2.60-2.59 (m, 1H), 2.49-2.44 (m, 1H), 2.27-2.14 (m, 4H), 1.95-1.86 (m, 6H), 1.77-1.72 (m, 2H), 1.67-1.61 (m, 2H), 0.96-0.94 (m, 2H).

LCMS m/z=864.5 [M+1]$^+$.

Example 16

5-[4-[3-[3-[4-[4-amino-3-(4-phenoxyphenyl)pyrazolo[3,4-d]pyrimidin-1-yl]-1-piperidyl]pyrrolidin-1-yl]azetidin-1-yl]-1-piperidyl]-2-(2,6-dioxo-3-piperidyl)isoindoline-1,3-dione (Compound 16)

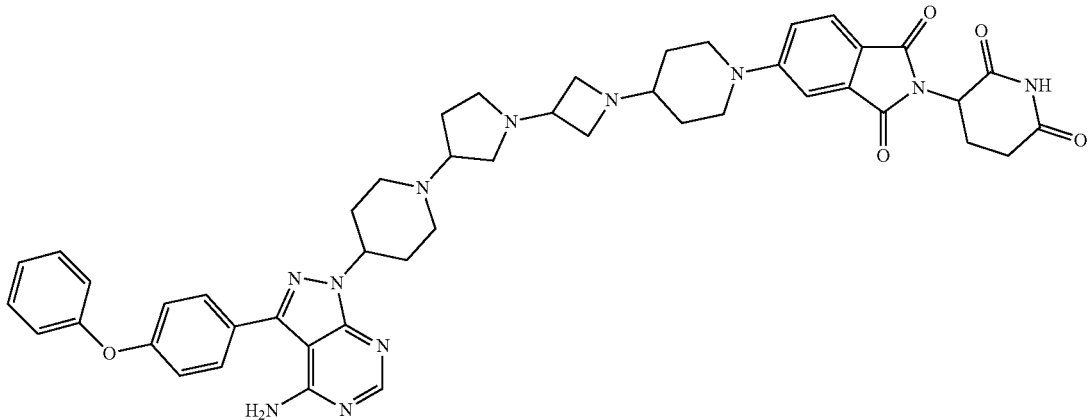

287 288
-continued
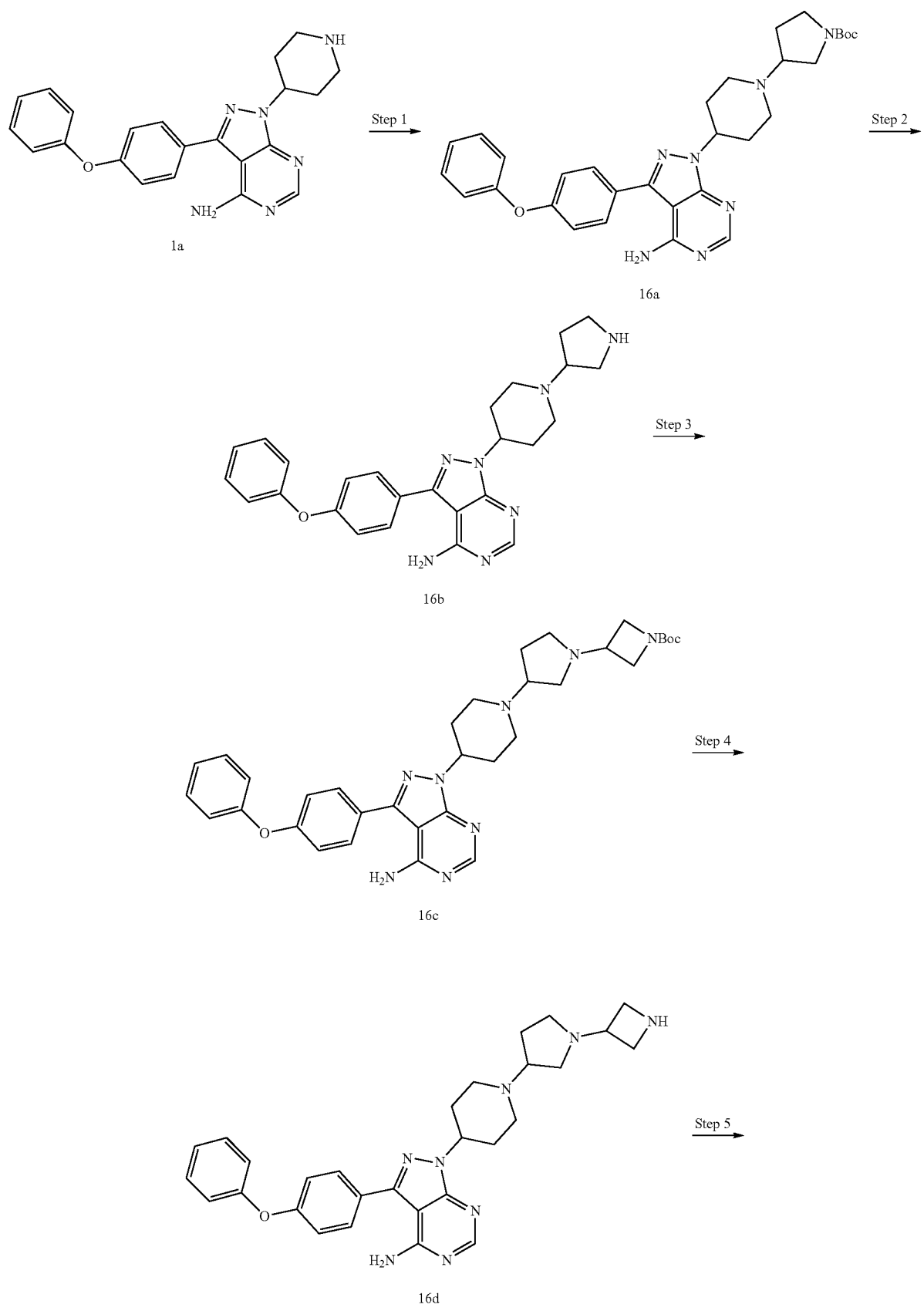

-continued
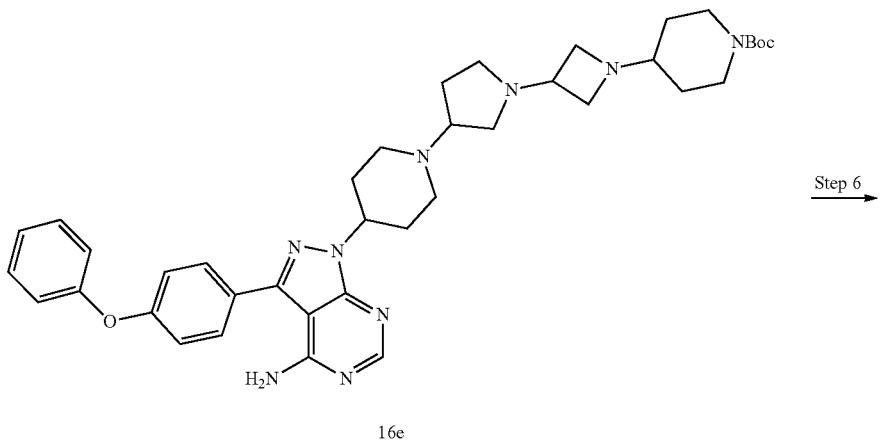
16e
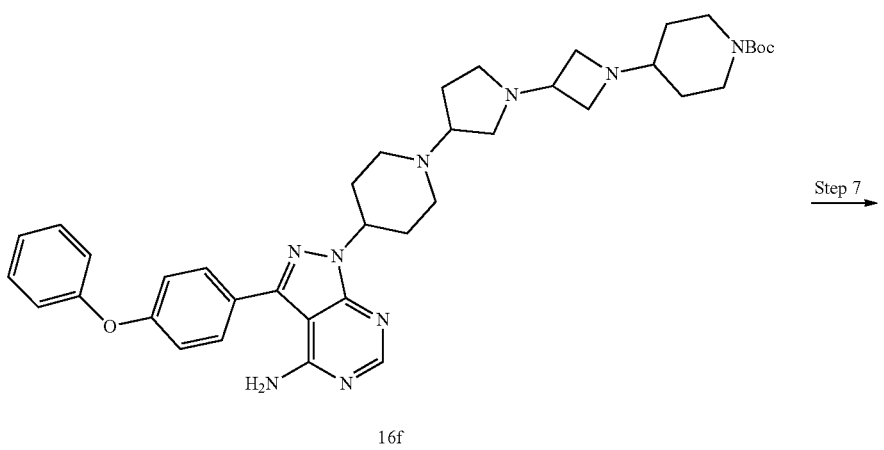
16f
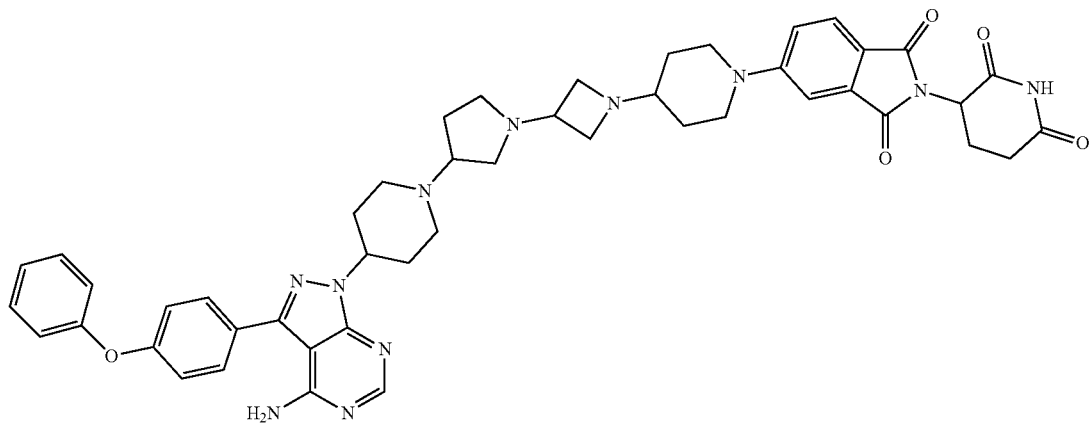
Compound 16

Step 1

Tert-butyl 3-[4-[4-amino-3-(4-phenoxyphenyl)pyrazolo[3,4-d]pyrimidin-1-yl]-1-piperidyl]pyrrolidine-1-carboxylate (16a)

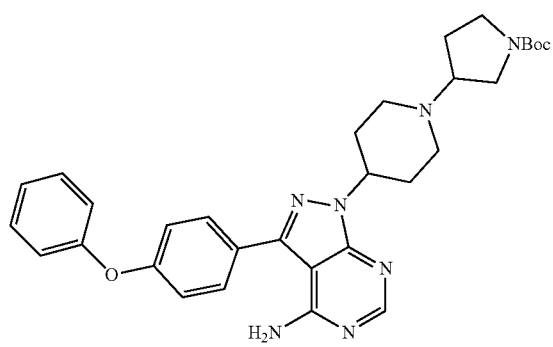 [SMILES: CC(C)(C)OC(=O)N1CCC(N2CCC(n3nc(-c4ccc(Oc5ccccc5)cc4)c4c(N)ncnc43)CC2)C1]

To a 50 mL reaction flask was successively added 3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.16 g, 3 mmol), acetic acid (180 mg, 3 mmol), tert-butyl 3-oxo-pyrrolidine-1-carboxylate (555.7 mg, 3 mmol), sodium triacetoxyborohydride (953.7 mg, 4.5 mmol) and dichloromethane (40 mL). Upon completion of the addition, the reaction was stirred at room temperature for 3 h. The reaction solution was filtered off with suction, and the filtrate was washed with saturated sodium bicarbonate solution (30 mL). The liquid separation was conducted, then the organic layer was dried over anhydrous sodium sulfate, filtered off with suction, and the filtrate was concentrated under reduced pressure, to obtain tert-butyl 3-[4-[4-amino-3-(4-phenoxyphenyl)pyrazolo[3,4-d]pyrimidin-1-yl]-1-piperidyl]pyrrolidine-1-carboxylate (16a) (1.2 g, yield: 72%).

Step 2

3-(4-phenoxyphenyl)-1-(1-pyrrolidin-3-yl-4-piperidyl)pyrazolo[3,4-b]pyridin-4-amine (16b)

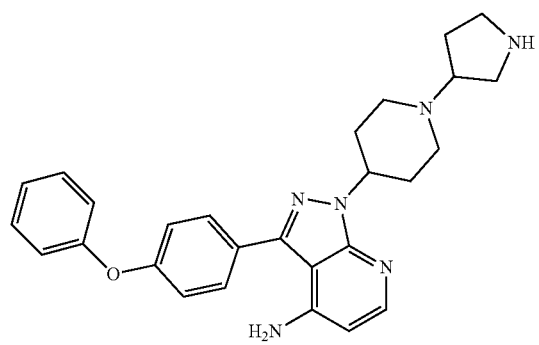 [SMILES: Nc1ccnc2c1c(-c1ccc(Oc3ccccc3)cc1)nn2C1CCN(C2CCNC2)CC1]

Tert-butyl 3-[4-[4-amino-3-(4-phenoxyphenyl)pyrazolo[3,4-d]pyrimidin-1-yl]-1-piperidyl]pyrrolidin-1-carboxylate (16a) (1.1 g, 2 mmol) was dissolved in 10 mL of 4N ethyl acetate hydrochloride solution, and 5 mL of methanol was added, the reaction was carried out at room temperature for 2 h. The reaction solution was directly concentrated, then the reaction system was diluted with ethyl acetate (30 mL), quenched with saturated sodium bicarbonate (10 mL), and extracted with ethyl acetate (5 mL×3). The organic phase was combined, dried over anhydrous sodium sulfate, and filtered, and the filtrate was concentrated under reduced pressure, to obtain 3-(4-phenoxyphenyl)-1-(1-pyrrolidin-3-yl-4-piperidyl)pyrazolo[3,4-b]pyridin-4-amine (16b) (837 mg, yield: 92%).

Step 3

Tert-butyl 3-[3-[4-[4-amino-3-(4-phenoxyphenyl)pyrazolo[3,4-d]pyrimidin-1-yl]-1-piperidyl]pyrrolidin-1-yl]azetidine-1-carboxylate (16c)

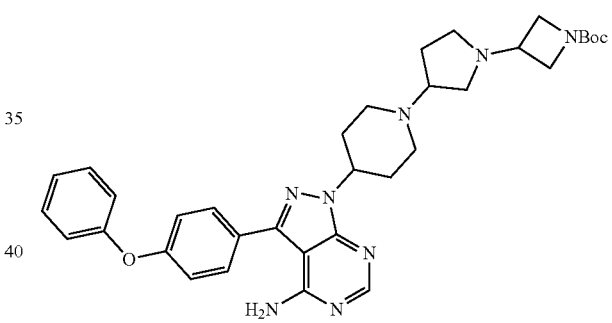

To a 50 mL reaction flask was successively added 3-(4-phenoxyphenyl)-1-(1-pyrrolidin-3-yl-4-piperidyl)pyrazolo[3,4-b]pyridin-4-amine (16b) (837 mg, 1.84 mmol), acetic acid (110.4 mg, 1.84 mmol), tert-butyl 3-oxo azetidine-1-carboxylate (315 mg, 1.84 mmol), sodium triacetoxyborohydride (924 mg, 4.36 mmol) and dichloromethane (40 mL). Upon completion of the addition, the reaction was stirred at room temperature for 3 h. The reaction solution was filtered off with suction, and the filtrate was washed with saturated sodium bicarbonate solution (20 mL). The liquid separation was conducted, then the organic layer was dried over anhydrous sodium sulfate, filtered off with suction, and the filtrate was concentrated under reduced pressure, to obtain tert-butyl 3-[3-[4-[4-amino-3-(4-phenoxyphenyl)pyrazolo[3,4-d]pyrimidin-1-yl]-1-piperidyl]pyrrolidin-1-yl]azetidine-1-carboxylate (16c) (680 mg, yield: 61%).

LCMS m/z=611.4 [M+1]$^+$.

Step 4

1-[1-[1-(azetidin-3-yl)pyrrolidin-3-yl]-4-piperidyl]-3-(4-phenoxyphenyl)pyrazolo[3,4-d]pyrimidin-4-amine (16d)

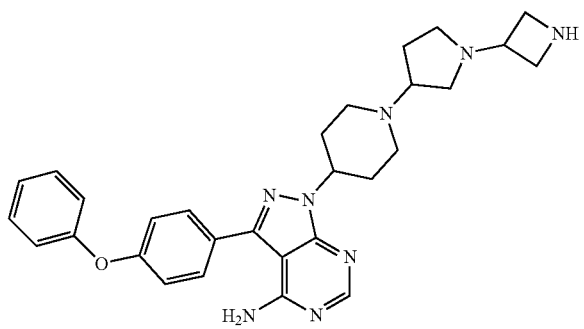 [SMILES: Nc1ncnc2c1c(-c1ccc(Oc3ccccc3)cc1)nn2C1CCN(C2CCN(C3CNC3)C2)CC1]

Tert-butyl 3-[3-[4-[4-amino-3-(4-phenoxyphenyl)pyrazolo[3,4-d]pyrimidin-1-yl]-1-piperidyl]pyrrolidin-1-yl]azetidine-1-carboxylate (16c) (680 mg, 1.11 mmol) was dissolved in 8 mL of 4N ethyl acetate hydrochloride solution, and 5 mL of methanol was added, the reaction was carried out at room temperature for 2 h. The reaction solution was directly concentrated, then the reaction system was diluted with ethyl acetate (30 mL), quenched with saturated sodium bicarbonate (10 mL), and extracted with ethyl acetate (5 mL×3). The organic phase was combined, dried over anhydrous sodium sulfate, and filtered, and the filtrate was concentrated under reduced pressure, to obtain 1-[1-[1-(azetidin-3-yl)pyrrolidin-3-yl]-4-piperidyl]-3-(4-phenoxyphenyl)pyrazolo[3,4-d]pyrimidin-4-amine (16d) (420 mg, yield: 74%).

Step 5

Tert-butyl 4-[3-[3-[4-[4-amino-3-(4-phenoxyphenyl)pyrazolo[3,4-d]pyrimidin-1-yl]-1-piperidyl]pyrrolidin-1-yl]azetidin-1-yl]piperidine-1-carboxylate (16e)

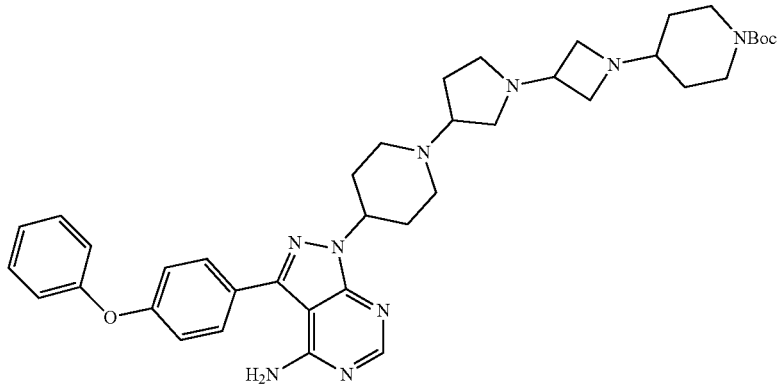 [SMILES: CC(C)(C)OC(=O)N1CCC(N2CC(N3CCC(N4CCC(n5nc(-c6ccc(Oc7ccccc7)cc6)c6c(N)ncnc65)CC4)C3)C2)CC1]

To a 50 mL reaction flask was successively added 1-[1-[1-(azetidin-3-yl)pyrrolidin-3-yl]-4-piperidyl]-3-(4-phenoxyphenyl)pyrazolo[3,4-d]pyrimidin-4-amine (16d) (420 mg, 0.82 mmol), acetic acid (49.2 mg, 0.82 mmol), tert-butyl 4-oxopiperidine-1-carboxylate (163.4 mg, 0.82 mmol), sodium triacetoxyborohydride (348 mg, 1.64 mmol) and dichloromethane (35 mL). Upon completion of the addition, the reaction was stirred at room temperature for 3 h. The reaction solution was filtered off with suction, and the filtrate was washed with saturated sodium bicarbonate solution (15 mL). The liquid separation was conducted, then the organic layer was dried over anhydrous sodium sulfate, filtered off with suction, and the filtrate was concentrated under reduced pressure, to obtain tert-butyl 4-[3-[3-[4-[4-amino-3-(4-phenoxyphenyl)pyrazolo[3,4-d]pyrimidin-1-yl]-1-piperidyl]pyrrolidin-1-yl]azetidin-1-yl]piperidine-1-carboxylate (16e) (320 mg, yield: 56%)

Step 6

3-(4-phenoxyphenyl)-1-[1-[1-[1-(4-piperidyl)azetidin-3-yl]pyrrolidin-3-yl]-4-piperidyl]pyrazolo[3,4-d]pyrimidin-4-amine (16f)

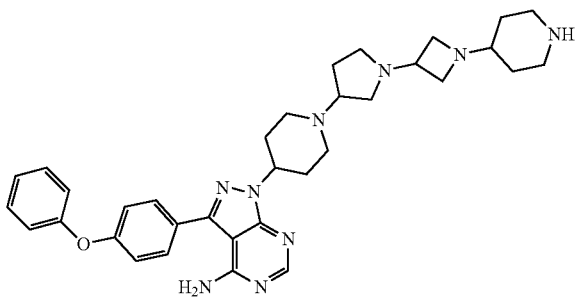 [SMILES: Nc1ncnc2c1c(-c1ccc(Oc3ccccc3)cc1)nn2C1CCN(C2CCN(C3CN(C4CCNCC4)C3)C2)CC1]

Tert-butyl 4-[3-[3-[4-[4-amino-3-(4-phenoxyphenyl)pyrazolo[3,4-d]pyrimidin-1-yl]-1-piperidyl]pyrrolidin-1-yl]azetidin-1-yl]piperidine-1-carboxylate (16e) (320 mg, 0.46 mmol) was dissolved in 8 mL of 4N ethyl acetate hydrochloride solution, and 5 mL of methanol was added, the reaction was carried out at room temperature for 2 h. The reaction solution was directly concentrated, then the reaction system was diluted with ethyl acetate (30 mL), quenched with saturated sodium bicarbonate (10 mL), and extracted with ethyl acetate (5 mL×3). The organic phase was combined, dried over anhydrous sodium sulfate, and filtered, and the filtrate was concentrated under reduced pressure, to obtain 3-(4-phenoxyphenyl)-1-[1-[1-[1-(4-piperidyl)azetidin-3-yl]pyrrolidin-3-yl]-4-piperidyl]pyrazolo[3,4-d]pyrimidin-4-amine (16f) (210 mg, yield: 77%).

Step 7

5-[4-[3-[3-[4-[4-amino-3-(4-phenoxyphenyl)pyrazolo[3,4-d]pyrimidin-1-yl]-1-piperidyl]pyrrolidin-1-yl]azetidin-1-yl]-1-piperidyl]-2-(2,6-dioxo-3-piperidyl)isoindoline-1,3-dione (Compound 16)

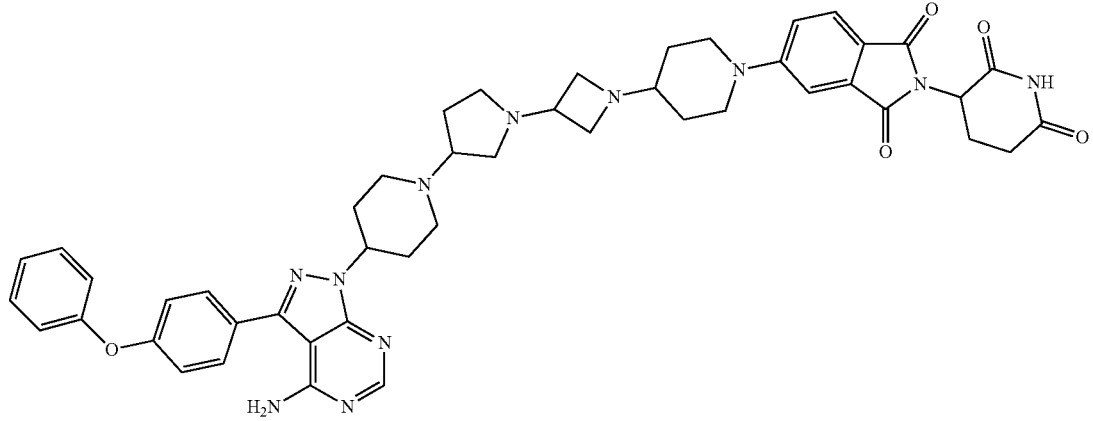 [SMILES: Nc1ncnc2c1c(-c1ccc(Oc3ccccc3)cc1)nn2C1CCN(C2CCN(C3CN(C4CCN(c5ccc6c(c5)C(=O)N(C5CCC(=O)NC5=O)C6=O)CC4)C3)C2)CC1]

3-(4-phenoxyphenyl)-1-[1-[1-[1-(4-piperidyl)azetidin-3-yl]pyrrolidin-3-yl]-4-piperidyl]pyrazolo[3,4-d]pyrimidin-4-amine (16f) (210 mg, 0.35 mmol) was dissolved in DMSO (20 mL), and 2-(2,6-dioxopiperidin-3-yl)-5-fluoroisoindoline-1,3-dione (see WO 2017197056 for the synthetic method) (96.7 mg, 0.35 mmol) and DIPEA (174.4 mg, 1.35 mmol) were added at room temperature, the reaction was stirred at 90° C. for 2 h. To the reaction solution was added 50 mL of water, and the layers were separated. The aqueous phase was extracted with ethyl acetate (50 mL×3), and the organic phase was combined, washed with water (20 mL×2), dried over anhydrous sodium sulfate, and concentrated. The crude product was separated and purified by silica gel column chromatography (dichloromethane/methanol (v/v) =100:1-20:1), to obtain a crude product. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from concentration of 5% to concentration of 60% (elution time: 15 min), the prepared product was alkalized and concentrated to obtain 5-[4-[3-[3-[4-[4-amino-3-(4-phenoxyphenyl)pyrazolo[3,4-d]pyrimidin-1-yl]-1-piperidyl]pyrrolidin-1-yl]azetidin-1-yl]-1-piperidyl]-2-(2,6-dioxo-3-piperidyl)isoindoline-1,3-dione (Compound 16) (58 mg, yield: 32%).

$^1$H NMR (400 MHz, CDCl$_3$) δ 8.38 (s, 1H), 7.75-7.50 (m, 4H), 7.42-7.35 (m, 2H), 7.256-7.25 (m, 1H), 7.19-7.10 (m, 3H), 7.08-7.06 (m, 2H), 7.04-6.98 (m, 1H), 5.72 (s, 2H), 5.00-4.90 (m, 2H), 4.67 (s, 2H), 4.38-4.18 (m, 1H), 3.86-3.74 (m, 2H), 3.47-3.42 (m, 2H), 3.13-2.98 (m, 6H), 2.90-2.64 (m, 6H), 2.45-2.43 (m, 1H), 2.37-2.32 (m, 2H), 2.19-2.10 (m, 5H), 2.05-2.03 (m, 2H), 1.81-1.77 (m, 2H), 0.98-0.90 (m, 2H).

LCMS m/z=425.8 [M/2+1]$^+$.

Example 17
5-[3-[3-[4-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 17)
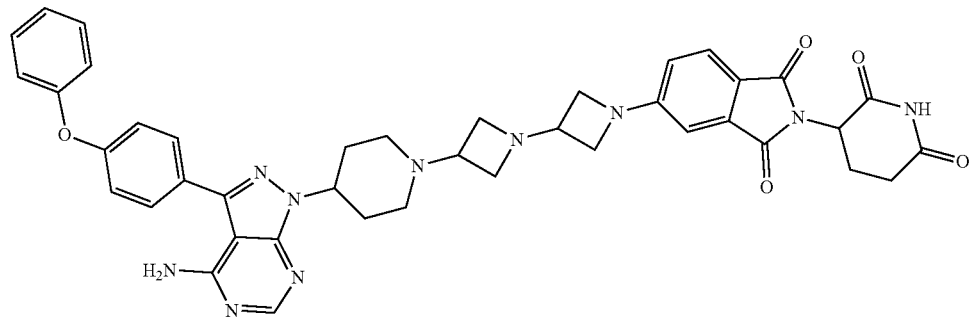
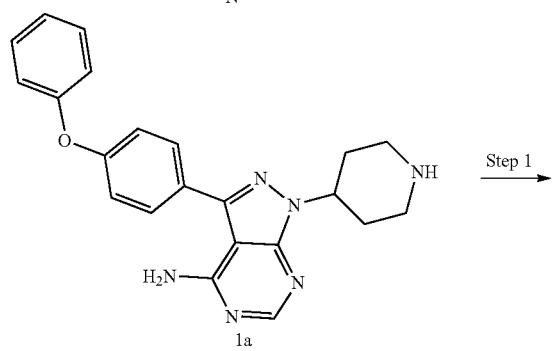
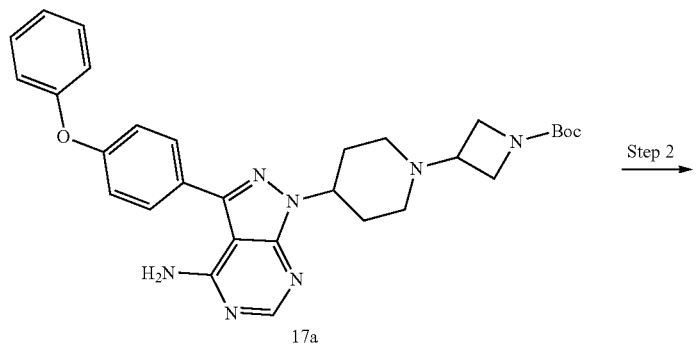
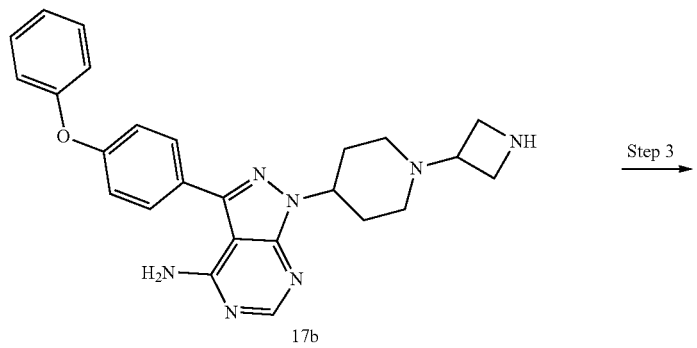

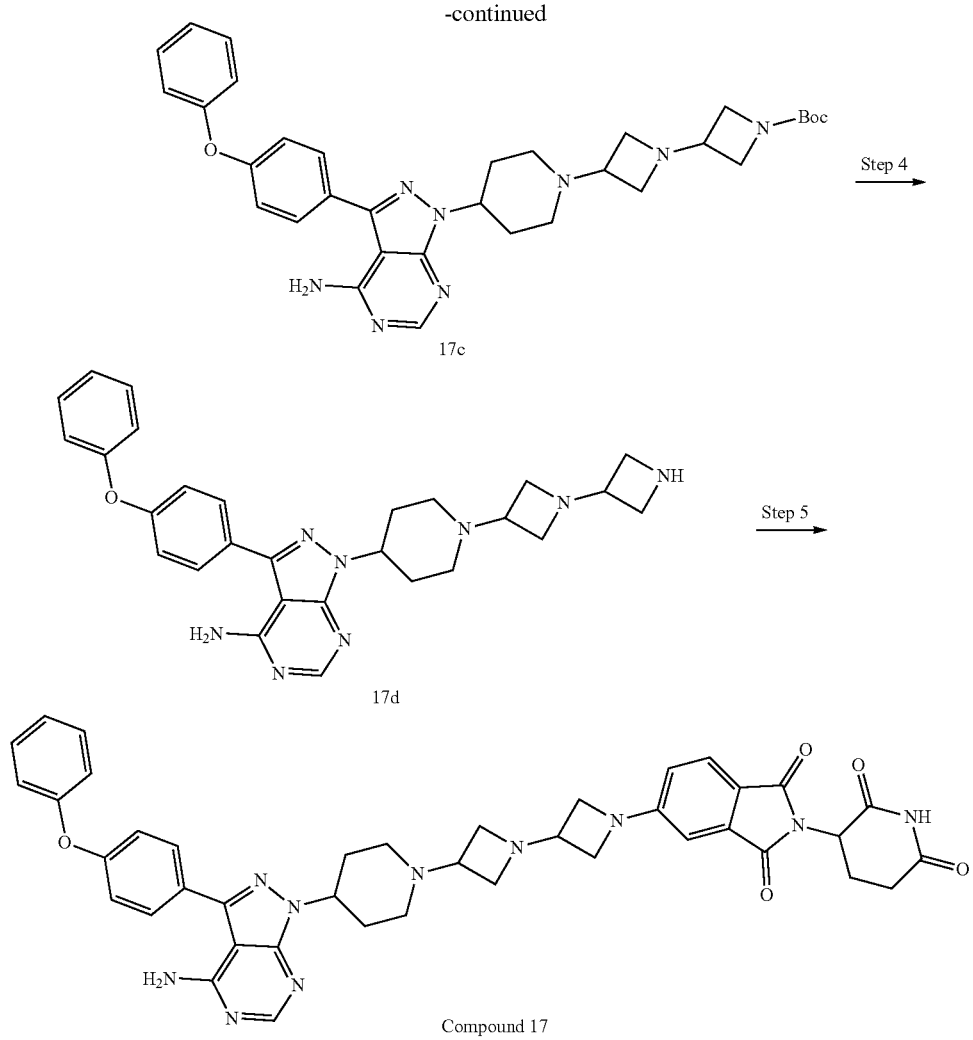

Compound 17

Step 1 tert-butyl 3-[4-[4-amino-3-(4-phenoxyphenyl)pyrazolo[3,4-d]pyrimidin-1-yl]-1-piperidyl]azetidine-1-carboxylate (17a)

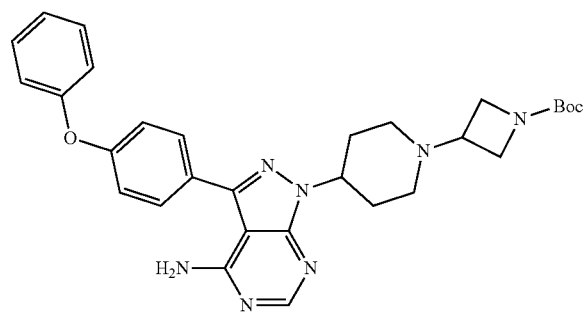 [SMILES: CC(C)(C)OC(=O)N1CC(N2CCC(n3nc(-c4ccc(Oc5ccccc5)cc4)c4c(N)ncnc43)CC2)C1]

3-(4-phenoxyphenyl)-1-(piperidin-4-yl)-1H-pyrazolo[3,4-d]pyrimidin-4-amine (1a) (see J. Med. Chem. 2015, 58, 9625-9638 for the synthetic method) (0.500 g, 1.29 mmol) was dissolved in 5 mL of 1,2-dichloroethane, and tert-butyl 3-oxoazetidine-1-carboxylate (0.266 g, 1.55 mmol) and glacial acetic acid (0.412 g, 6.86 mmol) were successively added. Upon completion of the addition, the reaction was carried out at 65° C. for 3 h. The reaction solution was cooled to room temperature, and sodium triacetoxyborohydride (0.548 g, 2.59 mmol) was added.

Upon completion of the addition, the reaction was carried out at room temperature overnight. To the reaction solution was added dropwise saturated sodium bicarbonate solution to adjust the pH to 9-10, and same was concentrated under reduced pressure, then the crude product was separated and purified by silica gel column chromatography (dichloromethane/methanol (v/v)=100:0-19:1), to obtain tert-butyl 3-[4-[4-amino-3-(4-phenoxyphenyl)pyrazolo[3,4-d]pyrimidin-1-yl]-1-piperidyl]azetidine-1-carboxylate (17a) (0.700 g, yield: >99%).

LCMS m/z=542.3 [M+1]$^+$.

Step 2

1-[1-(azetidin-3-yl)-4-piperidyl]-3-(4-phenoxyphenyl)pyrazolo[3,4-d]pyrimidin-4-amine (17b)

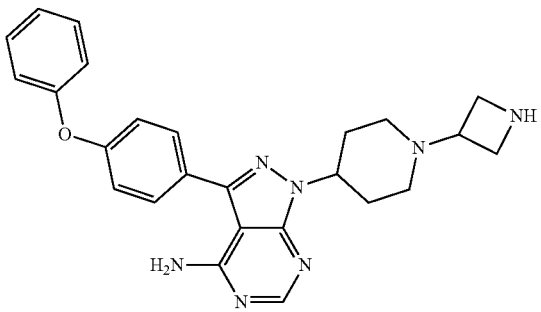 [SMILES: Nc1ncnc2c1c(-c1ccc(Oc3ccccc3)cc1)nn2C1CCN(C2CNC2)CC1]

Tert-butyl 3-[4-[4-amino-3-(4-phenoxyphenyl)pyrazolo[3,4-d]pyrimidin-1-yl]-1-piperidyl]azetidine-1-carboxylate (17a) (0.700 g, 1.29 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 1-[1-(azetidin-3-yl)-4-piperidyl]-3-(4-phenoxyphenyl)pyrazolo[3,4-d]pyrimidin-4-a mine (17b) (0.410 g, yield: 72%).

LCMS m/z=442.2 [M+1]$^+$.

Step 3

Tert-butyl 3-[3-[4-[4-amino-3-(4-phenoxyphenyl)pyrazolo[3,4-d]pyrimidin-1-yl]-1-piperidyl]azetidin-1-yl]azetidine-1-carboxylate (17c)

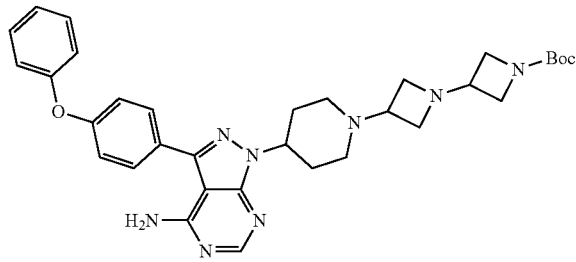 [SMILES: CC(C)(C)OC(=O)N1CC(N2CC(N3CCC(n4nc(-c5ccc(Oc6ccccc6)cc5)c5c(N)ncnc54)CC3)C2)C1]

1-[1-(azetidin-3-yl)-4-piperidyl]-3-(4-phenoxyphenyl)pyrazolo[3,4-d]pyrimidin-4-amine (17b) (0.200 g, 0.453 mmol) was dissolved in 5 mL of 1,2-dichloroethane, and tert-butyl 3-oxoazetidine-1-carboxylate (0.116 g, 0.680 mmol) and glacial acetic acid (0.0544 g, 0.906 mmol) were successively added. Upon completion of the addition, the reaction was carried out at 65° C. for 3 h. The reaction solution was cooled to room temperature, and sodium triacetoxyborohydride (0.192 g, 0.906 mmol) was added. Upon completion of the addition, the reaction was carried out at room temperature overnight. The pH was adjusted to 9-10 by adding dropwise saturated sodium bicarbonate solution to the reaction solution. The reaction solution was concentrated under reduced pressure, and then the crude product was separated and purified by silica gel column chromatography (dichloromethane/methanol (v/v)=100:0-19:1), to obtain tert-butyl 3-[3-[4-[4-amino-3-(4-phenoxyphenyl)pyrazolo[3,4-d]pyrimidin-1-yl]-1-piperidyl]azetidin-1-yl]azetidine-1-carboxylate (17c) (0.150 g, yield: 56%).

LCMS m/z=597.3 [M+1]$^+$.

Step 4

1-[1-[1-(azetidin-3-yl)azetidin-3-yl]-4-piperidyl]-3-(4-phenoxyphenyl)pyrazolo[3,4-d]pyrimidin-4-amine (17d)

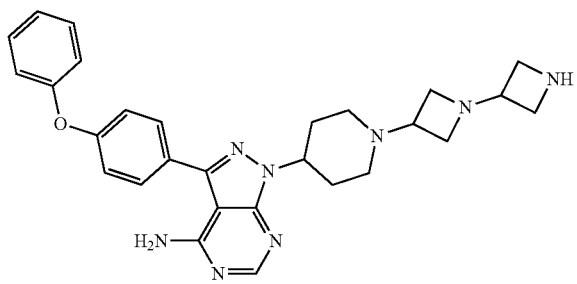 [SMILES: Nc1ncnc2c1c(-c1ccc(Oc3ccccc3)cc1)nn2C1CCN(C2CN(C3CNC3)C2)CC1]

Tert-butyl 3-[3-[4-[4-amino-3-(4-phenoxyphenyl)pyrazolo[3,4-d]pyrimidin-1-yl]-1-piperidyl]azetidin-1-yl]azetidine-1-carboxylate (17c) (0.140 g, 0.235 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 1-[1-[1-(azetidin-3-yl)azetidin-3-yl]-4-piperidyl]-3-(4-phenoxyphenyl)pyrazolo[3,4-d]pyrimidin-4-amine (17d) (0.100 g, yield: 86%).

LCMS m/z=497.3 [M+1]$^+$.

Step 5

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 17)

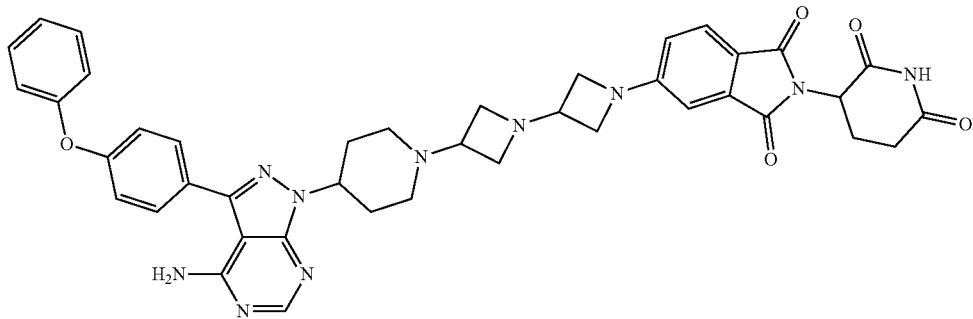

1-[1-[1-(azetidin-3-yl)azetidin-3-yl]-4-piperidyl]-3-(4-phenoxyphenyl)pyrazolo[3,4-d]pyrimidin-4-amine (17d) (0.100 g, 0.201 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.0667 g, 0.242 mmol) and diisopropylethylamine (0.130 g, 1.01 mmol) were successively added. Upon completion of the addition, the reaction was carried out at 90° C. for 2 h. The reaction solution was cooled to room temperature, to which 10 mL of water was slowly added dropwise, and filtered. The filter cake was dissolved with 20 mL of dichloromethane, and then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-19:1), to obtain 5-[3-[3-[4-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 17) (0.063 g, yield: 42%).

$^1$H NMR (400 MHz, CDCl$_3$) δ 9.99 (s, 1H), 8.39 (s, 1H), 7.72-7.57 (m, 3H), 7.45-7.32 (m, 2H), 7.21-7.11 (m, 3H), 7.10-7.04 (m, 2H), 6.78 (d, 1H), 6.52 (dd, 1H), 5.81 (brs, 2H), 4.92 (dd, 1H), 4.87-4.71 (m, 1H), 4.08-3.99 (m, 2H), 3.94-3.83 (m, 2H), 3.76-3.65 (m, 1H), 3.64-3.49 (m, 2H), 3.20-3.04 (m, 3H), 3.00-2.64 (m, 5H), 2.52-2.34 (m, 2H), 2.18-1.89 (m, 5H).

LCMS m/z=377.3 [M/2+1]$^+$.

Example 17-1

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3R)-2,6-dioxo-3-piperidyl]isoindoline-1,3-dione (Compound 17-a)

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3S)2,6-dioxo-3-piperidyl]isoindoline-1,3-dione (Compound 17-b)

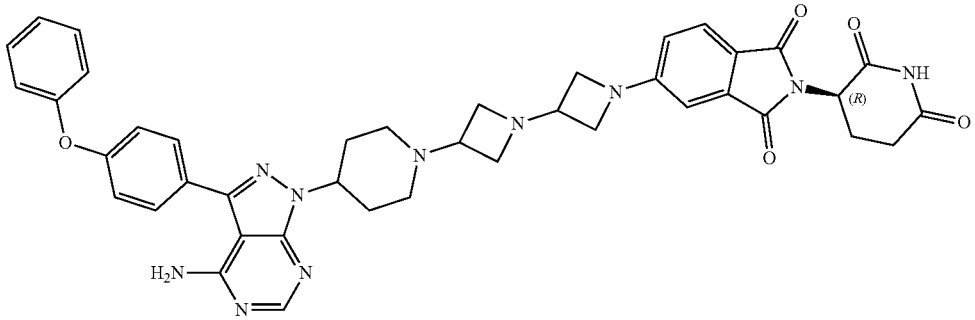

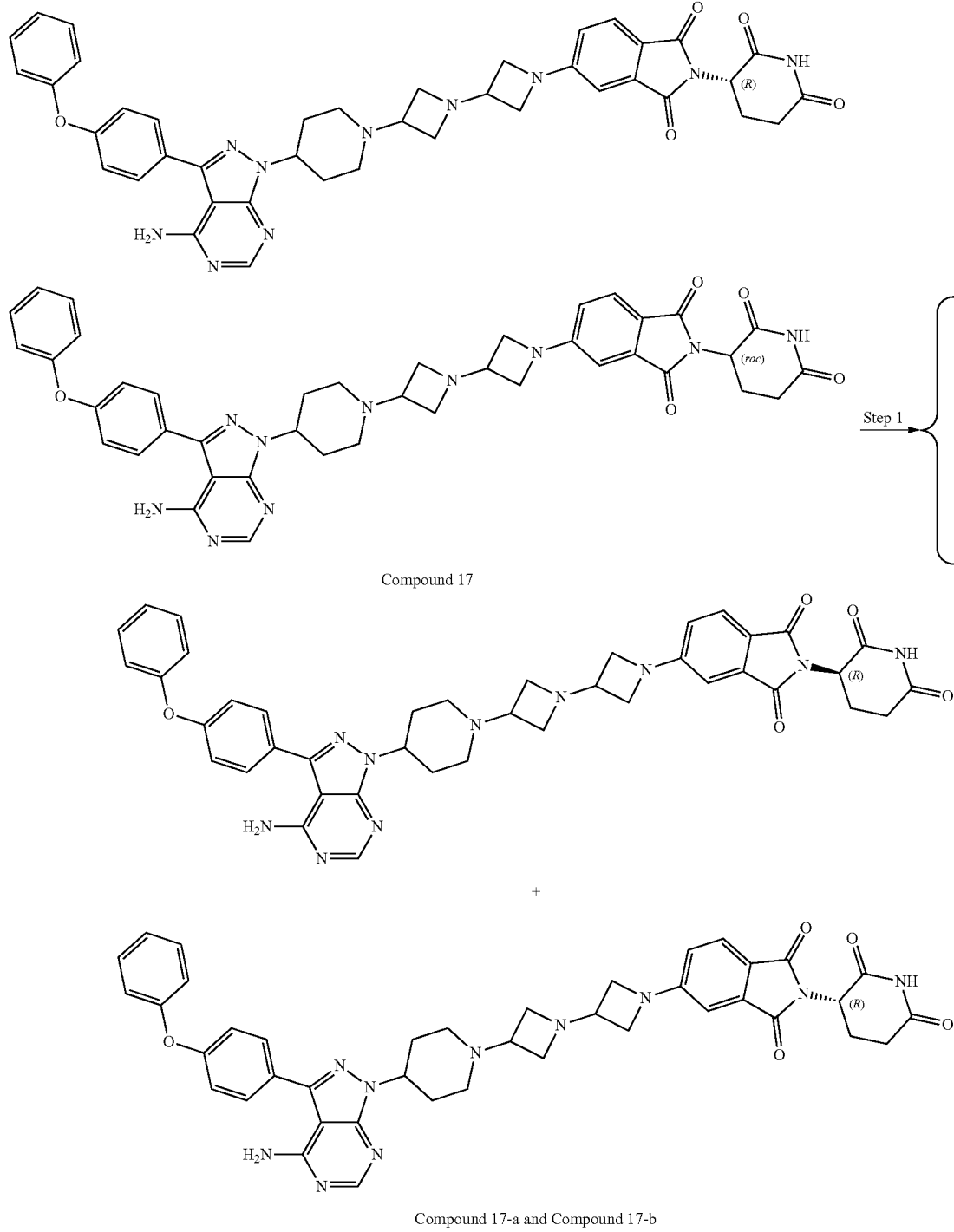

Compound 17

Compound 17-a and Compound 17-b

Step 1: Preparation of Compounds 17-a and 17-b

Compounds 17-a and 17-b were separated and prepared from compound 17 by means of high performance liquid chromatography. The preparation conditions were as follows:

instrument and preparative column: using Thar 200 preparative SFC (SFC-7) to prepare the liquid phase, preparative column model: ChiralCel OJ, 250×50 mm I.D., 10 μm.

Preparation method: the crude product was dissolved with methanol/dichloromethane, to prepare into a sample solution.

Mobile phase system: $sCO_2$ (supercritical $CO_2$)/ethanol, isocratic elution: $sCO_2$/ethanol=55/45.

Flow rate: 200 mL/min

Analysis method for compounds 17-a and 17-b:

Instrument: Agilent HPLC1260

Chromatographic column: Daicel CHIRALPAK IC

Specification: 4.6 mm×250 mm, 5 μm

Mobile phase A: 20 mM of ammonium bicarbonate solution (adjusting pH to 9.0 with diethylamine)
Mobile phase B: Acetonitrile
Column temperature: 35° C.
Flow rate: 0.8 mL/min
Wavelength: 264 nm
Elution program: mobile phase A:B=20:80, equal elution for 50 min.

Retention time of compound 17-a: 32.234 min;
$^1$H NMR (400 MHz, CDCl$_3$) δ 9.04 (s, 1H), 8.38 (s, 1H), 7.69-7.60 (m, 3H), 7.42-7.34 (m, 2H), 7.21-7.11 (m, 3H), 7.11-7.05 (m, 2H), 6.78 (d, 1H), 6.52 (dd, 1H), 5.63 (brs, 2H), 4.92 (dd, 1H), 4.85-4.72 (m, 1H), 4.09-3.98 (m, 2H), 3.93-3.82 (m, 2H), 3.74-3.64 (m, 1H), 3.61-3.50 (m, 2H), 3.16-3.01 (m, 3H), 2.99-2.64 (m, 5H), 2.52-2.34 (m, 2H), 2.17-1.95 (m, 5H).

Retention time of compound 17-b: 36.797 min. $^1$H NMR (400 MHz, CDCl$_3$) δ 8.37 (s, 1H), 7.68-7.57 (m, 3H), 7.43-7.33 (m, 2H), 7.20-7.10 (m, 3H), 7.10-7.04 (m, 2H), 6.78 (d, 1H), 6.52 (dd, 1H), 5.71 (brs, 2H), 4.92 (dd, 1H), 4.84-4.72 (m, 1H), 4.08-3.98 (m, 2H), 3.91-3.82 (m, 2H), 3.76-3.64 (m, 1H), 3.60-3.50 (m, 2H), 3.16-3.01 (m, 3H), 2.98-2.62 (m, 5H), 2.51-2.34 (m, 2H), 2.17-1.97 (m, 5H).

Example 17-A

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3R)-2,6-dioxo-3-piperidyl]isoindoline-1,3-di one (Compound 17-a)

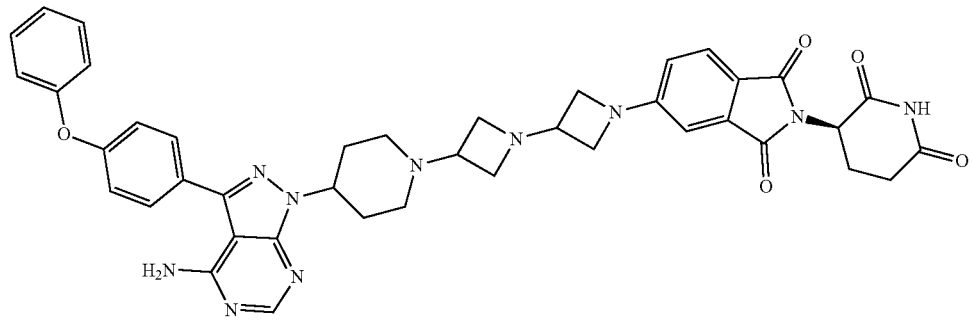

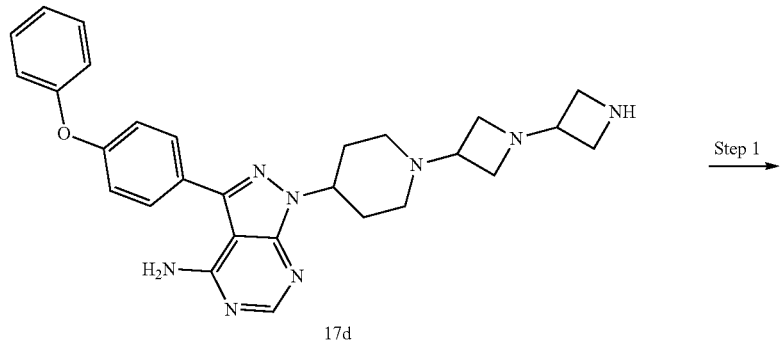

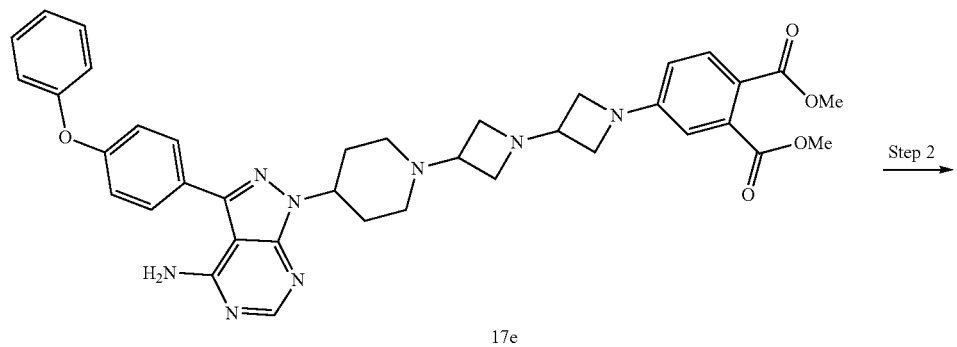

-continued

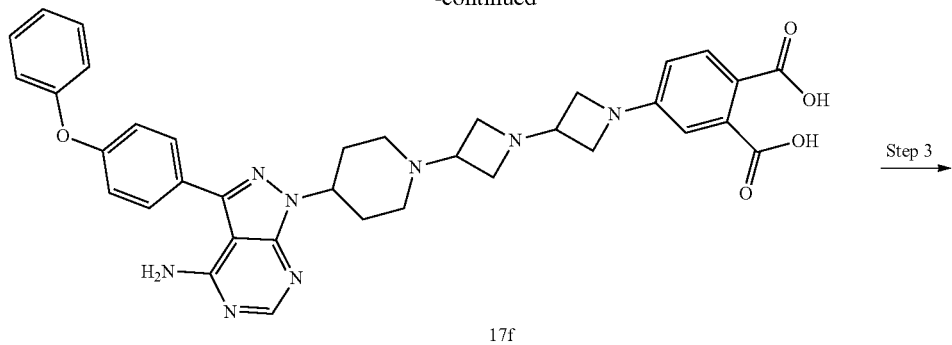

17f

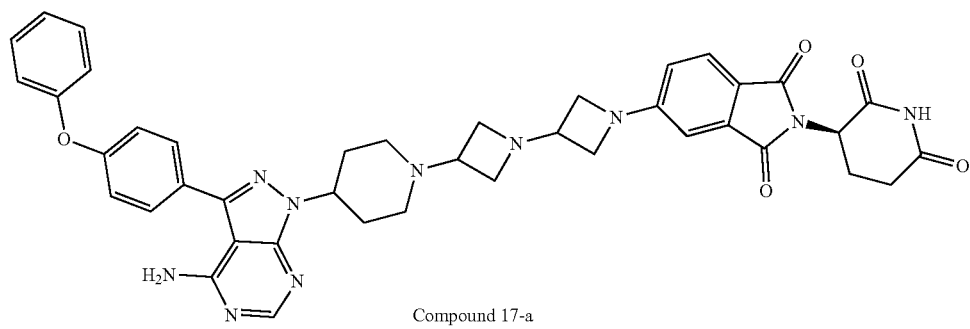

Compound 17-a

Step 1

Dimethyl 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalate (17e)

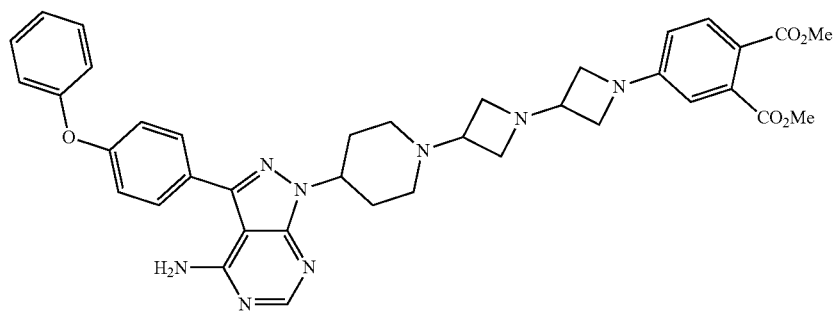 [SMILES: COC(=O)c1ccc(N2CC(N3CC(N4CCC(n5nc(-c6ccc(Oc7ccccc7)cc6)c6c(N)ncnc65)CC4)C3)C2)cc1C(=O)OC]

1-[1-[1-(azetidin-3-yl)azetidin-3-yl]-4-piperidyl]-3-(4-phenoxyphenyl)pyrazolo[3,4-d]pyrimidin-4-amine (17d) (83 g, 0.167 mol) was dissolved in 400 mL of DMSO, and dimethyl 4-fluorophthalate (40 g, 0.188 mol) (see *Beilstein J. Org. Chem.* 2017, 13, 2659-2662 for the synthetic method) and DIPEA (43.17 g, 0.334 mol) were added, the reaction was stirred at 85° C. for 5 h. The reaction solution was cooled to room temperature, and by addition of 4 L of water, a yellow solid was precipitated, which was filtered off with suction and dried, to obtain the crude product 4-(3-(4-(4-amino-3-(4-phenoxyphenyl)-1H-pyrazolo[3,4-d]pyrimidin-1-yl)piperidin-1-yl)[1,3'-biazetidin]-1'-yl)phthalate (17e) (120 g).

LC-MS m/z=689.3 [M+1]$^+$.

Step 2

4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f)

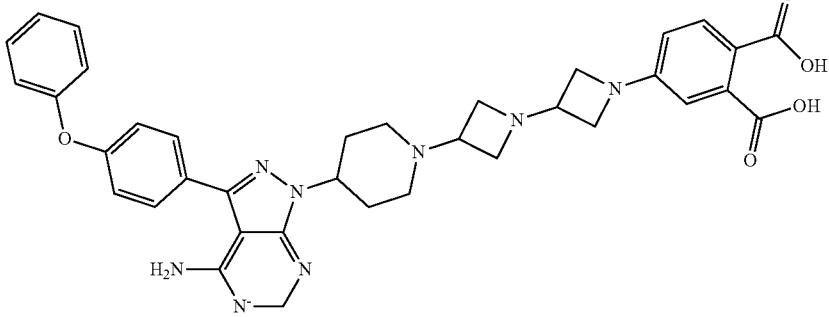

The above crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalate (17e) (120 g) was dissolved in 400 mL of 1,4-dioxane, and 300 mL of methanol and 200 mL of 5 mol/L sodium hydroxide solution were added, and the reaction was stirred at 75° C. for 1 h. The reaction solution was cooled to room temperature, and concentrated under reduced pressure to remove most of methanol and 1,4-dioxane, the remaining was added 1 L of water, and extracted with 1 L of the mixed solvent of dichloromethane/methanol (v/v)=9:1. The aqueous phase was separated (adjusting the pH of the aqueous phase to 5.0 with acetic acid), and then extracted with 1 L of the mixed solvent of dichloromethane/methanol (v/v)=9:1. The organic phase was separated, dried over anhydrous sodium sulfate, and concentrated under reduced pressure, to obtain the crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f) (93 g).

LCMS m/z=661.3 [M+1]$^+$.

Step 3

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3R)-2,6-dioxo-3-piperidyl]isoindoline-1,3-di one (Compound 17-a)

The above crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f) (40.0 g) was dissolved in 200 mL N,N-dimethylformamide, and N-methylimidazole (7.20 g, 87.7 mmol) was added, then tetramethylchlorourea hexafluorophosphate (20.0 g, 71.3 mmol) was added, the mixture was stirred at room temperature for 30 min, added 200 mL of anhydrous methanol, and stirred at room temperature for 16 h. The reaction solution was concentrated under reduced pressure, and the residue was added 500 mL of water and slurried for 1 h, and filtered off with suction under reduced pressure. The filter cake was washed with 100 mL of water once, collected and dried, to obtain a crude product (40 g). The crude product (28.0 g) was dissolved in 175 mL of N,N-dimethylformamide, and diisopropylethylamine (8.03 g, 62.1 mmol) was added, then HATU (18.9 g, 49.7 mmol) was added. The mixture was stirred at room temperature for 30 min, and (R)-3-aminopiperidine-2,6-dione hydrochloride (8.90 g, 54.1 mmol) (see *Heterocycles* 2015, 91, 764-781 for the synthetic method) and diisopropylethylamine (8.03 g, 62.1 mmol) were successively added, and the stirring was continued at room temperature for 30 min. The reaction solution was slowly added dropwise to 700 mL of water with stirring, and filtered off with suction under reduced pressure. The filter cake was washed with 50 mL of water, collected, dissolved with 300 mL of the mixed solvent of methanol and dichloromethane (v/v)=1:9, dried over anhydrous sodium sulfate, and concentrated under reduced pressure, then to the residue was added 350 mL of dichloromethane and diisopropylethylamine (8.03 g, 62.1 mmol), and the mixture was stirred at room temperature for 18 h. To the reaction solution was added 100 mL of water and 100 mL of dichloromethane. The liquid

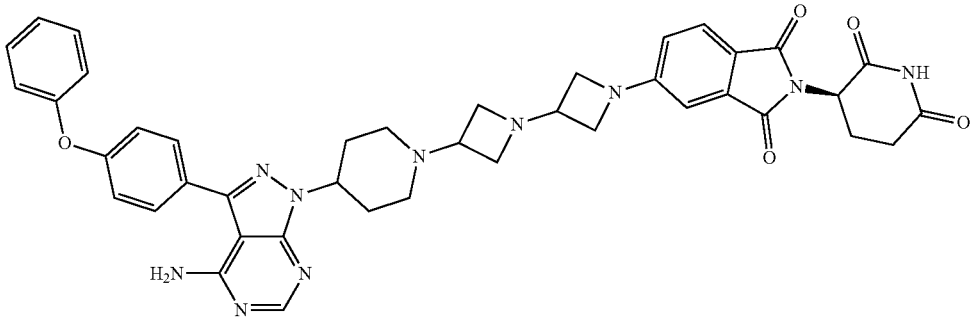 [SMILES: Nc1ncnc2c1c(-c1ccc(Oc3ccccc3)cc1)nn2C1CCN(C2CN(C3CN(c4ccc5c(c4)C(=O)N([C@@H]4CCC(=O)NC4=O)C5=O)C3)C2)CC1]

separation was conducted, and the organic layer was washed with 100 mL of saturated sodium chloride solution, dried over anhydrous sodium sulfate, and concentrated under reduced pressure, then the crude product was separated and purified by silica gel column chromatography (dichloromethane/methanol (v/v)=100:0-93:7), to obtain 5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3R)-2,6-dioxo-3-piperidyl]isoindoline-1,3-dione (Compound 17-a) (16.0 g, three-step yield calculated from compound 17d: 42%, ee=96%).

$^1$H NMR (400 MHz, CDCl$_3$) δ 9.04 (s, 1H), 8.38 (s, 1H), 7.69-7.60 (m, 3H), 7.42-7.34 (m, 2H), 7.21-7.11 (m, 3H), 7.11-7.05 (m, 2H), 6.78 (d, 1H), 6.52 (dd, 1H), 5.63 (brs, 2H), 4.92 (dd, 1H), 4.85-4.72 (m, 1H), 4.09-3.98 (m, 2H), 3.93-3.82 (m, 2H), 3.74-3.64 (m, 1H), 3.61-3.50 (m, 2H), 3.16-3.01 (m, 3H), 2.99-2.64 (m, 5H), 2.52-2.34 (m, 2H), 2.17-1.95 (m, 5H).

LCMS m/z=753.3 [M+1]$^+$.

Example 17-B

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3S)-2,6-dioxo-3-piperidyl]isoindoline-1,3-dione (Compound 17-b)

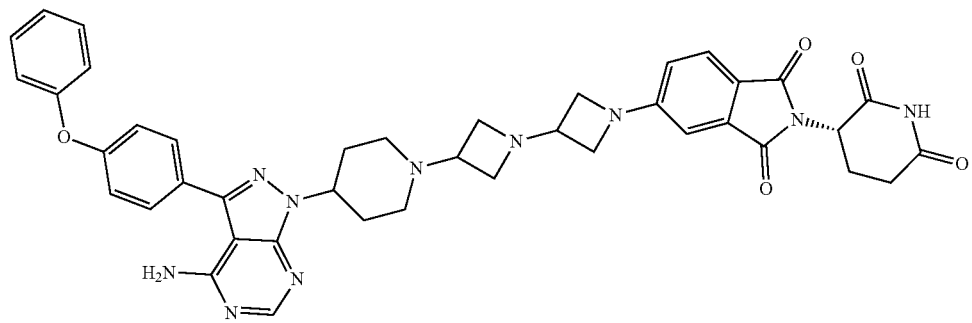

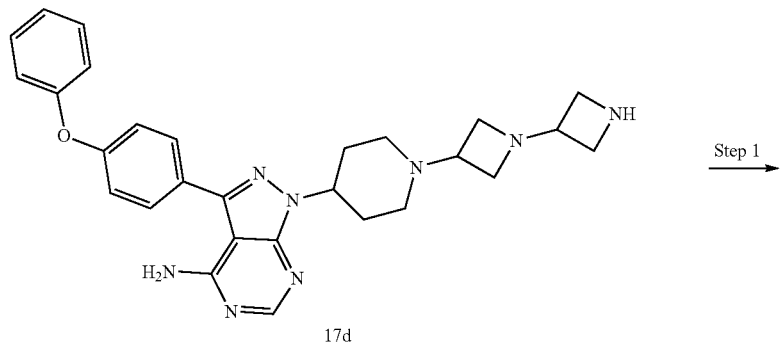

17d

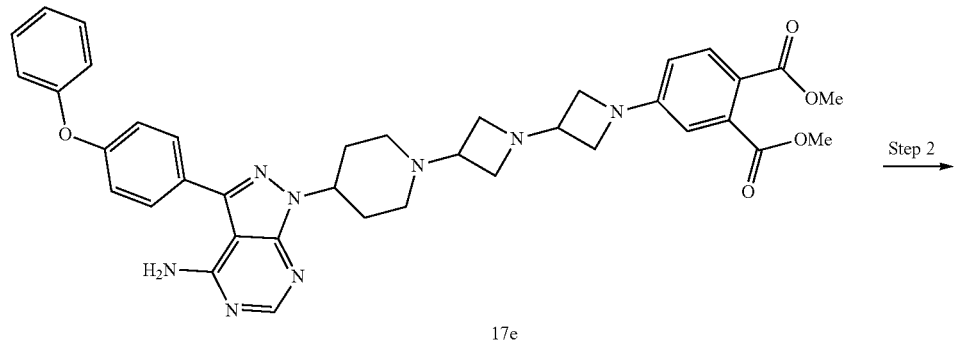

17e

-continued

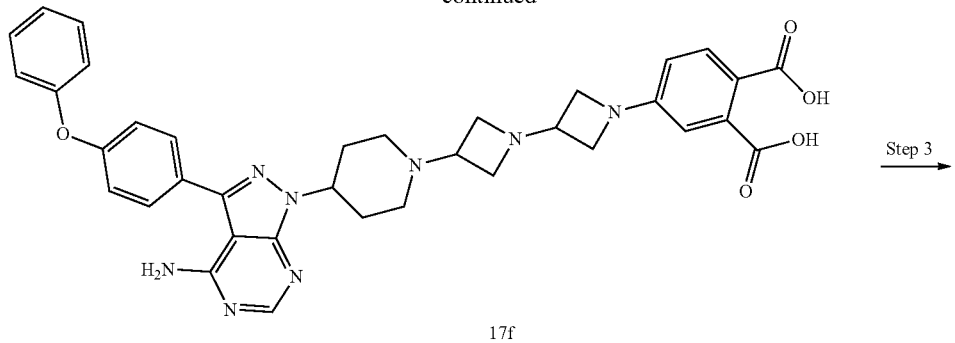

17f

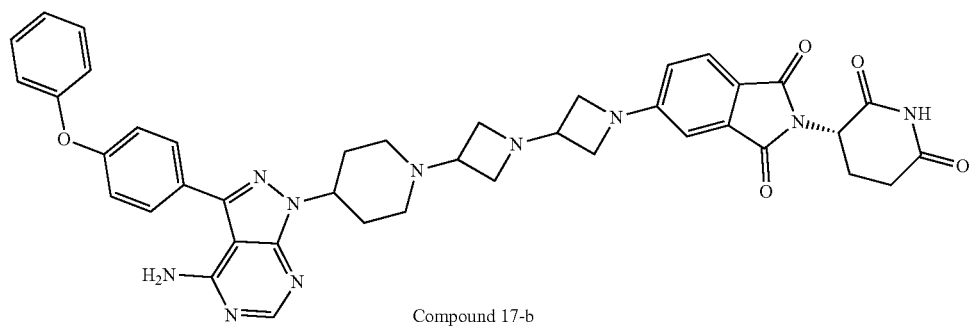

Compound 17-b

Step 1

Dimethyl 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalate (17e)

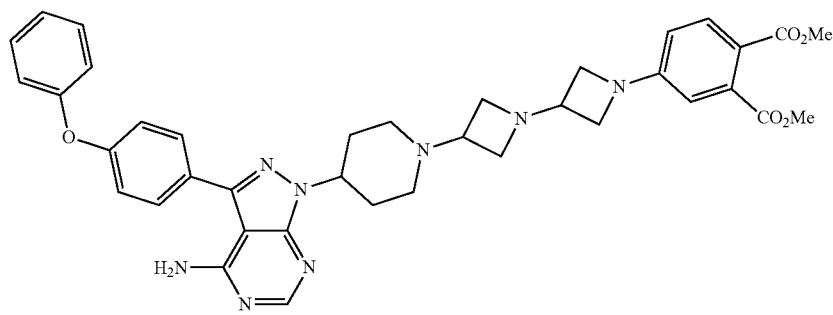 [SMILES: COC(=O)c1ccc(N2CC(N3CC(N4CCC(n5nc(-c6ccc(Oc7ccccc7)cc6)c6c(N)ncnc65)CC4)C3)C2)cc1C(=O)OC]

1-[1-[1-(azetidin-3-yl)azetidin-3-yl]-4-piperidyl]-3-(4-phenoxyphenyl)pyrazolo[3,4-d]pyrimidin-4-amine (17d) (83 g, 0.167 mol) was dissolved in 400 mL of DMSO, and dimethyl 4-fluorophthalate (40 g, 0.188 mol) (see *Beilstein J. Org. Chem.* 2017, 13, 2659-2662 for the synthetic method) and DIPEA (43.17 g, 0.334 mol) were added, the reaction was stirred at 85° C. for 5 h. The reaction solution was cooled to room temperature, and by addition of 4 L of water, a yellow solid was precipitated, which was suction-filtered and dried, to obtain the crude product 4-(3-(4-(4-amino-3-(4-phenoxyphenyl)-1H-pyrazolo[3,4-d]pyrimidin-1-yl)piperidin-1-yl)[1,3'-biazetidin]-1'-yl)phthalate (17e) (120 g).

LC-MS m/z=689.3 [M+1]$^+$.

Step 2

4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f)

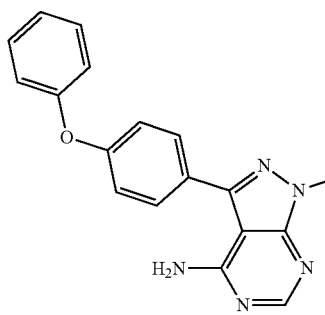

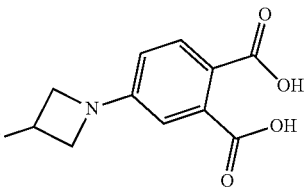

The above crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)[1,3'-biazetidin]-1'-yl)phthalate (17e) (120 g) was dissolved in 400 mL of 1,4-dioxane, and 300 mL of methanol and 200 mL of 5 mol/L sodium hydroxide solution were added, and the reaction was stirred at 75° C. for 1 h. The reaction solution was cooled to room temperature, and concentrated under reduced pressure to remove most of methanol and 1,4-dioxane, the remaining was added 1 L of water, and extracted with 1 L of the mixed solvent of dichloromethane/methanol (v/v)=9:1. The aqueous phase was separated (adjusting the pH of the aqueous phase to 5.0 with acetic acid), and then extracted with 1 L of the mixed solvent of dichloromethane/methanol (v/v)=9:1. The organic phase was separated, dried over anhydrous sodium sulfate, and concentrated under reduced pressure, to obtain the crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f) (93 g).

LCMS m/z=661.3 [M+1]$^+$.

Step 3

5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3S)-2,6-dioxo-3-piperidyl]isoindoline-1,3-dione (Compound 17-b)

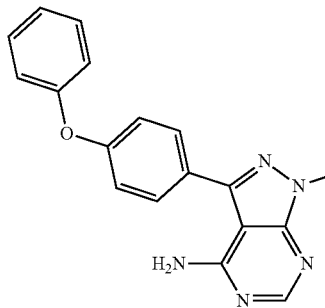

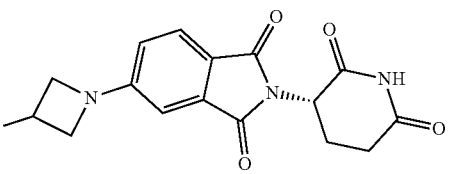

The above crude product 4-(3-(4-(4-amino-3-(4-phenoxyphenyl)-1H-pyrazolo[3,4-d]pyrimidin-1-yl)piperidin-1-yl)-[1,3'-biazetidin]-1'-yl)phthalic acid (17f) (40.0 g) was dissolved in 200 mL N,N-dimethylformamide, and N-methylimidazole (7.20 g, 87.7 mmol) was added, then tetramethylchlorourea hexafluorophosphate (20.0 g, 71.3 mmol) was added, the mixture was stirred at room temperature for 30 min, added 200 mL of anhydrous methanol, and stirred at room temperature for 16 h. The reaction solution was concentrated under reduced pressure, and the residue was added 500 mL of water and slurried for 1 h, and filtered off with suction under reduced pressure. The filter cake was washed with 100 mL of water once, collected and dried, to obtain a crude product (40 g). The crude product (40.0 g) was dissolved in 200 mL of N,N-dimethylformamide, and diisopropylethylamine (11.5 g, 89.0 mmol) was added, then HATU (27.0 g, 71.0 mmol) was added. The mixture was stirred at room temperature for 30 min. and (S)-3-aminopiperidine-2,6-dione hydrochloride (12.7 g, 77.2 mmol) (see *Heterocycles* 2015, 91, 764-781 for the synthetic method) and diisopropylethylamine (11.5 g, 89.0 mmol) were successively added, and the stirring was continued at room temperature for 30 min. The reaction solution was slowly added dropwise to 800 mL of water with stirring, and filtered off with suction under reduced pressure. The filter cake was washed with 100 mL of water, collected, dissolved with 600 mL of the mixed solvent of methanol and dichloromethane (v/v)=1:9, dried over anhydrous sodium sulfate, and concentrated under reduced pressure, then to the residue was added 400 mL of dichloromethane and diisopropylethylamine (11.5 g, 89.0 mmol), and the mixture was stirred at room temperature for 18 h. To the reaction solution was added 100 mL of water and 100 mL of dichloromethane. The liquid separation was conducted, and the organic layer was washed with 100 mL of saturated sodium chloride solution, dried over anhydrous sodium sulfate, and concentrated under reduced pressure, then the crude product was separated and purified by silica gel column chromatography (dichloromethane/methanol (v/v)=100:0-93:7), to obtain 5-[3-[3-[4-[4-amino-3-(4-phenoxyphenyl)pyrazolo[3,4-d]pyrimidin-1-yl]-1-piperidyl]azetidin-1-yl]azetidin-1-yl]-2-[(3S)-2,6-dioxo-3-piperidyl]isoindoline-1,3-dione (Compound 17-b) (20.0 g, three-step yield calculated from compound 17d: 37%, ee=93%).

$^1$H NMR (400 MHz, CDCl$_3$) δ 8.37 (s, 1H), 7.68-7.57 (m, 3H), 7.43-7.33 (m, 2H), 7.20-7.10 (m, 3H), 7.10-7.04 (m, 2H), 6.78 (d, 1H), 6.52 (dd, 1H), 5.71 (brs, 2H), 4.92 (dd, 1H), 4.84-4.72 (m, 1H), 4.08-3.98 (m, 2H), 3.91-3.82 (m, 2H), 3.76-3.64 (m, 1H), 3.60-3.50 (m, 2H), 3.16-3.01 (m, 3H), 2.98-2.62 (m, 5H), 2.51-2.34 (m, 2H), 2.17-1.97 (m, 5H).

LCMS m/z=753.3 [M+1]$^+$.

Example 18 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione trifluoroacetate (Compound 18)

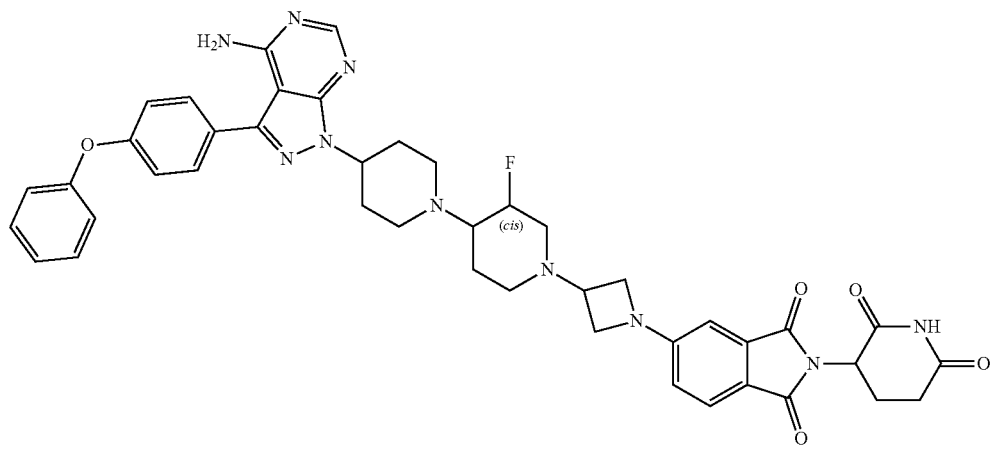

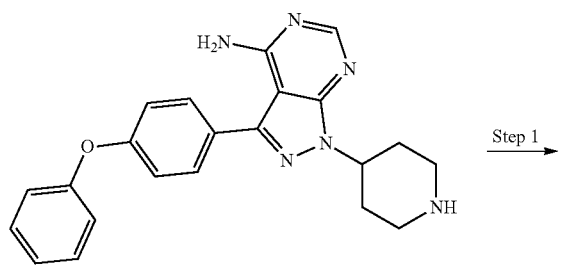

1a

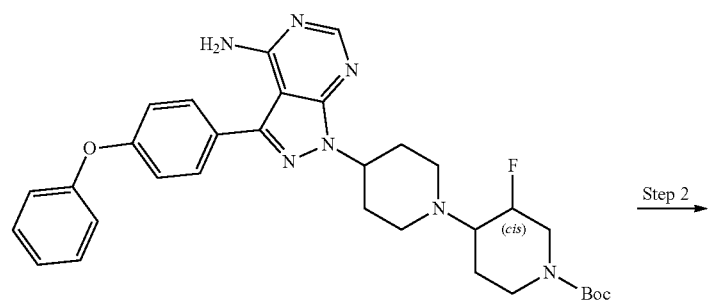

18a

-continued
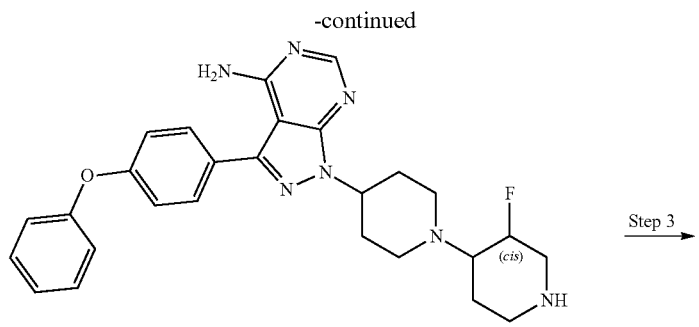
18b
Step 3
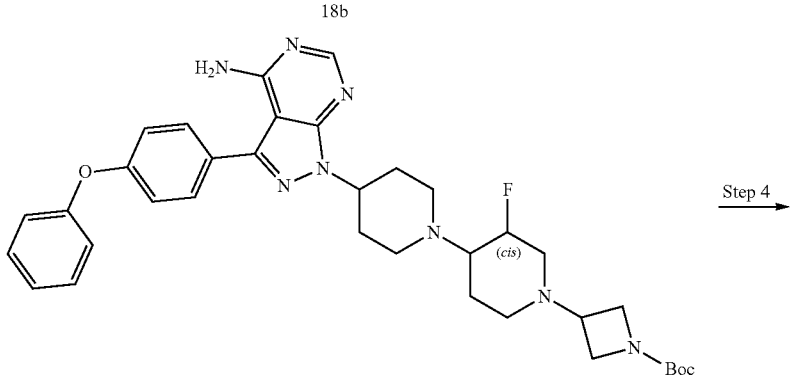
18c
Step 4
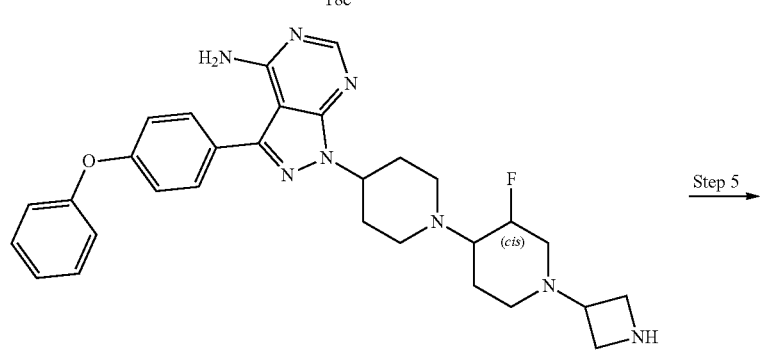
18d
Step 5
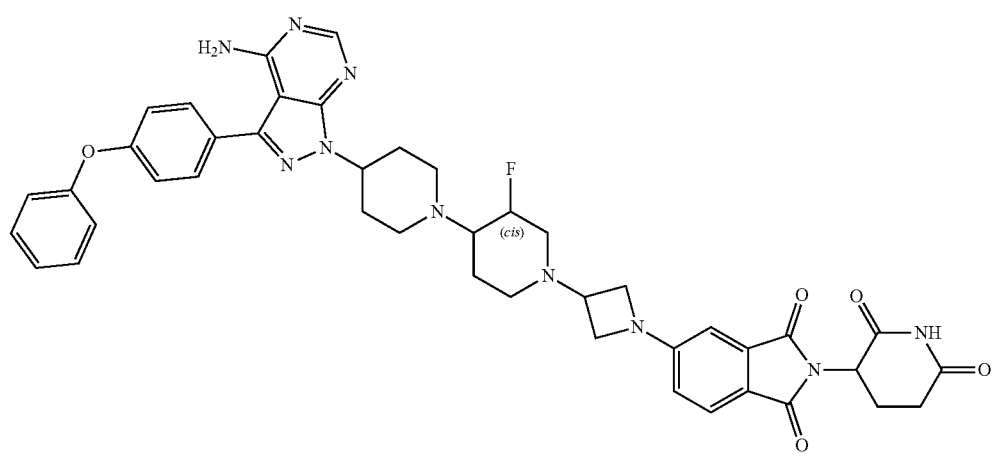
Compound 18

Step 1 cis-tert-butyl 4-(4-amino-3-(4-phenoxyphenyl)-1H-pyrazolo[3,4-d]pyrimidin-1-yl)-3'-fluoro-[1,4'-bipiperidine]-1'-carboxylate (18a)

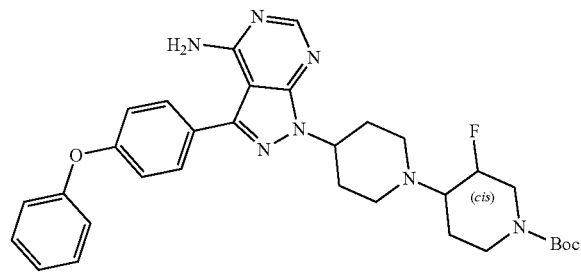 [SMILES: CC(C)(C)OC(=O)N1CCC(N2CCC(n3nc(-c4ccc(Oc5ccccc5)cc4)c4c(N)ncnc43)CC2)C(F)C1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.5 g, 3.88 mmol) was dissolved in 10 mL of DMSO and 50 mL of DCE, and N-Boc-3-fluoro-4-piperidone (2.1 g, 9.70 mmol) was added, the mixture was stirred at room temperature for 10 minutes, and then sodium triacetoxyborohydride (4.1 g, 19.40 mmol) was added, the mixture was stirred at room temperature overnight. To the reaction solution was slowly added dropwise 80 mL of saturated sodium bicarbonate solution, and the mixed solution was extracted with 100 mL of dichloromethane. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain cis tert-butyl-4-(4-amino-3-(4-phenoxyphenyl)-1H-pyrazolo[3,4-d]pyrimidin-1-yl)-3'-fluoro-[1,4'-bipiperidine]-1-carboxylate (18a) (980 mg, yield: 43%).

LC-MS m/z=588.3 [M+1]$^+$.

Step 2 cis-1-(3'-fluoro-[1,4'-bipiperidin]-4-yl)-3-(4-phenoxyphenyl)-1H-pyrazolo[3,4-d]pyrimidin-4-amine Trifluoroacetate (18b)

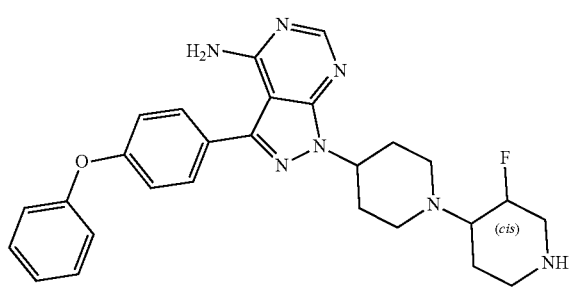 [SMILES: Nc1ncnc2c1c(-c1ccc(Oc3ccccc3)cc1)nn2C1CCN(C2CCNCC2F)CC1]

cis-tert-butyl 4-(4-amino-3-(4-phenoxyphenyl)-1H-pyrazolo[3,4-d]pyrimidin-1-yl)-3'-fluoro-[1,4'-bipiperidine]-1-carboxylate (18a) (0.5 g, 0.85 mmol) was dissolved in 50 mL of DCM, and 10 mL of trifluoroacetic acid was added, the mixture was stirred at room temperature for 4 h. The reaction system was directly concentrated under reduced pressure to obtain cis-1-(3'-fluoro-[1,4'-bipiperidin]-4-yl)-3-(4-phenoxyphenyl)-1H-pyrazolo[3,4-d]pyrimidin-4-amine Trifluoroacetate (18b) (0.60 g).

LCMS m/z=488.5 [M+1]$^+$.

Step 3 cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate (18c)

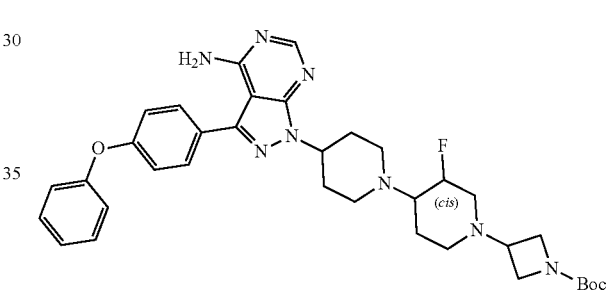

cis-1-(3'-fluoro-[1,4'-bipiperidin]-4-yl)-3-(4-phenoxyphenyl)-1H-pyrazolo[3,4-d]pyrimidin-4-amine Trifluoroacetate (18b) (540 mg) was dissolved in 15 mL of 1,2-dichloroethane and 2 mL of DMSO, and tert-butyl 3-oxoazetidine-1-carboxylate (564 mg, 3.30 mmol) was added, the mixture was stirred at room temperature for 10 minutes. Sodium triacetoxyborohydride (1.4 g, 6.60 mmol) was added, and the mixture was stirred at room temperature overnight. To the reaction solution was slowly added dropwise 80 mL of saturated sodium bicarbonate solution, and the mixed solution was extracted with 50 mL of DCM. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate (18c) (290 mg).

LCMS m/z=643.3 [M+1]$^+$.

Step 4 cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine Trifluoroacetate (18d)

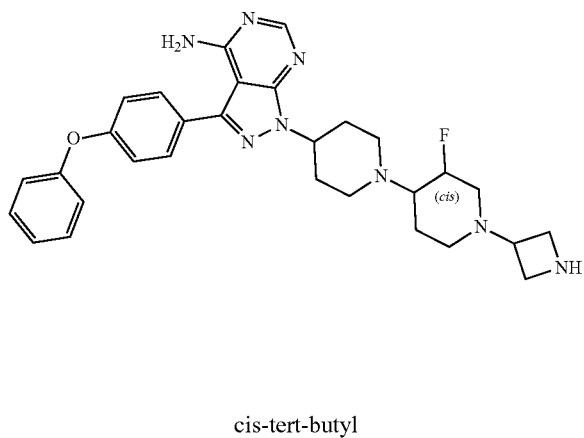

cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate (18c) (290 mg, 0.45 mmol) was dissolved in 10 mL of DCM, and 2 mL of trifluoroacetic acid was added, the mixture was stirred at room temperature for 4 h. The reaction system was directly concentrated under reduced pressure to obtain cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine Trifluoroacetate (18d) (0.30 g).
LCMS m/z=543.5 [M+1]$^+$.

Step 5 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione Trifluoroacetate (Compound 18)

cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine Trifluoroacetate (18d) (0.3 g) was dissolved in 8.5 mL of DMSO, and 1.5 mL of DIPEA and 2-(2,6-dioxopiperidin-3-yl)-5-fluoroisoindoline-1,3-dione (see WO 2017197056 for the synthetic method) (250 mg, 0.90 mmol) were added, the mixture was stirred at 80° C. for 5 h. The reaction solution was cooled to room temperature, added 10 mL of water, and extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione trifluoroacetate (Compound 18) (80 mg).

$^1$H NMR (400 MHz, DMSO-d$_6$) δ 11.05 (s, 1H), 8.23 (s, 1H), 7.71-7.61 (m, 3H), 7.47-7.39 (m, 2H), 7.22-7.08 (m, 5H), 6.82-6.78 (m, 1H), 6.66 (dd, 1H), 5.11-4.92 (m, 2H), 4.71-4.58 (m, 1H), 4.15-4.05 (m, 2H), 3.92-3.77 (m, 2H), 3.45-3.36 (m, 1H), 3.17-3.02 (m, 3H), 2.99-2.82 (m, 2H), 2.64-2.53 (m, 3H), 2.47-2.39 (m, 2H), 2.23-1.97 (m, 5H), 1.96-1.79 (m, 3H), 1.75-1.64 (m, 1H).

LCMS m/z=799.3 [M+1]$^+$.

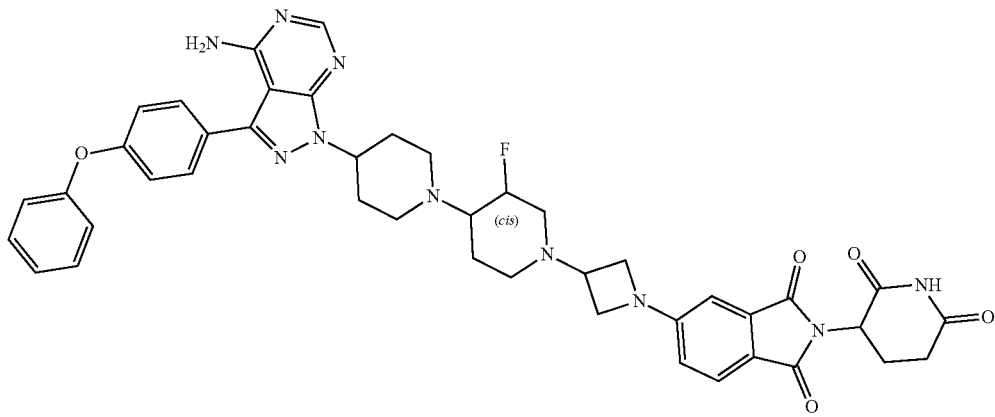 [SMILES: Nc1ncnc2c1c(-c1ccc(Oc3ccccc3)cc1)nn2C1CCN(C2CCN(C3CN(c4ccc5c(c4)C(=O)N(C4CCC(=O)NC4=O)C5=O)C3)CC2F)CC1]

Example 18-1 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione (Compound 18-1)

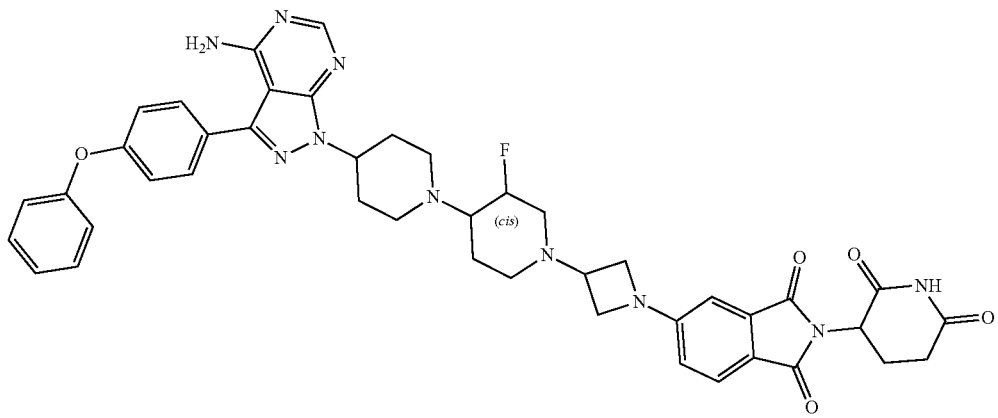 [SMILES: Nc1ncnc2c1c(-c1ccc(Oc3ccccc3)cc1)nn2C1CCN(C2CCN(C3CN(c4ccc5c(c4)C(=O)N(C4CCC(=O)NC4=O)C5=O)C3)CC2F)CC1]

The compound 18 (50 mg) was dissolved in 10 mL of concentrated ammonia water with a mass fraction of 28%, the mixed solution was extracted with DCM (12 mL×3). The organic phase was combined, and washed concentrated ammonia water with a mass fraction of 28% (12 mL×3), the organic layer was dried over anhydrous sodium sulfate, and concentrated under reduced pressure. To the residue was added 10 mL of petroleum ether and slurried for 0.5 h, and the slurry was filtered, to obtain free base cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione (Compound 18-1) (35 mg).

$^1$H NMR (400 MHz, CDCl$_3$) δ 9.16 (s, 1H), 8.38 (s, 1H), 7.69-7.59 (m, 3H), 7.43-7.34 (m, 2H), 7.21-7.03 (m, 5H), 6.78 (d, 1H), 6.52 (dd, 1H), 5.72 (brs, 2H), 5.20-4.97 (m, 1H), 4.96-4.88 (m, 1H), 4.87-4.73 (m, 1H), 4.16-4.04 (m, 2H), 4.00-3.85 (m, 2H), 3.52-3.43 (m, 1H), 3.36-3.13 (m, 3H), 3.10-3.00 (m, 1H), 2.95-2.62 (m, 5H), 2.59-2.35 (m, 3H), 2.25-2.00 (m, 6H), 1.89-1.79 (m, 1H).

LCMS m/z=799.3 [M+1]$^+$.

Example 19 trans-5-(3-(4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione Trifluoroacetate (Compound 19)

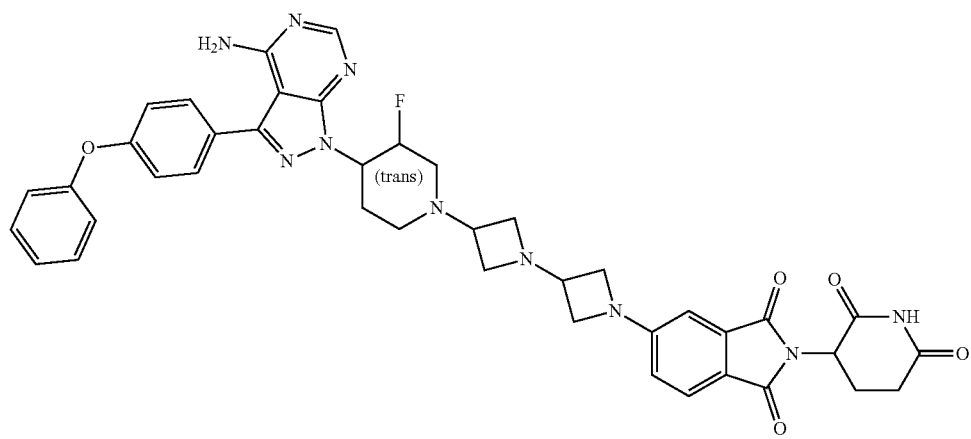

-continued
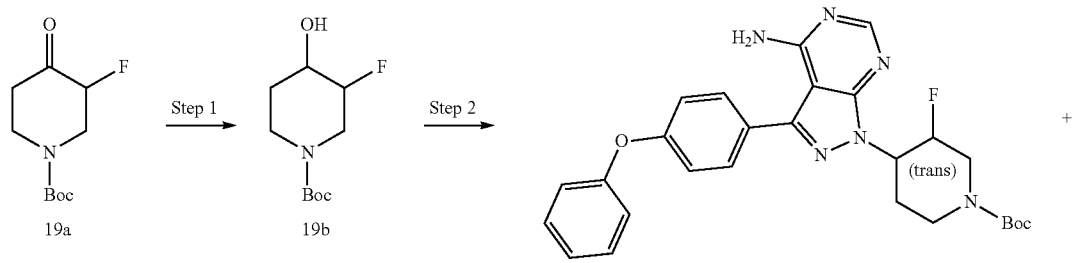
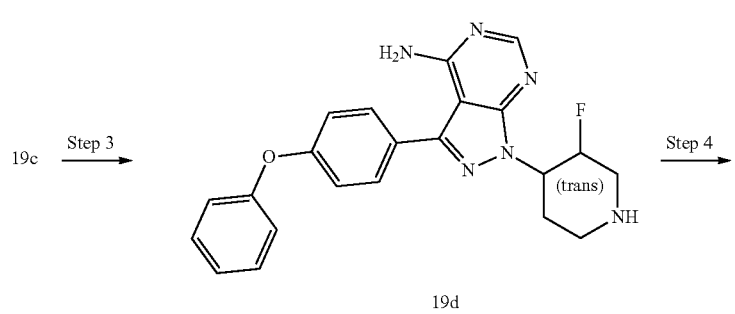
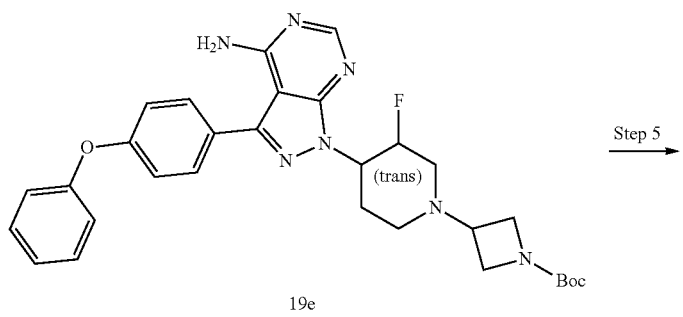
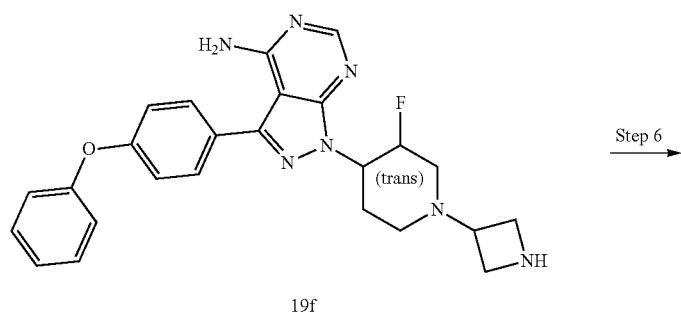

-continued

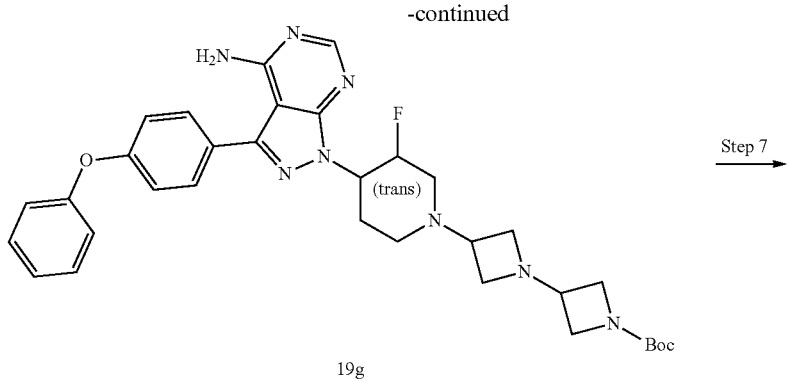

19g

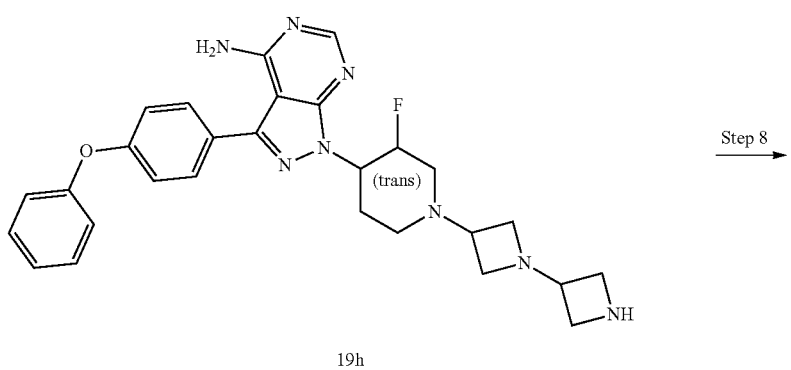

19h

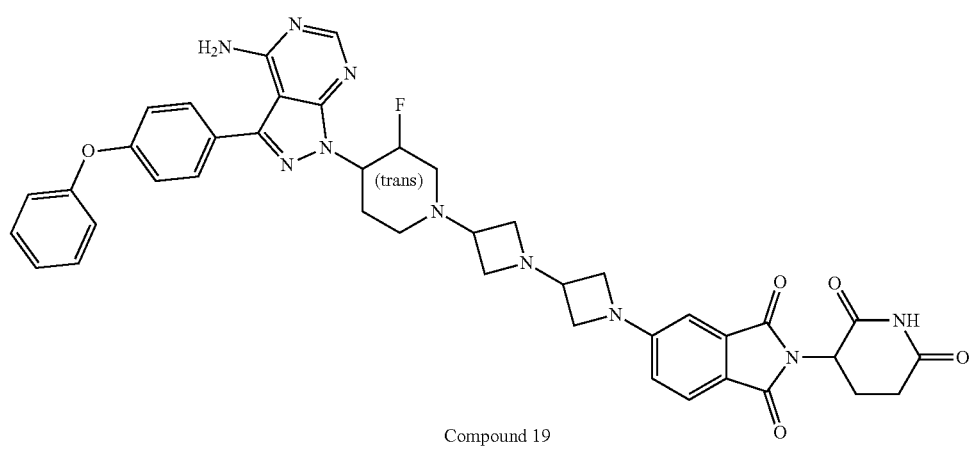

Compound 19

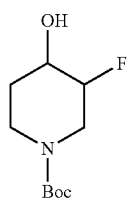

Tert-butyl 3-fluoro-4-piperidone-carboxylate (19a) (6.51 g, 30.0 mmol) was dissolved in 80 mL of anhydrous methanol, and sodium borohydride (2.28 g, 60.0 mmol) was slowly added in portions at room temperature. Upon completion of the addition, the mixture was stirred at room temperature for 30 minutes. The reaction solution was quenched with 150 mL of saturated sodium bicarbonate solution, and extracted with 100 mL of dichloromethane. The organic phase was washed with 100 mL of water, dried over anhydrous sodium sulfate, and concentrated under reduced pressure, then the crude product was separated and purified by silica gel column chromatography (petroleum ether/ethyl acetate (v/v)=2:1), to obtain the mixture of cis and trans isomers tert-butyl 3-fluoro-4-hydroxypiperidine-1-carboxylate (19b) (5.7 g, cis/trans=2.5:1, yield: 87%).

LC-MS m/z=220.1 [M+1]$^+$.

Step 2 trans-tert-butyl 4-(4-amino-3-(4-phenoxyphenyl)-1H-pyrazolo[3,4-d]pyrimidin-1-yl)-3-fluoropiperidine-1-carboxylate (19c)

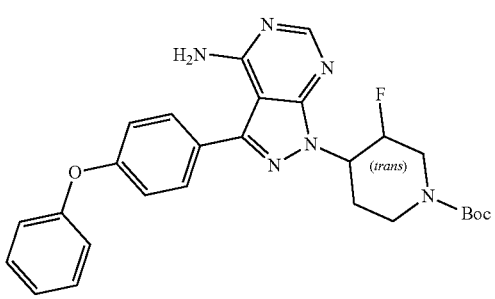 [SMILES: CC(C)(C)OC(=O)N1CCC(n2nc(-c3ccc(Oc4ccccc4)cc3)c3c(N)ncnc32)C(F)C1]

The mixture of cis and trans isomers tert-butyl 3-fluoro-4-hydroxypiperidine-1-carboxylate (19b) (cis/trans=2.5:1) (1.0 g, 4.56 mmol) and 3-(4-phenoxyphenyl)-1H-pyrazolo[3,4-d]pyrimidin-4-amine (1.15 g, 3.80 mmol) was dissolved in 40 mL of THF, and triphenylphosphine (1.5 g, 5.72 mmol) was added. DIAD (1.15 g, 5.69 mmol) was slowly added dropwise under nitrogen atmosphere. Upon completion of the addition, the mixture was stirred at room temperature overnight. Upon completion of the reaction, to the system was slowly added 50 mL of saturated sodium bicarbonate solution, the mixed solution was extracted with 100 mL of dichloromethane. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain trans-tert-butyl 4-(4-amino-3-(4-phenoxyphenyl)-1H-pyrazolo[3,4-d]pyrimidin-1-yl)-3-fluoropiperidine-1-carboxylate (19c) (0.8 g, yield: 35%)

LCMS m/z=505.4 [M+1]+.

Step 3 trans-1-(3-fluoropiperidin-4-yl)-3-(4-phenoxyphenyl)-1H-pyrazolo[3,4-d]pyrimidin-4-amine Trifluoroacetate (19d)

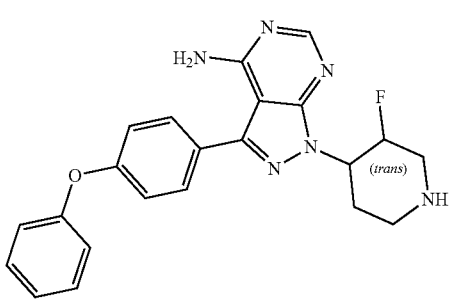 [SMILES: Nc1ncnc2c1c(-c1ccc(Oc3ccccc3)cc1)nn2C1CCNCC1F]

Trans-tert-butyl 4-(4-amino-3-(4-phenoxyphenyl)-1H-pyrazolo[3,4-d]pyrimidin-1-yl)-3-fluoropiperidine-1-carboxylate (19c) (800 mg, 1.59 mmol) was dissolved in 20 mL of DCM, and 5 mL of trifluoroacetic acid was added, the mixture was stirred at room temperature for 4 h. Upon completion of the reaction, the system was directly concentrated under reduced pressure, to obtain trans-1-(3-fluoropiperidin-4-yl)-3-(4-phenoxyphenyl)-1H-pyrazolo[3,4-d]pyrimidin-4-amine Trifluoroacetate (19d) (0.90 g).

LCMS m/z=405.3 [M+1]+.

Step 4 trans-tert-butyl 3-(4-(4-amino-3-(4-phenoxyphenyl)-1H-pyrazolo[3,4-d]pyrimidin-1-yl)-3-fluoropiperidin-1-yl)azetidine-1-carboxylate (19e)

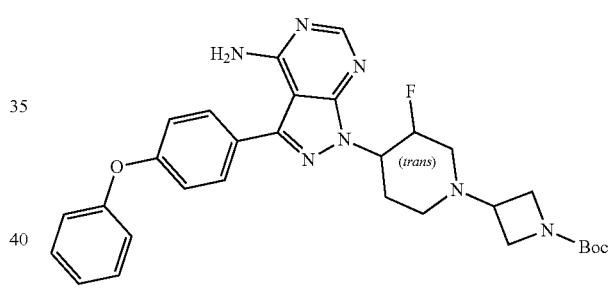

trans-1-(3-fluoropiperidin-4-yl)-3-(4-phenoxyphenyl)-1H-pyrazolo[3,4-d]pyrimidin-4-amine Trifluoroacetate (19d) (0.8 g) was dissolved in 35 mL of DCE and 5 mL of DMSO, and tert-butyl 3-oxoazetidine-1-carboxylate (542 mg, 3.17 mmol) was added, the mixture was stirred at room temperature for 10 minutes, then sodium triacetoxyborohydride (1.68 g, 7.92 mmol) was added, and the mixture was stirred at room temperature overnight. To the reaction solution was slowly added 30 mL of saturated sodium bicarbonate aqueous solution, and the mixed solution was with extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain trans-tert-butyl 3-(4-(4-amino-3-(4-phenoxyphenyl)-1H-pyrazolo[3,4-d]pyrimidin-1-yl)-3-fluoropiperidin-1-yl)azetidine-1-carboxylate (19e) (930 mg).

LCMS m/z=560.5 [M+1]+.

Step 5 trans-1-(1-(azetidin-3-yl)-3-fluoropiperidin-4-yl)-3-(4-phenoxyphenyl)-1H-pyrazolo[3,4-d]pyrimidin-4-amine Trifluoroacetate (19f)

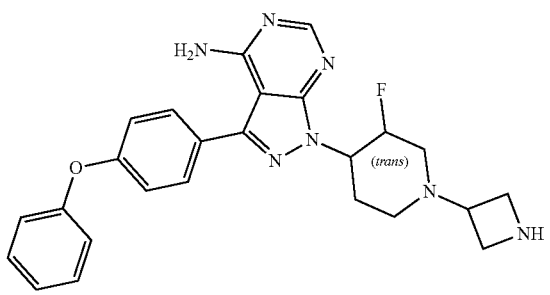 [SMILES: Nc1ncnc2c1c(-c1ccc(Oc3ccccc3)cc1)nn2C1CCN(C2CNC2)CC1F]

trans-tert-butyl 3-(4-(4-amino-3-(4-phenoxyphenyl)-1H-pyrazolo[3,4-d]pyrimidin-1-yl)-3-fluoropiperidin-1-yl)azetidine-1-carboxylate (19e) (500 mg, 0.89 mmol) was dissolved in 20 mL of DCM, and 5 mL of trifluoroacetic acid was added, the mixture was stirred at room temperature for 4 h. Upon completion of the reaction, the system was directly concentrated under reduced pressure, to obtain trans-1-(1-(azetidin-3-yl)-3-fluoropiperidin-4-yl)-3-(4-phenoxyphenyl)-1H-pyrazolo[3,4-d]pyrimidin-4-amine Trifluoroacetate (19f) (0.65 g).

LCMS m/z=460.3 [M+1]$^+$.

Step 6 trans-tert-butyl 3-(4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (19g)

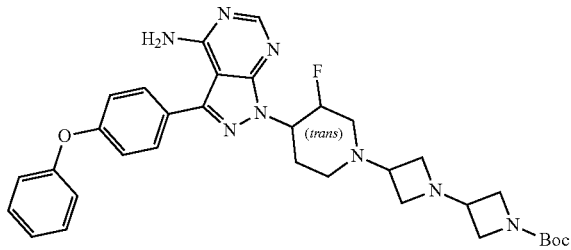 [SMILES: CC(C)(C)OC(=O)N1CC(N2CC(N3CCC(n4nc(-c5ccc(Oc6ccccc6)cc5)c5c(N)ncnc54)C(F)C3)C2)C1]

trans-1l-(1-(azetidin-3-yl)-3-fluoropiperidin-4-yl)-3-(4-phenoxyphenyl)-1H-pyrazolo[3,4-d]pyrimidin-4-amine Trifluoroacetate (19f) (650 mg) was dissolved in 25 mL of DCE and 2 mL of DMSO, and tert-butyl 3-oxoazetidine-1-carboxylate (485 mg, 2.83 mmol) was added, the mixture was stirred at room temperature for 10 minutes, then sodium triacetoxyborohydride (1.12 g, 5.28 mmol) was added, and the mixture was stirred at room temperature overnight. To the reaction system was slowly added 60 mL of saturated sodium bicarbonate solution, and the mixed solution was extracted with 60 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v) =20:1), to obtain trans-tert-butyl 3-(4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (19g) (450 mg).

LCMS m/z=615.6 [M+1]$^+$.

Step 7 trans-1-(1-([1,3'-biazetidin]-3-yl)-3-fluoropiperidin-4-yl)-3-(4-phenoxyphenyl)-1H-pyrazolo[3,4-d]pyrimidin-4-amine Trifluoroacetate (19h)

trans-tert-butyl 3-(4-(4-amino-3-(4-phenoxyphenyl)-1H-pyrazolo[3,4-d]pyrimidin-1-yl)-3-fluoropiperidin-1-yl)-[1,3'-biazetidin]-1'-carboxylate (19g) (400 mg, 0.65 mmol) was dissolved in 20 mL of DCM, and 4 mL of trifluoroacetic acid was added, the mixture was stirred at room temperature for 4 h. The reaction system was directly concentrated under reduced pressure, to obtain trans-1-(1-([1,3'-biazetidin]-3-yl)-3-fluoropiperidin-4-yl)-3-(4-phenoxyphenyl)-1H-pyrazolo[3,4-d]pyrimidin-4-amine Trifluoroacetate (19h) (0.56 g).

LCMS m/z=515.5 [M+1]$^+$.

Step 8 trans-5-(3-(4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione trifluoroacetate (Compound 19)

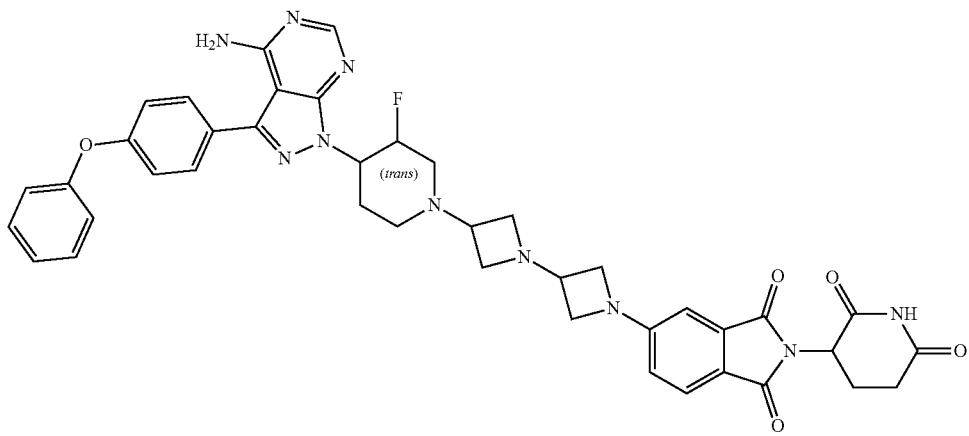 [SMILES: Nc1ncnc2c1c(-c1ccc(Oc3ccccc3)cc1)nn2C1CCN(C2CN(C3CN(c4ccc5c(c4)C(=O)N(C4CCC(=O)NC4=O)C5=O)C3)C2)CC1F]

trans-1-(1-([1,3'-biazetidin]-3-yl)-3-fluoropiperidin-4-yl)-3-(4-phenoxyphenyl)-1H-pyrazolo[3,4-d]pyrimidin-4-amine Trifluoroacetate (19h) (0.5 g) was dissolved in 25 mL of DMSO, and 3 mL of DIPEA and 2-(2,6-dioxopiperidin-3-yl)-5-fluoroisoindoline-1,3-dione (see WO 2017197056 for the synthetic method) (352 mg, 1.28 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=20:1), to obtain trans-5-(3-(4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione trifluoroacetate (Compound 19) (120 mg).

$^1$H NMR (400 MHz, DMSO-$d_6$) δ 11.05 (s, 1H), 8.25 (s, 1H), 7.73-7.60 (m, 3H), 7.48-7.40 (m, 2H), 7.23-7.10 (m, 5H), 6.80 (d, 1H), 6.66 (dd, 1H), 5.25-5.00 (m, 2H), 4.88-4.75 (m, 1H), 4.12-4.00 (m, 2H), 3.89-3.78 (m, 2H), 3.75-3.62 (m, 1H), 3.54-3.39 (m, 2H), 3.28-2.96 (m, 4H), 2.95-2.77 (m, 2H), 2.64-2.53 (m, 2H), 2.30-2.08 (m, 3H), 2.07-1.92 (m, 2H).

LCMS m/z=771.3 [M+1]$^+$.

Example 19-1 trans-5-(3-(4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 19-1)

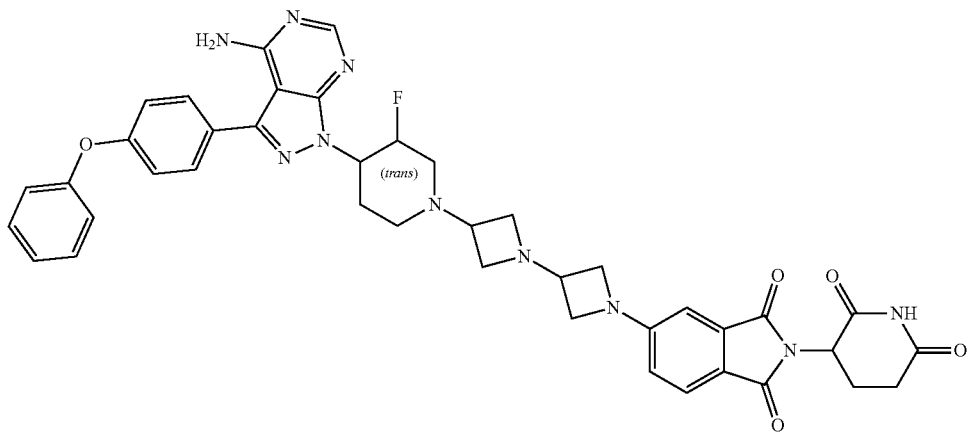 [SMILES: Nc1ncnc2c1c(-c1ccc(Oc3ccccc3)cc1)nn2C1CCN(C2CN(C3CN(c4ccc5c(c4)C(=O)N(C4CCC(=O)NC4=O)C5=O)C3)C2)CC1F]

The compound 19 (95 mg) was dissolved in 17 mL of concentrated ammonia water with a mass fraction of 28%, the mixed solution was extracted with DCM (20 mL×3). The organic phase was combined, and washed concentrated ammonia water with a mass fraction of 28% (20 mL×3), the organic layer was dried over anhydrous sodium sulfate, and concentrated under reduced pressure. To the residue was added 17 mL of petroleum ether and slurried for 0.5 h, and the slurry was filtered, to obtain free base trans-5-(3-(4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 19-1) (80 mg).

¹H NMR (400 MHz, CDCl₃) δ 9.30 (brs, 1H), 8.40 (s, 1H), 7.69-7.61 (m, 3H), 7.43-7.35 (m, 2H), 7.21-7.04 (m, 5H), 6.79 (d, 1H), 6.53 (dd, 1H), 5.73 (brs, 2H), 5.36-5.13 (m, 1H), 4.97-4.83 (m, 2H), 4.11-4.00 (m, 2H), 3.94-3.84 (m, 2H), 3.76-3.56 (m, 3H), 3.30-3.05 (m, 4H), 2.93-2.64 (m, 4H), 2.54-2.39 (m, 1H), 2.23-2.02 (m, 4H).

LCMS m/z=771.3 [M+1]⁺.

Example 20 trans-5-(3-(4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione trifluoroacetate (Compound 20)

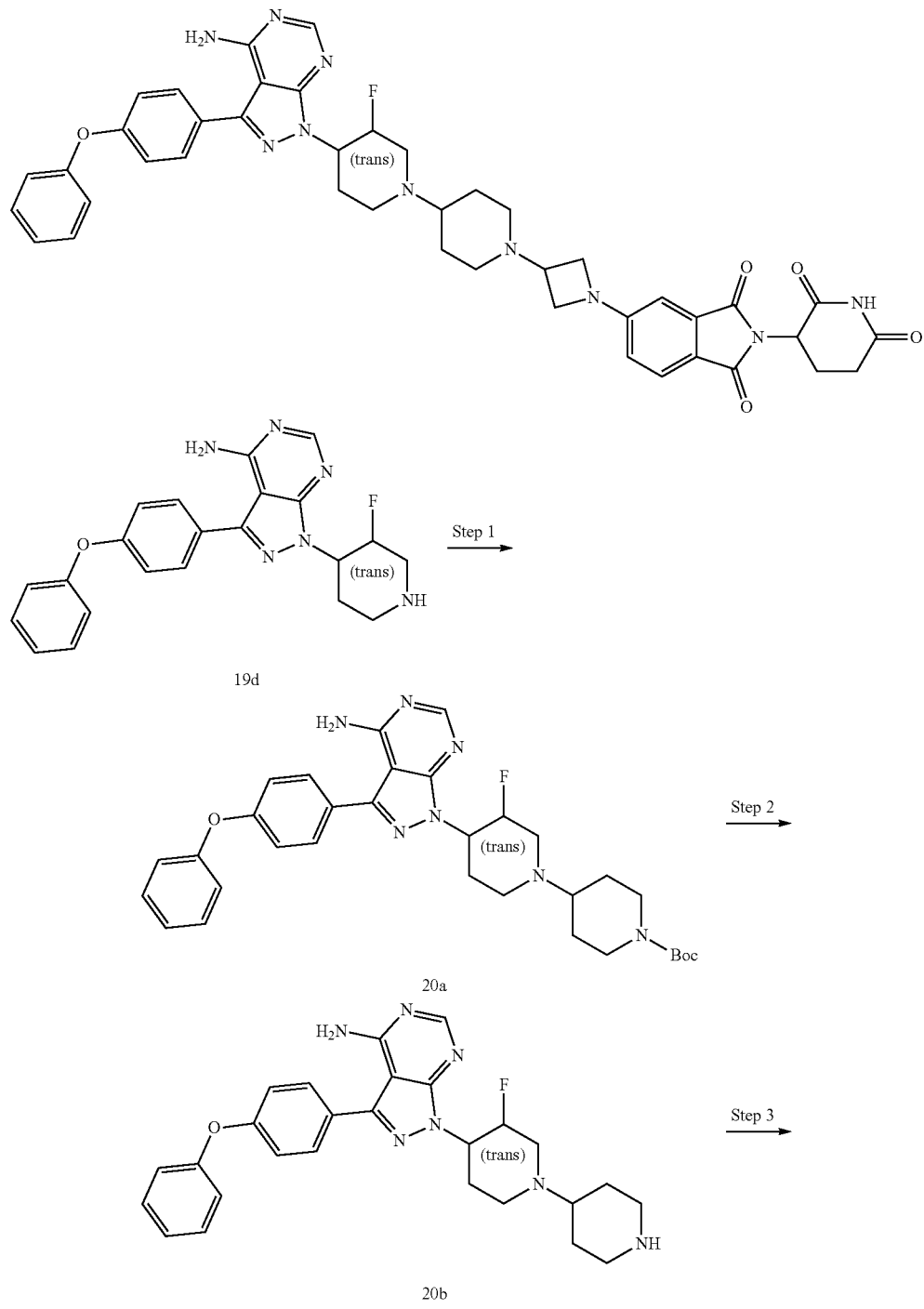

-continued
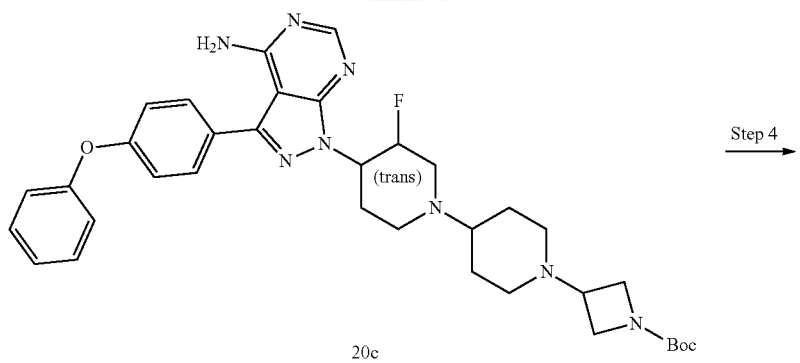
20c
Step 4
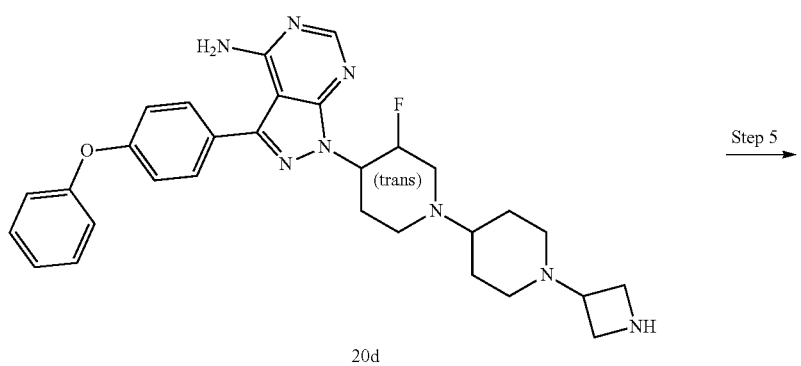
20d
Step 5
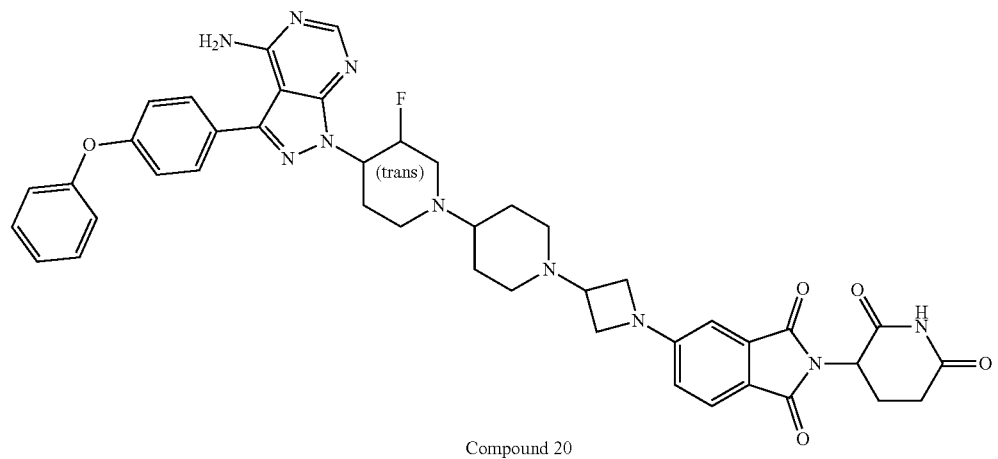
Compound 20

Step 1 trans-tert-butyl 4-(4-amino-3-(4-phenoxyphenyl)-1H-pyrazolo[3,4-d]pyrimidin-1-yl)-3-fluoro-[1,4'-bipiperidine]-1'-carboxylate (20a)

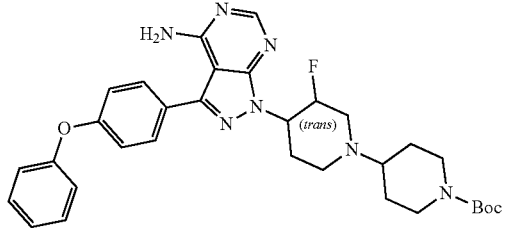 [SMILES: CC(C)(C)OC(=O)N1CCC(N2CCC(n3nc(-c4ccc(Oc5ccccc5)cc4)c4c(N)ncnc43)C(F)C2)CC1]

trans-1-(3-fluoropiperidin-4-yl)-3-(4-phenoxyphenyl)-1H-pyrazolo[3,4-d]pyrimidin-4-amine Trifluoroacetate (19d) (520 mg) was dissolved in 15 mL of DCE and 2 mL of DMSO, and N-Boc-4-piperidone (1.05 g, 5.27 mmol) was added, the mixture was stirred at room temperature for 10 minutes, then sodium triacetoxyborohydride (1.12 g, 5.28 mmol) was added, and the mixture was stirred at room temperature overnight. To the reaction system was slowly added 50 mL of saturated sodium bicarbonate solution, and the mixed solution was extracted with 50 mL of DCM. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain trans-tert-butyl 4-(4-amino-3-(4-phenoxyphenyl)-1H-pyrazolo[3,4-d]pyrimidin-1-yl)-3-fluoro-[1,4'-bipiperidine]-1'-carboxylate (20a) (500 mg).

LCMS m/z=588.4 [M+1]$^+$.

Step 2 trans-1-(3-fluoro-[1,4'-bipiperidin]-4-yl)-3-(4-phenoxyphenyl)-1H-pyrazolo[3,4-d]pyrimidin-4-amine Trifluoroacetate (20b)

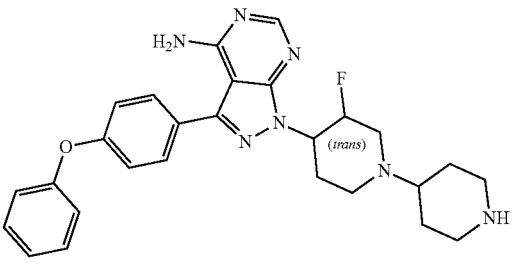 [SMILES: Nc1ncnc2c1c(-c1ccc(Oc3ccccc3)cc1)nn2C1CCN(C2CCNCC2)CC1F]

trans-tert-butyl 4-(4-amino-3-(4-phenoxyphenyl)-1H-pyrazolo[3,4-d]pyrimidin-1-yl)-3-fluoro-[1,4'-bipiperidine]-1'-carboxylate (20a) (500 mg, 0.85 mmol) was dissolved in 20 mL of DCM, and 5 mL of trifluoroacetic acid was added, the mixture was stirred at room temperature for 4 h. The reaction system was directly concentrated under reduced pressure, to obtain trans-1-(3-fluoro-[1,4'-bipiperidin]-4-yl)-3-(4-phenoxyphenyl)-1H-pyrazolo[3,4-d]pyrimidin-4-amine Trifluoroacetate (20b) (0.60 g).

LCMS m/z=488.3 [M+1]$^+$.

Step 3 trans-tert-butyl 3-(4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (20c)

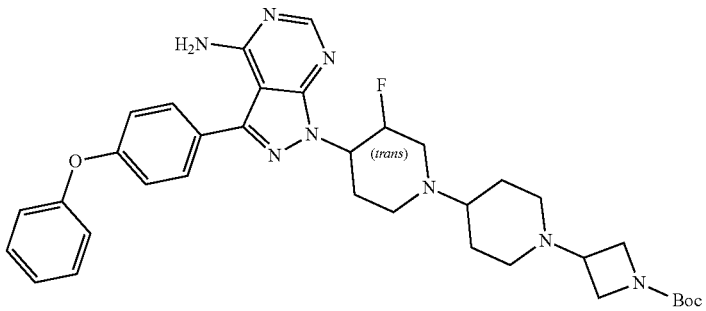 [SMILES: CC(C)(C)OC(=O)N1CC(N2CCC(N3CCC(n4nc(-c5ccc(Oc6ccccc6)cc5)c5c(N)ncnc54)C(F)C3)CC2)C1]

trans-1-(3-fluoro-[1,4'-bipiperidin]-4-yl)-3-(4-phenoxyphenyl)-1H-pyrazolo[3,4-d]pyrimidin-4-amine Trifluoroacetate (20b) (600 mg) was dissolved in 35 mL of DCE and 2 mL of DMSO, and tert-butyl 3-oxoazetidine-1-carboxylate (727 mg, 4.25 mmol) was added, the mixture was stirred at room temperature for 10 minutes, then sodium triacetoxyborohydride (900 mg, 4.25 mmol) was added, and the mixture was stirred at room temperature overnight. To the reaction system was slowly added 80 mL of saturated sodium bicarbonate solution, and the mixed solution was extracted with 50 mL of DCM. The organic phase was washed with 50 mL of water, dried over anhydrous sodium sulfate, and concentrated under reduced pressure, then the crude product was separated and purified by silica gel column chromatography (dichloromethane/methanol (v/v)= 20:1), to obtain trans-tert-butyl 3-(4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (20c) (550 mg).

LCMS m/z=643.4 [M+1]⁺.

Step 4 trans-1-(1'-(azetidin-3-yl)-3-fluoro-[1,4'-bipiperidin]-4-yl)-3-(4-phenoxyphenyl)-1H-pyrazolo[3,4-d]pyrimidin-4-amine Trifluoroacetate (20d)

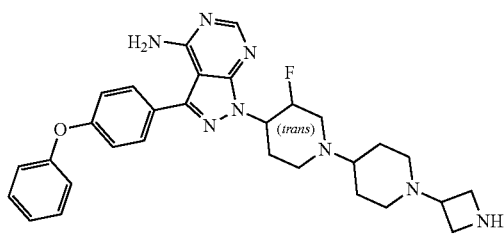 [SMILES: Nc1ncnc2c1c(-c1ccc(Oc3ccccc3)cc1)nn2C1CCN(C2CCN(C3CNC3)CC2)CC1F]

trans-tert-butyl 3-(4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (20c) (500 mg, 0.78 mmol) was dissolved in 25 mL of DCM, and 5 mL of trifluoroacetic acid was added, the mixture was stirred at room temperature for 4 h. The reaction system was directly concentrated under reduced pressure, to obtain trans-1-(1'-(azetidin-3-yl)-3-fluoro-[1,4'-bipiperidin]-4-yl)-3-(4-phenoxyphenyl)-1H-pyrazolo[3,4-d]pyrimidin-4-amine Trifluoroacetate (20d) (0.55 g).

LCMS m/z=543.2 [M+1]⁺.

Step 5 trans-5-(3-(4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione trifluoroacetate (Compound 20)

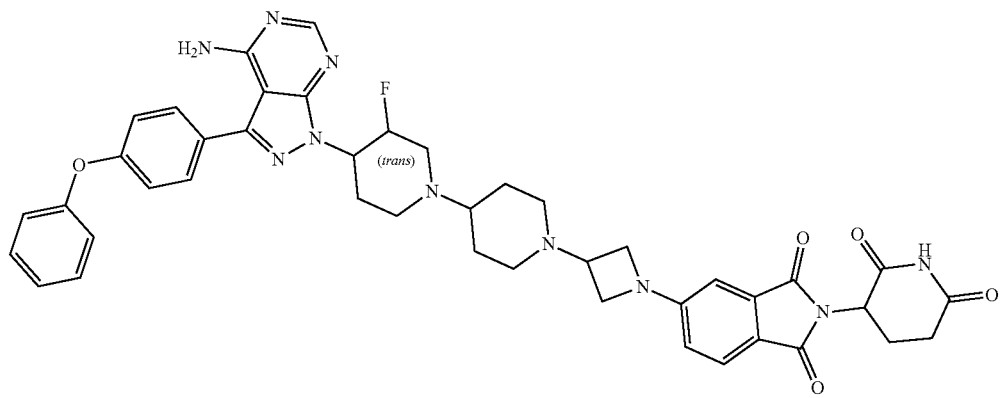 [SMILES: Nc1ncnc2c1c(-c1ccc(Oc3ccccc3)cc1)nn2C1CCN(C2CCN(C3CN(c4ccc5c(c4)C(=O)N(C4CCC(=O)NC4=O)C5=O)C3)CC2)CC1F]

trans-1-(1'-(azetidin-3-yl)-3-fluoro-[1,4'-bipiperidin]-4-yl)-3-(4-phenoxyphenyl)-1H-pyrazolo[3,4-d]pyrimidin-4-amine Trifluoroacetate (20d) (0.5 g) was dissolved in 25 mL of DMSO, and 3 mL of DIPEA and 2-(2,6-dioxopiperidin-3-yl)-5-fluoroisoindoline-1,3-dione (see WO 2017197056 for the synthetic method) (310 mg, 1.12 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol=15:1-8:1), to obtain trans-5-(3-(4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione trifluoroacetate (Compound 20) (120 mg).

¹H NMR (400 MHz, DMSO-d₆) δ 11.05 (s, 1H), 8.24 (s, 1H), 7.72-7.61 (m, 3H), 7.47-7.40 (m, 2H), 7.22-7.10 (m, 5H), 6.79 (d, 1H), 6.65 (dd, 1H), 5.19-4.94 (m, 2H), 4.83-4.70 (m, 1H), 4.15-4.05 (m, 2H), 3.89-3.76 (m, 2H), 3.41-3.34 (m, 1H), 3.00-2.81 (m, 4H), 2.63-2.52 (m, 2H), 2.49-2.32 (m, 4H), 2.24-2.10 (m, 1H), 2.07-1.94 (m, 2H), 1.94-1.82 (m, 2H), 1.82-1.70 (m, 2H), 1.57-1.41 (m, 2H).

LCMS m/z=799.3 [M+1]⁺.

Example 20-1 trans-5-(3-(4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 20-1)

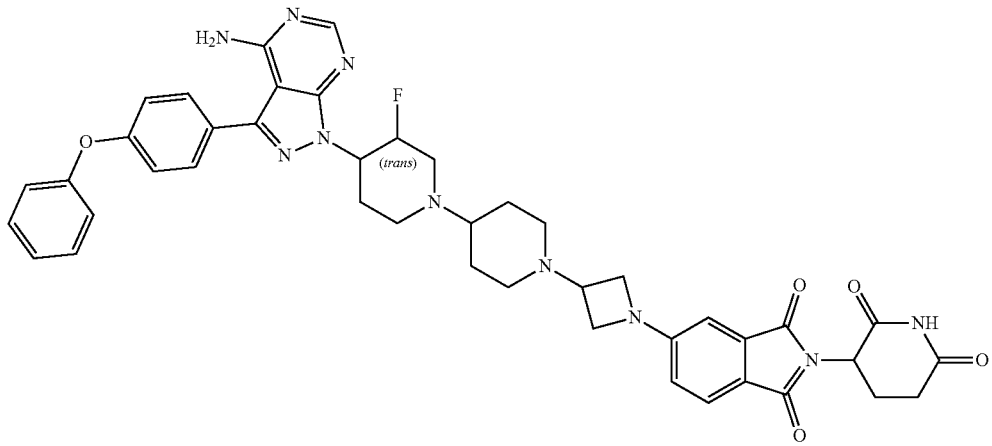

The compound 20 (90 mg) was dissolved in 17 mL of concentrated ammonia water with a mass fraction of 28%, the mixed solution was extracted with DCM (20 mL×3). The organic phase was combined, and washed concentrated ammonia water with a mass fraction of 28% (20 mL×3), the organic layer was dried over anhydrous sodium sulfate, and concentrated under reduced pressure. To the residue was added 17 mL of petroleum ether and slurried for 0.5 h, and the slurry was filtered, to obtain free base trans-5-(3-(4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 20-1) (70 mg).

$^1$H NMR (400 MHz, CDCl$_3$) δ 8.86 (brs, 1H), 8.39 (s, 1H), 7.71-7.60 (m, 3H), 7.43-7.35 (m, 2H), 7.21-7.11 (m, 3H), 7.11-7.04 (m, 2H), 6.79 (d, 1H), 6.53 (dd, 1H), 5.78 (brs, 2H), 5.33-5.10 (m, 1H), 4.97-4.81 (m, 2H), 4.16-4.06 (m, 2H), 4.00-3.86 (m, 2H), 3.48-3.34 (m, 2H), 3.08-2.94 (m, 3H), 2.93-2.65 (m, 3H), 2.59-2.36 (m, 4H), 2.17-1.97 (m, 4H), 1.96-1.85 (m, 2H), 1.78-1.62 (m, 2H).

LCMS m/z=799.3 [M+1]$^+$.

Example 21

5-(3-(4-(4-amino-3-(4-phenoxyphenyl)-1H-pyrazolo[3,4-d]pyrimidin-1-yl)piperidin-1-yl)-[1,3'-biazetidin]-1'-yl)-2-(2,6-dioxopiperidin-3-yl)-6-fluoroisoindoline-1,3-dione (Compound 21)

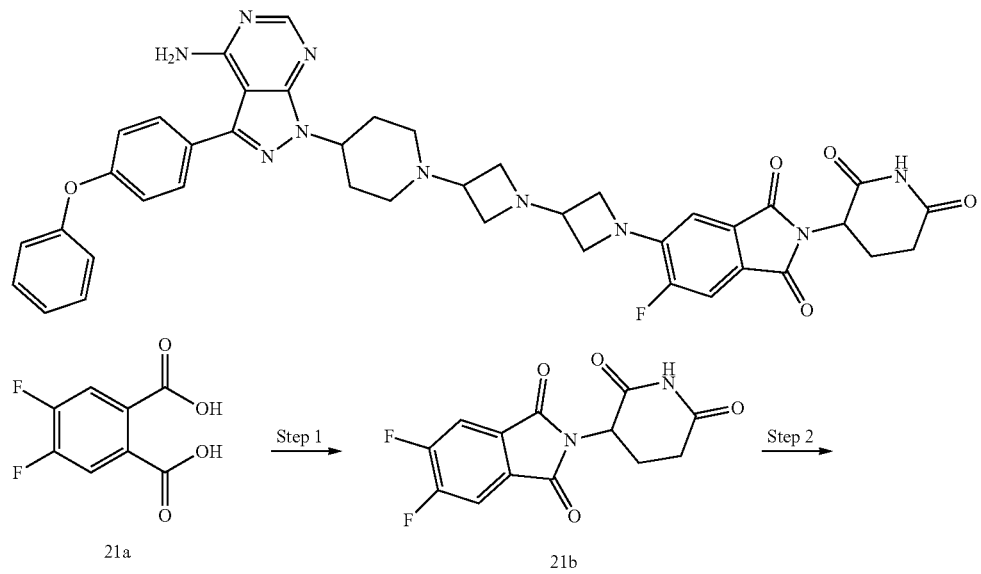

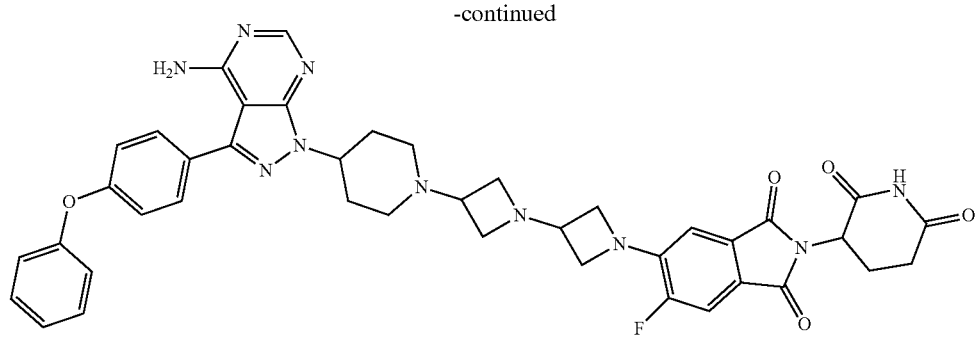

Compound 21

Step 1

2-(2,6-dioxopiperidin-3-yl)-5,6-difluoroisoindoline-1,3-dione (21b)

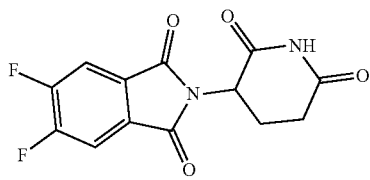 [SMILES: O=C1CCC(N2C(=O)c3cc(F)c(F)cc3C2=O)C(=O)N1]

4,5-difluorophthalic acid (21a) (500 mg, 2.47 mmol) was dissolved in 25 mL of acetonitrile, and 3-aminopiperidine-2,6-dione hydrochloride (0.41 g, 2.49 mmol) and CDI (0.8 g, 4.94 mmol) were added, the mixture was heated to reflux in external bath, and reacted for 4 h. The reaction system was directly concentrated under reduced pressure, and the crude product was separated and purified by silica gel column chromatography (petroleum ether/ethyl acetate (v/v)=2:1), to obtain 2-(2,6-dioxopiperidin-3-yl)-5,6-difluoroisoindoline-1,3-dione (21b) (0.4 g, yield: 55.0%).

LCMS m/z=295.2 [M+1]$^+$.

Step 2

5-(3-(4-(4-amino-3-(4-phenoxyphenyl)-1H-pyrazolo[3,4-d]pyrimidin-1-yl)piperidin-1-yl)-[1,3'-biazetidin]-1'-yl)-2-(2,6-dioxopiperidin-3-yl)-6-fluoroisoindoline-1,3-dione (Compound 21)

1-[1-[1-(azetidin-3-yl)azetidin-3-yl]-4-piperidyl]-3-(4-phenoxyphenyl)pyrazolo[3,4-d]pyrimidin-4-amine (17d) (0.25 g, 0.50 mmol) was dissolved in 10 mL of DMSO, and 1 mL of DIPEA and 2-(2,6-dioxopiperidin-3-yl)-5,6-difluoroisoindoline-1,3-dione (21b) (180 mg, 0.61 mmol) were added, the mixture was stirred in external bath at 80° C. for 5 h. The reaction solution was cooled to room temperature, quenched by adding 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-(4-(4-amino-3-(4-phenoxyphenyl)-1H-pyrazolo[3,4-d]pyrimidin-1-yl)piperidin-1-yl)-[1,3'-biazetidin]-1'-yl)-2-(2,6-dioxopiperidin-3-yl)-6-fluoroisoindoline-1,3-dione (Compound 21) (100 mg, yield: 26%).

$^1$H NMR (400 MHz, DMSO-d$_6$) δ 11.07 (s, 1H), 8.23 (s, 1H), 7.70-7.63 (m, 2H), 7.58 (d, 1H), 7.48-7.40 (m, 2H), 7.22-7.09 (m, 5H), 6.92 (d, 1H), 5.06 (dd, 1H), 4.74-4.61 (m, 1H), 4.24-4.14 (m, 2H), 4.00-3.88 (m, 2H), 3.66-3.55 (m, 1H), 3.49-3.39 (m, 2H), 3.08-2.78 (m, 6H), 2.64-2.52 (m, 2H), 2.29-2.13 (m, 2H), 2.09-1.96 (m, 3H), 1.96-1.85 (m, 2H).

LCMS m/z=771.3 [M+1]$^+$.

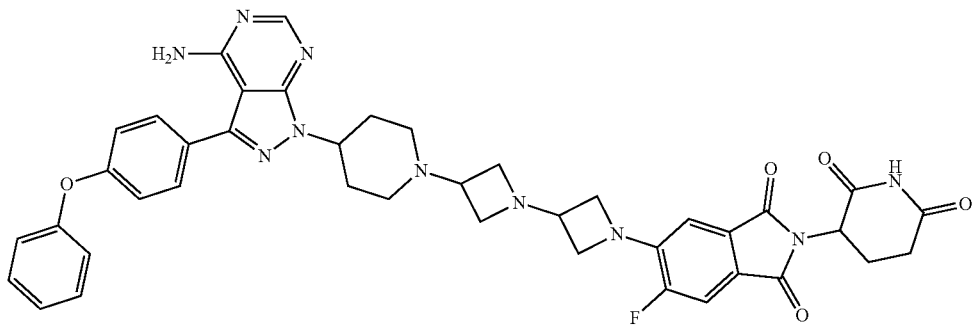 [SMILES: Nc1ncnc2c1c(-c1ccc(Oc3ccccc3)cc1)nn2C1CCN(C2CN(C3CN(c4cc5c(cc4F)C(=O)N(C4CCC(=O)NC4=O)C5=O)C3)C2)CC1]

Example 22

4-[3-[4-[4-[4-amino-3-(4-phenoxyphenyl)pyrazolo[3,4-d]pyrimidin-1-yl]-1-piperidyl]-1-piperidyl]azetidin-1-yl]-2-(2,6-dioxo-3-piperidyl)isoindoline-1,3-dione (Compound 22)

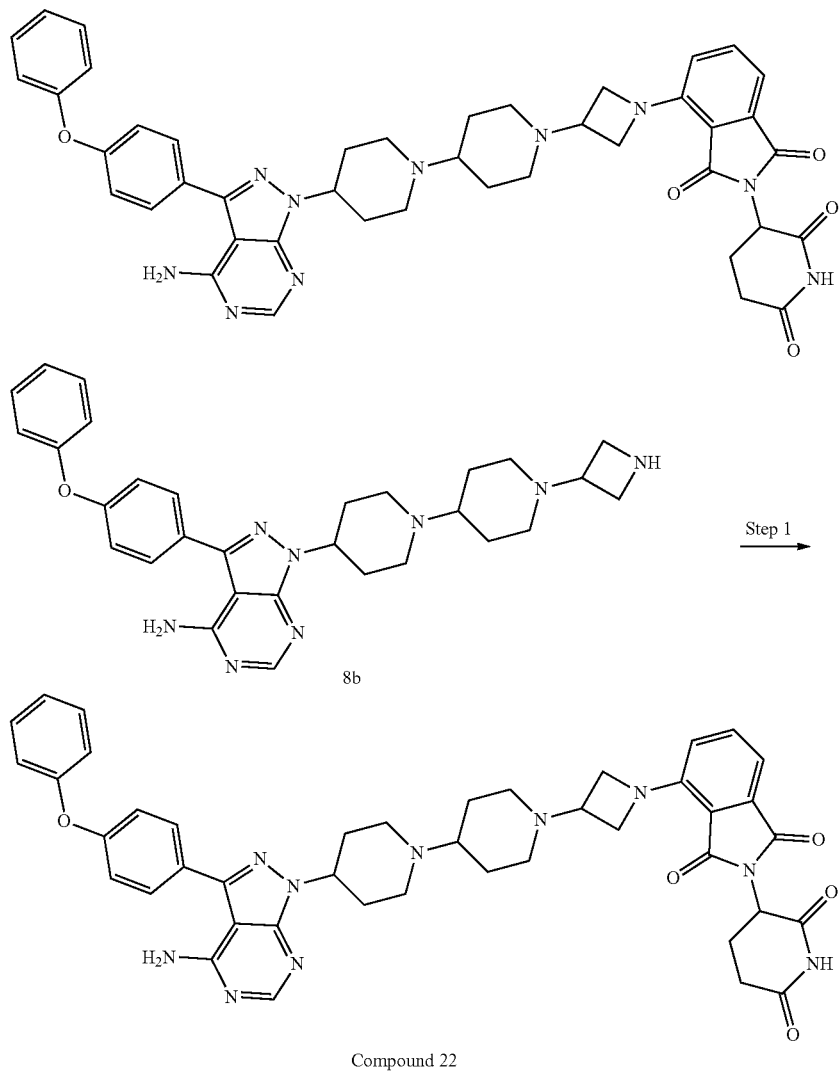

Compound 22

1-(1'-(azetidin-3-yl)-[1,4'-bipiperidin]-4-yl)-3-(4-phenoxyphenyl)-1H-pyrazolo[3,4-d]pyrimidin-4-amine (8b) (0.12 g, 0.23 mmol) was dissolved in 3 mL of DMSO, and 0.2 mL of DIPEA and 2-(2,6-dioxopiperidin-3-yl)-4-fluoroisoindoline-1,3-dione (see WO 2017197056 for the synthetic method) (90 mg, 0.30 mmol) were added, the mixture was stirred in external bath at 90° C. for 5 h. The reaction solution was cooled to room temperature, and extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain 4-[3-[4-[4-[4-amino-3-(4-phenoxyphenyl)pyrazolo[3,4-d]pyrimidin-1-yl]-1-piperidyl]-1-piperidyl]azetidin-1-yl]-2-(2,6-dioxo-3-piperidyl)isoindoline-1,3-dione (Compound 22) (58 mg, yield: 32%)

$^1$H NMR (400 MHz, CDCl$_3$) δ 8.41 (s, 1H), 8.34 (s, 1H), 7.63 (d, 2H), 7.48-7.35 (m, 3H), 7.22-7.11 (m, 4H), 7.10-7.05 (m, 2H), 6.60 (d, 1H), 5.80 (brs, 2H), 4.92 (dd, 1H), 4.87-4.68 (m, 1H), 4.44-4.31 (m, 2H), 4.11-4.01 (m, 2H), 3.30-3.08 (m, 3H), 3.02-2.93 (m, 2H), 2.92-2.68 (m, 4H), 2.63-2.39 (m, 4H), 2.14-2.09 (m, 3H), 1.99-1.89 (m, 4H), 1.77-1.62 (in, 2H).

LCMS m/z=781.3 [M+1]$^+$.

Example 23
5-[4-[3-[4-[4-amino-3-(4-phenoxyphenyl)pyrazolo[3,4-d]pyrimidin-1-yl]-1-piperidyl]azetidin-1-yl]-1-piperidyl]-2-(2,6-dioxo-3-piperidyl)isoindoline-1,3-dione (Compound 23)
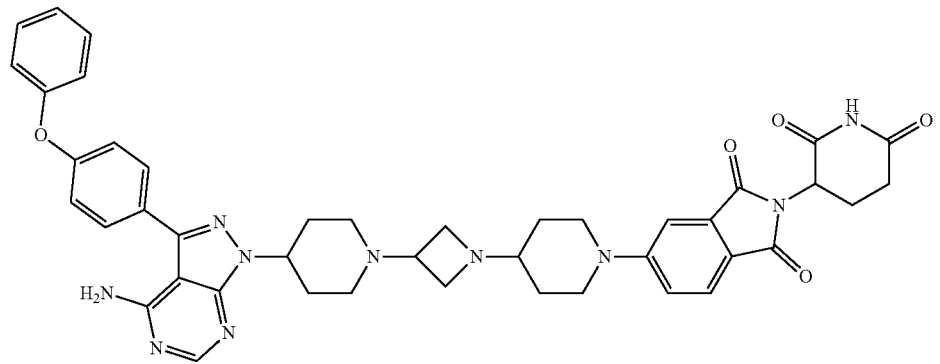 [SMILES: Nc1ncnc2c1c(-c1ccc(Oc3ccccc3)cc1)nn2C1CCN(C2CN(C3CCN(c4ccc5c(c4)C(=O)N(C4CCC(=O)NC4=O)C5=O)CC3)C2)CC1]
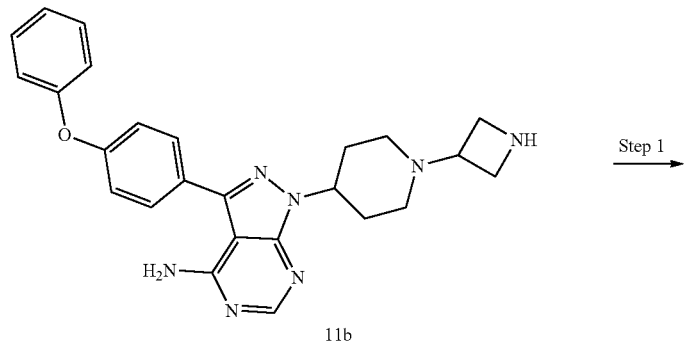
11b
Step 1 →
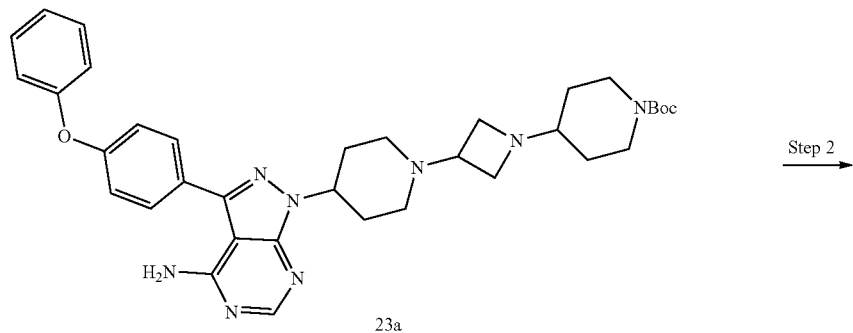
23a
Step 2 →
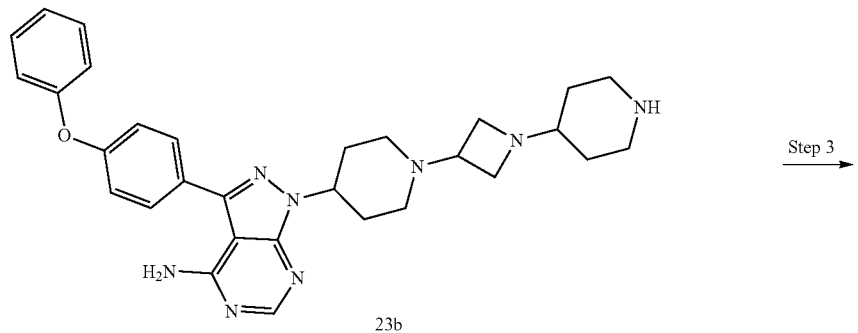
23b
Step 3 →

-continued

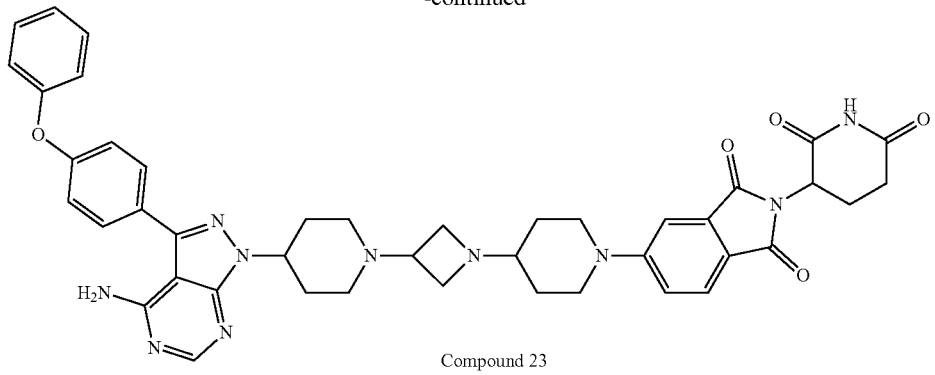

Compound 23

Step 1 tert-butyl
4-[3-[4-[4-amino-3-(4-phenoxyphenyl)pyrazolo[3,4-d]pyrimidin-1-yl]-1-piperidyl]azetidin-1-yl]piperidine-1-carboxylate (23a)

Step 2

3-(4-phenoxyphenyl)-1-[1-[1-(4-piperidyl)azetidin-3-yl]-4-piperidyl]pyrazolo[3,4-d]pyrimidin-4-amine (23b)

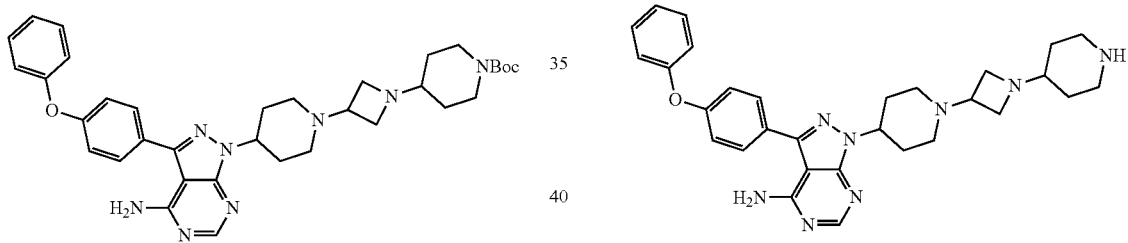

1-[1-(azetidin-3-yl)-4-piperidyl]-3-(4-phenoxyphenyl)pyrazolo[3,4-d]pyrimidin-4-amine (11b) (0.12 g, 0.27 mmol) was dissolved in 5 mL of DCE, and tert-butyl 4-oxopiperidine-1-carboxylate (0.5 g, 3.0 mmol) was added. The mixture was stirred at room temperature for 10 minutes, then sodium triacetoxyborohydride (0.6 g, 3.0 mmol) was added, and the mixture was stirred at room temperature overnight. To the reaction solution was slowly added dropwise 30 mL of saturated sodium bicarbonate solution, and the mixed solution was extracted with 30 mL of dichloromethane. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain tert-butyl 4-[3-[4-[4-amino-3-(4-phenoxyphenyl)pyrazolo[3,4-d]pyrimidin-1-yl]-1-piperidyl]azetidin-1-yl]piperidine-1-carboxylate (23a) (0.15 g, yield: 88%).

LC-MS m/z=625.3 [M+1]$^+$.

Tert-butyl

4-[3-[4-[4-amino-3-(4-phenoxyphenyl)pyrazolo[3,4-d]pyrimidin-1-yl]-1-piperidyl]azetidin-1-yl]piperidine-1-carboxylate (23a) (0.15 g, 0.24 mmol) was dissolved in 5 mL of DCM, and 1.5 mL of trifluoroacetic acid was added, the mixture was stirred at room temperature for 3 h. To the reaction solution was slowly added dropwise saturated sodium bicarbonate solution to adjust the pH to 9-10, and the mixed solution was extracted with 30 mL of dichloromethane. The organic phase was washed with 50 mL of water, dried over anhydrous sodium sulfate, and concentrated under reduced pressure to obtain 3-(4-phenoxyphenyl)-1-[1-[1-(4-piperidyl)azetidin-3-yl]-4-piperidyl]pyrazolo[3,4-d]pyrimidin-4-amine (23b) (0.12 g, yield: 95%).

LCMS m/z=525.3 [M+1]$^+$.

Step 3

5-[4-[3-[4-[4-amino-3-(4-phenoxyphenyl)pyrazolo[3,4-d]pyrimidin-1-yl]-1-piperidyl]azetidin-1-yl]-1-piperidyl]-2-(2,6-dioxo-3-piperidyl)isoindoline-1,3-dione (Compound 23)

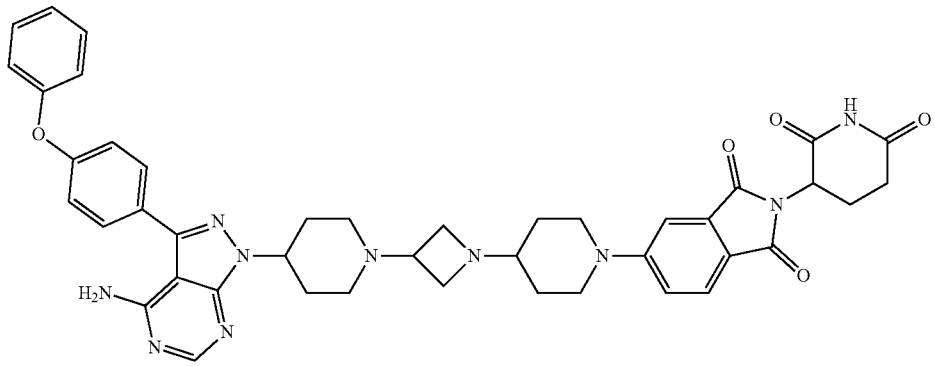

3-(4-phenoxyphenyl)-1-[1-[1-(4-piperidyl)azetidin-3-yl]-4-piperidyl]pyrazolo[3,4-d]pyrimidin-4-amine (23b) (0.12 g, 0.23 mmol) was dissolved in 3 mL of DMSO, and 0.4 mL of DIPEA and 2-(2,6-dioxopiperidin-3-yl)-5-fluoroisoindoline-1,3-dione (see WO 2017197056 for the synthetic method) (90 mg, 0.30 mmol) were added, the mixture was stirred in external bath at 90° C. for 5 h. The reaction solution was cooled to room temperature, and extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain 5-[4-[3-[4-[4-amino-3-(4-phenoxyphenyl)pyrazolo[3,4-d]pyrimidin-1-yl]-1-piperidyl]azetidin-1-yl]-1-piperidyl]-2-(2,6-dioxo-3-piperidyl)isoindoline-1,3-dione (Compound 23) (6 mg, yield: 4%).

$^1$H NMR (400 MHz, CDCl$_3$) δ 8.55 (s, 1H), 8.33 (s, 1H), 7.67 (d, 1H), 7.64-7.58 (m, 2H), 7.41-7.34 (m, 2H), 7.27-7.24 (m, 1H), 7.19-7.10 (m, 3H), 7.09-7.01 (m, 3H), 5.80 (brs, 2H), 4.92 (dd, 1H), 4.86-4.75 (m, 1H), 4.22-4.04 (m, 2H), 3.98-3.88 (m, 2H), 3.54-3.34 (m, 3H), 3.03-2.68 (m, 8H), 2.49-2.33 (m, 3H), 2.28-2.06 (m, 5H), 2.00-1.93 (m, 3H).

LCMS m/z=781.3 [M+1]$^+$.

Example 24

5-[3-[3-[4-[4-amino-3-(4-phenoxyphenyl)pyrazolo[3,4-d]pyrimidin-1-yl]-1-piperidyl]pyrrolidin-1-yl]azetidin-1-yl]-2-(2,6-dioxo-3-piperidyl)isoindoline-1,3-dione (Compound 24)

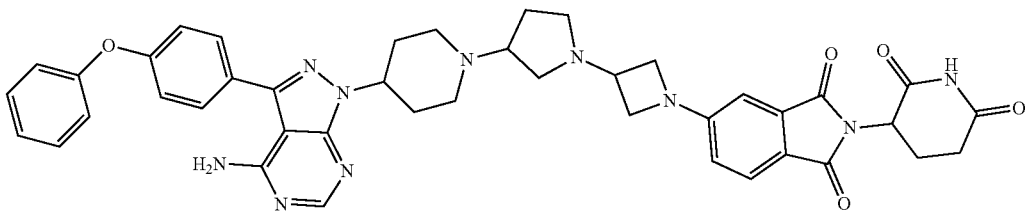

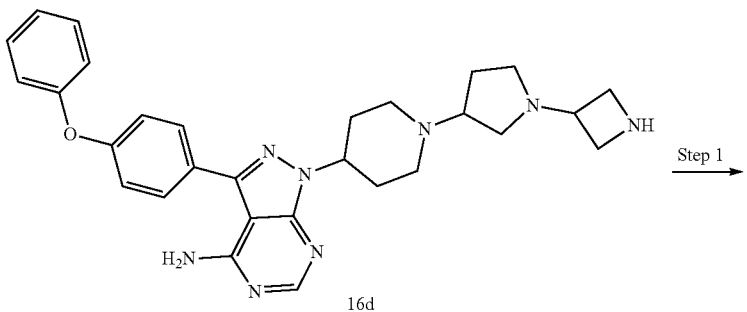

Step 1

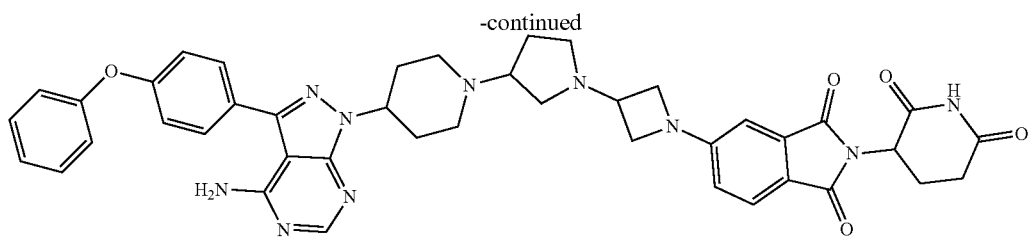

Compound 24

1-[1-[1-(azetidin-3-yl)pyrrolidin-3-yl]-4-piperidyl]-3-(4-phenoxyphenyl)pyrazolo[3,4-d]pyrimidin-4-amine (16d) (0.1 g, 0.20 mmol) was dissolved in 3 mL of DMSO, and 0.2 mL of DIPEA and 2-(2,6-dioxopiperidin-3-yl)-5-fluoroisoindoline-1,3-dione (see WO 2017197056 for the synthetic method) (75 mg, 0.27 mmol) were added, the mixture was stirred in external bath at 90° C. for 5 h. The reaction solution was cooled to room temperature, extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain 5-[3-[3-[4-[4-amino-3-(4-phenoxyphenyl)pyrazolo[3,4-d]pyrimidin-1-yl]-1-piperidyl]pyrrolidin-1-yl]azetidin-1-yl]-2-(2,6-dioxo-3-piperidyl)isoindoline-1,3-dione (Compound 24) (30 mg, yield: 20%).

$^1$H NMR (400 MHz, CDCl$_3$) δ 8.75 (s, 1H), 8.36 (s, 1H), 7.67-7.62 (m, 3H), 7.43-7.36 (m, 2H), 7.21-7.12 (m, 3H), 7.11-7.07 (m, 2H), 6.79 (d, 1H), 6.52 (dd, 1H), 5.74 (brs, 2H), 4.93 (dd, 1H), 4.88-4.76 (m, 1H), 4.14-4.06 (m, 2H), 3.97-3.89 (m, 2H), 3.62-3.53 (m, 1H), 3.28-3.16 (m, 1H), 3.15-3.00 (m, 2H), 2.97-2.70 (m, 6H), 2.67-2.58 (m, 1H), 2.57-2.39 (m, 4H), 2.35-2.23 (m, 2H), 2.16-2.09 (m, 3H).

LCMS m/z=767.3 [M+1]$^+$.

Example 25

3-[5-[3-[4-[4-[4-amino-3-(4-phenoxyphenyl)pyrazolo[3,4-d]pyrimidin-1-yl]-1-piperidyl]-1-piperidyl]azetidin-1-yl]-1-oxo-isoindolin-2-yl]piperidine-2,6-dione (Compound 25)

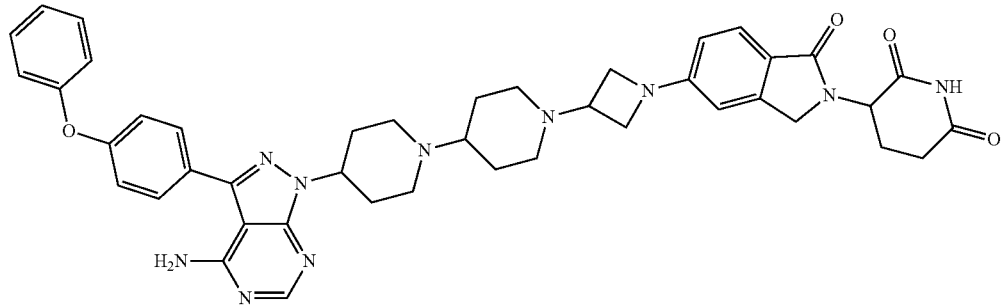

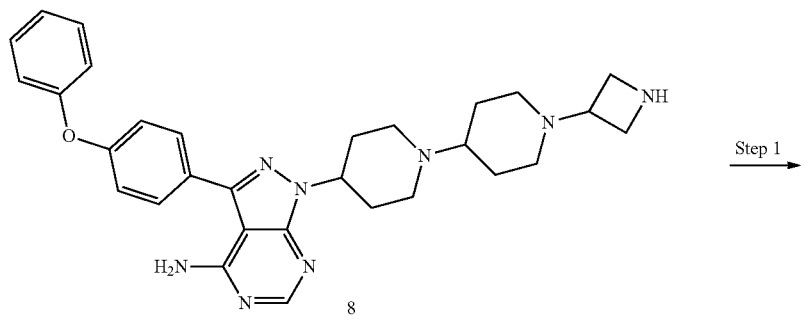

Step 1

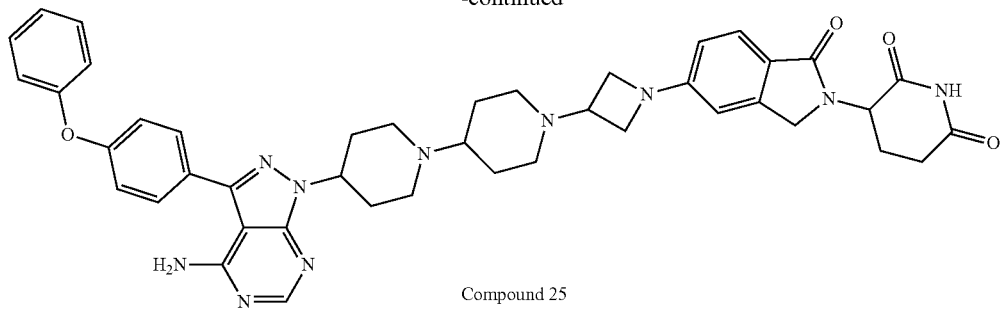

Compound 25

1-(1'-(azetidin-3-yl)-[1,4'-bipiperidin]-4-yl)-3-(4-phenoxyphenyl)-1H-pyrazolo[3,4-d]pyrimidin-4-amine (8b) (0.635 g, 1.21 mmol) was dissolved in 12 mL of 1,4-dioxane, and 3-(5-bromo-1-oxo-isoindolin-2-yl) piperidine-2,6-dione (see *J. Med. Chem.* 2018, 61, 492-503 for the synthetic method) (0.587 g, 1.82 mmol) and cesium carbonate (1.17 g, 3.63 mmol) were successively added. Nitrogen replacement was carried out three times, and methanesulfonic acid(2-dicyclohexylphosphino-2',6'-diisopropoxy-1,1'-biphenyl)(2-amino-1,1'-biphenyl-2-yl)palladium (II) (Ru-Phos-Pd-G3) (0.300 g, 0.363 mmol) was added. Upon completion of the addition, nitrogen replacement was carried out three times, and the reaction was stirred in a sealed tube at 100° C. for 2 h. The reaction solution was cooled to room temperature, and added 20 mL of dichloromethane and 10 mL of water. The liquid separation was conducted, the aqueous layer was further extracted with 20 mL of dichloromethane, and the organic layers were combined, dried over anhydrous sodium sulfate, and concentrated under reduced pressure, then the crude product was separated and purified by silica gel column chromatography (dichloromethane/methanol (v/v)=100:0-19:1), to obtain 3-[5-[3-[4-[4-[4-amino-3-(4-phenoxyphenyl)pyrazolo[3,4-d]pyrimidin-1-yl]-1-piperidyl]-1-piperidyl]azetidin-1-yl]-1-oxo-isoindolin-2-yl]piperidine-2,6-dione (Compound 25) (0.045 g, yield 5%).

¹H NMR (400 MHz, DMSO-d₆) δ 10.92 (s, 1H), 8.24 (s, 1H), 7.69-7.63 (m, 2H), 7.49 (d, 1H), 7.47-7.40 (m, 2H), 7.22-7.08 (m, 5H), 6.54-6.46 (m, 2H), 5.03 (dd, 1H), 4.80-4.62 (m, 1H), 4.25 (dd, 2H), 4.05-3.95 (m, 2H), 3.74-3.63 (m, 2H), 3.36-3.28 (m, 1H), 3.20-2.97 (m, 2H), 2.96-2.83 (m, 3H), 2.64-2.09 (m, 7H), 2.05-1.74 (m, 7H), 1.65-1.43 (m, 2H).

LCMS m/z=767.4 [M+1]⁺.

Example 26

3-[5-[3-[3-[4-[4-amino-3-(4-phenoxyphenyl)pyrazolo[3,4-d]pyrimidin-1-yl]-1-piperidyl]azetidin-1-yl] azetidin-1-yl]-1-oxo-isoindolin-2-yl]piperidine-2,6-dione (Compound 26)

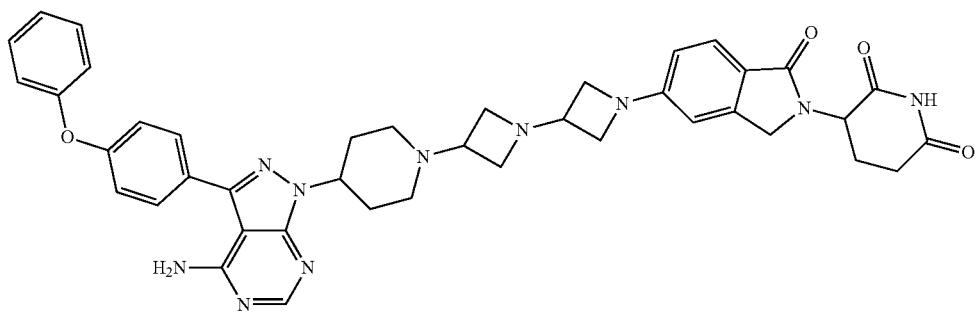

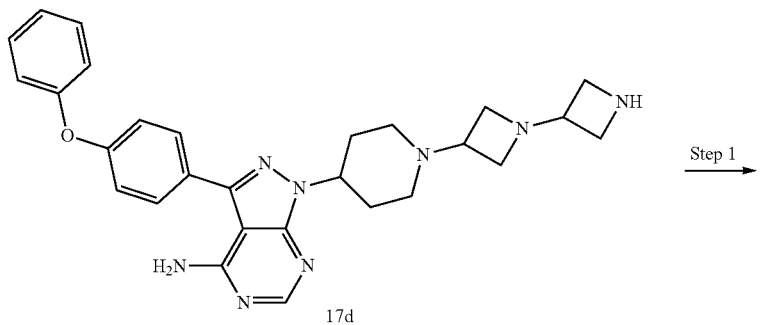

Step 1

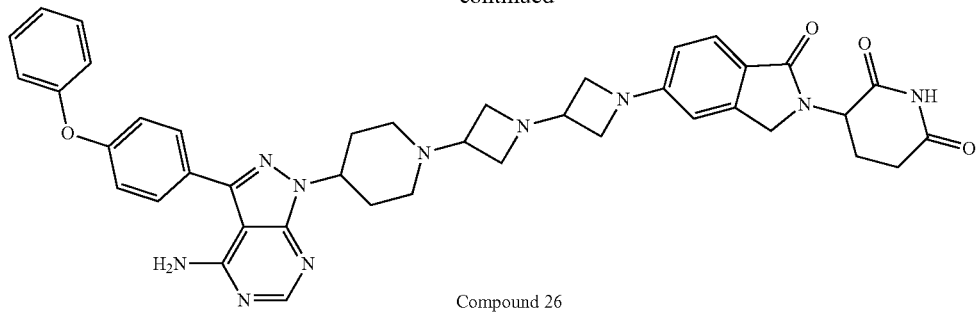

Compound 26

1-[1-[1-(azetidin-3-yl)azetidin-3-yl]-4-piperidyl]-3-(4-phenoxyphenyl)pyrazolo[3,4-d]pyrimidin-4-amine (17d) (0.600 g, 1.21 mmol) was dissolved in 12 mL of 1,4-dioxane, and 3-(5-bromo-1-oxo-isoindolin-2-yl) piperidine-2,6-dione (see J. Med. Chem. 2018, 61, 492-503 for the synthetic method) (0.586 g, 1.81 mmol) and cesium carbonate (1.17 g, 3.63 mmol) were successively added. Nitrogen replacement was carried out three times, and methanesulfonic acid(2-dicyclohexylphosphino-2',6'-diisopropoxy-1,1'-biphenyl)(2-amino-1,1'-biphenyl-2-yl)palladium (II) (RuPhos-Pd-G3) (0.300 g, 0.363 mmol) was added. Upon completion of the addition, nitrogen replacement was carried out three times, and the mixture was stirred in a sealed tube at 100° C. for 2 h. The reaction solution was cooled to room temperature, and added 20 mL of dichloromethane and 10 mL of water. The liquid separation was conducted, the aqueous layer was further extracted with 20 mL of dichloromethane, and the organic layers were combined, dried over anhydrous sodium sulfate, and concentrated under reduced pressure, then the crude product was separated and purified by silica gel column chromatography (dichloromethane/methanol (v/v)= 100:0-19:1), to obtain 3-[5-[3-[3-[4-[4-amino-3-(4-phenoxyphenyl)pyrazolo[3,4-d]pyrimidin-1-yl]-1-piperidyl]azetidin-1-yl]azetidin-1-yl]-1-oxo-isoindolin-2-yl]piperidine-2,6-dione (Compound 26) (0.053 g, yield: 6%).

$^1$H NMR (400 MHz, DMSO-d$_6$) δ 10.91 (s, 1H), 8.23 (s, 1H), 7.70-7.63 (m, 2H), 7.52-7.40 (m, 3H), 7.23-7.08 (m, 5H), 6.55-6.44 (m, 2H), 5.03 (dd, 1H), 4.72-4.61 (m, 1H), 4.24 (dd, 2H), 3.99-3.87 (m, 2H), 3.74-3.58 (m, 3H), 3.48-3.36 (m, 2H), 3.04-2.78 (m, 6H), 2.64-2.52 (m, 1H), 2.41-2.28 (m, 1H), 2.25-2.14 (m, 2H), 2.07-1.83 (m, 5H).

LCMS m/z=739.3 [M+1]$^+$.

Example 27

4-[3-[3-[4-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 27)

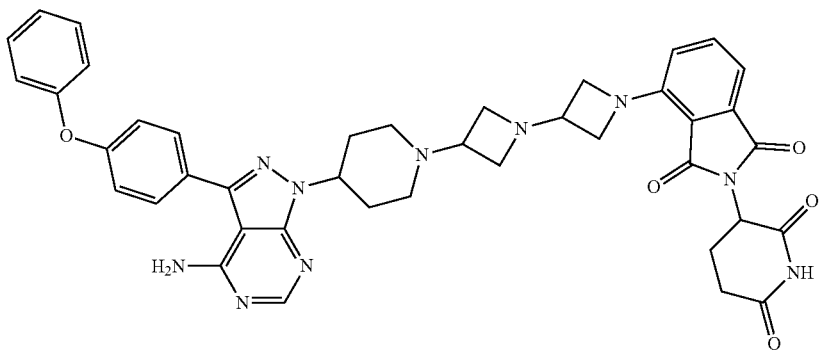

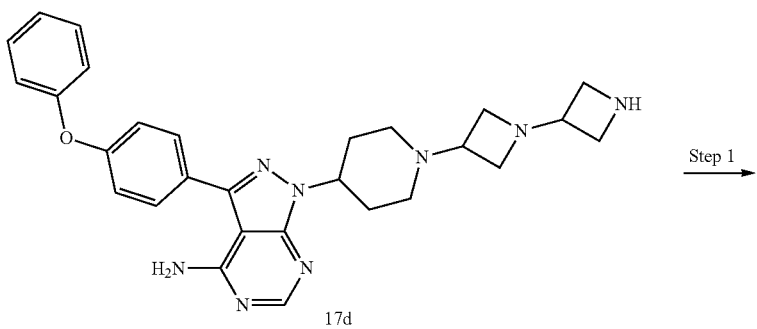

17d

Step 1

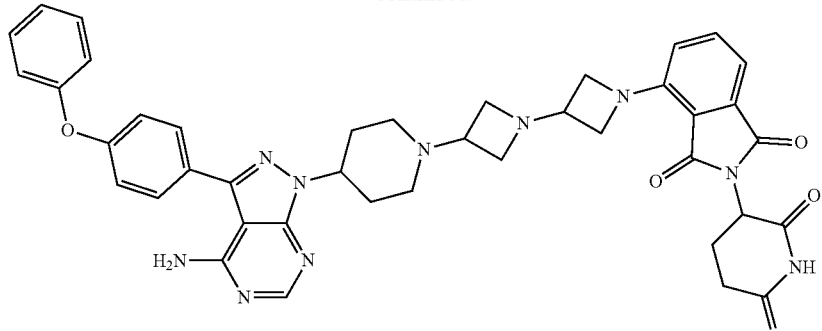

Compound 27

1-[1-[1-(azetidin-3-yl)azetidin-3-yl]-4-piperidyl]-3-(4-phenoxyphenyl)pyrazolo[3,4-d]pyrimidin-4-amine (17d) (0.100 g, 0.201 mmol) was dissolved in 2 mL of dimethyl sulfoxide, and 2-(2,6-dioxopiperidin-3-yl)-4-fluoroisoindoline-1,3-dione (see WO 2017197056 for the synthetic method) (0.0667 g, 0.242 mmol) and diisopropylethylamine (0.130 g, 1.01 mmol) were successively added. Upon completion of the addition, the reaction was carried out at 90° C. for 2 h. The reaction solution was cooled to room temperature, to which 10 mL of water was slowly added dropwise, and filtered. The filter cake was dissolved with 20 mL of dichloromethane, then washed with 5 mL of saturated sodium chloride solution. The liquid separation was conducted, dried over anhydrous sodium sulfate, and concentrated under reduced pressure, then the crude product was separated and purified by silica gel column chromatography (dichloromethane/methanol (v/v)=100:0-19:1), to obtain 4-[3-[3-[4-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 27) (0.063 g, yield: 42%).

$^1$H NMR (400 MHz, DMSO-d$_6$) δ 11.05 (s, 1H), 8.23 (s, 1H), 7.69-7.63 (m, 2H), 7.56 (dd, 1H), 7.47-7.40 (m, 2H), 7.23-7.08 (m, 6H), 6.79 (d, 1H), 5.05 (dd, 1H), 4.72-4.62 (m, 1H), 4.25-4.14 (m, 2H), 4.00-3.90 (m, 2H), 3.57-3.48 (m, 1H), 3.47-3.39 (m, 2H), 3.04-2.78 (m, 6H), 2.63-2.45 (m, 2H), 2.27-2.13 (m, 2H), 2.07-1.83 (m, 5H).

LCMS m/z=753.3 [M+1]$^+$.

Example 28

5-[3-[3-[(3R)-3-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 28)

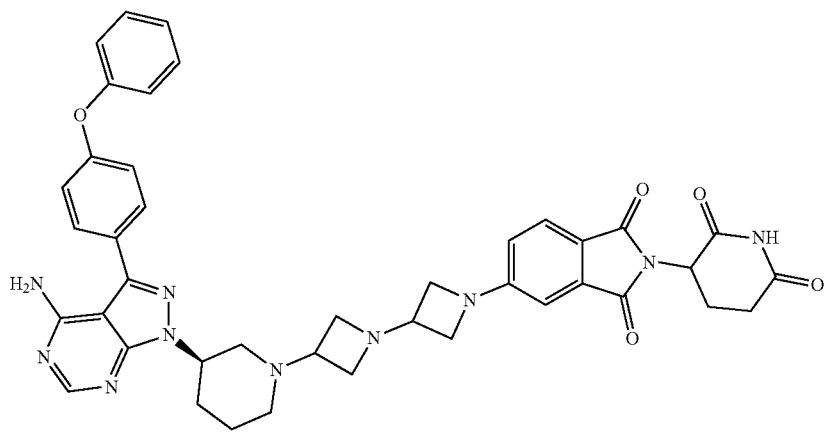

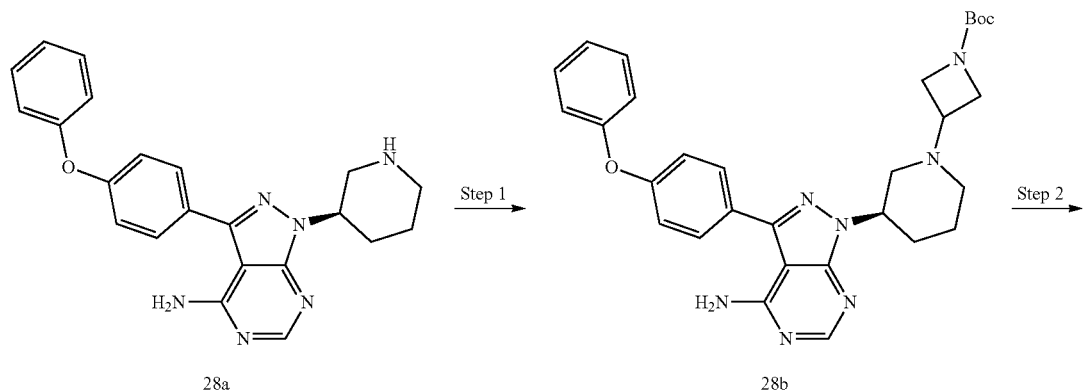
28a → 28b
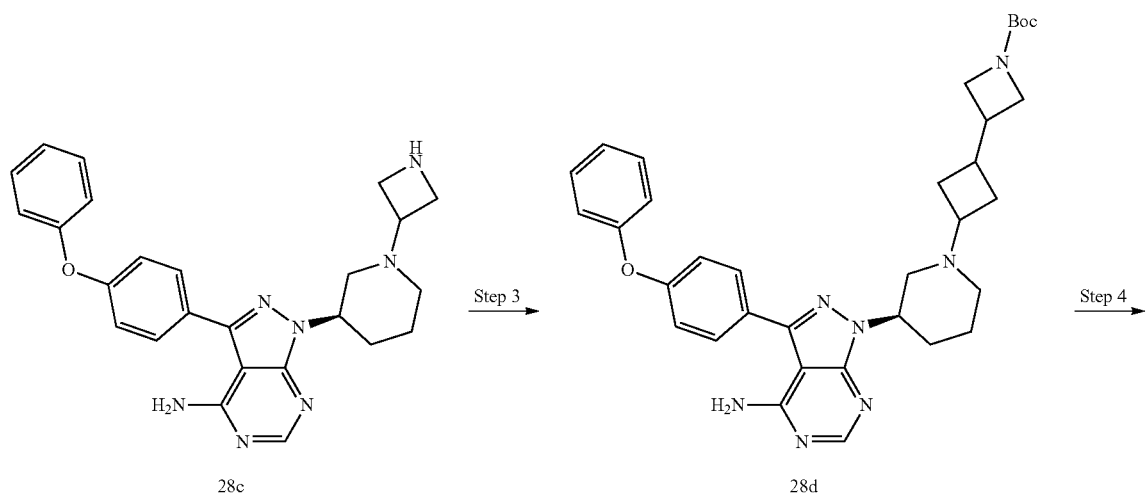
28c → 28d
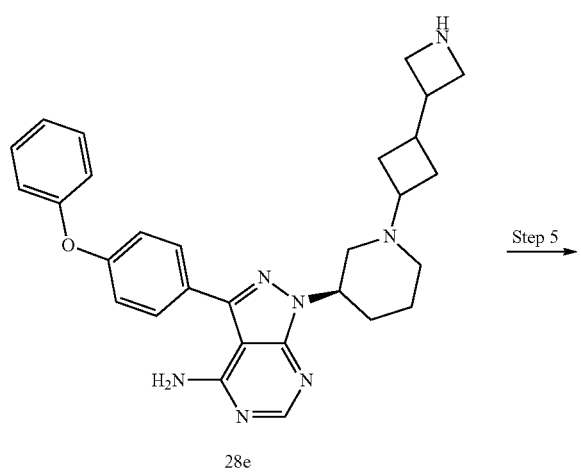
28e

-continued

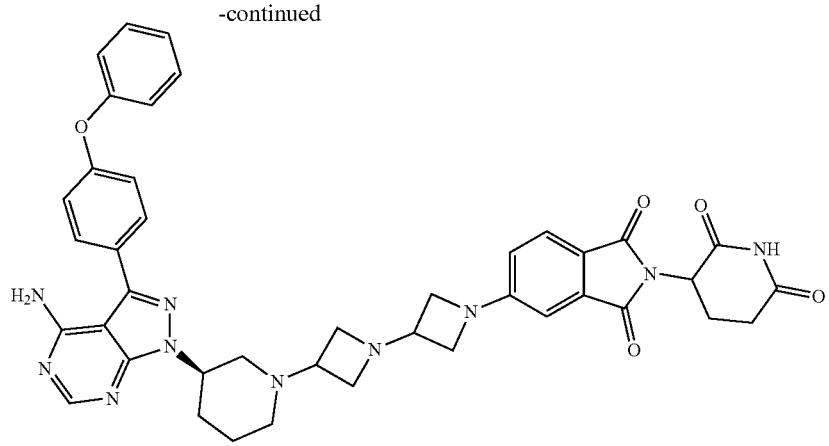

Compound 28

Step 1 tert-butyl 3-[(3R)-3-[4-amino-3-(4-phenoxyphenyl)pyrazolo[3,4-d]pyrimidin-4-yl]-1-piperidyl]azetidine-1-carboxylate (28b)

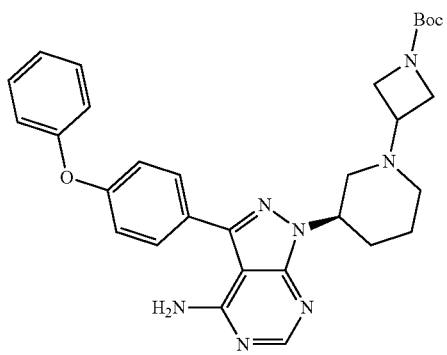 [SMILES: CC(C)(C)OC(=O)N1CC(N2CCC[C@@H](n3nc(-c4ccc(Oc5ccccc5)cc4)c4c(N)ncnc43)C2)C1]

(R)-3-(4-phenoxyphenyl)-1-(piperidin-3-yl)-1H-pyrazolo[3,4-d]pyrimidin-4-a mine (28a) (1.00 g, 2.59 mmol) was dissolved in 10 mL of chloroform, and tert-butyl 3-oxoazetidine-1-carboxylate (0.665 g, 3.88 mmol) and glacial acetic acid (0.311 g, 5.18 mmol) were successively added. Upon completion of the addition, the reaction was carried out at 70° C. for 3 h, and cooled to room temperature, then sodium triacetoxyborohydride (1.10 g, 5.18 mmol) was added. Upon completion of the addition, the reaction was carried out at room temperature for 2 h. Upon completion of the reaction, the pH was adjusted to 9-10 by adding dropwise saturated sodium bicarbonate solution. The reaction solution was concentrated under reduced pressure, then the crude product was separated and purified by silica gel column chromatography (dichloromethane/methanol (v/v)=100:0-19:1), to obtain tert-butyl 3-[(3R)-3-[4-amino-3-(4-phenoxyphenyl)pyrazolo[3,4-d]pyrimidin-1-yl]-1-piperidyl]azetidine-1-carboxylate (28b) (0.600 g, yield: 43%).

LCMS m/z=542.2 [M+1]$^+$.

Step 2

1-[(3R)-1-(azetidin-3-yl)-3-piperidyl]-3-(4-phenoxyphenyl)pyrazolo[3,4-d]pyrimidin-4-amine (28c)

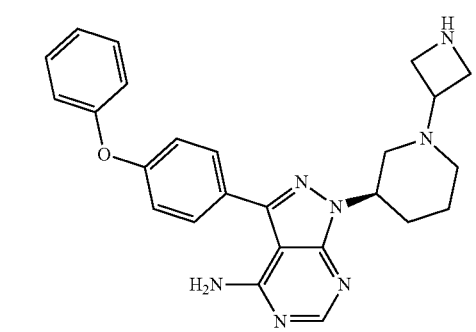 [SMILES: Nc1ncnc2c1c(-c1ccc(Oc3ccccc3)cc1)nn2[C@@H]1CCCN(C2CNC2)C1]

Tert-butyl 3-[(3R)-3-[4-amino-3-(4-phenoxyphenyl)pyrazolo[3,4-d]pyrimidin-1-yl]-1-piperidyl]azetidine-1-carboxylate (28b) (0.600 g, 1.11 mmol) was dissolved in 2 mL of dichloromethane, and 10 mL of 4N ethyl acetate hydrochloride solution was added, the mixture was stirred at room temperature for 2 h. The reaction solution was concentrated under reduced pressure, then to the residue was added 20 mL of dichloromethane, and the pH was adjusted to 9-10 with saturated sodium bicarbonate solution. The liquid separation was conducted, dried over anhydrous sodium sulfate, and concentrated under reduced pressure to obtain 1-[(3R)-1-(azetidin-3-yl)-3-piperidyl]-3-(4-phenoxyphenyl)pyrazolo[3,4-d]pyrimidin-4-amine (28c) (0.450 g, yield: 92%).

LCMS m/z=442.2 [M+1]$^+$.

Step 3 tert-butyl
3-[3-[(3R)-3-[4-amino-3-(4-phenoxyphenyl)pyrazolo[3,4-d]pyrimidin-1-yl]-1-piperidyl]azetidin-1-yl]azetidine-1-carboxylate (28d)

Step 4

1-[(3R)-1-[1-(azetidin-3-yl)azetidin-3-yl]-3-piperidyl]-3-(4-phenoxyphenyl)pyrazolo[3,4-d]pyrimidin-4-amine (28e)

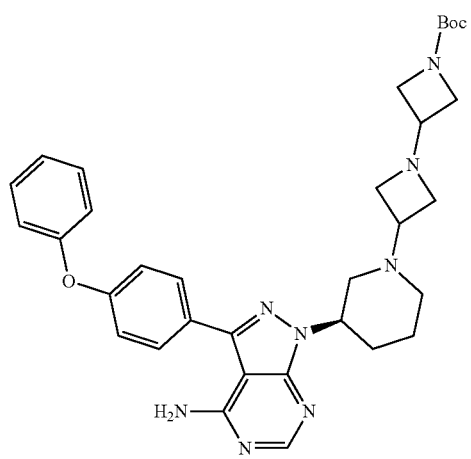 [SMILES: CC(C)(C)OC(=O)N1CC(N2CC(N3CCC[C@@H](n4nc(-c5ccc(Oc6ccccc6)cc5)c5c(N)ncnc54)C3)C2)C1]

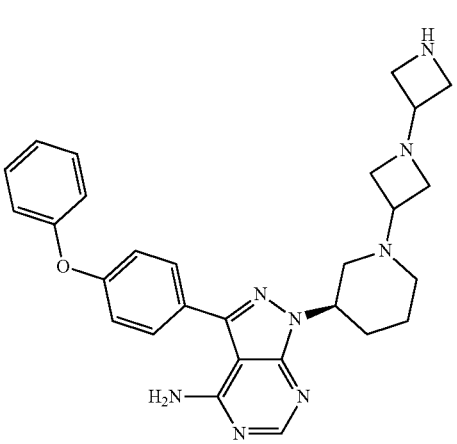 [SMILES: Nc1ncnc2c1c(-c1ccc(Oc3ccccc3)cc1)nn2[C@@H]1CCCN(C2CN(C3CNC3)C2)C1]

1-[(3R)-1-(azetidin-3-yl)-3-piperidyl]-3-(4-phenoxyphenyl)pyrazolo[3,4-d]pyrimidin-4-amine (28c) (0.300 g, 0.680 mmol) was dissolved in 10 mL of chloroform, tert-butyl 3-oxoazetidine-1-carboxylate (0.174 g, 1.02 mmol) and glacial acetic acid (0.0816 g, 1.36 mmol) were added. Upon completion of the addition, the reaction was carried at 70° C. for 3 h, and cooled to room temperature, then sodium triacetoxyborohydride (0.288 g, 1.36 mmol) was added. Upon completion of the addition, the reaction was carried out at room temperature for 2 h. Upon completion of the reaction, the pH was adjusted to 9-10 by adding dropwise saturated sodium bicarbonate solution. The reaction solution was concentrated under reduced pressure, then the crude product was separated and purified by silica gel column chromatography (dichloromethane/methanol (v/v)=100:0-19:1), to obtain tert-butyl 3-[3-[(3R)-3-[4-amino-3-(4-phenoxyphenyl)pyrazolo[3,4-d]pyrimidin-1-yl]-1-piperidyl]azetidin-1-yl]azetidine-1-carboxylate (28d) (0.090 g, yield: 22%).

LCMS m/z=597.3 [M+1]$^+$.

Tert-butyl
3-[3-[(3R)-3-[4-amino-3-(4-phenoxyphenyl)pyrazolo[3,4-d]pyrimidin-1-yl]-1-piperidyl]azetidin-1-yl]azetidine-1-carboxylate (28d) (0.090 g, 0.15 mmol) was dissolved in 2 mL of dichloromethane, and 5 mL of 4N ethyl acetate hydrochloride solution was added, the mixture was stirred at room temperature for 2 h. The reaction solution was concentrated under reduced pressure, then to the residue was added 20 mL of dichloromethane, and the pH was adjusted to 9-10 with saturated sodium bicarbonate solution. The liquid separation was conducted, dried over anhydrous sodium sulfate, and concentrated under reduced pressure to obtain 1-[(3R)-1-[1-(azetidin-3-yl)azetidin-3-yl]-3-piperidyl]-3-(4-phenoxyphenyl)pyrazolo[3,4-d]pyrimidin-4-amine (28e) (0.075 g).

LCMS m/z=497.3 [M+1]$^+$.

Step 5

5-[3-[3-[(3R)-3-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 28)

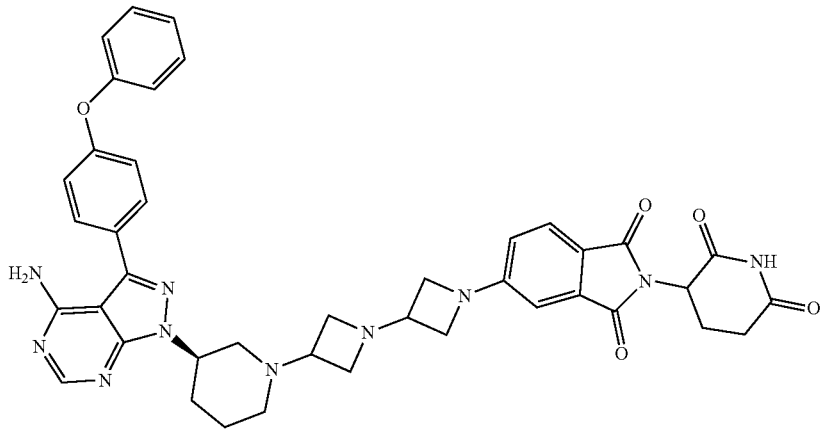 [SMILES: Nc1ncnc2c1c(-c1ccc(Oc3ccccc3)cc1)nn2[C@@H]1CCCN(C2CN(C3CN(c4ccc5c(c4)C(=O)N(C4CCC(=O)NC4=O)C5=O)C3)C2)C1]

1-[(3R)-1-[1-(azetidin-3-yl)azetidin-3-yl]-3-piperidyl]-3-(4-phenoxyphenyl)pyrazolo[3,4-d]pyrimidin-4-amine (28e) (0.075 g, 0.201 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.050 g, 0.066 mmol) and diisopropylethylamine (0.098 g, 0.76 mmol) were added. Upon completion of the addition, the reaction was carried out at 90° C. for 2 h. The reaction solution was cooled to room temperature, to which 10 mL of water was slowly added dropwise, and filtered. The filter cake was dissolved with 20 mL of dichloromethane, then washed with 5 mL of saturated sodium chloride solution. The liquid separation was conducted, dried over anhydrous sodium sulfate, and concentrated under reduced pressure, then the crude product was separated and purified by silica gel column chromatography (dichloromethane/methanol (v/v)=100:0-9:1), to obtain 5-[3-[3-[(3R)-3-[4-amino-3-(4-phenoxyphenyl)pyrazolo[3,4-d]pyrimidin-1-yl]-1-piperidyl]azetidin-1-yl]azetidin-1-yl]-2-(2,6-dioxo-3-piperidyl)isoindoline-1,3-dione (Compound 28) (0.050 g, yield: 44%).

$^1$H NMR (400 MHz, DMSO-$d_6$) δ 11.04 (s, 1H), 8.24 (s, 1H), 7.68-7.59 (m, 3H), 7.47-7.39 (m, 2H), 7.22-7.09 (m, 5H), 6.77 (d, 1H), 6.64 (dd, 1H), 5.04 (dd, 1H), 4.83-4.72 (m, 1H), 4.06-3.98 (m, 2H), 3.82-3.73 (m, 2H), 3.66-3.56 (m, 1H), 3.45-3.32 (m, 2H), 3.06-2.72 (m, 6H), 2.63-2.45 (m, 2H), 2.37-2.27 (m, 1H), 2.07-1.95 (m, 3H), 1.90-1.78 (m, 2H), 1.72-1.58 (m, 1H).

LCMS m/z=753.4 [M+1]$^+$.

Example 29

5-(3-(3-(4-amino-3-(4-phenoxyphenyl)-1H-pyrazolo[3,4-d]pyrimidin-1-yl)pyrrolidin-1-yl)-[1,3'-biazetidin]-1'-yl)-2-(2,6-dioxopiperidin-3-yl)isoindoline-1,3-dione trifluoroacetate (Compound 29)

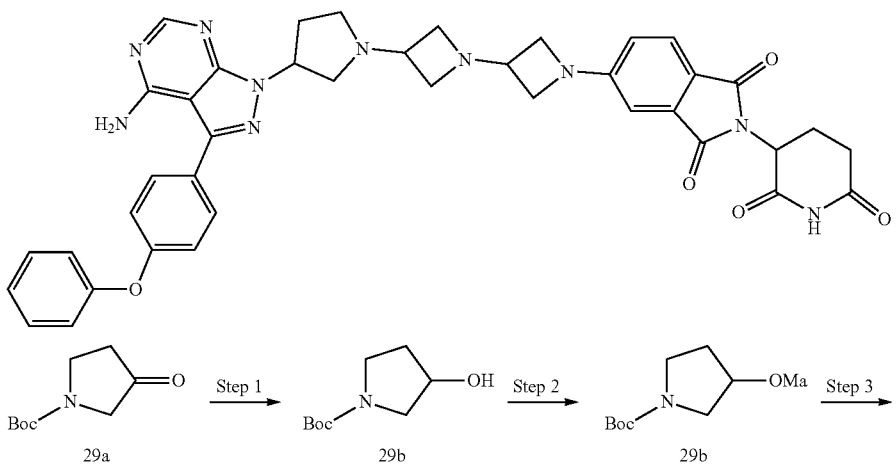

-continued
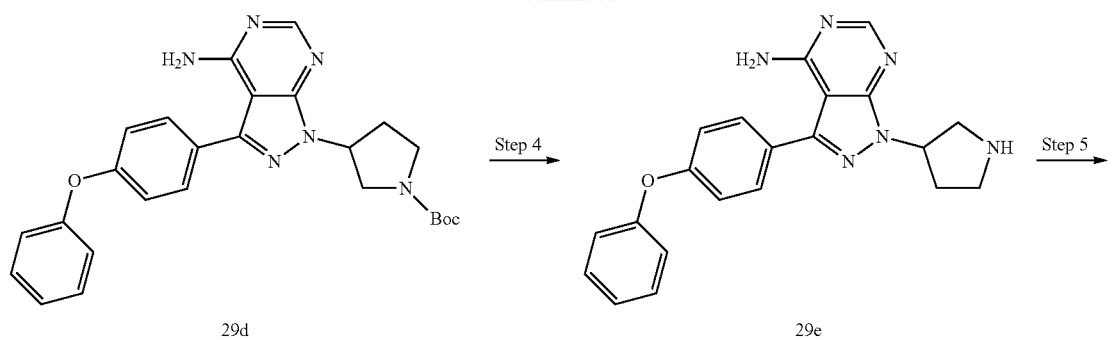
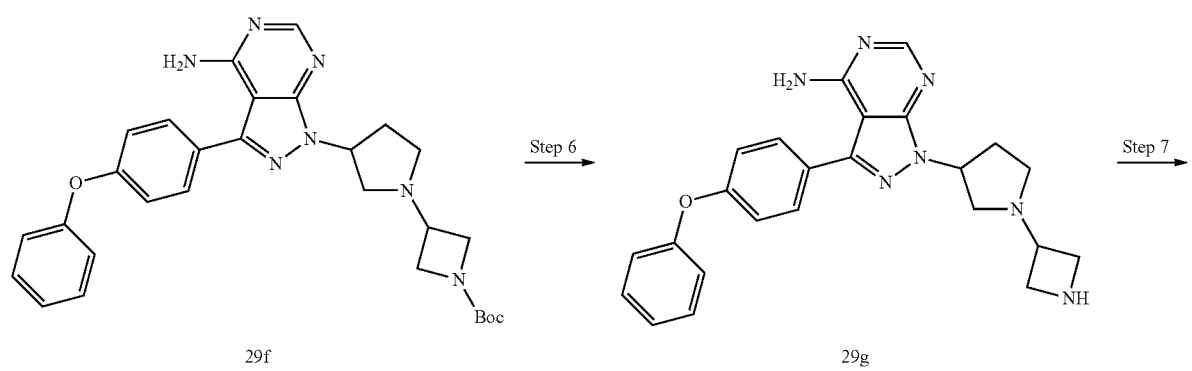
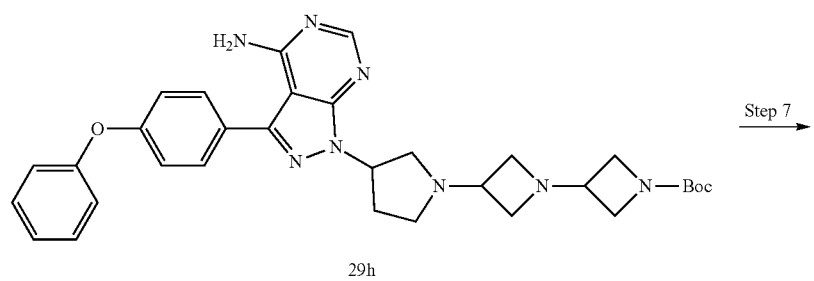
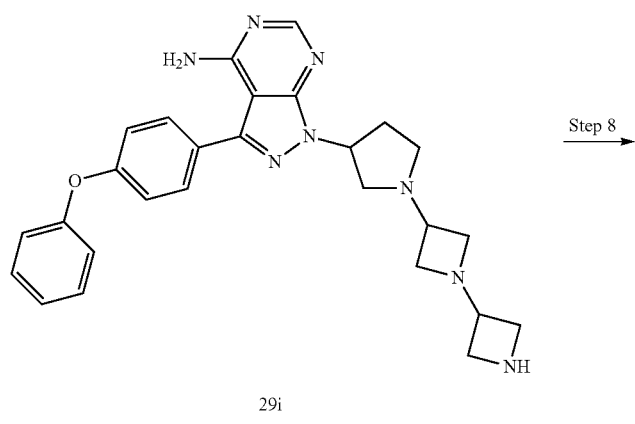

-continued

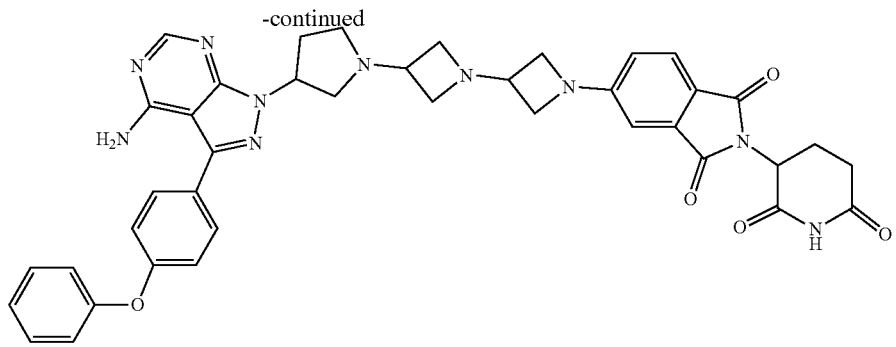

Compound 29

Step 1 tert-butyl 3-hydroxypyrrolidine-1-carboxylate (29b)

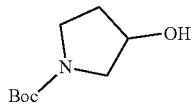

Tert-butyl 3-oxo pyrrolidine-1-carboxylate (29a) (5.56 g, 30.0 mmol) was dissolved in 80 mL of anhydrous methanol, and sodium borohydride (2.28 g, 60.0 mmol) was slowly added in portions. Upon completion of the addition, the mixture was stirred at room temperature for 30 minutes. Upon completion of the reaction, the reaction was quenched by adding 150 mL of saturated sodium bicarbonate solution, and extracted with 200 mL of DCM. The organic phase was washed with 100 mL of water, dried over anhydrous sodium sulfate, and concentrated under reduced pressure, then the crude product was separated and purified by silica gel column chromatography (petroleum ether/ethyl acetate (v/v) =2:1), to obtain tert-butyl 3-hydroxypyrrolidine-1-carboxylate (29b) (4.7 g, yield: 84%).

LC-MS m/z=188.1 [M+1]$^+$.

Step 2 tert-butyl 3-((methylsulfonyl)oxy)pyrrolidine-1-carboxylate (29c)

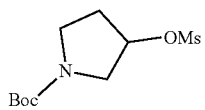

Tert-butyl 3-hydroxypyrrolidine-1-carboxylate (29b) (1.0 g, 5.34 mmol) was dissolved in 30 mL of dichloromethane, and DIPEA (2.1 g, 16.25 mmol) was added, then MsCl (0.74 g, 6.41 mmol) was slowly added dropwise at room temperature. Upon completion of the addition, the mixture was stirred at room temperature for 2 h. To the reaction solution was added 40 mL of water, and the resulted solution was extracted with 100 mL of DCM. The organic phase was washed with 100 mL of water, dried over anhydrous sodium sulfate, and concentrated under reduced pressure, then the crude product was separated and purified by silica gel column chromatography (petroleum ether/ethyl acetate (v/v) =5:1), to obtain tert-butyl 3-((methylsulfonyl)oxy)pyrrolidine-1-carboxylate (29c) (1.4 g, yield: 98%).

LC-MS m/z=266.2 [M+1]$^+$.

Step 3 tert-butyl 3-(4-amino-3-(4-phenoxyphenyl)-1H-pyrazolo[3,4-d]pyrimidin-1-yl) pyrrolidine-1-carboxylate (29d)

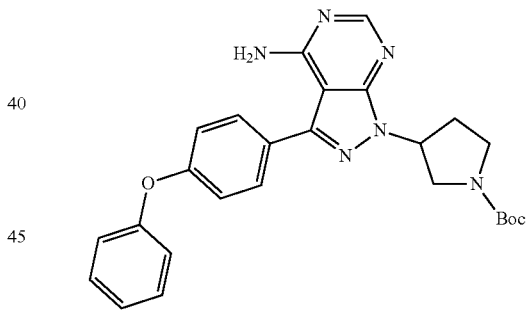

Tert-butyl 3-((methylsulfonyl)oxy)pyrrolidine-1-carboxylate (29c) (1.0 g, 3.77 mmol) and 3-(4-phenoxyphenyl)-1H-pyrazolo[3,4-d]pyrimidin-4-amine (0.75 g, 2.48 mmol) was dissolved in 40 mL of DMF, and potassium carbonate (1.24 g, 8.99 mmol) was added, the reaction was stirred at 80° C. for 4 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain tert-butyl 3-(4-amino-3-(4-phenoxyphenyl)-1H-pyrazolo[3,4-d]pyrimidin-1-yl)pyrrolidine-1-carboxylate (29d) (0.91 g, yield: 78%).

LCMS m/z=473.4 [M+1]$^+$.

Step 4

3-(4-phenoxyphenyl)-1-(pyrrolidin-3-yl)-1H-pyrazolo[3,4-d]pyrimidin-4-amine trifluoroacetate (29e)

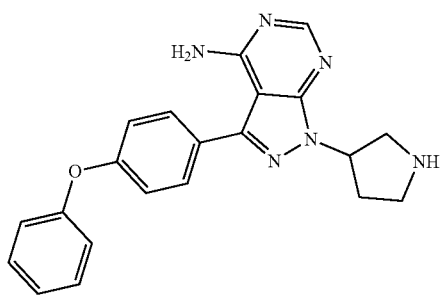 [SMILES: Nc1ncnc2c1c(-c1ccc(Oc3ccccc3)cc1)nn2C1CCNC1]

Tert-butyl 3-(4-amino-3-(4-phenoxyphenyl)-1H-pyrazolo[3,4-d]pyrimidin-1-yl)pyrrolidine-1-carboxylate (29d) (910 mg, 1.87 mmol) was dissolved in 20 mL of DCM, and 8 mL of trifluoroacetic acid was added, the mixture was stirred at room temperature for 4 h. The reaction system was directly concentrated under reduced pressure, to obtain 3-(4-phenoxyphenyl)-1-(pyrrolidin-3-yl)-1H-pyrazolo[3,4-d]pyrimidin-4-amine trifluoroacetate (29e) (1.1 g).

LCMS m/z=373.3 [M+1]$^+$.

Step 5 tert-butyl 3-(3-(4-amino-3-(4-phenoxyphenyl)-1H-pyrazolo[3,4-d]pyrimidin-1-yl)pyrrolidin-1-yl)azetidine-1-carboxylate (29f)

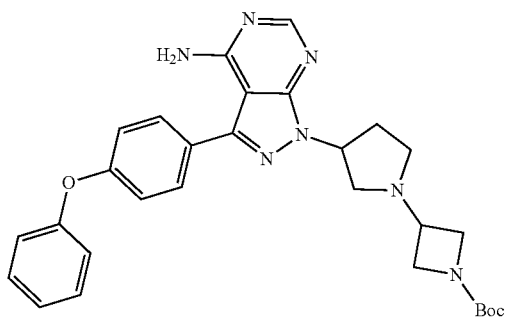 [SMILES: CC(C)(C)OC(=O)N1CC(N2CCC(n3nc(-c4ccc(Oc5ccccc5)cc4)c4c(N)ncnc43)C2)C1]

3-(4-phenoxyphenyl)-1-(pyrrolidin-3-yl)-1H-pyrazolo[3,4-d]pyrimidin-4-amine trifluoroacetate (29e) (420 mg) was dissolved in 15 mL of DCE and 2 mL of DMSO, and Boc-azetidinone (253 mg, 1.48 mmol) was added, the mixture was stirred at room temperature for 10 minutes, then sodium triacetoxyborohydride (628 mg, 2.96 mmol) was added, and the mixture was stirred at room temperature overnight. To the reaction system was slowly added 30 mL of saturated sodium bicarbonate solution, and the resulted solution was extracted with 100 mL of DCM. The organic phase was washed with 100 mL of water, dried over anhydrous sodium sulfate, and concentrated under reduced pressure, then the crude product was separated and purified by silica gel column chromatography (dichloromethane/methanol (v/v)=20:1), to obtain tert-butyl 3-(3-(4-amino-3-(4-phenoxyphenyl)-1H-pyrazolo[3,4-d]pyrimidin-1-yl)pyrrolidin-1-yl)azetidine-1-carboxylate (29f) (320 mg).

LCMS m/z=528.5 [M+1]$^+$.

Step 6

1-(1-(azetidin-3-yl)pyrrolidin-3-yl)-3-(4-phenoxyphenyl)-1H-pyrazolo[3,4-d]pyrimidin-4-amine Trifluoroacetate (29g)

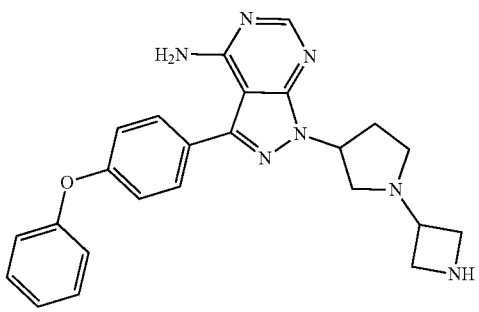 [SMILES: Nc1ncnc2c1c(-c1ccc(Oc3ccccc3)cc1)nn2C1CCN(C2CNC2)C1]

Tert-butyl 3-(3-(4-amino-3-(4-phenoxyphenyl)-1H-pyrazolo[3,4-d]pyrimidin-1-yl)pyrrolidin-1-yl)azetidine-1-carboxylate (29f) (320 mg, 0.61 mmol) was dissolved in 20 mL of DCM, and 5 mL of trifluoroacetic acid was added, the mixture was stirred at room temperature for 4 h. The reaction system was directly concentrated under reduced pressure, to obtain 1-(1-(azetidin-3-yl)pyrrolidin-3-yl)-3-(4-phenoxyphenyl)-1H-pyrazolo[3,4-d]pyrimidin-4-amine Trifluoroacetate (29g) (380 mg).

LCMS m/z=428.4 [M+1]$^+$.

Step 7 tert-butyl 3-(3-(4-amino-3-(4-phenoxyphenyl)-1H-pyrazolo[3,4-d]pyrimidin-1-yl)pyrrolidin-1-yl)-[1,3'-biazetidine]-1'-carboxylate (29h)

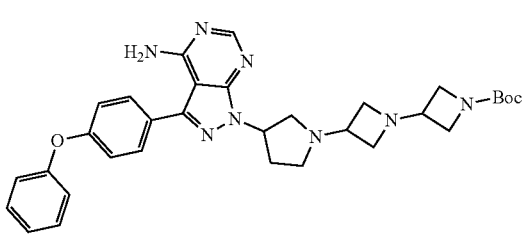 [SMILES: CC(C)(C)OC(=O)N1CC(N2CC(N3CCC(n4nc(-c5ccc(Oc6ccccc6)cc5)c5c(N)ncnc54)C3)C2)C1]

1-(1-(azetidin-3-yl)pyrrolidin-3-yl)-3-(4-phenoxyphenyl)-1H-pyrazolo[3,4-d]pyrimidin-4-amine Trifluoroacetate (29g) (380 mg) was dissolved in 15 mL of DCE and 2 mL of DMSO, and Boc-azetidinone (210 mg, 1.22 mmol) was added, the mixture was stirred at room temperature for 10 minutes, then sodium triacetoxyborohydride (515 mg, 2.44 mmol) was added, and the mixture was stirred at room temperature overnight. To the reaction system was slowly added 30 mL of saturated sodium bicarbonate solution, and the resulted solution was extracted with 100 mL of DCM. The organic phase was washed with 100 mL of water, dried over anhydrous sodium sulfate, and concentrated under reduced pressure, then the crude product was separated and purified by silica gel column chromatography (dichloromethane/methanol (v/v)=20:1), to obtain tert-butyl 3-(3-(4-amino-3-(4-phenoxyphenyl)-1H-pyrazolo[3,4-d]pyrimidin-1-yl)pyrrolidin-1-yl)-[1,3'-biazetidine]-1'-carboxylate (29h) (300 mg).

LCMS m/z=583.6 [M+1]⁺.

Step 8

1-(1-([1,3'-biazetidin]-3-yl)pyrrolidin-3-yl)-3-(4-phenoxyphenyl)-1H-pyrazolo[3,4-d]pyrimidin-4-amine Trifluoroacetate (29i)

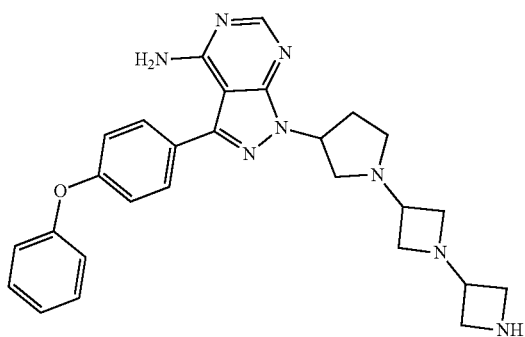 [SMILES: Nc1ncnc2c1c(-c1ccc(Oc3ccccc3)cc1)nn2C1CCN(C2CN(C3CNC3)C2)C1]

Tert-butyl 3-(3-(4-amino-3-(4-phenoxyphenyl)-1H-pyrazolo[3,4-d] pyrimidin-1-yl)pyrrolidin-1-yl)-[1,3'-biazetidine]-1'-carboxylate (29h) (300 mg, 0.51 mmol) was dissolved in 10 mL of DCM, and 5 mL of trifluoroacetic acid was added, the mixture was stirred at room temperature for 4 h. The reaction system was directly concentrated under reduced pressure, to obtain 1-(1-([1,3'-biazetidin]-3-yl)pyrrolidin-3-yl)-3-(4-phenoxyphenyl)-1H-pyrazolo[3,4-d]pyrimidin-4-amine Trifluoroacetate (29i) (0.38 g).

LCMS m/z=483.4 [M+1]⁺.

Step 9

5-(3-(3-(4-amino-3-(4-phenoxyphenyl)-1H-pyrazolo[3,4-d]pyrimidin-1-yl)pyrrolidin-1-yl)-[1,3'-biazetidin]-1'-yl)-2-(2,6-dioxopiperidin-3-yl)isoindoline-1,3-dione trifluoroacetate (Compound 29)

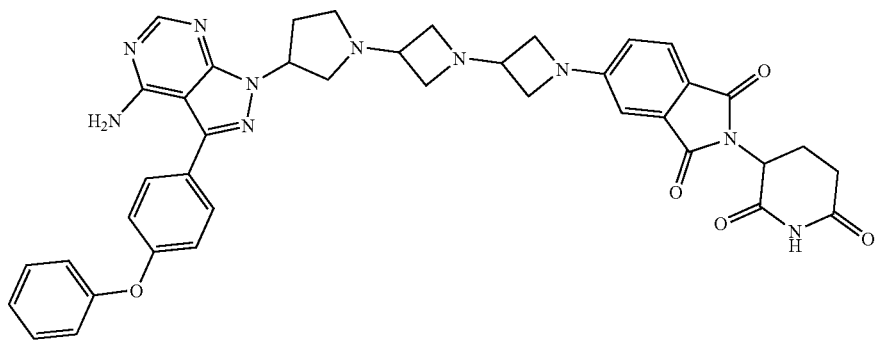 [SMILES: Nc1ncnc2c1c(-c1ccc(Oc3ccccc3)cc1)nn2C1CCN(C2CN(C3CN(c4ccc5c(c4)C(=O)N(C4CCC(=O)NC4=O)C5=O)C3)C2)C1]

1-(1-([1,3'-biazetidin]-3-yl)pyrrolidin-3-yl)-3-(4-phenoxyphenyl)-1H-pyrazolo[3,4-d]pyrimidin-4-amine Trifluoroacetate (29i) (0.38 g) was dissolved in 25 mL of DMSO, and 3 mL of DIPEA and 2-(2,6-dioxopiperidin-3-yl)-5-fluoroisoindoline-1,3-dione (see WO 2017197056 for the synthetic method) (211 mg, 0.77 mmol) were added, the reaction was stirred at 80° C. for 5 h. The reaction solution was cooled to room temperature, added 50 mL of water, and extracted with 100 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=15:1-5:1), to obtain 5-(3-(3-(4-amino-3-(4-phenoxyphenyl)-1H-pyrazolo[3,4-d]pyrimidin-1-yl)pyrrolidin-1-yl)-[1,3'-biazetidin]-1'-yl)-2-(2,6-dioxopiperidin-3-yl)isoindoline-1,3-dione trifluoroacetate (Compound 29) (130 mg).

¹H NMR (400 MHz, DMSO-d₆) δ 11.06 (s, 1H), 8.25 (s, 1H), 7.78-7.57 (m, 3H), 7.49-7.35 (m, 2H), 7.27-7.05 (m, 5H), 6.78 (d, 1H), 6.64 (dd, 1H), 5.49-5.31 (m, 1H), 5.05 (dd, 1H), 4.14-3.97 (m, 2H), 3.87-3.76 (m, 2H), 3.71-3.61 (m, 1H), 3.53-3.39 (m, 3H), 3.23-3.06 (m, 3H), 2.96-2.70 (m, 4H), 2.65-2.45 (m, 2H), 2.41-2.24 (m, 2H), 2.07-1.95 (m, 1H).

LCMS m/z=739.3 [M+1]⁺.

Example 30
(7S)-7-[1-[1-[1-[2-(2,6-dioxo-3-piperidyl)-1,3-dioxo-isoindolin-5-yl]azetidin-3-yl]-4-piperidyl]-4-piperidyl]-2-(4-phenoxyphenyl)-4,5,6,7-tetrahydro-pyrazolo[1,5-a]pyrimidine-3-carboxamide trifluoroacetate (Compound 30)
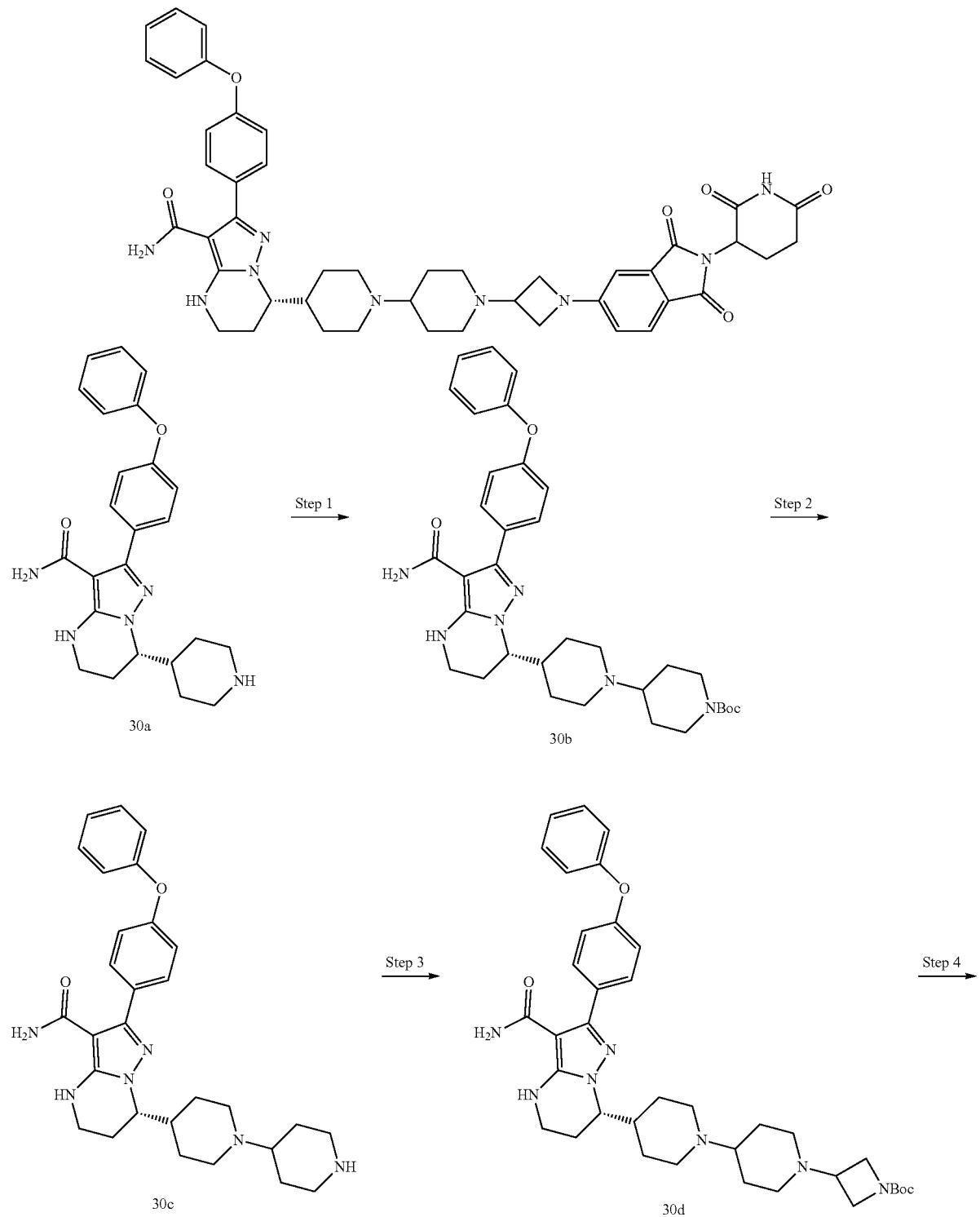

-continued
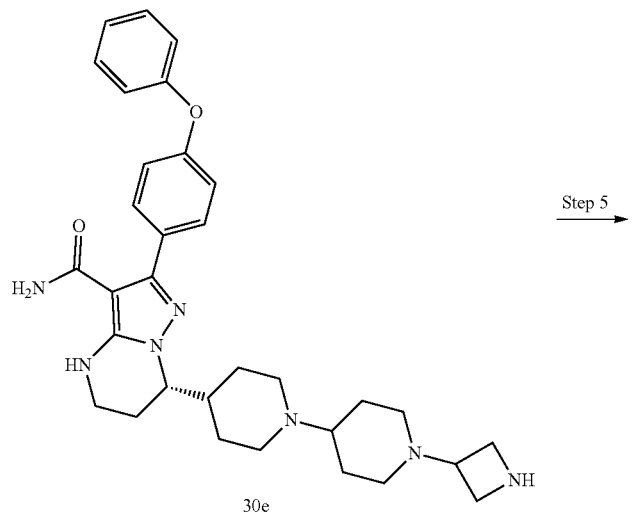
30e
Step 5
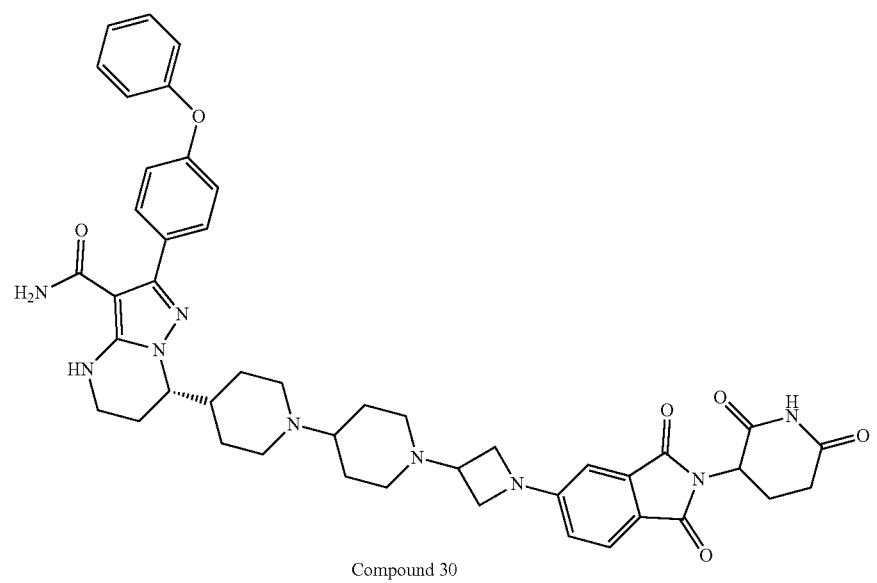
Compound 30

Step 1

4-[4-[(7S)-3-carbamoyl-2-(4-phenoxyphenyl)-4,5,6,7-tetrahydropyrazolo[1,5-a]pyrimidin-7-yl]-1-piperidyl]piperidine-1-carboxylate (30b)

Step 2

(7S)-2-(4-phenoxyphenyl)-7-[1-(4-piperidyl)-4-piperidyl]-4,5,6,7-tetrahydropyrazolo[1,5-a]pyrimidine-3-carboxamide (30c)

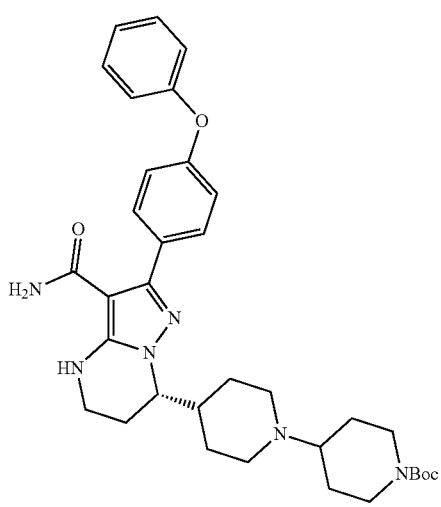 [SMILES: CC(C)(C)OC(=O)N1CCC(N2CCC([C@@H]3CCNc4c(C(N)=O)c(-c5ccc(Oc6ccccc6)cc5)nn43)CC2)CC1]

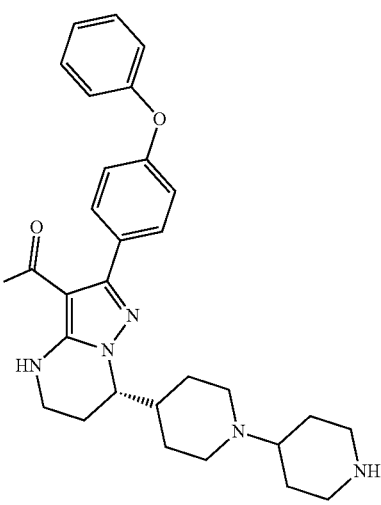

(S)-2-(4-phenoxyphenyl)-7-(piperidin-4-yl)-4,5,6,7-tetrahydropyrazolo[1,5-a]pyrimidine-3-carboxamide (30a) (95% ee) (see WO 2018033853 for the synthetic method) (0.2 g, 0.48 mmol) and tert-butyl 4-oxopiperidine-1-carboxylate (0.57 g, 2.87 mmol) were dissolved in 20 mL of chloroform, and acetic acid (0.14 g, 2.4 mmol) was added, then 1 g of 4 Å molecular sieve and 1 g of anhydrous sodium sulfate were added. The mixture was warmed to 65° C. and stirred for 2 h, sodium triacetoxyborohydride (0.61 g, 2.87 mmol) was added, and stirring was continued at this temperature overnight. The reaction solution was filtered, and the filtrate was concentrated under reduced pressure. The residue was separated and purified by silica gel column chromatography (dichloromethane/methanol (v/v)=50:1-7:1), to obtain tert-butyl 4-[4-[(7S)-3-carbamoyl-2-(4-phenoxyphenyl)-4,5,6,7-tetrahydropyrazolo[1,5-a]pyrimidin-7-yl]-1-piperidyl]piperidine-1-carboxylate (30b) (0.2 g, yield: 69%).

LCMS m/z=601.3 [M+1]$^+$.

Tert-butyl 4-[4-[(7S)-3-carbamoyl-2-(4-phenoxyphenyl)-4,5,6,7-tetrahydropyrazolo[1,5-a]pyrimidin-7-yl]-1-piperidyl]piperidine-1-carboxylate (30b) (0.2 g, 0.33 mmol) was dissolved in 5 mL of dichloromethane, and 5 mL of trifluoroacetic acid was added, the mixture was stirred at room temperature for 2 h. The solvent was removed from the reaction solution under reduced pressure, and the mixed solution of 20 mL of dichloromethane and 2 mL of ethanol was added. The resulting solution was washed with 50 mL of saturated sodium bicarbonate solution, the aqueous phase was further extracted with the mixed solution of 20 mL of dichloromethane and 2 mL ethanol, and the organic layers were combined, dried over anhydrous sodium sulfate, and concentrated under reduced pressure to obtain (7S)-2-(4-phenoxyphenyl)-7-[1-(4-piperidyl)-4-piperidyl]-4,5,6,7-tetrahydropyrazolo[1,5-a]pyrimidine-3-carboxamide (30c) (0.16 g, yield: 96%).

LCMS m/z=501.3 [M+1]$^+$.

Step 3 tert-butyl 3-[4-[4-[(7S)-3-carbamoyl-2-(4-phenoxyphenyl)-4,5,6,7-tetrahydropyrazolo[1,5-a]pyrimidin-7-yl]-1-piperidyl]-1-piperidyl]azetidine-1-carboxylate (30d)

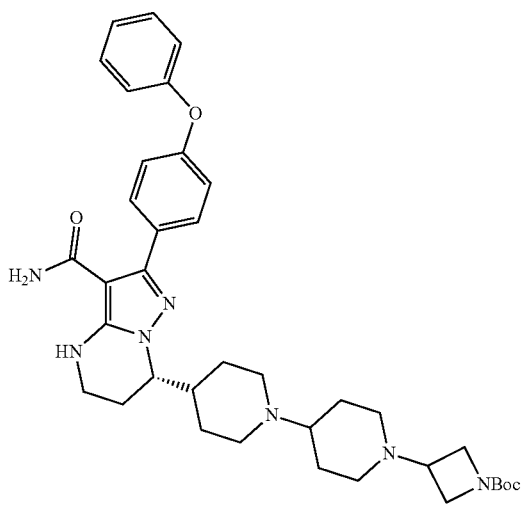 [SMILES: CC(C)(C)OC(=O)N1CC(N2CCC(N3CCC([C@@H]4CCNc5c(C(N)=O)c(-c6ccc(Oc7ccccc7)cc6)nn54)CC3)CC2)C1]

(7S)-2-(4-phenoxyphenyl)-7-[1-(4-piperidyl)-4-piperidyl]-4,5,6,7-tetrahydropyrazolo[1,5-a]pyrimidine-3-carboxamide (30c) (0.14 g, 0.28 mmol) and tert-butyl 3-oxoazetidine-1-carboxylate (0.24 g, 1.4 mmol) were dissolved in 20 mL of chloroform, and acetic acid (0.08 g, 1.4 mmol) was added, then 1 g of 4 Å molecular sieve and 1 g of anhydrous sodium sulfate were added, and the mixture was warmed to 65° C. and stirred for 2 h. Sodium triacetoxyborohydride (0.3 g, 1.4 mmol) was added, and the stirring was continued at this temperature overnight. The reaction solution was filtered, and the filtrate was concentrated under reduced pressure. The residue was separated and purified by silica gel column chromatography (dichloromethane/methanol (v/v)=50:1-7:1), to obtain tert-butyl 3-[4-[4-[(7S)-3-carbamoyl-2-(4-phenoxyphenyl)-4,5,6,7-tetrahydropyrazolo[1,5-a]pyrimidin-7-yl]-1-piperidyl]-1-piperidyl]azetidine-1-carboxylate (30d) (0.1 g, yield: 55%).

LCMS m/z=656.4 [M+1]⁺.

Step 4

(7S)-7-[1-[1-(azetidin-3-yl)-4-piperidyl]-4-piperidyl]-2-(4-phenoxyphenyl)-4,5,6,7-tetrahydropyrazolo[1,5-a]pyrimidine-3-carboxamide trifluoroacetate (30e)

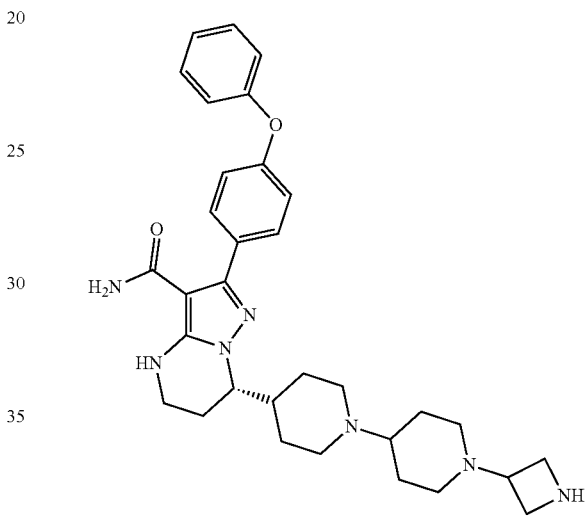

Tert-butyl 3-[4-[4-[(7S)-3-carbamoyl-2-(4-phenoxyphenyl)-4,5,6,7-tetrahydropyrazolo[1,5-a]pyrimidin-7-yl]-1-piperidyl]-1-piperidyl]azetidine-1-carboxylate (30d) (0.1 g, 0.15 mmol) was dissolved in 2 mL of dichloromethane, and 2 mL of trifluoroacetic acid was added, the mixture was stirred at room temperature overnight. The solvent was removed from the reaction solution under reduced pressure, to obtain (7S)-7-[1-[1-(azetidin-3-yl)-4-piperidyl]-4-piperidyl]-2-(4-phenoxyphenyl)-4,5,6,7-tetrahydropyrazolo[1,5-a]pyrimidine-3-carboxamide trifluoroacetate (30e) (0.12 g).

LCMS m/z=556.3 [M+1]⁺.

Step 5

(7S)-7-[1-[1-[1-[2-(2,6-dioxo-3-piperidyl)-1,3-di-oxo-isoindolin-5-yl]azetidin-3-yl]-4-piperidyl]-4-piperidyl]-2-(4-phenoxyphenyl)-4,5,6,7-tetrahydro-pyrazolo[1,5-a]pyrimidine-3-carboxamide trifluoroacetate (Compound 30)

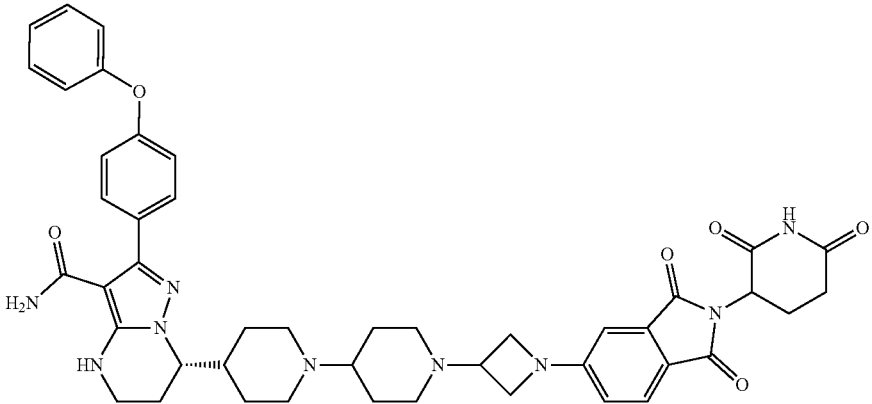 [SMILES: NC(=O)c1c(-c2ccc(Oc3ccccc3)cc2)nn2c1NCC[C@H]2C1CCN(C2CCN(C3CN(c4ccc5c(c4)C(=O)N(C4CCC(=O)NC4=O)C5=O)C3)CC2)CC1]

(7S)-7-[1-[1-(azetidin-3-yl)-4-piperidyl]-4-piperidyl]-2-(4-phenoxyphenyl)-4,5,6,7-tetrahydropyrazolo[1,5-a]pyrimidine-3-carboxamide trifluoroacetate (30e) (0.12 g) was dissolved in 3 mL of DMSO, and 2-(2,6-dioxopiperidin-3-yl)-5-fluoroisoindoline-1,3-dione (see WO 2017197056 for the synthetic method) (0.04 g, 0.16 mmol) and triethylamine (0.07 g, 0.67 mmol) were added, the mixture was warmed to 120° C. and stirred for 4 h. The reaction solution was cooled to room temperature, added 10 mL of water and 20 mL of ethyl acetate, and extracted, then the solvent was removed from the organic layer under reduced pressure, and the residue was separated and purified by silica gel column chromatography (dichloromethane/methanol (v/v)=50:1-10:1), to obtain (7S)-7-[1-[1-[1-[2-(2,6-dioxo-3-piperidyl)-1,3-dioxo-isoindolin-5-yl]azetidin-3-yl]-4-piperidyl]-4-piperidyl]-2-(4-phenoxyphenyl)-4,5,6,7-tetrahydropyrazolo[1,5-a]pyr imidine-3-carboxamide trifluoroacetate (Compound 30) (45 mg).

$^1$H NMR (400 MHz, DMSO-d$_6$) δ 11.05 (s, 1H), 7.64 (d, 1H), 7.50 (d, 2H), 7.45-7.38 (m, 2H), 7.21-7.14 (m, 1H), 7.12-7.02 (m, 4H), 6.78 (d, 1H), 6.72-6.61 (m, 2H), 5.05 (dd, 1H), 4.16-3.96 (m, 3H), 3.87-3.73 (m, 2H), 3.35-3.28 (m, 1H), 2.97-2.78 (m, 3H), 2.58-2.52 (m, 11H), 2.10-1.73 (m, 8H), 1.72-1.45 (m, 4H).

LCMS m/z=812.4 [M+1]$^+$.

Example 31

(7S)-7-[1-[1-[1-[2-(2,6-dioxo-3-piperidyl)-1,3-di-oxo-isoindolin-5-yl]azetidin-3-yl]azetidin-3-yl]-4-piperidyl]-2-(4-phenoxyphenyl)-4,5,6,7-tetrahydro-pyrazolo[1,5-a]pyrimidine-3-carboxamide trifluoroacetate (Compound 31)

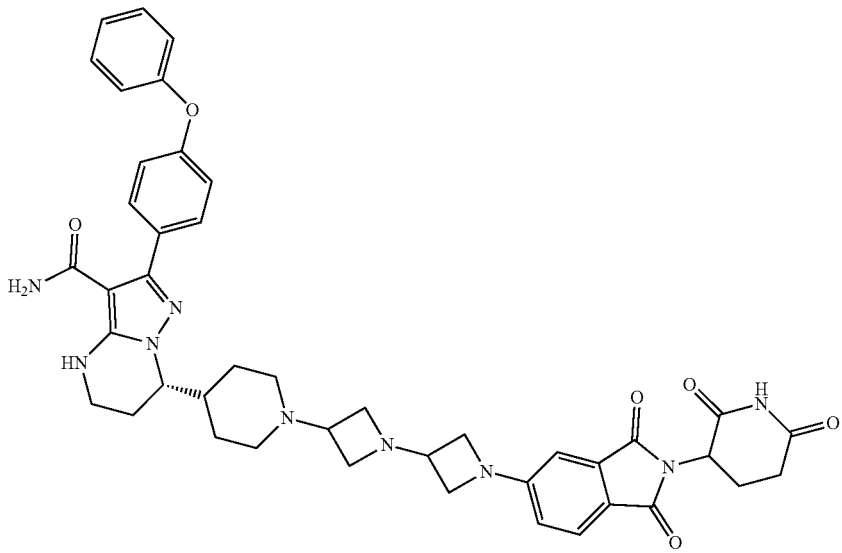

393
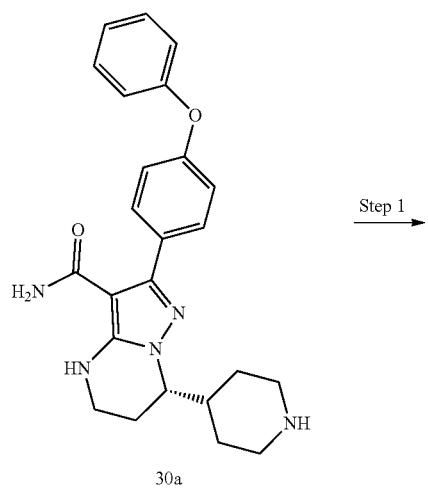
30a
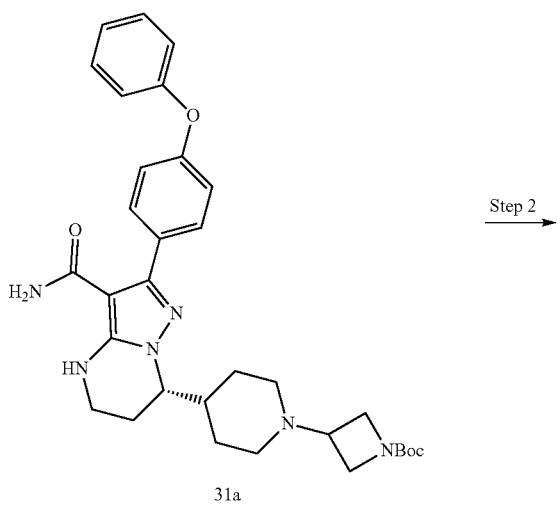
31a
-continued
394
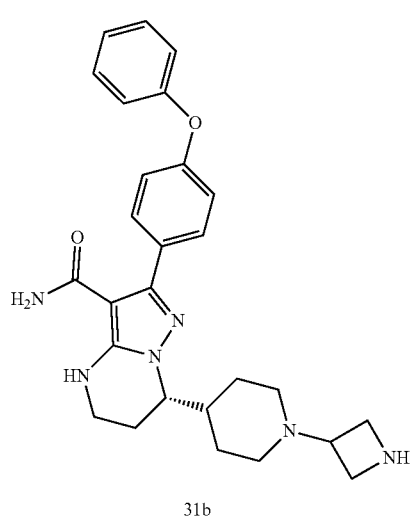
31b
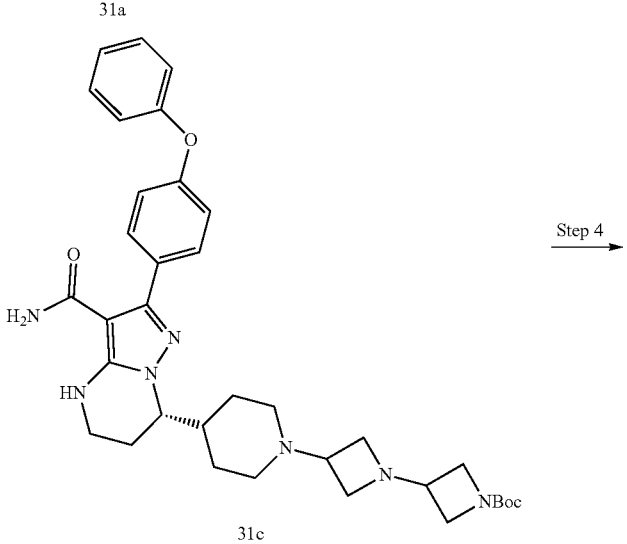
31c
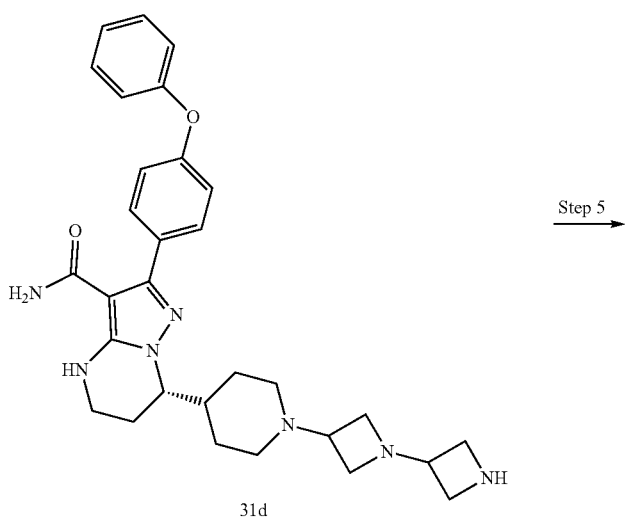
31d
Step 1
Step 2
Step 3
Step 4
Step 5

-continued

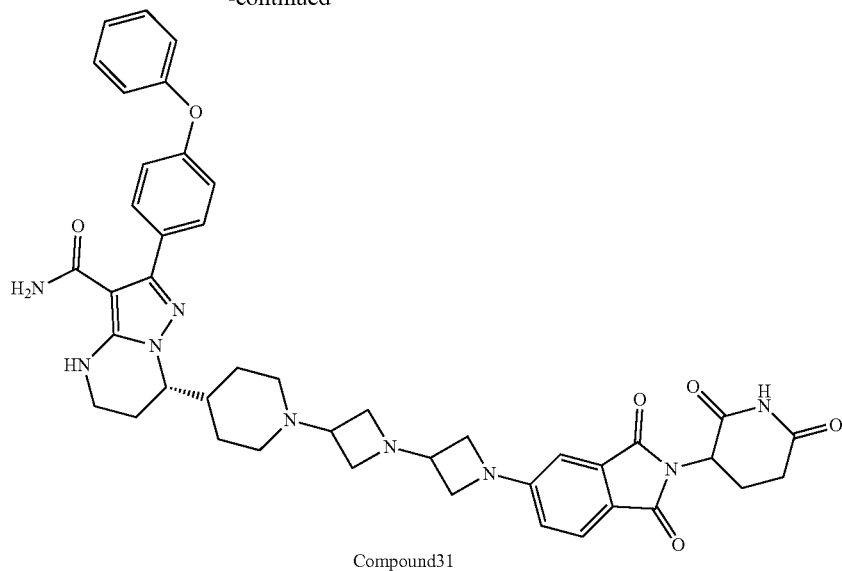

Compound31

Step 1 tert-butyl 3-[4-[(7S)-3-carbamoyl-2-(4-phenoxyphenyl)-4,5,6,7-tetrahydropyrazolo[1,5-a]pyrimidin-7-yl]-1-piperidyl]azetidine-1-carboxylate (31a)

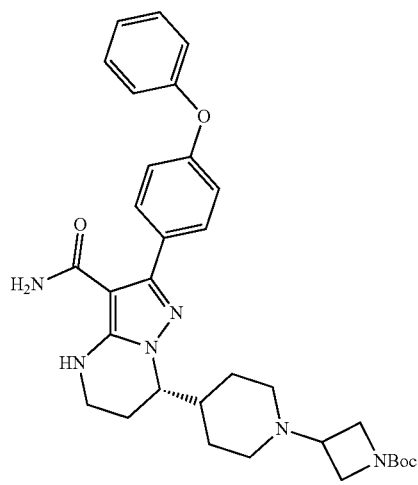 [SMILES: CC(C)(C)OC(=O)N1CC(N2CCC([C@@H]3CCNc4c(C(N)=O)c(-c5ccc(Oc6ccccc6)cc5)nn43)CC2)C1]

(S)-2-(4-phenoxyphenyl)-7-(piperidin-4-yl)-4,5,6,7-tetrahydropyrazolo[1,5-a]pyrimidine-3-carboxamide (30a) (95% ee) (see WO 2018033853 for the synthetic method) (0.2 g, 0.48 mmol) and tert-butyl 3-oxoazetidine-1-carboxylate (0.41 g, 2.40 mmol) were dissolved in 20 mL of chloroform, and acetic acid (0.14 g, 2.4 mmol) was added, then 1 g of 4 Å molecular sieve and 1 g of anhydrous sodium sulfate were added. The mixture was warmed to 65° C. and stirred for 2 h, sodium triacetoxyborohydride (0.61 g, 2.87 mmol) was added, and stirring was continued at this temperature overnight. The reaction solution was filtered, and the filtrate was concentrated under reduced pressure. The residue was separated and purified by silica gel column chromatography (dichloromethane/methanol (v/v)=50:1-7:1), to obtain tert-butyl 3-[4-[(7S)-3-carbamoyl-2-(4-phenoxyphenyl)-4,5,6,7-tetrahydropyrazolo[1,5-a]pyrimidin-7-yl]-1-piperidyl]azetidine-1-carboxylate (31a) (0.25 g, yield: 91%).

LCMS m/z=573.4 [M+1]$^+$.

Step 2

(7S)-7-[1-(azetidin-3-yl)-4-piperidyl]-2-(4-phenoxyphenyl)-4,5,6,7-tetrahydropyrazolo[1,5-a]pyrimidine-3-carboxamide (31b)

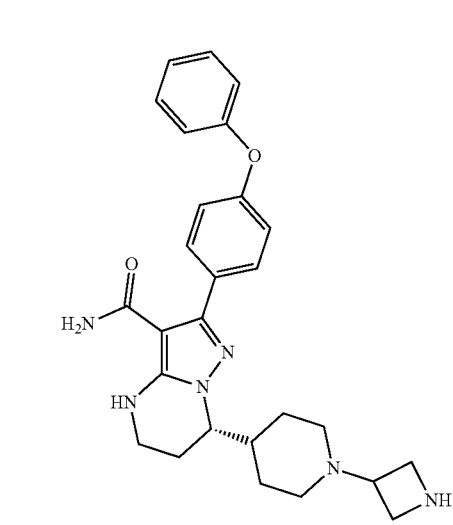 [SMILES: NC(=O)c1c(-c2ccc(Oc3ccccc3)cc2)nn2c1NCC[C@H]2C1CCN(C2CNC2)CC1]

Tert-butyl 3-[4-[(7S)-3-carbamoyl-2-(4-phenoxyphenyl)-4,5,6,7-tetrahydropyrazolo[1,5-a]pyrimidin-7-yl]-1-piperidyl]azetidine-1-carboxylate (31a)

(0.25 g, 0.44 mmol) was dissolved in 5 mL of dichloromethane, and 5 mL of trifluoroacetic acid was added, the mixture was stirred at room temperature for 2 h. The solvent was removed from the reaction solution under reduced pressure, and the mixed solution of 20 mL of dichloromethane and 2 mL of ethanol was added. The resulting solution was washed with 50 mL of saturated sodium bicarbonate solution, the aqueous phase was further extracted with the mixed solution of 20 mL of dichloromethane and 2 mL ethanol, and the organic layers were combined, dried over anhydrous sodium sulfate, and concentrated under reduced pressure to obtain (7S)-7-[1-(azetidin-3-yl)-4-piperidyl]-2-(4-phenoxyphenyl)-4,5,6,7-tetrahydropyrazolo[1,5-a]pyrimidine-3-carboxamide (31b) (0.19 g, yield: 92%).

LCMS m/z=473.4 [M+1]⁺.

Step 3 tert-butyl 3-[3-[4-[(7S)-3-carbamoyl-2-(4-phenoxyphenyl)-4,5,6,7-tetrahydropyrazolo[1,5-a]pyrimidin-7-yl]-1-piperidyl]azetidin-1-yl]azetidine-1-carboxylate (31c)

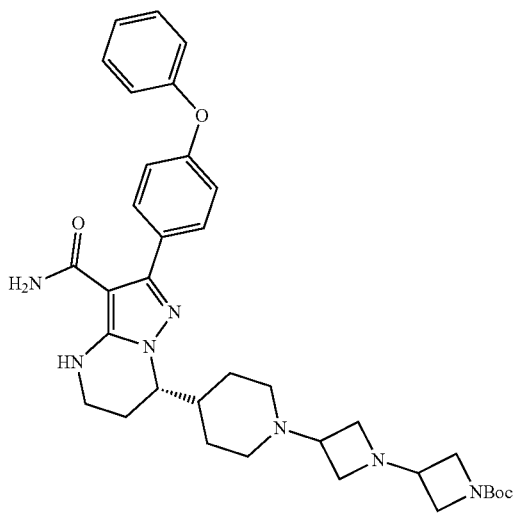 [SMILES: CC(C)(C)OC(=O)N1CC(N2CC(N3CCC([C@@H]4CCNc5c(C(N)=O)c(-c6ccc(Oc7ccccc7)cc6)nn54)CC3)C2)C1]

(7S)-7-[1-(azetidin-3-yl)-4-piperidyl]-2-(4-phenoxyphenyl)-4,5,6,7-tetrahydropyrazolo[1,5-a]pyrimidine-3-carboxamide (31b) (0.19 g, 0.40 mmol) and tert-butyl 3-oxoazetidine-1-carboxylate (0.34 g, 2.01 mmol) were dissolved in 20 mL of chloroform, and acetic acid (0.12 g, 2.01 mmol) was added, then 1 g of 4 Å molecular sieve and 1 g of anhydrous sodium sulfate were added, and the mixture was warmed to 65° C. and stirred for 2 h. Sodium triacetoxyborohydride (0.43 g, 2.01 mmol) was added, and the stirring was continued at this temperature overnight. The reaction solution was filtered, and the filtrate was concentrated under reduced pressure. The residue was separated and purified by silica gel column chromatography (dichloromethane/methanol (v/v)=50:1-7:1), to obtain tert-butyl 3-[3-[4-[(7S)-3-carbamoyl-2-(4-phenoxyphenyl)-4,5,6,7-tetrahydropyrazolo[1,5-a]pyrimidin-7-yl]-1-piperidyl]azetidin-1-yl]azetidine-1-carboxylate (31c) (0.14 g, yield: 46%).

LCMS m/z=628.3 [M+1]⁺.

Step 4

(7S)-7-[1-[1-(azetidin-3-yl)azetidin-3-yl]-4-piperidyl]-2-(4-phenoxyphenyl)-4,5,6,7-tetrahydropyrazolo[1,5-a]pyrimidine-3-carboxamide (31d)

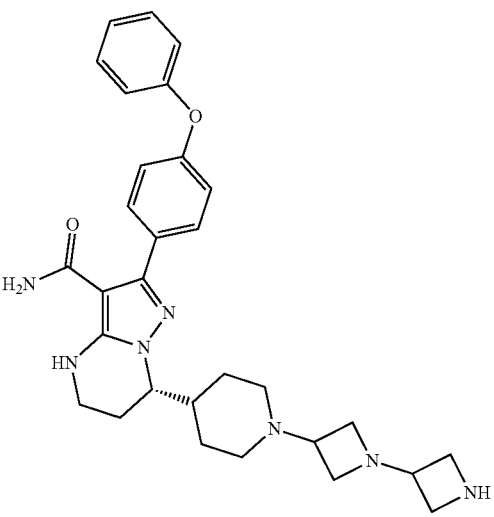 [SMILES: NC(=O)c1c(-c2ccc(Oc3ccccc3)cc2)nn2c1NCC[C@H]2C1CCN(C2CN(C3CNC3)C2)CC1]

Tert-butyl 3-[3-[4-[(7S)-3-carbamoyl-2-(4-phenoxyphenyl)-4,5,6,7-tetrahydropyrazolo[1,5-a]pyrimidin-7-yl]-1-piperidyl]azetidin-1-yl]azetidine-1-carboxylate (31c) (0.14 g, 0.22 mmol) was dissolved in 5 mL of dichloromethane, and 5 mL of trifluoroacetic acid was added, the mixture was stirred at room temperature for 2 h. The solvent was removed from the reaction solution under reduced pressure, and the mixed solution of 20 mL of dichloromethane and 2 mL of ethanol was added. The resulting solution was washed with 50 mL of saturated sodium bicarbonate solution, the aqueous phase was further extracted with the mixed solution of 20 mL of dichloromethane and 2 mL ethanol, and the organic layers were combined, dried over anhydrous sodium sulfate, and concentrated under reduced pressure to obtain (7S)-7-[1-[1-(azetidin-3-yl)azetidin-3-yl]-4-piperidyl]-2-(4-phenoxyphenyl)-4,5,6,7-tetrahydropyrazolo[1,5-a]pyrimidine-3-carboxamide (31d) (0.10 g, yield: 85%).

LCMS m/z=528.3 [M+1]⁺.

Step 5

(7S)-7-[1-[1-[1-[2-(2,6-dioxo-3-piperidyl)-1,3-di-oxo-isoindolin-5-yl]azetidin-3-yl]azetidin-3-yl]-4-piperidyl]-2-(4-phenoxyphenyl)-4,5,6,7-tetrahydro-pyrazolo[1,5-a]pyrimidine-3-carboxamide trifluoroacetate (Compound 31)

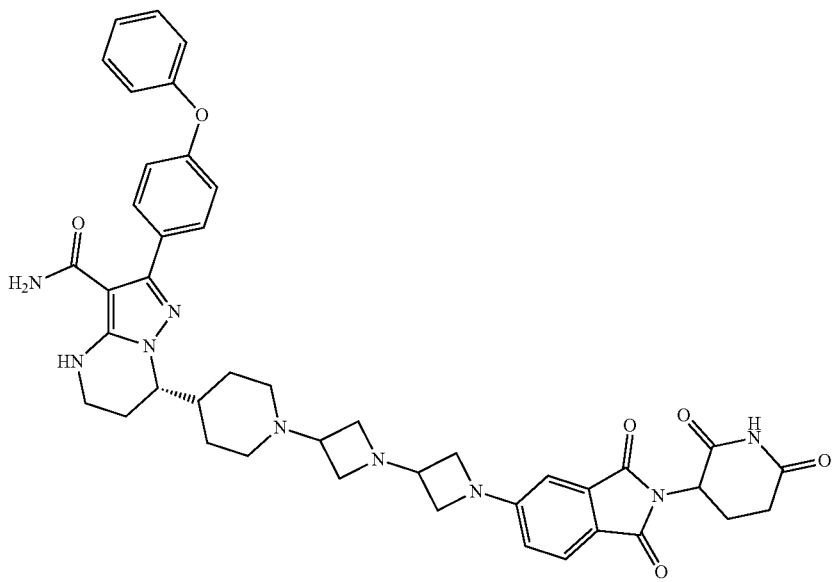 [SMILES: NC(=O)c1c(-c2ccc(Oc3ccccc3)cc2)nn2c1NCC[C@H]2C1CCN(C2CN(C3CN(c4ccc5c(c4)C(=O)N(C4CCC(=O)NC4=O)C5=O)C3)C2)CC1]

(7S)-7-[1-[1-(azetidin-3-yl)azetidin-3-yl]-4-piperidyl]-2-(4-phenoxyphenyl)-4,5,6,7-tetrahydropyrazolo[1,5-a]pyrimidine-3-carboxamide (31d) (0.03 g, 0.057 mmol) was dissolved in 3 mL of DMSO, and 2-(2,6-dioxopiperidin-3-yl)-5-fluoroisoindoline-1,3-dione (see WO 2017197056 for the synthetic method) (0.019 g, 0.068 mmol) and triethylamine (0.022 g, 0.17 mmol) were added, the mixture was warmed to 120° C. and stirred for 4 h. The reaction solution was cooled to room temperature, added 10 mL of water, and extracted with 20 mL of ethyl acetate. The solvent was removed from the organic layer under reduced pressure, and the residue was passed through Pre-HPLC (instrument and preparative column: using Glison GX-281 to prepare the liquid phase, preparative column model: Sunfire C18, 5 μm, inner diameter×length=30 mm×150 mm).

Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from 5% to 60% (elution time: 15 min), the reaction system was lyophilized to obtain (7S)-7-[1-[1-[1-[2-(2,6-dioxo-3-piperidyl)-1,3-dioxo-isoindolin-5-yl]azetidin-3-yl]azetidin-3-yl]-4-piperidyl]-2-(4-phenoxyphenyl)-4,5,6,7-tetrahydropyrazolo[1,5-a]pyrimidine-3-carboxamide trifluoroacetate (Compound 31) (15 mg).

$^1$H NMR (400 MHz, DMSO-$d_6$) δ 11.05 (s, 1H), 7.68 (d, 1H), 7.53-7.47 (m, 2H), 7.45-7.38 (m, 2H), 7.21-7.14 (m, 1H), 7.13-6.98 (m, 4H), 6.96-6.44 (m, 3H), 5.06 (dd, 1H), 4.22-3.60 (m, 11H), 3.45-3.26 (m, 4H), 2.97-2.64 (m, 3H), 2.63-2.45 (m, 2H), 2.34-2.15 (m, 1H), 2.12-1.50 (m, 7H).

LCMS m/z=784.3 [M+1]$^+$.

Example 32

5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)-6-fluoroisoindoline-1,3-dione (Compound 32)

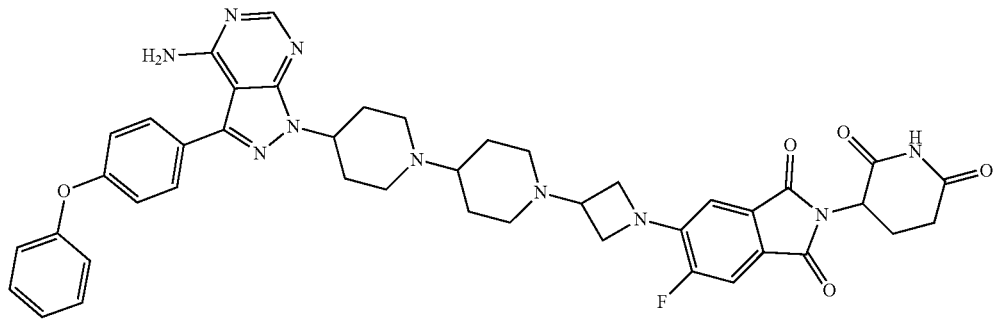

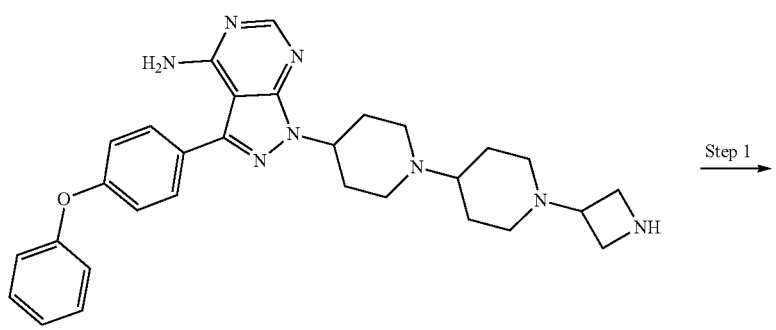

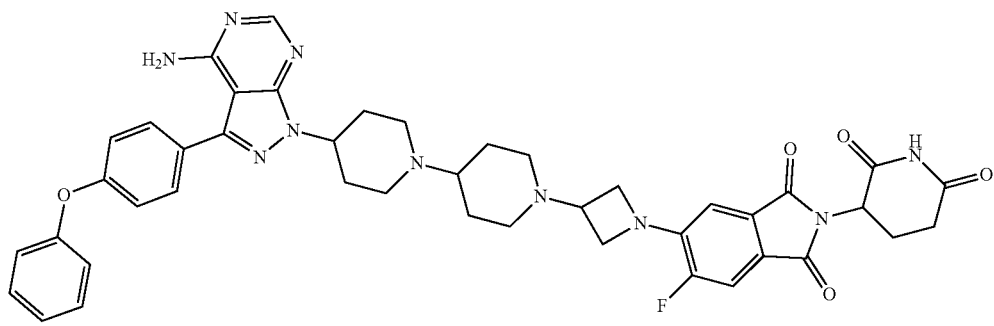

Compound 32

1-(1'-(azetidin-3-yl)-[1,4'-bipiperidin]-4-yl)-3-(4-phenoxyphenyl)-1H-pyrazolo[3,4-d]pyrimidin-4-amine (8b) (290 mg, 0.55 mmol) was dissolved in 10 mL of DMSO, and 1 mL of DIPEA and 2-(2,6-dioxopiperidin-3-yl)-5,6-difluoroisoindoline-1,3-dione (21b) (150 mg, 0.51 mmol) were added, the mixture was stirred in external bath at 80° C. for 5 h. The reaction solution was cooled to room temperature, added 50 mL of water, and extracted with 100 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=15:1), to obtain 5-(3-(4-(4-amino-3-(4-phenoxyphenyl)-1H-pyrazolo[3,4-d]pyrimidin-1-yl)-[1,4'-bipiperidin]-1'-yl)azetidin-1-yl)-2-(2,6-dioxopiperidin-3-yl)-6-fluoroisoindoline-1,3-di one (Compound 32) (150 mg, yield: 34%).

$^1$H NMR (400 MHz, DMSO-d$_6$) δ 11.06 (s, 1H), 8.23 (s, 1H), 7.70-7.63 (m, 2H), 7.60 (d, 1H), 7.48-7.39 (m, 2H), 7.23-7.09 (m, 5H), 6.92 (d, 1H), 5.07 (dd, 1H), 4.69-4.57 (m, 1H), 4.28-4.18 (m, 2H), 4.02-3.90 (m, 2H), 3.30-3.21 (m, 1H), 3.07-2.96 (m, 2H), 2.94-2.80 (m, 3H), 2.69-2.52 (m, 2H), 2.41-2.27 (m, 3H), 2.24-2.08 (m, 2H), 2.07-1.96 (m, 1H), 1.96-1.70 (m, 6H), 1.56-1.39 (m, 2H).

LCMS m/z=799.3 [M+1]$^+$.

Example 33
4-[8-amino-3-[(2S)-1-[1-[1-[2-(2,6-dioxo-3-piperidyl)-1,3-dioxo-isoindolin-5-yl]azetidin-3-yl]-4-piperidyl]pyrrolidin-2-yl]imidazo[1,5-a]pyrazin-1-yl]-N-(2-pyridyl)benzamide (Compound 33)
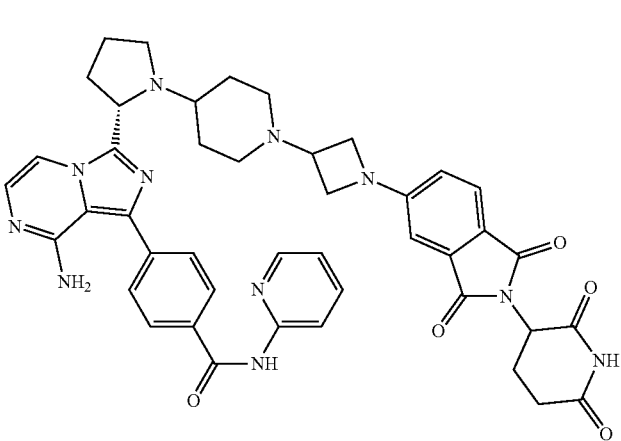
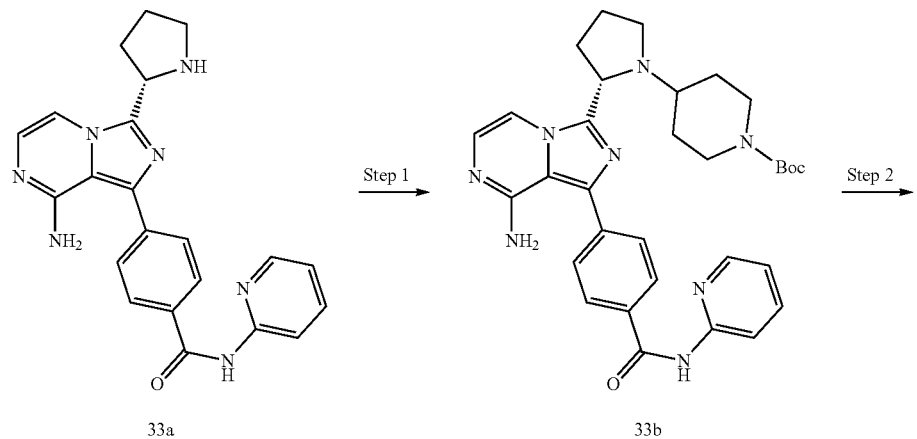
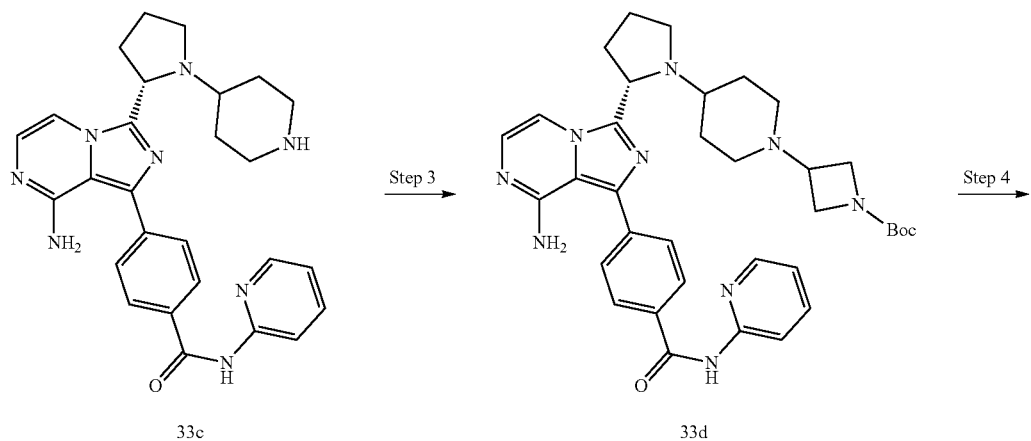

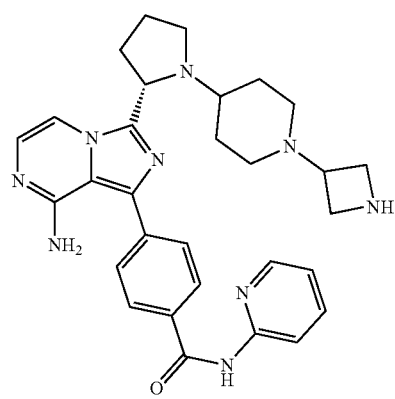

33e

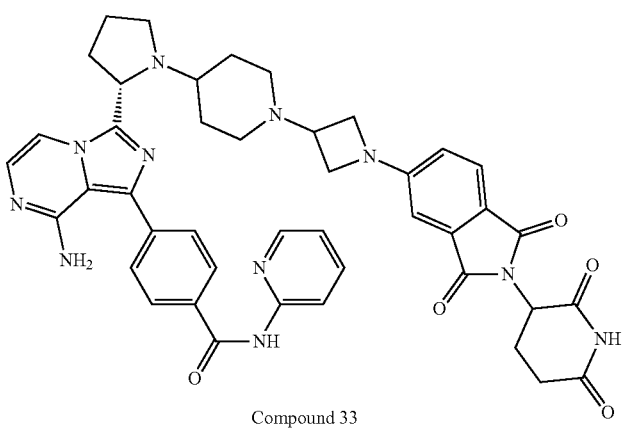

Compound 33

Step 1 tert-butyl 4-[(2S)-2-[8-amino-1-[4-(2-pyridylcarbamoyl)phenyl]imidazo[1,5-a]pyrazin-3-yl]pyrrolidin-1-yl]piperidine-1-carboxylate (33b)

Step 2

4-[8-amino-3-[(2S)-1-(4-piperidyl)pyrrolidin-2-yl]imidazo[1,5-a]pyrazin-1-yl]-N-(2-pyridyl)benzamide (33c)

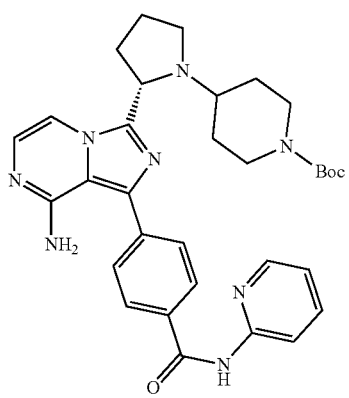 [SMILES: CC(C)(C)OC(=O)N1CCC(N2CCC[C@H]2c2nc(-c3ccc(C(=O)Nc4ccccn4)cc3)c3c(N)nccn23)CC1]

Tert-butyl

4-[(2S)-2-[8-amino-1-[4-(2-pyridylcarbamoyl)phenyl]imidazo[1,5-a]pyrazin-3-yl]pyrrolidin-1-yl]piperidine-1-carboxylate (33b)

(S)-4-(8-amino-3-(pyrrolidin-2-yl)imidazo[1,5-a]pyrazin-1-yl)-N-(pyridin-2-yl)benzamide (33a) (0.500 g, 1.25 mmol) was dissolved in 5 mL of 1,2-dichloroethane, and N-tert-butoxycarbonyl-4-piperidone (0.374 g, 1.88 mmol) and glacial acetic acid (0.150 g, 2.50 mmol) were added. Upon completion of the addition, the reaction was carried out at 65° C. for 3 h, cooled to room temperature, and sodium triacetoxyborohydride (0.531 g, 2.50 mmol) was added. Upon completion of the addition, the reaction was carried out at room temperature overnight. To the reaction system was added dropwise saturated sodium bicarbonate solution to adjust the pH to 9-10, and same was concentrated under reduced pressure, then the crude product was separated and purified by silica gel column chromatography (dichloromethane/methanol (v/v)=100:0-19:1), to obtain tert-butyl 4-[(2S)-2-[8-amino-1-[4-(2-pyridylcarbamoyl)phenyl]imidazo[1,5-a]pyrazin-3-yl]pyrrolidin-1-yl]piperidine-1-carboxylate (33b) (0.340 g, yield: 47%).

LCMS m/z=583.3 [M+1]⁺.

4-[(2S)-2-[8-amino-1-[4-(2-pyridylcarbamoyl)phenyl]imidazo[1,5-a]pyrazin-3-yl]pyrrolidin-1-yl]piperidine-1-carboxylate (33b) (0.340 g, 0.583 mmol) was dissolved in 2 mL of dichloromethane, and 5 mL of 4N dioxane hydrochloride solution was added, the mixture was stirred at room temperature for 1 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure, then the crude product was separated and purified by silica gel column chromatography (dichloromethane/methanol (v/v)=19:0-1:1), to obtain 4-[8-amino-3-[(2S)-1-(4-piperidyl)pyrrolidin-2-yl]imidazo[1,5-a]pyrazin-1-yl]-N-(2-pyridyl)benzamide (33c) (0.206 g, yield: 73%).

LCMS m/z=483.3 [M+1]⁺.

Step 3 tert-butyl
3-[4-[(2S)-2-[8-amino-1-[4-(2-pyridylcarbamoyl)
phenyl]imidazo[1,5-a]pyrazin-3-yl]pyrrolidin-1-yl]-
1-piperidyl]azetidine-1-carboxylate (33d)

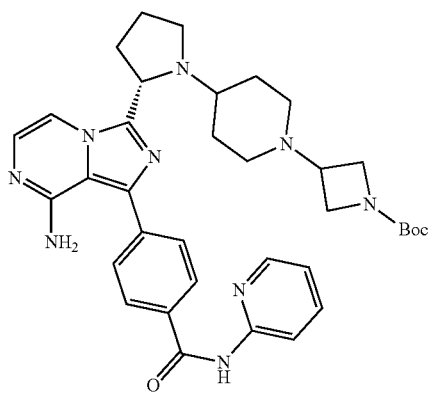 [SMILES: CC(C)(C)OC(=O)N1CC(N2CCC(N3CCC[C@H]3c3nc(-c4ccc(C(=O)Nc5ccccn5)cc4)c4c(N)nccn34)CC2)C1]

4-[8-amino-3-[(2S)-1-(4-piperidyl)pyrrolidin-2-yl]imidazo[1,5-a]pyrazin-1-yl]-N-(2-pyridyl)benzamide (33c) (0.200 g, 0.414 mmol) was dissolved in 5 mL of 1,2-dichloroethane, and 2 mL of dimethyl sulfoxide was added, then tert-butyl 3-oxoazetidine-1-carboxylate (0.106 g, 0.622 mmol) and glacial acetic acid (0.0498 g, 0.829 mmol) were added. Upon completion of the addition, the reaction was carried out at 65° C. for 3 h, cooled to room temperature, and sodium triacetoxyborohydride (0.176 g, 0.829 mmol) was added. Upon completion of the addition, the reaction was carried out at room temperature for 2 h. To the reaction system was added dropwise saturated sodium bicarbonate solution to adjust the pH to 9-10, and same was concentrated under reduced pressure, then the crude product was separated and purified by silica gel column chromatography (dichloromethane/methanol (v/v)=100:0-19:1), to obtain tert-butyl 3-[4-[(2S)-2-[8-amino-1-[4-(2-pyridylcarbamoyl)phenyl]imidazo[1,5-a]pyrazin-3-yl]pyrrolidin-1-yl]-1-piperidyl]azetidine-1-carboxylate (33d) (0.090 g, yield: 34%).

Step 4

4-[8-amino-3-[(2S)-1-[1-(azetidin-3-yl)-4-piperidyl]
pyrrolidin-2-yl]imidazo[1,5-a]pyrazin-1-yl]-N-(2-
pyridyl)benzamide (33e)

Tert-butyl
3-[4-[(2S)-2-[8-amino-1-[4-(2-pyridylcarbamoyl)phenyl]
imidazo[1,5-a]pyrazin-3-yl]pyrrolidin-1-yl]-1-piperidyl]
azetidine-1-carboxylate (33d) (0.090 g, 0.14 mmol) was dissolved in 2 mL of dichloromethane, and 5 mL of 4N dioxane hydrochloride solution was added, and the mixture was stirred at room temperature for 1 h. The reaction solution was concentrated under reduced pressure, and then to the residue was added 20 mL of dichloromethane. The pH was adjusted to 9-10 with saturated sodium bicarbonate solution. The liquid separation was conducted, and the organic layer was dried over anhydrous sodium sulfate, and concentrated under reduced pressure to obtain 4-[8-amino-3-[(2S)-1-[1-(azetidin-3-yl)-4-piperidyl]pyrrolidin-2-yl]imidazo[1,5-a]pyrazin-1-yl]-N-(2-pyridyl)benzamide (33e) (0.076 g, yield: >99%).

LCMS m/z=538.3 [M+1]$^+$.

Step 5

4-[8-amino-3-[(2S)-1-[1-[1-[2-(2,6-dioxo-3-pip-
eridyl)-1,3-dioxo-isoindolin-5-yl]azetidin-3-yl]-4-
piperidyl]pyrrolidin-2-yl]imidazo[1,5-a]pyrazin-1-
yl]-N-(2-pyridyl)benzamide (Compound 33)

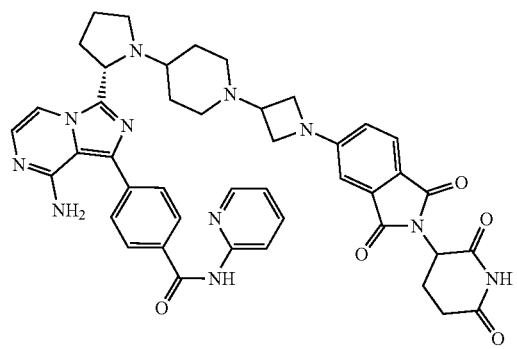 [SMILES: Nc1nccn2c([C@@H]3CCCN3C3CCN(C4CN(c5ccc6c(c5)C(=O)N(C5CCC(=O)NC5=O)C6=O)C4)CC3)nc(-c3ccc(C(=O)Nc4ccccn4)cc3)c12]

4-[8-amino-3-[(2S)-1-[1-(azetidin-3-yl)-4-piperidyl]pyrrolidin-2-yl]imidazo[1,5-a]pyrazin-1-yl]-N-(2-pyridyl)benzamide (33e) (0.076 g, 0.141 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.0468 g, 0.170 mmol) and diisopropylethylamine (0.0913 g, 0.707 mmol) were added. Upon completion of the addition, the reaction was carried out at 90° C. for 2 h. The reaction solution was cooled to room temperature, to which 10 mL of water was slowly added dropwise, and filtered. The filter cake was dissolved with 20 mL of dichloromethane, then washed with 5 mL of saturated sodium chloride solution. The liquid separation was conducted, and the organic layer was dried over anhydrous sodium sulfate, and concentrated under reduced pressure, then the crude product was separated and purified by silica gel column chromatography (dichloromethane/methanol (v/v)=100:0-19:1), to obtain 4-[8-amino-3-[(2S)-1-[1-[1-[2-(2,6-dioxo-3-piperidyl)-1,3-dioxo-isoindolin-5-yl]azetidin-3-yl]-4-piperidyl]pyrrolidin-2-yl]imidazo[1,5-a]pyrazin-1-yl]-N-(2-pyridyl)benzamide (Compound 33) (0.055 g, yield: 49%).

$^1$H NMR (400 MHz, CDCl$_3$) δ 8.53-8.37 (m, 2H), 8.20-7.98 (m, 3H), 7.83-7.75 (m, 1H), 7.73-7.56 (m, 2H), 7.51-7.38 (m, 1H), 7.29-7.21 (m, 1H), 7.16-7.05 (m, 2H), 6.80-6.71 (m, 1H), 6.48-6.40 (m, 1H), 5.50 (brs, 2H), 4.99-4.89 (m, 1H), 4.53-4.41 (m, 1H), 4.13-4.02 (m, 1H), 3.99-3.83 (m, 1H), 3.82-3.32 (m, 4H), 2.97-2.58 (m, 6H), 2.56-2.30 (m, 2H), 2.25-1.55 (m, 11H).

LCMS m/z=794.3 [M+1]$^+$.

Example 34

5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-a)

5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-b)

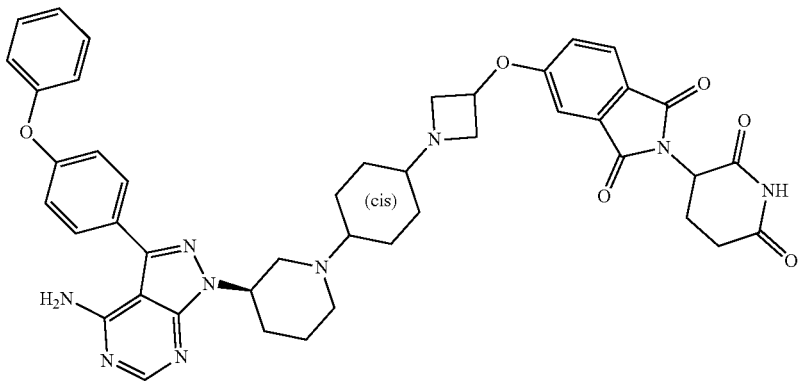

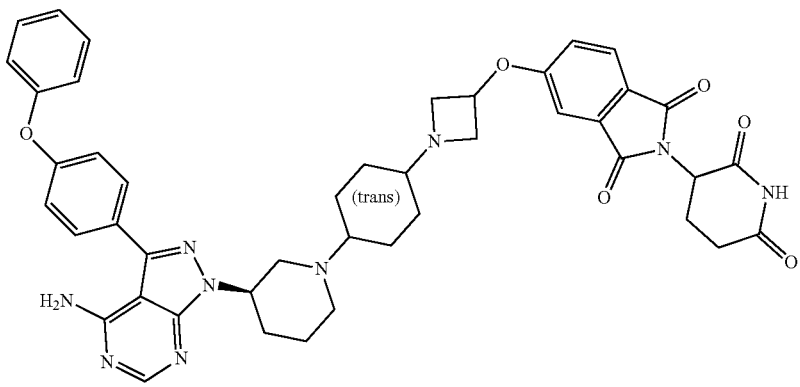

413
-continued
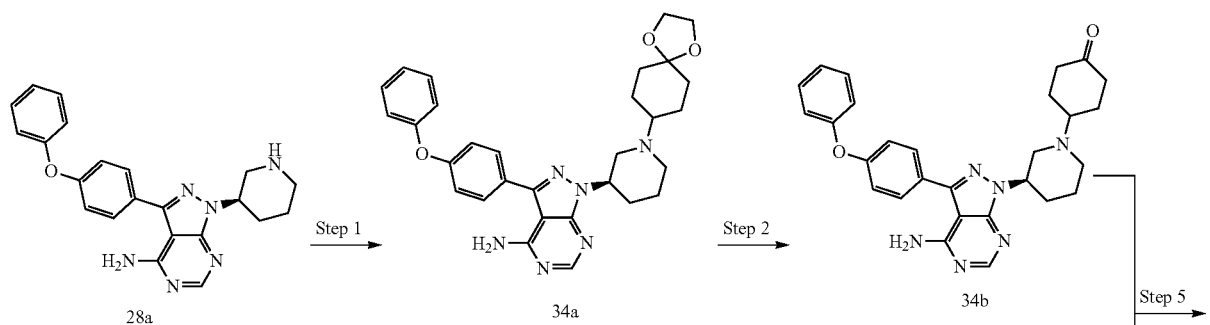
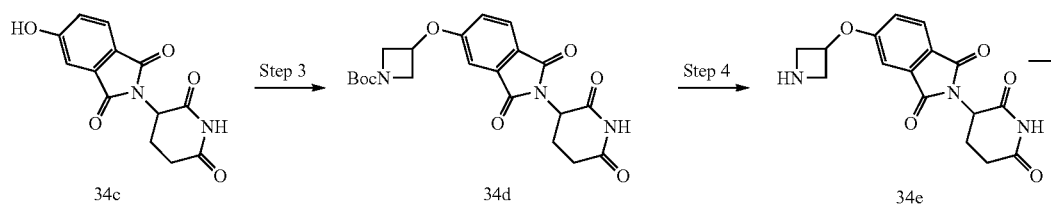
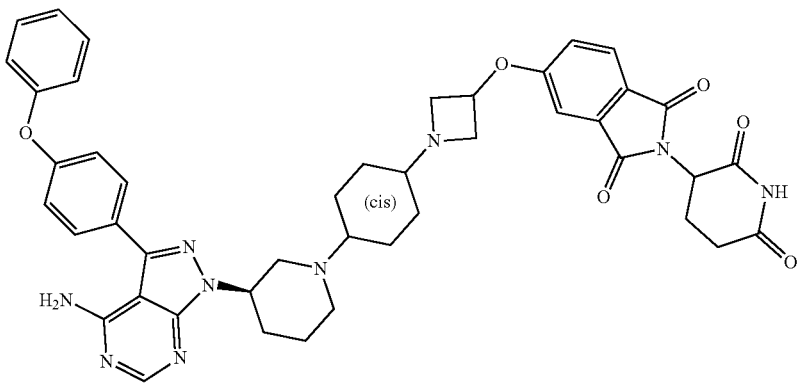
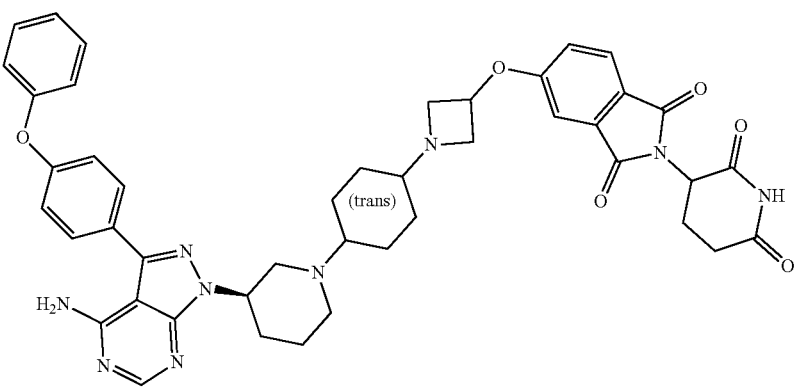
Compound 34-a and Compound 34-b

415

Step 1

1-[(3R)-1-(1,4-dioxaspiro[4.5]decan-8-yl)-3-piperidyl]-3-(4-phenoxyphenyl)pyrazolo[3,4-d]pyrimidin-4-amine (34a)

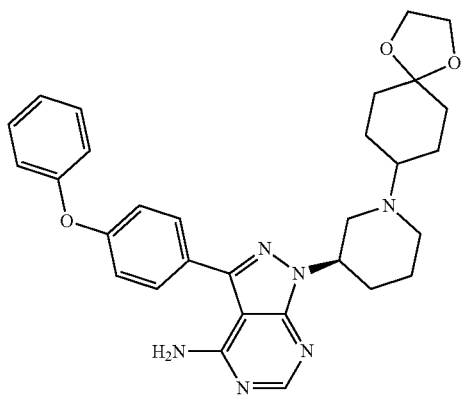 [SMILES: Nc1ncnc2c1c(-c1ccc(Oc3ccccc3)cc1)nn2[C@@H]1CCCN(C2CCC3(CC2)OCCO3)C1]

(R)-3-(4-phenoxyphenyl)-1-(piperidin-3-yl)-1H-pyrazolo[3,4-d]pyrimidin-4-amine (28a) (1.00 g, 2.59 mmol) was dissolved in 10 mL of chloroform, and 1,4-dioxaspiro[4.5]decan-8-one (0.606 g, 3.88 mmol) and glacial acetic acid (0.311 g, 5.18 mmol) were added. Upon completion of the addition, the reaction was carried out at 70° C. for 3 h, then cooled to room temperature, and sodium triacetoxyborohydride (1.10 g, 5.18 mmol) was added. Upon completion of the addition, the reaction was carried out at room temperature for 2 h. To the reaction system was added dropwise saturated sodium bicarbonate solution to adjust the pH to 9-10, and same was concentrated under reduced pressure, then the crude product was separated and purified by silica gel column chromatography (dichloromethane/methanol (v/v)=100:0-19:1), to obtain 1-[(3R)-1-(1,4-dioxaspiro[4.5]decan-8-yl)-3-piperidyl]-3-(4-phenoxyphenyl)pyrazolo[3,4-d]pyrimidin-4-amine (34a) (0.530 g, yield: 39%).

LCMS m/z=527.3 [M+1]$^+$.

Step 2

4-[(3R)-3-[4-amino-3-(4-phenoxyphenyl)pyrazolo[3,4-d]pyrimidin-1-yl]-1-piperidyl]cyclohexanone (34b)

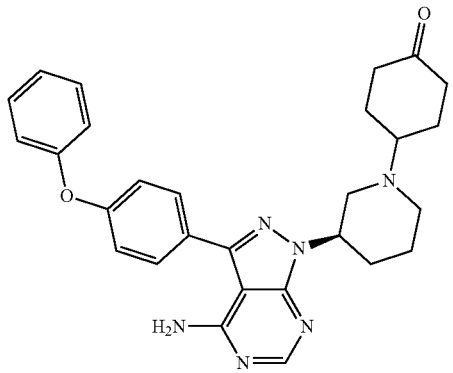 [SMILES: Nc1ncnc2c1c(-c1ccc(Oc3ccccc3)cc1)nn2[C@@H]1CCCN(C2CCC(=O)CC2)C1]

416

1-[(3R)-1-(1,4-dioxaspiro[4.5]decan-8-yl)-3-piperidyl]-3-(4-phenoxyphenyl)pyrazolo[3,4-d]pyrimidin-4-amine (34a) (0.530 g, 1.01 mmol) was dissolved in 5 mL of tetrahydrofuran, and 5 mL of 4N hydrochloric acid aqueous solution was added, the mixture was stirred at room temperature for 1 h. The reaction solution was concentrated, and then to the residue was added 20 mL of dichloromethane. The pH was adjusted to 9-10 with saturated sodium bicarbonate solution. The liquid separation was conducted, the aqueous layer was further extracted with 20 mL of dichloromethane, and the organic layers were combined, dried over anhydrous sodium sulfate, and concentrated under reduced pressure to obtain 4-[(3R)-3-[4-amino-3-(4-phenoxyphenyl)pyrazolo[3,4-d]pyrimidin-1-yl]-1-piperidyl]cyclohexanone (34b) (0.480 g, yield: 99%).

Step 3 tert-butyl 3-[2-(2,6-dioxo-3-piperidyl)-1,3-dioxo-isoindolin-5-yl]oxyazetidine-1-carboxylate (34d)

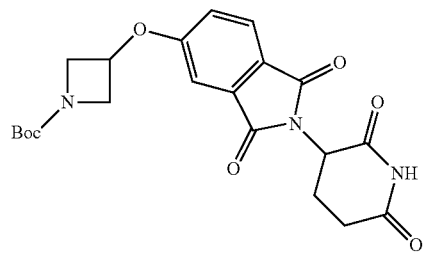 [SMILES: CC(C)(C)OC(=O)N1CC(Oc2ccc3c(c2)C(=O)N(C2CCC(=O)NC2=O)C3=O)C1]

2-(2,6-dioxopiperidin-3-yl)-5-hydroxyl isoindoline-1,3-dione (34c) (see US20180099940 for the synthetic method) (1.00 g, 3.65 mmol) was dissolved in 10 mL of DMF, and tert-butyl 3-((methylsulfonyl)oxy)azetidine-1-carboxylate (1.01 g, 4.01 mmol) and cesium carbonate (2.38 g, 7.29 mmol) were added. Upon completion of the addition, the reaction was carried out at 110° C. under microwave for 2 h. The reaction solution was cooled to room temperature, and 20 mL of water and 50 mL of ethyl acetate were added. The liquid separation was conducted, the aqueous layer was further extracted with 20 mL of ethyl acetate, and the organic layers were combined. The organic phase was washed with 20 mL of saturated sodium chloride, dried over anhydrous sodium sulfate, and concentrated under reduced pressure. The resulting crude product was separated and purified by silica gel column chromatography (petroleum ether/ethyl acetate (v/v)=4:1-1:1), to obtain tert-butyl 3-[2-(2,6-dioxo-3-piperidyl)-1,3-dioxo-isoindolin-5-yl]oxyazetidine-1-carboxylate (34d) (0.670 g, yield: 43%).

Step 4

5-(azetidin-3-yloxy)-2-(2,6-dioxo-3-piperidyl)isoindoline-1,3-dione hydrochloride (34e)

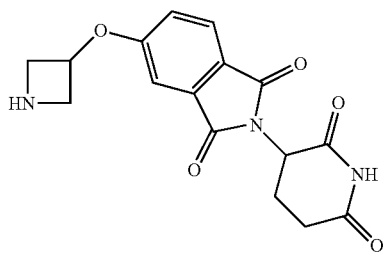 [SMILES: O=C1CCC(N2C(=O)c3ccc(OC4CNC4)cc3C2=O)C(=O)N1]

Tert-butyl 3-[2-(2,6-dioxo-3-piperidyl)-1,3-dioxo-isoindolin-5-yl]oxyazetidine-1-carboxylate (34d) (0.670 g, 1.56 mmol) was dissolved in 2 mL of dichloromethane, and 10 mL of 2N ethyl acetate hydrochloride solution was added, the mixture was stirred at room temperature for 2 h. The reaction solution was filtered, and the filter cake was collected, and dried to obtain 5-(azetidin-3-yloxy)-2-(2,6-dioxo-3-piperidyl)isoindoline-1,3-dione hydrochloride (34e) (0.484 g).

LCMS m/z=330.1 [M+1]$^+$.

Step 5

5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-a)

5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-b)

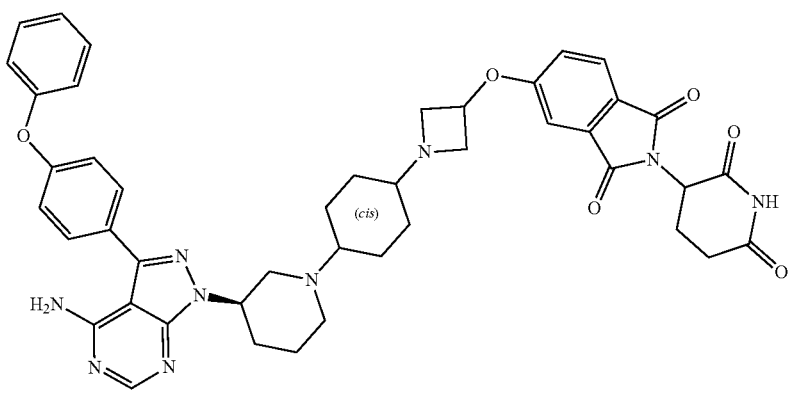

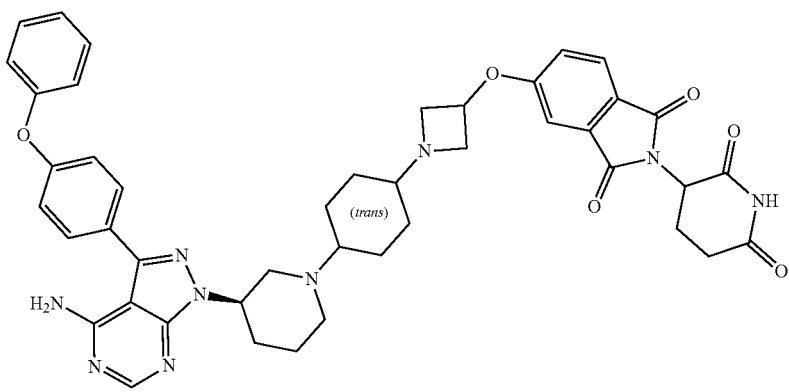

5-(azetidin-3-yloxy)-2-(2,6-dioxo-3-piperidyl)isoindoline-1,3-dione hydrochloride (34e) (0.066 g) was dissolved in 2 mL of anhydrous methanol, and sodium bicarbonate solid (0.020 g, 0.24 mmol) was added. The mixture was stirred at room temperature for 20 minutes, and filtered, the filter cake was washed with 1 mL of methanol, and the filtrate was combined and concentrated, then the residue was dissolved in 2 mL of chloroform. 0.5 mL of DMSO, glacial acetic acid (0.022 g, 0.36 mmol) and 4-[(3R)-3-[4-amino-3-(4-phenoxyphenyl)pyrazolo[3,4-d]pyrimidin-1-yl]-1-piperidyl]cyclohexanone (34b) (0.13 g, 0.27 mmol) were added. Upon completion of the addition, the reaction was stirred at 70° C. for 5 h, and cooled to room temperature. Sodium triacetoxyborohydride (0.077 g, 0.36 mmol) was added, and the reaction was carried out at room temperature overnight. To the reaction system was added dropwise saturated sodium bicarbonate solution to adjust the pH to 9-10, and 20 mL of dichloromethane was added. The liquid separation was conducted, the aqueous layer was further extracted with 10 mL of dichloromethane once, and the organic layers were combined, dried over anhydrous sodium sulfate, and concentrated under reduced pressure, then the crude product was separated and purified by silica gel column chromatography (dichloromethane/methanol (v/v) =100:0-6:1), to obtain two pure products, 5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-a) (23 mg) and 5-[1-[4-[(3R)-3-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 34-b) (25 mg).

Compound 34-a: (developing solvent: dichloromethane/methanol=10:1, Rf value=0.45)

$^1$H NMR (400 MHz, CDCl$_3$) δ 8.79 (s, 1H), 8.39 (s, 1H), 7.77 (d, 1H), 7.67-7.61 (m, 2H), 7.42-7.34 (m, 2H), 7.21-7.12 (m, 4H), 7.11-7.05 (m, 3H), 5.64 (brs, 2H), 5.54-5.37 (m, 1H), 4.95 (dd, 1H), 4.88-4.79 (m, 1H), 3.89-3.77 (m, 2H), 3.54-3.40 (m, 1H), 3.36-3.15 (m, 2H), 3.12-3.01 (m, 2H), 2.95-2.65 (m, 5H), 2.46-2.40 (m, 1H), 2.28-2.09 (m, 4H), 2.06-1.95 (m, 3H), 1.92-1.72 (m, 5H), 1.49-1.44 (m, 1H).

LCMS m/z=796.3 [M+1]$^+$.

Compound 34-b: (developing solvent: dichloromethane/methanol=10:1, Rf value=0.35)

$^1$H NMR (400 MHz, CDCl$_3$) δ 8.77 (s, 1H), 8.37 (s, 1H), 7.78 (d, 1H), 7.66-7.60 (m, 2H), 7.42-7.36 (m, 2H), 7.20-7.05 (m, 7H), 5.60 (brs, 2H), 5.32-5.16 (m, 1H), 4.99-4.88 (m, 2H), 3.99-3.87 (m, 2H), 3.42-3.00 (m, 5H), 2.94-2.62 (m, 5H), 2.58-2.46 (m, 1H), 2.27-2.06 (m, 8H), 1.98-1.88 (m, 2H), 1.53-1.44 (m, 1H), 1.20-1.11 (m, 2H).

LCMS m/z=796.4 [M+1]$^+$.

Example 35

5-[4-[4-[4-[4-amino-3-(4-phenoxyphenyl)pyrazolo[3,4-d]pyrimidin-1-yl]-1-piperidyl]pyrazol-1-yl]-1-piperidyl]-2-(2,6-dioxo-3-piperidyl)isoindoline-1,3-dione (Compound 35)

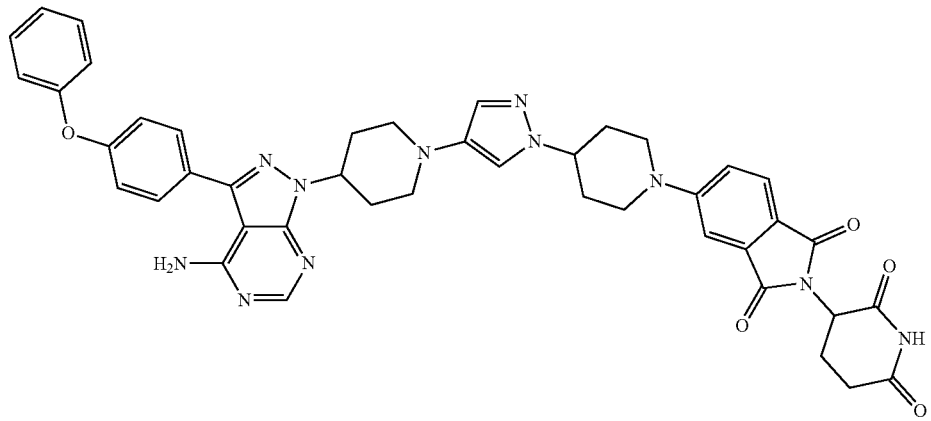

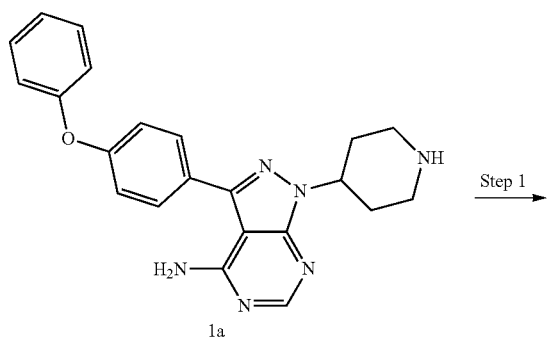

-continued

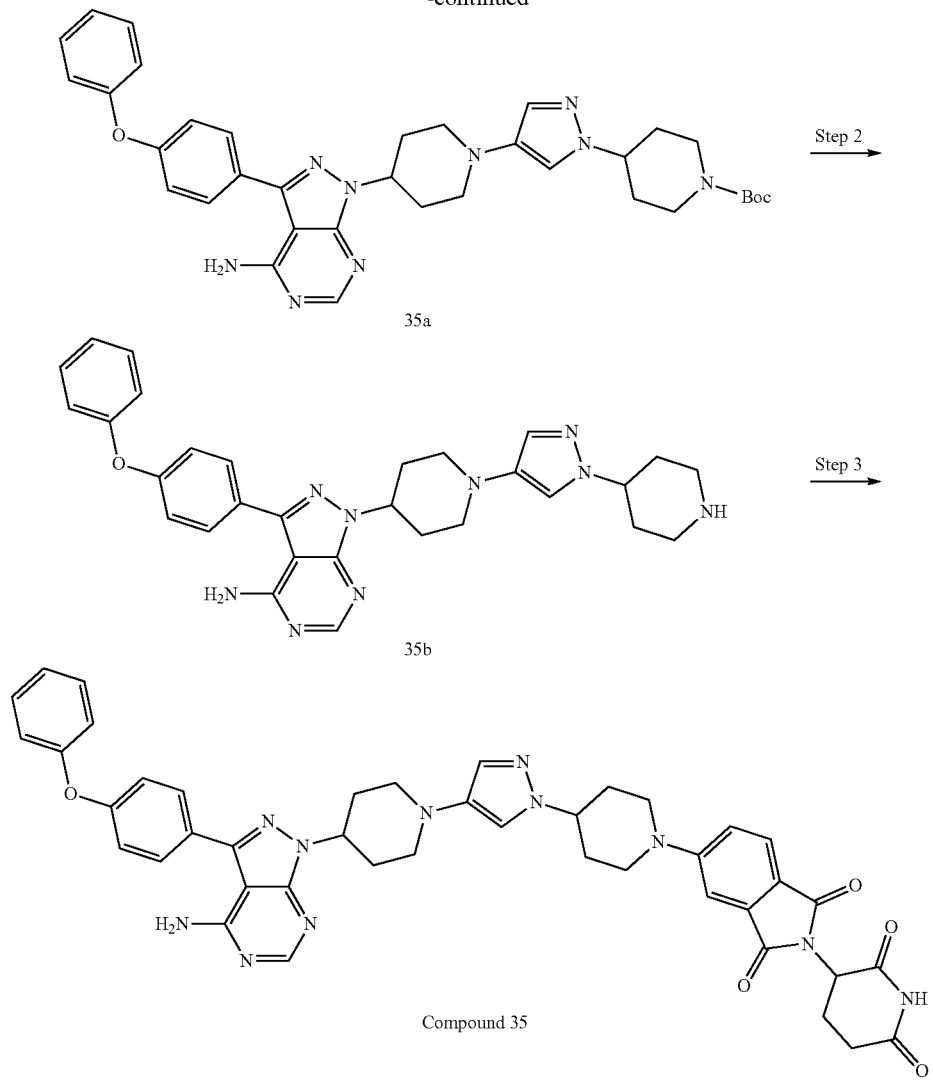

35a

35b

Compound 35

Step 1 tert-butyl 4-[4-[4-[4-amino-3-(4-phenoxyphenyl)pyrazolo[3,4-d]pyrimidin-1-yl]-1-piperidyl]pyrazol-1-yl]piperidine-1-carboxylate (35a)

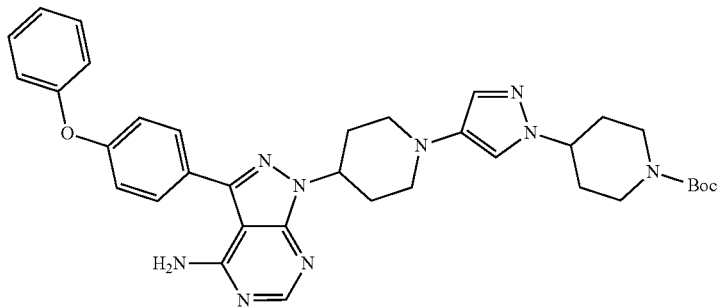 [SMILES: CC(C)(C)OC(=O)N1CCC(n2cc(N3CCC(n4nc(-c5ccc(Oc6ccccc6)cc5)c5c(N)ncnc54)CC3)cn2)CC1]

Tert-butyl 4-(4-iodopyrazol-1-yl)piperidine-1-carboxylate (0.500 g, 1.33 mmol) was dissolved in 2 mL of dimethyl sulfoxide, and 3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (0.615 g, 1.59 mmol), L-proline (0.0610 g, 0.530 mmol) and potassium carbonate (0.550 g, 3.98 mmol) were successively added. Nitrogen replacement was carried out three times, and cuprous iodide (0.0505 g, 0.265 mmol) was added. Upon completion of the addition, the mixture was heated to 100° C. and reacted for 5 h. The reaction solution was cooled to room temperature, and 5 mL of water and 10 mL of ethyl acetate were added. The liquid separation was conducted, the aqueous layer was further extracted with 10 mL of ethyl acetate, and the organic layers were combined. The organic phase was washed with 10 mL of saturated sodium chloride, dried over anhydrous sodium sulfate, and concentrated under reduced pressure. The resulting crude product was separated and purified by silica gel column chromatography (dichloromethane/methanol (v/v)=100:0-19:1), to obtain tert-butyl 4-[4-[4-[4-[4-amino-3-(4-phenoxyphenyl)pyrazolo[3,4-d]pyrimidin-1-yl]-1-piperidyl]pyrazol-1-yl]piperidine-1-carboxylate (35a) (0.0730 g, yield: 9%).

Step 2

3-(4-phenoxyphenyl)-1-[1-[1-(4-piperidyl)pyrazol-4-yl]-4-piperidyl]pyrazolo[3,4-d]pyrimidin-4-amine (35b)

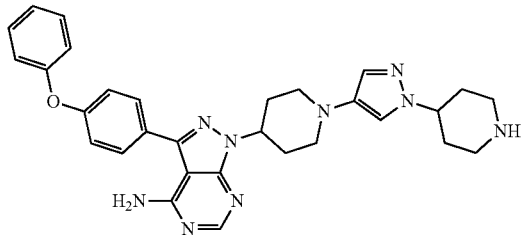 [SMILES: Nc1ncnc2c1c(-c1ccc(Oc3ccccc3)cc1)nn2C1CCN(c2cnn(C3CCNCC3)c2)CC1]

Tert-butyl

4-[4-[4-[4-[4-amino-3-(4-phenoxyphenyl)pyrazolo[3,4-d]pyrimidin-1-yl]-1-piperidyl]pyrazol-1-yl]piperidine-1-carboxylate (35a) (0.0730 g, 0.115 mmol) was dissolved in 2 mL of dichloromethane, and 5 mL of 4N ethyl acetate hydrochloride solution was added, the mixture was stirred at room temperature for 2 h. The reaction solution was concentrated, then to the crude product was added 20 mL of dichloromethane, and the pH was adjusted to 9-10 with saturated sodium bicarbonate solution. The liquid separation was conducted, the organic layer was dried over anhydrous sodium sulfate, and concentrated under reduced pressure to obtain 3-(4-phenoxyphenyl)-1-[1-[1-(4-piperidyl)pyrazol-4-yl]-4-piperidyl]pyrazolo[3,4-d]pyrimidin-4-amine (35b) (0.0615g, yield: >99%).

Step 3

5-[4-[4-[4-[4-amino-3-(4-phenoxyphenyl)pyrazolo[3,4-d]pyrimidin-1-yl]-1-piperidyl]pyrazol-1-yl]-1-piperidyl]-2-(2,6-dioxo-3-piperidyl)isoindoline-1,3-dione (Compound 35)

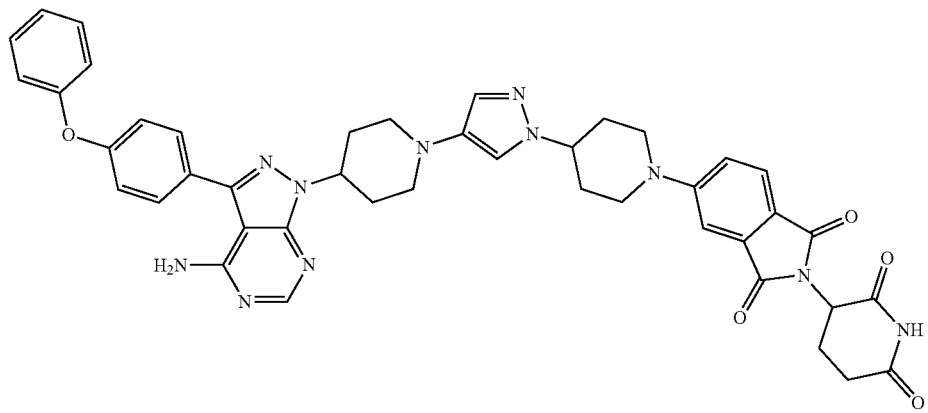 [SMILES: Nc1ncnc2c1c(-c1ccc(Oc3ccccc3)cc1)nn2C1CCN(c2cnn(C3CCN(c4ccc5c(c4)C(=O)N(C4CCC(=O)NC4=O)C5=O)CC3)c2)CC1]

3-(4-phenoxyphenyl)-1-[1-[1-(4-piperidyl)pyrazol-4-yl]-4-piperidyl]pyrazolo[3,4-d]pyrimidin-4-amine (35b) (0.0600 g, 0.112 mmol) was dissolved in 2 mL of dimethyl sulfoxide, and 2-(2,6-dioxopiperidin-3-yl)-5-fluoroisoindoline-1,3-dione (see WO 2017197056 for the synthetic method) (0.0402 g, 0.146 mmol) and diisopropylethylamine (0.0724 g, 0.560 mmol) were added. Upon completion of the addition, the reaction was stirred at 90° C. for 2 h. The reaction solution was cooled to room temperature, added 10 mL of water, and filtered. The filter cake was dissolved with 20 mL of dichloromethane, then washed with 5 mL of saturated sodium chloride, dried over anhydrous sodium sulfate, and concentrated under reduced pressure. The resulting crude product was separated and purified by silica gel column chromatography (dichloromethane/methanol (v/v) =100:0-92:8), to obtain 5-[4-[4-[4-[4-amino-3-(4-phenoxyphenyl)pyrazolo[3,4-d]pyrimidin-1-yl]-1-piperidyl]pyrazol-1-yl]-1-piperidyl]-2-(2,6-dioxo-3-piperidyl)isoindoline-1,3-dione (Compound 35) (0.0350 g, yield: 40%).

$^1$H NMR (400 MHz, CDCl$_3$) δ 8.36 (s, 1H), 8.23 (s, 1H), 7.73-7.69 (m, 1H), 7.68-7.60 (m, 2H), 7.43-7.36 (m, 2H), 7.33 (d, 1H), 7.29-7.26 (m, 2H), 7.21-7.05 (m, 6H), 6.15 (brs, 2H), 4.99-4.83 (m, 2H), 4.36-4.28 (m, 1H), 4.12-4.02 (m, 2H), 3.58-3.49 (m, 2H), 3.23-3.12 (m, 2H), 2.95-2.67 (m, 5H), 2.63-2.50 (m, 2H), 2.30-2.21 (m, 2H), 2.18-2.05 (m, 5H).

LCMS m/z=792.3 [M+1]$^+$.

Example 36
5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 36-a) 5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione trifluoroacetate (Compound 36-b)
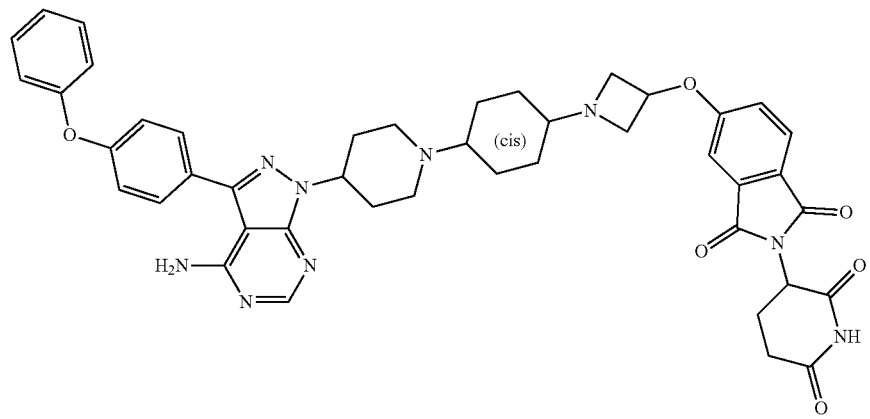
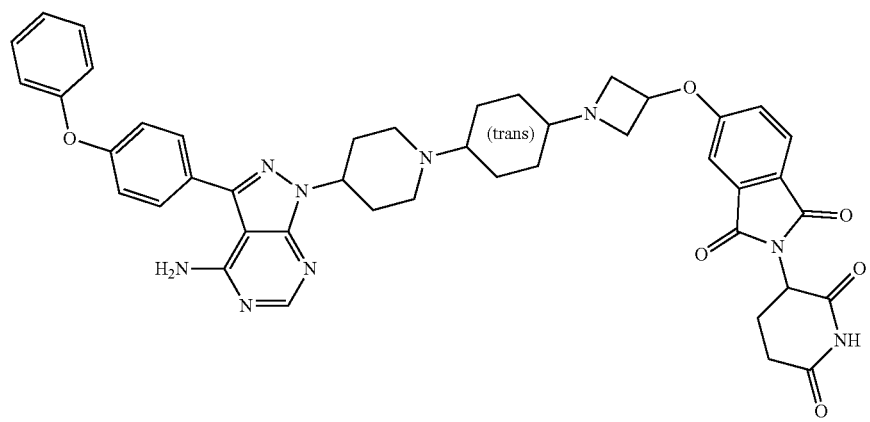
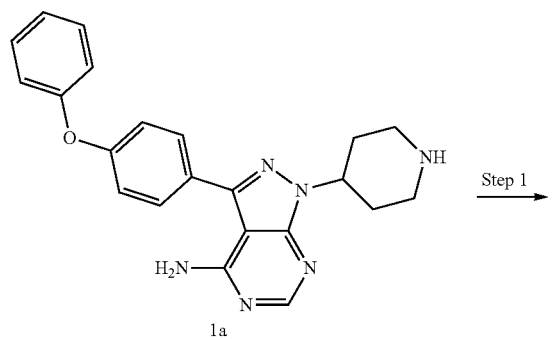

-continued
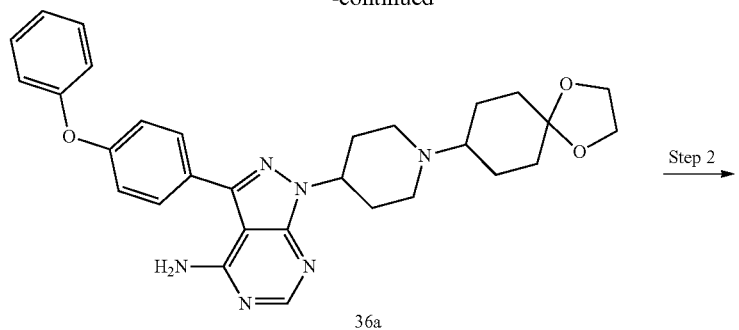
36a
Step 2 →
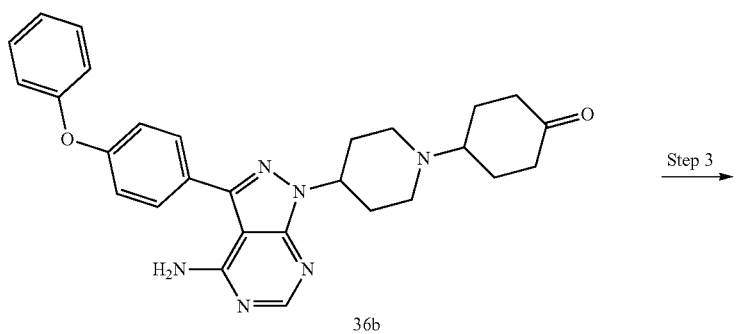
36b
Step 3 →
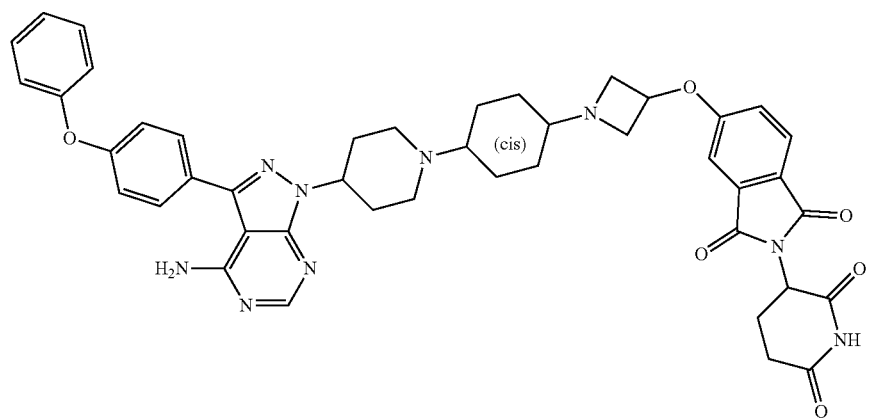
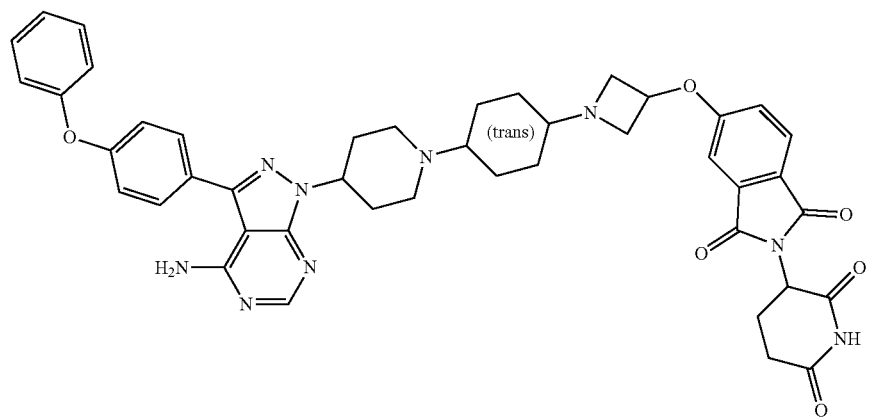
Compound 36-a and Compound 36-b

Step 1

1-[1-(1,4-dioxaspiro[4.5]decan-8-yl)-4-piperidyl]-3-(4-phenoxyphenyl)pyrazolo[3,4-d]pyrimidin-4-amine (36a)

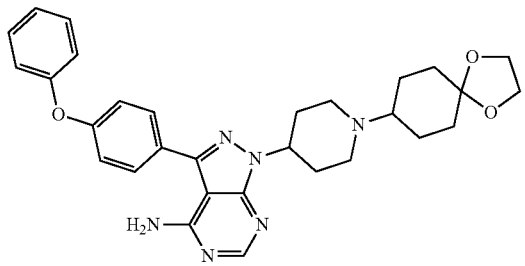 [SMILES: Nc1ncnc2c1c(-c1ccc(Oc3ccccc3)cc1)nn2C1CCN(C2CCC3(CC2)OCCO3)CC1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.00 g, 2.59 mmol) was dissolved in 5 mL of 1,2-dichloroethane, and 1,4-dioxaspiro[4.5]decan-8-one (0.606 g, 3.88 mmol) and glacial acetic acid (0.311 g, 5.18 mmol) was added. Upon completion of the addition, the reaction was stirred at 65° C. for 3 h, then cooled to room temperature, and sodium triacetoxyborohydride (1.10 g, 5.18 mmol) was added. Upon completion of the addition, the reaction was carried out at room temperature for 2 h. To the reaction solution was added dropwise saturated sodium bicarbonate solution to adjust the pH to 9-10, and same was concentrated under reduced pressure, then the crude product was separated and purified by silica gel column chromatography (dichloromethane/methanol (v/v)=100:0-19:1), to obtain 1-[1-(1,4-dioxaspiro[4.5]decan-8-yl)-4-piperidyl]-3-(4-phenoxyphenyl)pyrazolo[3,4-d]pyrimidin-4-amine (36a) (0.800 g, yield: 59%).

LCMS m/z=527.3 [M+1]$^+$.

Step 2

4-[4-[4-amino-3-(4-phenoxyphenyl)pyrazolo[3,4-d]pyrimidin-1-yl]-1-piperidyl]cyclohexanone (36b)

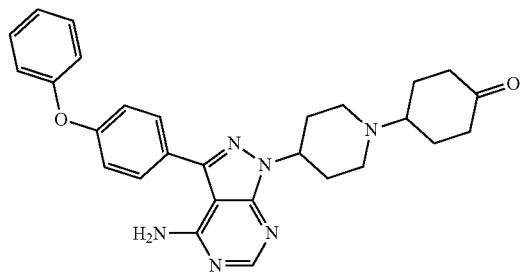 [SMILES: Nc1ncnc2c1c(-c1ccc(Oc3ccccc3)cc1)nn2C1CCN(C2CCC(=O)CC2)CC1]

1-[1-(1,4-dioxaspiro[4.5]decan-8-yl)-4-piperidyl]-3-(4-phenoxyphenyl)pyrazolo[3,4-d]pyrimidin-4-amine (36a) (0.800 g, 1.52 mmol) was dissolved in 10 mL of tetrahydrofuran, and 10 mL of 4N hydrochloric acid aqueous solution was added, the mixture was stirred at room temperature for 1 h. The reaction solution was concentrated, and to the residue was added 20 mL of dichloromethane. The pH was adjusted to 9-10 with saturated sodium bicarbonate solution. The aqueous phase was further extracted with 20 mL of dichloromethane, and the organic layers were combined, dried over anhydrous sodium sulfate, and concentrated under reduced pressure. The resulting product was separated and purified by silica gel column chromatography (dichloromethane/methanol (v/v)=19:1-9:1), to obtain 4-[4-[4-amino-3-(4-phenoxyphenyl)pyrazolo[3,4-d]pyrimidin-1-yl]-1-piperidyl]cyclohexanone (36b) (0.600 g, yield: 82%).

LCMS m/z=483.3 [M+1]$^+$.

Step 3

5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 36-a)

5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione trifluoroacetate (Compound 36-b)

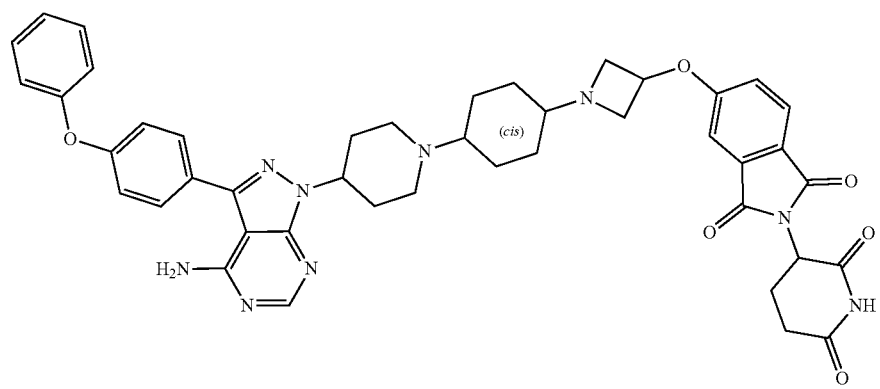

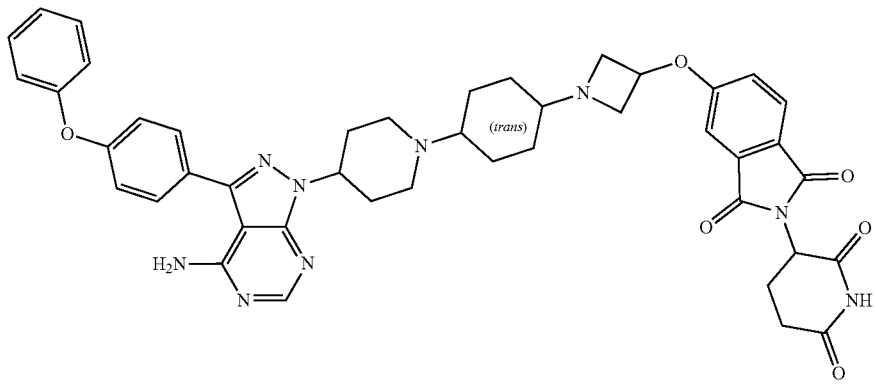

5-(azetidin-3-yloxy)-2-(2,6-dioxo-3-piperidyl)isoindoline-1,3-dione hydrochloride (34e) (0.056 g, 0.15 mmol) was dissolved in 2 mL of anhydrous methanol, and sodium bicarbonate solid (0.017 g, 0.20 mmol) was added. The mixture was stirred at room temperature for 20 minutes, and filtered, the filter cake was washed with 1 mL of methanol, and the filtrate was combined and concentrated, then the residue was dissolved in 2 mL of chloroform. 0.5 mL of DMSO, glacial acetic acid (0.018 g, 0.30 mmol) and 4-[4-[4-amino-3-(4-phenoxyphenyl)pyrazolo[3,4-d]pyrimidin-1-yl]-1-piperidyl]cyclohexanone (36b) (0.11 g, 0.23 mmol) were successively added. Upon completion of the addition, the reaction was stirred at 70° C. for 5 h, and cooled to room temperature. Sodium triacetoxyborohydride (0.064 g, 0.30 mmol) was added, and the reaction was carried out at room temperature overnight. To the reaction system was added dropwise saturated sodium bicarbonate solution to adjust the pH to 9-10, and 20 mL of dichloromethane was added. The liquid separation was conducted, the aqueous layer was further extracted with 10 mL of dichloromethane once, and the organic layers were combined, dried over anhydrous sodium sulfate, and concentrated under reduced pressure, then the crude product was separated and purified by silica gel column chromatography (dichloromethane/methanol (v/v)=100:0-6:1), to obtain the pure product 5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione (Compound 36-a) (0.020 g) and another isomer crude product. The crude product was passed through Pre-HPLC (instrument and preparative column: using Glison GX-281 to prepare the liquid phase, preparative column model: Sunfire C18, 5 μm, inner diameter×length=30 mm×150 mm). Preparation method: The crude product was dissolved with methanol and dimethyl sulfoxide, and filtered with 0.45 μm filter membrane, to prepare into a sample solution. Mobile phase system: acetonitrile/water (containing 0.1% TFA). Gradient elution method: gradient elution with acetonitrile from concentration of 5% to concentration of 60% (elution time: 15 min), the reaction system was lyophilized to obtain the pure product 5-[1-[4-[4-[4-amino-3-(4-phenoxyphenyl)pyrazolo[3,4-d]pyrimidin-1-yl]-1-piperidyl]cyclohexyl]azetidin-3-yl]oxy-2-(2,6-dioxo-3-piperidyl)isoindoline-1,3-dione trifluoroacetate (Compound 36-b) (7 mg).

Compound 36-a: (developing solvent: dichloromethane/methanol=10:1, Rf value=0.45)

$^1$H NMR (400 MHz, DMSO-$d_6$) δ 11.09 (s, 1H), 8.27 (s, 1H), 7.89-7.83 (m, 1H), 7.66 (d, 2H), 7.47-7.41 (m, 2H), 7.33-7.28 (m, 2H), 7.23-7.10 (m, 5H), 5.16-5.00 (m, 3H), 3.87-3.75 (m, 2H), 3.58-3.39 (m, 4H), 3.22-3.05 (m, 3H), 2.95-2.84 (m, 1H), 2.68-2.53 (m, 3H), 2.46-2.40 (m, 1H), 2.26-2.14 (m, 2H), 2.09-1.95 (m, 2H), 1.84-1.68 (m, 5H), 1.49-1.37 (m, 3H).

LCMS m/z=796.3 [M+1]$^+$.

Compound 36-b: (developing solvent: dichloromethane/methanol=10:1, Rf value=0.35)

$^1$H NMR (400 MHz, DMSO-$d_6$) δ 11.11 (s, 1H), 8.30 (s, 1H), 7.92 (d, 1H), 7.74-7.61 (m, 2H), 7.50-7.32 (m, 4H), 7.26-7.09 (m, 5H), 5.38-5.29 (m, 1H), 5.18-5.05 (m, 2H), 4.78-4.63 (m, 2H), 4.43-4.24 (m, 2H), 3.66-3.56 (m, 2H), 3.28-3.21 (m, 3H), 2.95-2.84 (m, 1H), 2.68-2.54 (m, 2H), 2.29-1.94 (m, 8H), 1.60-1.45 (m, 2H), 1.36-1.22 (m, 4H).

LCMS m/z=796.2 [M+1]$^+$.

Example 37
5-[4-[3-[4-[4-amino-3-(4-phenoxyphenyl)pyrazolo[3,4-d]pyrimidin-1-yl]-1-piperidyl]azetidin-1-yl]cyclohexoxy]-2-(2,6-dioxo-3-piperidyl)isoindoline-1,3-dione (Compound 37)
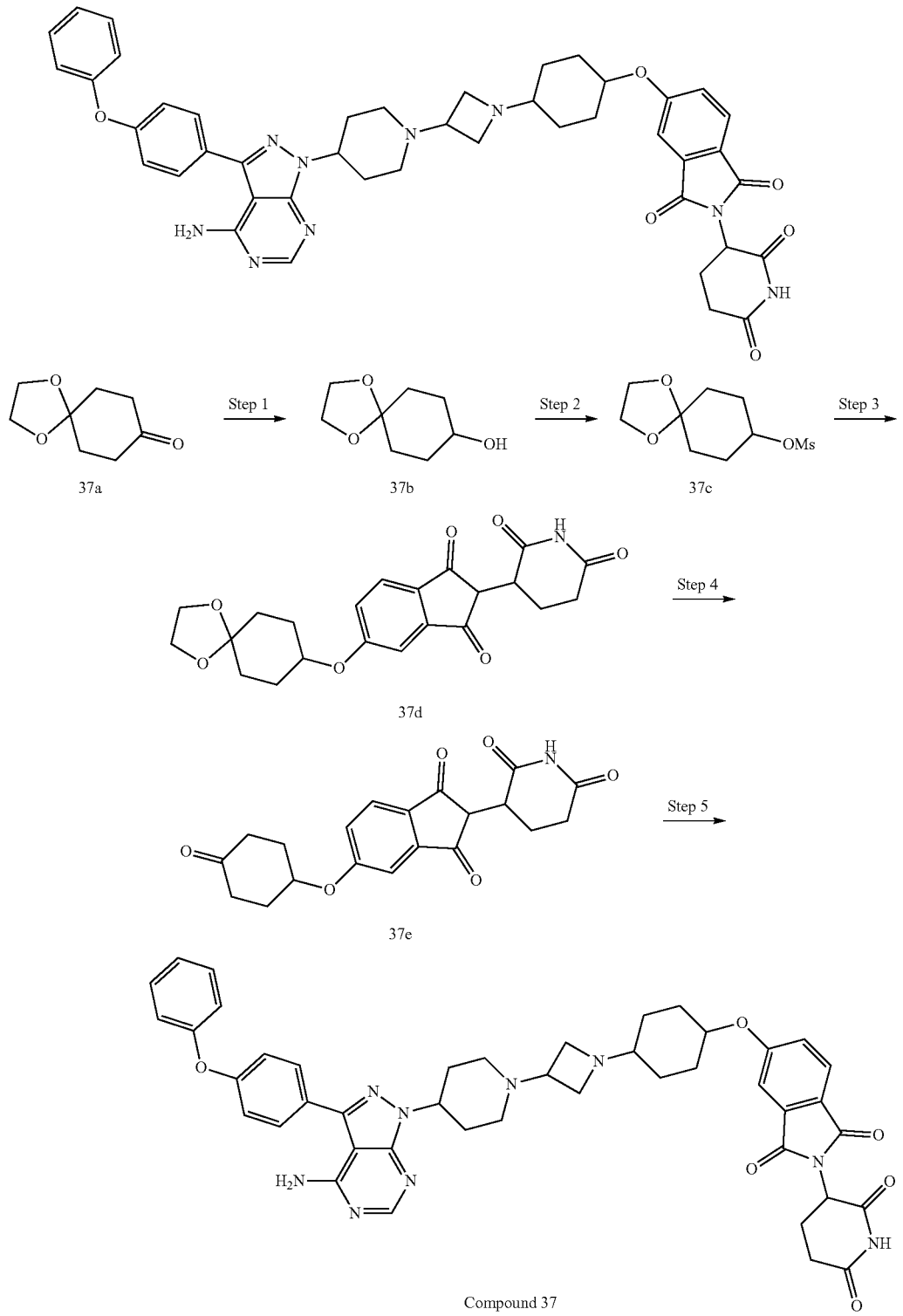

Step 1

1,4-dioxaspiro[4.5]decan-8-ol (37b)

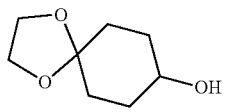

1,4-dioxaspiro[4.5]decan-8-one (37a) (1.00 g, 6.40 mmol) was dissolved in 10 mL of anhydrous methanol, and sodium borohydride (0.484 g, 12.8 mmol) was slowly added. Upon completion of the addition, the reaction was carried out at room temperature for 20 minutes. To the reaction system was slowly added dropwise 20 mL of saturated ammonium chloride aqueous solution, and the resulted solution was extracted with dichloromethane (30 mL×2). The organic layers were combined, dried over anhydrous sodium sulfate, and concentrated under reduced pressure to obtain 1,4-dioxaspiro[4.5]decan-8-ol (37b) (0.800 g, yield: 79%).

Step 2

1,4-dioxaspiro[4.5]decan-8-yl methanesulfonate (37c)

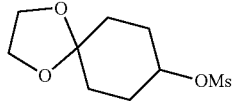 [SMILES: CS(=O)(=O)OC1CCC2(CC1)OCCO2]

1,4-dioxaspiro[4.5]decan-8-ol (37b) (0.800 g, 5.06 mmol) was dissolved in 10 mL of dichloromethane, and triethylamine (1.28 g, 12.6 mmol) was added, and the mixture was cooled to 0° C. in an ice bath, and then methanesulfonyl chloride (1.16 g, 10.1 mmol) was slowly added. Upon completion of the addition, the mixture was slowly warmed to room temperature and reacted for 2 h. To the reaction system was added 20 mL of saturated sodium bicarbonate solution and 20 mL of dichloromethane. The liquid separation was conducted, and the organic layer was dried over anhydrous sodium sulfate, and concentrated under reduced pressure. The crude product was separated and purified by silica gel column chromatography (ethyl acetate/petroleum ether (v/v)=1:4-3:7), to obtain 1,4-dioxaspiro[4.5]decan-8-yl methanesulfonate (37c) (0.640 g, yield: 54%).

Step 3

5-(1,4-dioxaspiro[4.5]decan-8-yloxy)-2-(2,6-dioxo-3-piperidyl)isoindoline-1,3-dione (37d)

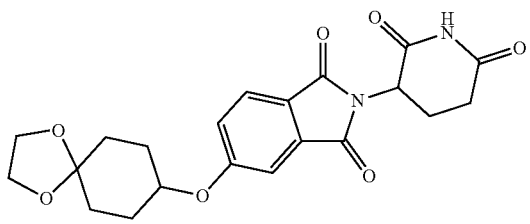 [SMILES: O=C1CCC(N2C(=O)c3ccc(OC4CCC5(CC4)OCCO5)cc3C2=O)C(=O)N1]

2-(2,6-dioxopiperidin-3-yl)-5-hydroxyl isoindoline-1,3-dione (34c) (see US20180099940 for the synthetic method) (0.0500 g, 0.182 mmol) was dissolved in 2 mL of DMF, and 1,4-dioxaspiro[4.5]decan-8-yl methanesulfonate (37c) (0.0474 g, 0.201 mmol) and cesium carbonate (0.119 g, 0.365 mmol) were added. Upon completion of the addition, the reaction was stirred at 110° C. under microwave for 2 h. The reaction solution was cooled to room temperature, and 20 mL of water and 50 mL of ethyl acetate were added. The liquid separation was conducted, the aqueous layer was further extracted with 20 mL of ethyl acetate, and the organic layers were combined. The organic phase was washed with 20 mL of saturated sodium chloride, dried over anhydrous sodium sulfate, and concentrated under reduced pressure. The crude product was separated and purified by silica gel column chromatography (ethyl acetate/petroleum ether (v/v)=1:4-1:1), to obtain 5-(1,4-dioxaspiro[4.5]decan-8-yloxy)-2-(2,6-dioxo-3-piperidyl)isoindoline-1,3-dione (37d) (0.0240 g, yield: 32%).

LCMS m/z=415.1 [M+1]$^+$.

Step 4

2-(2,6-dioxo-3-piperidyl)-5-(4-oxocyclohexoxy)isoindoline-1,3-dione (37e)

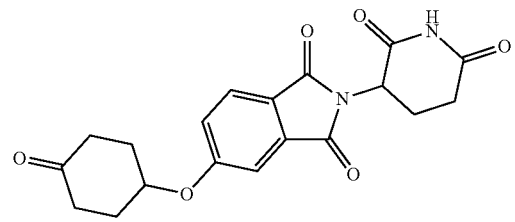 [SMILES: O=C1CCC(Oc2ccc3c(c2)C(=O)N(C2CCC(=O)NC2=O)C3=O)CC1]

5-(1,4-dioxaspiro[4.5]decan-8-yloxy)-2-(2,6-dioxo-3-piperidyl)isoindoline-1,3-dione (37d) (0.024 g, 0.058 mmol) was dissolved in 5 mL of tetrahydrofuran, and 5 mL of 4N hydrochloric acid aqueous solution was added, the mixture was stirred at room temperature for 1 h. The reaction solution was concentrated, and to the crude product was added 20 mL of dichloromethane. The pH was adjusted to 9-10 with saturated sodium bicarbonate solution. The liquid separation was conducted, the aqueous layer was further extracted with 20 mL of dichloromethane, and the organic layers were combined, dried over anhydrous sodium sulfate, and concentrated under reduced pressure to obtain 2-(2,6-dioxo-3-piperidyl)-5-(4-oxocyclohexoxy)isoindoline-1,3-dione (37e) (0.021 g, yield: >99%).

LCMS m/z=371.1 [M+1]$^+$.

Step 5

5-[4-[3-[4-[4-amino-3-(4-phenoxyphenyl)pyrazolo[3,4-d]pyrimidin-1-yl]-1-piperidyl]azetidin-1-yl]cyclohexoxy]-2-(2,6-dioxo-3-piperidyl)isoindoline-1,3-dione (Compound 37)

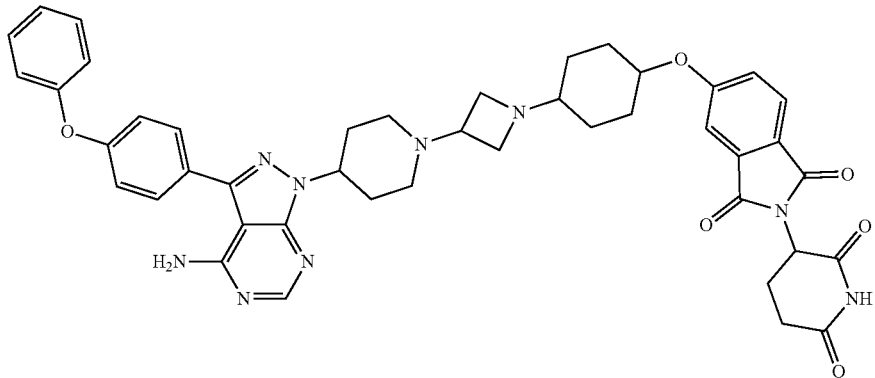 [SMILES: Nc1ncnc2c1c(-c1ccc(Oc3ccccc3)cc1)nn2C1CCN(C2CN(C3CCC(Oc4ccc5c(c4)C(=O)N(C4CCC(=O)NC4=O)C5=O)CC3)C2)CC1]

1-[1-(azetidin-3-yl)-4-piperidyl]-3-(4-phenoxyphenyl)pyrazolo[3,4-d]pyrimidin-4-amine (17b) (0.025 g, 0.057 mmol) was dissolved in 2 mL of chloroform, and glacial acetic acid (0.0068 g, 0.11 mmol) and 2-(2,6-dioxo-3-piperidyl)-5-(4-oxocyclohexoxy)isoindoline-1,3-dione (37e) (0.021 g, 0.057 mmol) were added. Upon completion of the addition, the reaction was stirred at 70° C. for 5 h, and cooled to room temperature. Sodium triacetoxyborohydride (0.024 g, 0.11 mmol) was added, and the reaction was carried out at room temperature overnight. To the reaction solution was added dropwise saturated sodium bicarbonate solution to adjust the pH to 9-10, and 20 mL of dichloromethane was added. The liquid separation was conducted, the aqueous phase was further extracted with 10 mL of dichloromethane, and the organic layers were combined, dried over anhydrous sodium sulfate, and concentrated under reduced pressure, then the crude product was separated and purified by silica gel column chromatography (dichloromethane/methanol (v/v)=100:0-6:1), to obtain 5-[4-[3-[4-[4-amino-3-(4-phenoxyphenyl)pyrazolo[3,4-d]pyrimidin-1-yl]-1-piperidy l]azetidin-1-yl]cyclohexoxy]-2-(2,6-dioxo-3-piperidyl)isoindoline-1,3-dione (Compound 37) (0.020 g, yield: 44%).

$^1$H NMR (400 MHz, DMSO-$d_6$) δ 11.09 (s, 1H), 8.26-8.20 (m, 1H), 7.86-7.77 (m, 1H), 7.69-7.63 (m, 2H), 7.50-7.39 (m, 3H), 7.38-7.32 (m, 1H), 7.23-7.08 (m, 5H), 5.15-5.07 (m, 1H), 4.81-4.59 (m, 2H), 3.60-3.39 (m, 3H), 2.95-2.81 (m, 4H), 2.64-2.53 (m, 2H), 2.26-2.11 (m, 3H), 2.10-1.73 (m, 9H), 1.70-1.36 (m, 5H).

LCMS m/z=796.3 [M+1]$^+$.

Example 38

5-[3-[3-[(3S,4R)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 38)

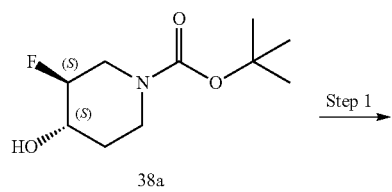
38a
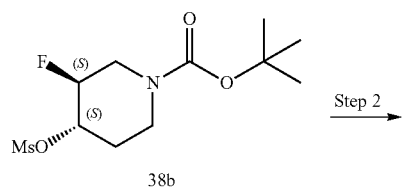
38b
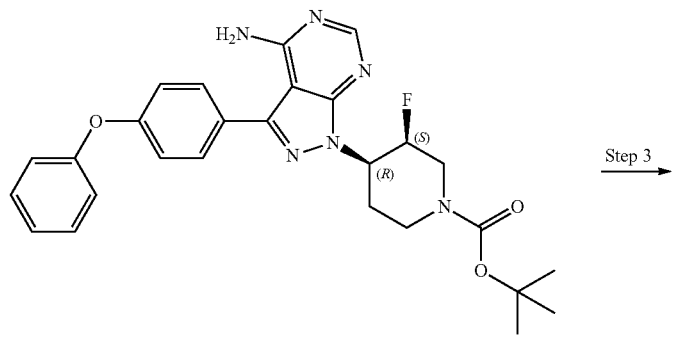
38c
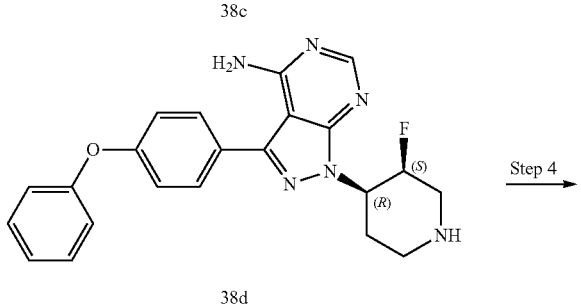
38d
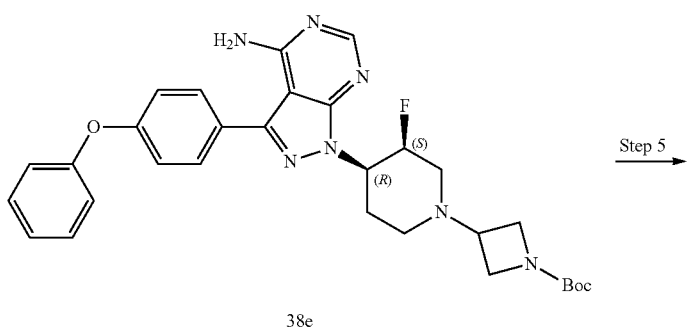
38e
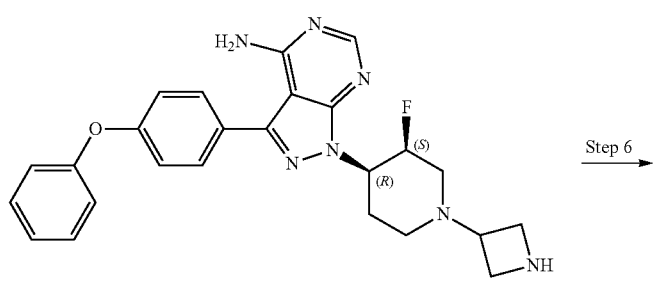
38f -continued

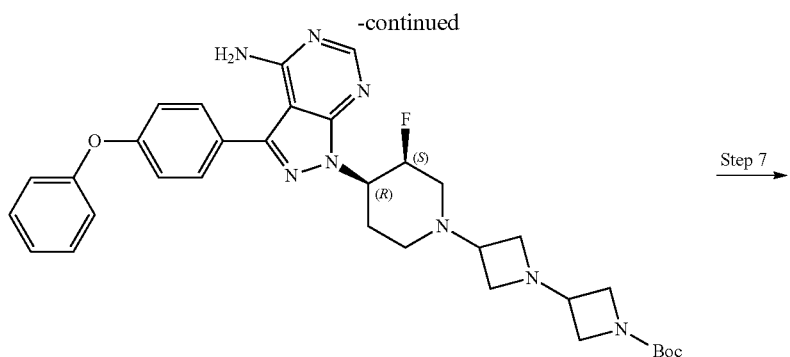

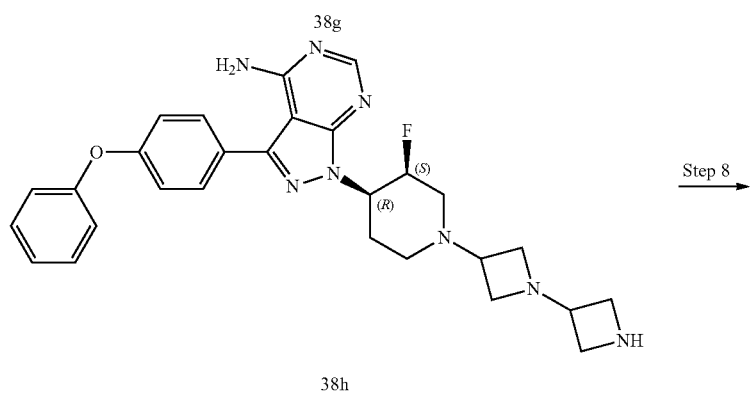

38h

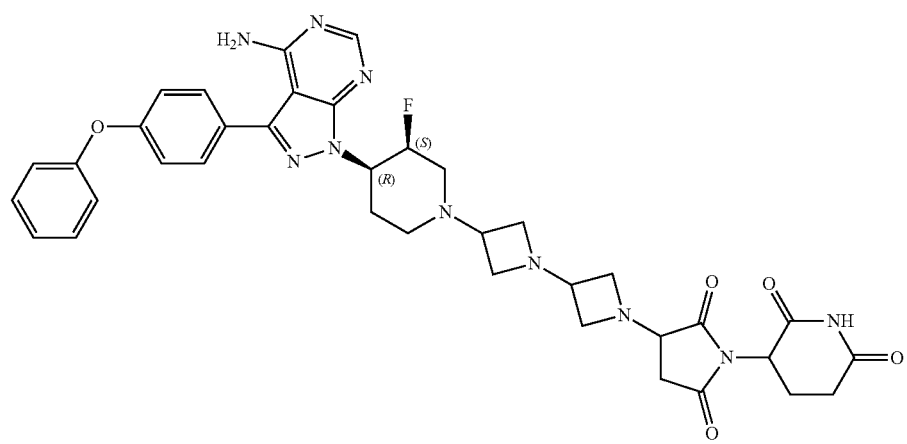

Compound 38

Step 1 tert-butyl (3S,4S)-3-fluoro-4-methylsulfonyloxy-piperidine-1-carboxylate (38b)

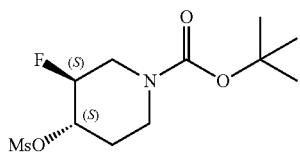

Tert-butyl (3S,4S)-3-fluoro-4-hydroxypiperidine-1-carboxylate (38a) (2.0 g, 9.13 mmol) was dissolved in 30 mL of dichloromethane, and DIPEA (4.48 g, 34.66 mmol) was added, then methanesulfonyl chloride (1.6 g, 13.97 mmol) was slowly added dropwise. Upon completion of the addition, the mixture was stirred at room temperature for 2 h. The reaction solution was quenched with 40 mL of water, and extracted with 100 mL of DCM three times. The organic phase was washed with 100 mL of water, dried over anhydrous sodium sulfate, and concentrated under reduced pressure. The crude product was separated and purified by silica gel column chromatography (petroleum ether/ethyl acetate (v/v)=5:1), to obtain tert-butyl (3S,4S)-3-fluoro-4-methylsulfonyloxy-piperidine-1-carboxylate (38b) (2.65 g, yield: 98%).

Step 2 tert-butyl (3S,4R)-4-[4-amino-3-(4-phenoxyphenyl)pyrazolo[3,4-d]pyrimidin-1-yl]-3-fluoro-piperidine-1-carboxylate (38c)

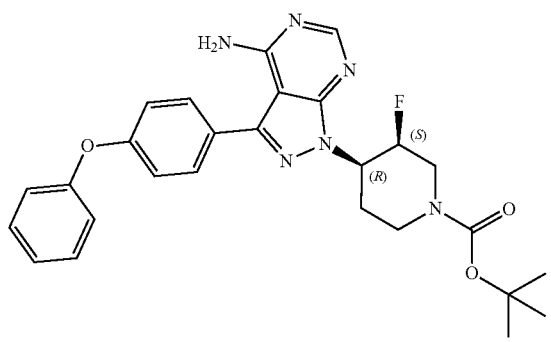

Tert-butyl (3S,4S)-3-fluoro-4-methylsulfonyloxy-piperidine-1-carboxylate (38b) (2.45 g, 8.25 mmol) and 3-(4-phenoxyphenyl)-1H-pyrazolo[3,4-d]pyrimidin-4-amine (1.0 g, 3.30 mmol) were dissolved in 20 mL of DMF, and cesium carbonate (2.14 g, 6.6 mmol) was added, the reaction was stirred at 100° C. for 7 h. The reaction was cooled to room temperature, and the reaction system was added 50 mL of water, and extracted with 100 mL of ethyl acetate three times. The organic phase was washed with 100 mL of water, dried over anhydrous sodium sulfate, and concentrated under reduced pressure. The crude product was separated and purified by silica gel column chromatography (dichloromethane/methanol (v/v)=15:1), to obtain tert-butyl (3S,4R)-4-[4-amino-3-(4-phenoxyphenyl)pyrazolo[3,4-d]pyrimidin-1-yl]-3-fluoro-piperidine-1-carboxylate (38c) (0.9 g, yield: 54%).

LCMS m/z=505.3 [M+1]$^+$.

Step 3

1-[(3S,4R)-3-fluoro-4-piperidyl]-3-(4-phenoxyphenyl)pyrazolo[3,4-d]pyrimidin-4-amine (38d)

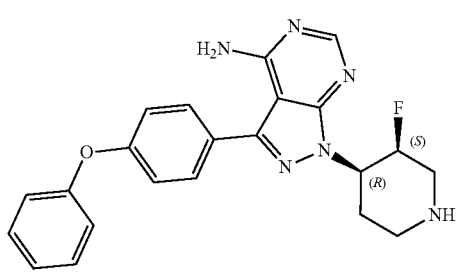

Tert-butyl (3S,4R)-4-[4-amino-3-(4-phenoxyphenyl)pyrazolo[3,4-d]pyrimidin-1-yl]-3-fluoro-piperidine-1-carboxylate (38c) (0.9 g, 1.79 mmol) was dissolved in 10 mL of DCM, and 5 mL of trifluoroacetic acid was added, the mixture was stirred at room temperature for 4 h. The reaction system was directly concentrated under reduced pressure, and the residue was dissolved with 60 mL of 5N sodium hydroxide solution, extracted with 100 mL of dichloromethane three times, dried over anhydrous sodium sulfate, and concentrated under reduced pressure, to obtain 1-[(3S,4R)-3-fluoro-4-piperidyl]-3-(4-phenoxyphenyl)pyrazolo[3,4-d]pyrimidin-4-a mine (38d) (0.7 g, yield: 97%).

LCMS m/z=405.2 [M+1]$^+$.

Step 4 tert-butyl 3-[(3S,4R)-4-[4-amino-3-(4-phenoxyphenyl)pyrazolo[3,4-d]pyrimidin-1-yl]-3-fluoro-1-piperidyl] azetidine-1-carboxylate (38e)

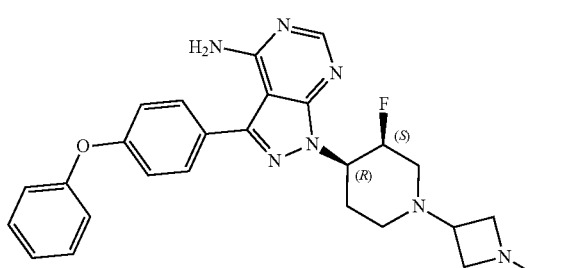

1-[(3S,4R)-3-fluoro-4-piperidyl]-3-(4-phenoxyphenyl)pyrazolo[3,4-d]pyrimidin-4-amine (38d) (0.7 g, 1.73 mmol) was dissolved in 35M1 of DCE and 5 mL of DMSO, and tert-butyl 3-oxoazetidine-1-carboxylate (542 mg, 3.17 mmol) were added, the mixture was stirred at room temperature for 10 minutes, then sodium triacetoxyborohydride (1.68 g, 7.93 mmol) was added, and the mixture was stirred at room temperature overnight. To the reaction solution was slowly added 30 mL of saturated sodium bicarbonate solution, and the mixed solution was extracted with 50 mL of ethyl acetate three times. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain tert-butyl 3-[(3S,4R)-4-[4-amino-3-(4-phenoxyphenyl)pyrazolo[3,4-d]pyrimidin-1-yl]-3-fluoro-1-piperidyl] azetidine-1-carboxylate (38e) (0.88 g, yield: 91%).

LCMS m/z=560.5 [M+1]$^+$.

Step 5

1-((3S,4R)-1-(azetidin-3-yl)-3-fluoropiperidin-4-yl)-3-(4-phenoxyphenyl)-1H-pyrazolo[3,4-d]pyrimidin-4-amine (38f)

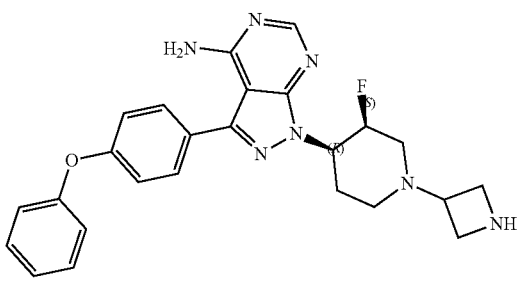

Tert-butyl 3-[(3S,4R)-4-[4-amino-3-(4-phenoxyphenyl)pyrazolo[3,4-d]pyrimidin-1-yl]-3-fluoro-1-piperidyl]azetidine-1-carboxylate (38e) (880 mg, 1.57 mmol) was dissolved in 20 mL of DCM, and 5 mL of trifluoroacetic acid was added, the mixture was stirred at room temperature for 4 h. Upon completion of the reaction, the system was directly concentrated under reduced pressure, and the residue was dissolved with 50 mL of 5N sodium hydroxide solution, and extracted with 50 mL of DCM three times. The organic phase was washed with 30 mL of 1N sodium hydroxide solution twice, dried over anhydrous sodium sulfate, and concentrated under reduced pressure, to obtain 1-((3S,4R)-1-(azetidin-3-yl)-3-fluoropiperidin-4-yl)-3-(4-phenoxyphenyl)-1H-pyrazole[3,4-d]pyrimidin-4-amine (38f) (0.65 g, yield: 90%).

LCMS m/z=460.3 [M+1]⁺.

Step 6 tert-butyl 3-[3-[(3S,4R)-4-[4-amino-3-(4-phenoxyphenyl)pyrazolo[3,4-d]pyrimidin-1-yl]-3-fluoro-1-piperidyl]azetidin-1-yl]azetidine-1-carboxylate (38g)

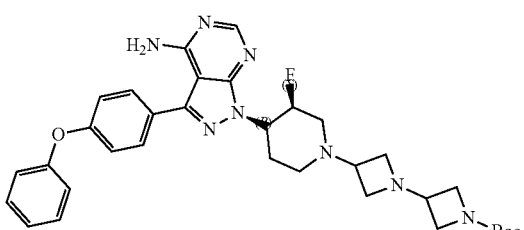

1-((3S,4R)-1-(azetidin-3-yl)-3-fluoropiperidin-4-yl)-3-(4-phenoxyphenyl)-1H-pyrazole[3,4-d]pyrimidin-4-amine (38f) (650 mg, 1.42 mmol) was dissolved in 25 mL of DCE and 2 mL of DMSO, and tert-butyl 3-oxoazetidine-1-carboxylate (485 mg, 2.84 mmol) was added, the mixture was stirred at room temperature for 10 minutes, then sodium triacetoxyborohydride (1.12 g, 5.28 mmol) was added, and the mixture was stirred at room temperature overnight. To the reaction system was slowly added 60 mL of saturated sodium bicarbonate solution, and the mixed solution was extracted with 60 mL of ethyl acetate three times. The organic phase was washed with 50 mL of water, dried over anhydrous sodium sulfate, and concentrated under reduced pressure, then the crude product was separated and purified by silica gel column chromatography (dichloromethane/methanol (v/v)=1), to obtain tert-butyl 3-[3-[(3S,4R)-4-[4-amino-3-(4-phenoxyphenyl)]pyrazolo[3,4-d]pyrimidin-1-yl]-3-fluoro-1-piperidyl]azetidin-1-yl]azetidine-1-carboxylate (38g) (0.46 g, yield: 53%).

LCMS m/z=615.6 [M+1]⁺.

Step 7

1-[(3S,4R)-1-[1-(azetidin-3-yl)azetidin-3-yl]-3-fluoro-4-piperidyl]-3-(4-phenoxyphenyl) pyrazolo[3,4-d]pyrimidin-4-amine (38h)

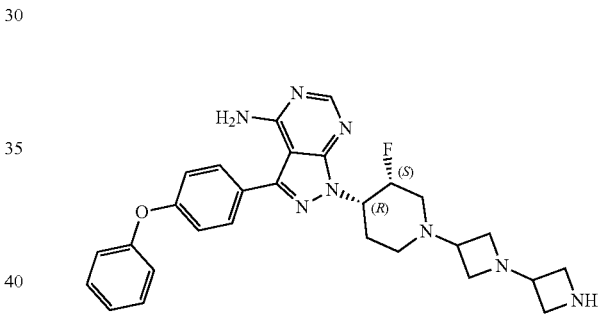

Tert-butyl 3-[3-[(3S,4R)-[4-[4-amino-3-(4-phenoxyphenyl)]pyrazolo[3,4-d]pyrimidin-1-yl]-3-fluoro-1-piperidyl]azetidin-1-yl]azetidine-1-carboxylate (38g) (400 mg, 0.65 mmol) was dissolved in 20 mL of DCM, and 4 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure, to obtain 1-[(3S,4R)-1-[1-(azetidin-3-yl)azetidin-3-yl]-3-fluoro-4-piperidyl]-3-(4-phenoxyphenyl) pyrazolo[3,4-d]pyrimidin-4-amine (38h) (0.28 g, yield: 84%).

LCMS m/z=515.5 [M+1]⁺.

Step 8

5-[3-[3-[(3S,4R)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 38)

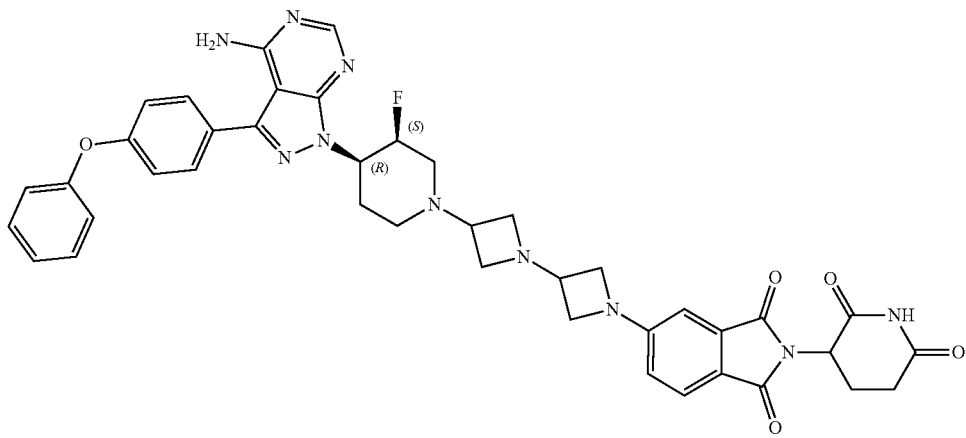

1-[(3S,4R)-1-[1-(azetidin-3-yl)azetidin-3-yl]-3-fluoro-4-piperidyl]-3-(4-phenoxyphenyl) pyrazolo[3,4-d]pyrimidin-4-amine (38h) (0.28 g, 0.54 mmol) was dissolved in 25 mL of DMSO, and 3 mL of DIPEA and 2-(2,6-dioxopiperidin-3-yl)-5-fluoroisoindoline-1,3-dione (see WO 2017197056 for the synthetic method) (300 mg, 1.09 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=20:1), to obtain 5-[3-[3-[(3S,4R)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 38) (0.126 g, yield: 30%).

$^1$H NMR (400 MHz, CDCl$_3$) δ 8.91 (s, 1H), 8.38 (s, 1H), 7.69-7.61 (m, 3H), 7.43-7.35 (m, 2H), 7.21-7.05 (m, 5H), 6.79 (d, 1H), 6.53 (dd, 1H), 5.68 (brs, 2H), 5.20-5.01 (m, 1H), 4.99-4.82 (m, 2H), 4.10-4.02 (m, 2H), 3.96-3.87 (m, 2H), 3.80-3.66 (m, 1H), 3.66-3.56 (m, 2H), 3.32-2.97 (m, 6H), 2.92-2.65 (m, 3H), 2.49-2.29 (m, 1H), 2.29-2.19 (m, 1H), 2.17-2.07 (m, 2H).

LCMS m/z=771.3 [M+1]$^+$.

Example 39

5-(3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 39)

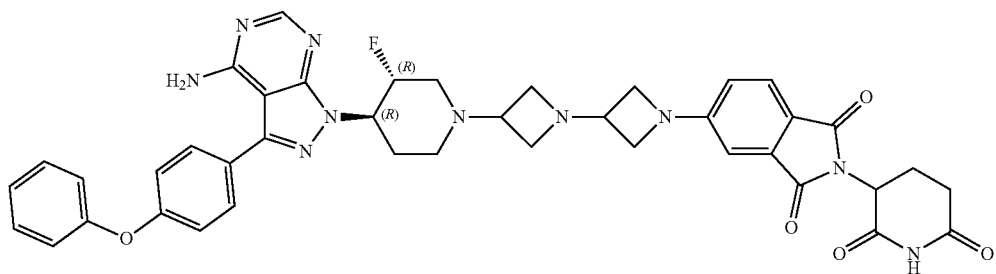

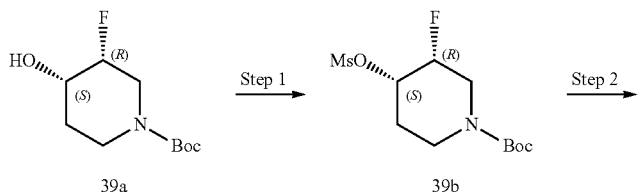

449 450
-continued
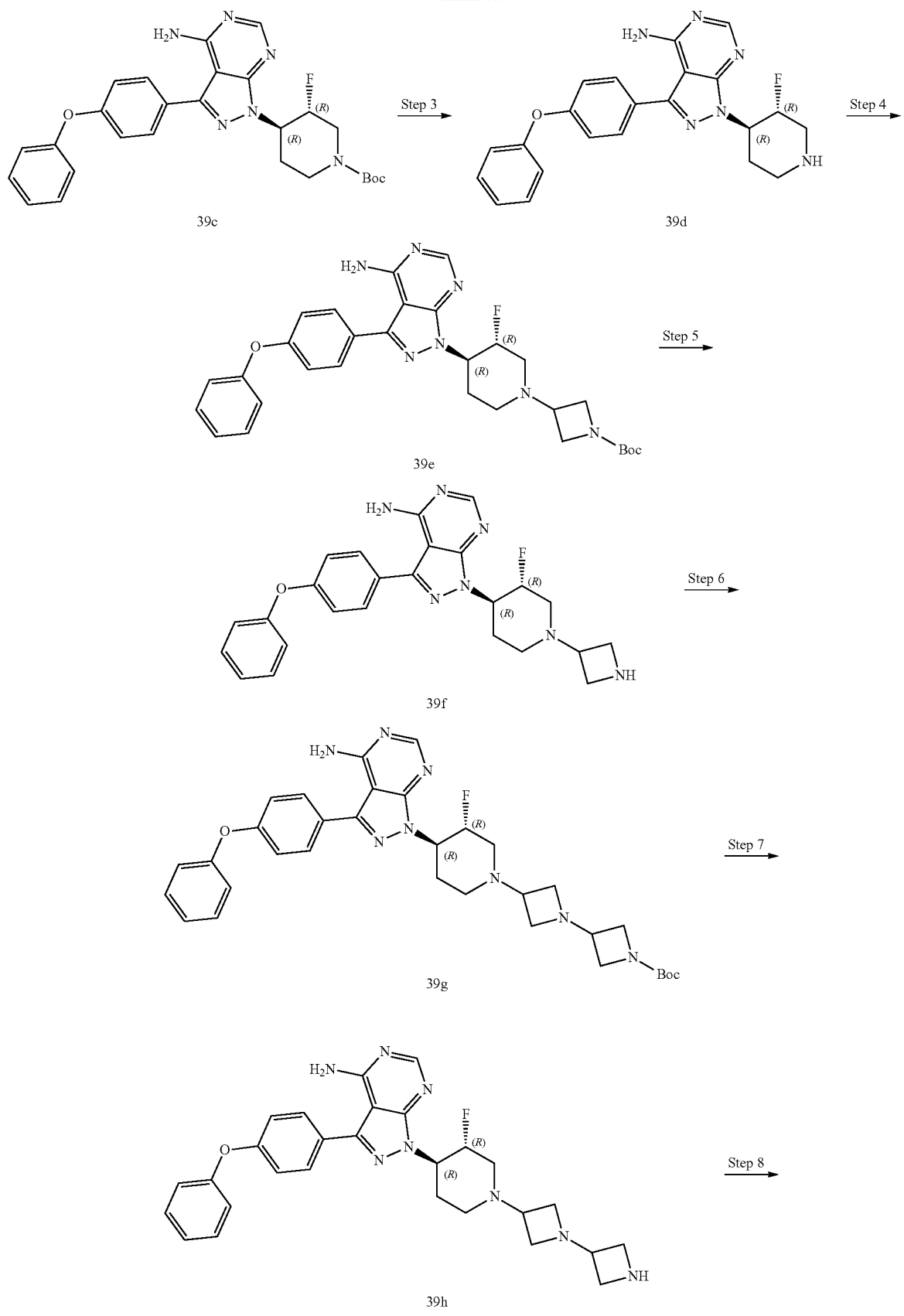

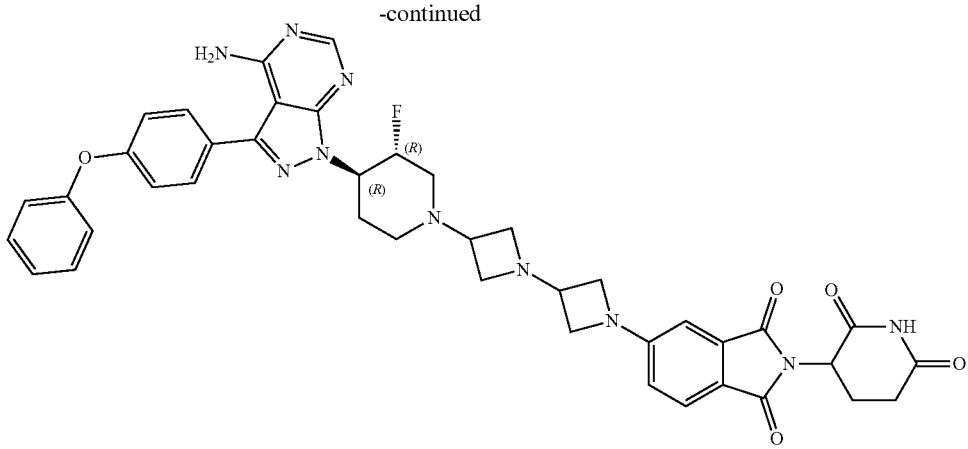

Compound 39

Step 1 tert-butyl(3R,4S)-3-fluoro-4-((methylsulfonyl)oxy)piperidine-1-carboxylate (39b)

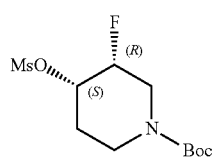

Tert-butyl (3R,4S)-3-fluoro-4-hydroxypiperidine-1-carboxylate (39a) (2.0 g, 9.13 mmol) was dissolved in 30 mL of dichloromethane, and DIPEA (2.76 g, 21.35 mmol) was added. The mixture was cooled to 0° C., and methanesulfonyl chloride (1.25 g, 10.91 mmol) was slowly added dropwise. Upon completion of the addition, the mixture was stirred at room temperature for 30 minutes. Upon completion of the reaction, the reaction was quenched by adding 40 mL of water, and extracted with 50 mL of dichloromethane. The organic phase was washed with 50 mL of water, dried over anhydrous sodium sulfate, and concentrated under reduced pressure, then the crude product was separated and purified by silica gel column chromatography (petroleum ether/ethyl acetate (v/v)=3:1), to obtain tert-butyl (3R,4S)-3-fluoro-4-((methylsulfonyl)oxy)piperidine-1-carboxylate (39b) (2.7 g, yield: >99%).

Step 2 tert-butyl (3R,4R)-4-(4-amino-3-(4-phenoxyphenyl)-1H-pyrazolo[3,4-d]pyrimidin-1-yl)-3-fluoropiperidine-1-carboxylate (39c)

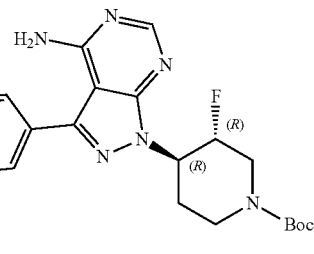

Tert-butyl (3R,4S)-3-fluoro-4-((methylsulfonyl)oxy)piperidine-1-carboxylate (39b) (2.20 g, 7.41 mmol) and 3-(4-phenoxyphenyl)-1H-pyrazolo[3,4-d]pyrimidin-4-amine (1.0 g, 3.30 mmol) were dissolved in 30 mL of DMF, and cesium carbonate (3.23 g, 9.91 mmol) was added, the reaction was stirred at 100° C. for 4 h. The reaction solution was cooled to room temperature, to same was added 50 mL of water, and extracted with 50 mL of ethyl acetate. The organic phase was washed with 50 mL of water, dried over anhydrous sodium sulfate, and concentrated under reduced pressure, then the crude product was separated and purified by silica gel column chromatography (dichloromethane/methanol (v/v)=50:1), to obtain tert-butyl (3R,4R)-4-(4-amino-3-(4-phenoxyphenyl)-1H-pyrazolo[3,4-d]pyrimidin-1-yl)-3-fluoropiperidine-1-carboxylate (39c) (900 mg, yield: 54%).

LCMS m/z=505.3 [M+1]$^+$.

Step 3

1-((3R,4R)-3-fluoropiperidin-4-yl)-3-(4-phenoxyphenyl)-1H-pyrazolo[3,4-d]pyrimidin-4-amine (39d)

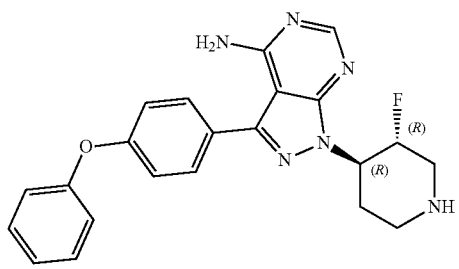

(3R,4R)-4-(4-amino-3-(4-phenoxyphenyl)-1H-pyrazolo[3,4-d]pyrimidin-1-yl)-3-fluoropiperidine-1-carboxylate (39c) (900 mg, 1.79 mmol) was dissolved in 15 mL of dichloromethane, and 10 mL of trifluoroacetic acid was added, the mixture was stirred at room temperature for 4 h. The reaction system was directly concentrated under reduced pressure, and the residue was dissolved with 30 mL of 5N sodium hydroxide solution, extracted with 50 mL of dichloromethane, dried over anhydrous sodium sulfate, and concentrated under reduced pressure, to obtain 1-((3R,4R)-3-fluoropiperidin-4-yl)-3-(4-phenoxyphenyl)-1H-pyrazolo[3,4-d]pyrimidin-4-amine (39d) (670 mg, yield: 93%).

LCMS m/z=405.3 [M+1]$^+$.

Step 4 tert-butyl 3-((3R,4R)-4-(4-amino-3-(4-phenoxyphenyl)-1H-pyrazolo[3,4-d]pyrimidin-1-yl)-3-fluoropiperidin-1-yl)azetidine-1-carboxylate (39e)

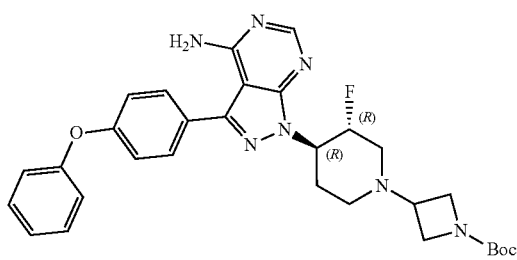

1-((3R,4R)-3-fluoropiperidin-4-yl)-3-(4-phenoxyphenyl)-1H-pyrazolo[3,4-d]pyrimidin-4-amine (39d) (670 mg, 1.66 mmol) was dissolved in 35 mL of DCE, and tert-butyl 3-oxoazetidine-1-carboxylate (566 mg, 3.31 mmol) was added, the mixture was stirred at room temperature for 10 minutes, then sodium triacetoxyborohydride (1.4 g, 6.61 mmol) was added, and the mixture was stirred at room temperature overnight. To the reaction solution was slowly added 30 mL of saturated sodium bicarbonate solution, and the mixed solution was extracted with 30 mL of dichloromethane three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4R)-4-(4-amino-3-(4-phenoxyphenyl)-1H-pyrazolo[3,4-d]pyrimidin-1-yl)-3-fluoropiperidin-1-yl)azetidine-1-carboxylate (39e) (860 mg, yield: 93%).

LCMS m/z=560.3 [M+1]$^+$.

Step 5

1-((3R,4R)-1-(azetidin-3-yl)-3-fluoropiperidin-4-yl)-3-(4-phenoxyphenyl)-1H-pyrazolo[3,4-d]pyrimidin-4-amine (39f)

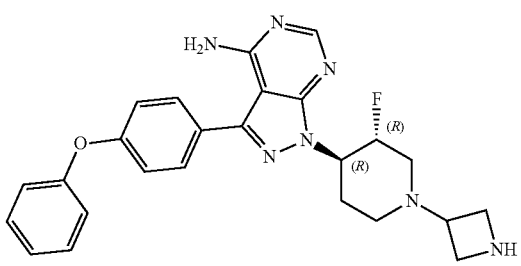

3-((3R,4R)-4-(4-amino-3-(4-phenoxyphenyl)-1H-pyrazolo[3,4-d]pyrimidin-1-yl)-3-fluoropiperidin-1-yl)azetidine-1-carboxylate (39e) (810 mg, 1.45 mmol) was dissolved in 20 mL of DCM, and 5 mL of trifluoroacetic acid was added, the mixture was stirred at room temperature for 4 h. Upon completion of the reaction, the system was directly concentrated under reduced pressure, and the residue was dissolved with 30 mL of 5N sodium hydroxide aqueous solution, and extracted with 30 mL of DCM three times. The organic phase was washed with 30 mL of 1N sodium hydroxide solution twice, dried over anhydrous sodium sulfate, and concentrated to obtain 1-((3R,4R)-1-(azetidin-3-yl)-3-fluoropiperidin-4-yl)-3-(4-phenoxyphenyl)-1H-pyrazolo[3,4-d]pyrimidin-4-amine (39f)(0.63 g, yield: 95%).

LCMS m/z=460.2 [M+1]$^+$.

Step 6 tert-butyl 3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (39g)

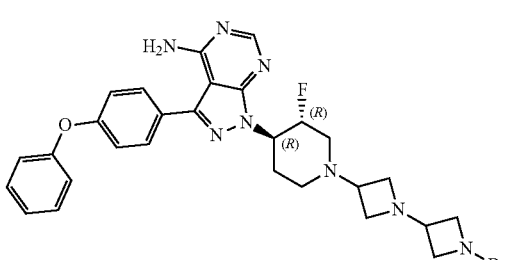

1-((3R,4R)-1-(azetidin-3-yl)-3-fluoropiperidin-4-yl)-3-(4-phenoxyphenyl)-1H-pyrazolo[3,4-d]pyrimidin-4-amine (39f) (580 mg, 1.26 mmol) was dissolved in 30 mL of DCE, and tert-butyl 3-oxoazetidine-1-carboxylate (432 mg, 2.53 mmol) was added, the mixture was stirred at room temperature for 10 minutes, then sodium triacetoxyborohydride (1.07 g, 5.05 mmol) was added, and the mixture was stirred at room temperature overnight. To the reaction system was slowly added 30 mL of saturated sodium bicarbonate solution, and the mixed solution was extracted with 30 mL of dichloromethane three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (39g) (600 mg, yield: 77%).

LCMS m/z=615.3 [M+1]$^+$.

Step 7

1-((3R,4R)-1-([1,3'-biazetidin]-3-yl)-3-fluoropiperidin-4-yl)-3-(4-phenoxyphenyl)-1H-pyrazolo[3,4-d]pyrimidin-4-amine (39h)

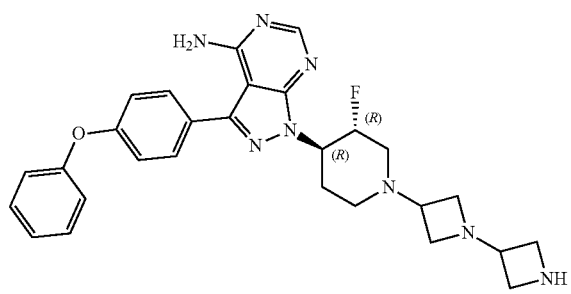

Tert-butyl 3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (39g) (550 mg, 0.896 mmol) was dissolved in 20 mL of DCM, and 4 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated to obtain 1-((3R,4R)-1-([1,3'-biazetidin]-3-yl)-3-fluoropiperidin-4-yl)-3-(4-phenoxyphenyl)-1 H-pyrazolo[3,4-d]pyrimidin-4-amine (39h) (0.43 g, yield: 93%).

LCMS m/z=515.2 [M+1]$^+$.

Step 8

5-(3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 39)

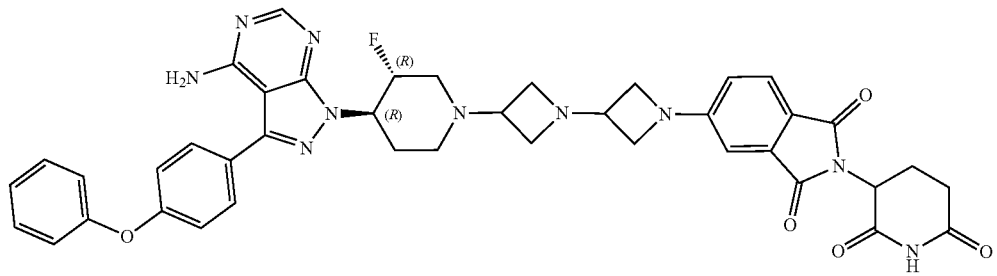

1-((3R,4R)-1-([1,3'-biazetidin]-3-yl)-3-fluoropiperidin-4-yl)-3-(4-phenoxyphenyl)-1H-pyrazolo[3,4-d]pyrimidin-4-amine (39h) (300 mg, 0.584 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (274 mg, 0.993 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3R,4R)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoli ne-1,3-dione (Compound 39) (300 mg, yield: 67%).

$^1$H NMR (400 MHz, CDCl$_3$) δ 9.61 (s, 1H), 8.41 (s, 1H), 7.69-7.61 (m, 3H), 7.43-7.35 (m, 2H), 7.20-7.05 (m, 5H), 6.79 (d, 1H), 6.53 (dd, 1H), 5.80 (brs, 2H), 5.35-5.14 (m, 1H), 4.97-4.83 (m, 2H), 4.09-4.01 (m, 2H), 3.93-3.85 (m, 2H), 3.75-3.55 (m, 3H), 3.29-3.05 (m, 4H), 2.92-2.64 (m, 4H), 2.53-2.39 (m, 1H), 2.22-2.05 (in, 4H).

LCMS m/z=771.3 [M+1]$^+$.

Example 40
5-(3-((3R,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 40)
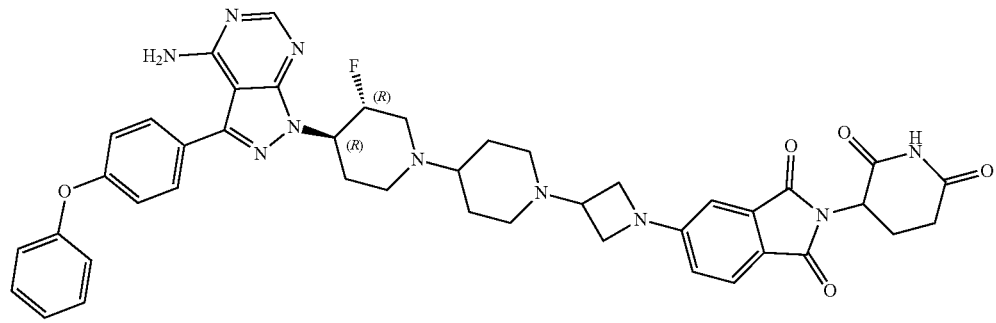
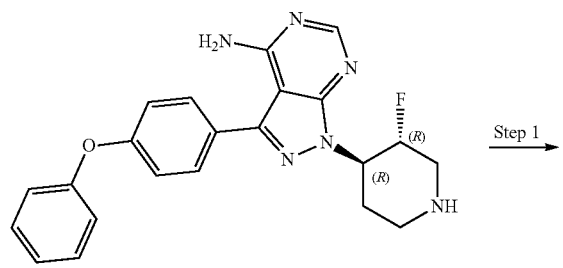
39d
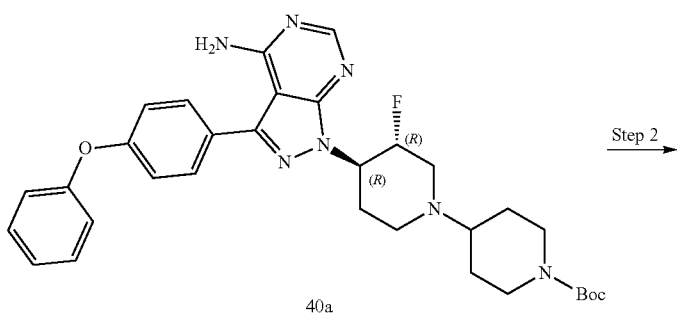
40a
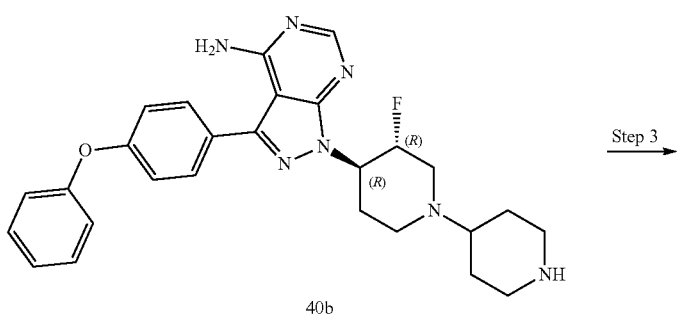
40b -continued
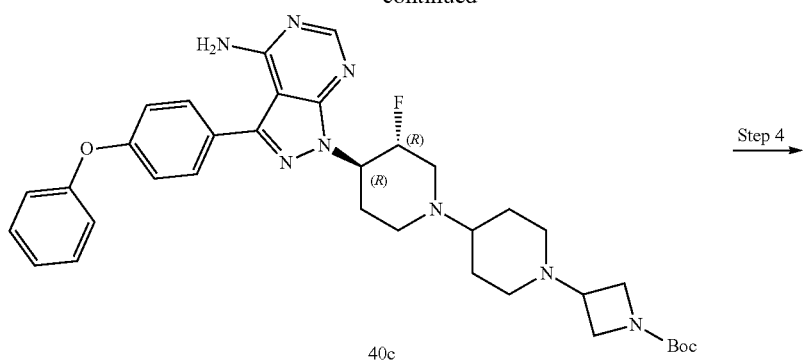
40c
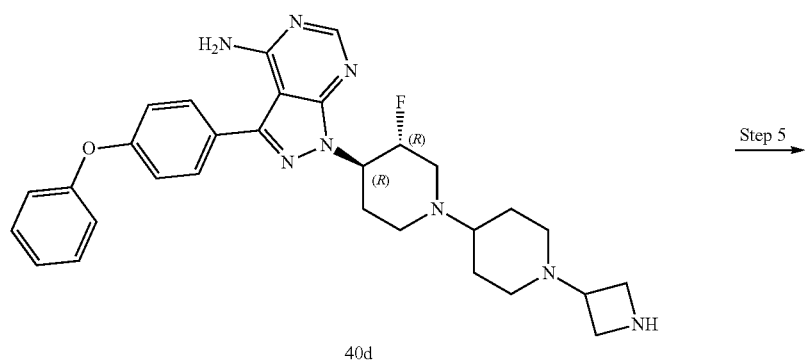
40d
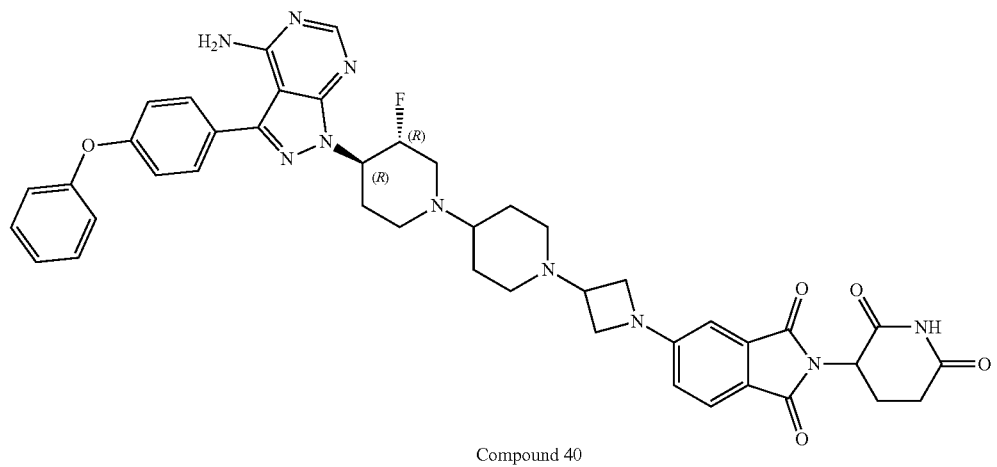
Compound 40

Step 1 tert-butyl (3R,4R)-4-(4-amino-3-(4-phenoxyphenyl)-1H-pyrazolo[3,4-d]pyrimidin-1-yl)-3-fluoro-[1,4'-bipiperidine]-1'-carboxylate (40a)

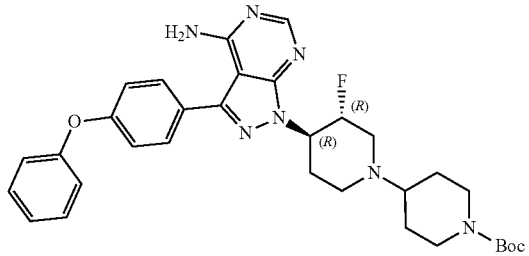

1-((3R,4R)-3-fluoropiperidin-4-yl)-3-(4-phenoxyphenyl)-1H-pyrazolo[3,4-d]pyrimidin-4-amine (39d) (800 mg, 1.98 mmol) was dissolved in 35 mL of DCE, and tert-butyl 4-oxopiperidine-1-carboxylate (787 mg, 3.95 mmol) was added, the mixture was stirred at room temperature for 10 minutes, then sodium triacetoxyborohydride (1.68 g, 7.93 mmol) was added, and the mixture was stirred at room temperature overnight. To the reaction solution was slowly added 30 mL of saturated sodium bicarbonate solution, and the mixed solution was extracted with 30 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl (3R,4R)-4-(4-amino-3-(4-phenoxyphenyl)-1H-pyrazolo[3,4-d]pyrimidin-1-yl)-3-fluoro-[1,4'-bipiperidine]-1'-carboxylate (40a) (970 mg, yield: 83%).

LCMS m/z=588.3 [M+1]$^+$.

Step 2

1-((3R,4R)-3-fluoro-[1,4'-bipiperidin]-4-yl)-3-(4-phenoxyphenyl)-1H-pyrazolo[3,4-d]pyrimidin-4-amine (40b)

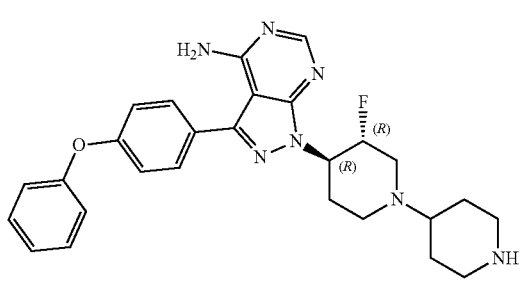

Tert-butyl (3R,4R)-4-(4-amino-3-(4-phenoxyphenyl)-1H-pyrazolo[3,4-d]pyrimidin-1-yl)-3-fluoro-[1,4'-bipiperidine]-1'-carboxylate (40a) (960 mg, 1.64 mmol) was dissolved in 20 mL of DCM, and 8 mL of trifluoroacetic acid was added, the mixture was stirred at room temperature for 4 h. Upon completion of the reaction, the system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure to obtain 1-((3R,4R)-3-fluoro-[1,4'-bipiperidin]-4-yl)-3-(4-phenoxyphenyl)-1H-pyrazolo[3,4-d]pyrimidin-4-amine (40b) (0.79 g, yield: 99%).

LCMS m/z=488.3 [M+1]$^+$.

Step 3 tert-butyl 3-((3R,4R)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (40c)

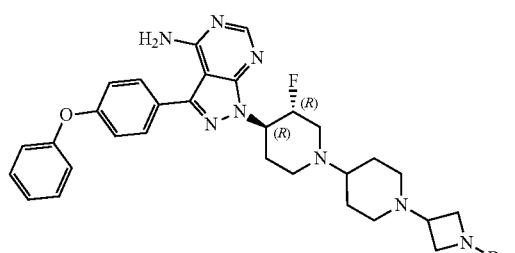

1-((3R,4R)-3-fluoro-[1,4'-bipiperidin]-4-yl)-3-(4-phenoxyphenyl)-1H-pyrazolo[3,4-d]pyrimidin-4-amine (40b) (540 mg, 1.11 mmol) was dissolved in 30 mL of DCE, and tert-butyl 3-oxoazetidine-1-carboxylate (380 mg, 2.22 mmol) was added, the mixture was stirred at room temperature for 10 minutes, then sodium triacetoxyborohydride (940 mg, 4.44 mmol) was added, and the mixture was stirred at room temperature overnight. To the reaction system was slowly added 30 mL of saturated sodium bicarbonate solution, and the mixed solution was extracted with 30 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4R)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (40c) (630 mg, yield: 88%).

LCMS m/z=643.4 [M+1]$^+$.

Step 4

1-((3R,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (40d)

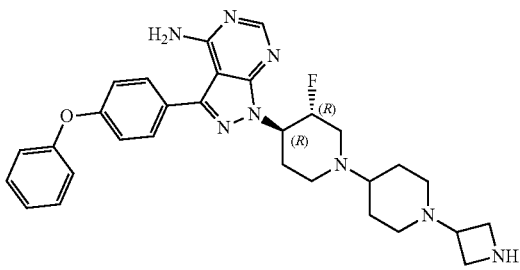

Tert-butyl 3-((3R,4R)-4-(4-amino-3-(4-phenoxyphenyl)-1H-pyrazolo[3,4-d]pyrimidin-1-yl)-3-fluoro-[1,4'-bipiperidin]-1'-yl) azetidine-1-carboxylate (40c) (600 mg, 0.93 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of dichloromethane three times. The organic phase was washed with 30 mL of 1N sodium hydroxide solution twice, dried over anhydrous sodium sulfate, and concentrated under reduced pressure to obtain 1-((3R,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (40d) (0.47 g, yield: 93%).

LCMS m/z=543.3 [M+1]+.

Step 5

5-(3-((3R,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 40)

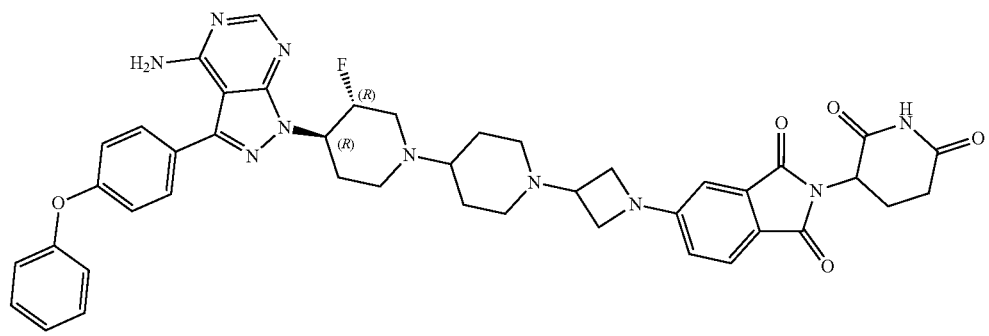

1-((3R,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (40d) (350 mg, 0.65 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (267 mg, 0.97 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3R,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoli ne-1,3-dione (Compound 40) (380 mg, yield: 74%).

$^1$H NMR (400 MHz, CDCl$_3$) δ 9.76 (s, 1H), 8.41 (s, 1H), 7.69-7.61 (m, 3H), 7.42-7.34 (m, 2H), 7.20-7.11 (m, 3H), 7.11-7.05 (m, 2H), 6.79 (d, 1H), 6.52 (dd, 1H), 5.83 (brs, 2H), 5.29-5.10 (m, 1H), 4.97-4.80 (m, 2H), 4.12-4.06 (m, 2H), 3.95-3.85 (m, 2H), 3.45-3.31 (m, 2H), 3.06-2.92 (m, 3H), 2.91-2.68 (m, 3H), 2.56-2.35 (m, 4H), 2.16-1.93 (m, 4H), 1.92-1.82 (m, 2H), 1.74-1.58 (m, 2H).

LCMS m/z=799.3 [M+1]+.

Example 41
5-(3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 41)
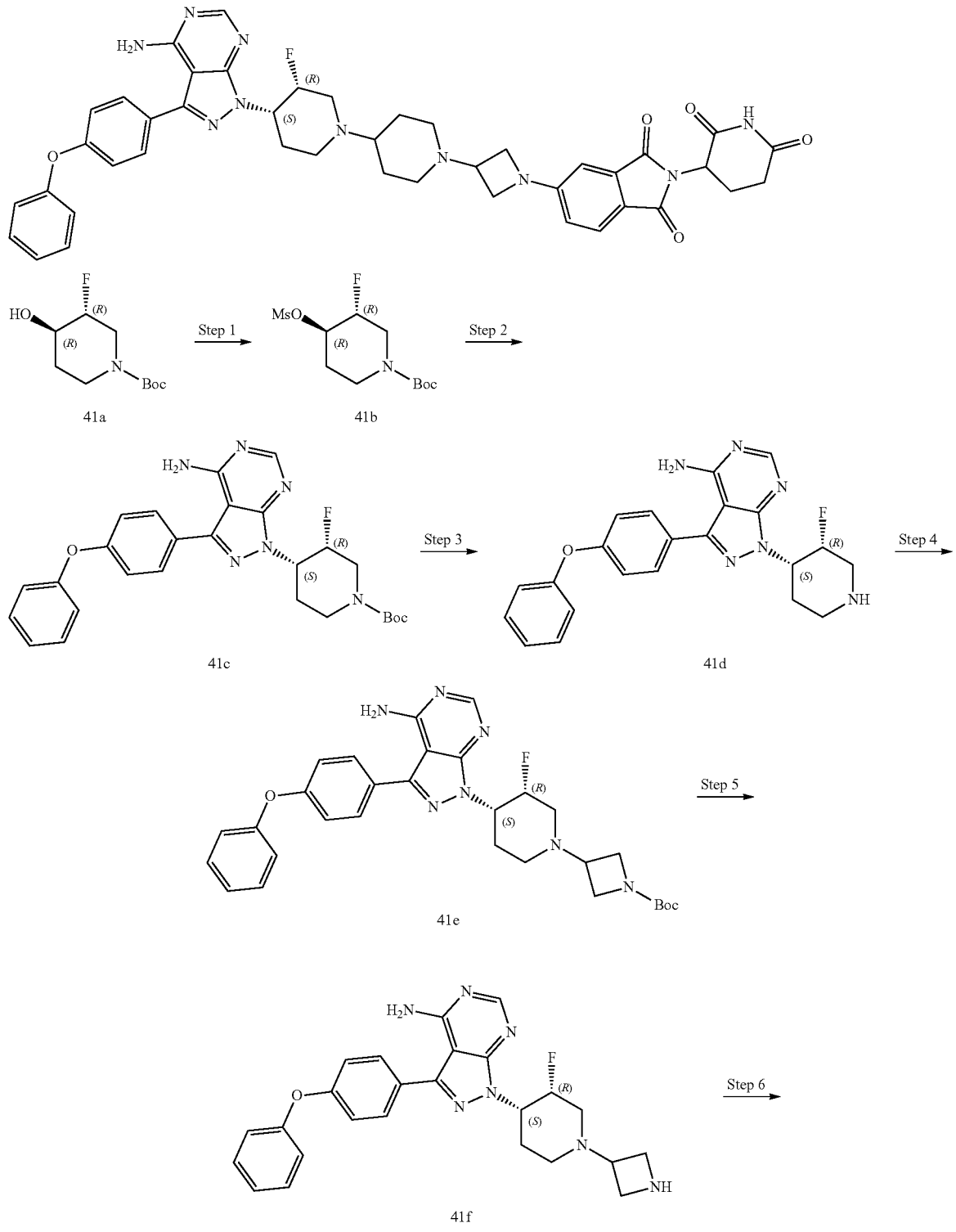

-continued

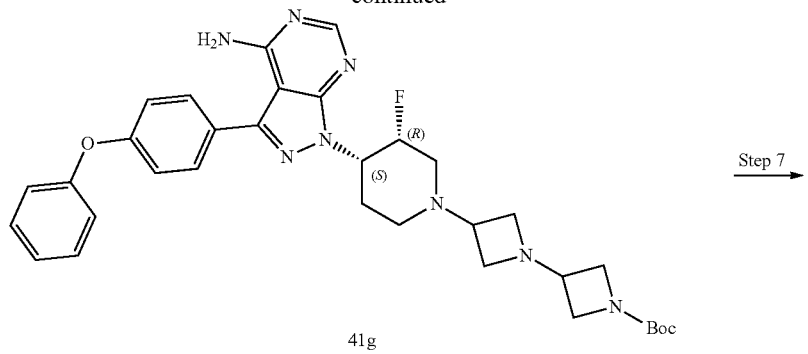

41g

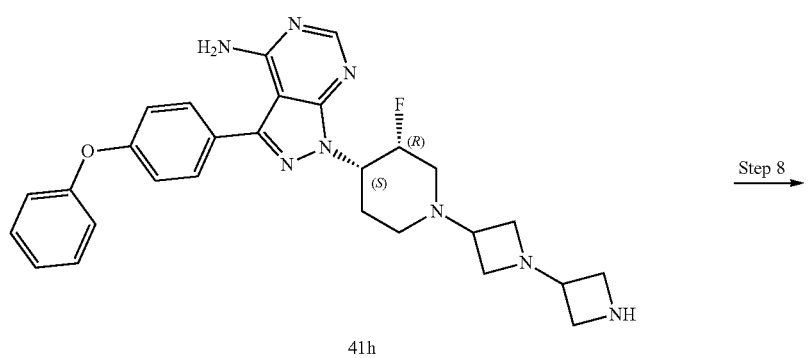

41h

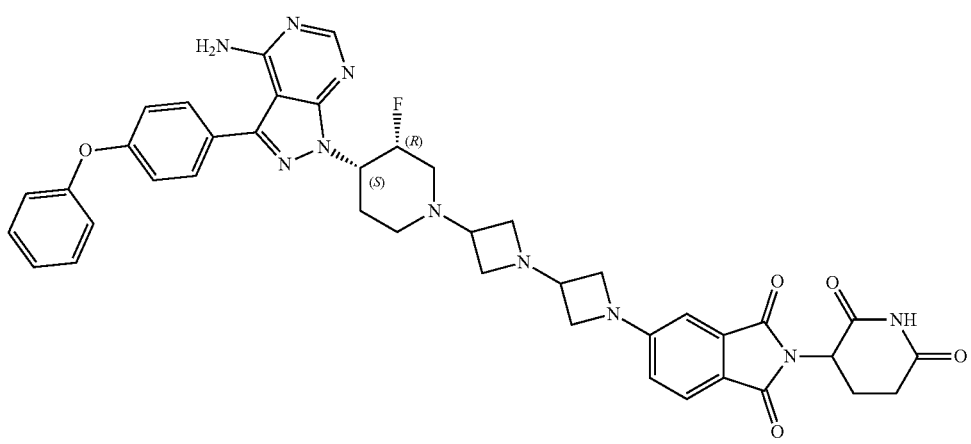

Compound 41

Step 1

Tert-butyl (3R,4R)-3-fluoro-4-((methylsulfonyl)oxy)piperidine-1-carboxylate (41b)

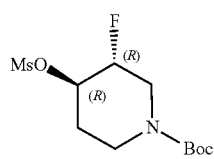

Tert-butyl (3R,4R)-3-fluoro-4-hydroxypiperidine-1-carboxylate (41a) (3.0 g, 13.70 mmol) was dissolved in 80 mL of dichloromethane, and triethylamine (4.15 g, 41.09 mmol) was added, the mixture was cooled to 0° C., then methanesulfonyl chloride (1.88 g, 16.41 mmol) was slowly added dropwise. Upon completion of the addition, the reaction was stirred at room temperature for 30 minutes. The reaction solution was quenched with 40 mL of water, and extracted with 100 mL of DCM three times. The organic phase was washed with 100 mL of water, dried over anhydrous sodium sulfate, and concentrated under reduced pressure. The crude product was separated and purified by silica gel column chromatography (petroleum ether/ethyl acetate (v/v)=3:1), to obtain tert-butyl (3R,4R)-3-fluoro-4-((methylsulfonyl)oxy)piperidine-1-carboxylate (41b) (4.1 g, yield: >99%).

Step 2 tert-butyl (3R,4S)-4-(4-amino-3-(4-phenoxyphenyl)-1H-pyrazolo[3,4-d]pyrimidin-1-yl)-3-fluoropiperidine-1-carboxylate (41c)

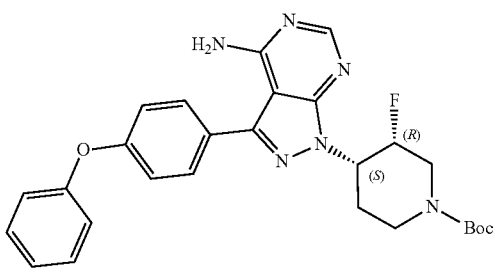

Tert-butyl (3R,4R)-3-fluoro-4-((methylsulfonyl)oxy)piperidine-1-carboxylate (41b) (3.92 g, 13.20 mmol) and 3-(4-phenoxyphenyl)-1H-pyrazolo[3,4-d]pyrimidin-4-amine (2.0 g, 6.60 mmol) were dissolved in 50 mL of DMF, and cesium carbonate (6.45 g, 19.80 mmol) was added, the reaction was stirred at 100° C. for 4 h. The reaction was cooled to room temperature, and the reaction system was added 80 mL of water, and extracted with 100 mL of ethyl acetate three times. The organic phase was washed with 100 mL of water, dried over anhydrous sodium sulfate, and concentrated under reduced pressure. The crude product was separated and purified by silica gel column chromatography (dichloromethane/methanol (v/v)=50:1), to obtain tert-butyl (3R,4S)-4-(4-amino-3-(4-phenoxyphenyl)-1H-pyrazolo[3,4-d]pyrimidin-1-yl)-3-fluoropiperidine-1-carboxylate (41c) (2.5 g, yield: 75%).

LCMS m/z=505.3 [M+1]$^+$.

Step 3

1-((3R,4S)-3-fluoropiperidin-4-yl)-3-(4-phenoxyphenyl)-1H-pyrazolo[3,4-d]pyrimidin-4-amine (41d)

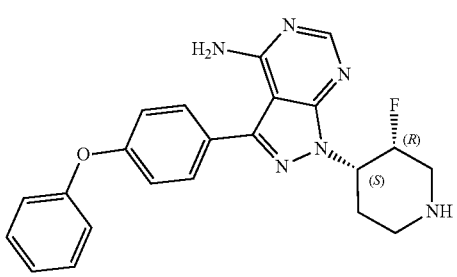

Tert-butyl (3R,4S)-4-(4-amino-3-(4-phenoxyphenyl)-1H-pyrazolo[3,4-d]pyrimidin-1-yl)-3-fluoropiperidine-1-carboxylate (41c) (2.5 g, 4.96 mmol) was dissolved in 60 mL of DCM, and 20 mL of trifluoroacetic acid was added, the mixture was stirred at room temperature for 4 h. The reaction system was directly concentrated under reduced pressure, and the residue was dissolved with 60 mL of 5N sodium hydroxide solution, extracted with 100 mL of dichloromethane, dried over anhydrous sodium sulfate, and concentrated under reduced pressure, to obtain 1-((3R,4S)-3-fluoropiperidin-4-yl)-3-(4-phenoxyphenyl)-1H-pyrazolo[3,4-d]pyrimidin-4-amine (41d) (2.1 g, yield: >99%).

LCMS m/z=405.3 [M+1]$^+$.

Step 4 tert-butyl 3-((3R,4S)-4-(4-amino-3-(4-phenoxyphenyl)-1H-pyrazolo[3,4-d]pyrimidin-1-yl)-3-fluoropiperidin-1-yl)azetidine-1-carboxylate (41e)

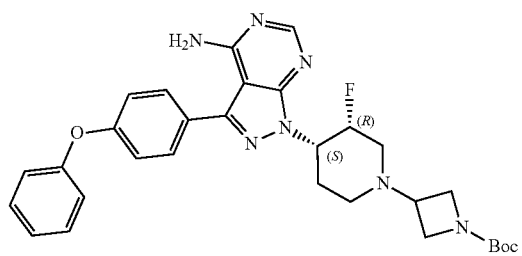

1-((3R,4S)-3-fluoropiperidin-4-yl)-3-(4-phenoxyphenyl)-1H-pyrazolo[3,4-d]pyrimidin-4-amine (41d) (900 mg, 2.23 mmol) was dissolved in 35 mL of DCE, and tert-butyl 3-oxoazetidine-1-carboxylate (762 mg, 4.46 mmol) was added, the mixture was stirred at room temperature for 10 minutes, then sodium triacetoxyborohydride (1.89 g, 8.92 mmol) was added, and the mixture was stirred at room temperature overnight. To the reaction solution was slowly added 50 mL of saturated sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4S)-4-(4-amino-3-(4-phenoxyphenyl)-1H-pyrazolo[3,4-d]pyrimidin-1-yl)-3-fluoropiperidin-1-yl)azetidine-1-carboxylate (41e) (1.18 g, yield: 95%).

LCMS m/z=560.3 [M+1]$^+$.

Step 5

1-((3R,4S)-1-(azetidin-3-yl)-3-fluoropiperidin-4-yl)-3-(4-phenoxyphenyl)-1H-pyrazolo[3,4-d]pyrimidin-4-amine (41f)

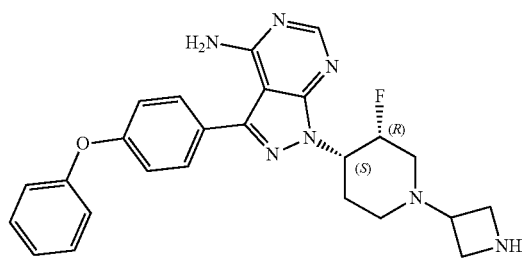

Tert-butyl 3-((3R,4S)-4-(4-amino-3-(4-phenoxyphenyl)-1H-pyrazolo[3,4-d]pyrimidin-1-yl)-3-fluoropiperidin-1-yl)azetidine-1-carboxylate (41e) (800 mg, 1.43 mmol) was dissolved in 20 mL of DCM, and 8 mL of trifluoroacetic acid was added, the mixture was stirred at room temperature for 4 h. Upon completion of the reaction, the system was directly concentrated under reduced pressure, and the residue was dissolved with 50 mL of 5N sodium hydroxide solution, and extracted with 50 mL of DCM three times. The organic phase was washed with 30 mL of 1N sodium hydroxide solution twice, dried over anhydrous sodium sulfate, and concentrated under reduced pressure, to obtain 1-((3R,4S)-1-(azetidin-3-yl)-3-fluoropiperidin-4-yl)-3-(4-phenoxyphenyl)-1H-pyrazolo[3,4-d]pyrimidin-4-amine (41f) (0.57 g, yield: 87%).

LCMS m/z=460.2 [M+1]$^+$.

Step 6 tert-butyl 3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidine]-1'-carboxylate (41g)

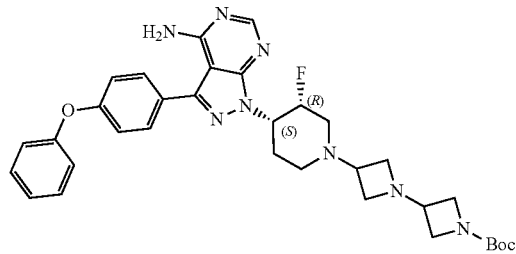

1-((3R,4S)-1-(azetidin-3-yl)-3-fluoropiperidin-4-yl)-3-(4-phenoxyphenyl)-1H-pyrazolo[3,4-d]pyrimidin-4-amine (41f) (500 mg, 1.09 mmol) was dissolved in 30 mL of DCE, and tert-butyl 3-oxoazetidine-1-carboxylate (372 mg, 2.18 mmol) was added, the mixture was stirred at room temperature for 10 minutes, then sodium triacetoxyborohydride (0.93 g, 4.39 mmol) was added, and the mixture was stirred at room temperature overnight. To the reaction system was slowly added 50 mL of saturated sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidin]-1'-carboxylate (41g) (480 mg, yield: 72%).

LCMS m/z=615.3 [M+1]$^+$.

Step 7

1-((3R,4S)-1-([1,3'-biazetidin]-3-yl)-3-fluoropiperidin-4-yl)-3-(4-phenoxyphenyl)-1H-pyrazolo[3,4-d]pyrimidin-4-amine (41h)

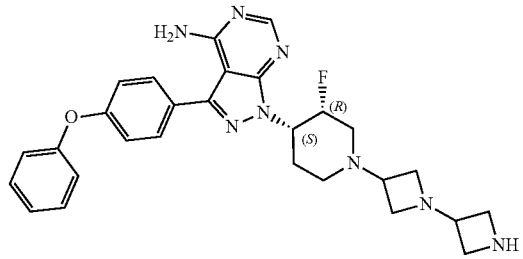

Tert-butyl 3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidin]-1'-carboxylate (41g) (480 mg, 0.78 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure, to obtain 1-((3R,4S)-1-([1,3'-biazetidin]-3-yl)-3-fluoropiperidin-4-yl)-3-(4-phenoxyphenyl)-1 H-pyrazolo[3,4-d]pyrimidin-4-amine (41h) (0.40 g, yield: >99%).

LCMS m/z=515.2 [M+1]$^+$.

Step 8

5-(3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 41)

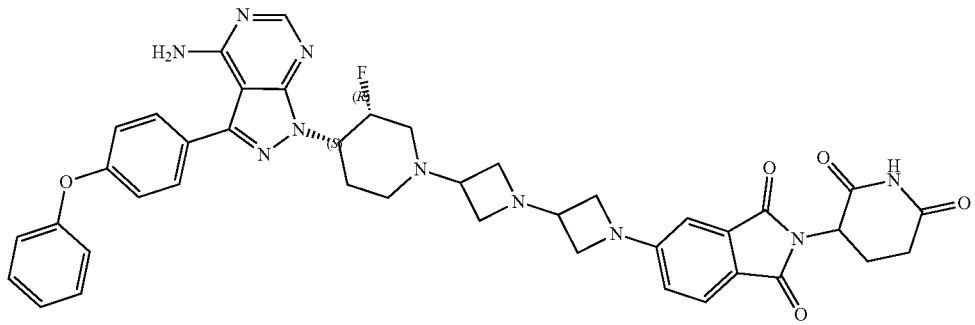

1-((3R,4S)-1-([1,3'-biazetidin]-3-yl)-3-fluoropiperidin-4-yl)-3-(4-phenoxyphenyl)-1H-pyrazolo[3,4-d]pyrimidin-4-amine (41h) (300 mg, 0.58 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (242 mg, 0.88 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3R,4S)-4-(4-amino-3-(4-phenoxyphenyl)-1H-pyrazolo[3,4-d]pyrimidin-1-yl)-3-fluoropiperidin-1-yl)-[1,3'-biazetidin]-1'-yl)-2-(2,6-dioxopiperidin-3-yl)isoindoline-1,3-dione (Compound 41) (280 mg, yield: 63%).

¹H NMR (400 MHz, CDCl₃) δ 10.07 (s, 1H), 8.39 (s, 1H), 7.68-7.60 (m, 3H), 7.41-7.34 (m, 2H), 7.19-7.04 (m, 5H), 6.78 (d, 1H), 6.51 (dd, 1H), 5.86 (brs, 2H), 5.18-5.00 (m, 1H), 4.98-4.81 (m, 2H), 4.08-4.00 (m, 2H), 3.92-3.84 (m, 2H), 3.74-3.66 (m, 1H), 3.66-3.56 (m, 2H), 3.26-2.95 (m, 6H), 2.90-2.65 (m, 3H), 2.46-2.29 (m, 1H), 2.28-2.17 (m, 1H), 2.16-2.05 (m, 2H).

LCMS m/z=771.3 [M+1]⁺.

Example 42

5-(3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 42)

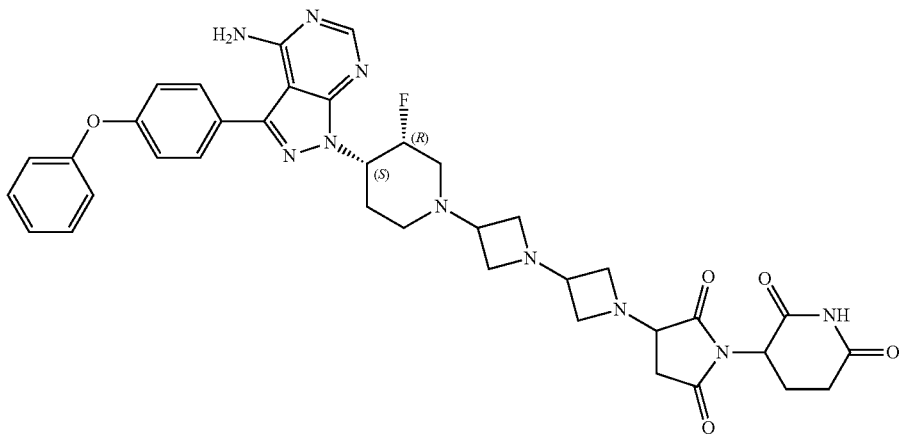

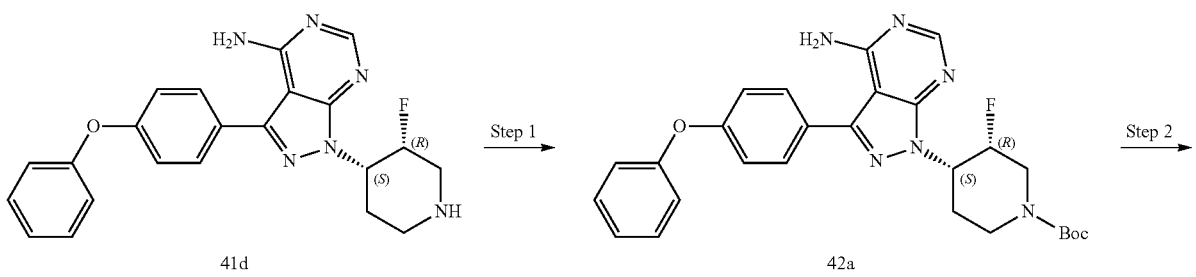

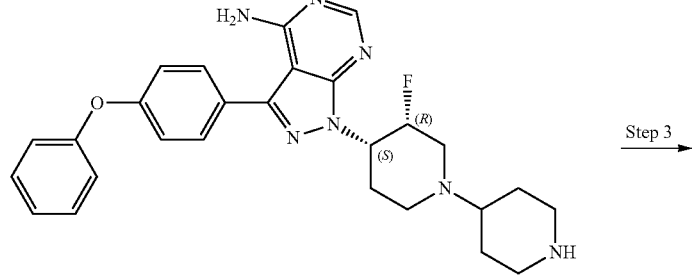

-continued
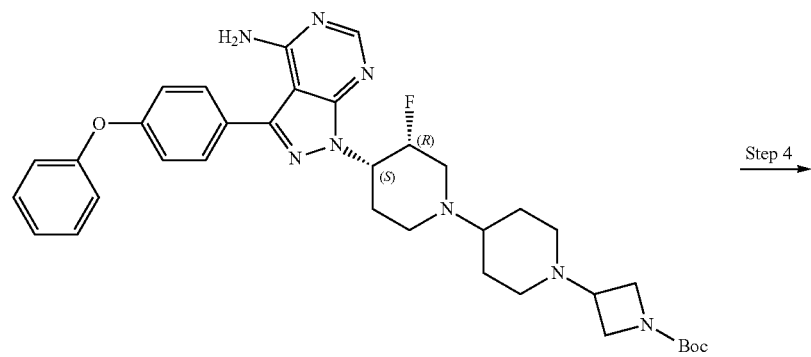
42c
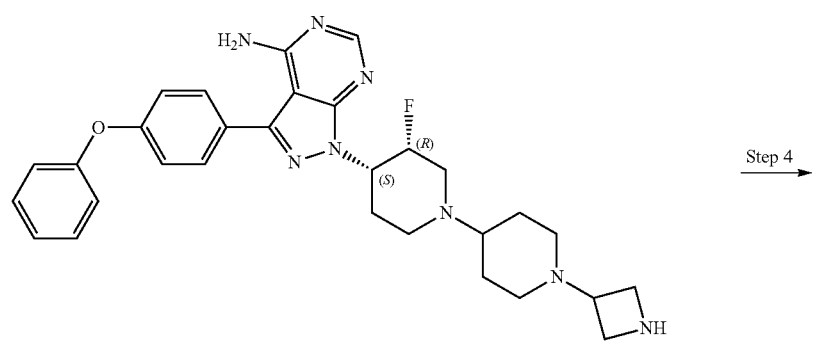
42d
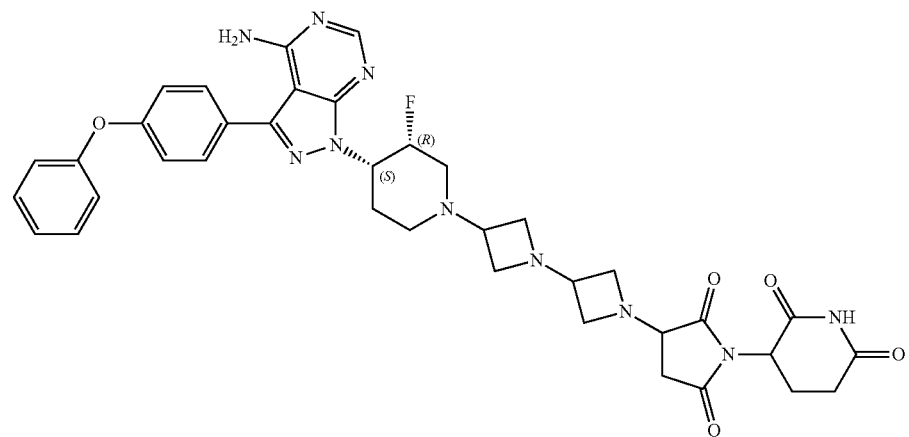
Compound 42

Step 1 tert-butyl (3R,4S)-4-(4-amino-3-(4-phenoxyphenyl)-1H-pyrazolo[3,4-d]pyrimidin-1-yl)-3-fluoro-[1,4'-bipiperidine]-1'-carboxylate (42a)

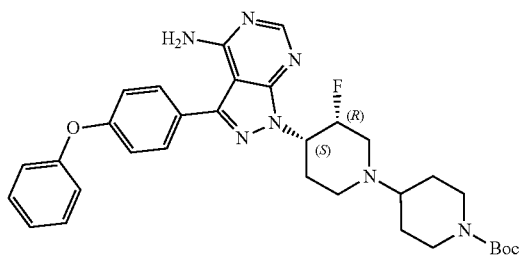

1-((3R,4S)-3-fluoropiperidin-4-yl)-3-(4-phenoxyphenyl)-1H-pyrazolo[3,4-d]pyrimidin-4-amine (41d) (0.9 g, 2.23 mmol) was dissolved in 35 mL of DCE, and tert-butyl 4-oxopiperidine-1-carboxylate (887 mg, 4.46 mmol) was added, the mixture was stirred at room temperature for 10 minutes, then sodium triacetoxyborohydride (1.89 g, 8.92 mmol) was added, and the mixture was stirred at room temperature overnight. To the reaction solution was slowly added 50 mL of saturated sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl (3R,4S)-4-(4-amino-3-(4-phenoxyphenyl)-1H-pyrazolo[3,4-d]pyrimidin-1-yl)-3-fluoro-[1,4'-bipiperidine]-1'-carboxylate (42a) (1.08 g, yield: 83%).

LCMS m/z=588.3 [M+1]$^+$.

Step 2

1-((3R,4S)-3-fluoro-[1,4'-bipiperidin]-4-yl)-3-(4-phenoxyphenyl)-1H-pyrazolo[3,4-d]pyrimidin-4-amine (42b)

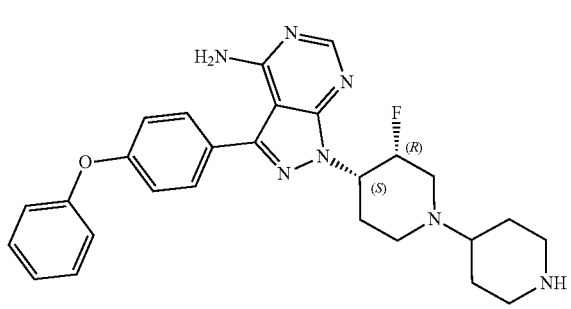

Tert-butyl (3R,4S)-4-(4-amino-3-(4-phenoxyphenyl)-1H-pyrazolo[3,4-d]pyrimidin-1-yl)-3-fluoro-[1,4'-bipiperidine]-1'-carboxylate (42a) (800 mg, 1.36 mmol) was dissolved in 30 mL of DCM, and 10 mL of trifluoroacetic acid was added, the mixture was stirred at room temperature for 4 h. Upon completion of the reaction, the reaction system was directly concentrated under reduced pressure, and the residue was dissolved with 50 mL of 5N sodium hydroxide solution, and extracted with 50 mL of DCM three times. The organic phase was washed with 50 mL of 1N sodium hydroxide solution twice, dried over anhydrous sodium sulfate, and concentrated under reduced pressure to obtain 1-((3R,4S)-3-fluoro-[1,4'-bipiperidin]-4-yl)-3-(4-phenoxyphenyl)-1H-pyrazolo[3,4-d]pyrimidin-4-amine (42b) (600 mg, yield: 91%).

LCMS m/z=488.3 [M+1]$^+$.

Step 3 tert-butyl 3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (42c)

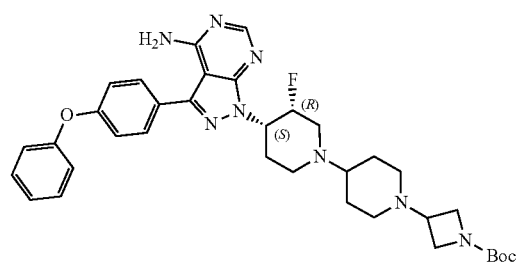

1-((3R,4S)-3-fluoro-[1,4'-bipiperidin]-4-yl)-3-(4-phenoxyphenyl)-1H-pyrazolo[3,4-d]pyrimidin-4-amine (42b) (550 mg, 1.13 mmol) was dissolved in 30 mL of DCE, and tert-butyl 3-oxoazetidine-1-carboxylate (380 mg, 2.22 mmol) was added, the mixture was stirred at room temperature for 10 minutes, then sodium triacetoxyborohydride (0.95 g, 4.48 mmol) was added, and the mixture was stirred at room temperature overnight. To the reaction system was slowly added 50 mL of saturated sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (42c) (620 mg, yield: 85%).

LCMS m/z=643.4 [M+1]$^+$.

Step 4

1-((3R,4S)-1'-(azetidin-3-yl)-3-fluoro-[1,4'-bipiperidin]-4-yl)-3-(4-phenoxyphenyl)-1H-pyrazolo[3,4-d]pyrimidin-4-amine (42d)

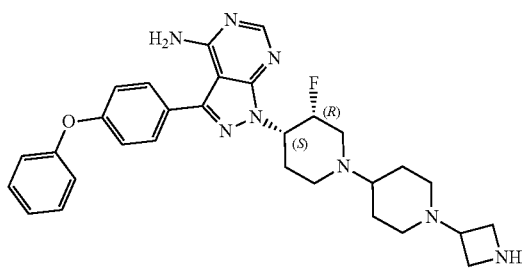

Tert-butyl 3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (42c) (580 mg, 0.90 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure, to obtain 1-((3R,4S)-1'-(azetidin-3-yl)-3-fluoro-[1,4'-bipiperidin]-4-yl)-3-(4-phenoxyphenyl)-1H-pyrazolo[3,4-d]pyrimidin-4-amine (42d) (480 mg, yield: 98%).

LCMS m/z=543.3 [M+1]$^+$.

Step 5

5-(3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 42)

1-((3R,4S)-1'-(azetidin-3-yl)-3-fluoro-[1,4'-bipiperidin]-4-yl)-3-(4-phenoxyphenyl)-1H-pyrazolo[3,4-d]pyrimidin-4-amine (42d) (300 mg, 0.55 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (229 mg, 0.83 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3R,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 42) (340 mg, yield: 77%).

$^1$H NMR (400 MHz, CDCl$_3$) δ 9.63-9.46 (m, 1H), 8.39 (s, 1H), 7.68-7.61 (m, 3H), 7.41-7.34 (m, 2H), 7.20-7.04 (m, 5H), 6.79 (d, 1H), 6.52 (dd, 1H), 5.78 (brs, 2H), 5.23-5.00 (m, 1H), 4.97-4.77 (m, 2H), 4.13-4.06 (m, 2H), 3.93-3.84 (m, 2H), 3.42-3.29 (m, 2H), 3.27-3.14 (m, 1H), 3.08-2.92 (m, 3H), 2.92-2.65 (m, 4H), 2.65-2.46 (m, 2H), 2.18-2.06 (m, 2H), 2.02-1.84 (m, 4H), 1.76-1.61 (m, 2H).

LCMS m/z=799.3 [M+1]$^+$.

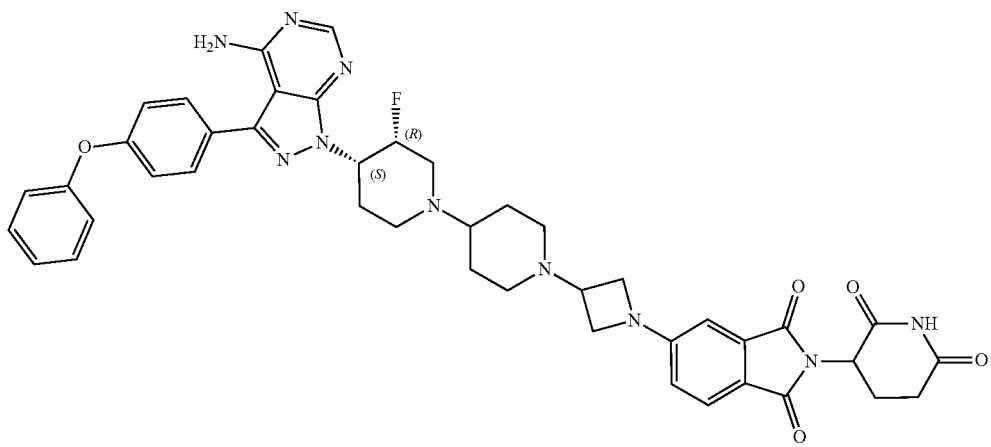

Example 43
5-[3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 43)
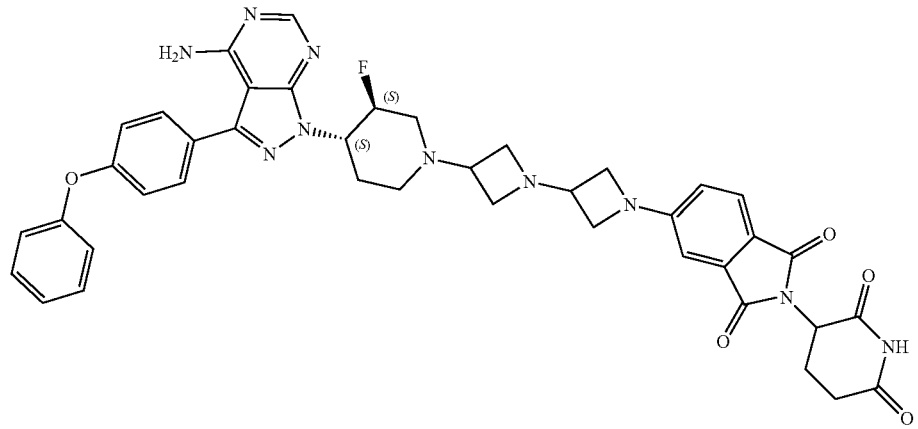
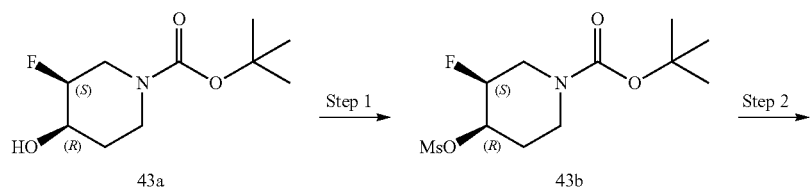
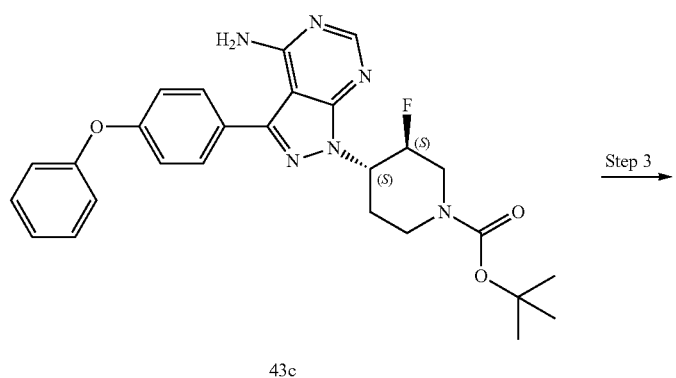
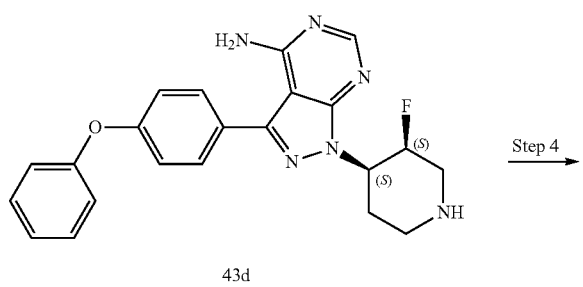

-continued
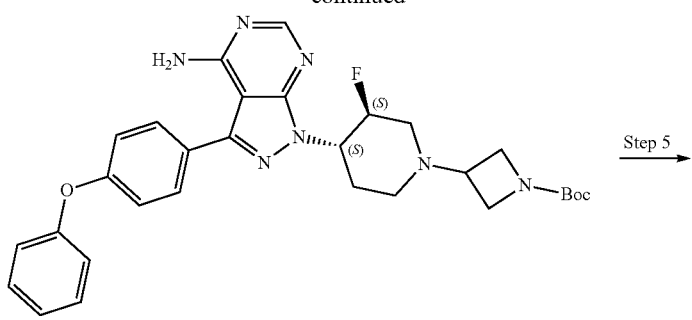
43e
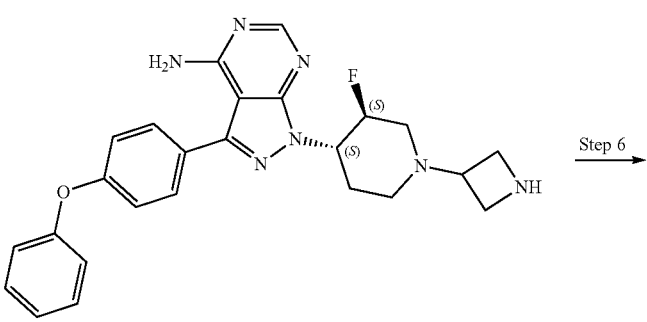
43f
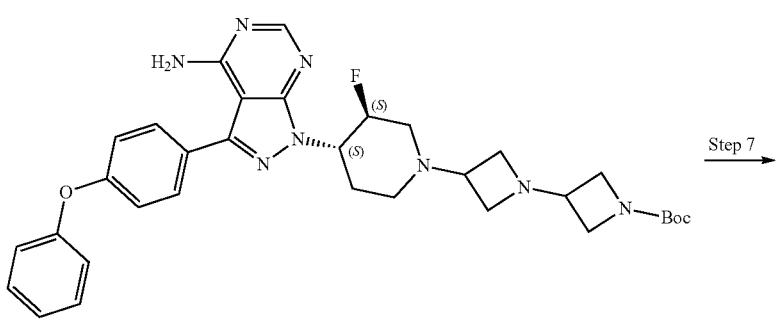
43g
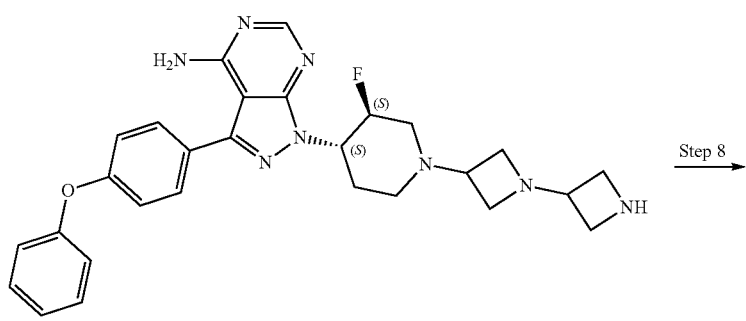
43h

-continued

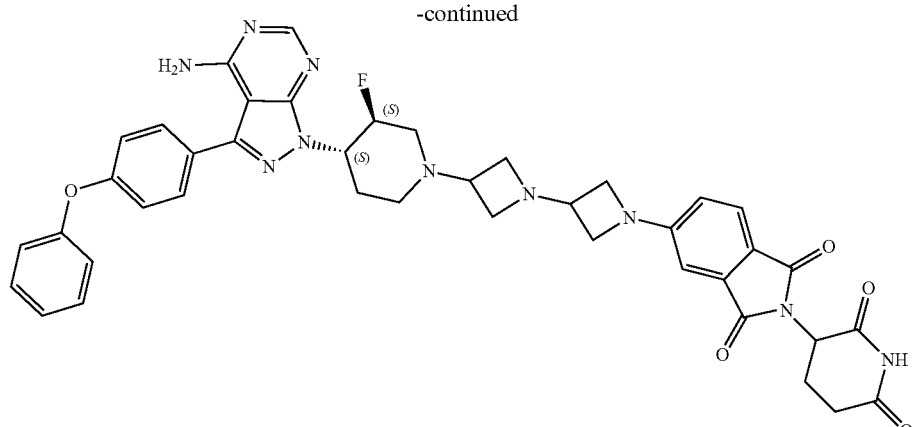

Compound 43

Step 1 tert-butyl (3S,4R)-3-fluoro-4-methylsulfonyloxy-piperidine-1-carboxylate (43b)

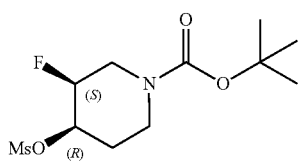

Tert-butyl (3S,4R)-3-fluoro-4-hydroxypiperidine-1-carboxylate (43a) (6.0 g, 27.39 mmol) was dissolved in 30 mL of dichloromethane, and DIPEA (7.06 g, 54.62 mmol) was added, then methanesulfonyl chloride (0.376 g, 3.28 mmol) was slowly added dropwise. Upon completion of the addition, the mixture was stirred at room temperature for 2 h. The reaction solution was quenched with 40 mL of water, and extracted with 100 mL of DCM three times. The organic phase was washed with 100 mL of water, dried over anhydrous sodium sulfate, and concentrated under reduced pressure. The crude product was separated and purified by silica gel column chromatography (petroleum ether/ethyl acetate (v/v)=5:1), to obtain tert-butyl (3S,4R)-3-fluoro-4-methylsulfonyloxy-piperidine-1-carboxylate (43b) (7.97 g, yield: 98%).

Step 2 tert-butyl (3S,4S)-4-[4-amino-3-(4-phenoxyphenyl)pyrazolo[3,4-d]pyrimidin-1-yl]-3-fluoro-piperidine-1-carboxylate (43c)

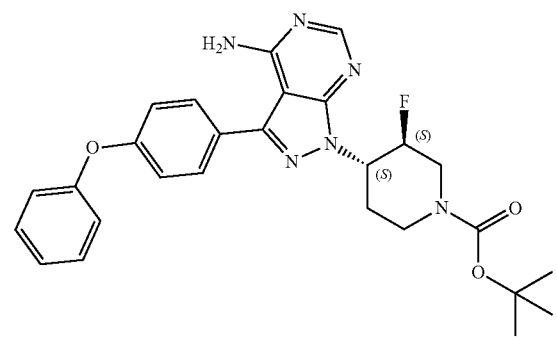

Tert-butyl (3S,4R)-3-fluoro-4-methylsulfonyloxy-piperidine-1-carboxylate (43b) (2.45 g, 8.25 mmol) and 3-(4-phenoxyphenyl)-1H-pyrazolo[3,4-d]pyrimidin-4-amine (1.0 g, 3.30 mmol) was dissolved in 20 mL of DMF, and cesium carbonate (2.14 g, 6.57 mmol) was added, the reaction was stirred at 100° C. for 7 h. The reaction was cooled to room temperature, and the reaction system was added 50 mL of water, and extracted with 100 mL of ethyl acetate three times. The organic phase was washed with 100 mL of water, dried over anhydrous sodium sulfate, and concentrated under reduced pressure. The crude product was separated and purified by silica gel column chromatography (dichloromethane/methanol (v/v)=15:1), to obtain tert-butyl (3S,4S)-4-[4-amino-3-(4-phenoxyphenyl)pyrazolo[3,4-d]pyrimidin-1-yl]-3-fluoro-piperidine-1-carboxylate (43c) (0.9 g, yield: 54%).

LCMS m/z=505.3 [M+1]$^+$.

Step 3

1-[(3S,4S)-3-fluoro-4-piperidyl]-3-(4-phenoxyphenyl)pyrazolo[3,4-d]pyrimidin-4-amine (43d)

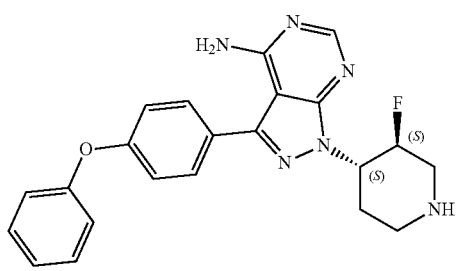

Tert-butyl (3S,4S)-4-[4-amino-3-(4-phenoxyphenyl)pyrazolo[3,4-d]pyrimidin-1-yl]-3-fluoro-piperidine-1-carboxylate (43c) (0.9 g, 1.79 mmol) was dissolved in 20 mL of DCM, and 5 mL of trifluoroacetic acid was added, the mixture was stirred at room temperature for 4 h. The reaction system was directly concentrated under reduced pressure, and the residue was dissolved with 60 mL of 5N sodium hydroxide solution, extracted with 100 mL of dichloromethane three times, dried over anhydrous sodium sulfate, and concentrated under reduced pressure, to obtain 1-[(3S,4S)-3-fluoro-4-piperidyl]-3-(4-phenoxyphenyl)pyrazolo[3,4-d]pyrimidin-4-a mine (43d) (0.7 g, yield: 97%).

LCMS m/z=405.3 [M+1]+.

Step 4 tert-butyl 3-[(3S,4S)-4-[4-amino-3-(4-phenoxyphenyl)pyrazolo[3,4-d]pyrimidin-1-yl]-3-fluoro-1-piperidyl]azetidine-1-carboxylate (43e)

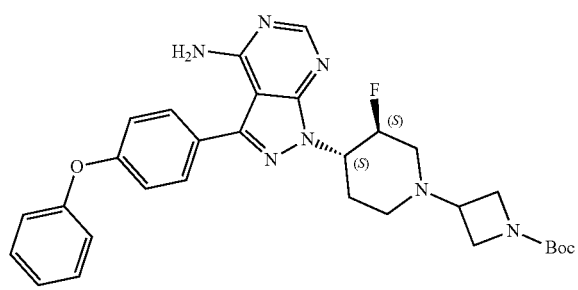

1-[(3S,4S)-3-fluoro-4-piperidyl]-3-(4-phenoxyphenyl)pyrazolo[3,4-d]pyrimidin-4-amine (43d) (0.7 g, 1.73 mmol) was dissolved in 35 mL of DCE and 5 mL of DMSO, and tert-butyl 3-oxoazetidine-1-carboxylate (542 mg, 3.17 mmol) was added, the mixture was stirred at room temperature for 10 minutes, then sodium triacetoxyborohydride (1.68 g, 7.93 mmol) was added, and the mixture was stirred at room temperature overnight. To the reaction solution was slowly added 30 mL of saturated sodium bicarbonate solution, and the mixed solution was extracted with 50 mL of ethyl acetate three times. The organic phase was washed with 50 mL of water, dried over anhydrous sodium sulfate, and concentrated under reduced pressure, then the crude product was separated and purified by silica gel column chromatography (dichloromethane/methanol (v/v)=20:1), to obtain tert-butyl 3-[(3S,4S)-4-[4-amino-3-(4-phenoxyphenyl)pyrazolo[3,4-d]pyrimidin-1-yl]-3-fluoro-1-piperidyl]azetidine-1-carboxylate (43e) (800 mg, yield: 83%).

LCMS m/z=560.3 [M+1]+.

Step 5

1-[(3S,4S)-1-(azetidin-3-yl)-3-fluoro-4-piperidyl]-3-(4-phenoxyphenyl)pyrazolo[3,4-d]pyrimidin-4-amine (43f)

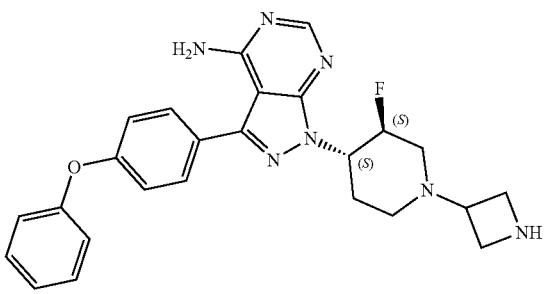

Tert-butyl 3-[(3S,4S)-4-[4-amino-3-(4-phenoxyphenyl)pyrazolo[3,4-d]pyrimidin-1-yl]-3-fluoro-1-piperidyl]azetidine-1-carboxylate (43e) (500 mg, 0.89 mmol) was dissolved in 20 mL of DCM, and 5 mL of trifluoroacetic acid was added, the mixture was stirred at room temperature for 4 h. Upon completion of the reaction, the system was directly concentrated under reduced pressure, and the residue was dissolved with 50 mL of 5N sodium hydroxide solution, and extracted with 50 mL of DCM three times. The organic phase was washed with 30 mL of 1N sodium hydroxide solution twice, dried over anhydrous sodium sulfate, and concentrated under reduced pressure, to obtain 1-[(3S,4S)-1-(azetidin-3-yl)-3-fluoro-4-piperidyl]-3-(4-phenoxyphenyl)pyrazolo[3,4-d]pyrimidin-4-amine (43f) (0.4 g, yield: 98%).

LCMS m/z=460.2 [M+1]+.

Step 6 tert-butyl 3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidine-1-carboxylate (43g)

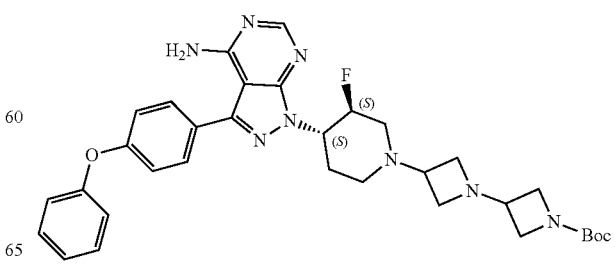

1-[(3S,4S)-1-(azetidin-3-yl)-3-fluoro-4-piperidyl]-3-(4-phenoxyphenyl)pyrazolo[3,4-d]pyrimidin-4-amine (43f) (0.4 g, 0.87 mmol) was dissolved in 25 mL of DCE and 2 mL of DMSO, and tert-butyl 3-oxoazetidine-1-carboxylate (485 mg, 2.83 mmol) was added, the mixture was stirred at room temperature for 10 minutes, then sodium triacetoxyborohydride (1.12 g, 5.28 mmol) was added, and the mixture was stirred at room temperature overnight. To the reaction system was slowly added 60 mL of saturated sodium bicarbonate solution, and the mixed solution was extracted with 60 mL of ethyl acetate three times. The organic phase was washed with 50 mL of water, dried over anhydrous sodium sulfate, and concentrated under reduced pressure, then the crude product was separated and purified by silica gel column chromatography (dichloromethane/methanol (v/v) =20:1), to obtain tert-butyl 3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidine-1-carboxylate (43g) (450 mg, yield: 84%).

LCMS m/z=615.3 [M+1]$^+$.

was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure, to obtain 1-[(3S,4S)-1-[1-(azetidin-3-yl)azetidin-3-yl]-3-fluoro-4-piperidyl]-3-(4-phenoxyphenyl) pyrazolo[3,4-d]pyrimidin-4-amine (43h) (0.33 g, yield: 99/a).

LCMS m/z=515.2 [M+1]$^+$.

Step 8

5-[3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 43)

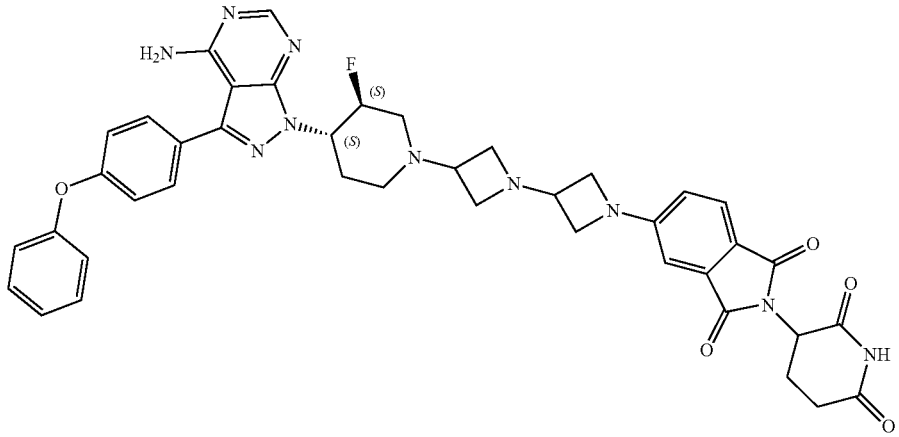

Step 7

1-[(3S,4S)-1-[1-(azetidin-3-yl)azetidin-3-yl]-3-fluoro-4-piperidyl]-3-(4-phenoxyphenyl)pyrazolo[3,4-d]pyrimidin-4-amine (43h)

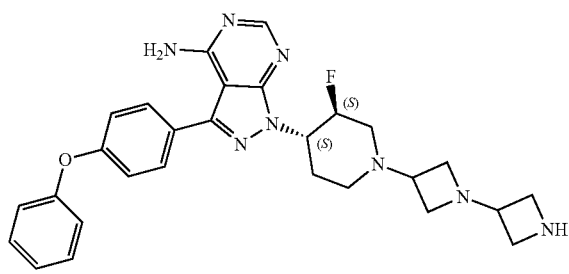

Tert-butyl

3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidine-1-carboxylate (43g) (400 mg, 0.65 mmol) was dissolved in 20 mL of DCM, and 4 mL of trifluoroacetic acid 1-[(3S,4S)-1-[1-(azetidin-3-yl)azetidin-3-yl]-3-fluoro-4-piperidyl]-3-(4-phenoxyphenyl)pyrazolo[3,4-d]pyrimidin-4-amine (43h) (0.33 g, 0.64 mmol) was dissolved in 25 mL of DMSO, and 3 mL of DIPEA and 2-(2,6-dioxopiperidin-3-yl)-5-fluoroisoindoline-1,3-dione (see WO 2017197056 for the synthetic method) (352 mg, 1.28 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=20:1), to obtain 5-[3-[3-[(3S,4S)-4-[4-amino-3-(4-phenoxyphenyl)pyrazolo[3,4-d]pyrimidin-1-yl]-3-fluoro-1-piperidyl]azetidin-1-yl]azetidin-1-yl]-2-(2,6-dioxo-3-piperidyl)isoindoline-1,3-dione (Compound 43) (125 mg, yield: 25%).

$^1$H NMR (400 MHz, CDCl$_3$) δ 9.61 (s, 1H), 8.41 (s, 1H), 7.69-7.61 (m, 3H), 7.43-7.35 (m, 2H), 7.21-7.05 (m, 5H), 6.79 (d, 1H), 6.53 (dd, 1H), 5.80 (brs, 2H), 5.35-5.13 (m, 1H), 4.97-4.83 (m, 2H), 4.09-4.01 (m, 2H), 3.93-3.85 (m, 2H), 3.75-3.55 (m, 3H), 3.29-3.06 (m, 4H), 2.92-2.65 (m, 4H), 2.53-2.39 (m, 1H), 2.22-2.05 (in, 4H).

LCMS m/z=771.3 [M+1]$^+$.

Example 44
5-(3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 44)
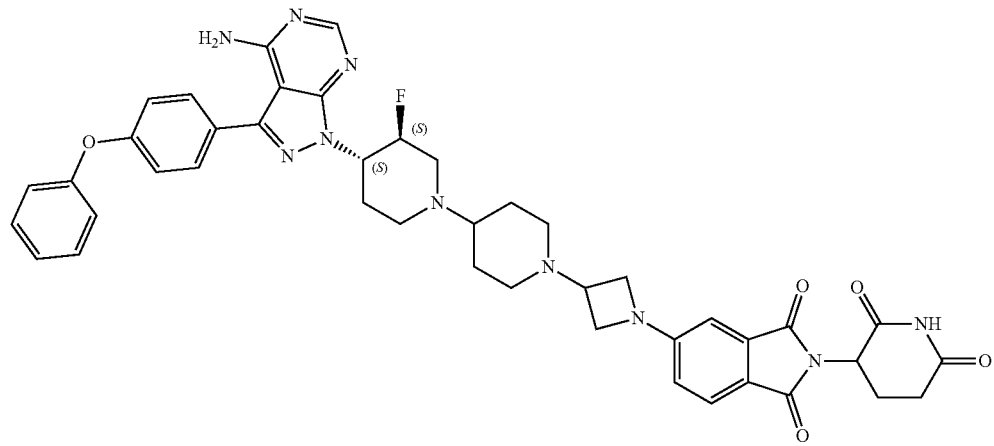
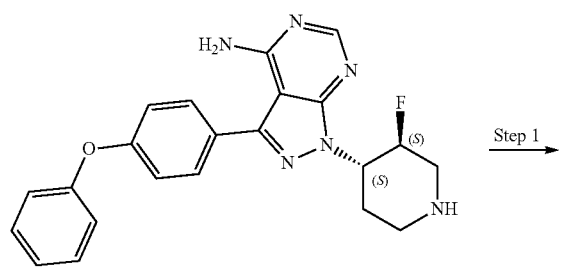
43d
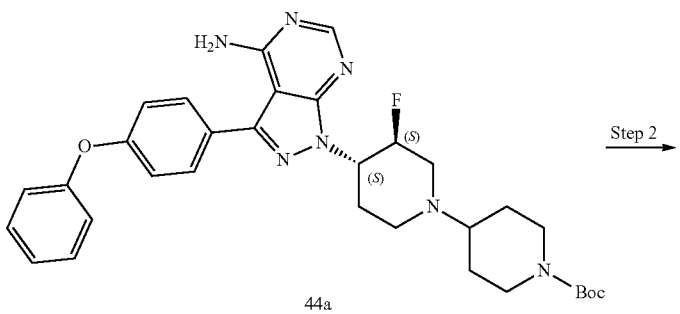
44a
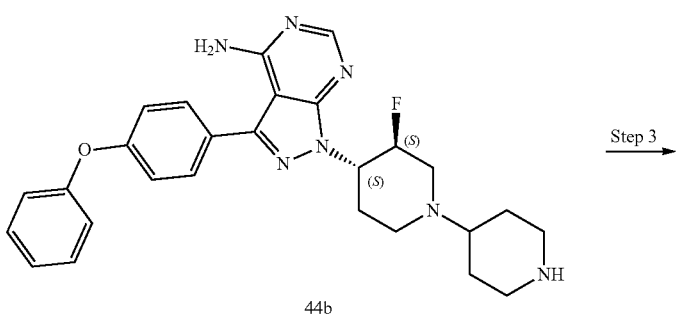
44b -continued
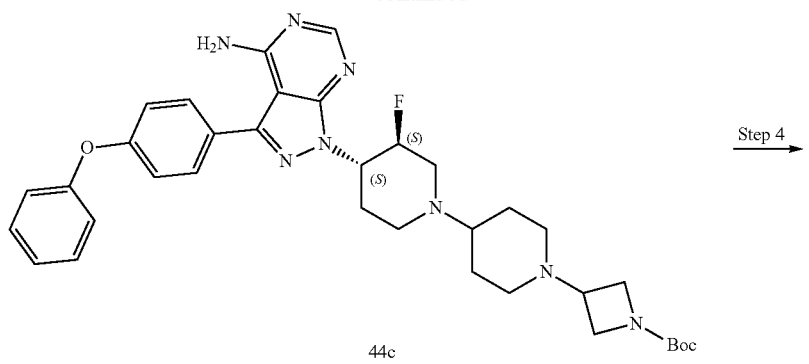
44c
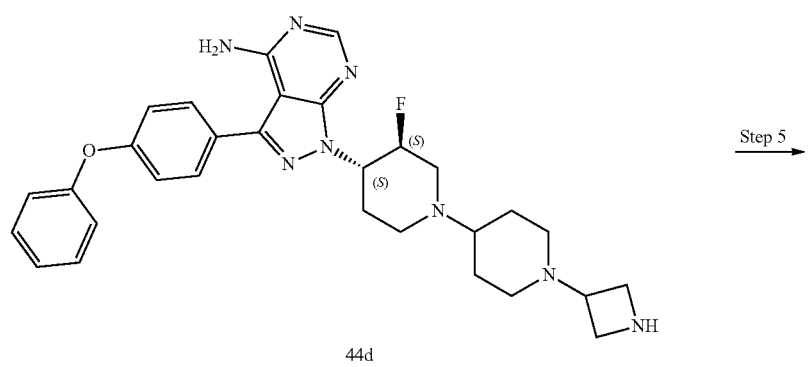
44d
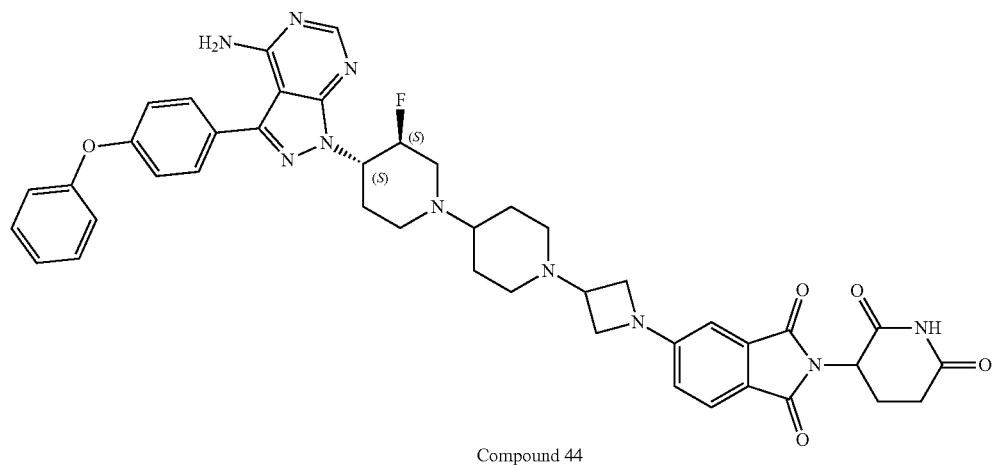
Compound 44

Step 1 tert-butyl (3S,4S)-4-(4-amino-3-(4-phenoxyphenyl)-1H-pyrazolo[3,4-d]pyrimidin-1-yl)-3-fluoro-[1,4'-bipiperidine]-1'-carboxylate (44a)

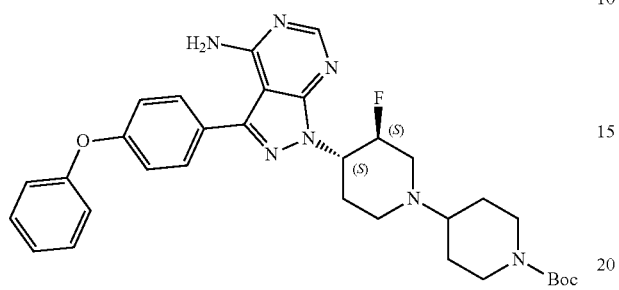

1-[(3S,4S)-3-fluoro-4-piperidyl]-3-(4-phenoxyphenyl)pyrazolo[3,4-d]pyrimidin-4-amine (43d) (800 mg, 1.98 mmol) was dissolved in 35 mL of DCE, and tert-butyl 4-oxopiperidine-1-carboxylate (787 mg, 3.95 mmol) was added, the mixture was stirred at room temperature for 10 minutes, then sodium triacetoxyborohydride (1.68 g, 7.93 mmol) was added, and the mixture was stirred at room temperature overnight. To the reaction solution was slowly added 30 mL of saturated sodium bicarbonate solution, and the mixed solution was extracted with 30 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl (3S,4S)-4-(4-amino-3-(4-phenoxyphenyl)-1H-pyrazolo[3,4-d]pyrimidin-1-yl)-3-fluoro-[1,4'-bipiperidine]-1'-carboxylate (44a) (970 mg, yield: 83%).

LCMS m/z=588.3 [M+1]⁺.

Step 2

1-((3S,4S)-3-fluoro-[1,4'-bipiperidin]-4-yl)-3-(4-phenoxyphenyl)-1H-pyrazolo[3,4-d]pyrimidin-4-amine (44b)

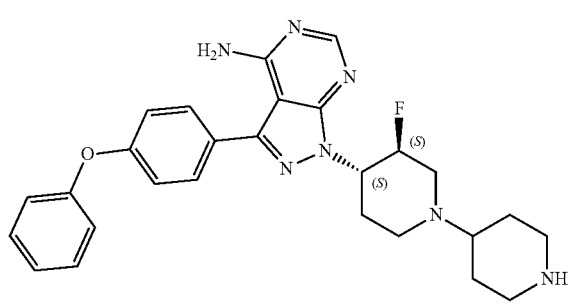

Tert-butyl (3S,4S)-4-(4-amino-3-(4-phenoxyphenyl)-1H-pyrazolo[3,4-d]pyrimidin-1-yl)-3-fluoro-[1,4'-bipiperidine]-1'-carboxylate (44a) (650 mg, 1.11 mmol) was dissolved in 20 mL of DCM, and 8 mL of trifluoroacetic acid was added, the mixture was stirred at room temperature for 4 h. Upon completion of the reaction, the system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure to obtain 1-((3S,4S)-3-fluoro-[1,4'-bipiperidin]-4-yl)-3-(4-phenoxyphenyl)-1H-pyrazolo[3,4-d]pyrimidin-4-amine (44b) (540 mg, yield: >99%).

LCMS m/z=488.3 [M+1]⁺.

Step 3 tert-butyl 3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (44c)

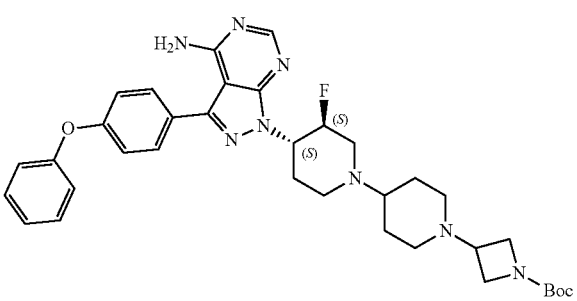

1-((3S,4S)-3-fluoro-[1,4'-bipiperidin]-4-yl)-3-(4-phenoxyphenyl)-1H-pyrazolo[3,4-d]pyrimidin-4-amine (44b) (500 mg, 1.03 mmol) was dissolved in 30 mL of DCE, and tert-butyl 3-oxoazetidine-1-carboxylate (350 mg, 2.05 mmol) was added, the mixture was stirred at room temperature for 10 minutes, then sodium triacetoxyborohydride (870 mg, 4.10 mmol) was added, and the mixture was stirred at room temperature overnight. To the reaction system was slowly added 30 mL of saturated sodium bicarbonate solution, and the mixed solution was extracted with 30 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (44c) (560 mg, yield: 85%).

LCMS m/z=643.4 [M+1]⁺.

Step 4

1-((3S,4S)-1'-(azetidin-3-yl)-3-fluoro-[1,4'-bipiperidin]-4-yl)-3-(4-phenoxy-phenyl)-1H-pyrazolo[3,4-d]pyrimidin-4-amine (44d)

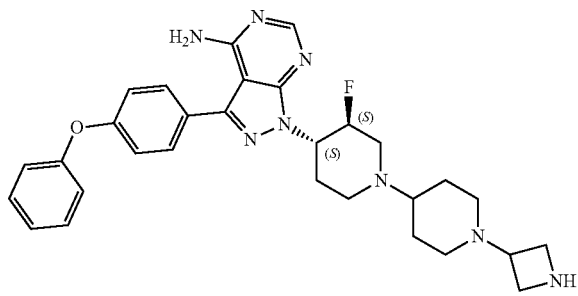

Tert-butyl 3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (44c) (500 mg, 0.78 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of dichloromethane three times. The organic phase was washed with 30 mL of 1N sodium hydroxide solution twice, dried over anhydrous sodium sulfate, and concentrated under reduced pressure, to obtain 1-((3S,4S)-1'-(azetidin-3-yl)-3-fluoro-[1,4'-bipiperidin]-4-yl)-3-(4-phenoxy-phenyl)-1H-pyrazolo[3,4-d]pyrimidin-4-amine (44d) (420 mg, yield: >99%).

LCMS m/z=543.3 [M+1]+.

Step 5

5-(3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 44)

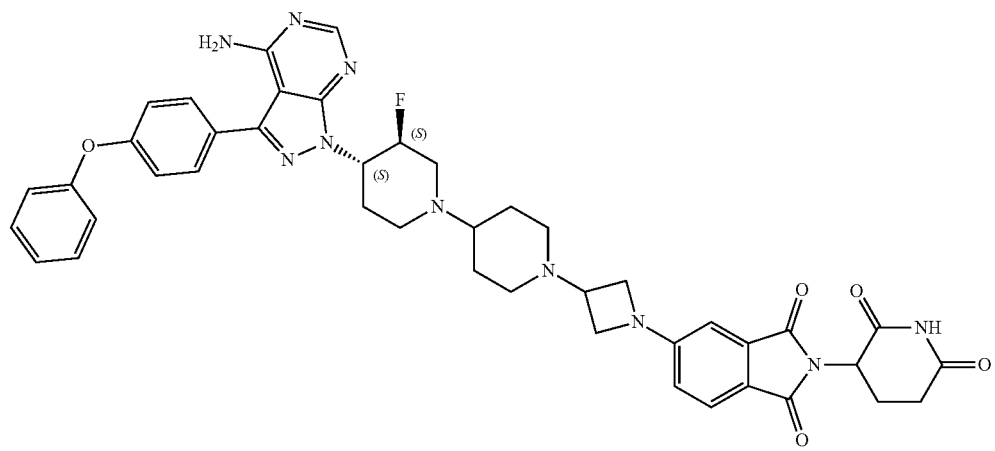

1-((3S,4S)-1'-(azetidin-3-yl)-3-fluoro-[1,4'-bipiperidin]-4-yl)-3-(4-phenoxyphenyl)-1H-pyrazolo[3,4-d]pyrimidin-4-amine (44d) (310 mg, 0.57 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (236 mg, 0.86 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3S,4S)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 44) (310 mg, yield: 68%).

$^1$H NMR (400 MHz, CDCl$_3$) δ 9.49 (s, 1H), 8.41 (s, 1H), 7.71-7.58 (m, 3H), 7.43-7.33 (m, 2H), 7.22-7.11 (m, 3H), 7.11-7.03 (m, 2H), 6.83-6.74 (m, 1H), 6.57-6.47 (m, 1H), 5.78 (brs, 2H), 5.33-5.09 (m, 1H), 4.98-4.79 (m, 2H), 4.16-4.04 (m, 2H), 3.96-3.85 (m, 2H), 3.46-3.31 (m, 2H), 3.07-2.91 (m, 3H), 2.91-2.65 (m, 3H), 2.57-2.34 (m, 4H), 2.18-1.93 (m, 4H), 1.92-1.82 (m, 2H), 1.74-1.58 (m, 2H).

LCMS m/z=799.3 [M+1]+.

Example 45
5-(3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 45)
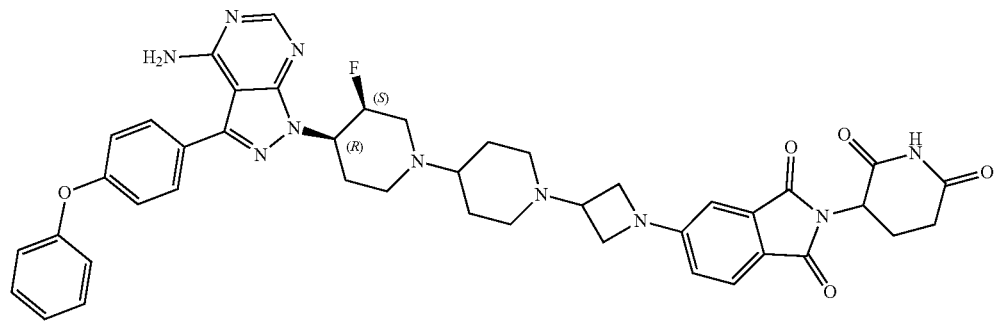
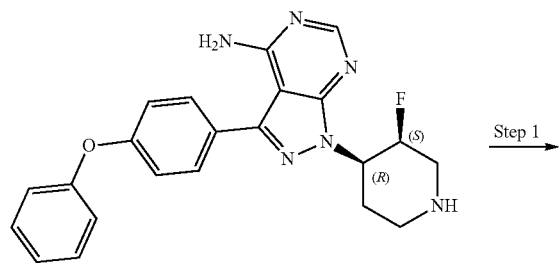
38d
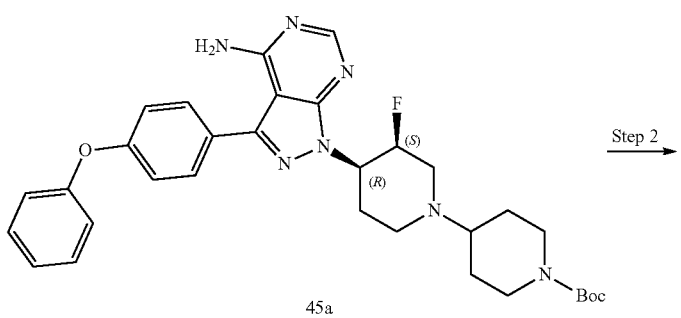
45a
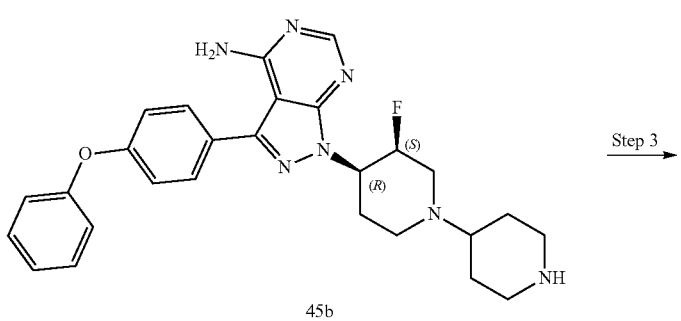
45b -continued
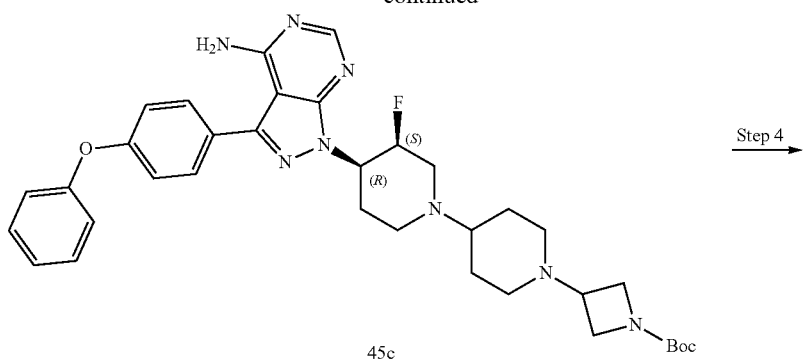
45c
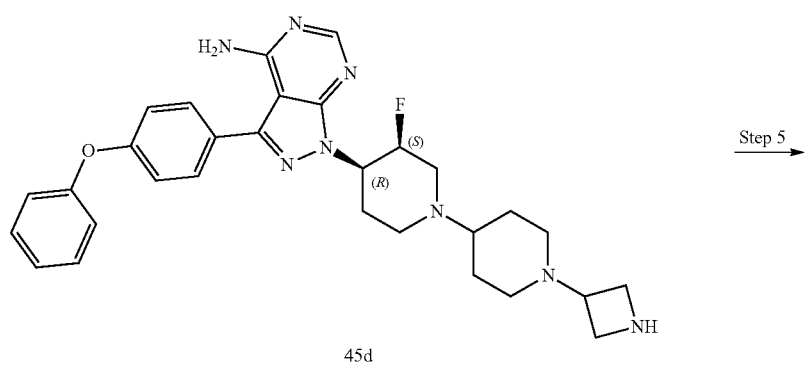
45d
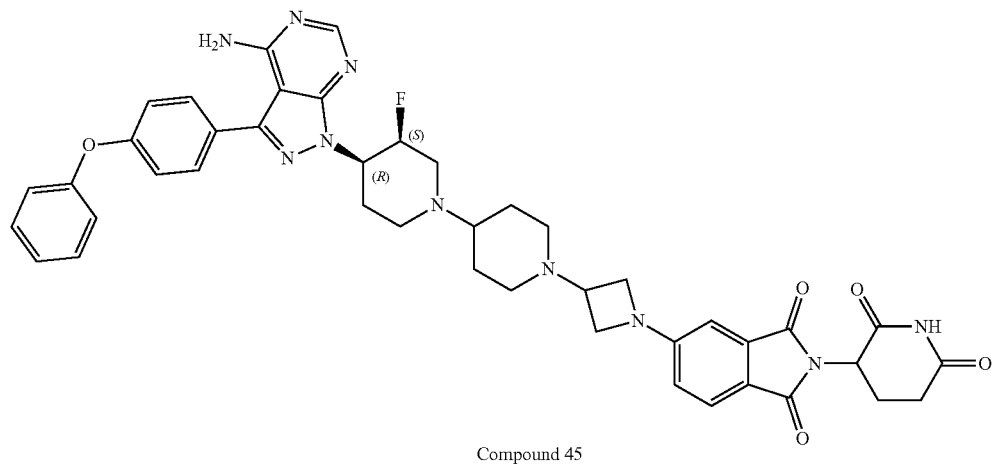
Compound 45

Step 1 tert-butyl (3S,4R)-4-(4-amino-3-(4-phenoxyphenyl)-1H-pyrazolo[3,4-d]pyrimidin-1-yl)-3-fluoro-[1,4'-bipiperidine]-1'-carboxylate (45a)

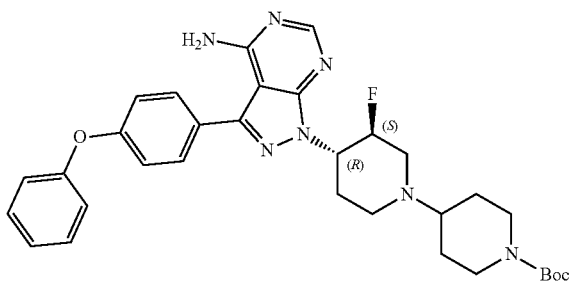

1-[(3S,4R)-3-fluoro-4-piperidyl]-3-(4-phenoxyphenyl)pyrazolo[3,4-d]pyrimidin-4-amine (38d) (1.1 g, 2.72 mmol) was dissolved in 35 mL of DCE, and tert-butyl 4-oxopiperidine-1-carboxylate (1.08 g, 5.43 mmol) was added, the mixture was stirred at room temperature for 10 minutes, then sodium triacetoxyborohydride (2.31 g, 10.90 mmol) was added, and the mixture was stirred at room temperature overnight. To the reaction solution was slowly added 50 mL of saturated sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl (3S,4R)-4-(4-amino-3-(4-phenoxyphenyl)-1H-pyrazolo[3,4-d]pyrimidin-1-yl)-3-fluoro-[1,4'-bipiperidine]-1'-carboxylate (45a) (1.4 g, yield: 88%).

LCMS m/z=588.3 [M+1]+.

Step 2

1-((3S,4R)-3-fluoro-[1,4'-bipiperidin]-4-yl)-3-(4-phenoxyphenyl)-1H-pyrazolo[3,4-d]pyrimidin-4-amine (45b)

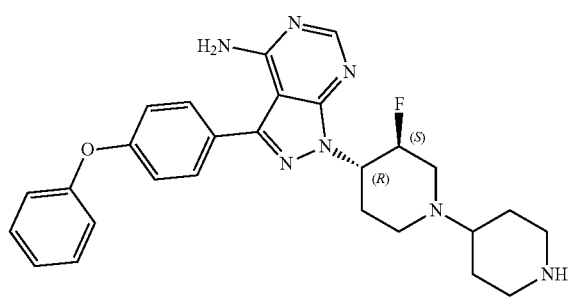

Tert-butyl (3S,4R)-4-(4-amino-3-(4-phenoxyphenyl)-1H-pyrazolo[3,4-d]pyrimidin-1-yl)-3-fluoro-[1,4'-bipiperidine]-1'-carboxylate (45a) (1.4 g, 2.38 mmol) was dissolved in 30 mL of DCM, and 10 mL of trifluoroacetic acid was added, the mixture was stirred at room temperature for 4 h. Upon completion of the reaction, the system was directly concentrated under reduced pressure, and the residue was dissolved with 50 mL of 5N sodium hydroxide solution, and extracted with 50 mL of DCM three times. The organic phase was washed with 30 mL of 1N sodium hydroxide solution twice, dried over anhydrous sodium sulfate, and concentrated under reduced pressure to obtain 1-((3S,4R)-3-fluoro-[1,4'-bipiperidin]-4-yl)-3-(4-phenoxyphenyl)-1H-pyrazolo[3,4-d]pyrimidin-4-amine (45b) (1.2 g, yield: >99%).

LCMS m/z=488.3 [M+1]+.

Step 3 tert-butyl 3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (45c)

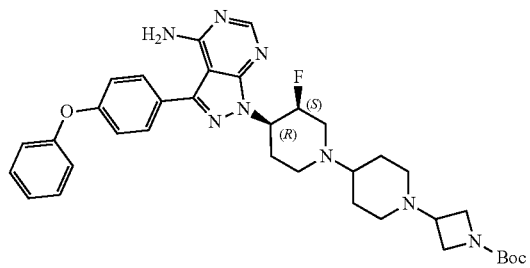

1-((3S,4R)-3-fluoro-[1,4'-bipiperidin]-4-yl)-3-(4-phenoxyphenyl)-1H-pyrazolo[3,4-d]pyrimidin-4-amine (45b) (600 mg, 1.23 mmol) was dissolved in 30 mL of DCE, and tert-butyl 3-oxoazetidine-1-carboxylate (421 mg, 2.46 mmol) was added, the mixture was stirred at room temperature for 10 minutes, then sodium triacetoxyborohydride (1.04 g, 4.91 mmol) was added, and the mixture was stirred at room temperature overnight. To the reaction system was slowly added 50 mL of sodium bicarbonate solution, and the mixed solution was extracted with 50 mL of DCM three times. The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (45c) (700 mg, yield: 89%).

LCMS m/z=643.4 [M+1]+.

Step 4

1-((3S,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (45d)

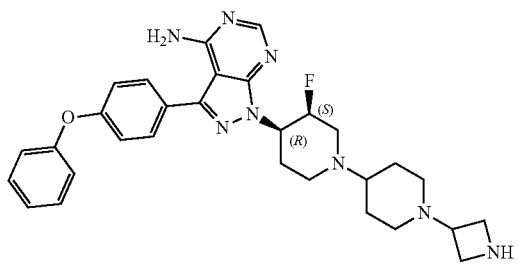

Tert-butyl 3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidine-1-carboxylate (45c) (600 mg, 0.93 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5N sodium hydroxide solution, and extracted with 30 mL of DCM three times. The organic phase was washed with 30 mL of 1N sodium hydroxide solution twice, dried over anhydrous sodium sulfate, and concentrated under reduced pressure, to obtain 1-((3S,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (45d) (0.44 g, yield: 87%).

LCMS m/z=543.3 [M+1]+.

Step 5

5-(3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 45)

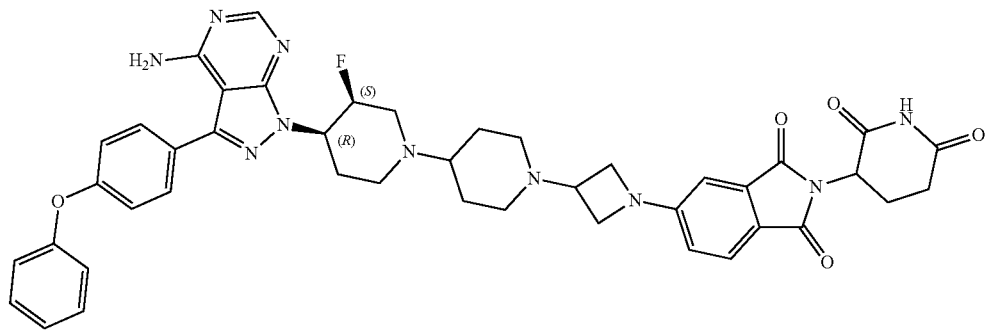

1-((3S,4R)-1'-(azetidin-3-yl)-3-fluoro-[1,4'-bipiperidin]-4-yl)-3-(4-phenoxyphenyl)-1H-pyrazolo[3,4-d]pyrimidin-4-amine (45d) (300 mg, 0.55 mmol) was dissolved in 25 mL of DMSO, and 1.5 mL of DIPEA and 2-(2,6-dioxopiperidin-3-yl)-5-fluoroisoindoline-1,3-dione (see WO 2017197056 for the synthetic method) (229 mg, 0.83 mmol) were added, the reaction was stirred in an external bath at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain 5-(3-((3S,4R)-4-(4-amino-3-(4-phenoxyphenyl)-1H-pyrazolo[3,4-d]pyrimidin-1-yl)-3-fluoro-[1,4'-bipiperidin]-1'-yl)azetidin-1-yl)-2-(2,6-dioxopiperidin-3-yl)isoindoline-1,3-dione (Compound 45) (220 mg, yield: 50%).

$^1$H NMR (400 MHz, CDCl$_3$) δ 9.37 (s, 1H), 8.39 (s, 1H), 7.68-7.60 (m, 3H), 7.42-7.34 (m, 2H), 7.20-7.04 (m, 5H), 6.79 (d, 1H), 6.52 (dd, 1H), 5.74 (brs, 2H), 5.23-5.02 (m, 1H), 4.97-4.79 (m, 2H), 4.14-4.05 (m, 2H), 3.94-3.84 (m, 2H), 3.41-3.29 (m, 2H), 3.27-3.15 (m, 1H), 3.07-2.92 (m, 3H), 2.92-2.66 (m, 4H), 2.65-2.48 (m, 2H), 2.18-2.06 (m, 2H), 2.03-1.84 (m, 4H), 1.75-1.61 (m, 2H).

LCMS m/z=799.3 [M+1]+.

Example 46-1
trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 46-1)
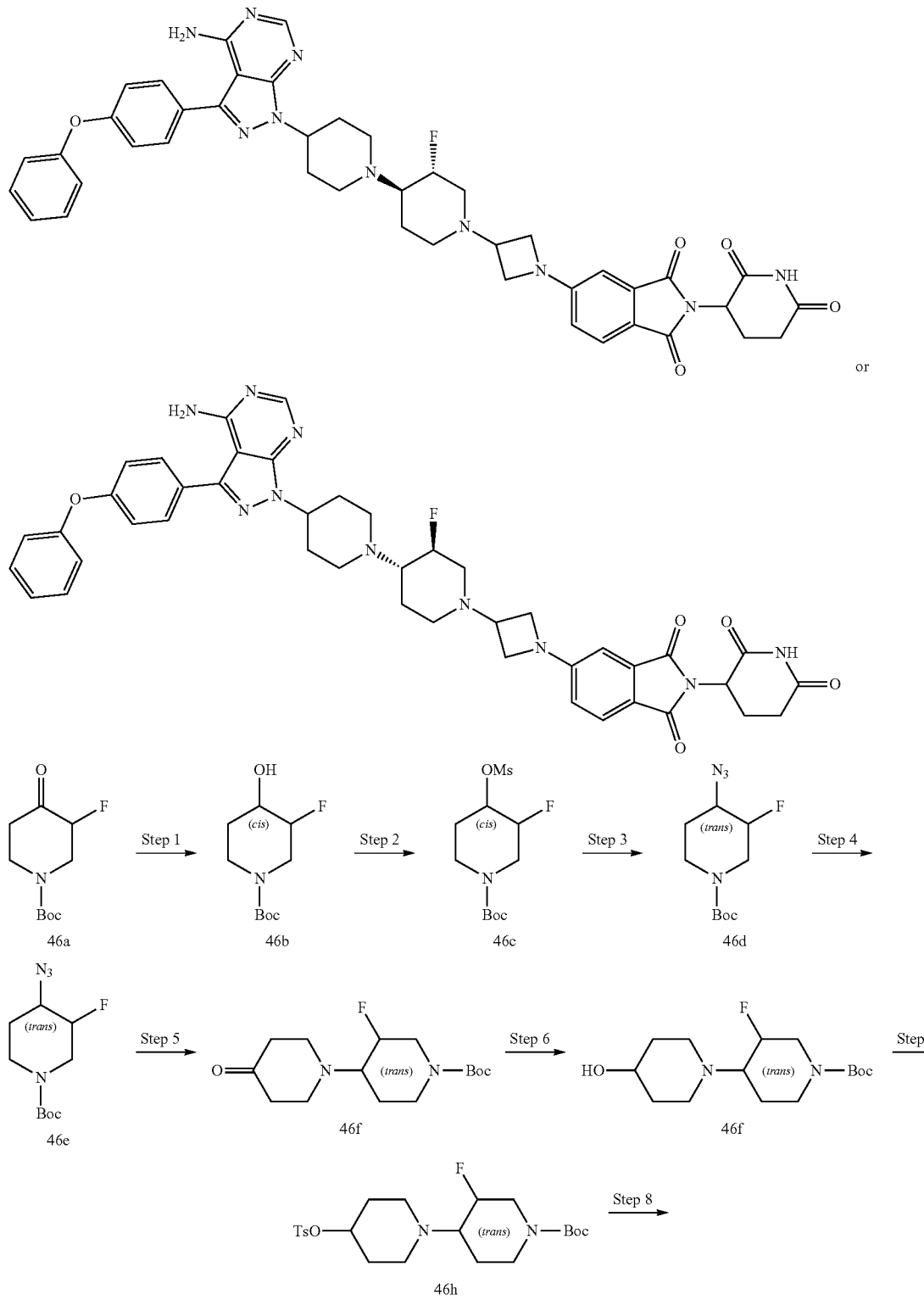

-continued
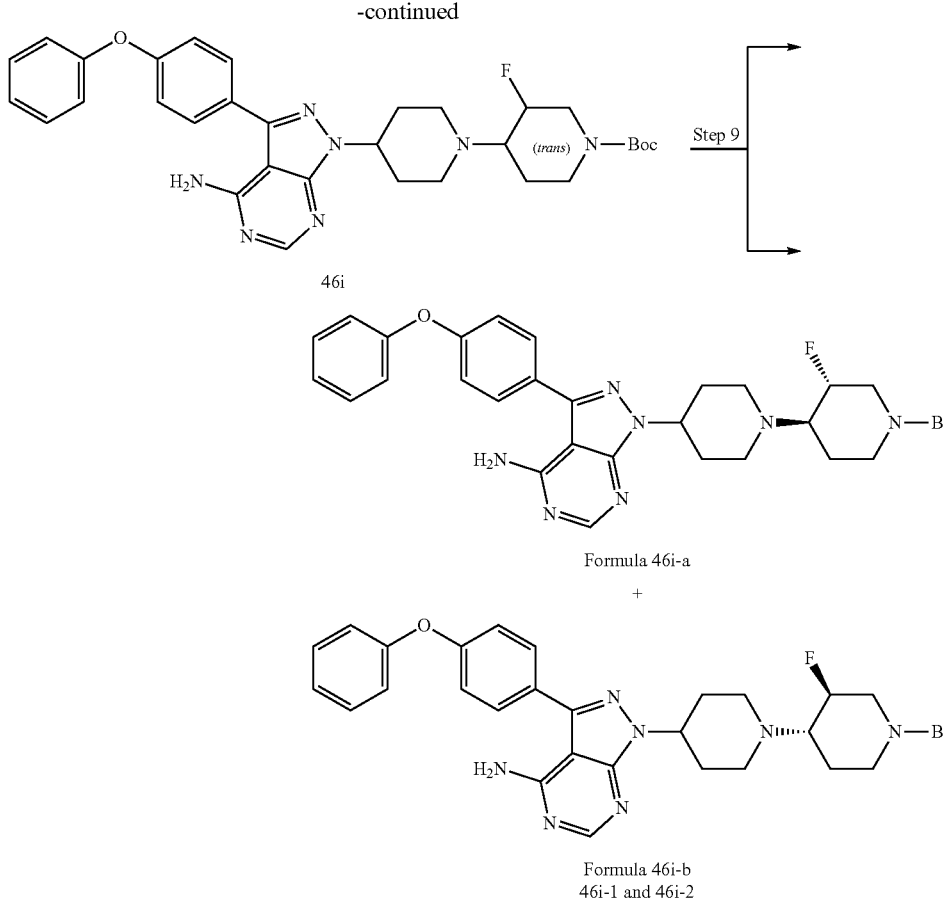
46i
Formula 46i-a
+
Formula 46i-b
46i-1 and 46i-2
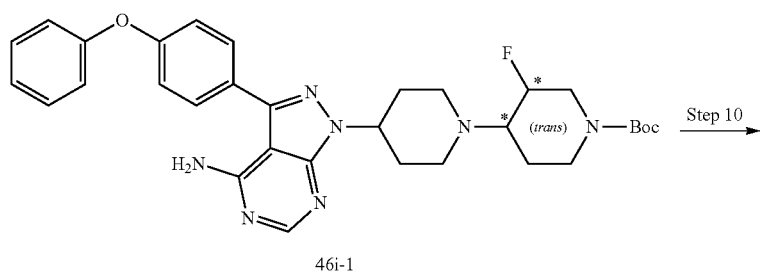
46i-1
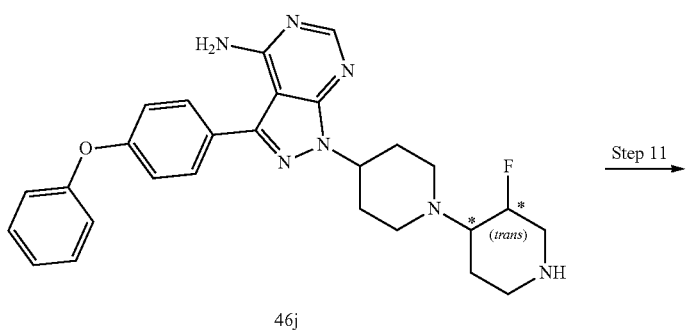
46j -continued
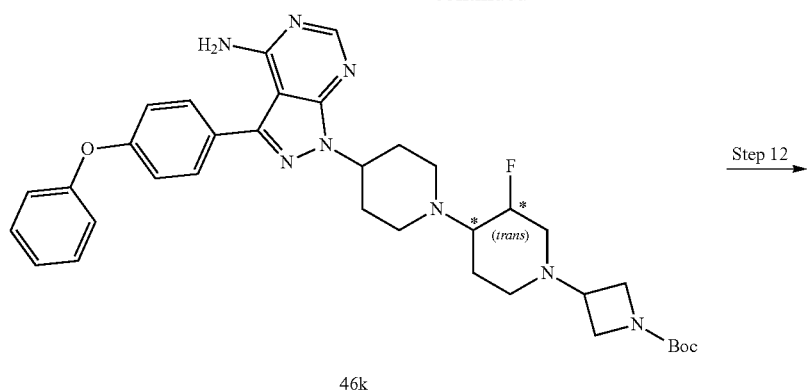
46k
Step 12 →
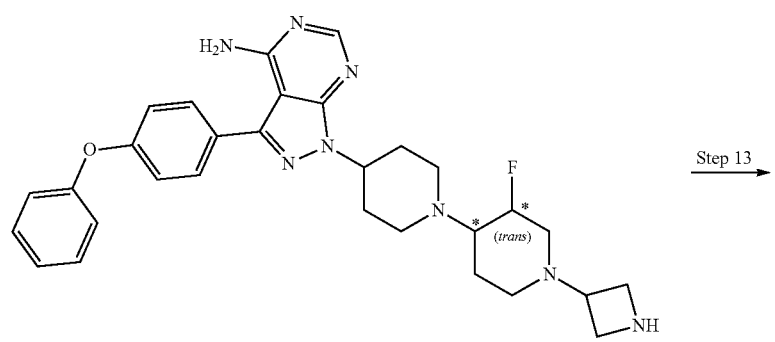
46l
Step 13 →
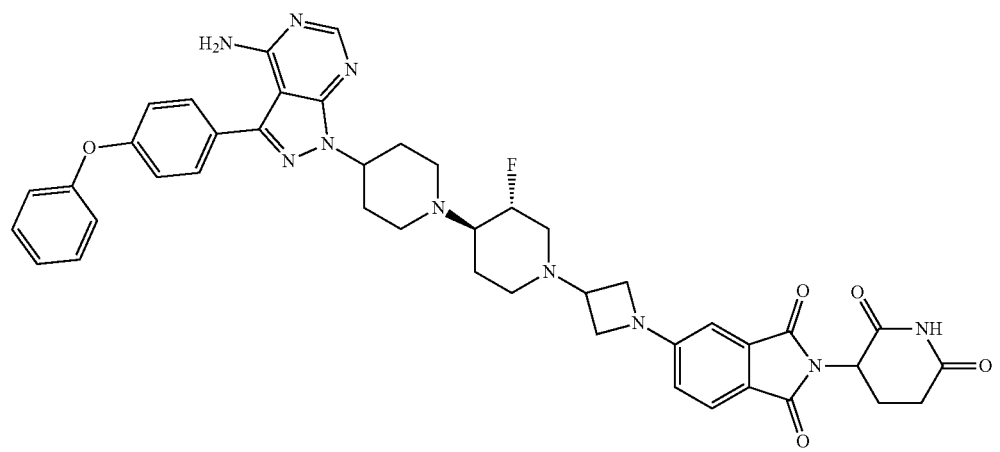
Formula 46-a
or -continued

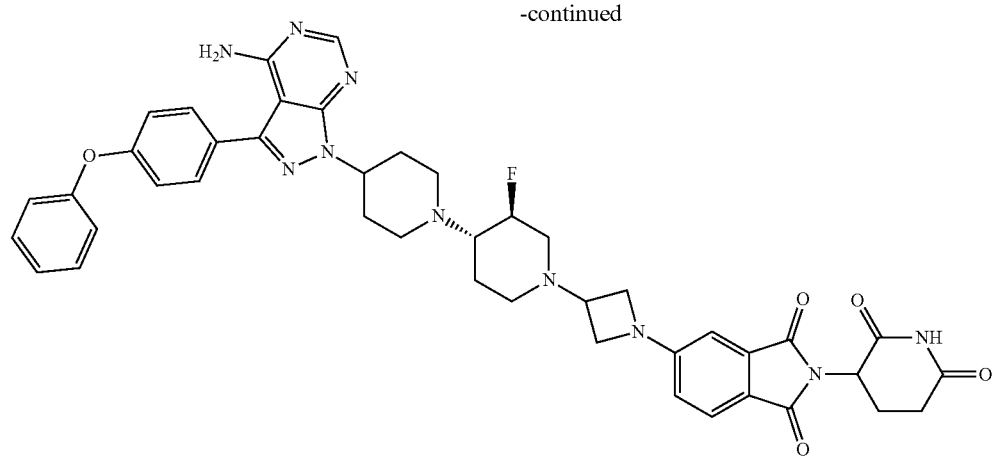

Formula 46-b
Compound 46-1

Step 1 cis-tert-butyl
3-fluoro-4-hydroxy-piperidine-1-carboxylate (46b)

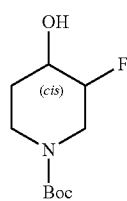

Tert-butyl 3-fluoro-tert-butyl 4-oxopiperidine-1-carboxylate (46a) (13.0 g, 59.8 mmol) was dissolved in 130 mL of anhydrous methanol, and sodium borohydride (4.52 g, 119.5 mmol) was slowly added. Upon completion of the addition, the mixture was stirred at room temperature for 30 minutes. The reaction solution was quenched with 60 mL of saturated ammonium chloride solution, and extracted with 200 mL of dichloromethane. The organic phase was washed with 100 mL of water, dried over anhydrous sodium sulfate, and concentrated under reduced pressure, then the crude product was separated and purified by silica gel column chromatography (petroleum ether/ethyl acetate (v/v)=4:1-7:3), to obtain cis-tert-butyl 3-fluoro-4-hydroxyl-piperidine-1-carboxylate (46b) (9.0 g, yield: 69%).

$^1$H NMR (400 MHz, CDCl$_3$) δ 4.70-4.51 (m, 1H), 3.99-3.83 (m, 2H), 3.79-3.60 (m, 1H), 3.52-3.33 (m, 1H), 3.25-3.10 (m, 1H), 1.95 (br.s, 1H), 1.89-1.69 (m, 2H), 1.46 (s, 9H).

Step 2

Cis-tert-butyl 3-fluoro-4-methylsulfonyloxy-piperidine-1-carboxylate (46c)

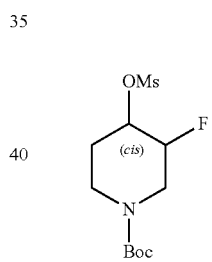

Cis-tert-butyl 3-fluoro-4-hydroxyl-piperidine-1-carboxylate (46b) (1.20 g, 5.47 mmol) was dissolved in 12 mL of dichloromethane, and triethylamine (0.720 g, 7.12 mmol) was added, then methanesulfonyl chloride (0.940 g, 8.21 mmol) was slowly added dropwise at 0° C. Upon completion of the addition, the reaction was carried out at 0° C. for 30 min. At 0° C., to the reaction solution was added dropwise 10 mL of saturated ammonium chloride solution to quench the reaction, until to room temperature. The liquid separation was conducted, the aqueous phase was further extracted with 20 mL of dichloromethane, and the organic phase was combined. The organic phase was washed with 20 mL of saturated sodium chloride solution once, dried over anhydrous sodium sulfate, and concentrated under reduced pressure, to obtain the crude product cis-tert-butyl 3-fluoro-4-methylsulfonyloxy-piperidine-1-carboxylate (46c) (1.60 g).

Step 3 trans-tert-butyl 4-azido-3-fluoro-piperidine-1-carboxylate (46d)

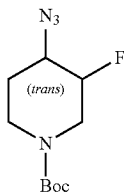

The above crude product cis-tert-butyl 3-fluoro-4-methylsulfonyloxy-piperidine-1-carboxylate (46c) (1.60 g) was dissolved in 10 mL of DMF, and sodium azide (1.05 g, 16.2 mmol) was added. Upon completion of the addition, the reaction was stirred at 95° C. for 5 h. The reaction solution was cooled to room temperature, added 10 mL of water, and extracted with 50 mL of ethyl acetate. The liquid separation was conducted, the organic phase was further washed with 20 mL of saturated sodium chloride solution, dried over anhydrous sodium sulfate, and concentrated under reduced pressure, then the crude product was separated and purified by silica gel column chromatography (petroleum ether/ethyl acetate (v/v)=9:1), to obtain trans-tert-butyl 4-azido-3-fluoro-piperidine-1-carboxylate (46d) (0.900 g, two-step yield calculated from compound 46b: 67%).

$^1$H NMR (400 MHz, CDCl$_3$) δ 4.46-4.25 (m, 1H), 4.21-4.00 (m, 1H), 3.87-3.77 (m, 1H), 3.71-3.59 (m, 1H), 3.19-2.97 (m, 2H), 2.06-1.94 (m, 1H), 1.59-1.49 (m, 1H), 1.46 (s, 9H).

Step 4: trans-tert-butyl 4-amino-3-fluoro-piperidine-1-carboxylate (46e)

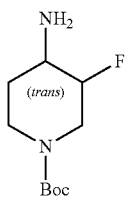

Trans-tert-butyl 4-azido-3-fluoro-piperidine-1-carboxylate (46d) (0.900 g, 3.68 mmol) was dissolved in 10 mL anhydrous ethanol, and 150 mg of 10% palladium carbon was added, the mixture was stirred under H$_2$ atmosphere at room temperature for 16 h. The reaction solution was filtered off with suction, and the filtrate was concentrated under reduced pressure, then the crude product was separated and purified by silica gel column chromatography (dichloromethane/methanol (v/v)=100:0-20:1), to obtain trans-tert-butyl 4-amino-3-fluoro-piperidine-1-carboxylate (46e) (0.500 g, yield: 62%).

$^1$H NMR (400 MHz, CDCl$_3$) δ 4.42-4.19 (m, 1H), 4.18-3.92 (m, 2H), 2.98-2.69 (m, 3H), 1.93-1.82 (m, 1H), 1.55 (br.s, 2H), 1.46 (s, 9H), 1.41-1.28 (m, 1H).

Step 5 trans-tert-butyl 3-fluoro-4-(4-oxo-1-piperidyl)piperidine-1-carboxylate (46f)

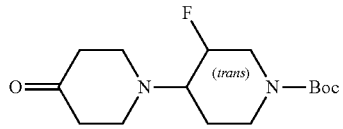 [SMILES: CC(C)(C)OC(=O)N1CCC(N2CCC(=O)CC2)C(F)C1]

Pentan-1,4-dien-3-ol (5.0 g, 59.4 mmol) was dissolved in 50 mL of 1,2-dichloroethane, and 2-iodoxybenzoic acid (IBX) (33 g, 117.8 mmol) was added, the reaction was stirred at 70° C. for 3 h. The reaction solution was cooled to room temperature, and filtered off with suction, and the filtrate was directly used in the next step.

Trans-tert-butyl 4-amino-3-fluoro-piperidine-1-carboxylate (46e) (3.6 g, 16.5 mmol) was dissolved in 10 mL of anhydrous methanol, and diisopropylethylamine (4.26 g, 33.0 mmol) was added, then the above filtrate was added, the reaction was stirred at 70° C. for 3 h. The reaction solution was cooled to room temperature, and concentrated under reduced pressure, then the crude product was separated and purified by silica gel column chromatography (petroleum ether/ethyl acetate (v/v)=4:1-2:3), to obtain trans-tert-butyl 3-fluoro-4-(4-oxo-1-piperidyl)piperidine-1-carboxylate (46f) (4.0 g, yield: 81%).

$^1$H NMR (400 MHz, CDCl$_3$) δ 4.61-4.31 (m, 2H), 4.16-4.00 (m, 1H), 3.06-2.91 (m, 4H), 2.87-2.66 (m, 3H), 2.45 (t, 4H), 1.90-1.79 (m, 1H), 1.60-1.48 (m, 1H), 1.46 (s, 9H).

LCMS m/z=301.3 [M+1]$^+$.

Step 6 trans-tert-butyl 3-fluoro-4-(4-hydroxy-1-piperidyl)piperidine-1-carboxylate (46g)

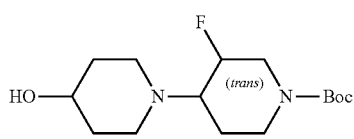

Trans-tert-butyl 3-fluoro-4-(4-oxo-1-piperidyl)piperidine-1-carboxylate (46f) (4.0 g, 13.3 mmol) was dissolved in 40 mL of anhydrous methanol, and sodium borohydride (0.505 g, 13.3 mmol) was added. Upon completion of the addition, the reaction was carried out at room temperature for 10 min. To the reaction solution was added dropwise 25 mL of saturated ammonium chloride solution to quench the reaction, and the resulted solution was extracted with 50 mL of ethyl acetate twice. The organic phase was combined, washed with 30 mL of saturated sodium chloride solution, dried over anhydrous sodium sulfate, and concentrated under reduced pressure, then the crude product was separated and purified by silica gel column chromatography (dichloromethane/methanol (v/v)=100:0-9:1), to obtain trans-tert-butyl 3-fluoro-4-(4-hydroxy-1-piperidyl)piperidine-1-carboxylate (46g) (3.2 g, yield: 80%).

$^1$H NMR (400 MHz, CDCl$_3$) δ 4.65-4.40 (m, 1H), 4.38-4.22 (m, 1H), 4.09-3.91 (m, 1H), 3.76-3.61 (m, 1H), 2.99-2.39 (m, 7H), 2.00-1.71 (m, 3H), 1.65-1.41 (m, 12H).

LCMS m/z=303.3 [M+1]$^+$.

Step 7 trans-tert-butyl 3-fluoro-4-[4-(p-tosyloxy)-1-piperidyl]piperidine-1-carboxylate (46h)

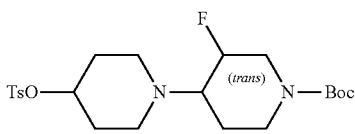

Trans-tert-butyl 3-fluoro-4-(4-hydroxy-1-piperidyl)piperidine-1-carboxylate (46g) (1.80 g, 5.95 mmol) was dissolved in 18 mL of pyridine, and p-toluenesulfonyl chloride (2.27 g, 11.9 mmol) was added. Upon completion of the addition, the reaction was stirred at 70° C. for 2 hours. The reaction solution was cooled to room temperature, and 30 mL of water and 60 mL of ethyl acetate were added. The liquid separation was conducted, and the organic phase was washed successively with 20 mL of saturated sodium bicarbonate solution, 40 mL of 0.5 mol/L hydrochloric acid and 20 mL of saturated sodium chloride solution, dried over anhydrous sodium sulfate, and concentrated under reduced pressure, to obtain the crude product trans-tert-butyl 3-fluoro-4-[4-(p-tosyloxy)-1-piperidyl]piperidine-1-carboxylate (46h) (2.48 g).

Step 8 trans-tert-butyl-4-[4-[4-amino-3-(4-phenoxyphenyl)pyrazolo[3,4-d]pyrimidin-1-yl]-1-piperidyl]-3-fluoro-piperidine-1-carboxylate (46i)

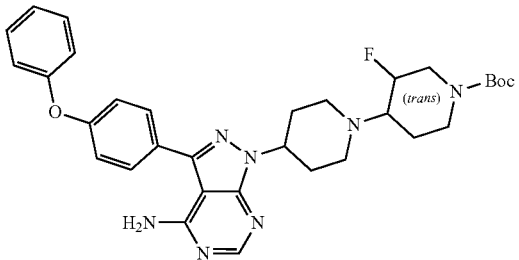 [SMILES: CC(C)(C)OC(=O)N1CCC(N2CCC(n3nc(-c4ccc(Oc5ccccc5)cc4)c4c(N)ncnc43)CC2)C(F)C1]

3-(4-phenoxyphenyl)-1H-pyrazolo[3,4-d]pyrimidin-4-amine (1.50 g, 4.95 mmol) was dissolved in 10 mL of DMF, and the above crude product trans-tert-butyl 3-fluoro-4-[4-(p-tosyloxy)-1-piperidyl]piperidine-1-carboxylate (46h) (2.48 g) and cesium carbonate (3.24 g, 9.94 mmol) were successively added.

Upon completion of the addition, the reaction was stirred at 60° C. for 2 h. The reaction solution was cooled to room temperature, and 10 mL of water and 20 mL of ethyl acetate were added. The liquid separation was conducted, and the organic phase was washed with 5 mL of saturated sodium chloride solution, dried over anhydrous sodium sulfate, and concentrated under reduced pressure, then the crude product was separated and purified by silica gel column chromatography (dichloromethane/methanol (v/v)=100:0-50:1), to obtain trans-tert-butyl 4-[4-[4-amino-3-(4-phenoxyphenyl)pyrazolo[3,4-d]pyrimidin-1-yl]-1-piperidyl]-3-fluoro-piperidine-1-carboxylate (46i) (0.900 g, yield: 31%).

$^1$H NMR (400 MHz, CDCl$_3$) δ 8.36 (s, 1H), 7.69-7.62 (m, 2H), 7.43-7.35 (m, 2H), 7.21-7.11 (m, 3H), 7.11-7.05 (m, 2H), 5.64 (br.s, 2H), 4.86-4.74 (m, 1H), 4.69-4.46 (m, 1H), 4.42-4.25 (m, 1H), 4.12-3.94 (m, 1H), 3.19-3.03 (m, 2H), 2.87-2.63 (m, 5H), 2.50-2.34 (m, 2H), 2.12-2.01 (m, 2H), 1.93-1.84 (m, 1H), 1.63-1.50 (m, 1H), 1.47 (s, 9H).

Step 9 trans-tert-butyl-4-[4-[4-amino-3-(4-phenoxyphenyl)pyrazolo[3,4-d]pyrimidin-1-yl]-1-piperidyl]-3-fluoro-piperidine-1-carboxylate-P1 (46i-1)

trans-tert-butyl-4-[4-[4-amino-3-(4-phenoxyphenyl)pyrazolo[3,4-d]pyrimidin-1-yl]-1-piperidyl]-3-fluoro-piperidine-1-carboxylate-P2 (46i-2)

formula 46i-a

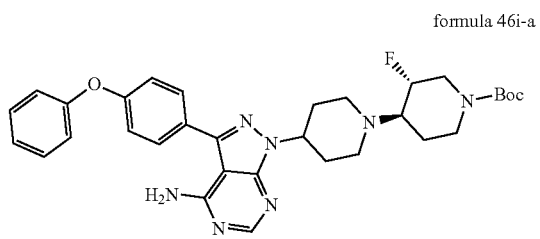

and formula 46i-b

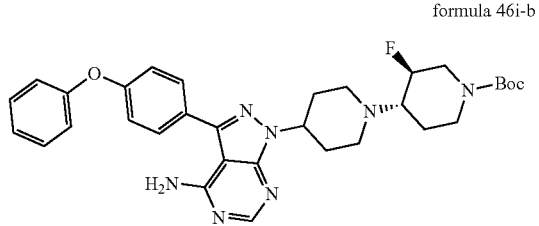

Compounds 46i-1 and 46i-2 were separated and prepared from compound 46i by means of high performance liquid chromatography. The preparation conditions were as follows: instrument and preparative column: using MG II preparative SFC (SFC-1) to prepare the liquid phase, preparative column model: ChiralPak IC, 250×30 mm I.D., 10 μm.

Preparation method: the crude product was dissolved with methanol/dichloromethane, to prepare into a sample solution.

Mobile phase system: sCO$_2$/isopropanol (containing 0.1% ammonia water), isocratic elution: sCO$_2$/isopropanol (containing 0.1% ammonia water)=55/45.

Flow rate: 80 mL/min
Analysis method for compounds 46i-1 and 46i-2:
Instrument: Waters UPC2 analytical SFC (SFC-H)
Chromatographic column: CHIRALPAK IC
Specification: 150 mm×4.6 mm, 3 μm
Mobile phase A: sCO$_2$
Mobile phase B: isopropanol (containing 0.05% diethylamine)
Column temperature: 35° C.
Flow rate: 2.5 mL/min
Wavelength: 254 nm
Isocratic elution: mobile phase A:B=60:40.
Retention time of compound 46i-1: 6.576 min (the absolute configuration had not been determined, and its structure was one of the above formulas 46i-a and 46i-b);
Retention time of compound 46i-2: 8.951 min (the absolute configuration had not been determined, and its structure was one of the above formulas 46i-a and 46i-b, as well as it was an isomer of compound 46i-1, namely, when the structure of compound 46i-1 was the structure of formula 46i-a, the structure of compound 46i-2 was the structure of formula 46i-b; when the structure of compound 46i-1 was the structure of formula 46i-b, the structure of compound 46i-2 was the structure of formula 46i-a).

Step 10 trans-1-(3'-fluoro-[1,4'-bipiperidin]-4-yl)-3-(4-phenoxyphenyl)-1H-pyrazolo[3,4-d]pyrimidin-4-amine-P1 (46j)

Trans-tert-butyl 4-[4-[4-amino-3-(4-phenoxyphenyl)pyrazolo[3,4-d]pyrimidin-1-yl]-1-piperidyl]-3-fluoro-piperidine-1-carboxylate-P1 (46i-1, its structure was one of formula 46i-a and formula 46i-b) (420 mg, 0.71 mmol) was dissolved in 20 mL of DCM, and 8 mL of trifluoroacetic acid was added, the mixture was stirred at room temperature for 4 hours. The reaction solution was directly concentrated under reduced pressure, and the residue was dissolved with 30 mL of 5 mol/L NaOH solution, and extracted with DCM (30 mL×4). The organic phase was combined, washed with 1 mol/L NaOH solution (30 mL×2), dried over anhydrous sodium sulfate, and concentrated under reduced pressure, to obtain trans-1-(3'-fluoro-[1,4'-bipiperidin]-4-yl)-3-(4-phenoxyphenyl)-1H-pyrazolo[3,4-d]pyrimidin-4-amine-P1 (46j) (340 mg, yield: 98%), and the configuration of the chiral carbon thereof was consistent with that of the corresponding chiral carbon of the raw material (Compound 46i-1) in the tenth step.

$^1$H NMR (400 MHz, CDCl$_3$) δ 8.36 (s, 1H), 7.71-7.61 (m, 2H), 7.43-7.33 (m, 2H), 7.20-7.11 (m, 3H), 7.11-7.04 (m, 2H), 5.52 (br.s, 2H), 4.84-4.72 (m, 1H), 4.71-4.46 (m, 1H), 3.43-3.33 (m, 1H), 3.17-2.99 (m, 3H), 2.86-2.75 (m, 1H), 2.74-2.50 (m, 4H), 2.49-2.31 (m, 2H), 2.11-1.97 (m, 2H), 1.94-1.84 (m, 1H), 1.84-1.70 (m, 1H), 1.62-1.48 (m, 1H).

LCMS m/z=488.3 [M+1]$^+$.

Step 11 trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (46k)

Trans-1-(3'-fluoro-[1,4'-bipiperidin]-4-yl)-3-(4-phenoxyphenyl)-1H-pyrazolo[3,4-d]pyrimidin-4-amine-P1 (46j) (300 mg, 0.62 mmol) was dissolved in 30 mL of DCE, and tert-butyl 3-oxoazetidine-1-carboxylate (211 mg, 1.23 mmol) was added, the mixture was stirred at room temperature for 10 min, then sodium triacetoxyborohydride (522 mg, 2.46 mmol) was added, and the mixture was stirred at room temperature for 16 h. The reaction solution was extracted with DCM (30 mL×3), and the organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (46k) (380 mg, yield: 95%), and the configuration of the chiral carbon thereof was consistent with that of the corresponding chiral carbon of the raw material (Compound 46i-1) in the tenth step.

LCMS m/z=643.4 [M+1]$^+$.

Step 12 trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (46l)

Trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (46k) (380 mg, 0.59 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5 mol/L NaOH solution, and extracted with DCM (30 mL×4). The organic phase was combined, washed with 1 mol/L NaOH solution (30 mL×2), dried over anhydrous sodium sulfate, and concentrated under reduced pressure, to obtain the crude product trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (46l) (260 mg), and the configuration of the chiral carbon thereof was consistent with that of the corresponding chiral carbon of the raw material (Compound 46i-1) in the tenth step.

LCMS m/z=543.3 [M+1]$^+$.

Step 13 trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 46-1)

formula 46-a

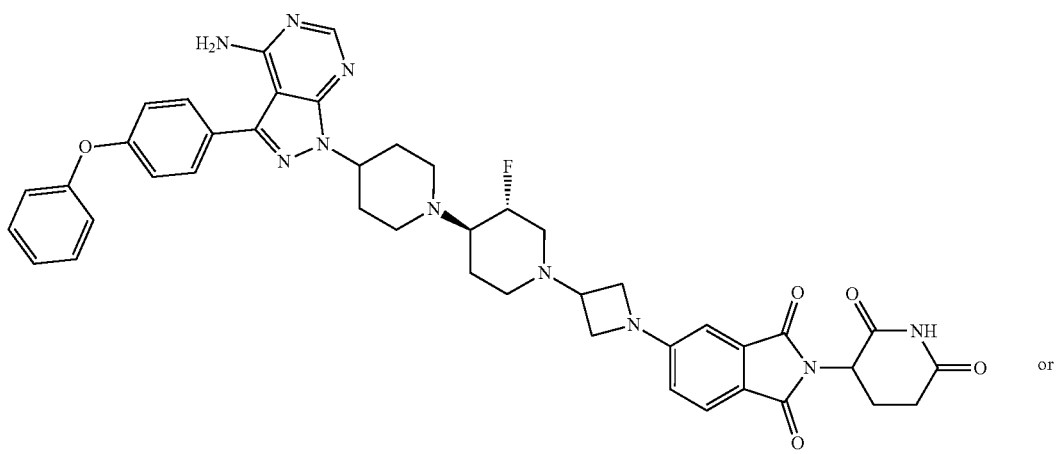

or formula 46-b

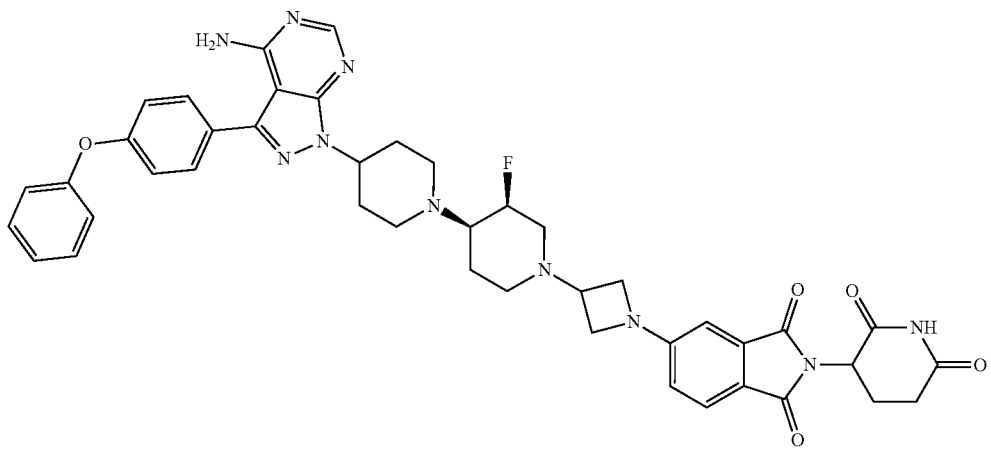

The above crude product trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (46l) (260 mg) was dissolved in 15 mL of DMSO, and 1.5 mL of DIPEA and 2-(2,6-dioxopiperidin-3-yl)-5-fluoroisoindoline-1,3-dione (see WO 2017197056 for the synthetic method) (191 mg, 0.69 mmol) were added, the reaction was stirred at 80° C. for 5 h. The reaction solution was cooled to room temperature, quenched by adding 30 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=15:1), to obtain trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 46-1) (220 mg, two-step yield calculated from compound 46k: 47%). The structure of compound 46-1 was one of the structures shown in 46-a and 46-b above, and the configuration of the chiral carbon thereof was consistent with that of the corresponding chiral carbon of the raw material (Compound 46i-1) in the tenth step.

$^1$H NMR (400 MHz, CDCl$_3$) δ 9.28 (s, 1H), 8.39 (s, 1H), 7.69-7.60 (m, 3H), 7.42-7.34 (m, 2H), 7.20-7.11 (m, 3H), 7.10-7.04 (m, 2H), 6.79 (d, 1H), 6.53 (dd, 1H), 5.71 (br.s, 2H), 4.93 (dd, 1H), 4.87-4.60 (m, 2H), 4.14-4.07 (m, 2H), 3.90-3.81 (m, 2H), 3.50-3.40 (m, 1H), 3.24-2.98 (m, 3H), 2.94-2.62 (m, 7H), 2.50-2.33 (m, 2H), 2.17-1.94 (m, 6H), 1.70-1.60 (m, 1H).

LCMS m/z=799.3 [M+1]$^+$.

Example 46-2 trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 46-2)

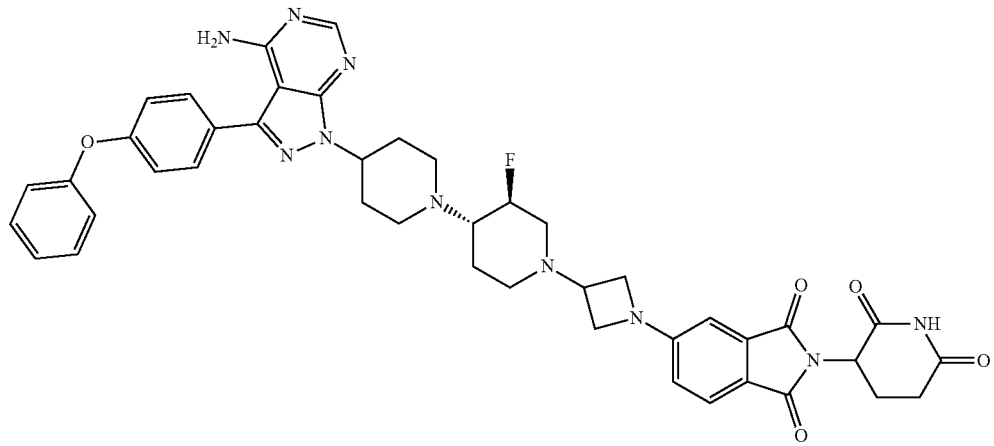

or

-continued
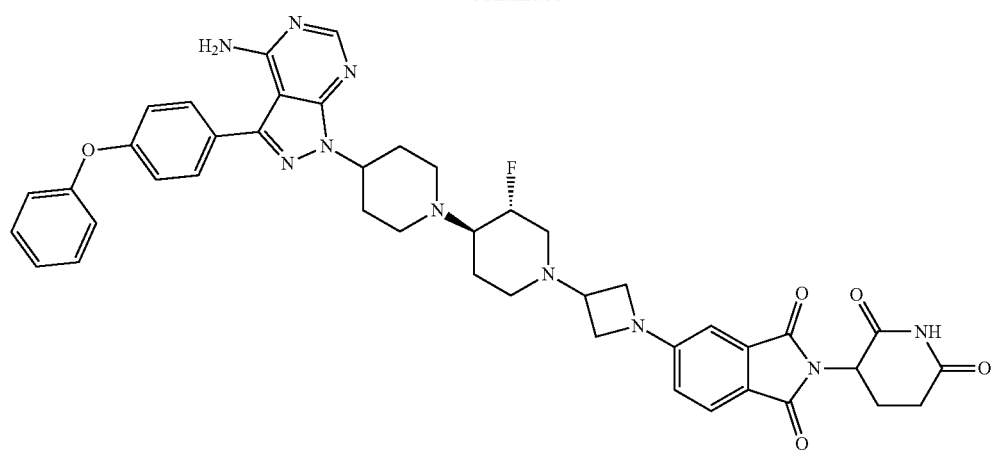
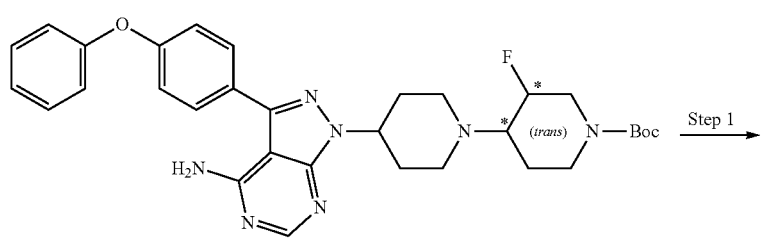
46i-2
Step 1 →
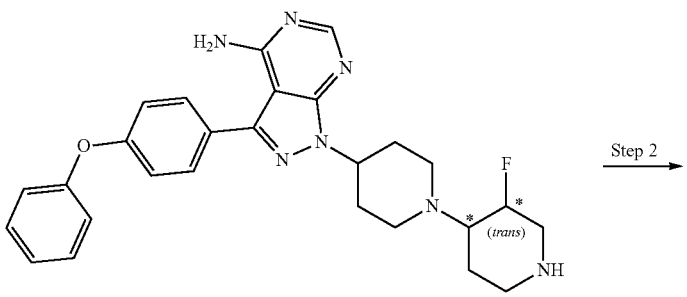
46m
Step 2 →
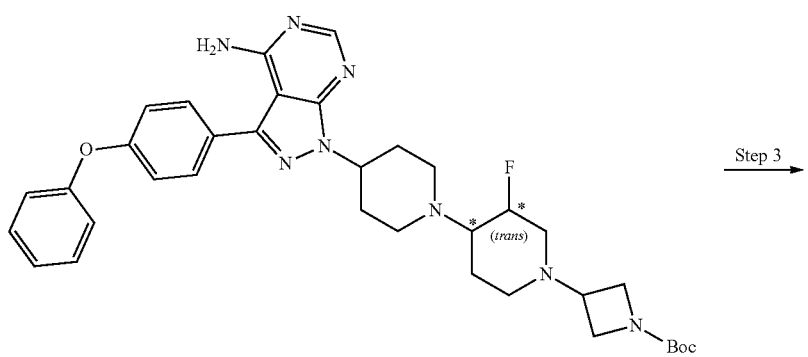
46n
Step 3 →

-continued
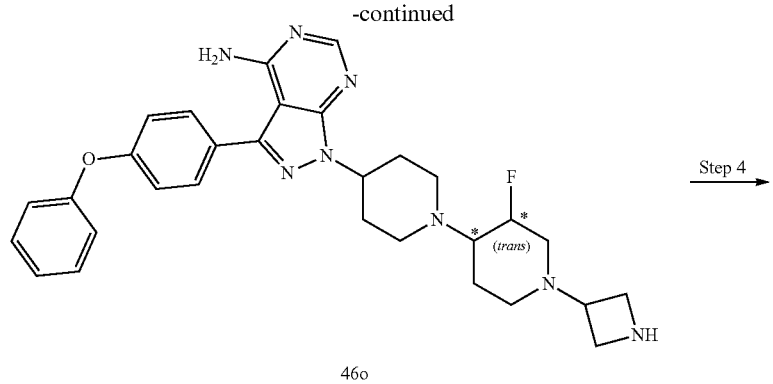
46o
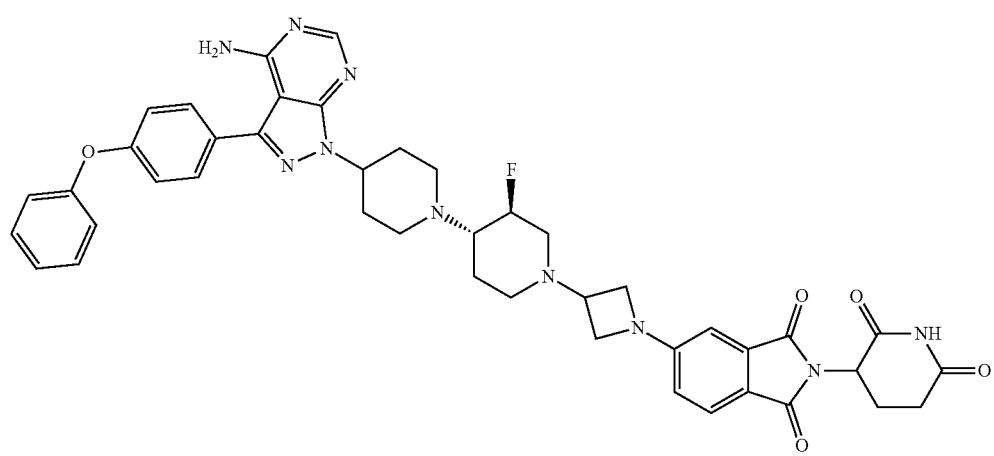
Formula 46-b
or
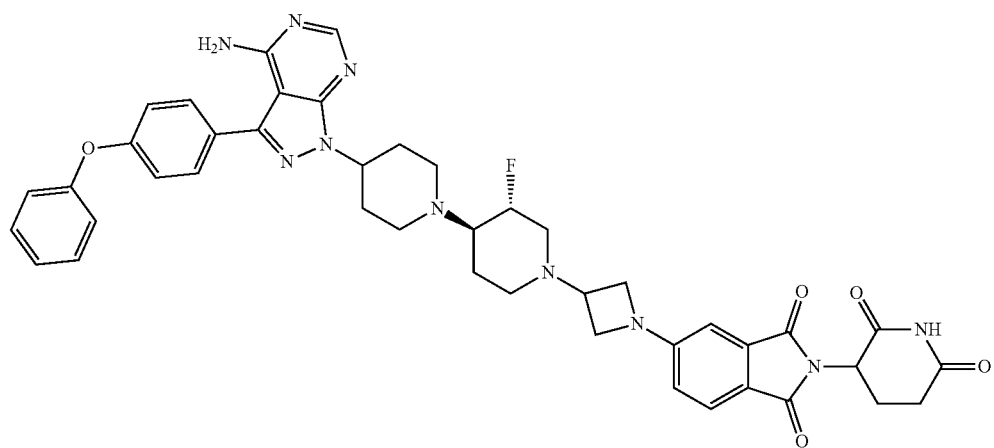
Formula 46-a
Compound 46-2

Step 1 trans-1-(3'-fluoro-[1,4'-bipiperidin]-4-yl)-3-(4-phenoxyphenyl)-1H-pyrazolo[3,4-d]pyrimidin-4-amine-P2 (46m)

Trans-tert-butyl

4-[4-[4-amino-3-(4-phenoxyphenyl)pyrazolo[3,4-d]pyrimidin-1-yl]-1-piperidyl]-3-fluoro-piperidine-1-carboxylate-P2 (46i-2, an isomer of compound 46i-1 in example 46-1) (420 mg, 0.71 mmol) was dissolved in 20 mL of DCM, and 8 mL of trifluoroacetic acid was added, the mixture was stirred at room temperature for 4 h. Upon completion of the reaction, the system was directly concentrated under reduced pressure, and the residue was dissolved with 30 mL of 5 mol/L NaOH solution, and extracted with DCM (30 mL×4). The organic phase was combined, washed with 1 mol/L NaOH solution (30 mL×2), dried over anhydrous sodium sulfate, and concentrated under reduced pressure, to obtain 2% trans-1-(3'-fluoro-[1,4'-bipiperidin]-4-yl)-3-(4-phenoxyphenyl)-1H-pyrazolo[3,4-d]pyrimidin-4-amine-P2 (46m) (330 mg, yield: 95%), and the configuration of the chiral carbon thereof was consistent with that of the corresponding chiral carbon of (Compound 46i-2).

$^1$H NMR (400 MHz, CDCl$_3$) δ 8.36 (s, 1H), 7.70-7.61 (m, 2H), 7.43-7.34 (m, 2H), 7.20-7.11 (m, 3H), 7.10-7.05 (m, 2H), 5.54 (brs, 2H), 4.85-4.72 (m, 1H), 4.68-4.46 (m, 1H), 3.43-3.33 (m, 1H), 3.17-2.99 (m, 3H), 2.86-2.75 (m, 1H), 2.74-2.50 (m, 4H), 2.48-2.31 (m, 2H), 2.10-1.96 (m, 2H), 1.93-1.81 (m, 1H), 1.79-1.62 (m, 1H), 1.61-1.46 (m, 1H).

LCMS m/z=488.3 [M+1]$^+$.

Step 2 trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P2 (46n)

Trans-1-(3'-fluoro-[1,4'-bipiperidin]-4-yl)-3-(4-phenoxyphenyl)-1H-pyrazolo[3,4-d]pyrimidin-4-amine-P2 (46m) (300 mg, 0.62 mmol) was dissolved in 30 mL of DCE, and tert-butyl 3-oxoazetidine-1-carboxylate (211 mg, 1.23 mmol) was added, the mixture was stirred at room temperature for 10 min, then sodium triacetoxyborohydride (522 mg, 2.46 mmol) was added, and the mixture was stirred at room temperature for 16 h. The reaction solution was extracted with DCM (30 mL×3), and the organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P2 (46n) (390 mg, yield: 98%), and the configuration of the chiral carbon thereof was consistent with that of the corresponding chiral carbon of (Compound 46i-2).

LCMS m/z=643.4 [M+1]$^+$.

Step 3 trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2 (46o)

Trans-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P2 (46n) (370 mg, 0.58 mmol) was dissolved in 20 mL of DCM, and 8 mL of trifluoroacetic acid was added, the mixture was stirred at room temperature for 4 h. The reaction system was directly concentrated under reduced pressure, and the residue was dissolved with 30 mL of 5 mol/L NaOH solution, and extracted with DCM (30 mL×4). The organic phase was combined, washed with 1 mol/L NaOH solution (30 mL×2), dried over anhydrous sodium sulfate, and concentrated under reduced pressure, to obtain the crude product trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2 (46o) (270 mg), and the configuration of the chiral carbon thereof was consistent with that of the corresponding chiral carbon of (Compound 46i-2).

LCMS m/z=543.3 [M+1]$^+$.

Step 4 trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 46-2)

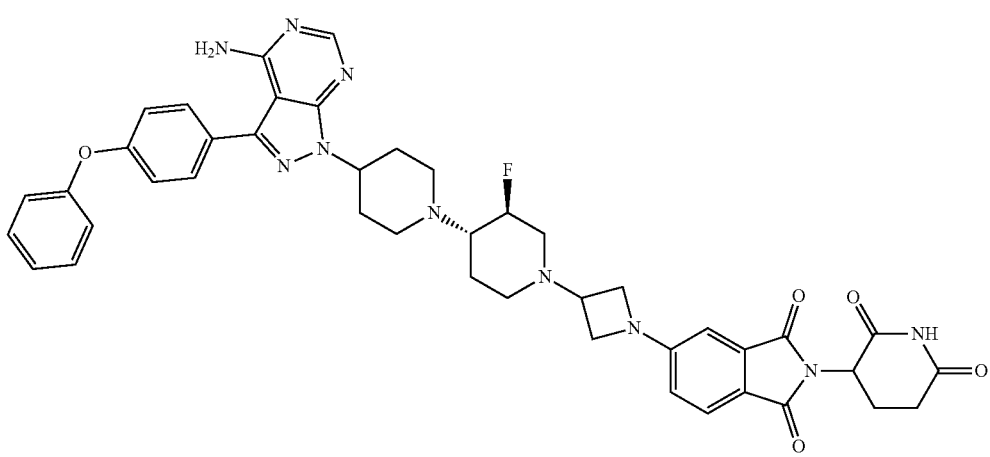

formula46-b or

-continued formula 46-a

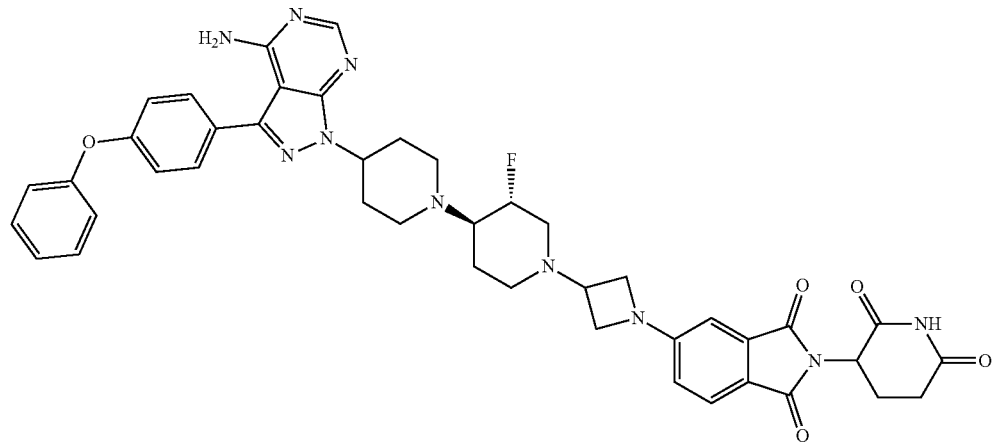

The above crude product trans-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2 (46o) (270 mg) was dissolved in 15 mL of DMSO, and 1.5 mL of DIPEA and 2-(2,6-dioxopiperidin-3-yl)-5-fluoroisoindoline-1,3-dione (see WO 2017197056 for the synthetic method) (191 mg, 0.69 mmol) were added, the reaction was stirred at 80° C. for 5 h. The reaction solution was cooled to room temperature, added 30 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=1), to obtain trans-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 46-2) (260 mg, two-step yield calculated from compound 46n: 56%). The structure of compound 46-2 was one of the structures shown in 46-b and 46-a above, and the configuration of the chiral carbon thereof was consistent with that of the corresponding chiral carbon of the raw material (Compound 46i-2) in the first step; namely, compound 46-2 was an isomer of compound 46-1 in example 46-1.

$^1$H NMR (400 MHz, CDCl$_3$) δ 8.86 (s, 1H), 8.38 (s, 1H), 7.69-7.60 (m, 3H), 7.43-7.34 (m, 2H), 7.21-7.11 (m, 3H), 7.10-7.04 (m, 2H), 6.79 (d, 1H), 6.53 (dd, 1H), 5.63 (brs, 2H), 4.93 (dd, 1H), 4.87-4.59 (m, 2H), 4.14-4.07 (m, 2H), 3.90-3.81 (m, 2H), 3.50-3.40 (m, 1H), 3.25-3.00 (m, 3H), 2.94-2.62 (m, 7H), 2.51-2.35 (m, 2H), 2.18-1.94 (m, 6H), 1.77-1.62 (m, 1H).

LCMS m/z=799.3 [M+1]$^+$.

Example 47

(7S)-7-(1-(1-(2-(2,6-dioxopiperidin-3-yl)-1,3-dioxo-isoindolin-5-yl)azetidin-3-yl)piperidin-4-yl)-2-(4-phenoxyphenyl)-4,5,6,7-tetrahydropyrazolo[1,5-a]pyrimidine-3-carboxamide (Compound 47)

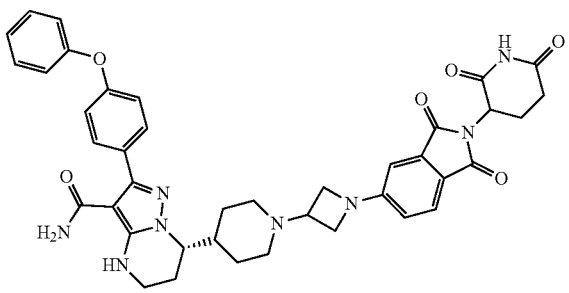

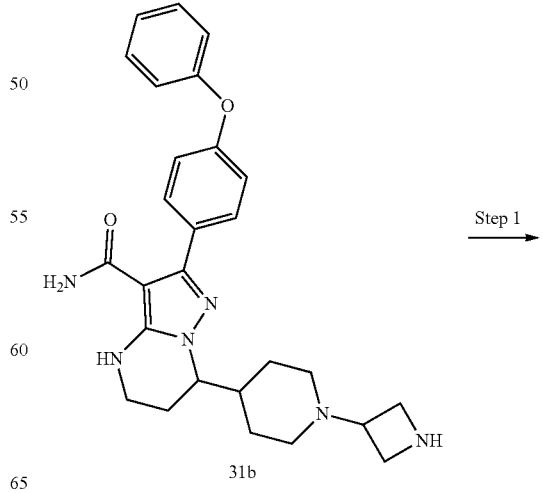

Step 1

531

-continued

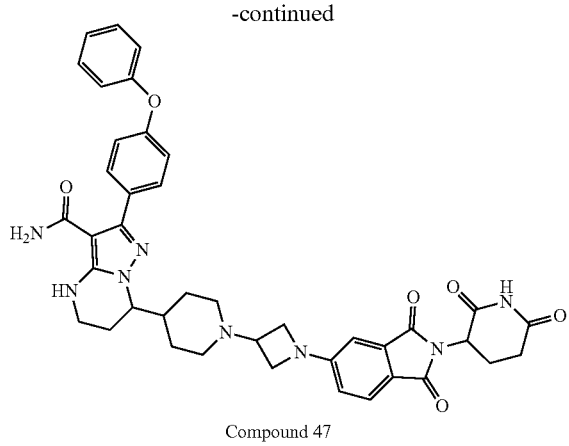

Compound 47

(7S)-7-[1-(azetidin-3-yl)-4-piperidyl]-2-(4-phenoxyphenyl)-4,5,6,7-tetrahydropyrazolo[1,5-a]pyrimidine-3-carboxamide (31b) (250 mg, 0.53 mmol) was dissolved in 25 mL of DMSO, and 1.0 mL of DIPEA and 2-(2,6-dioxopiperidin-3-yl)-5-fluoroisoindoline-1,3-dione (see WO 2017197056 for the synthetic method) (220 mg, 0.80 mmol) were added, the reaction was stirred at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=1), to obtain (7S)-7-(1-(1-(2-(2,6-dioxopiperidin-3-yl)-1,3-dioxo-isoindolin-5-yl)azetidin-3-yl)piperidin-4-yl)-2-(4-phenoxyphenyl)-4,5,6,7-tetrahydropyrazolo[1,5-a]pyrimidine-3-c arboxamide (Compound 47) (210 mg, yield: 54%).

$^1$H NMR (400 MHz, CDCl$_3$) δ 8.53-8.41 (m, 1H), 7.63 (d, 1H), 7.53-7.46 (m, 2H), 7.40-7.32 (m, 2H), 7.18-7.11 (m, 1H), 7.10-7.01 (m, 4H), 6.78 (d, 1H), 6.63-6.57 (m, 1H), 6.52 (dd, 1H), 5.21 (br.s, 2H), 4.95-4.87 (m, 1H), 4.14-4.05 (m, 2H), 3.98-3.78 (m, 2H), 3.47-3.29 (m, 3H), 3.06-2.64 (m, 5H), 2.35-2.05 (m, 4H), 2.02-1.86 (m, 2H), 1.86-1.76 (m, 1H), 1.74-1.38 (m, 4H).

LCMS m/z=729.3 [M+1]$^+$.

Example 48

(7S)-7-(1'-(2-(2,6-dioxopiperidin-3-yl)-1,3-dioxo-isoindolin-5-yl)-[1,4'-bipiperidin]-4-yl)-2-(4-phenoxyphenyl)-4,5,6,7-tetrahydropyrazolo[1,5-a]pyrimidine-3-carboxamide (Compound 48)

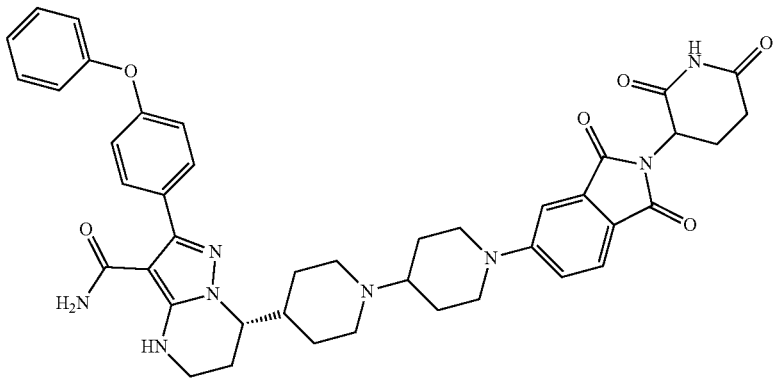

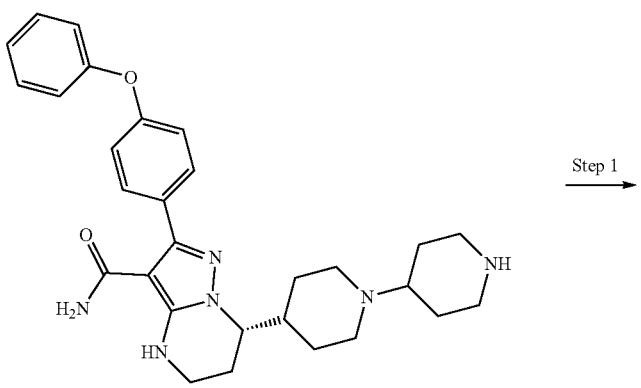

Step 1

30c

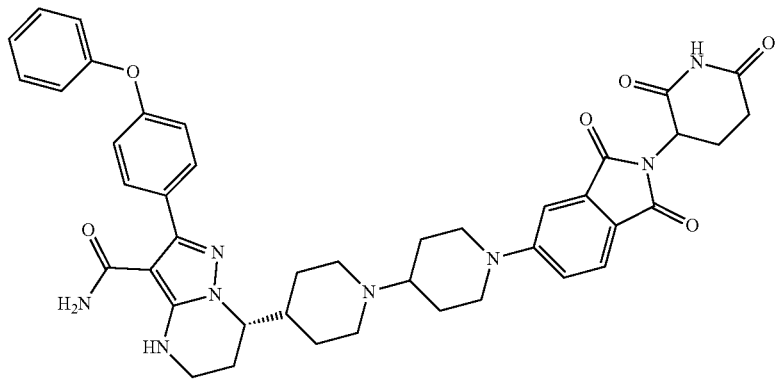

Compound 48

(7S)-2-(4-phenoxyphenyl)-7-[1-(4-piperidyl)-4-piperidyl]-4,5,6,7-tetrahydropyrazolo[1,5-a]pyrimidine-3-carboxamide (30c) (250 mg, 0.50 mmol) was dissolved in 25 mL of DMSO, and 1.0 mL of DIPEA and 2-(2,6-dioxopiperidin-3-yl)-5-fluoroisoindoline-1,3-dione (see WO 2017197056 for the synthetic method) (207 mg, 0.75 mmol) were added, the reaction was stirred at 80° C. for 5 h. The reaction solution was cooled to room temperature, added 50 mL of water, and extracted with 100 mL of ethyl acetate. The organic phase was washed with 100 mL of water, dried over anhydrous sodium sulfate, and concentrated under reduced pressure, then the crude product was separated and purified by silica gel column chromatography (dichloromethane/methanol (v/v)=1), to obtain (7S)-7-(1'-(2-(2,6-dioxopiperidin-3-yl)-1,3-dioxo-isoindolin-5-yl)-[1,4'-bipiperidin]-4-yl)-2-(4-phenoxyphenyl)-4,5,6,7-tetrahydropyrazolo[1,5-a]pyrimidine-3-carboxamide (Compound 48) (200 mg, yield: 53%).

$^1$H NMR (400 MHz, CDCl$_3$) δ 8.81 (br.s, 1H), 7.66 (d, 1H), 7.53-7.45 (m, 2H), 7.40-7.32 (m, 2H), 7.29-7.24 (m, 1H), 7.19-7.10 (m, 1H), 7.10-6.99 (m, 5H), 6.62-6.57 (m, 1H), 5.26 (br.s, 2H), 4.97-4.88 (m, 1H), 4.16-4.06 (m, 1H), 4.04-3.94 (m, 2H), 3.46-3.36 (m, 2H), 3.21-3.03 (m, 2H), 3.03-2.91 (m, 2H), 2.90-2.65 (m, 4H), 2.47-2.22 (m, 3H), 2.22-2.02 (m, 5H), 1.87-1.58 (m, 6H).

LCMS m/z=757.3 [M+1]$^+$.

Example 49-1 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 49-1)

or

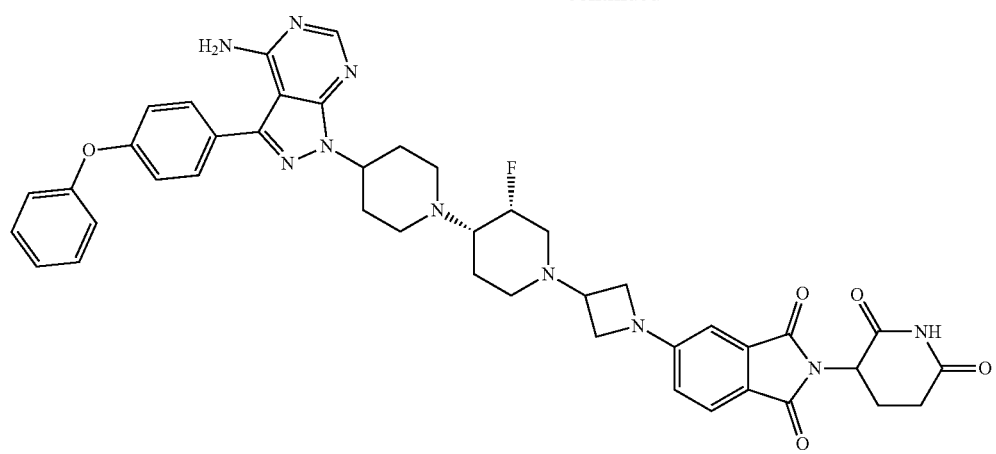
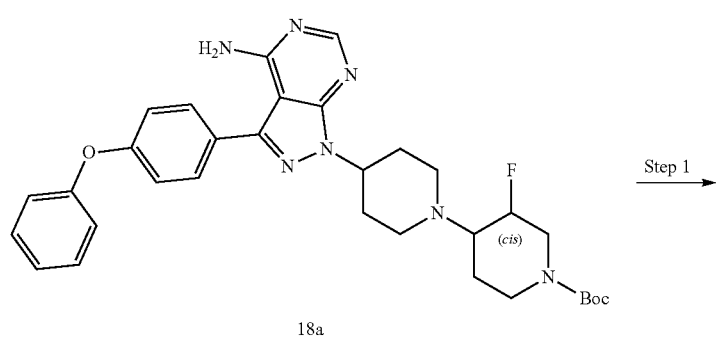
18a
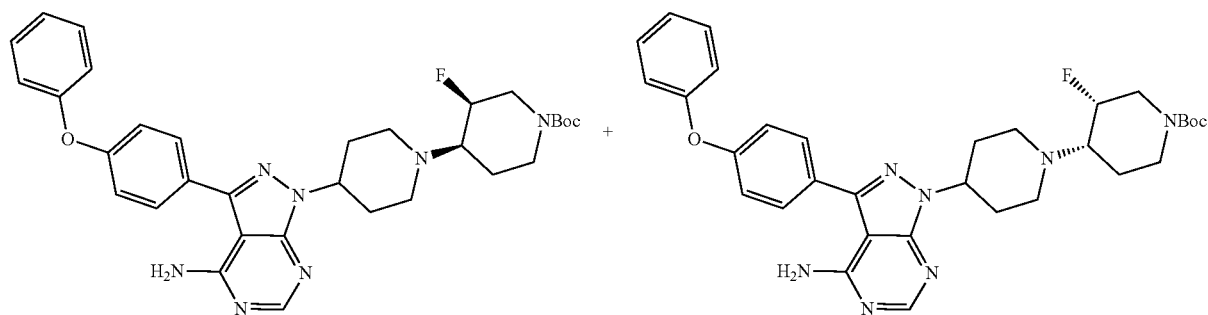
18a-1 and 18a-2
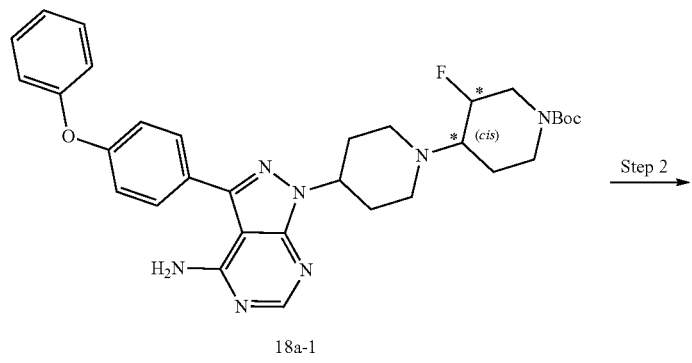
18a-1

-continued
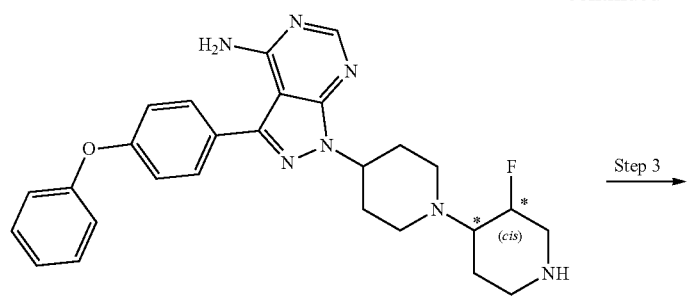
49a
Step 3 →
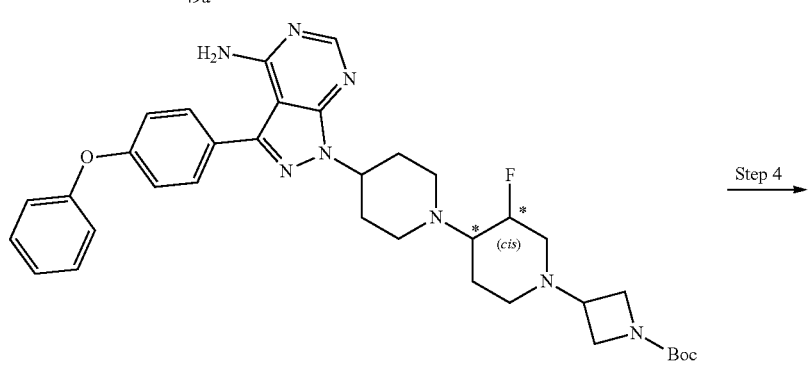
49b
Step 4 →
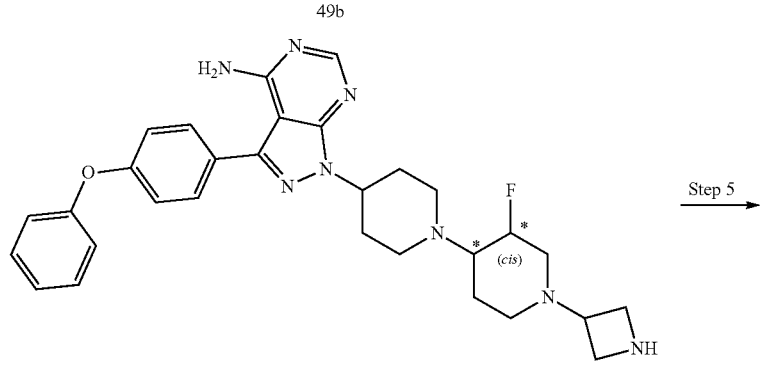
49c
Step 5 →
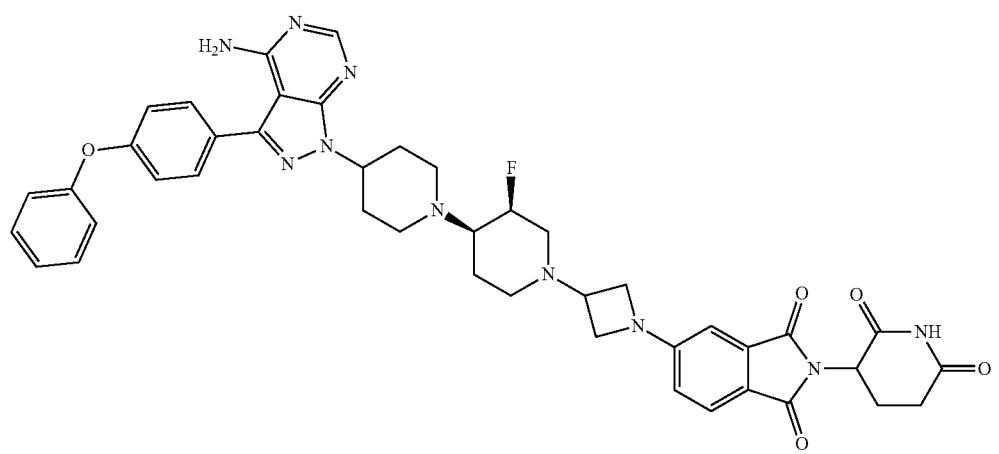
or

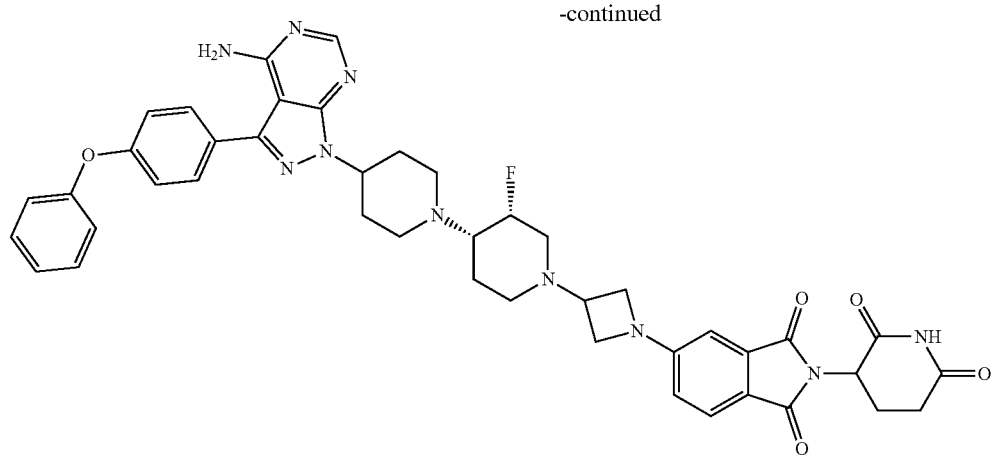

Compound 49-1

Step 1 cis-tert-butyl 4-(4-amino-3-(4-phenoxyphenyl)-1H-pyrazolo[3,4-d]pyrimidin-1-yl)-3'-fluoro-[1,4'-bipiperidine]-1'-carboxylate-P1 (18a-1)

and cis-tert-butyl 4-(4-amino-3-(4-phenoxyphenyl)-1H-pyrazolo[3,4-d]pyrimidin-1-yl)-3'-fluoro-[1,4'-bipiperidine]-1'-carboxylate-P2 (18a-2)

formula 18a-a

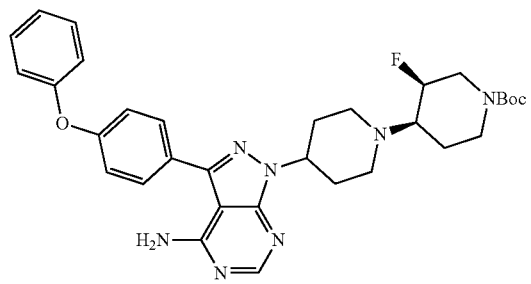

and formula 18a-b

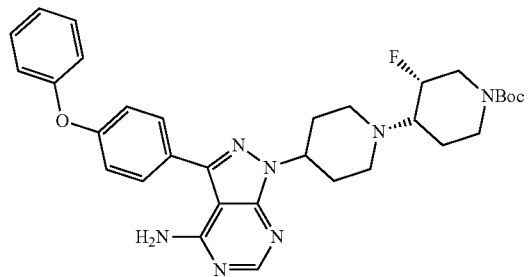

Compounds 18a-1 and 18a-2 were separated and prepared from compound 18a by means of high performance liquid chromatography. The preparation conditions were as follows:

instrument and preparative column: using MG II preparative SFC (SFC-1) to prepare the liquid phase, preparative column model: Cellulose-2, 250×30 mm I.D., 5 μm.

Preparation method: the crude product was dissolved with methanol/dichloromethane, to prepare into a sample solution.

Mobile phase system: $sCO_2$/ethanol (containing 0.1% ammonia water), isocratic elution: $sCO_2$/ethanol (containing 0.1% ammonia water)=60/40.

Flow rate: 50 mL/min

Analysis method for compounds 18a-1 and 18a-2:

Instrument: Waters UPC2 analytical SFC (SFC-H)

Chromatographic column: Cellulose-2, I.D.

Specification: 150 mm×4.6 mm, 3 μm

Mobile phase A: $sCO_2$

Mobile phase B: ethanol (containing 0.05% diethylamine)

Column temperature: 35° C.

Flow rate: 2.5 mL/min

Wavelength: 220 nm

Isocratic elution: mobile phase A:B=60:40.

Retention time of compound 18a-1: 7.201 min; the absolute configuration had not been determined, and its structure was one of the above formulas 18a-a and 18a-b;

$^1$H NMR (400 MHz, $CDCl_3$) δ 8.29 (s, 1H), 7.58 (d, 1H), 7.35-7.27 (m, 2H), 7.23-7.16 (m, 1H), 7.13-7.04 (m, 3H), 7.03-6.97 (m, 2H), 5.51 (br.s, 2H), 4.99-4.62 (m, 2H), 4.46-4.10 (m, 2H), 3.14-2.94 (m, 2H), 2.87-2.25 (m, 7H), 2.01-1.86 (m, 3H), 1.65-1.57 (m, 1H), 1.39 (s, 9H).

Retention time of compound 18a-2: 8.585 min. the absolute configuration had not been determined, and its structure was one of the above formulas 18a-a and 18a-b, as well as it was an isomer of compound 18a-1, namely, when the structure of compound 18a-1 was the structure of formula 18a-a, the structure of compound 18a-2 was the structure of formula 18a-b; when the structure of compound 18a-1 was the structure of formula 18a-b, the structure of compound 18a-2 was the structure of formula 18a-a.

$^1$H NMR (400 MHz, $CDCl_3$) δ 8.29 (s, 1H), 7.58 (d, 1H), 7.35-7.27 (m, 2H), 7.21-7.16 (m, 1H), 7.13-7.04 (m, 3H), 7.03-6.97 (m, 2H), 5.41 (br.s, 2H), 5.00-4.60 (m, 2H), 4.53-4.03 (m, 2H), 3.15-3.00 (m, 2H), 2.92-2.22 (m, 7H), 2.02-1.85 (m, 3H), 1.69-1.51 (m, 1H), 1.39 (s, 9H).

Step 2 cis-1-(3'-fluoro-[1,4'-bipiperidin]-4-yl)-3-(4-phenoxyphenyl)-1H-pyrazolo[3,4-d]pyrimidin-4-amine-P1 (49a)

Cis-tert-butyl 4-(4-amino-3-(4-phenoxyphenyl)-1H-pyrazolo[3,4-d]pyrimidin-1-yl)-3'-fluoro-[1,4'-bipiperidine]-1'-carboxylate-P1 (18a-1, its structure was one of formula 18a-a and formula 18a-b) (1.0 g, 1.7 mmol) was dissolved in 20 mL of DCM, and 5 mL of trifluoroacetic acid was added, the mixture was stirred at room temperature for 3 h. To the reaction solution was slowly added dropwise 30 mL of saturated sodium bicarbonate solution, and 30 mL of dichloromethane and 50 mL of water were added. The organic phase was separated, dried over anhydrous sodium sulfate, and concentrated under reduced pressure, to obtain the crude product cis-1-(3'-fluoro-[1,4'-bipiperidin]-4-yl)-3-(4-phenoxyphenyl)-1H-pyrazolo[3,4-d]pyrimidin-4-amine-P1 (49a) (0.8 g), and the configuration of the chiral carbon thereof was consistent with that of the corresponding chiral carbon of (Compound 18a-1).

LC-MS m/z=488.3 [M+1]$^+$.

Step 3

Cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (49b)

The above crude product cis-1-(3'-fluoro-[1,4'-bipiperidin]-4-yl)-3-(4-phenoxyphenyl)-1H-pyrazolo[3,4-d]pyrimidin-4-amine-P1 (49a) (0.8 g) was dissolved in 30 mL of DCE, and tert-butyl 3-oxazetidine-1-carboxylate (0.6 g, 3.5 mmol) was added, the mixture was stirred at room temperature for 10 min, then sodium triacetoxyborohydride (0.7 g, 3.3 mmol) was added, and the reaction was stirred at room temperature for 16 h. To the reaction solution was added 30 mL of saturated sodium bicarbonate solution, and 50 mL of dichloromethane and 50 mL of water were added. The organic phase was separated, dried over anhydrous sodium sulfate, and concentrated under reduced pressure, then the crude product was separated and purified by silica gel column chromatography (dichloromethane/methanol (v/v) =20:1), to obtain cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (49b) (1.0 g, two-step yield calculated from compound 18a-1:92%), and the configuration of the chiral carbon thereof was consistent with that of the corresponding chiral carbon of (compound 18a-1).

LC-MS m/z=643.4 [M+1]$^+$.

Step 4

Cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (49c)

Cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P1 (49b) (1.0 g, 1.56 mmol) was dissolved in 20 mL of DCM, and 5 mL of trifluoroacetic acid was added, the mixture was stirred at room temperature for 3 h. To the reaction solution was slowly added dropwise 30 mL of saturated sodium bicarbonate solution, and 30 mL of dichloromethane and 50 mL of water were added. The organic phase was separated, dried over anhydrous sodium sulfate, and concentrated under reduced pressure, to obtain the crude product cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (49c) (0.7 g), and the configuration of the chiral carbon thereof was consistent with that of the corresponding chiral carbon of (Compound 18a-1).

LCMS m/z=543.3 [M+1]$^+$.

Step 5 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 49-1)

formula 49-a

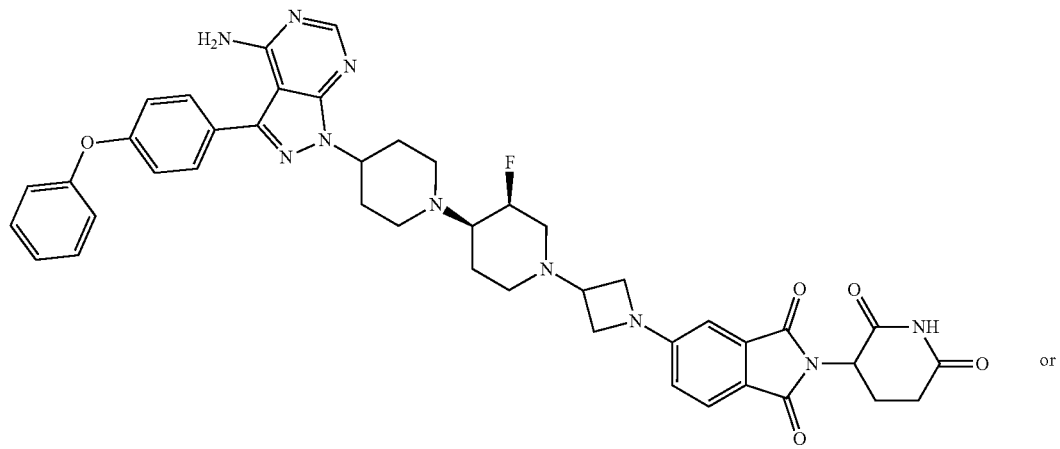

or formula 49-b

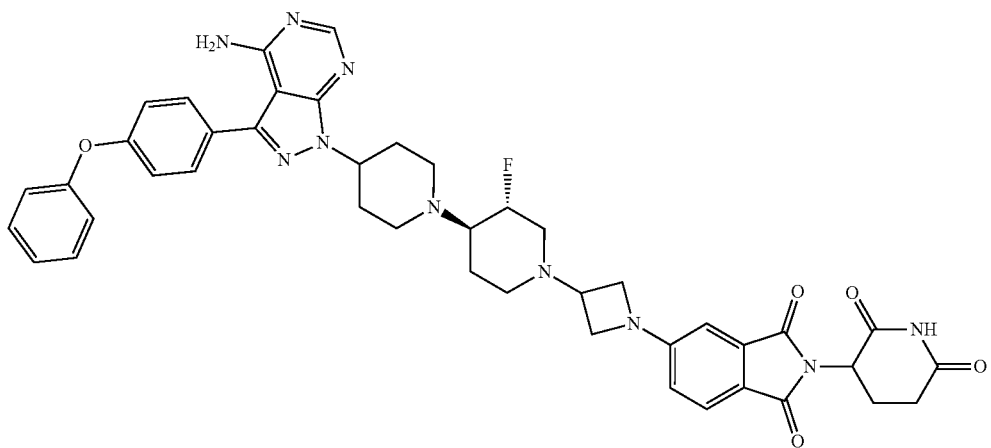

The above crude product cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P1 (49c) (0.2 g) was dissolved in 5 mL of DMSO, and DIPEA (0.21 g, 1.6 mmol) and 2-(2,6-dioxopiperidin-3-yl)-5-fluoroisoindoline-1,3-dione (see WO 2017197056 for the synthetic method) (0.14 g, 0.5 mmol) were added, the reaction was stirred at 90° C. for 3 h. The reaction solution was cooled to room temperature, and 50 mL of ethyl acetate and 50 mL of water were added. The organic phase was separated, dried over anhydrous sodium sulfate, and concentrated under reduced pressure, then the crude product was separated and purified by silica gel column chromatography (dichloromethane/methanol (v/v)=20:1), to obtain cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P1 (Compound 49-1) (0.05 g, two-step yield calculated from compound 49b: 14%). The structure of compound 49-1 was one of the structures shown in 49-a and 49-b above, and the configuration of the chiral carbon thereof was consistent with that of the corresponding chiral carbon of the raw material (Compound 18a-1) in the second step.

$^1$H NMR (400 MHz, CDCl$_3$) δ 8.97 (s, 1H), 8.38 (s, 1H), 7.69-7.59 (m, 3H), 7.43-7.34 (m, 2H), 7.20-7.04 (m, 5H), 6.78 (d, 1H), 6.52 (dd, 1H), 5.69 (brs, 2H), 5.13-4.88 (m, 2H), 4.84-4.73 (m, 1H), 4.15-4.05 (m, 2H), 3.99-3.87 (m, 2H), 3.52-3.43 (m, 1H), 3.28-3.12 (m, 3H), 3.09-3.00 (m, 1H), 2.93-2.33 (m, 8H), 2.24-2.00 (m, 6H), 1.84-1.76 (m, 1H).

LCMS m/z=799.3 [M+1]$^+$.

Example 49-2 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 49-2)

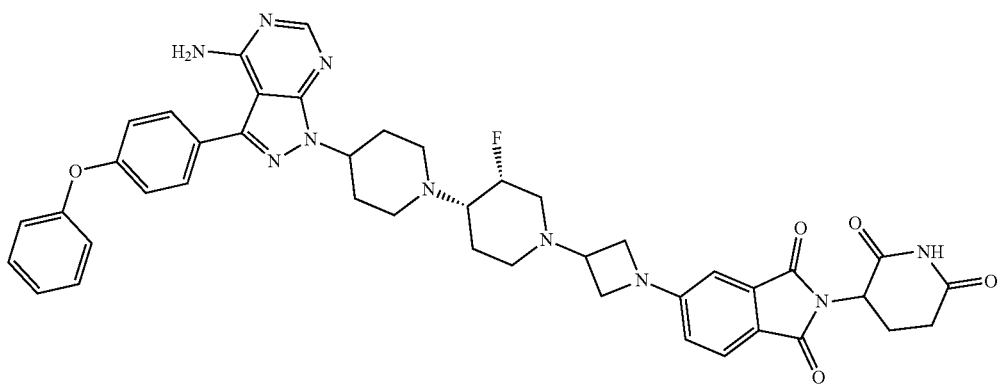

or

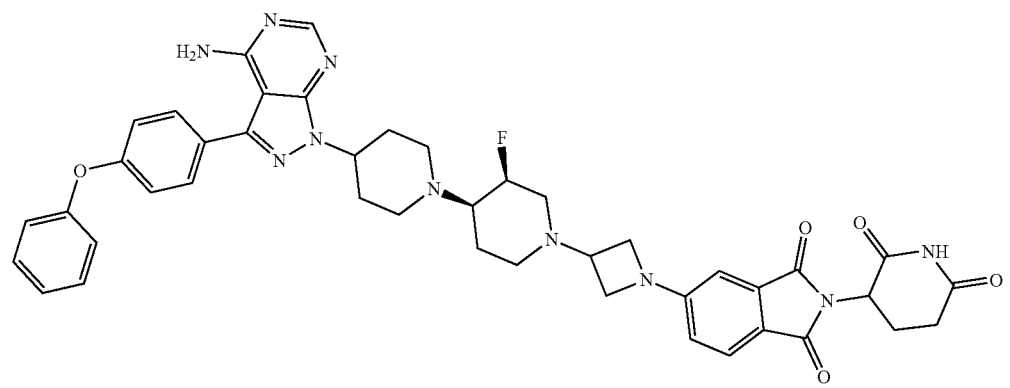

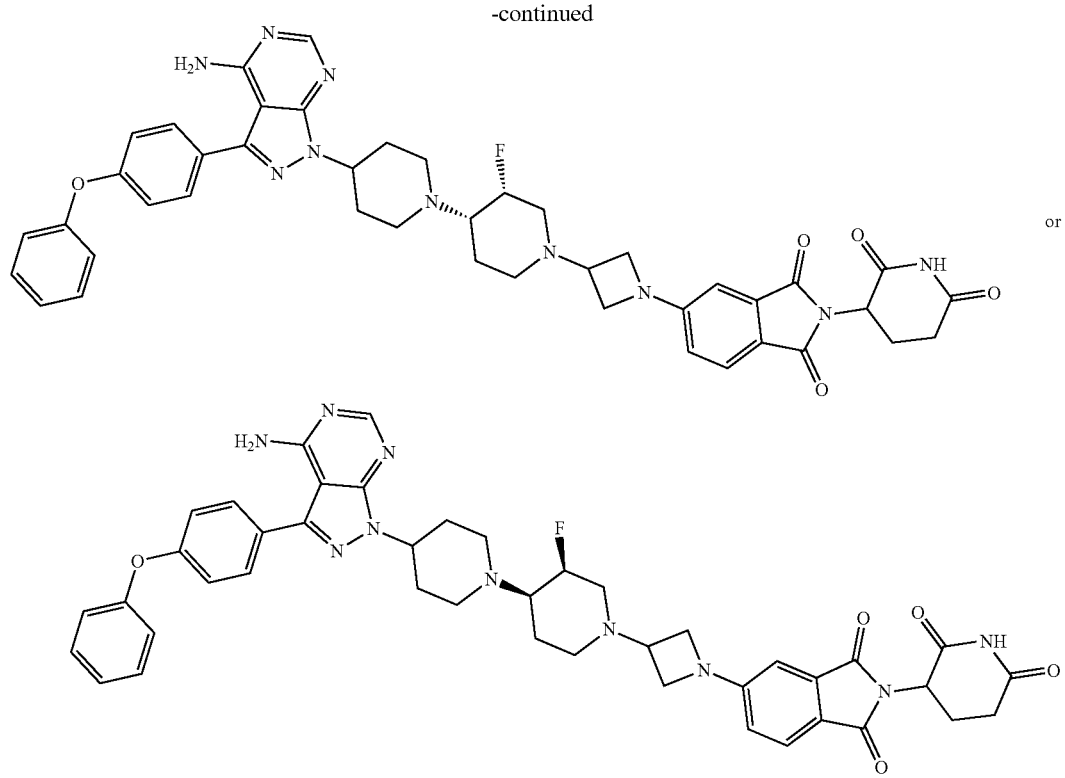

Compound 49-2

Step 1 cis-1-(3'-fluoro-[1,4'-bipiperidin]-4-yl)-3-(4-phenoxyphenyl)-1H-pyrazolo[3,4-d]pyrimidin-4-amine-P2 (49d)

Cis-tert-butyl 4-(4-amino-3-(4-phenoxyphenyl)-1H-pyrazolo[3,4-d]pyrimidin-1-yl)-3'-fluoro-[1,4'-bipiperidine]-1'-carboxylate-P2 (18a-2, its structure was one of formula 18a-a and formula 18a-b, an isomer of compound 18a-1) (0.82 g, 1.4 mmol) was dissolved in 20 mL of DCM, and 5 mL of trifluoroacetic acid was added, the mixture was stirred at room temperature for 3 h. To the reaction solution was slowly added dropwise 30 mL of saturated sodium bicarbonate solution, and 30 mL of dichloromethane and 50 mL of water were added. The organic phase was separated, dried over anhydrous sodium sulfate, and concentrated under reduced pressure, to obtain the crude product cis-1-(3'-fluoro-[1,4'-bipiperidin]-4-yl)-3-(4-phenoxyphenyl)-1H-pyrazolo[3,4-d]pyrimidin-4-amine-P2 (49d) (0.62 g), and the configuration of the chiral carbon thereof was consistent with that of the corresponding chiral carbon of compound 18a-2.

LC-MS m/z=488.3 [M+1]$^+$.

Step 2

Cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P2 (49e)

The above crude product cis-1-(3'-fluoro-[1,4'-bipiperidin]-4-yl)-3-(4-phenoxyphenyl)-1H-pyrazolo[3,4-d]pyrimidin-4-amine-P2 (49d) (0.62 g) was dissolved in 30 mL of DCE, and tert-butyl 3-oxazetidine-1-carboxylate (0.43 g, 2.5 mmol) was added, the mixture was stirred at room temperature for 10 min, then sodium triacetoxyborohydride (0.64 g, 3.0 mmol) was added, and the reaction was stirred at room temperature for 16 h. To the reaction solution was added 30 mL of saturated sodium bicarbonate solution, and 50 mL of dichloromethane and 50 mL of water were added. The organic phase was separated, dried over anhydrous sodium sulfate, and concentrated under reduced pressure, then the crude product was separated and purified by silica gel column chromatography (dichloromethane/methanol (v/v) =20:1), to obtain cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine-1-carboxylate-P2 (49e) (0.6 g, two-step yield calculated from compound 18a-2: 67%), and the configuration of the chiral carbon thereof was consistent with that of the corresponding chiral carbon of compound 18a-2.

LC-MS m/z=643.4 [M+1]$^+$.

Step 3

Cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2 (49f)

Cis-tert-butyl 3-(4-(4-amino-3-(4-phenoxyphenyl)-1H-pyrazolo[3,4-d]pyrimidin-1-yl)-3'-fluoro-[1,4'-bipiperidin]-1'-yl)azetidine- 1-carboxylate-P2 (49e) (0.6 g, 0.93 mmol) was dissolved in 20 mL of DCM, and 5 mL of trifluoroacetic acid was added, the mixture was stirred at room temperature for 3 h. To the reaction solution was slowly added dropwise 30 mL of saturated sodium bicarbonate solution, and 30 mL of dichloromethane and 50 mL of water were added. The organic phase was separated, dried over anhydrous sodium sulfate, and concentrated under reduced pressure, to obtain the crude product cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2 (49f) (0.45 g), and the configuration of the chiral carbon thereof was consistent with that of the corresponding chiral carbon of compound 18a-2.

LCMS m/z=543.3 [M+1]$^+$.

Step 4 cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 49-2)

0.5 mmol) were added, the reaction was stirred at 90° C. for 3 h. The reaction solution was cooled to room temperature, and 50 mL of ethyl acetate and 50 mL of water were added. The organic phase was separated, dried over anhydrous sodium sulfate, and concentrated under reduced pressure, then the crude product was separated and purified by silica gel column chromatography (dichloromethane/methanol (v/v)=20:1), to obtain cis-5-(3-(4-(4-amino-3-(4-phenoxyphenyl)-1H-pyrazolo[3,4-d]pyrimidin-1-yl)-3'-fluoro-[1,4'-bipiperidin]-1'-yl)azetidin-1-yl)-2-(2,6-dioxopiperidin-3-yl)isoindoline-1,3-dione-P2 (Compound 49-2) (0.27 g, two-step yield calculated from compound 49e: 82%). The structure of compound 49-2 was one of the structures shown in 49-a and 49-b above, and the configuration of the chiral carbon thereof was consistent with that of the corresponding chiral carbon of the raw material (Compound 18a-2) in the first step, namely, compound 49-2 was an isomer of compound 49-1.

$^1$H NMR (400 MHz, CDCl$_3$) δ 9.66 (s, 1H), 8.38 (s, 1H), 7.67-7.60 (m, 3H), 7.42-7.34 (m, 2H), 7.20-7.11 (m, 3H),

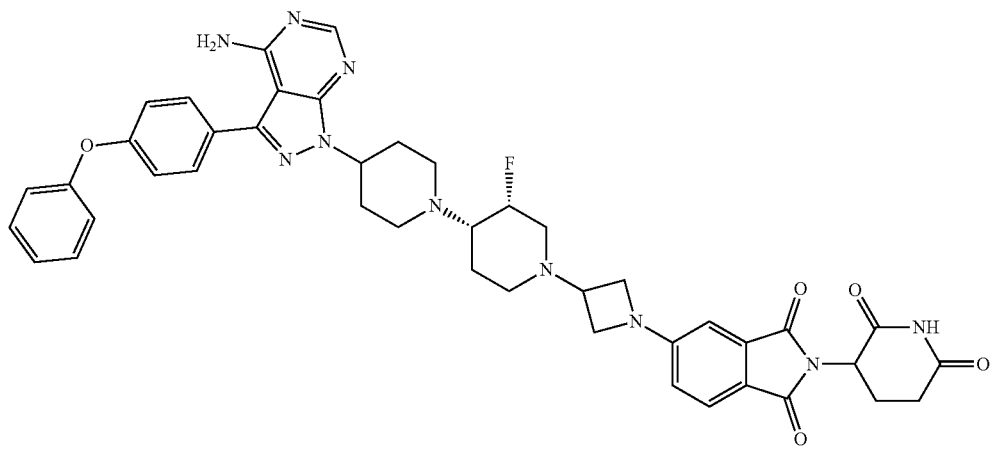

formula 49-b

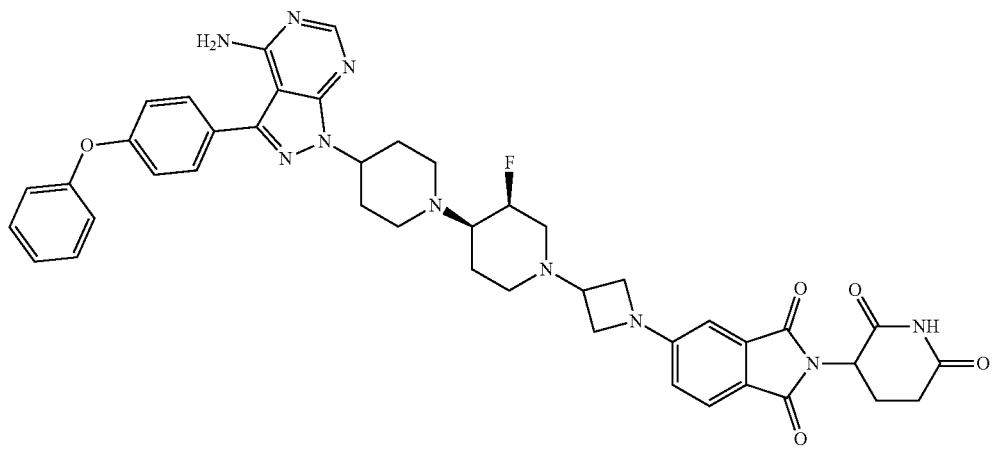

formula 49-a

The above crude product cis-1-(1'-(azetidin-3-yl)-3'-fluoro-[1,4'-bipiperidin]-4-yl)-3-(4-phenoxyphenyl)-1H-pyrazolo[3,4-d]pyrimidin-4-amine-P2(49f) (0.2 g) was dissolved in 5 mL of DMSO, and DIPEA (0.21 g, 1.6 mmol) and 2-(2,6-dioxopiperidin-3-yl)-5-fluoroisoindoline-1,3-dione (see WO 2017197056 for the synthetic method) (0.14 g, 7.10-7.04 (m, 2H), 6.78 (d, 1H), 6.52 (dd, 1H), 5.79 (brs, 2H), 5.13-4.88 (m, 2H), 4.83-4.72 (m, 1H), 4.16-4.04 (m, 2H), 4.00-3.86 (m, 2H), 3.52-3.42 (m, 1H), 3.24-3.12 (m, 3H), 3.09-3.00 (m, 1H), 2.91-2.32 (m, 8H), 2.23-1.98 (m, 6H), 1.84-1.76 (m, 1H).

LCMS m/z=799.4 [M+1]$^+$.

Example 50
5-(3-(2-(4-(4-amino-3-(4-phenoxyphenyl)-1H-pyra-
zolo[3,4-d]pyrimidin-1-yl)piperidin-1-yl)-7-azaspiro
[3.5]nonan-7-yl)azetidin-1l-yl)-2-(2,6-dioxopiperi-
din-3-yl)isoindoline-1,3-dione (Compound 50)
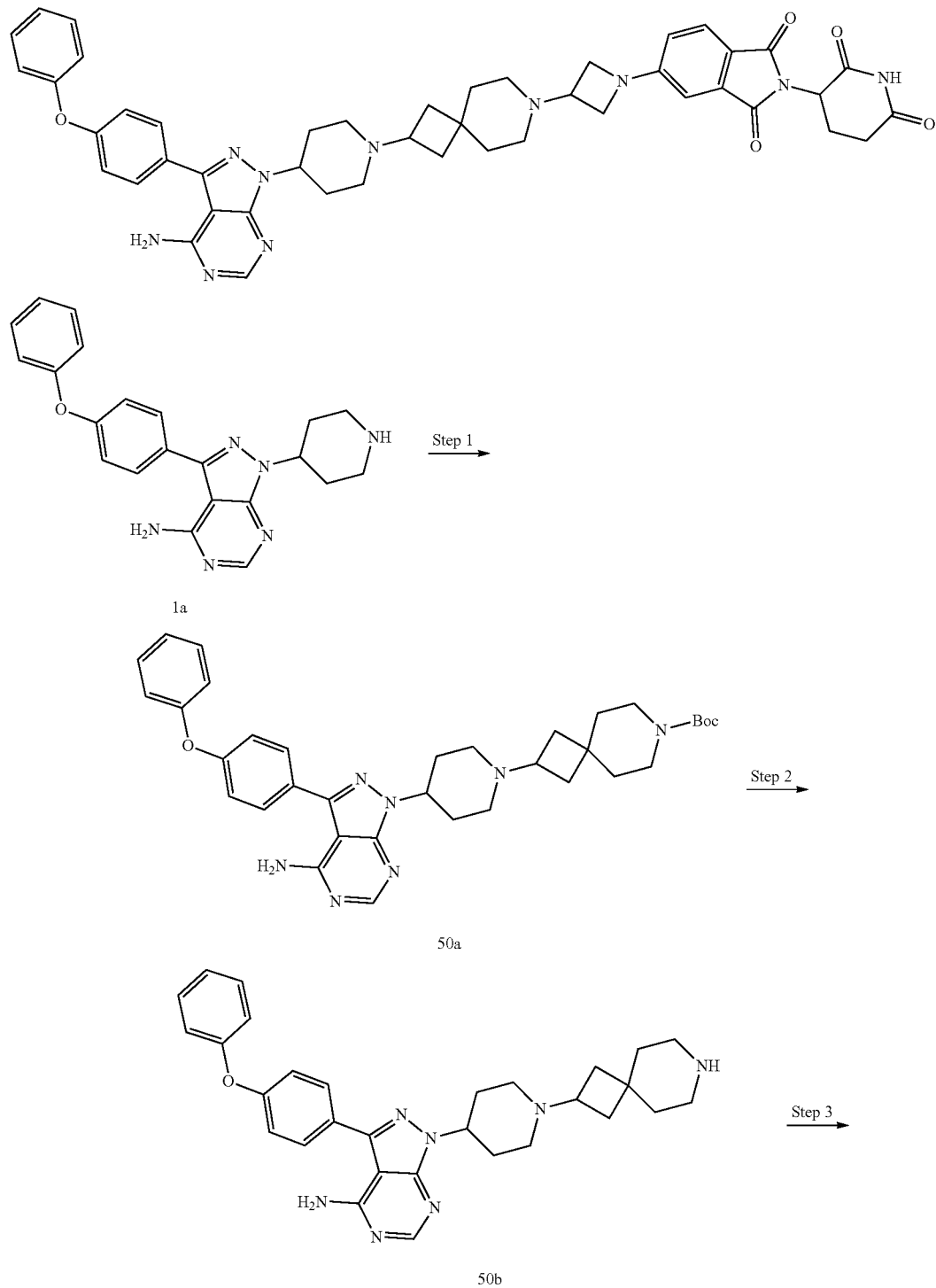

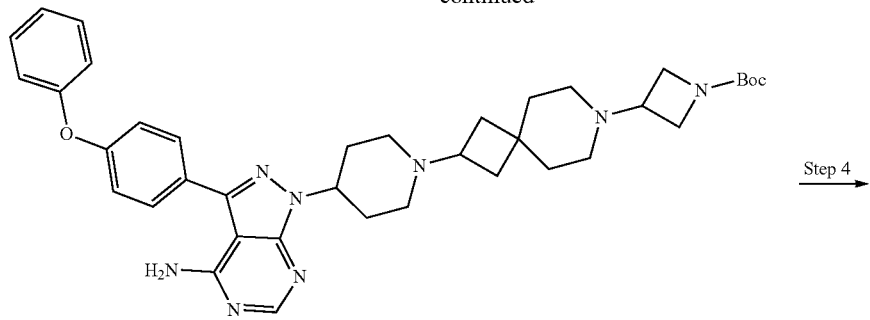

50c

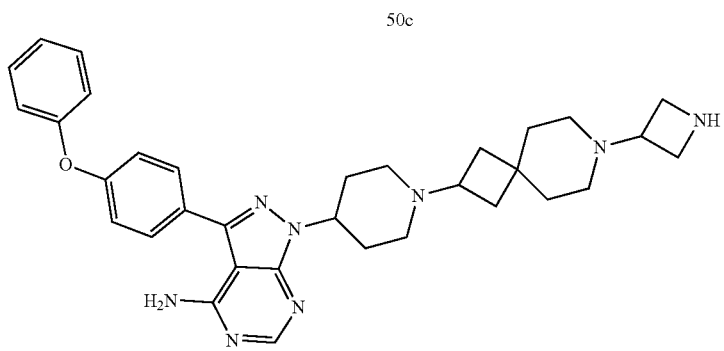

50d

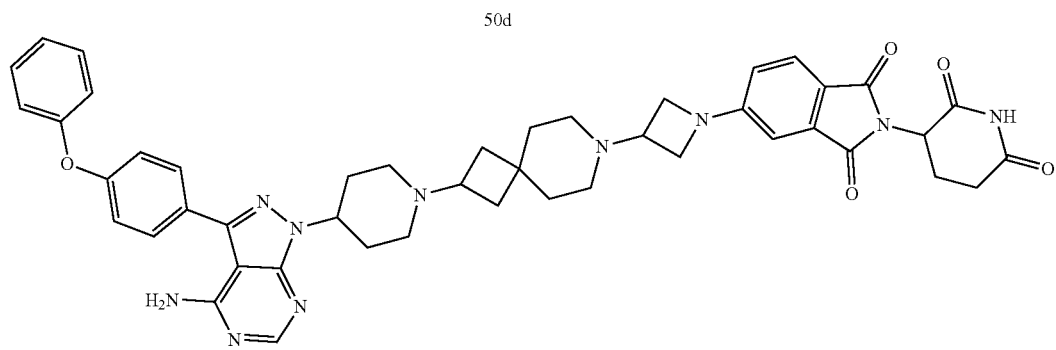

Compound 50

Step 1 tert-butyl 2-(4-(4-amino-3-(4-phenoxyphenyl)-1H-pyrazolo[3,4-d]pyrimidin-1-yl)piperidin-11-yl)-7-azaspiro[3.5]nonane-7-carboxylate (50a)

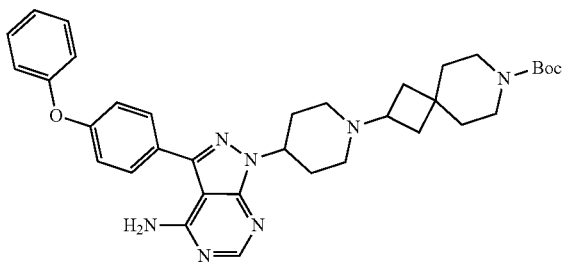 [SMILES: CC(C)(C)OC(=O)N1CCC2(CC1)CC(N1CCC(n3nc(-c4ccc(Oc5ccccc5)cc4)c4c(N)ncnc43)CC1)C2]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (400 mg, 1.04 mmol) was dissolved in 5 mL of DCE, and tert-butyl 2-oxo-7-azaspiro[3.5]nonane-7-carboxylate (493 mg, 2.06 mmol), glacial acetic acid (0.15 mL, 2.6 mmol) and anhydrous sodium sulfate (700 mg) were successively added at room temperature, the mixture was stirred for 5 min, then sodium triacetoxyborohydride (655 mg, 3.09 mmol) was added, and the mixture was stirred at room temperature for 16 h. To the reaction solution was added 50 mL of water, the pH of the aqueous phase was adjusted to 10 with 2 mol/L sodium hydroxide aqueous solution, and the resulted solution was extracted with dichloromethane (30 mL×3). The organic phase was combined, washed with water (20 mL×2), dried over anhydrous sodium sulfate, and concentrated under reduced pressure, then the crude product was separated and purified by silica gel column chromatography (dichloromethane/methanol (v/v)=10:1-8:1), to obtain tert-butyl 2-(4-(4-amino-3-(4-phenoxyphenyl)-1H-pyrazolo[3,4-d]pyrimidin-1-yl)piperidin-1-yl)-7-azaspiro[3.5]nonane-7-carboxylate (50a) (600 mg, yield: 95%).

LCMS m/z=610.4 [M+1]$^+$.

Step 2

1-(1-(7-azaspiro[3.5]nonan-2-yl)piperidin-4-yl)-3-(4-phenoxyphenyl)-1H-pyrazolo[3,4-d]pyrimidin-4-amine (50b)

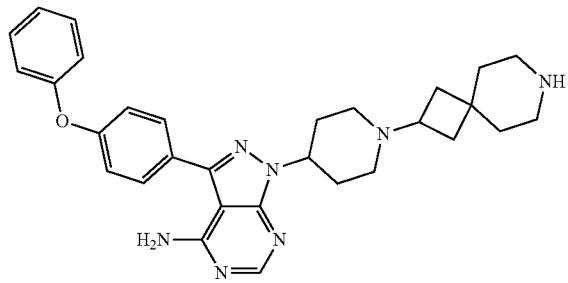 [SMILES: Nc1ncnc2c1c(-c1ccc(Oc3ccccc3)cc1)nn2C1CCN(C2CC3(CCNCC3)C2)CC1]

Tert-butyl 2-(4-(4-amino-3-(4-phenoxyphenyl)-1H-pyrazolo[3,4-d]pyrimidin-1-yl]piperidin-1-yl)-7-azaspiro[3.5]nonane-7-carboxylate (50a) (600 mg, 0.98 mmol) was dissolved in 4 mL of dichloromethane, and 2 mL of trifluoroacetic acid was added, the reaction was carried out at room temperature for 2 h. The pH of the reaction solution was adjusted to 10 with 2 mol/L sodium hydroxide solution, and the aqueous phase was extracted with dichloromethane (10 mL×3). The organic phase was combined, dried over anhydrous sodium sulfate, and concentrated under reduced pressure, to obtain the crude product 1-(1-(7-azaspiro[3.5]nonan-2-yl)piperidin-4-yl)-3-(4-phenoxyphenyl)-1H-pyrazolo[3,4-d]pyrimidin-4-amine (50b) (458 mg).

LCMS m/z=510.3 [M+1]⁺.

Step 3 tert-butyl 3-(2-(4-(4-amino-3-(4-phenoxyphenyl)-1H-pyrazolo[3,4-d]pyrimidin-1-yl)piperidin-1-yl)-7-azaspiro[3.5]nonan-7-yl)azetidine-1-carboxylate (50c)

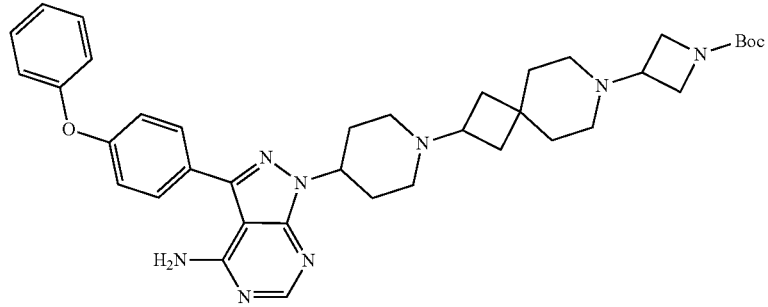 [SMILES: CC(C)(C)OC(=O)N1CC(N2CCC3(CC2)CC(N2CCC(n4nc(-c5ccc(Oc6ccccc6)cc5)c5c(N)ncnc54)CC2)C3)C1]

The above crude product 1-(1-(7-azaspiro[3.5]nonan-2-yl)piperidin-4-yl)-3-(4-phenoxyphenyl)-1H-pyrazolo[3,4-d]pyrimidin-4-amine (50b) (458 mg) was dissolved in 5 mL of DCE, and 1-Boc-3-azetidinone (308 mg, 1.80 mmol), glacial acetic acid (0.13 mL, 2.25 mmol) and anhydrous sodium sulfate (700 mg) were successively added at room temperature, the mixture was stirred for 30 min, then sodium triacetoxyborohydride (634 mg, 2.99 mmol) was added, and the mixture was stirred at room temperature for 16 h. To the reaction solution was added 50 mL of water, the pH of the aqueous phase was adjusted to 10 with 2 mol/L sodium hydroxide solution, and the resulted solution was extracted with dichloromethane (30 mL×3). The organic phase was combined, washed with water (20 mL×2), dried over anhydrous sodium sulfate, and concentrated under reduced pressure, then the crude product was separated and purified by silica gel column chromatography (dichloromethane/methanol (v/v)=10:1-8:1), to obtain tert-butyl 3-(2-(4-(4-amino-3-(4-phenoxyphenyl)-1H-pyrazolo[3,4-d]pyrimidin-1-yl)piperidin-1-yl)-7-azaspiro[3.5]nonan-7-yl)azetidine-1-carboxylate (50c) (501 mg, two-step yield calculated from compound 50a: 77%).

LCMS m/z=665.4 [M+1]⁺.

Step 4

1-(1-(7-(azetidin-3-yl)-7-azaspiro[3.5]nonan-2-yl)piperidin-4-yl)-3-(4-phenoxy phenyl)-1H-pyrazolo[3,4-d]pyrimidin-4-amine (50d)

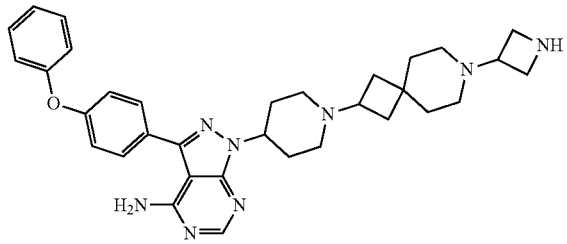 [SMILES: Nc1ncnc2c1c(-c1ccc(Oc3ccccc3)cc1)nn2C1CCN(C2CC3(CCN(C4CNC4)CC3)C2)CC1]

Tert-butyl 3-(2-(4-(4-amino-3-(4-phenoxyphenyl)-1H-pyrazolo[3,4-d]pyrimidin-1-yl)piperidin-1-yl)-7-azaspiro[3.5]nonan-7-yl)azetidine-1-carboxylate (50c) (501 mg, 0.75 mmol) was dissolved in 5 mL of dichloromethane, and 2 mL of trifluoroacetic acid was added, the reaction was carried out at room temperature for 2.5 h. The pH of the reaction solution was adjusted to 10 with 2 mol/L sodium hydroxide solution, and the aqueous phase was extracted with dichloromethane (10 mL×3). The organic phase was combined, dried over anhydrous sodium sulfate, and concentrated under reduced pressure, to obtain the crude product 1-(1-(7-(azetidin-3-yl)-7-azaspiro[3.5]nonan-2-yl)piperidin-4-yl)-3-(4-phenoxyphenyl)-1H-pyrazolo[3,4-d]pyrimidin-4-amine (50d) (350 mg).

LCMS m/z=565.4 [M+1]⁺.

Step 5

5-(3-(2-(4-(4-amino-3-(4-phenoxyphenyl)-1H-pyrazolo[3,4-d]pyrimidin-1-yl)piperidin-1-yl)-7-azaspiro[3.5]nonan-7-yl)azetidin-1-yl)-2-(2,6-dioxopiperidin-3-yl)isoindoline-1,3-dione (Compound 50)

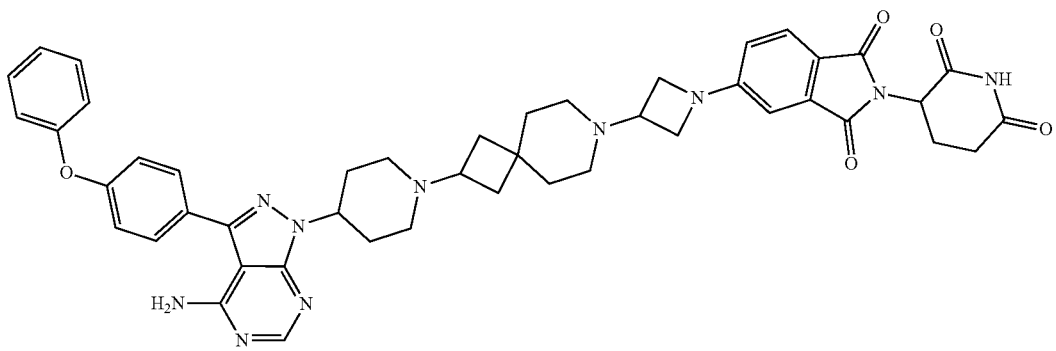 [SMILES: Nc1ncnc2c1c(-c1ccc(Oc3ccccc3)cc1)nn2C1CCN(C2CC3(CCN(C4CN(c5ccc6c(c5)C(=O)N(C5CCC(=O)NC5=O)C6=O)C4)CC3)C2)CC1]

The above crude product 1-(1-(7-(azetidin-3-yl)-7-azaspiro[3.5]nonan-2-yl)piperidin-4-yl)-3-(4-phenoxyphenyl)-1H-pyrazolo[3,4-d]pyrimidin-4-amine (50d) (192 mg) was dissolved in 5 mL of DMSO, and 2-(2,6-dioxopiperidin-3-yl)-5-fluoroisoindoline-1,3-dione (see WO 2017197056 for the synthetic method) (102 mg, 0.37 mmol) and diisopropylethylamine (220 mg, 1.70 mmol) were added at room temperature, the reaction was stirred at 80° C. for 4 h. The reaction solution was poured into 20 mL of water, and the aqueous phase was extracted with the mixed solvent of dichloromethane/methanol (v/v)=10:1 (30 mL×3). The organic phase was combined, washed with 50 mL of water, dried over anhydrous sodium sulfate, and concentrated under reduced pressure, then the crude product was separated and purified by silica gel column chromatography (dichloromethane/methanol (v/v)=15:1-8:1), to obtain 5-(3-(2-(4-(4-amino-3-(4-phenoxyphenyl)-1-pyrazolo[3,4-d]pyrimidin-1-yl)piperidin-1-yl)-7-azaspiro[3.5]nonan-7-yl)azetidin-1-yl)-2-(2,6-dioxopiperidin-3-yl)isoindoline-1,3-dione (Compound 50) (112 mg, two-step yield calculated from compound 50c: 33%).

¹H NMR (400 MHz, CDCl₃) δ 8.29 (s, 1H), 7.61-7.52 (m, 3H), 7.36-7.28 (m, 2H), 7.16-6.97 (m, 5H), 6.70 (d, 1H), 6.44 (dd, 1H), 5.76 (br.s, 2H), 4.85 (dd, 1H), 4.80-4.66 (m, 1H), 4.06-3.96 (m, 2H), 3.86-3.76 (m, 2H), 3.28-3.18 (m, 1H), 3.07-2.96 (m, 1H), 2.86-2.57 (m, 5H), 2.43-2.31 (m, 3H), 2.31-2.17 (m, 3H), 2.09-1.92 (m, 7H), 1.77-1.66 (m, 2H), 1.65-1.54 (m, 4H).

LCMS m/z=821.4 [M+1]⁺.

Example 51
5-(2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonan]-7-yl)-2-(2,6-dioxopiperidin-3-yl)isoindoline-1,3-dione (Compound 51)
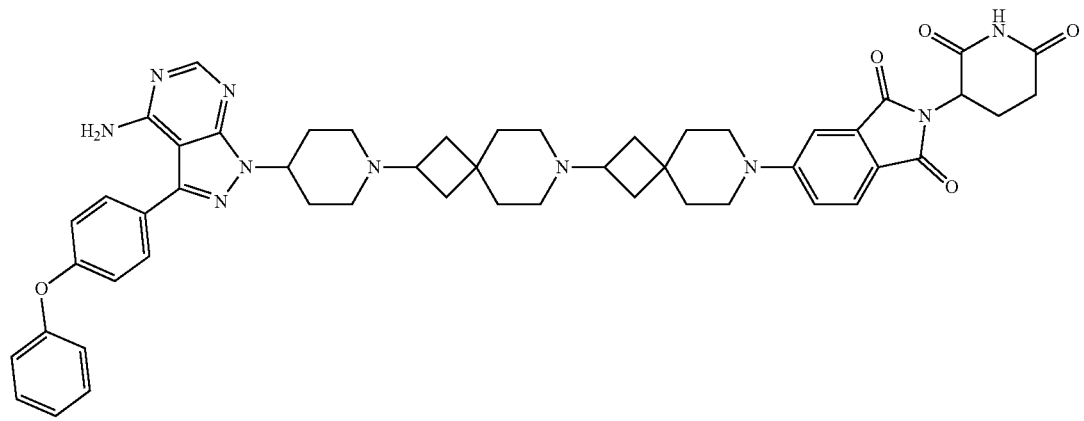
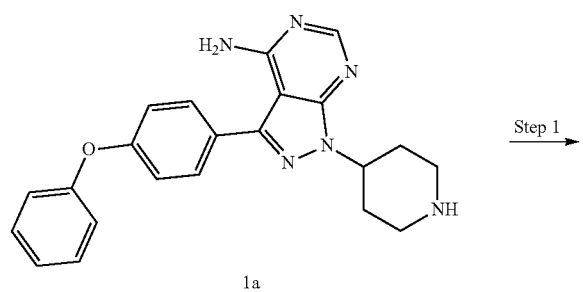
1a
Step 1 →
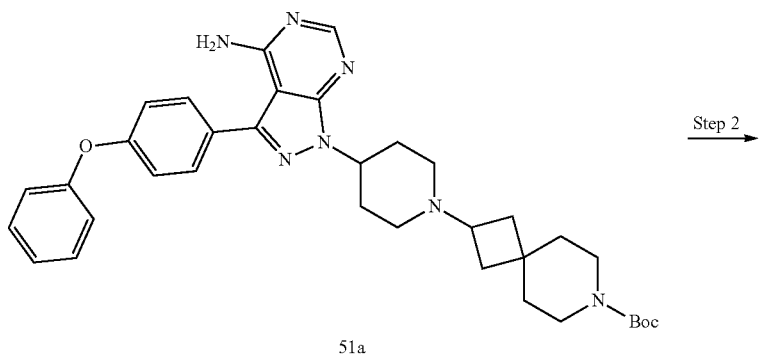
51a
Step 2 →
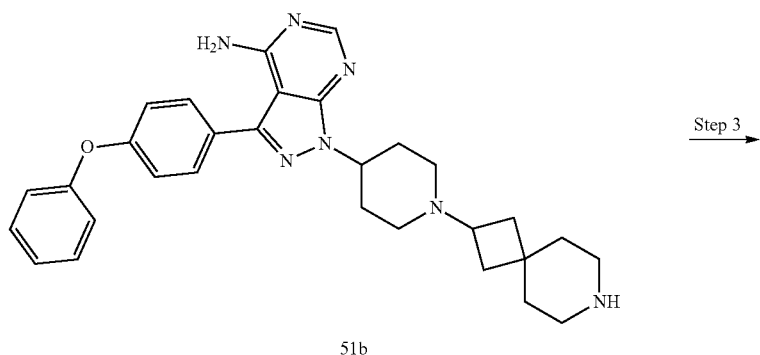
51b
Step 3 →

-continued
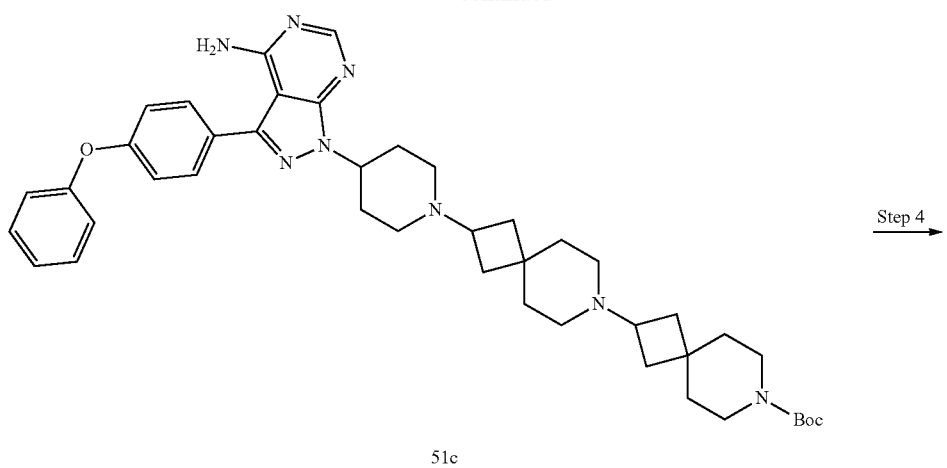
51c
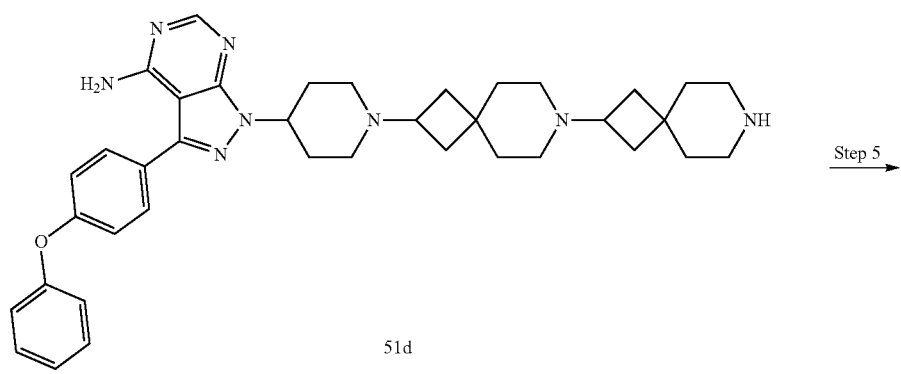
51d
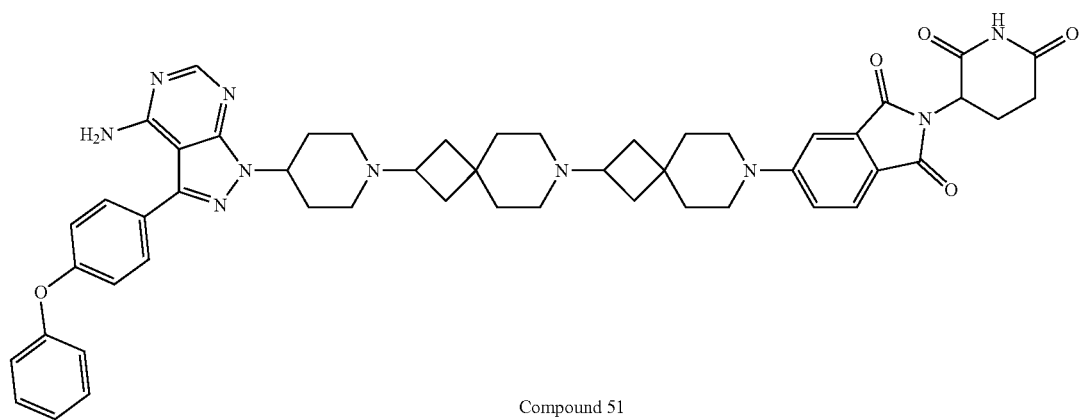
Compound 51

Step 1 tert-butyl 2(4-(4-amino-3-(4-phenoxyphenyl)-1H-pyrazolo[3,4-d]pyrimidin-1-yl)piperidine-1-yl)-7-azaspiro[3.5]nonane-7-carboxylate (51a)

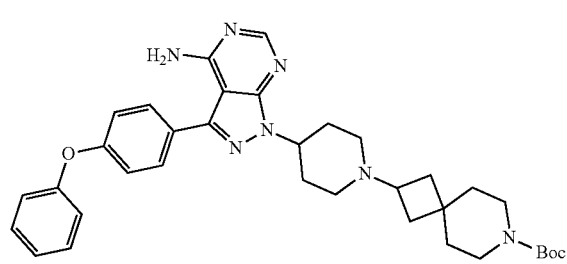 [SMILES: CC(C)(C)OC(=O)N1CCC2(CC1)CC(N1CCC(n3nc(-c4ccc(Oc5ccccc5)cc4)c4c(N)ncnc43)CC1)C2]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.0 g, 2.59 mmol) was dissolved in 35 mL of DCE, and tert-butyl 2-oxo-7-azaspiro[3.5]nonane-7-carboxylate (1.24 g, 5.18 mmol) was added, the mixture was stirred at room temperature for 10 min, then sodium triacetoxyborohydride (1.37 g, 6.46 mmol) was added, and the mixture was stirred at room temperature for 16 h. To the reaction solution was slowly added 30 mL of saturated sodium bicarbonate aqueous solution, and the mixed solution was extracted with dichloromethane (30 mL×3). The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 2-(4-(4-amino-3-(4-phenoxyphenyl)-1H-pyrazolo[3,4-d]pyrimidin-1-yl)piperidin-1-yl)-7-azaspiro[3.5]nonane-7-carboxylate (51a) (1.5 g, yield: 95%).

LCMS m/z=610.4 [M+1]⁺.

Step 2

1-(1-(7-azaspiro[3.5]nonan-2-yl)piperidin-4-yl)-3-(4-phenoxyphenyl)-1H-pyrazolo[3,4-d]pyrimidin-4-amine Trifluoroacetate (51b)

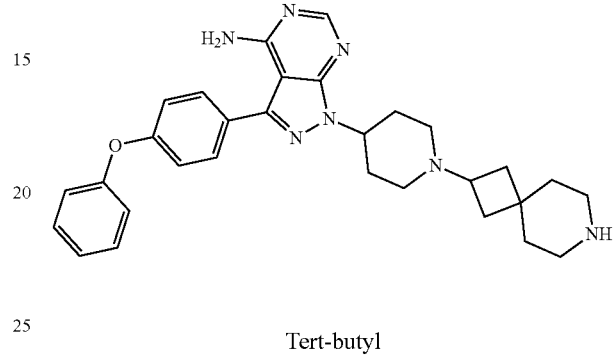

Tert-butyl 2-(4-(4-amino-3-(4-phenoxyphenyl)-1H-pyrazolo[3,4-d]pyrimidin-1-yl)piperidin-1-yl)-7-azaspiro[3.5]nonane-7-carboxylate (51a) (1.5 g, 2.46 mmol) was dissolved in 20 mL of dichloromethane, and 8 mL of trifluoroacetic acid was added, the mixture was stirred at room temperature for 4 h. Upon completion of the reaction, the reaction system was directly concentrated under reduced pressure, to obtain the crude product 1-(1-(1-(7-azaspiro[3.5]nonan-2-yl)piperidin-4-yl)-3-(4-phenoxyphenyl)-1H-pyrazolo[3,4-d]pyrimidin-4-amine Trifluoroacetate (51b) (1.8 g).

LCMS m/z=510.3 [M+1]⁺.

Step 3 tert-butyl 2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonane]-7-carboxylate (51c)

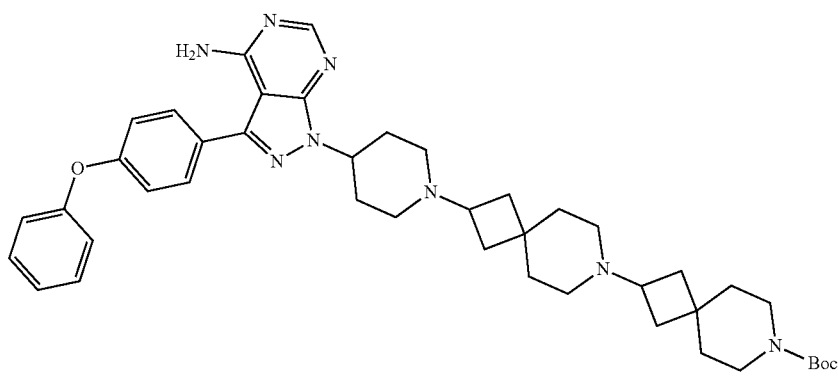 [SMILES: CC(C)(C)OC(=O)N1CCC2(CC1)CC(N1CCC3(CC1)CC(N1CCC(n4nc(-c5ccc(Oc6ccccc6)cc5)c5c(N)ncnc54)CC1)C3)C2]

The above crude product 1-(1-(1-(7-azaspiro[3.5]nonan-2-yl)piperidin-4-yl)-3-(4-phenoxyphenyl)-1H-pyrazolo[3,4-d]pyrimidin-4-amine Trifluoroacetate (51b) (1.8 g) was dissolved in 40 mL of DCE, and solid sodium bicarbonate (620 mg, 7.38 mmol) was added, the mixture was stirred at room temperature for 20 min, then tert-butyl 2-oxo-7-azaspiro[3.5]nonane-7-carboxylate (1.18 g, 4.93 mmol) was added, and the mixture was stirred at room temperature for 10 min, then sodium triacetoxyborohydride (1.56 g, 7.36 mmol) was added, and the mixture was stirred at room temperature for 16 h. To the reaction system was slowly added 60 mL of saturated sodium bicarbonate aqueous solution, and the mixed solution was extracted with dichloromethane (80 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonane]-7-carboxylate (51c) (1.2 g, two-step yield calculated from compound 51a: 67%).

LCMS m/z=733.3 [M+1]$^+$.

Step 4

1-(1-(7,7'-diaza[2,7'-bispiro[3.5]nonan]-2'-yl)piperidin-4-yl)-3-(4-phenoxy-phenyl)-1H-pyrazolo[3,4-d]pyrimidin-4-amine hydrochloride (51d)

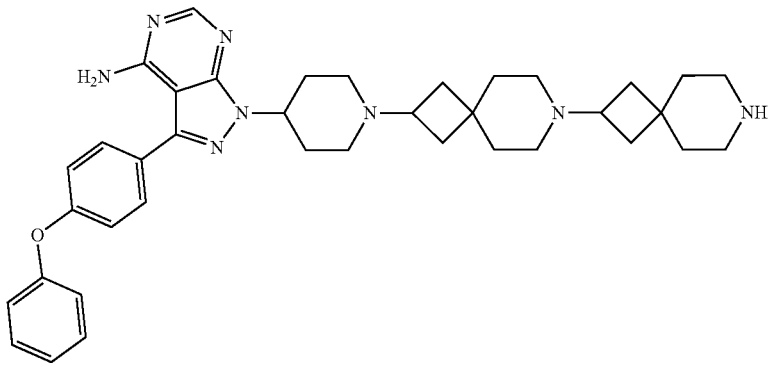 [SMILES: Nc1ncnc2c1c(-c1ccc(Oc3ccccc3)cc1)nn2C1CCN(C2CC3(CCN(C4CC5(CCNCC5)C4)CC3)C2)CC1]

Tert-butyl 2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonane]-7-carboxylate (51c) (300 mg, 0.41 mmol) was dissolved in 5 mL of methanol, and 10 mL 2N ethyl acetate hydrochloride solution was added, the mixture was stirred at room temperature for 4 h. The reaction system was directly concentrated under reduced pressure, to obtain the crude product 1-(1-(7,7'-diaza[2,7'-bispiro[3.5]nonane]-2'-yl)piperidin-4-yl)-3-(4-phenoxyphenyl)-1H-pyrazolo[3,4-d]pyrimidin-4-amine hydrochloride (51d) (0.36 g).

LCMS m/z=633.5 [M+1]$^+$.

Step 5

5-(2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonan]-7-yl)-2-(2,6-dioxopiperidin-3-yl)isoindoline-1,3-dione (Compound 51)

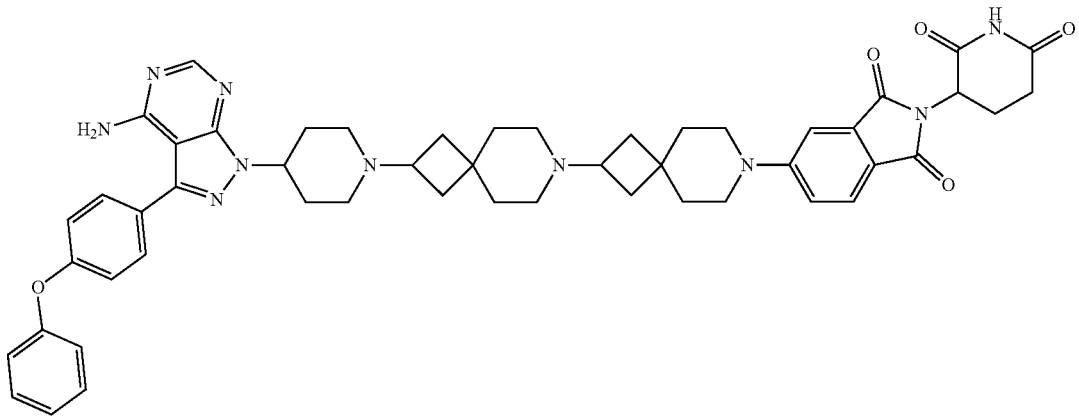 [SMILES: Nc1ncnc2c1c(-c1ccc(Oc3ccccc3)cc1)nn2C1CCN(C2CC3(CCN(C4CC5(CCN(c6ccc7c(c6)C(=O)N(C6CCC(=O)NC6=O)C7=O)CC5)C4)CC3)C2)CC1]

The above crude product 1-(1-(7,7'-diaza[2,7'-bispiro[3.5]nonane]-2'-yl)piperidin-4-yl)-3-(4-phenoxyphenyl)-1H-pyrazolo[3,4-d]pyrimidin-4-amine hydrochloride (51d) (0.36 g) was dissolved in 25 mL of DMSO, and solid sodium bicarbonate (138 mg, 1.64 mmol) was added, the mixture was stirred at room temperature for 10 min, then 1.5 mL of DIPEA and 2-(2,6-dioxopiperidin-3-yl)-5-fluoroisoindoline-1,3-dione (see WO 2017197056 for the synthetic method) (166 mg, 0.60 mmol) were added, the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=1), to obtain 5-(2'-(4-(4-amino-3-(4-phenoxyphenyl)-1H-pyrazolo[3,4-d]pyrimidin-1-yl)piperidin-1-yl)-7,7'-diaza[2,7'-bispiro[3.5]nonan]-7-yl)-2-(2,6-dioxopiperidin-3-yl)isoindoli ne-1,3-dione (Compound 51) (120 mg, two-step yield calculated from compound 51c: 33%).

$^1$H NMR (400 MHz, CDCl$_3$) δ 8.38 (s, 1H), 7.70-7.59 (m, 3H), 7.43-7.34 (m, 2H), 7.29-7.24 (m, 1H), 7.22-6.98 (m, 6H), 5.75 (br.s, 2H), 4.93 (dd, 1H), 4.84-4.71 (m, 1H), 3.48-3.26 (m, 4H), 3.09-2.98 (m, 2H), 2.93-2.80 (m, 2H), 2.79-2.65 (m, 3H), 2.50-2.17 (m, 5H), 2.17-1.91 (m, 10H), 1.90-1.48 (m, 12H).

LCMS m/z=889.5 [M+1]$^+$.

Example 52

5-(2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonan-7-yl)-2-(2,6-dioxopiperidin-3-yl)isoindoline-1,3-dione (Compound 52)

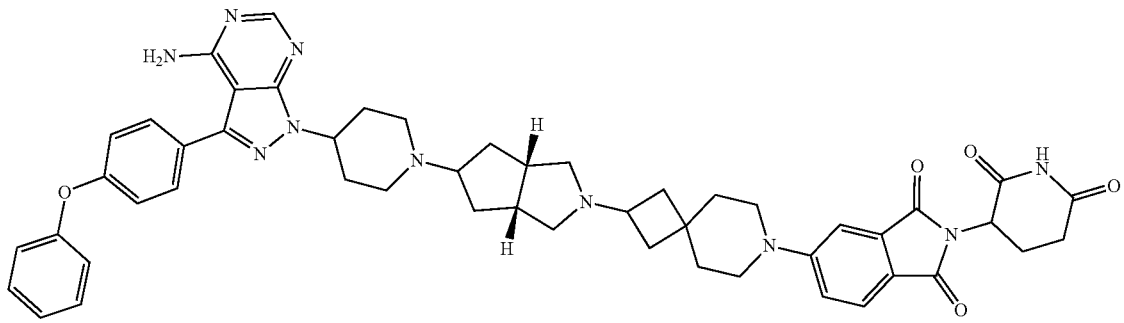

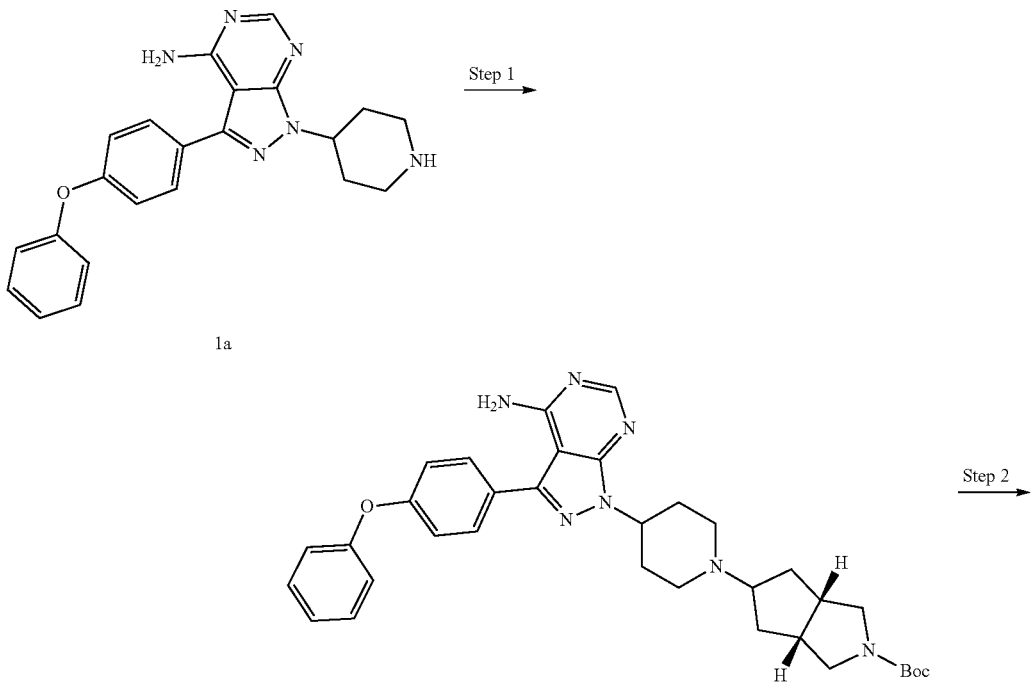

-continued
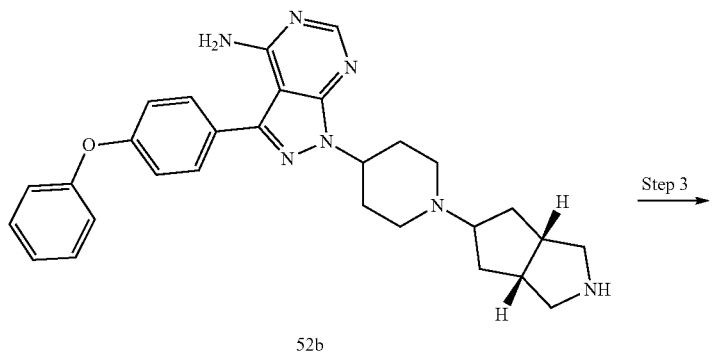
52b
Step 3 →
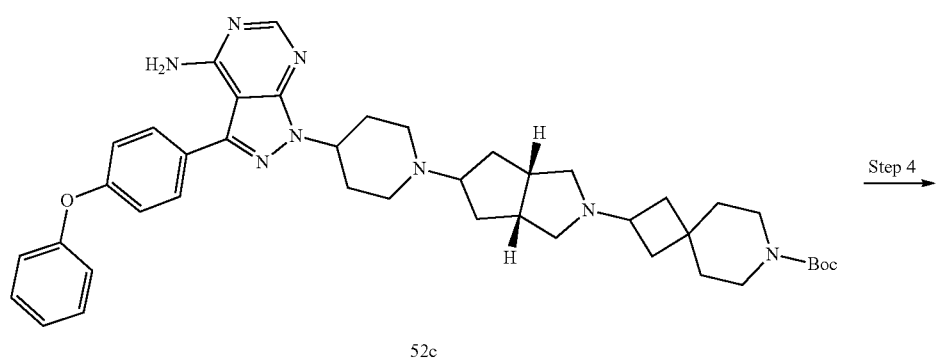
52c
Step 4 →
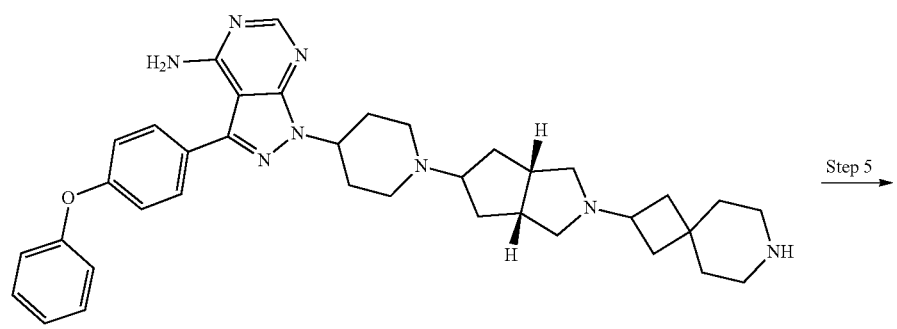
52d
Step 5 →
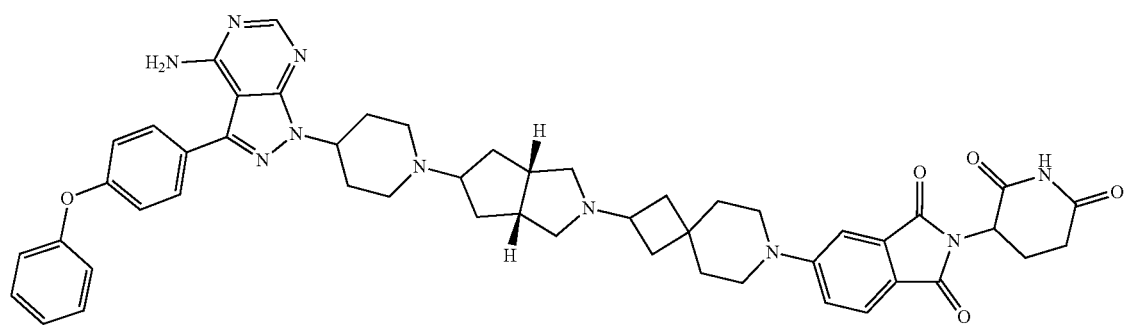
Compound 52

Step 1 tert-butyl (3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrole-2(1H)-carboxylate (52a)

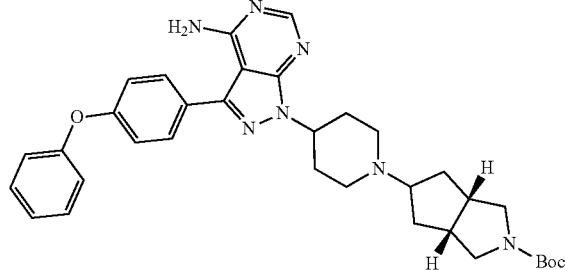 [SMILES: CC(C)(C)OC(=O)N1C[C@H]2CC(N3CCC(n4nc(-c5ccc(Oc6ccccc6)cc5)c5c(N)ncnc54)CC3)C[C@H]2C1]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.0 g, 2.59 mmol) was dissolved in 35 mL of DCE, and tert-butyl (3aR,6aS)-5-oxo hexahydrocyclopenta[c]pyrrole-2(1H)-carboxylate (1.17 g, 5.19 mmol) was added, the mixture was stirred at room temperature for 10 min, then sodium triacetoxyborohydride (1.37 g, 6.46 mmol) was added, and the mixture was stirred at room temperature for 16 h. To the reaction solution was slowly added 30 mL of saturated sodium bicarbonate aqueous solution, and the mixed solution was extracted with dichloromethane (30 mL×3). The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl (3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrole-2(1H)-carboxylate (52a) (1.4 g, yield: 91%).

LCMS m/z=596.4 [M+1]$^+$.

Step 2

1-(1-((3aR,6aS)-octahydrocyclopenta[c]pyrrol-5-yl)piperidin-4-yl)-3-(4-phenoxyphenyl)-1H-pyrazolo[3,4-d]pyrimidin-4-amine Trifluoroacetate (52b)

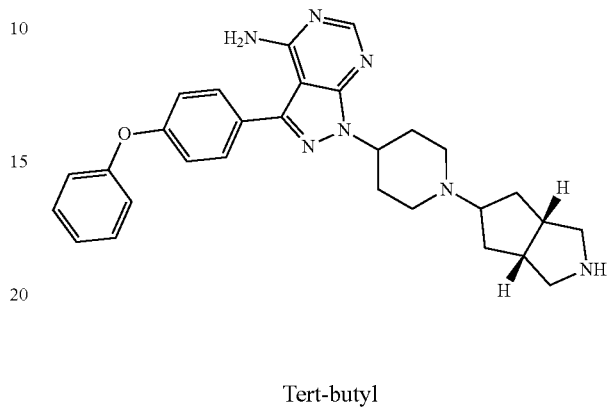

Tert-butyl (3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrole-2(1H)-carboxylate (52a) (1.5 g, 2.52 mmol) was dissolved in 20 mL of DCM, and 8 mL of trifluoroacetic acid was added, the mixture was stirred at room temperature for 4 h. Upon completion of the reaction, the reaction system was directly concentrated under reduced pressure, to obtain the crude product 1-(1-((3aR,6aS)-octahydrocyclopenta[c]pyrrol-5-yl)piperidin-4-yl)-3-(4-phenoxyphenyl)-1H-pyrazolo[3,4-d]pyrimidin-4-amine Trifluoroacetate (52b) (1.6 g).

LCMS m/z=496.3 [M+1]$^+$.

Step 3 tert-butyl 2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonane-7-carboxylate (52c)

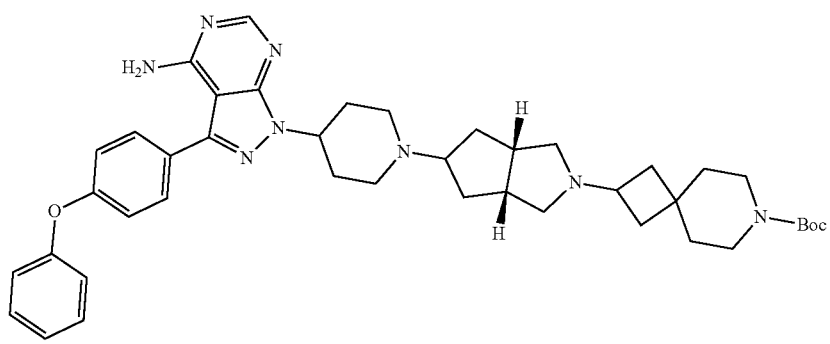 [SMILES: CC(C)(C)OC(=O)N1CCC2(CC1)CC(N1C[C@H]3CC(N4CCC(n5nc(-c6ccc(Oc7ccccc7)cc6)c6c(N)ncnc65)CC4)C[C@H]3C1)C2]

The above crude product 1-(1-((3aR,6aS)-octahydrocyclopenta[c]pyrrol-5-yl)piperidin-4-yl)-3-(4-phenoxyphenyl)-1H-pyrazolo[3,4-d]pyrimidin-4-amine Trifluoroacetate (52b) (0.8 g) was dissolved in 30 mL of DCE, and solid sodium bicarbonate (386 mg, 4.60 mmol) was added, the mixture was stirred at room temperature for 20 min, then tert-butyl 2-oxo-7-azaspiro[3.5]nonane-7-carboxylate (550 mg, 2.30 mmol) was added, and the mixture was stirred at room temperature for 10 min, then sodium triacetoxyborohydride (731 mg, 3.45 mmol) was added, and the mixture was stirred at room temperature for 16 h. To the reaction system was slowly added 60 mL of saturated sodium bicarbonate aqueous solution, and the mixed solution was extracted with DCM (80 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonane-7-carboxylate (52c) (0.63 g, two-step yield calculated from compound 52a: 70%).

LCMS m/z=719.5 [M+1]+.

Step 4

1-(1-((3aR,6aS)-2-(7-azaspiro[3.5]nonan-2-yl)octahydrocyclopenta[c]pyrrol-5-yl)piperidin-4-yl)-3-(4-phenoxyphenyl)-1H-pyrazolo[3,4-d]pyrimidin-4-amine hydrochloride (52d)

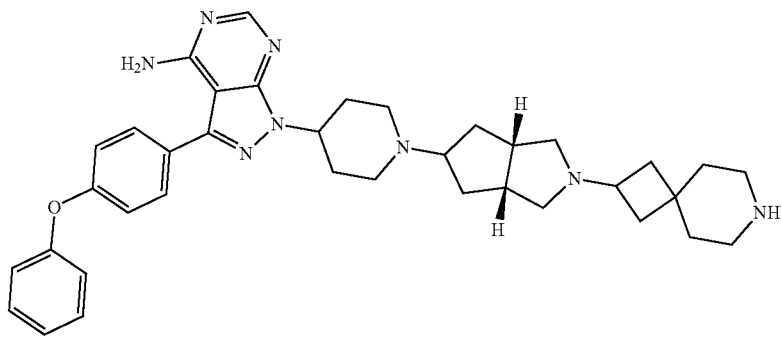 [SMILES: Nc1ncnc2c1c(-c1ccc(Oc3ccccc3)cc1)nn2C1CCN(C2C[C@@H]3CN(C4CC5(CCNCC5)C4)C[C@@H]3C2)CC1]

Tert-butyl 2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonane-7-carboxylate (52c) (300 mg, 0.42 mmol) was dissolved in 5 mL of methanol, and 10 mL of 2 mol/L ethyl acetate hydrochloride solution was added, the mixture was stirred at room temperature for 4 h. The reaction system was directly concentrated under reduced pressure, to obtain the crude product 1-(1-((3aR,6aS)-2-(7-azaspiro[3.5]nonan-2-yl)octahydrocyclopenta[c]pyrrol-5-yl)piperidin-4-yl)-3-(4-phenoxyphenyl)-1H-pyrazolo[3,4-d]pyrimidin-4-amine hydrochloride (52d) (0.36 g).

LCMS m/z=619.4 [M+1]+.

Step 5

5-(2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonan-7-yl)-2-(2,6-dioxopiperidin-3-yl)isoindoline-1,3-dione (Compound 52)

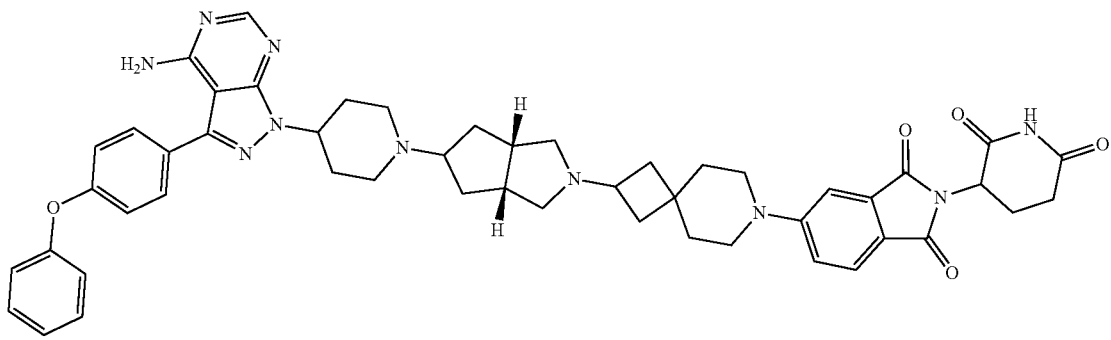 [SMILES: Nc1ncnc2c1c(-c1ccc(Oc3ccccc3)cc1)nn2C1CCN(C2C[C@@H]3CN(C4CC5(CCN(c6ccc7c(c6)C(=O)N(C6CCC(=O)NC6=O)C7=O)CC5)C4)C[C@@H]3C2)CC1]

The above crude product 1-(1-((3aR,6aS)-2-(7-azaspiro[3.5]nonan-2-yl)octahydrocyclopenta[c]pyrrol-5-yl)piperidin-4-yl)-3-(4-phenoxyphenyl)-1H-pyrazolo[3,4-d]pyrimidin-4-amine hydrochloride (52d) (0.36 g) was dissolved in 25 mL of DMSO, and solid sodium bicarbonate (138 mg, 1.64 mmol) was added, the mixture was stirred at room temperature for 10 min, then 1.5 mL of DIPEA and 2-(2,6-dioxopiperidin-3-yl)-5-fluoroisoindoline-1,3-dione (see WO 2017197056 for the synthetic method) (166 mg, 0.60 mmol) were added, and the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=1), to obtain 5-(2-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)-7-azaspiro[3.5]nonan-7-yl)-2-(2,6-dioxopiperidin-3-yl)isoindoline-1,3-dione (Compound 52) (100 mg, two-step yield calculated from compound 52c: 27%).

$^1$H NMR (400 MHz, CDCl$_3$) δ 10.06 (br.s, 1H), 8.39 (s, 1H), 7.68-7.60 (m, 3H), 7.42-7.34 (m, 2H), 7.29-7.24 (m, 1H), 7.20-6.99 (m, 6H), 5.84 (br.s, 2H), 4.98-4.90 (m, 1H), 4.83-4.71 (m, 1H), 3.44-3.29 (m, 4H), 3.25-3.14 (m, 2H), 2.94-2.66 (m, 4H), 2.64-2.31 (m, 9H), 2.30-2.07 (m, 5H), 2.07-1.93 (m, 4H), 1.89-1.59 (m, 6H), 1.46-1.32 (m, 2H).

LCMS m/z=875.4 [M+1]$^+$.

Example 53

5-((3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrol)]-2'(1'H)-yl)-2-(2,6-dioxopiperidin-3-yl)isoindoline-1,3-dione Trifluoroacetate (Compound 53)

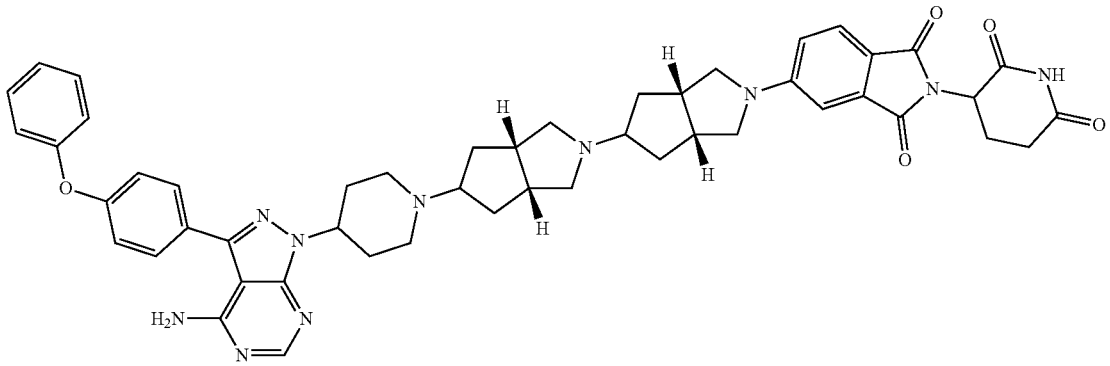

-continued
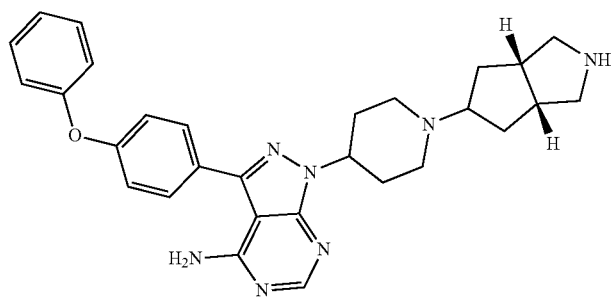
52b
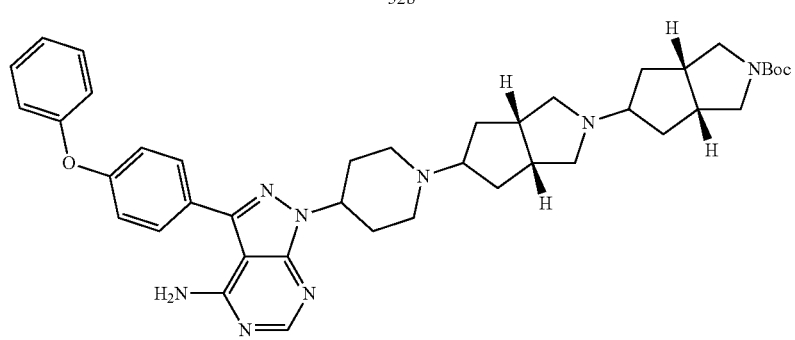
53a
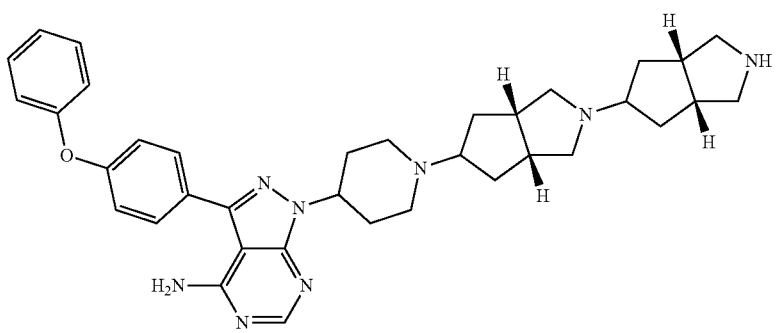
53b
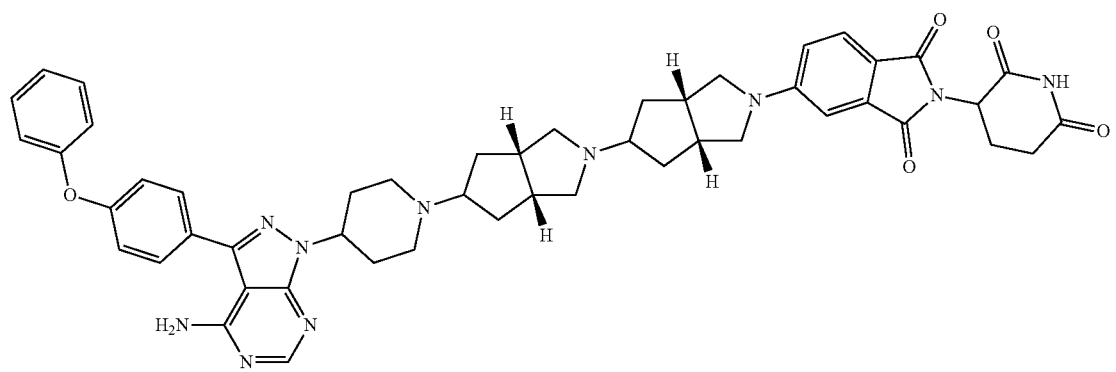
Compound 53

Step 1 tert-butyl (3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrole)]-2'(1'H)-carboxylate (53a)

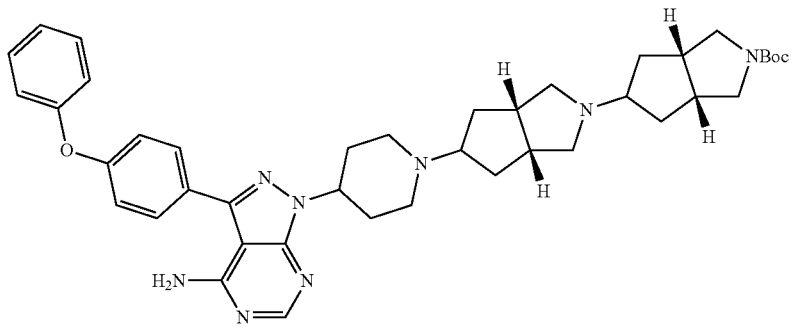 [SMILES: CC(C)(C)OC(=O)N1C[C@H]2CC(N3C[C@H]4CC(N5CCC(n6nc(-c7ccc(Oc8ccccc8)cc7)c7c(N)ncnc76)CC5)C[C@H]4C3)C[C@H]2C1]

Step 1

The above crude product 1-(1-((3aR,6aS)-octahydrocyclopenta[c]pyrrol-5-yl)piperidin-4-yl)-3-(4-phenoxyphenyl)-1H-pyrazolo[3,4-d]pyrimidin-4-amine Trifluoroacetate (52b) (0.5 g) was dissolved in 30 mL of DCE, and solid sodium bicarbonate (386 mg, 4.60 mmol) was added, the mixture was stirred at room temperature for 20 min, then tert-butyl (3aR,6aS)-5-oxo hexahydrocyclopenta[c]pyrrole-2(1H)-carboxylate (0.45 g, 2.0 mmol) was added, and the reaction was continued at 40° C. for 1 h, then sodium triacetoxyborohydride (0.42 g, 2.0 mmol) was added, and the mixture was stirred at room temperature for 16 h. To the reaction system was slowly added 60 mL of saturated sodium bicarbonate aqueous solution, and the mixed solution was extracted with DCM (80 mL×3). The organic phase was washed with 50 mL of water, dried over anhydrous sodium sulfate, and concentrated under reduced pressure. The crude product was separated and purified by silica gel column chromatography (dichloromethane/methanol (v/v) =10:1), to obtain tert-butyl (3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrole)]-2'(1'H)-carboxylate (53a) (0.25 g, two-step yield calculated from compound 52a: 45%).

LCMS m/z=705.5 [M+1]$^+$.

Step 2

3-(4-phenoxyphenyl)-1-(1-((3aR,3'aR,6aS,6'aS)-tetradecahydro-1H-[2,5'-bi(cyclopenta[c]pyrrol)]-5-yl)piperidin-4-yl)-1H-pyrazolo[3,4-d]pyrimidin-4-amine trifluoroacetate (53b)

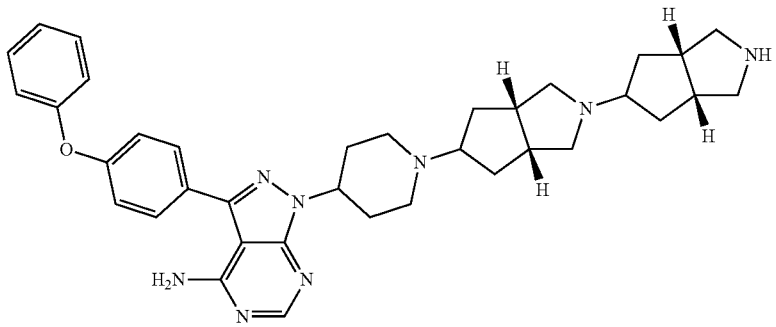 [SMILES: Nc1ncnc2c1c(-c1ccc(Oc3ccccc3)cc1)nn2C1CCN(C2C[C@@H]3CN(C4C[C@H]5CNC[C@H]5C4)C[C@@H]3C2)CC1]

Tert-butyl (3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrole)]-2'(1'H)-carboxylate (53a) (0.25 g, 0.35 mmol) was dissolved in 8 mL of dichloromethane, and 2 mL of trifluoroacetic acid was added, the mixture was stirred at room temperature for 4 h. The reaction system was concentrated under reduced pressure, to obtain the crude product 3-(4-phenoxyphenyl)-1-(1-((3aR,3'aR,6aS,6'aS)-tetradecahydro-1H-[2,5'-bi(cyclopenta[c]pyrrol)]-5-yl)piperidin-4-yl)-1H-pyrazolo[3,4-d]pyrimidin-4-amine trifluoroacetate (53b) (0.2 g).

LCMS m/z=605.4 [M+1]$^+$.

Step 3

5-((3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrol)]-2'(1'H)-yl)-2-(2,6-dioxopiperidin-3-yl)isoindoline-1,3-dione trifluoroacetate (compound 53)

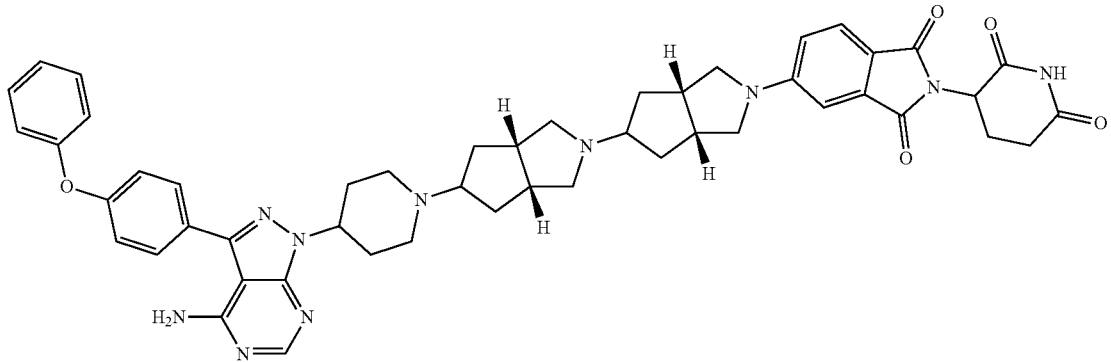 [SMILES: Nc1ncnc2c1c(-c1ccc(Oc3ccccc3)cc1)nn2C1CCN(C2C[C@@H]3CN(C4C[C@@H]5CN(c6ccc7c(c6)C(=O)N(C6CCC(=O)NC6=O)C7=O)C[C@@H]5C4)C[C@@H]3C2)CC1]

The above crude product 3-(4-phenoxyphenyl)-1-(1-((3aR,3'aR,6aS,6'aS)-tetradecahydro-1H-[2,5'-bi(cyclopenta[c]pyrrol)]-5-yl)piperidin-4-yl)-1H-pyrazolo[3,4-d]pyrimidin-4-amine trifluoroacetate (53b) (0.32 g) was dissolved in 10 mL of DMSO, and solid sodium bicarbonate (0.14 g, 1.67 mmol) was added, the mixture was stirred at room temperature for 10 min, then DIPEA (0.13 g, 1.0 mmol) and 2-(2,6-dioxopiperidin-3-yl)-5-fluoroisoindoline-1,3-dione (see WO 2017197056 for the synthetic method) (0.12 g, 0.43 mmol) were added, and the reaction was carried out at 90° C. for 4 h. The reaction solution was cooled to room temperature, and 50 mL of ethyl acetate and 50 mL of water were added. The organic phase was separated, dried over anhydrous sodium sulfate, and concentrated under reduced pressure, then the crude product was separated and purified by silica gel column chromatography (dichloromethane/methanol (v/v)=15:1), to obtain 5-((3aR,3'aR,6aS,6'aS)-5-(4-(4-amino-3-(4-phenoxyphenyl)-1H-pyrazolo[3,4-d]pyrimidin-1-yl)piperidin-1-yl)dodecahydro-1H-[2,5'-bi(cyclopenta[c]pyrrol]]-2'(1'H)-yl)-2-(2,6-dioxopiperidin-3-yl)isoindoline-1,3-dione trifluoroacetate (Compound 53) (50 mg).

$^1$H NMR (400 MHz, CDCl$_3$) δ 8.56 (br.s, 1H), 8.36 (s, 1H), 7.67-7.60 (m, 3H), 7.42-7.34 (m, 2H), 7.20-7.04 (m, 5H), 6.95 (d, 1H), 6.69 (dd, 1H), 5.56 (br.s, 2H), 4.92 (dd, 1H), 4.84-4.70 (m, 1H), 3.62-3.52 (m, 2H), 3.43-3.35 (m, 2H), 3.26-3.13 (m, 2H), 2.94-2.37 (m, 15H), 2.37-1.93 (m, 13H).

LCMS m/z=861.4 [M+1]$^+$.

Example 54

5-(7-(3-(4-(4-amino-3-(4-phenoxyphenyl)-1H-pyrazolo[3,4-d]pyrimidin-1-yl)piperidin-1-yl)azetidin-1-yl)-2-azaspiro[3.5]nonan-2-yl)-2-(2,6-dioxopiperidin-3-yl)isoindoline-1,3-dione (Compound 54)

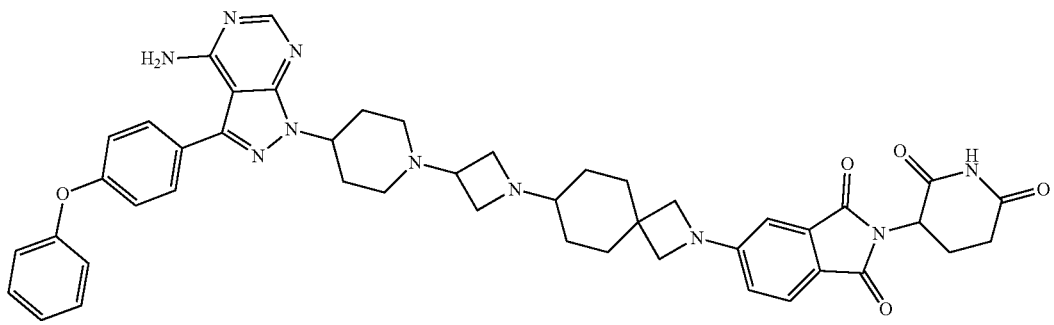

-continued
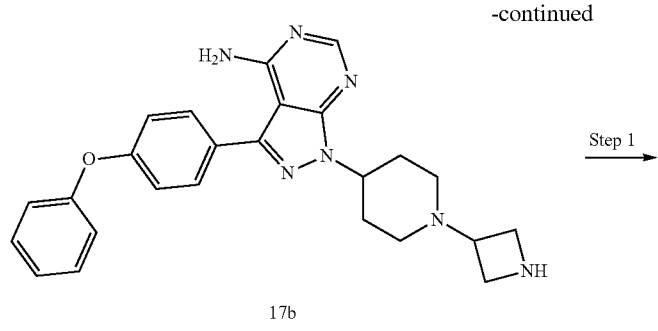
17b
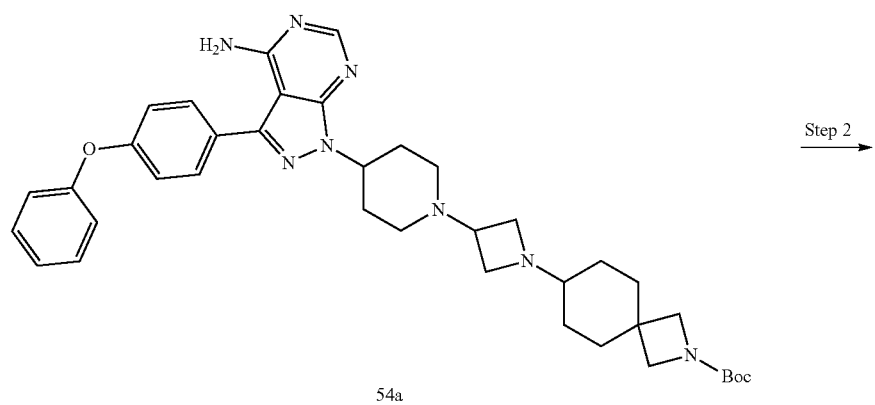
54a
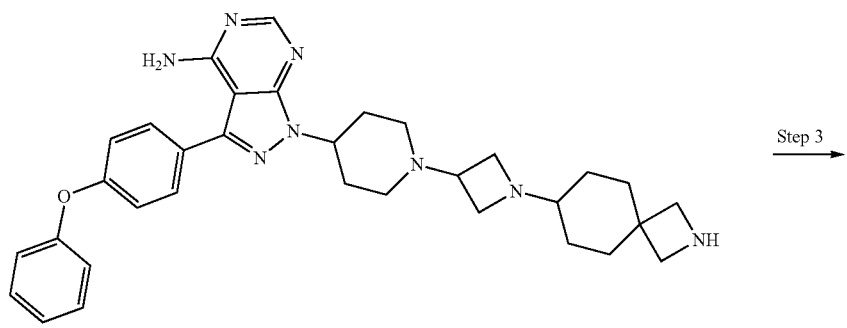
54b
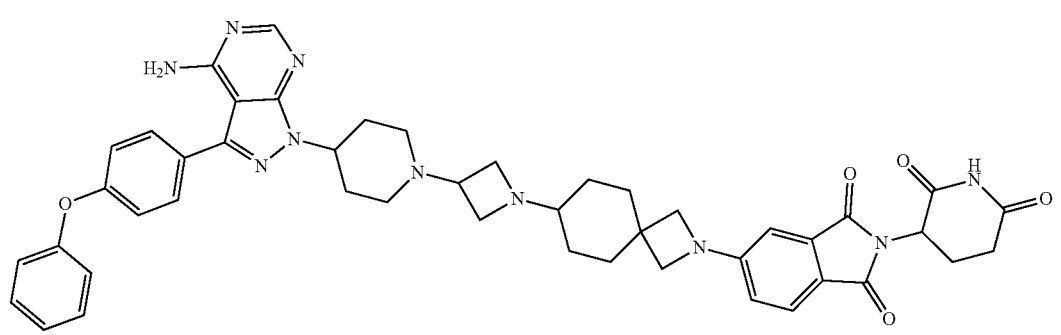
Compound 54

Step 1 tert-butyl 7-(3-(4-(4-amino-3-(4-phenoxyphenyl)-1H-pyrazolo[3,4-d]pyrimidin-1-yl)piperidin-1-yl)azetidin-1-yl)-2-azaspiro[3.5]nonane-2-carboxylate (54a)

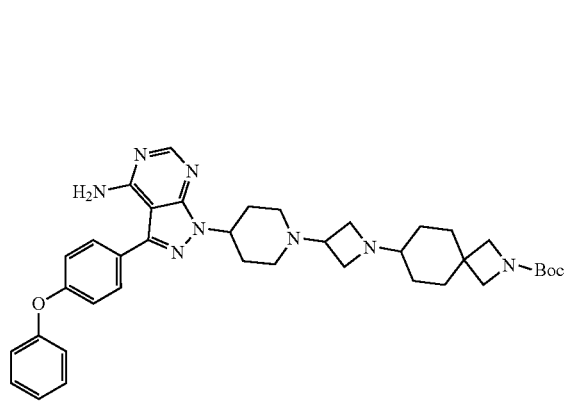 [SMILES: CC(C)(C)OC(=O)N1CC2(CCC(N3CC(N4CCC(n5nc(-c6ccc(Oc7ccccc7)cc6)c6c(N)ncnc65)CC4)C3)CC2)C1]

1-[1-(azetidin-3-yl)-4-piperidyl]-3-(4-phenoxyphenyl)pyrazolo[3,4-d]pyrimidin-4-amine (17b) (1.0 g, 2.26 mmol) was dissolved in 30 mL of DCE, and tert-butyl 7-oxo-2-azaspiro[3.5]nonane-2-carboxylate (0.82 g, 3.43 mmol) was added, the mixture was stirred at room temperature for 10 min, then sodium triacetoxyborohydride (1.2 g, 5.66 mmol) was added, and the mixture was stirred at room temperature for 16 h. To the reaction system was slowly added 60 mL of saturated sodium bicarbonate aqueous solution, and the mixed solution was extracted with DCM (80 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 7-(3-(4-(4-amino-3-(4-phenoxyphenyl)-1H-pyrazolo[3,4-d]pyrimidin-1-yl)piperidin-1-yl)azetidin-1-yl)-2-azaspiro[3.5]nonane-2-carboxylate (54a) (1.2 g, yield: 80%).

LCMS m/z=665.3 [M+1]$^+$.

Step 2

1-(1-(1-(2-azaspiro[3.5]nonan-7-yl)azetidin-3-yl)piperidin-4-yl)-3-(4-phenoxy-phenyl)-1H-pyrazolo[3,4-d]pyrimidin-4-amine Hydrochloride (54b)

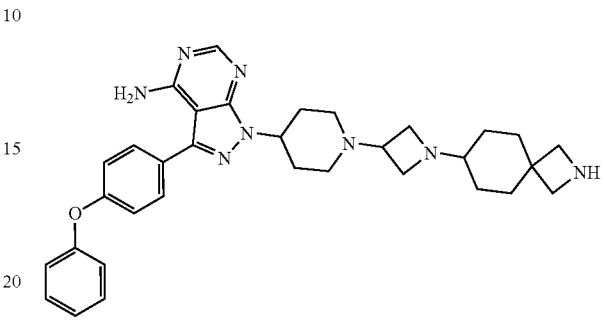

Tert-butyl 7-(3-(4-(4-amino-3-(4-phenoxyphenyl)-1H-pyrazolo[3,4-d]pyrimidin-1-yl)piperidin-1-yl)azetidin-1-yl)-2-azaspiro[3.5]nonane-2-carboxylate (54a) (300 mg, 0.45 mmol) was dissolved in 5 mL of methanol, and 10 mL of 2 mol/L ethyl acetate hydrochloride solution was added, the mixture was stirred at room temperature for 4 h. The reaction system was directly concentrated under reduced pressure, to obtain the crude product 1-(1-(1-(2-(azaspiro[3.5]nonan-7-yl)azetidin-3-yl)piperidin-4-yl)-3-(4-phenoxyphenyl)-1H-pyrazolo[3,4-d]pyrimidin-4-amine hydrochloride (54b) (0.35 g).

LCMS m/z=565.4 [M+1]$^+$.

Step 3

5-(7-(3-(4-(4-amino-3-(4-phenoxyphenyl)-1H-pyrazolo[3,4-d]pyrimidin-1-yl)piperidin-1-yl)azetidin-1-yl)-2-azaspiro[3.5]nonan-2-yl)-2-(2,6-dioxopiperidin-3-yl)isoindoline-1,3-dione (Compound 54)

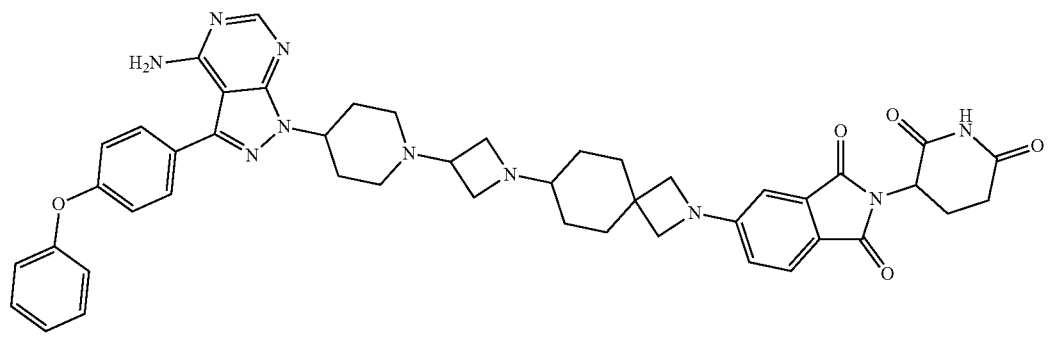 [SMILES: Nc1ncnc2c1c(-c1ccc(Oc3ccccc3)cc1)nn2C1CCN(C2CN(C3CCC4(CC3)CN(c3ccc5c(c3)C(=O)N(C3CCC(=O)NC3=O)C5=O)C4)C2)CC1]

The above crude product 1-(1-(1-(2-(azaspiro[3.5]nonan-7-yl)azetidin-3-yl)piperidin-4-yl)-3-(4-phenoxyphenyl)-1H-pyrazolo[3,4-d]pyrimidin-4-amine hydrochloride (54b) (0.35 g) was dissolved in 25 mL of DMSO, and solid sodium bicarbonate (152 mg, 1.81 mmol) was added, the mixture was stirred at room temperature for 10 min, then 1.5 mL of DIPEA and 2-(2,6-dioxopiperidin-3-yl)-5-fluoroisoindoline-1,3-dione (see WO 2017197056 for the synthetic method) (186 mg, 0.67 mmol) were added, and the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=15:1), to obtain 5-(7-(3-(4-(4-amino-3-(4-phenoxyphenyl)-1H-pyrazolo[3,4-d]pyrimidin-1-yl)piperi din-1-yl)azetidin-1-yl)-2-azaspiro[3.5]nonan-2-yl)-2-(2,6-dioxopiperidin-3-yl)isoindoline-1,3-dione (Compound 54) (95 mg, two-step yield calculated from compound 54a: 26%).

$^1$H NMR (400 MHz, CDCl$_3$) δ 9.23 (br.s, 1H), 8.38 (s, 1H), 7.68-7.59 (m, 3H), 7.43-7.35 (m, 2H), 7.21-7.11 (m, 3H), 7.11-7.05 (m, 2H), 6.76 (d, 1H), 6.49 (dd, 1H), 5.64 (br.s, 2H), 4.93 (dd, 1H), 4.84-4.72 (m, 1H), 3.78-3.56 (m, 6H), 3.15-2.65 (m, 8H), 2.49-2.36 (m, 2H), 2.16-1.94 (m, 8H), 1.81-1.72 (m, 2H), 1.59-1.49 (m, 2H), 1.26-1.16 (m, 2H).

LCMS m/z=821.4 [M+1]$^+$.

Example 55

5-(7-(4-(4-amino-3-(4-phenoxyphenyl)-1H-pyrazolo[3,4-d]pyrimidin-1-yl)pipe ridin-1-yl)-2,2'-diaza[2,7'-bispiro[3.5]nonan]-2'-yl)-2-(2,6-dioxopiperidin-3-yl)isoindoline-1,3-dione (Compound 55)

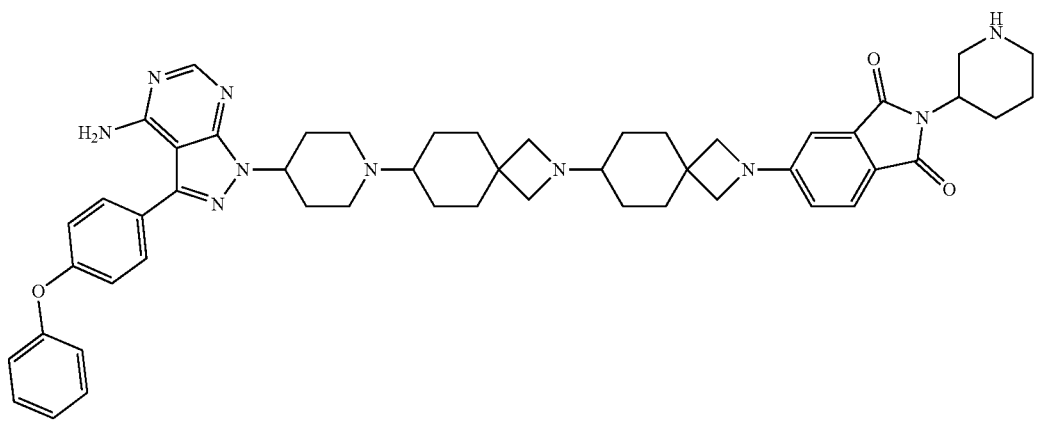

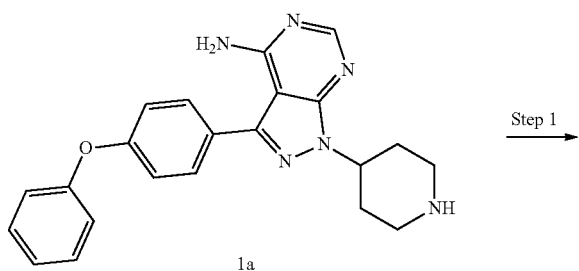

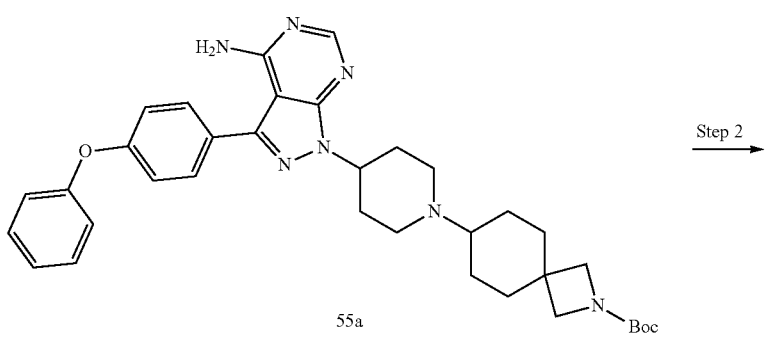

-continued
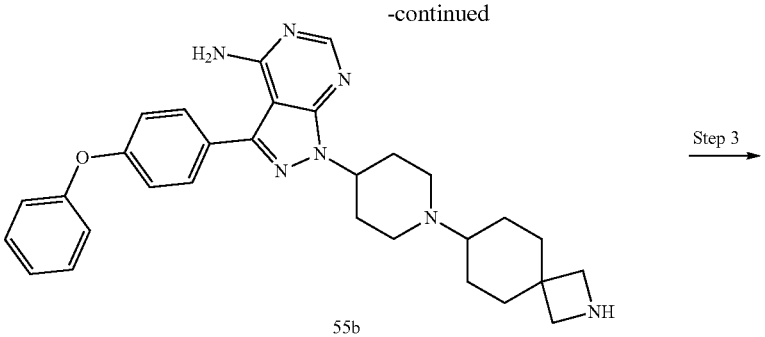
55b
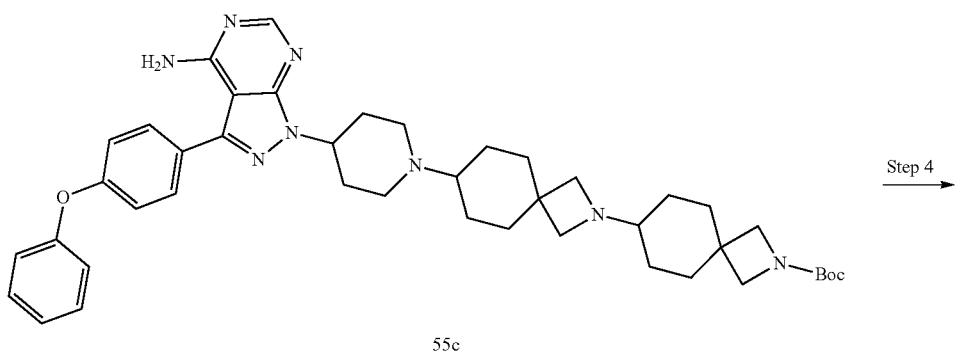
55c
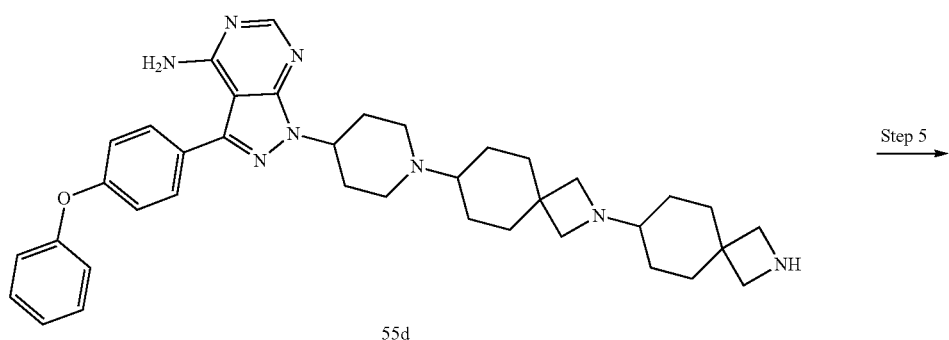
55d
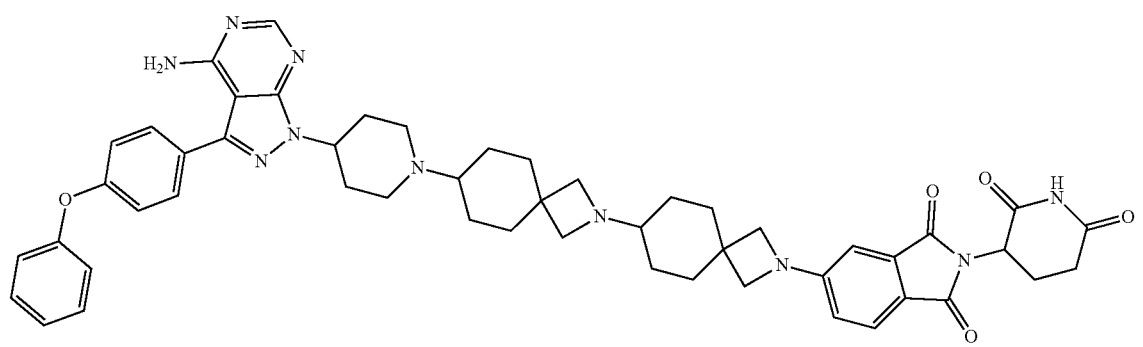
Compound 55

Step 1 tert-butyl 7-(4-(4-amino-3-(4-phenoxyphenyl)-1H-pyrazlo[3,4-d]pyrimidin-1-yl)piperidin-1-yl)-azaspiro[3.5]nonane-2-carboxylate (55a)

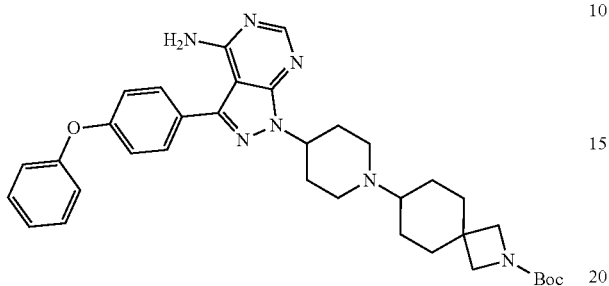

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (1.0 g, 2.59 mmol) was dissolved in 35 mL of DCE, and tert-butyl 7-oxo-2-azaspiro[3.5]nonane-2-carboxylate (0.93 g, 3.89 mmol) was added, the mixture was stirred at room temperature for 10 min, then sodium triacetoxyborohydride (1.37 g, 6.46 mmol) was added, and the mixture was stirred at room temperature for 16 h. To the reaction solution was slowly added 30 mL of saturated sodium bicarbonate aqueous solution, and the mixed solution was extracted with DCM (30 mL×3). The organic phase was washed with 50 mL of water, dried over anhydrous sodium sulfate, and concentrated under reduced pressure. The crude product was separated and purified by silica gel column chromatography (dichloromethane/methanol (v/v)=20:1), to obtain tert-butyl 7-(4-(4-amino-3-(4-phenoxyphenyl)-1H-pyrazolo[3,4-d]pyrimidin-1-yl)piperidin-1-yl)-2-azaspiro[3.5]nonane-2-carboxylate (55a) (1.4 g, yield: 89%).

LCMS m/z=610.4 [M+1]⁺.

Step 2

1-(1-(2-azaspiro[3.5]nonan-7-yl)piperidin-4-yl)-3-(4-phenoxyphenyl)-1H-pyrazolo[3,4-d]pyrimidin-4-amine hydrochloride (55b)

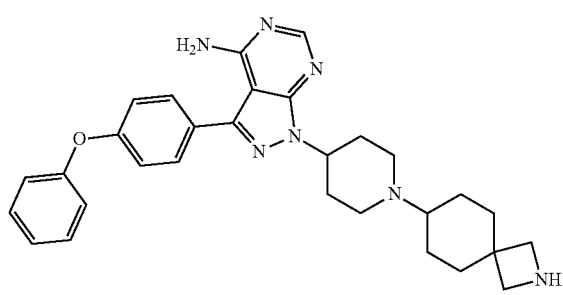 [SMILES: Nc1ncnc2c1c(-c1ccc(Oc3ccccc3)cc1)nn2C1CCN(C2CCC3(CC2)CNC3)CC1]

Tert-butyl 7-(4-(4-amino-3-(4-phenoxyphenyl)-1H-pyrazolo[3,4-d]pyrimidin-1-yl)piperidin-1-yl)-2-azaspiro[3.5]nonane-2-carboxylate (55a) (1.4 g, 2.30 mmol) was dissolved in 5 mL of methanol, and 25 mL of 2 mol/L ethyl acetate hydrochloride solution was added, the mixture was stirred at room temperature for 4 h. Upon completion of the reaction, the system was directly concentrated under reduced pressure, to obtain the crude product 1-(1-(2-azaspiro[3.5]nonan-7-yl)piperidin-4-yl)-3-(4-phenoxyphenyl)-1H-pyrazolo[3,4-d]pyrimidin-4-amine hydrochloride (55b) (1.5 g).

LCMS m/z=510.3 [M+1]⁺.

Step 3 tert-butyl 7-(4-(4-amino-3-(4-phenoxyphenyl)-1H-pyrazolo[3,4-d]pyrimidin-1-yl)piperidin-1-yl)-2,2'-diaza[2,7'-bispiro[3.5]nonane]-2'-carboxylate (55c)

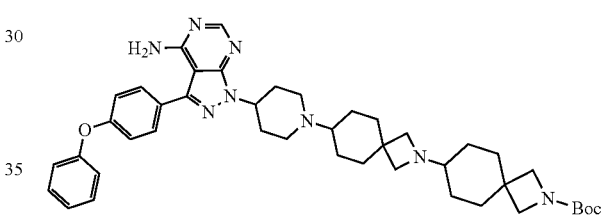

The above crude product 1-(1-(2-azaspiro[3.5]nonan-7-yl)piperidin-4-yl)-3-(4-phenoxyphenyl)-1H-pyrazolo[3,4-d]pyrimidin-4-amine hydrochloride (55b) (0.8 g) was dissolved in 40 mL of DCE, and solid sodium bicarbonate (330 mg, 3.93 mmol) was added, the mixture was stirred at room temperature for 20 min, tert-butyl 7-oxo-2-azaspiro[3.5]nonane-2-carboxylate (0.47 g, 1.96 mmol) was added, and the mixture was stirred at room temperature for 10 min, then sodium triacetoxyborohydride (0.70 g, 3.30 mmol) was added, and the mixture was stirred at room temperature for 16 h. To the reaction system was slowly added 60 mL of saturated sodium bicarbonate aqueous solution, and the mixed solution was extracted with DCM (80 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 7-(4-(4-amino-3-(4-phenoxyphenyl)-1H-pyrazolo[3,4-d]pyrimidin-1-yl)piperidin-1-yl)-2,2'-diaza[2,7'-bispiro[3.5]nonane]-2'-carboxylate (55c) (0.70 g, two-step yield calculated from compound 55a: 78%).

LCMS m/z=733.3 [M+1]⁺.

Step 4

1-(1-(2,2'-diaza[2,7'-bispiro[3.5]nonan]-7-yl)piperidin-4-yl)-3-(4-phenoxyphenyl)-1H-pyrazolo[3,4-d]pyrimidin-4-amine hydrochloride (55d)

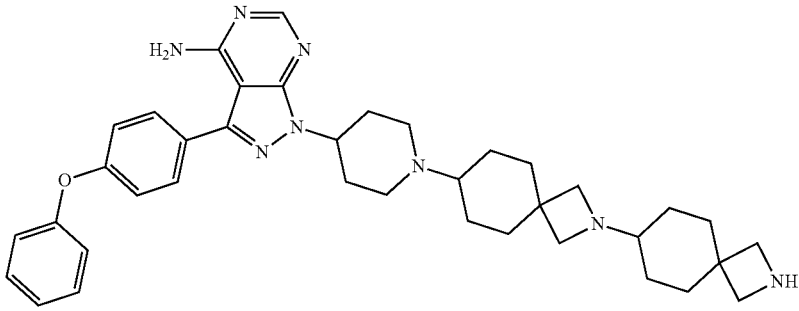 [SMILES: Nc1ncnc2c1c(-c1ccc(Oc3ccccc3)cc1)nn2C1CCN(C2CCC3(CC2)CN(C2CCC4(CC2)CNC4)C3)CC1]

Tert-butyl 7-(4-(4-amino-3-(4-phenoxyphenyl)-1H-pyrazolo[3,4-d]pyrimidin-1-yl)piperidin-1-yl)-2,2'-diaza[2,7'-bispiro[3.5]nonane]-2'-carboxylate (55c) (300 mg, 0.41 mmol) was dissolved in 5 mL of methanol, and 15 mL of 2 mol/L ethyl acetate hydrochloride solution was added, the mixture was stirred at room temperature for 4 h. The reaction system was directly concentrated under reduced pressure, to obtain the crude product 1-(1-(2,2'-diaza[2,7'-bispiro[3.5]nonan-7-yl]piperidin-4-yl)-3-(4-phenoxyphenyl)-1 H-pyrazolo[3,4-d]pyrimidin-4-amine hydrochloride (55d) (0.32 g).

LCMS m/z=633.5 [M+1]$^+$.

Step 5

5-(7-(4-(4-amino-3-(4-phenoxyphenyl)-1H-pyrazolo[3,4-d]pyrimidin-1-yl)piperidin-1-yl)-2,2'-bispiro[3.5]nonan]-2'-yl)-2-(2,6-dioxopiperidin-3-yl)isoindoline-1,3-dione (Compound 55)

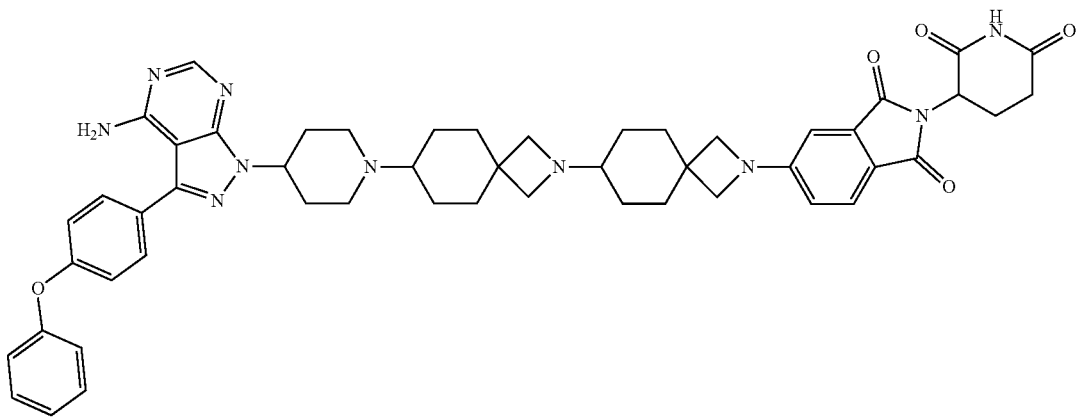 [SMILES: Nc1ncnc2c1c(-c1ccc(Oc3ccccc3)cc1)nn2C1CCN(C2CCC3(CC2)CN(C2CCC4(CC2)CN(c2ccc5c(c2)C(=O)N(C2CCC(=O)NC2=O)C5=O)C4)C3)CC1]

The above crude product 1-(1-(2,2'-diaza[2,7'-bispiro[3.5]nonan-7-yl]piperidin-4-yl)-3-(4-phenoxyphenyl)-1 H-pyrazolo[3,4-d]pyrimidin-4-amine hydrochloride (55d) (0.32 g) was dissolved in 25 mL of DMSO, and solid sodium bicarbonate (138 mg, 1.64 mmol) was added, the mixture was stirred at room temperature for 10 min, then 1.5 mL of DIPEA and 2-(2,6-dioxopiperidin-3-yl)-5-fluoroisoindoline-1,3-dione (see WO 2017197056 for the synthetic method) (166 mg, 0.60 mmol) were added, and the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=1), to obtain 5-(7-(4-(4-amino-3-(4-phenoxyphenyl)-1H-pyrazolo[3,4-d]pyrimidin-1-yl)piperidin-1-yl)-2,2'-diaza[2,7'-bispiro[3.5]nonan]-2'-yl)-2-(2,6-dioxopiperidin-3-yl)isoindoline-1,3-dione (Compound 55) (70 mg, two-step yield calculated from compound 55c: 19%).

¹H NMR (400 MHz, CDCl₃) δ 9.13 (br.s, 1H), 8.38 (s, 1H), 7.71-7.57 (m, 3H), 7.43-7.33 (m, 2H), 7.22-7.02 (m, 5H), 6.76 (d, 1H), 6.49 (dd, 1H), 5.62 (br.s, 2H), 4.97-4.88 (m, 1H), 4.83-4.68 (m, 1H), 3.76-3.60 (m, 4H), 3.40-2.60 (m, 9H), 2.50-2.26 (m, 5H), 2.19-1.92 (m, 8H), 1.88-1.70 (m, 4H), 1.58-1.41 (m, 4H), 1.35-1.23 (m, 4H).
LCMS m/z=889.4 [M+1]⁺.
Example 56
5-(3-(7-(4-(4-amino-3-(4-phenoxyphenyl)-1H-pyrazolo[3,4-d]pyrimidin-1-yl)piperidin-1-yl)-2-azaspiro[3.5]nonan-2-yl)azetidin-1-yl)-2-(2,6-dioxopiperidin-3-yl)isoindoline-1,3-dione (Compound 56)
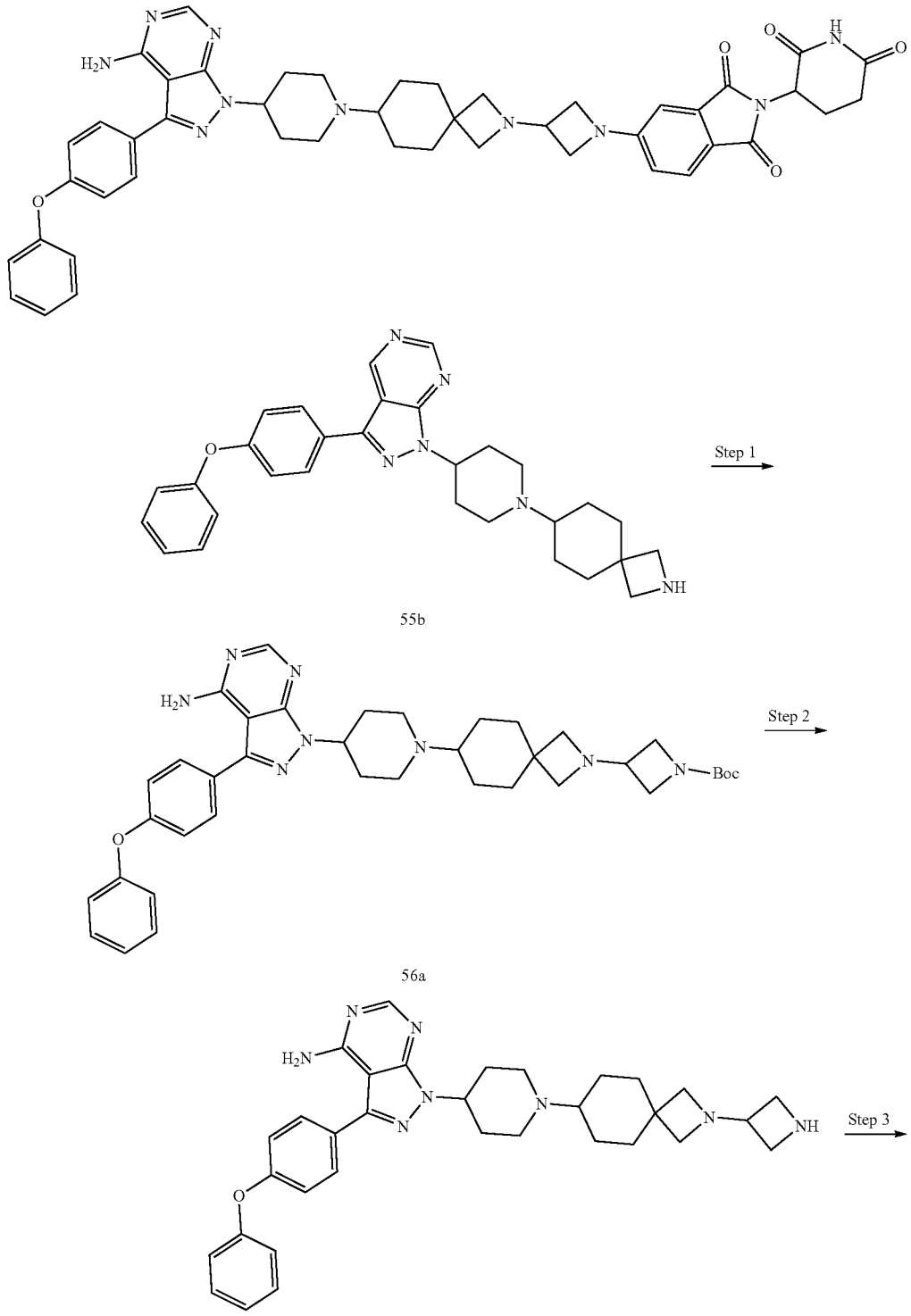

-continued

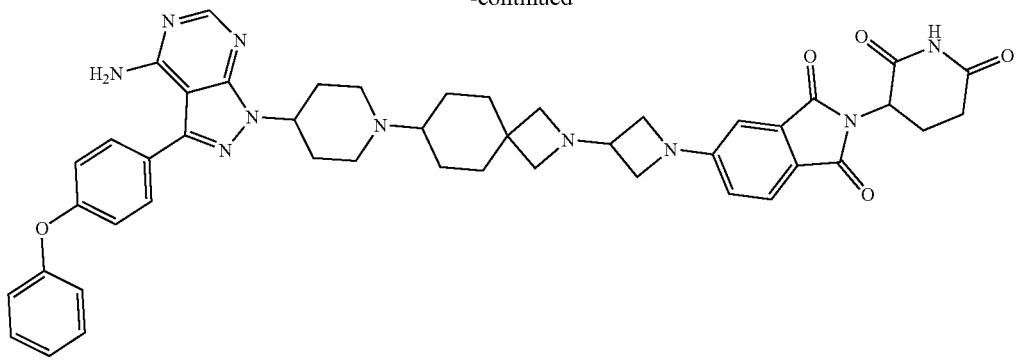

Compound 56

Step 1 tert-butyl 3-(7-(4-(4-amino-3-(4-phenoxyphenyl)-1H-pyrazolo[3,4-d]pyrimidin-1-yl)piperidin-1-yl)-2-azaspiro[3.5]nonan-2-yl)azetidine-1-carboxylate (56a)

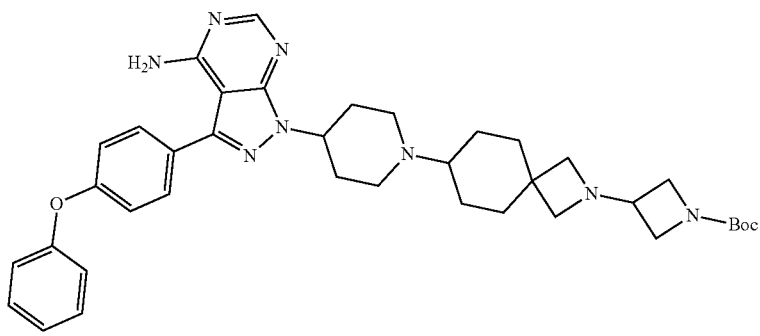 [SMILES: CC(C)(C)OC(=O)N1CC(N2CC3(CCC(N4CCC(n5nc(-c6ccc(Oc7ccccc7)cc6)c6c(N)ncnc65)CC4)CC3)C2)C1]

1-(1-(2-azaspiro[3.5]nonan-7-yl)piperidin-yl)-3-(4-phenoxyphenyl)-1H-pyrazolo[3,4-d]pyrimidin-4-amine hydrochloride (55b) (0.6 g) was dissolved in 40 mL of DCE, and solid sodium bicarbonate (247 mg, 2.94 mmol) was added, the mixture was stirred at room temperature for 20 min, then tert-butyl 3-oxoazetidine-1-carboxylate (337 mg, 1.97 mmol) was added, the mixture was stirred at room temperature for 10 min, then sodium triacetoxyborohydride (0.52 g, 2.45 mmol) was added, and the mixture was stirred at room temperature for 16 h. To the reaction system was slowly added 60 mL of saturated sodium bicarbonate aqueous solution, and the mixed solution was extracted with DCM (80 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 3-(7-(4-(4-amino-3-(4-phenoxyphenyl)-1H-pyrazolo[3,4-d]pyrimidin-1-yl)piperidin-1-yl)-2-azaspiro[3.5]nonan-2-yl)azetidine-1-carboxylate (56a) (0.44 g, two-step yield calculated from compound 55a: 72%).

LCMS m/z=665.4 [M+1]$^+$.

Step 2

1-(1-(2-(azetidin-3-yl)-2-azaspiro[3.5]nonan-7-yl)piperidin-4-yl)-3-(4-phenoxy phenyl)-1H-pyrazolo[3,4-d]pyrimidin-4-amine hydrochloride (56b)

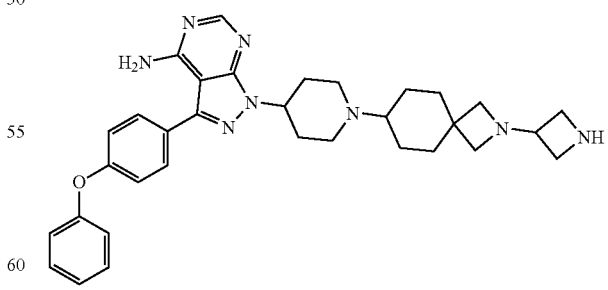

Tert-butyl 3-(7-(4-(4-amino-3-(4-phenoxyphenyl)-1H-pyrazolo[3,4-d]pyrimidin-1-yl)piperidin-1-yl)-2-azaspiro[3.5]nonan-2- yl)azetidine-1-carboxylate (56a) (250 mg, 0.38 mmol) was dissolved in 5 mL of methanol, and 15 mL of 2 mol/L ethyl acetate hydrochloride solution was added, the mixture was stirred at room temperature for 4 h. The reaction system was directly concentrated under reduced pressure, to obtain the crude product 1-(1-(2-(azetidin-3-yl)-2-azaspiro[3.5]nonan-7-yl)piperidin-4-yl)-3-(4-phenoxyphenyl)-1H-pyrazolo[3,4-d]pyrimidin-4-amine hydrochloride (56b) (0.28 g).

LCMS m/z=565.1 [M+1]$^+$.

Step 5

5-(3-(7-(4-(4-amino-3-(4-phenoxyphenyl)-1H-pyrazolo[3,4-d]pyrimidin-1-yl)piperidin-1-yl)-2-azaspiro[3.5]nonan-2-yl)azetidin-1-yl)-2-(2,6-dioxopiperidin-3-yl)isoindoline-1,3-dione (Compound 56)

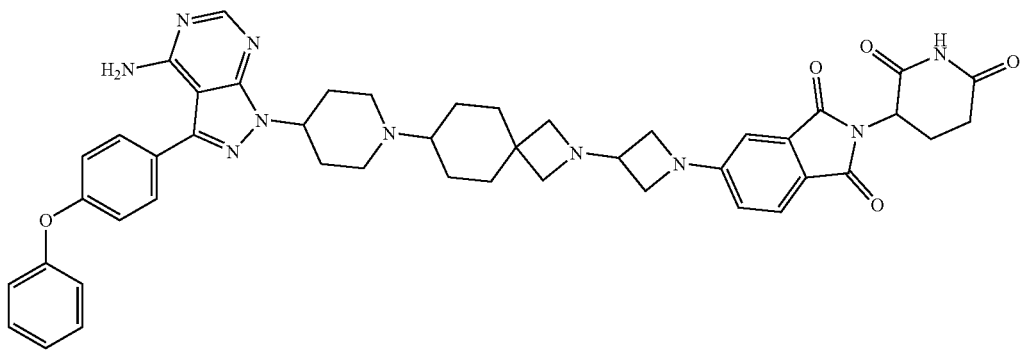 [SMILES: Nc1ncnc2c1c(-c1ccc(Oc3ccccc3)cc1)nn2C1CCN(C2CCC3(CC2)CN(C2CN(c4ccc5c(c4)C(=O)N(C4CCC(=O)NC4=O)C5=O)C2)C3)CC1]

1-(1-(2-(azetidin-3-yl)-2-azaspiro[3.5]nonan-7-yl)piperidin-4-yl)-3-(4-phenoxy phenyl)-1H-pyrazolo[3,4-d]pyrimidin-4-amine hydrochloride (56b) (0.28 g) was dissolved in 15 mL of DMSO, and solid sodium bicarbonate (127 mg, 1.51 mmol) was added, the mixture was stirred at room temperature for 10 min, then 1.5 mL of DIPEA and 2-(2,6-dioxopiperidin-3-yl)-5-fluoroisoindoline-1,3-dione (see WO 2017197056 for the synthetic method) (157 mg, 0.57 mmol) were added, and the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=15:1), to obtain 5-(3-(7-(4-(4-amino-3-(4-phenoxyphenyl)-1H-pyrazolo[3,4-d]pyrimidin-1-yl)piperi din-1-yl)-2-azaspiro[3.5]nonan-2-yl)azetidin-1-yl)-2-(2,6-dioxopiperidin-3-yl)isoindoline-1,3-dione (Compound 56) (110 mg, two-step yield calculated from compound 56a: 35%).

$^1$H NMR (400 MHz, CDCl$_3$) δ 9.64 (br.s, 1H), 8.38 (s, 1H), 7.68-7.59 (m, 3H), 7.42-7.34 (m, 2H), 7.20-7.10 (m, 3H), 7.10-7.04 (m, 2H), 6.77 (d, 1H), 6.50 (dd, 1H), 5.75 (br.s, 2H), 4.92 (dd, 1H), 4.85-4.68 (m, 1H), 4.07-3.96 (m, 2H), 3.88-3.78 (m, 2H), 3.72-3.62 (m, 1H), 3.20-2.96 (m, 6H), 2.92-2.65 (m, 3H), 2.58-2.28 (m, 5H), 2.17-2.07 (m, 2H), 2.07-2.03 (m, 2H), 2.03-1.97 (m, 1H), 1.91-1.81 (m, 2H), 1.53-1.42 (m, 2H), 1.39-1.30 (m, 2H).

LCMS m/z=821.2 [M+1]$^+$.

Example 57
5-(3-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)azetidin-1-yl)-2-(2,6-dioxopiperidin-3-yl)isoindoline-1,3-dione (Compound 57)
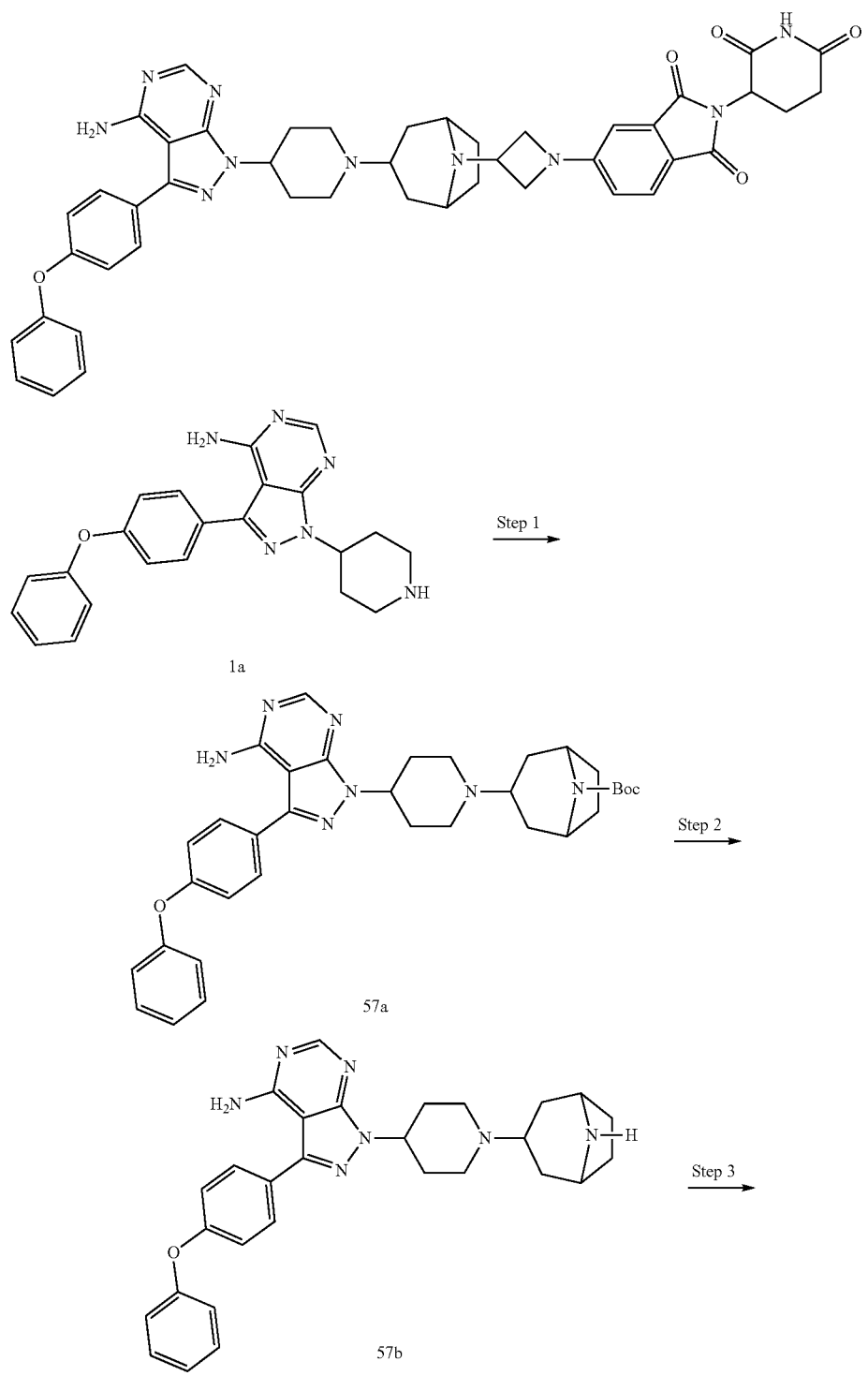

-continued
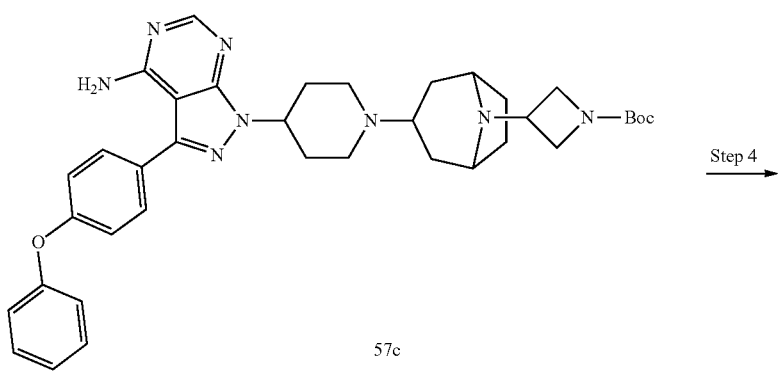
57c
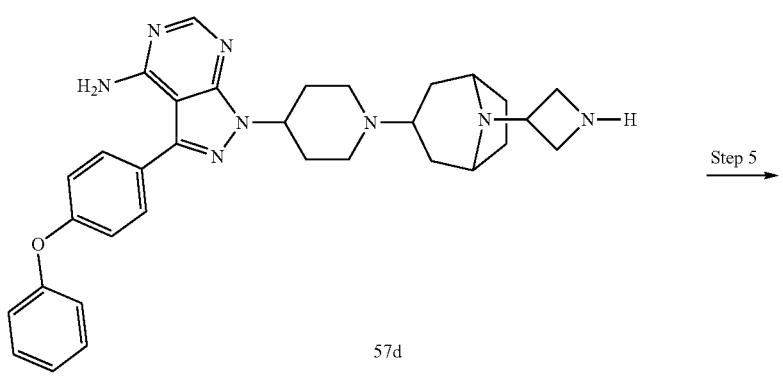
57d
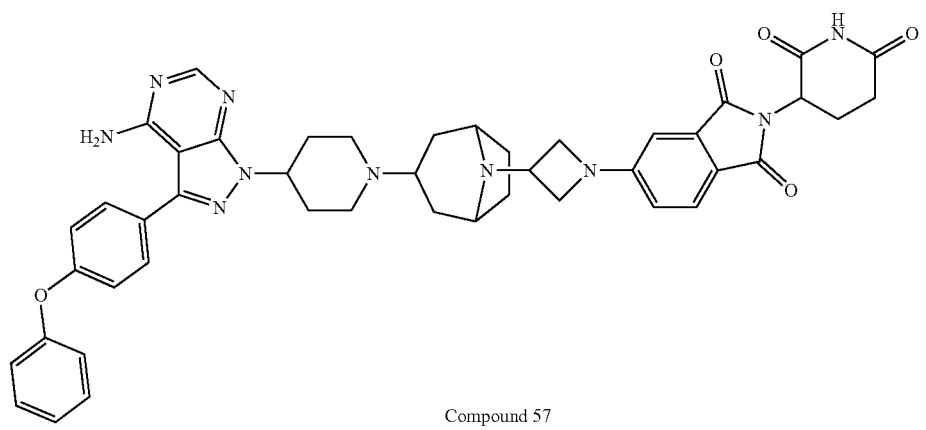
Compound 57

Step 1 tert-butyl 3-(4-(4-amino-3-(4-phenoxyphenyl)-1H-pyrazolo[3,4-d]pyrimidin-1-yl)piperidin-1-yl)-8-azabicyclo[3.2.1]octane-8-carboxylate (57a)

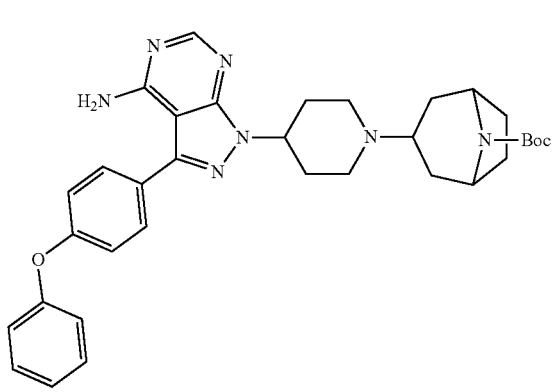 [SMILES: CC(C)(C)OC(=O)N1C2CCC1CC(N1CCC(n3nc(-c4ccc(Oc5ccccc5)cc4)c4c(N)ncnc43)CC1)C2]

3-(4-phenoxyphenyl)-1-(piperidin-4-yl)-1H-pyrazolo[3,4-d]pyrimidin-4-amine (1a) (see *J. Med. Chem.* 2015, 58, 9625-9638 for the synthetic method) (5.0 g, 12.94 mmol) was dissolved in 85 mL of DCE, and tert-butyl 3-oxo-8-azabicyclo[3.2.1]octane-8-carboxylate (5.82 g, 25.83 mmol) was added, the reaction was stirred at 55° C. for 2 h, and then cooled to room temperature. Sodium triacetoxyborohydride (8.23 g, 38.83 mmol) was added, and the mixture was stirred at room temperature for 16 h. To the reaction solution was slowly added 100 mL of saturated sodium bicarbonate aqueous solution, and the mixed solution was extracted with DCM (120 mL×3). The organic phase was washed with 150 mL of water, dried over anhydrous sodium sulfate, and concentrated under reduced pressure. The crude product was separated and purified by silica gel column chromatography (dichloromethane/methanol (v/v)=20:1), to obtain tert-butyl 3-(4-(4-(4-amino-3-(4-phenoxyphenyl)-1H-pyrazolo[3,4-d]pyrimidin-1-yl)piperidin-1-yl)-8-azabicyclo[3.2.1]octane-8-carboxylate (57a) (0.4 g, yield: 5%).

$^1$H NMR (400 MHz, CDCl$_3$) δ 8.36 (s, 1H), 7.68-7.61 (m, 2H), 7.42-7.35 (m, 2H), 7.21-7.05 (m, 5H), 5.53 (br.s, 2H), 4.85-4.65 (m, 1H), 4.40-4.15 (m, 2H), 3.18-2.99 (m, 2H), 2.98-2.82 (m, 1H), 2.48-2.30 (m, 4H), 2.11-1.91 (m, 4H), 1.83-1.59 (m, 6H), 1.47 (s, 9H).

LCMS m/z=596.4 [M+1]$^+$.

Step 2

1-(1-(8-azabicyclo[3.2.1]octan-3-yl)piperidin-4-yl)-3-(4-phenoxyphenyl)-1H-pyrazolo[3,4-d]pyrimidin-4-amine hydrochloride (57b)

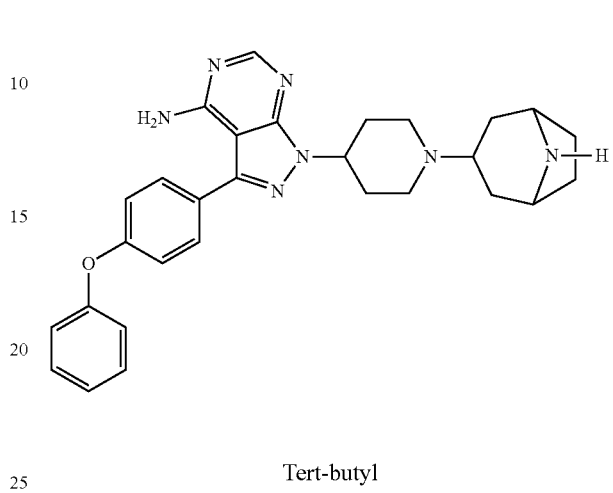

Tert-butyl 3-(4-(4-(4-amino-3-(4-phenoxyphenyl)-1H-pyrazolo[3,4-d]pyrimidin-1-yl)piperidin-1-yl)-8-azabicyclo[3.2.1]octane-8-carboxylate (57a) (0.38 g, 0.64 mmol) was dissolved in 5 mL of methanol, and 25 mL of 2 mol/L ethyl acetate hydrochloride solution was added, the mixture was stirred at room temperature for 4 h. Upon completion of the reaction, the system was directly concentrated under reduced pressure, to obtain the crude product 1-(1-(8-azabicyclo[3.2.1]octan-3-yl)piperidin-4-yl)-3-(4-phenoxyphenyl)-1H-pyrazolo[3,4-d]pyrimidin-4-amine hydrochloride (57b) (0.4 g). LCMS m/z=496.3 [M+1]$^+$.

Step 3 tert-butyl 3-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)azetidine-1-carboxylate (57c)

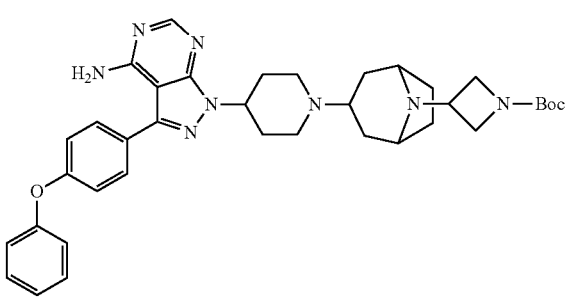 [SMILES: CC(C)(C)OC(=O)N1CC(N2C3CCC2CC(N2CCC(n4nc(-c5ccc(Oc6ccccc6)cc5)c5c(N)ncnc54)CC2)C3)C1]

The above crude product 1-(1-(8-azabicyclo[3.2.1]octan-3-yl)piperidin-4-yl)-3-(4-phenoxyphenyl)-1H-pyrazolo[3,4-d]pyrimidin-4-amine hydrochloride (57b) (0.17 g) was dissolved in 20 mL of DCE, and solid sodium bicarbonate (96 mg, 1.14 mmol) was added, the mixture was stirred at room temperature for 20 min, then N-Boc-azetidinone (96 mg, 0.56 mmol) was added, the mixture was stirred at room temperature for 10 min, then sodium triacetoxyborohydride (0.18 g, 0.85 mmol) was added, and the mixture was stirred at room temperature for 16 h. To the reaction system was slowly added 20 mL of saturated sodium bicarbonate aqueous solution, and the mixed solution was extracted with DCM (50 mL×3). The organic phase was washed with 50 mL of water, dried over anhydrous sodium sulfate, and concentrated under reduced pressure. The crude product was separated and purified by silica gel column chromatography (dichloromethane/methanol (v/v)=10:1), to obtain tert-butyl 3-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)azetidine-1-carboxylate (57c) (0.16 g, two-step yield calculated from compound 57a: 90%).

LCMS m/z=651.4 [M+1]$^+$.

Step 4

1-(1-(8-(azetidin-3-yl)-8-azabicyclo[3.2.1]octan-3-yl)piperidin-4-yl)-3-(4-phen oxyphenyl)-1H-pyrazolo[3,4-d]pyrimidin-4-amine hydrochloride (57d)

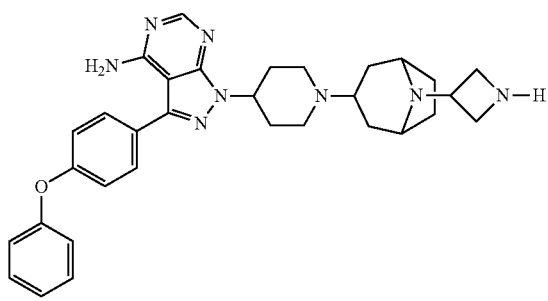 [SMILES: Nc1ncnc2c1c(-c1ccc(Oc3ccccc3)cc1)nn2C1CCN(C2CC3CCC(C2)N3C2CNC2)CC1]

Tert-butyl 3-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)azetidine-1-carboxylate (57c) (150 mg, 0.23 mmol) was dissolved in 5 mL of methanol, and 15 mL of 2 mol/L ethyl acetate hydrochloride solution was added, the mixture was stirred at room temperature for 4 h. The reaction system was directly concentrated under reduced pressure, to obtain the crude product 1-(1-(8-(azetidin-3-yl)-8-azabicyclo [3.2.1]octan-3-yl)piperidin-4-yl)-3-(4-phenoxyphenyl)-1H-pyrazolo[3,4-d]pyrimidin-4-amine hydrochloride (57d) (0.16 g).

LCMS m/z=551.3 [M+1]$^+$.

Step 5

5-(3-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)azetidin-1-yl)-2-(2,6-dioxopiperidin-3-yl)isoindoline-1,3-dione (Compound 57)

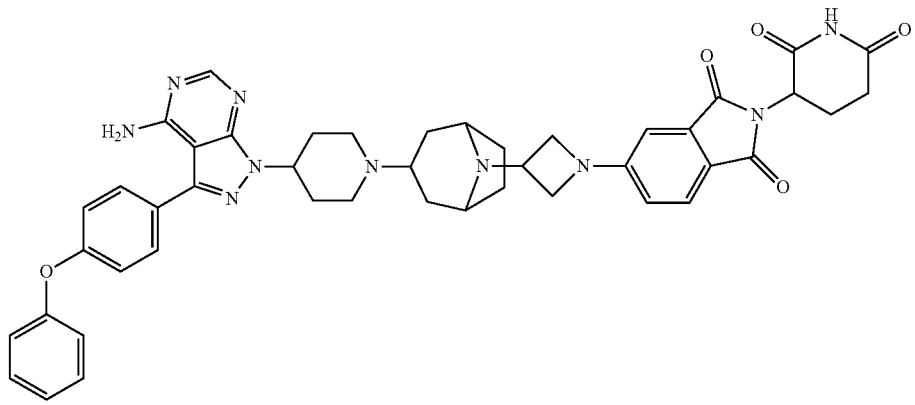 [SMILES: Nc1ncnc2c1c(-c1ccc(Oc3ccccc3)cc1)nn2C1CCN(C2CC3CCC(C2)N3C2CN(c3ccc4c(c3)C(=O)N(C3CCC(=O)NC3=O)C4=O)C2)CC1]

The above crude product 1-(1-(8-(azetidin-3-yl)-8-azabicyclo[3.2.1]octan-3-yl)piperidin-4-yl)-3-(4-phenoxyphenyl)-1H-pyrazolo[3,4-d]pyrimidin-4-amine hydrochloride (57d) (0.16 g) was dissolved in 10 mL of DMSO, and solid sodium bicarbonate (78 mg, 0.93 mmol) was added, the mixture was stirred at room temperature for 10 min, then 1.0 mL of DIPEA and 2-(2,6-dioxopiperidin-3-yl)-5-fluoroisoindoline-1,3-dione (see WO 2017197056 for the synthetic method) (95 mg, 0.34 mmol) were added, and the reaction was stirred at 80° C. for 5 h. The reaction solution was cooled to room temperature, added 50 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=15:1), to obtain 5-(3-(3-(4-(4-amino-3-(4-phenoxyphenyl)-1H-pyrazolo[3,4-d]pyrimidin-1-yl)piperi din-1-yl)-8-azabicyclo[3.2.1]octan-8-yl)azetidin-1-yl)-2-(2,6-dioxopiperidin-3-yl)isoindoline-1,3-dione (Compound 57) (80 mg, two-step yield calculated from compound 57c: 43%).

$^1$H NMR (400 MHz, CDCl$_3$) δ 9.30 (br.s, 1H), 8.38 (s, 1H), 7.68-7.59 (m, 3H), 7.43-7.34 (m, 2H), 7.21-7.03 (m, 5H), 6.77 (d, 1H), 6.50 (dd, 1H), 5.68 (br.s, 2H), 4.92 (dd, 1H), 4.83-4.67 (m, 1H), 4.18-4.04 (m, 2H), 3.86-3.77 (m, 2H), 3.76-3.62 (m, 1H), 3.36-3.26 (m, 2H), 3.22-3.03 (m, 2H), 2.93-2.65 (m, 4H), 2.51-2.27 (m, 4H), 2.17-1.92 (m, 5H), 1.84-1.60 (m, 6H).

LCMS m/z=807.1 [M+1]$^+$.

Example 58
5-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)-2-(2,6-dioxopiperidin-3-yl)isoindoline-1,3-dione (Compound 58)
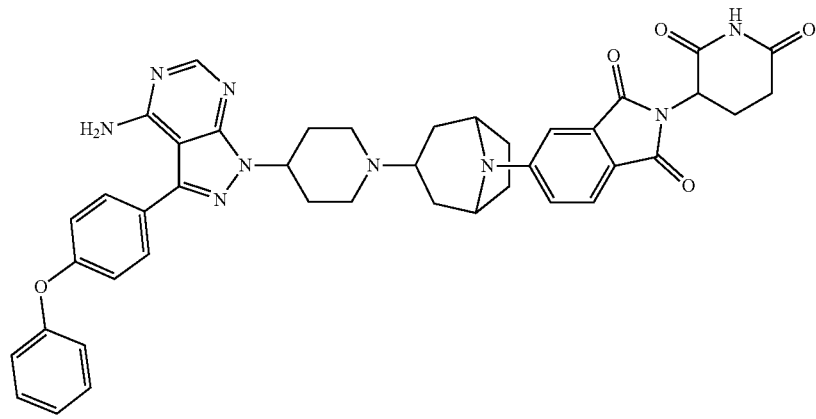
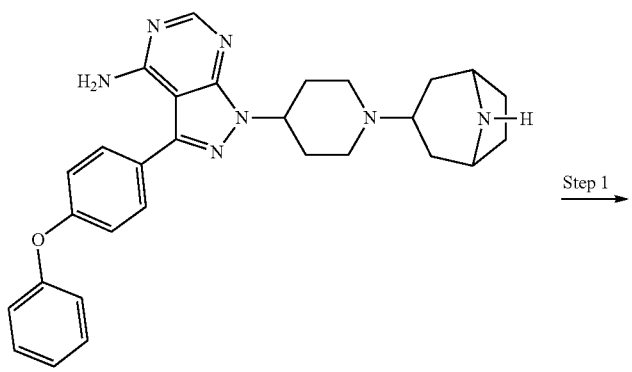
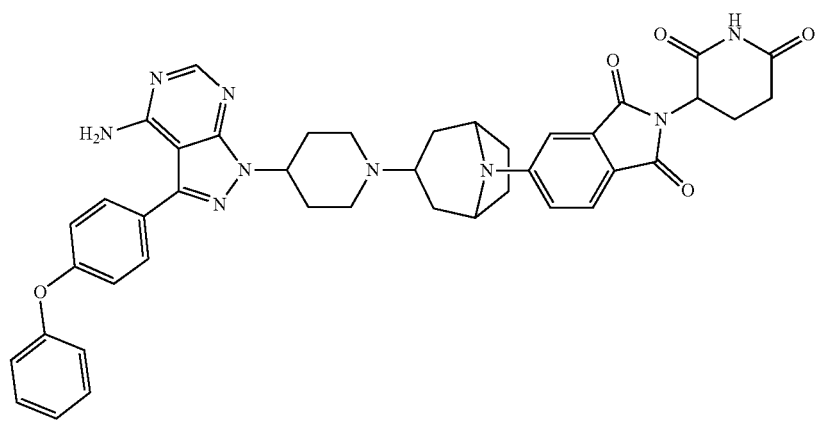
Compound 58

The above crude product 1-(1-(8-azabicyclo[3.2.1]octan-3-yl)piperidin-4-yl)-3-(4-phenoxyphenyl)-1H-pyrazolo[3,4-d]pyrimidin-4-amine hydrochloride (57b) (0.2 g) was dissolved in 10 mL of DMSO, and solid sodium bicarbonate (113 mg, 1.35 mmol) was added, the mixture was stirred at room temperature for 10 min, then 1.0 mL of DIPEA and 2-(2,6-dioxopiperidin-3-yl)-5-fluoroisoindoline-1,3-dione (see WO 2017197056 for the synthetic method) (139 mg, 0.50 mmol) were added, and the reaction was stirred at 80° C. for 5 h. The reaction solution was cooled to room temperature, added 20 mL of water, and filtered. The solid was collected, washed with water, and same was dissolved with 50 mL of dichloromethane, dried over anhydrous sodium sulfate, and concentrated under reduced pressure, then the crude product was separated and purified by silica gel column chromatography (dichloromethane/methanol (v/v)=1), to obtain 5-(3-(4-(4-amino-3-(4-phenoxyphenyl)-1H-pyrazolo[3,4-d]pyrimidin-1-yl)piperidin-1-yl)-8-azabicyclo[3.2.1]octan-8-yl)-2-(2,6-dioxopiperidin-3-yl)isoindoline-1,3-dione (Compound 58) (110 mg, two-step yield calculated from compound 57a: 46%).

$^1$H NMR (400 MHz, CDCl$_3$) δ 9.06 (br.s, 1H), 8.36 (s, 1H), 7.70-7.64 (m, 1H), 7.64-7.58 (m, 2H), 7.41-7.33 (m, 2H), 7.19-7.03 (m, 6H), 6.92 (dd, 1H), 5.64 (br.s, 2H), 4.97-4.89 (m, 1H), 4.77-4.64 (m, 1H), 4.47-4.39 (m, 2H), 3.10-2.65 (m, 6H), 2.42-2.24 (m, 4H), 2.18-2.08 (m, 3H), 2.04-1.94 (m, 2H), 1.92-1.82 (m, 2H), 1.82-1.74 (m, 4H). LCMS m/z=752.3 [M+1]$^+$.

Example 59

5-(3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)azetidin-1-yl)-2-(2,6-dioxopiperidin-3-yl)isoindoline-1,3-dione (Compound 59)

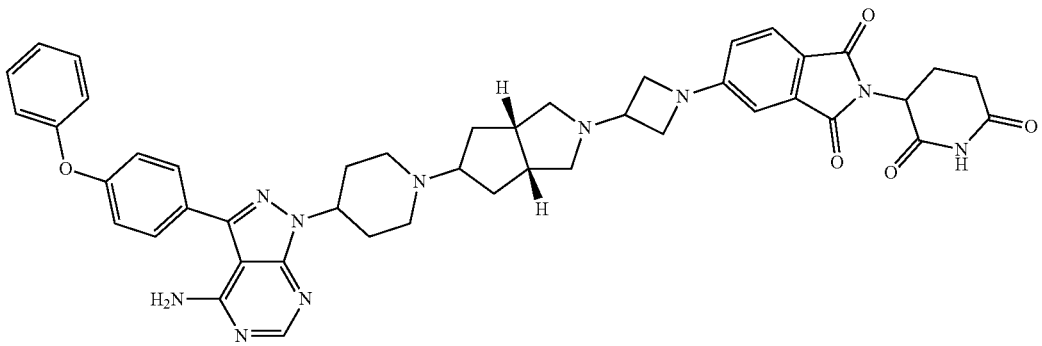

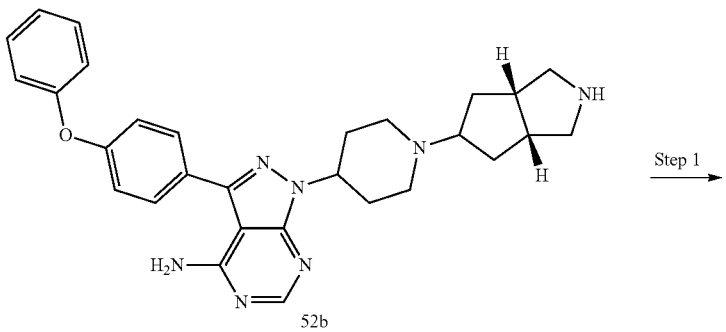

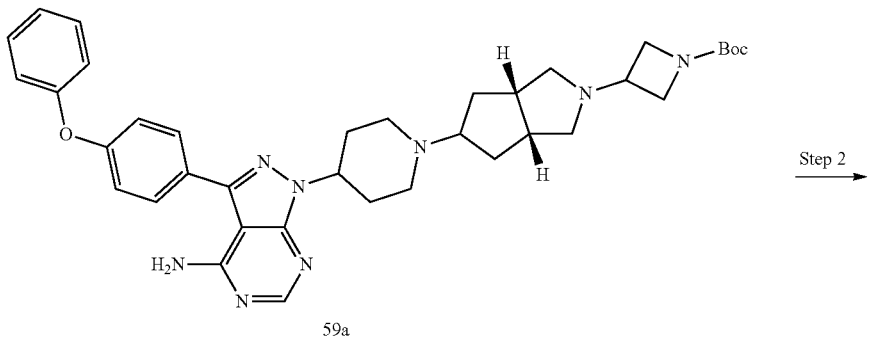

-continued

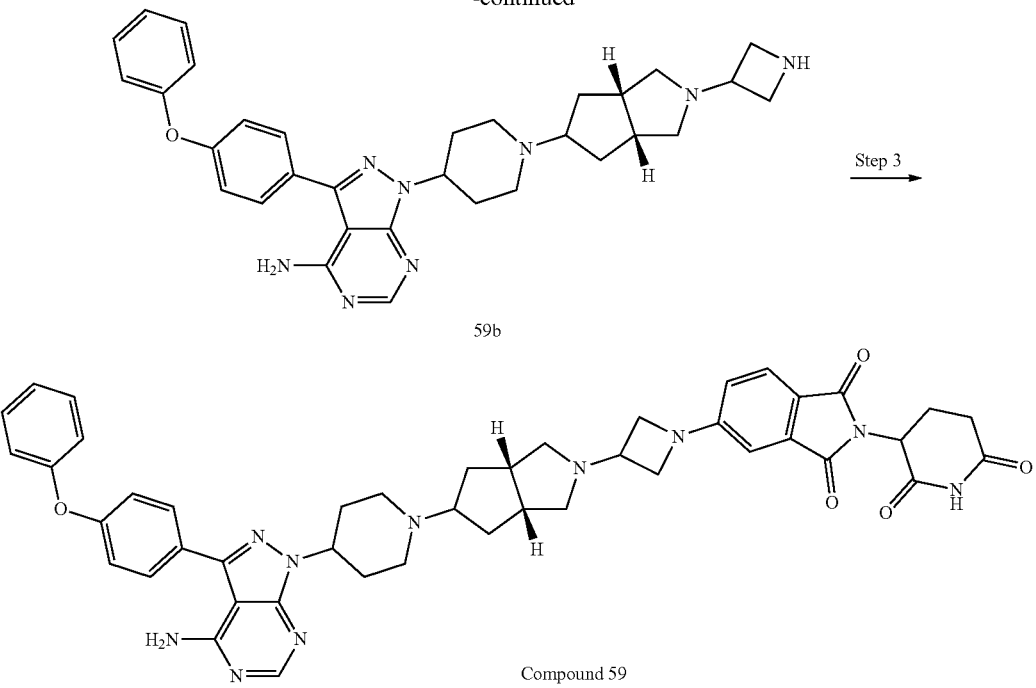

59b

Compound 59

Step 1 tert-butyl 3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)azetidine-1-carboxylate (59a)

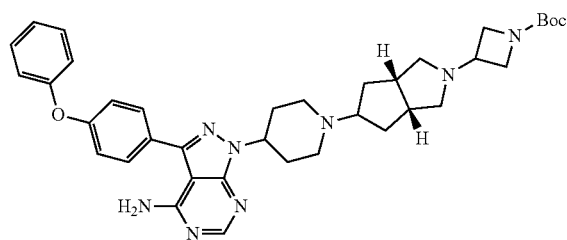 [SMILES: CC(C)(C)OC(=O)N1CC(N2C[C@H]3CC(N4CCC(n5nc(-c6ccc(Oc7ccccc7)cc6)c6c(N)ncnc65)CC4)C[C@H]3C2)C1]

The above crude product 1-(1-((3aR,6aS)-octahydrocyclopenta[c]pyrrol-5-yl)piperidin-4-yl)-3-(4-phenoxyphenyl)-1H-pyrazolo[3,4-d]pyrimidin-4-amine Trifluoroacetate (52b) (270 mg) was dissolved in 6 mL of DCE, and 1-Boc-3-azetidinone (188 mg, 1.10 mmol), glacial acetic acid (0.08 mL) and anhydrous sodium sulfate (400 mg) were successively added at room temperature, the mixture was stirred for 30 min, then sodium triacetoxyborohydride (400 mg, 1.89 mmol) was added, and the mixture was stirred at room temperature for 16 h. To the reaction solution was added 50 mL of water, the pH of the aqueous phase was adjusted to 10 with 2 mol/L sodium hydroxide aqueous solution, and the resulted solution was extracted with dichloromethane (30 mL×3). The organic phase was combined, washed with water (20 mL×2), dried over anhydrous sodium sulfate, and concentrated under reduced pressure. The crude product was separated and purified by silica gel column chromatography (dichloromethane/methanol (v/v)=10:1-8:1), to obtain tert-butyl 3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrole-2(1H)-yl) azetidine-1-carboxylate (59a) (265 mg, two-step yield calculated from compound 52a: 96%).

LCMS m/z=651.4 [M+1]$^+$.

Step 2

1-(1-((3aR,6aS)-2-(azetidin-3-yl)octahydrocyclopenta[c]pyrrol-5-yl)piperidin-4-yl)-3-(4-phenoxyphenyl)-1H-pyrazolo[3,4-d]pyrimidin-4-amine (59b)

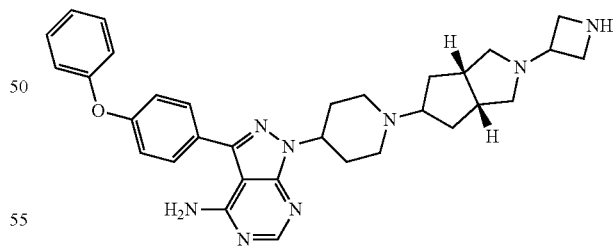

Tert-butyl 3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrole-2(1H)-yl)azetidine-1-carboxylate (59a) (210 mg, 0.32 mmol) was dissolved in 2 mL of dichloromethane, and 1 mL of trifluoroacetic acid was added, the mixture was reacted at room temperature for 2.5 h. The pH of the reaction solution was adjusted to 10 with 2 mol/L sodium hydroxide aqueous solution, and the aqueous phase was extracted with dichloromethane (10 mL×3). The organic phase was combined, dried over anhydrous sodium sulfate, and concentrated under reduced pressure, to obtain the crude product 1-(1-((3aR,6aS)-2-(azetidin-3-yl)hexahydrocyclopenta[c]pyrrol-5-yl)piperidin-4-yl)-3-(4-phenoxyphenyl)-1H-pyrazolo[3,4-d]pyrimidin-4-amine (59b) (165 mg).

LCMS m/z=551.4 [M+1]$^+$.

Step 3

5-(3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-yl)azetidin-1-yl)-2-(2,6-dioxopiperidin-3-yl)isoindoline-1,3-dione (Compound 59)

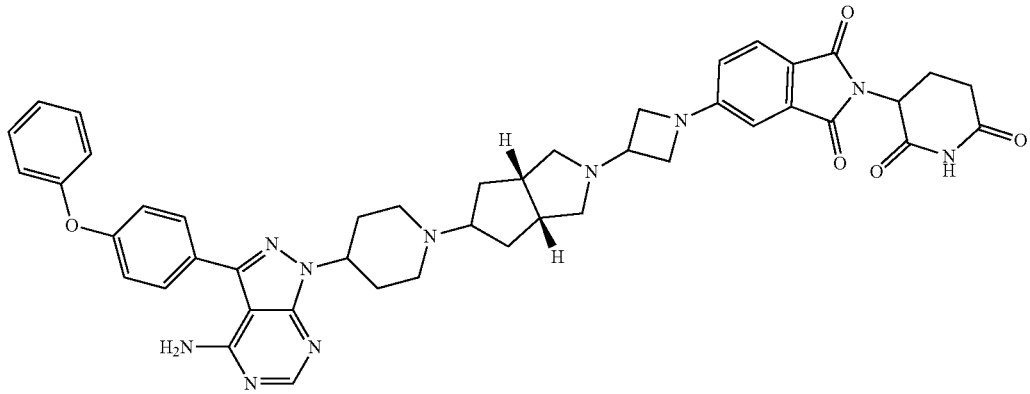 [SMILES: Nc1ncnc2c1c(-c1ccc(Oc3ccccc3)cc1)nn2C1CCN(C2C[C@@H]3CN(C4CN(c5ccc6c(c5)C(=O)N(C5CCC(=O)NC5=O)C6=O)C4)C[C@@H]3C2)CC1]

The above crude product 1-(1-((3aR,6aS)-2-(azetidin-3-yl)hexahydrocyclopenta[c]pyrrol-5-yl)piperidin-4-yl)-3-(4-phenoxyphenyl)-1H-pyrazolo[3,4-d]pyrimidin-4-amine (59b) (165 mg) was dissolved in 5 mL of DMSO, and 2-(2,6-dioxopiperidin-3-yl)-5-fluoroisoindoline-1,3-dione (see WO 2017197056 for the synthetic method) (82 mg, 0.30 mmol) and diisopropylethylamine (194 mg, 1.50 mmol) were added at room temperature, the mixture was warmed to 80° C. and reacted for 4 h. The reaction solution was cooled to room temperature, then poured into 20 mL of water, and the aqueous phase was extracted with the mixed solvent of dichloromethane/methanol (v/v)=10:1 (30 mL×3). The organic phase was combined, washed with 50 mL of water, dried over anhydrous sodium sulfate, and concentrated under reduced pressure, then the crude product was separated and purified by silica gel column chromatography (dichloromethane/methanol (v/v)=15:1-8:1), to obtain 5-(3-((3aR,6aS)-5-(4-(4-amino-3-(4-phenoxyphenyl)-1H-pyrazolo[3,4-d]pyrimidin-1-yl)piperidin-1-yl)hexahydrocyclopenta[c]pyrrol-2(1H)-azetidin-1-yl)-2-(2,6-dioxo piperidin-3-yl)isoindoline-1,3-dione (Compound 59) (108 mg, two-step yield calculated from compound 59a: 42%).

$^1$H NMR (400 MHz, CDCl$_3$) δ 8.36 (s, 1H), 8.13 (s, 1H), 7.68-7.58 (m, 3H), 7.43-7.33 (m, 2H), 7.22-7.02 (m, 5H), 6.77 (d, 1H), 6.50 (dd, 1H), 5.43 (br.s, 2H), 4.93 (dd, 1H), 4.82-4.68 (m, 1H), 4.11-4.03 (m, 2H), 3.94-3.83 (m, 2H), 3.51-3.42 (m, 1H), 3.23-3.11 (m, 2H), 2.94-2.63 (m, 4H), 2.62-2.30 (m, 8H), 2.28-2.16 (m, 3H), 2.16-2.08 (m, 1H), 2.06-1.95 (m, 2H), 1.44-1.22 (m, 3H).

LCMS m/z=807.4 [M+1]$^+$.

Example 60
5-(3-(4-(4-amino-3-(4-phenoxyphenyl)-1H-pyrazolo[3,4-d]pyrimidin-1-yl)piperidin-1-yl)-[1,3':1',3"-terazetidin]-1H-yl)-2-(2,6-dioxopiperidin-3-yl)isoindoline-1,3-dione (Compound 60)
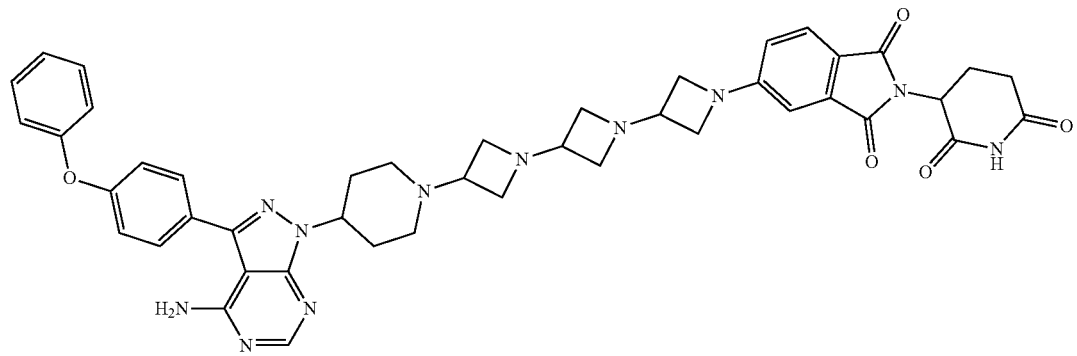
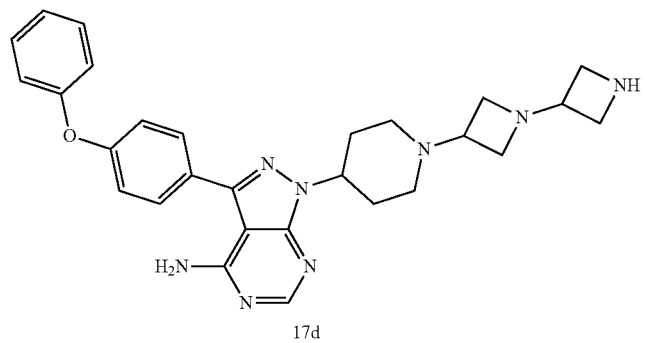
Step 1 →
17d
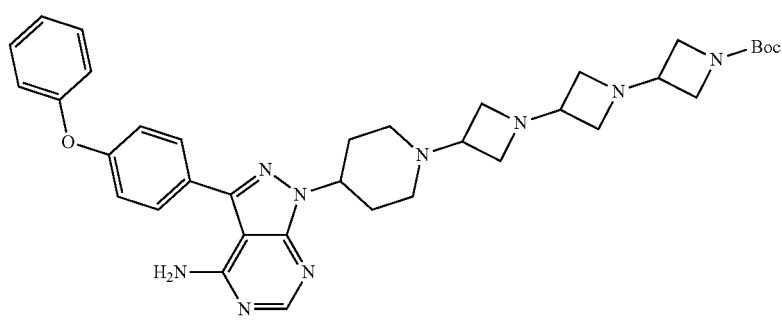
Step 2 →
60a
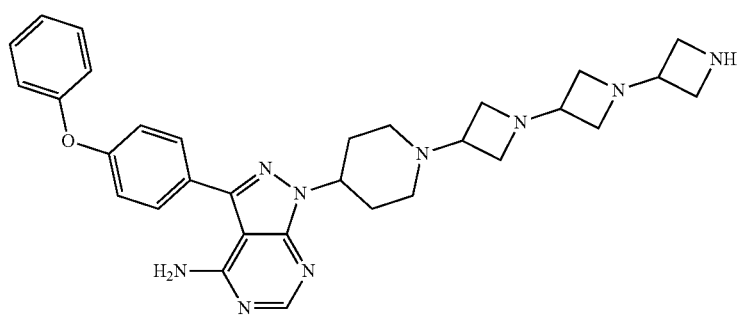
Step 3 →
60b

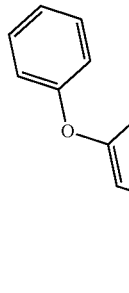

Compound 60

Step 1 tert-butyl 3-(4-(4-amino-3-(4-phenoxyphenyl)-1H-pyrazolo[3,4-d]pyrimidin-1-yl)piperidin-1-yl)-[1,3':1',3''-terazetidine]-1''-carboxylate (60a)

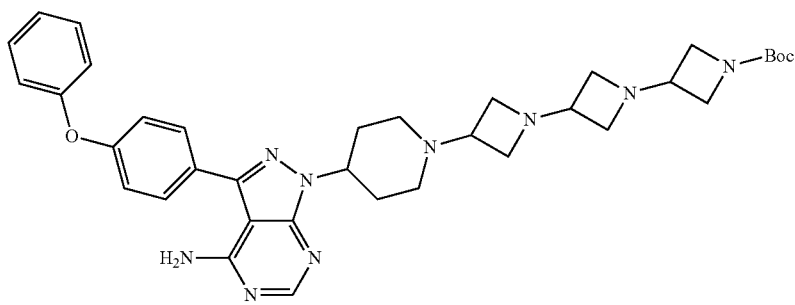 [SMILES: CC(C)(C)OC(=O)N1CC(N2CC(N3CC(N4CCC(n5nc(-c6ccc(Oc7ccccc7)cc6)c6c(N)ncnc65)CC4)C3)C2)C1]

1-[1-[1-(azetidin-3-yl)azetidin-3-yl]-4-piperidyl]-3-(4-phenoxyphenyl)pyrazolo[3,4-d]pyrimidin-4-amine (17d) (496 mg, 1.00 mmol) was dissolved in 10 mL of DCE, and 1-Boc-3-azetidinone (342 mg, 2.00 mmol), glacial acetic acid (0.15 mL) and anhydrous sodium sulfate (800 mg) were successively added at room temperature, the mixture was stirred at room temperature for 30 min, then sodium triacetoxyborohydride (726 mg, 3.43 mmol) was added, and the mixture was stirred at room temperature for 16 h. To the reaction solution was added 50 mL of water, the pH of the aqueous phase was adjusted to 10 with 2N sodium hydroxide aqueous solution, and the resulted solution was extracted with dichloromethane (30 mL×3). The organic phase was combined, washed with water (20 mL×2), dried over anhydrous sodium sulfate, and concentrated under reduced pressure. The crude product was separated and purified by silica gel column chromatography (dichloromethane/methanol (v/v)=10:1-8:1), to obtain tert-butyl 3-(4-(4-amino-3-(4-phenoxyphenyl)-1H-pyrazolo[3,4-d]pyrimidin-1-yl)piperidin-1-yl)-[1,3':1',3''-terazetidine]-1''-carboxylate (60a) (521 mg, yield: 80%).

LCMS m/z=652.5 [M+1]$^+$.

Step 2

1-(1-([1,3':1',3''-terazetidin]-3-yl)piperidin-4-yl)-3-(4-phenoxyphenyl)-1H-pyrazolo[3,4-d]pyrimidin-4-amine (60b)

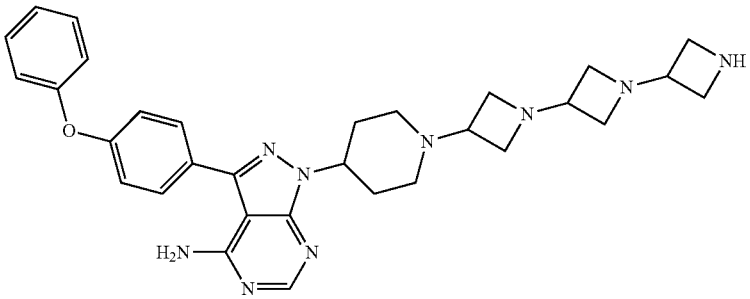 [SMILES: Nc1ncnc2c1c(-c1ccc(Oc3ccccc3)cc1)nn2C1CCN(C2CN(C3CN(C4CNC4)C3)C2)CC1]

Tert-butyl 3-(4-(4-amino-3-(4-phenoxyphenyl)-1H-pyrazolo[3,4-d]pyrimidin-1-yl)piperidin-1-yl)-[1,3':1',3''-terazetidine]-1H-carboxylate (60a) (143 mg, 0.22 mmol) was dissolved in 4 mL of dichloromethane, and 2 mL of trifluoroacetic acid was added, the mixture was reacted at room temperature for 1.5 h. The pH of the reaction solution was adjusted to 10 with 2 mol/L sodium hydroxide aqueous solution, and the aqueous phase was extracted with dichloromethane (10 mL×3). The organic phase was combined, dried over anhydrous sodium sulfate, and concentrated under reduced pressure, to obtain the crude product 1-(1-([1,3':1',3''-terazetidin]-3-yl)piperidin-4-yl)-3-(4-phenoxyphenyl)-1H-pyrazolo[3,4-d]pyrimidin-4-amine (60b) (113 mg).

LCMS m/z=552.4 [M+1]$^+$.

Step 3

5-(3-(4-(4-amino-3-(4-phenoxyphenyl)-1H-pyrazolo[3,4-d]pyrimidin-1-yl)piperidin-1-yl)-[1,3':1',3''-terazetidin]-1''-yl)-2-(2,6-dioxopiperidin-3-yl)isoindoline-1,3-dione (Compound 60)

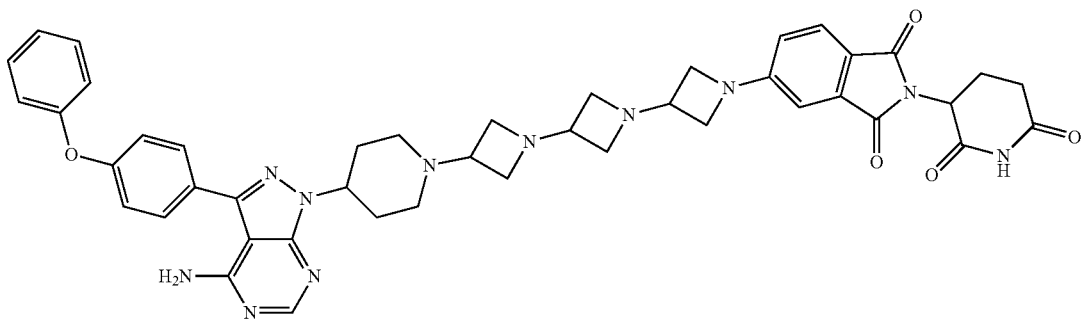 [SMILES: Nc1ncnc2c1c(-c1ccc(Oc3ccccc3)cc1)nn2C1CCN(C2CN(C3CN(C4CN(c5ccc6c(c5)C(=O)N(C5CCC(=O)NC5=O)C6=O)C4)C3)C2)CC1]

The above crude product 1-(1-([1,3':1',3''-terazetidin]-3-yl)piperidin-4-yl)-3-(4-phenoxyphenyl)-1H-pyrazolo[3,4-d]pyrimidin-4-amine (60b) (113 mg) was dissolved in 5 mL of DMSO, and 2-(2,6-dioxopiperidin-3-yl)-5-fluoroisoindoline-1,3-dione (see WO 2017197056 for the synthetic method) (55 mg, 0.20 mmol) and diisopropylethylamine (129 mg, 1.00 mmol) were added at room temperature, the mixture was warmed to 80° C. and reacted for 3.5 h. The reaction solution was cooled to room temperature, then poured into 20 mL of water, and the aqueous phase was extracted with the mixed solvent of dichloromethane/methanol (v/v)=10:1 (30 mL×3). The organic phase was combined, washed with 40 mL of water, dried over anhydrous sodium sulfate, and concentrated under reduced pressure, then the crude product was separated and purified by silica gel column chromatography (dichloromethane/methanol (v/v)=15:1-8:1), to obtain 5-(3-(4-(4-amino-3-(4-phenoxyphenyl)-1H-pyrazolo[3,4-d]pyrimidin-1-yl)piperidin-1-yl)-[1,3':1',3''-terazetidin]-1H-yl)-2-(2,6-dioxopiperidin-3-yl)isoindoline-1,3-dione (Compound 60) (99 mg, two-step yield calculated from compound 60a: 56%).

$^1$H NMR (400 MHz, CDCl$_3$) δ 8.37 (s, 1H), 7.68-7.59 (m, 3H), 7.43-7.35 (m, 2H), 7.21-7.11 (m, 3H), 7.11-7.05 (m, 2H), 6.76 (d, 1H), 6.49 (dd, 1H), 5.72 (br.s, 2H), 4.96-4.87 (m, 1H), 4.84-4.70 (m, 1H), 4.08-3.96 (m, 2H), 3.88-3.78 (m, 2H), 3.69-3.60 (m, 1H), 3.60-3.51 (m, 2H), 3.44-3.32 (m, 3H), 3.18-2.96 (m, 5H), 2.96-2.64 (m, 5H), 2.50-2.33 (m, 2H), 2.16-1.97 (m, 5H).

LCMS m/z=808.4 [M+1]$^+$.

Example 61
5-((3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrol-2(1H)-yl)-2-(2,6-dioxopiperidin-3-yl)isoindoline-1,3-dione (Compound 61)
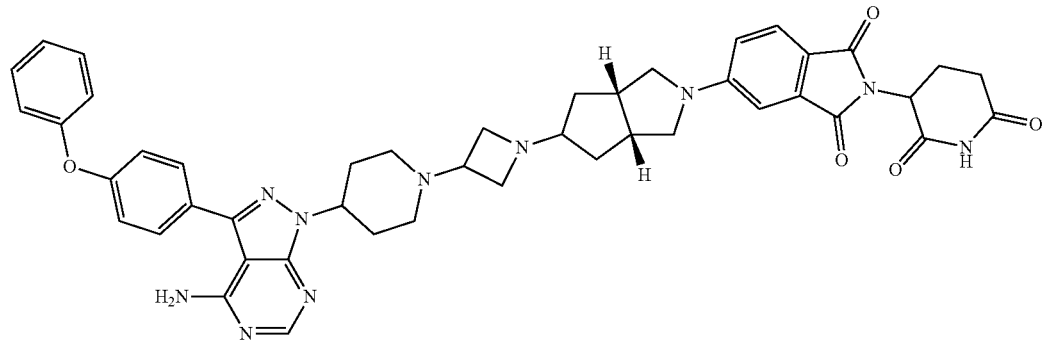
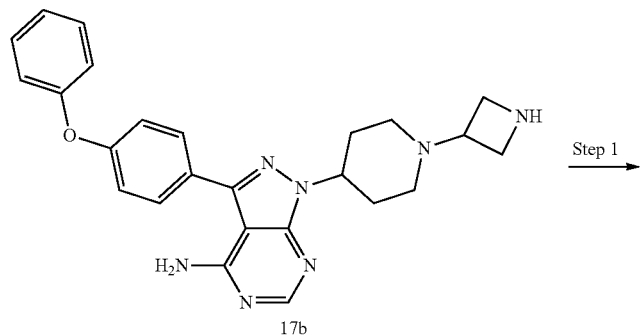
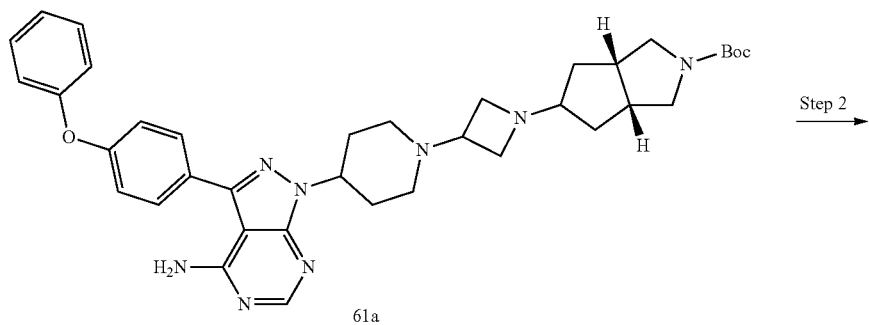
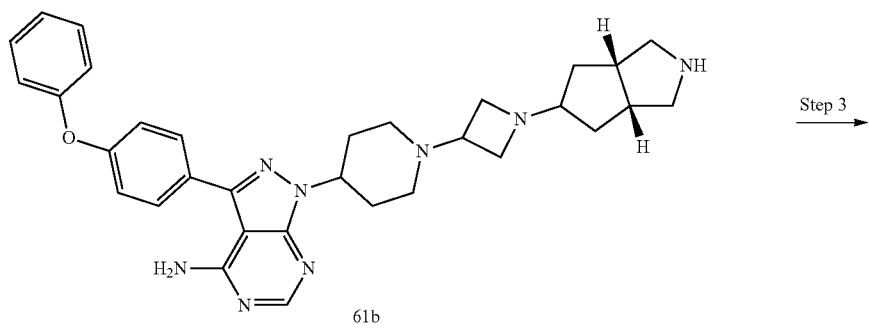

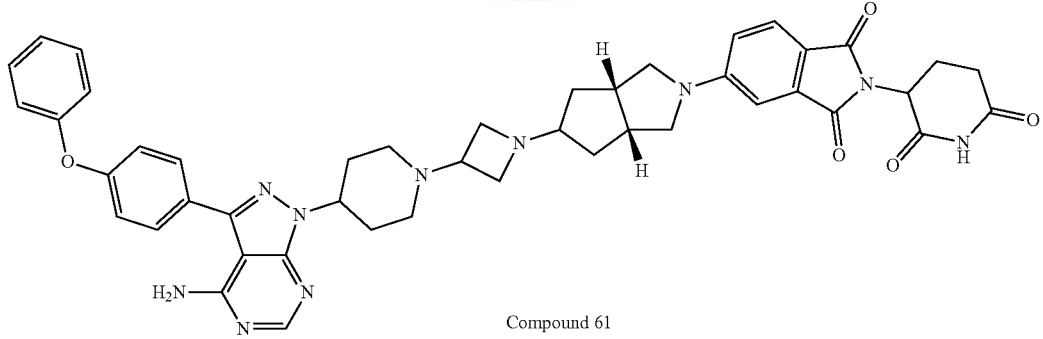

Compound 61

Step 1 tert-butyl (3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrole-2(1H)-carboxylate (61a)

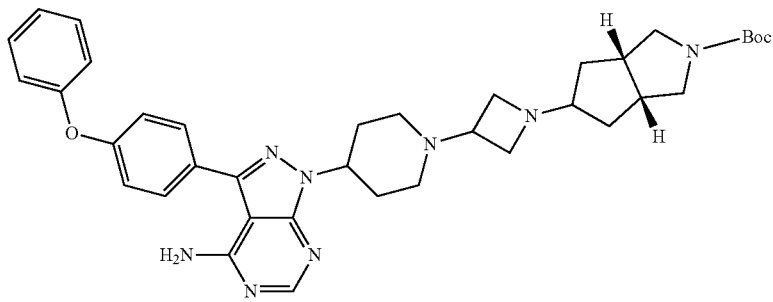 [SMILES: CC(C)(C)OC(=O)N1C[C@H]2CC(N3CC(N4CCC(n5nc(-c6ccc(Oc7ccccc7)cc6)c6c(N)ncnc65)CC4)C3)C[C@H]2C1]

1-[1-(azetidin-3-yl)-4-piperidyl]-3-(4-phenoxyphenyl)pyrazolo[3,4-d]pyrimidin-4-amine (17b) (650 mg, 1.47 mmol) was dissolved in 12 mL of DCE, and tert-butyl (3aR,6aS)-5-oxo hexahydrocyclopenta[c]pyrrol-2(1H)-carboxylate (451 mg, 2.00 mmol), glacial acetic acid (0.14 mL) and anhydrous sodium sulfate (700 mg) were successively added at room temperature, the mixture was stirred at room temperature for 30 min, then sodium triacetoxyborohydride (636 mg, 3.00 mmol) was added, and the mixture was stirred at room temperature for 16 h. To the reaction solution was added 50 mL of water, the pH of the aqueous phase was adjusted to 10 with 2 mol/L sodium hydroxide aqueous solution, and the resulted solution was extracted with dichloromethane (30 mL×3). The organic phase was combined, washed with water (20 mL×2), dried over anhydrous sodium sulfate, and concentrated. The crude product was separated and purified by silica gel column chromatography (dichloromethane/methanol (v/v)=10:1-8:1), to obtain tert-butyl (3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrol-2(1H)-carboxylate (61a) (310 mg, yield: 32%).

LCMS m/z=651.4 [M+1]$^+$.

Step 2

1-(1-((3aR,6aS)-2-(azetidin-3-yl)octahydrocyclopenta[c]pyrrol-5-yl)piperidin-4-yl)-3-(4-phenoxyphenyl)-1H-pyrazolo[3,4-d]pyrimidin-4-amine (61b)

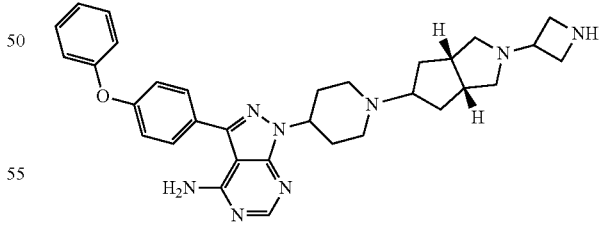

Tert-butyl (3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrol-2(1H)-carboxylate (61a) (310 mg, 0.48 mmol) was dissolved in 3 mL of dichloromethane, and 2 mL of trifluoroacetic acid was added, the mixture was reacted at room temperature for 2.5 h. The pH of the reaction solution was adjusted to 10 with 2 mol/L sodium hydroxide aqueous solution, and the aqueous phase was extracted with dichloromethane (10 mL×3). The organic phase was combined, dried over anhydrous sodium sulfate, and concentrated, to obtain the crude product 1-(1-((3aR,6aS)-2-(azetidin-3-yl)octahydrocyclopenta[c]pyrrol-5-yl)piperidin-4-yl)-3-(4-phenoxyphenyl)-1H-pyrazolo[3,4-d]pyrimidin-4-amine (61b) (255 mg).

LCMS m/z=551.4 [M+1]$^+$.

Step 3

5-((3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrol-2(1H)-yl)-2-(2,6-dioxopiperidin-3-yl)isoindoline-1,3-dione (Compound 61)

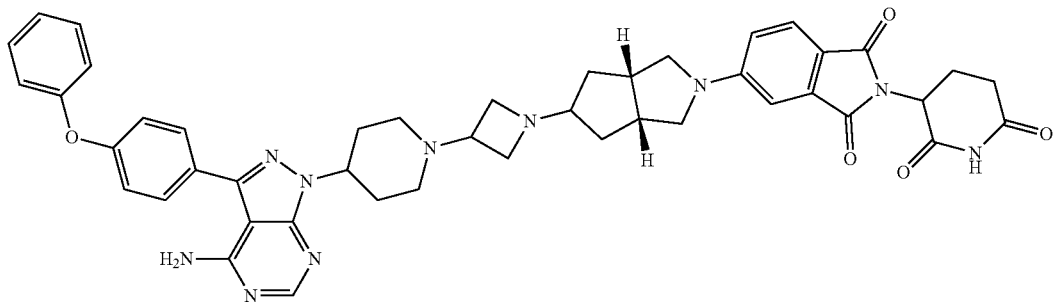 [SMILES: Nc1ncnc2c1c(-c1ccc(Oc3ccccc3)cc1)nn2C1CCN(C2CN(C3C[C@@H]4CN(c5ccc6c(c5)C(=O)N(C5CCC(=O)NC5=O)C6=O)C[C@@H]4C3)C2)CC1]

The above crude product 1-(1-((3aR,6aS)-2-(azetidin-3-yl)octahydrocyclopenta[c]pyrrol-5-yl)piperidin-4-yl)-3-(4-phenoxyphenyl)-1H-pyrazolo[3,4-d]pyrimidin-4-amine (61b) (200 mg) was dissolved in 8 mL of DMSO, and 2-(2,6-dioxopiperidin-3-yl)-5-fluoroisoindoline-1,3-dione (see WO 2017197056 for the synthetic method) (99 mg, 0.36 mmol) and diisopropylethylamine (233 mg, 1.80 mmol) were added at room temperature, the mixture was warmed to 80° C. and reacted for 4 h. The reaction solution was cooled to room temperature, then poured into 20 mL of water, and the aqueous phase was extracted with the mixed solvent of dichloromethane/methanol (v/v)=10:1 (30 mL×3). The organic phase was combined, washed with 50 mL of water, dried over anhydrous sodium sulfate, and concentrated under reduced pressure, then the crude product was separated and purified by silica gel column chromatography (dichloromethane/methanol (v/v)=1-8:1), to obtain 5-((3aR,6aS)-5-(3-(4-(4-amino-3-(4-phenoxyphenyl)-1H-pyrazolo[3,4-d]pyrimidin-1-yl)piperidin-1-yl)azetidin-1-yl)hexahydrocyclopenta[c]pyrrol-2(1H)-yl)-2-(2,6-di oxopiperidin-3-yl)isoindoline-1,3-dione (Compound 61) (148 mg, two-step yield calculated from compound 61a: 49%).

$^1$H NMR (400 MHz, CDCl$_3$) δ 8.52 (br.s, 1H), 8.37 (s, 1H), 7.69-7.60 (m, 3H), 7.44-7.34 (m, 2H), 7.24-7.02 (m, 5H), 6.96 (d, 1H), 6.67 (dd, 1H), 5.48 (br.s, 2H), 4.92 (dd, 1H), 4.83-4.70 (m, 1H), 3.70-3.43 (m, 4H), 3.42-3.30 (m, 2H), 3.10-2.65 (m, 10H), 2.49-2.32 (m, 2H), 2.16-1.94 (m, 6H), 1.52-1.20 (m, 4H).

LCMS m/z=807.4 [M+1]$^+$.

Example 62
5-(2-(3-(4-(4-amino-3-(4-phenoxyphenyl)-1H-pyrazolo[3,4-d]pyrimidin-1-yl)piperidin-1-yl)azetidin-1-yl)-7-azaspiro[3.5]nonan-7-yl)-2-(2,6-dioxopiperidin-3-yl)isoindoline-1,3-dione (Compound 62)
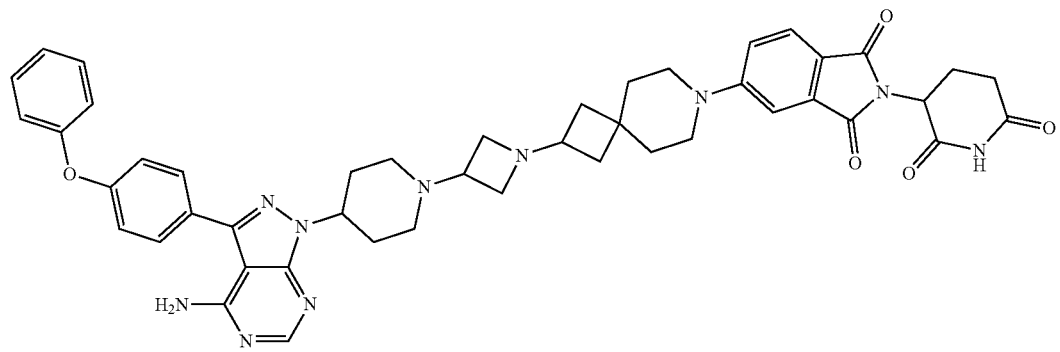
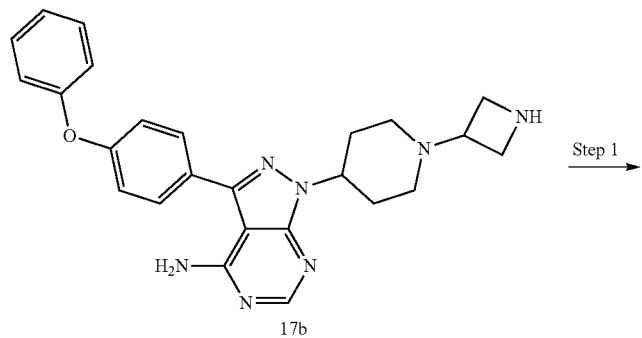
Step 1
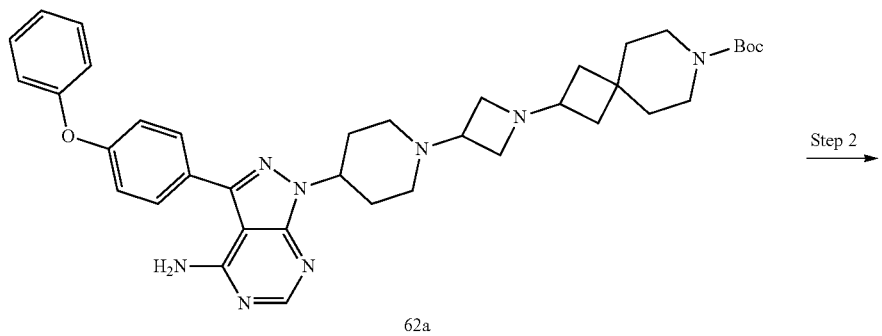
Step 2
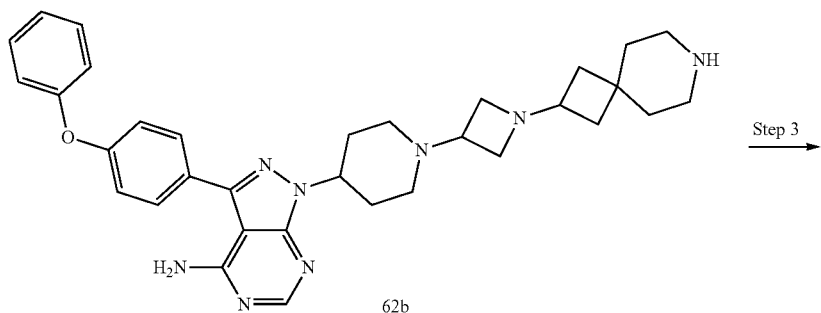
Step 3

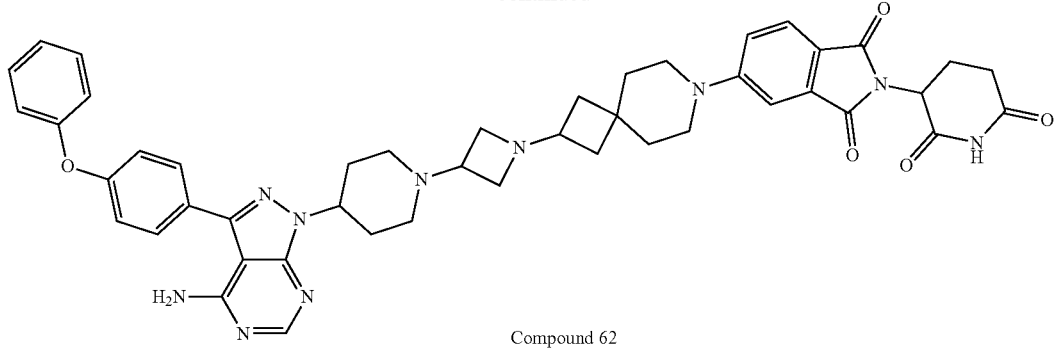

Compound 62

Step 1 tert-butyl 2-(3-(4-(4-amino-3-(4-phenoxyphenyl)-1H-pyrazolo[3,4-d]pyrimidin-1-yl)piperidin-1-yl)azetidin-1-yl)-7-azaspiro[3.5]nonane-7-carboxylate (62a)

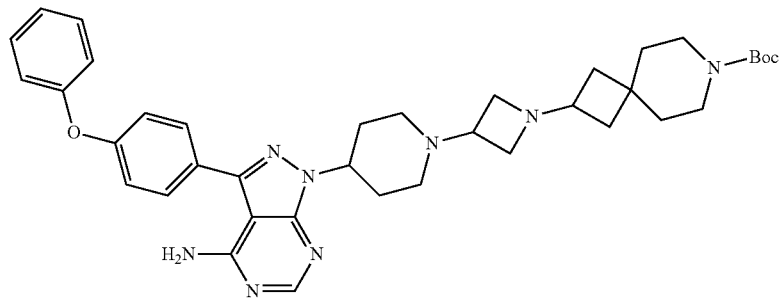 [SMILES: CC(C)(C)OC(=O)N1CCC2(CC1)CC(N1CC(N3CCC(n4nc(-c5ccc(Oc6ccccc6)cc5)c5c(N)ncnc54)CC3)C1)C2]

1-[1-(azetidin-3-yl)-4-piperidyl]-3-(4-phenoxyphenyl)pyrazolo[3,4-d]pyrimidin-4-amine (17b) (650 mg, 1.47 mmol) was dissolved in 12 mL of DCE, and tert-butyl 2-oxo-7-azaspiro[3.5]nonane-7-carboxylate (479 mg, 2.00 mmol), glacial acetic acid (0.14 mL) and anhydrous sodium sulfate (700 mg) were successively added at room temperature, the mixture was stirred at room temperature for 30 min, then sodium triacetoxyborohydride (636 mg, 3.00 mmol) was added, and the mixture was stirred at room temperature for 16 h. To the reaction solution was added 50 mL of water, the pH of the aqueous phase was adjusted to 10 with 2 mol/L sodium hydroxide aqueous solution, and the resulted solution was extracted with dichloromethane (30 mL×3). The organic phase was combined, washed with water (20 mL×2), dried over anhydrous sodium sulfate, and concentrated under reduced pressure. The crude product was separated and purified by silica gel column chromatography (dichloromethane/methanol (v/v)=10:1-8:1), to obtain tert-butyl 2-(3-(4-(4-amino-3-(4-phenoxyphenyl)-1H-pyrazolo[3,4-d]pyrimidin-1-yl)piperidin-1-yl)azetidin-1-yl)-7-azaspiro[3.5]nonane-7-carboxylate (62a) (404 mg, yield: 41%).

LCMS m/z=665.4 [M+1]$^+$.

Step 2

1-(1-(1-(7-azaspiro[3.5]nonan-2-yl)azetidin-3-yl)piperidin-4-yl)-3-(4-phenoxy phenyl)-1H-pyrazolo[3,4-d]pyrimidin-4-amine (62b)

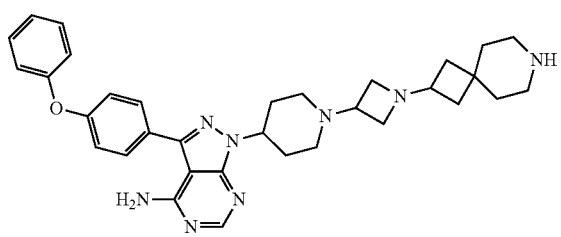 [SMILES: Nc1ncnc2c1c(-c1ccc(Oc3ccccc3)cc1)nn2C1CCN(C2CN(C3CC4(CCNCC4)C3)C2)CC1]

Tert-butyl 2-(3-(4-(4-amino-3-(4-phenoxyphenyl)-1H-pyrazolo[3,4-d]pyrimidin-1-yl)piperidin-1-yl)azetidin-1-yl)-7-azaspiro[3.5]nonane-7-carboxylate (62a) (200 mg, 0.30 mmol) was dissolved in 2 mL of dichloromethane, and 1 mL of trifluoroacetic acid was added, the mixture was reacted at room temperature for 2 h. The pH of the reaction solution was adjusted to 10 with 2 mol/L sodium hydroxide aqueous solution, and the aqueous phase was extracted with dichloromethane (10 mL×3). The organic phase was combined, dried over anhydrous sodium sulfate, and concentrated under reduced pressure, to obtain the crude product 1-(1-(1-(7-azaspiro[3.5]nonan-2-yl)azetidin-3-yl)piperidin-4-yl)-3-(4-phenoxyphenyl)-1H-pyrazolo[3,4-d]pyrimidin-4-amine (62b) (161 mg).

LCMS m/z=565.4 [M+1]$^+$.

Step 3

5-(2-(3-(4-(4-amino-3-(4-phenoxyphenyl)-1H-pyrazolo[3,4-d]pyrimidin-1-yl)piperidin-1-yl)azetidin-1-yl)-7-azaspiro[3.5]nonan-7-yl)-2-(2,6-dioxopiperidin-3-yl)isoindoline-1,3-dione (Compound 62)

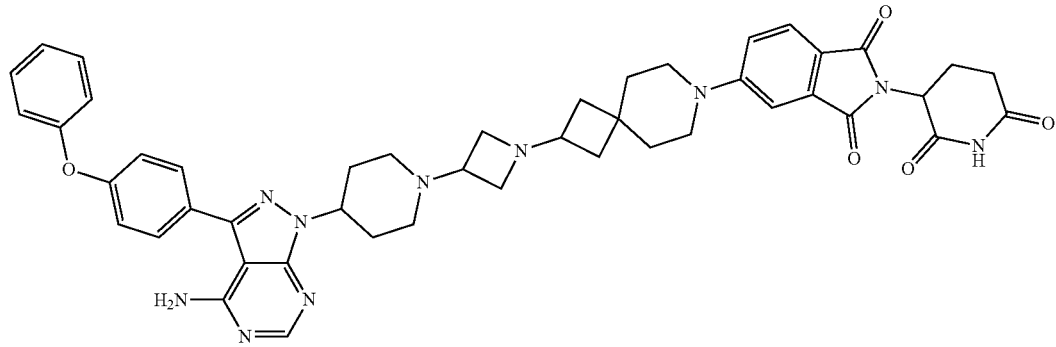 [SMILES: Nc1ncnc2c1c(-c1ccc(Oc3ccccc3)cc1)nn2C1CCN(C2CN(C3CC4(CCN(c5ccc6c(c5)C(=O)N(C5CCC(=O)NC5=O)C6=O)CC4)C3)C2)CC1]

The above crude product 1-(1-(1-(7-azaspiro[3.5]nonan-2-yl)azetidin-3-yl)piperidin-4-yl)-3-(4-phenoxyphenyl)-1H-pyrazolo[3,4-d]pyrimidin-4-amine (62b) (161 mg) was dissolved in 6 mL of DMSO, and 2-(2,6-dioxopiperidin-3-yl)-5-fluoroisoindoline-1,3-dione (see WO 2017197056 for the synthetic method) (80 mg, 0.29 mmol) and diisopropylethylamine (188 mg, 1.45 mmol) were added at room temperature, the mixture was warmed to 80° C. and reacted for 4 h. The reaction solution was cooled to room temperature, then poured into 20 mL of water, and the aqueous phase was extracted with the mixed solvent of dichloromethane/methanol (v/v)=10:1 (30 mL×3). The organic phase was combined, washed with 50 mL of water, dried over anhydrous sodium sulfate, and concentrated under reduced pressure, then the crude product was separated and purified by silica gel column chromatography (dichloromethane/methanol (v/v)=15:1-8:1), to obtain 5-(2-(3-(4-(4-amino-3-(4-phenoxyphenyl)-1H-pyrazolo[3,4-d]pyrimidin-1-yl)piperi din-1-yl)azetidin-1-yl)-7-azaspiro[3.5]nonan-7-yl)-2-(2,6-dioxopiperidin-3-yl)isoindoline-1,3-dione (Compound 62) (128 mg, two-step yield calculated from compound 62a: 52%).

$^1$H NMR (400 MHz, CDCl$_3$) δ 10.34 (br.s, 1H), 8.39 (s, 1H), 7.70-7.60 (m, 3H), 7.43-7.33 (m, 2H), 7.27-7.24 (m, 1H), 7.20-6.99 (m, 6H), 5.82 (br.s, 2H), 5.00-4.89 (m, 1H), 4.85-4.71 (m, 1H), 3.67-3.51 (m, 2H), 3.46-3.21 (m, 5H), 3.16-2.66 (m, 8H), 2.50-2.33 (m, 2H), 2.20-1.92 (m, 7H), 1.87-1.61 (m, 6H).

LCMS m/z=821.4 [M+1]$^+$.

Test Example

1. Experiment on Inhibiting Cell Proliferation

SU-DHL-4, Mino, and SU-DHL-6 cells, in the culture medium of RPMI1640+10% FBS, were cultured in an incubator at 37° C. under 5% CO$_2$. Cells were plated in a 96-well plate. Specifically, SU-DHL-4 cells were at 20000/well, Mino and SU-DHL-6 cells were at 5000/well, with 90 μL/well. 10 μL of the compounds at different concentrations were added to each well. There were 3 replicate wells for each concentration, and the last column, added with DMSO, was used as a vehicle control group. The cultures were continued for 72 hours at 37° C. under 5% CO$_2$. After 72 hours, 100 μL of detection reagent (Cell Viability Assay, Promega, G7573) was added to each well, and the cultures were uniformly mixed for 2 minutes, and incubated at room temperature for 10 minutes. The fluorescence signal value was measured with a microplate reader (PHERAstar FSX). The IC$_{50}$ value of the compound on cell proliferation inhibition was calculated using Origin 9.2 software, and the inhibition rate at the highest concentration of the compound (Max inhi. %) was calculated according to formula (1).

Max inhi. %=(1-T72 administration/T72 vehicle)×100     Formula (1).

OCI-LY10 and TMD-8 cells, in the culture medium of RPMI1640+10% FBS, were cultured in an incubator at 37° C. under 5% CO$_2$. Cells were plated in a 96-well plate. Specifically, OCI-LY10 cells were at 10000/well, and TMD-8 cells were at 8000/well, with 90 μL/well. These cells were cultured at 37° C. under 5% CO$_2$ overnight. On the next day, 10 μL of the compounds at different concentrations were added to each well. There were 3 replicate wells for each concentration, and the last column, added with DMSO, was used as a vehicle control group. The cultures were continued for 72 hours at 37° C. under 5% CO$_2$. After 72 hours, 50 μL of detection reagent (Cell Viability Assay, Promega, G7573) was added to each well, and the cultures were uniformly mixed for 2 minutes, and incubated at room temperature for 10 minutes. The fluorescence signal value was measured with an Envision2104 plate reader (PerkinElmer). The inhibition rate was calculated using formula (2), wherein RLU$_{compound}$ was the readout of the drug treated group, RLU$_{control}$ was the average value of the vehicle control group, and RLU$_{blank}$ was the average value of the cell-free wells. The IC$_{50}$ value was calculated using GraphPad Prism software.

IR (%)=(1-(RLU$_{compound}$-RLU$_{blank}$)/(RLU$_{control}$-RLU$_{blank}$))*100%     formula (2)

The results for IC$_{50}$ values on proliferation inhibition of Mino cells were shown in Table 1.

TABLE 1

IC$_{50}$ value on proliferation inhibition of Mino cells

| Serial No. | Compound No. | IC$_{50}$ (nM) |
|---|---|---|
| 1 | P13I* | 844 |
| 2 | Compound 2 | 633 |
| 3 | Compound 6 | 421 |
| 4 | Compound 8 | 309 |
| 5 | Compound 9 | 367 |
| 6 | Compound 10 | 405 |
| 7 | Compound 11 | 114 |
| 8 | Compound 12 | 183 |
| 9 | Compound 13 | 677 |
| 10 | Compound 17 | 20 |
| 11 | Compound 17-a | 8.0 |
| 12 | Compound 17-b | 7.2 |
| 13 | Compound 18-1 | 18 |
| 14 | Compound 19 | 48 |
| 15 | Compound 20-1 | 32 |
| 16 | Compound 23 | 295 |
| 17 | Compound 24 | 629 |
| 18 | Compound 25 | 282 |
| 19 | Compound 27 | 503 |
| 20 | Compound 32 | 188 |
| 21 | Compound 38 | 81 |
| 22 | Compound 39 | 41 |
| 23 | Compound 40 | 7.3 |
| 24 | Compound 41 | 10.3 |
| 25 | Compound 42 | 15 |
| 26 | Compound 43 | 10 |
| 27 | Compound 44 | 15 |
| 28 | Compound 45 | 9.6 |
| 29 | Compound 46-1 | 27 |
| 30 | Compound 49-1 | 113 |
| 31 | Compound 49-2 | 10 |
| 32 | Compound 50 | 112 |
| 33 | Compound 54 | 200 |
| 34 | Compound 59 | 501 |
| 35 | Compound 60 | 165 |
| 36 | Compound 61 | 100 |
| 37 | Compound 62 | 38 |

*Notes: denoting a trifluoroacetate thereof.

The results for Max inhi. % values on proliferation inhibition of Mino cells were shown in Table 1-1.

TABLE 1-1

Max inhi. % value on proliferation inhibition of Mino cells

| Serial No. | Compound No. | Mino Max inhi. % |
|---|---|---|
| 1 | Compound 15 | 99.8 |
| 2 | Compound 16 | 99.7 |
| 3 | Compound 26 | 74.3 |
| 4 | Compound 29 | 71.2 |
| 5 | Compound 30 | 82.5 |
| 6 | Compound 31 | 78.3 |
| 7 | Compound 48 | 95.7 |
| 8 | Compound 51 | 99.7 |
| 9 | Compound 52 | 99.7 |
| 10 | Compound 53 | 99.6 |
| 11 | Compound 55 | 99.9 |
| 12 | Compound 56 | 99.9 |
| 13 | Compound 57 | 99.2 |
| 14 | Compound 58 | 95.3 |

The results for IC$_{50}$ values on proliferation inhibition of SU-DHL-4 cells were shown in Table 2.

TABLE 2

IC$_{50}$ value on inhibition of SU-DHL-4 cells

| Serial No. | Compound No. | IC$_{50}$ (nM) |
|---|---|---|
| 1 | P13I* | 1184 |
| 2 | Compound 2 | 41 |
| 3 | Compound 8 | 255 |
| 4 | Compound 9 | 295 |
| 5 | Compound 11 | 189 |
| 6 | Compound 12 | 56 |
| 7 | Compound 13 | 70 |
| 8 | Compound 14 | 60 |
| 9 | Compound 17 | 367 |
| 10 | Compound 17-a | 481 |
| 11 | Compound 17-b | 460 |
| 12 | Compound 18-1 | 20 |
| 13 | Compound 19-1 | 394 |
| 14 | Compound 32 | 330 |
| 15 | Compound 37 | 631 |
| 16 | Compound 38 | 469 |
| 17 | Compound 40 | 74 |
| 18 | Compound 41 | 329 |
| 19 | Compound 42 | 382 |
| 20 | Compound 43 | 330 |
| 21 | Compound 45 | 110 |

*Notes: denoting a trifluoroacetate thereof.

The results for Max inhi. % values on proliferation inhibition of SU-DHL-4 cells were shown in Table 2-1.

TABLE 2-1

Max inhi. % value on proliferation inhibition of SU-DHL-4 cells

| Serial No. | Compound No. | SU-DHL-4 Max inhi. % |
|---|---|---|
| 1 | Compound 34-a | 94.4 |
| 2 | Compound 34-b | 99.2 |
| 3 | Compound 36-a | 99.6 |
| 4 | Compound 36-b | 99.8 |

The results for IC$_{50}$ values on proliferation inhibition of SU-DHL-6 cells were shown in Table 2-2.

TABLE 2-2

IC$_{50}$ value on inhibition of SU-DHL-6 cells

| Serial No. | Compound No. | IC$_{50}$ (nM) |
|---|---|---|
| 1 | P13I* | 1638 |
| 2 | Compound 2 | 26 |
| 3 | Compound 6 | 166 |
| 4 | Compound 8 | 399 |
| 5 | Compound 9 | 155 |
| 6 | Compound 10 | 77 |
| 7 | Compound 11 | 109 |
| 8 | Compound 12 | 106 |
| 9 | Compound 14 | 86 |
| 10 | Compound 17 | 744 |
| 11 | Compound 17-a | 524 |
| 12 | Compound 17-b | 662 |
| 13 | Compound 18-1 | 29 |
| 14 | Compound 19 | 782 |
| 15 | Compound 32 | 393 |
| 16 | Compound 38 | 888 |
| 17 | Compound 40 | 54 |
| 18 | Compound 41 | 670 |
| 19 | Compound 42 | 177 |
| 20 | Compound 43 | 407 |
| 21 | Compound 45 | 125 |

*Notes: denoting a trifluoroacetate thereof.

The results for IC$_{50}$ values on proliferation inhibition of OCI-LY10 cells were shown in Table 2-3.

TABLE 2-3

IC$_{50}$ value on inhibition of OCI-LY10 cells

| Serial No. | Compound No. | IC$_{50}$ (nM) |
|---|---|---|
| 1 | P13I* | 29 |
| 2 | Compound 8 | 3 |
| 3 | Compound 17 | 5 |
| 4 | Compound 18-1 | 4 |
| 5 | Compound 19-1 | 23 |
| 6 | Compound 40 | 3 |
| 7 | Compound 42 | 3 |
| 8 | Compound 45 | 3 |

*Notes: denoting a trifluoroacetate thereof.

The results for IC$_{50}$ values on proliferation inhibition of TMD-8 cells were shown in Table 2-4.

TABLE 2-4

IC$_{50}$ value on inhibition of TMD-8 cells

| Serial No. | Compound No. | IC$_{50}$ (nM) |
|---|---|---|
| 1 | P13I* | 104 |
| 2 | Compound 8 | 22 |
| 3 | Compound 17 | 22 |
| 4 | Compound 18-1 | 8 |
| 5 | Compound 19-1 | 14 |
| 6 | Compound 40 | 12 |
| 7 | Compound 42 | 16 |
| 8 | Compound 45 | 16 |

*Notes: denoting a trifluoroacetate thereof.

Conclusion: The compounds synthesized by using the technique of the present disclosure have a significant inhibitory effect on the proliferation of SU-DHL-4 cells and SU-DHL-6 cells (human B lymphoma cells), Mino cells (mantle cell lymphoma cells), and OCI-LY10 cells (diffuse large B cell lymphoma cells) and TMD-8 cells (human diffuse large B lymphoma cells).

2. Pharmacokinetic Experiment in Rats

Objective: In this experiment, a single dose of each test compound was administered to SD rats intravenously and intragastrically, the concentrations of the test compound in plasma of rats were measured, and the pharmacokinetic characteristics and bioavailability of the test compound in rats were evaluated.

Experimental animals: Male SD rats, 200-250 g, 6-8 weeks old, 6 rats/test compound. The experimental animals were purchased from CHENGDU DOSSY EXPERIMENTAL ANIMALS CO., LTD.

Experimental method: On the day of the experiment, 6 SD rats were randomly grouped according to their body weight. The animals were fasted with water available for 12 to 14 hours one day before the administration of a test compound, and were fed 4 hours after the administration. The administration information was shown in Table 3.

TABLE 3

Administration information

| Group | No. of rats Male | Test compound | Administration dosage* (mg/kg) | Administration concentration (mg/mL) | Administration volume (mL/kg) | Collected samples | Mode of administration | Vehicle |
|---|---|---|---|---|---|---|---|---|
| G1 | 3 | Compound of the present disclosure | 5 | 1 | 5 | Plasma | Intravenously | 5% DMSO + 5% Solutol + 90% Saline |
| G2 | 3 | Compound of the present disclosure | 20 | 2 | 10 | Plasma | Intragastrically | 0.5% MC |

*Dosage is calculated based on free base.

Sampling: Before and after the administration, 0.1 ml of blood was taken from the orbit of the rats under isoflurane anesthesia, and placed in an EDTAK2 centrifuge tube. Centrifugation was carried out at 5000 rpm at 4° C. for 10 min and the plasma was collected.

Time points for plasma collection in G1 group: 0, 5 m, 15 m, 30 m, 1 h, 2 h, 4 h, 6 h, 8 h, and 24 h.

Time points for plasma collection in G2 group: 0, 15 m, 30 m, 1 h, 2 h, 4 h, 6 h, 8 h, and 24 h.

Before analysis and detection, all samples were stored at −80° C. The samples were analyzed quantitatively by LC-MS/MS. The results were shown in Table 4.

TABLE 4

The pharmacokinetic parameters of compounds in plasma of rats

| Test compounds | Mode of administration* | AUC$_{0-t}$ (ng/ml · h) | F (%) |
|---|---|---|---|
| P13I** | i.g. (20 mg/kg) | 0$^\#$ | 0$^\#$ |
| Compound 1 | i.g. (20 mg/kg) | 479 ± 197 | N/A |
| Compound 2 | i.g. (20 mg/kg) | 18.6 ± 2.8 | N/A |
| Compound 3 | i.g. (20 mg/kg) | 211 ± 46 | N/A |
| Compound 4 | i.g. (20 mg/kg) | 36.0 ± 10 | N/A |
| Compound 5 | i.g. (20 mg/kg) | 81.7 ± 68 | N/A |
| Compound 6 | i.g. (20 mg/kg) | 328 ± 41 | N/A |
| Compound 7 | i.g. (20 mg/kg) | 105 ± 54 | N/A |
| Compound 8 | i.g. (20 mg/kg) | 634 ± 238 | 11.8 ± 4.4 |
| Compound 9 | i.g. (20 mg/kg) | 8.93 ± 4.3 | N/A |
| Compound 17 | i.g. (20 mg/kg) | 2344 ± 274 | 6.57 ± 0.77 |
| Compound 18-1 | i.g. (20 mg/kg) | 218 ± 68 | N/A |
| Compound 19-1 | i.g. (20 mg/kg) | 1263 ± 117 | N/A |
| Compound 20-1 | i.g. (20 mg/kg) | 891 ± 164 | N/A |

TABLE 4-continued

The pharmacokinetic parameters of compounds in plasma of rats

| Test compounds | Mode of administration* | $AUC_{0-t}$ (ng/ml · h) | F (%) |
|---|---|---|---|
| Compound 21 | i.g. (20 mg/kg) | 3205 ± 973 | 12.4 ± 3.8 |
| Compound 32 | i.g. (20 mg/kg) | 322 ± 64 | N/A |
| Compound 37 | i.g. (20 mg/kg) | 473 ± 105 | N/A |
| Compound 49-2 | i.g. (20 mg/kg) | 475 ± 237 | 4.14 ± 2.1 |

*Notes: i.g. (intragastrically) administration of the compounds.
**Notes: denoting a trifluoroacetate thereof;
Notes: The concentration at each detection point was lower than the lower limit of quantification by 0.5 ng/mL.

Conclusion: The compounds synthesized by using the technique of the present disclosure had a certain oral bioavailability in rats.

3. Pharmacokinetic Experiment in Mice

Objective: In this experiment, a single dose of each test compound was administered to ICR mice intravenously and intragastrically, the concentrations of the test compound in plasma of mice were measured, and the pharmacokinetic characteristics and bioavailability of the test compound in mice were evaluated.

Experimental animals: Male ICR mice, 20-25 g, 6-8 weeks old, 24 mice/compound. The experimental animals were purchased from CHENGDU DOSSY EXPERIMENTAL ANIMALS CO., LTD.

Experimental method: On the day of the experiment, 24 ICR mice were randomly grouped according to their body weight. The animals were fasted with water available for 12 to 14 hours one day before the administration of a test compound, and were fed 4 hours after the administration. The administration information was shown in Table 5.

TABLE 5

| | | | Administration information | | | | | |
|---|---|---|---|---|---|---|---|---|
| Group | No. of mice Male | Test compound | Administration dosage* (mg/kg) | Administration concentration (mg/mL) | Administration volume (mL/kg) | Collected samples | Mode of administration | Vehicle |
| G1 | 9 | Compound of the present disclosure | 5 | 1 | 5 | Plasma | Intravenously | 5% DMSO + 5% Solutol + 90% Saline |
| G2 | 15 | Compound Compound | 10 | 1 | 10 | Plasma | Oral (intragastrically) | 0.5% MC |

*Dosage is calculated based on free base;

Sampling: Before and after the administration, 0.06 ml of blood was taken from the orbit of the mice under isoflurane anesthesia, and placed in an $EDTAK_2$ centrifuge tube. Centrifugation was carried out at 5000 rpm at 4° C. for 10 min and the plasma was collected.

Time points for plasma collection in G1 group: 0, 5 min, 15 min, 30 min, 1 h, 2 h, 4 h, 6 h, 8 h, and 24 h;

Time points for plasma collection in G2 group: 0, 15 min, 30 min, 1 h, 2 h, 4 h, 6 h, 8 h, and 24 h;

Before analysis and detection, all samples were stored at −80° C. The samples were analyzed quantitatively by LC-MS/MS. The results were shown in Table 6.

TABLE 6

The pharmacokinetic parameters of test compounds in mice

| Test compounds | Mode of administration* | AUC0-t (ng/ml · h) | F (%) |
|---|---|---|---|
| Compound 17 | i.g. (10 mg/kg) | 2426 | 10.8 |

*Notes: i.g. (intragastrically) administration of the compounds.

Conclusion: The compounds synthesized by using the technique of the present disclosure had a certain oral bioavailability in mice.

4. Pharmacokinetic Experiment in Rats

Objective: In this experiment, a single dose of each test compound was administered to SD rats intravenously and intragastrically, the concentrations of the test compound in plasma of rats were measured, and the pharmacokinetic characteristics and bioavailability of the test compound in rats were evaluated.

Experimental animals: Male SD rats, 200-250 g, 6-8 weeks old, 6 rats/compound. The experimental animals were purchased from CHENGDU DOSSY EXPERIMENTAL ANIMALS CO., LTD.

Experimental method: On the day of the experiment, 6 SD rats were randomly grouped according to their body weight. The animals were fasted with water available for 12 to 14 hours one day before the administration of a test compound, and were fed 4 hours after the administration. The administration information was shown in Table 7.

TABLE 7

Administration information

| Group | No. of rats Male | Test compound | Administration dosage* (mg/kg) | Administration concentration (mg/mL) | Administration volume (mL/kg) | Collected samples | Mode of administration | Vehicle |
|---|---|---|---|---|---|---|---|---|
| G1 | 3 | Compound Compound | 5 | 1 | 5 | Plasma | Intravenously | 5% DMSO + 5% Solutol + 90% Saline |
| G2 | 3 | Compound Compound | 20 | 2 | 10 | Plasma | Oral (intragastrically) | 5% DMSO + 5% Solutol + 30% PEG-400 + 60% (20%SBE-β-CD) |

*Dosage is calculated based on free base.

Sampling: Before and after the administration, 0.1 mL of blood was taken from the orbit of the rats under isoflurane anesthesia, and placed in an EDTAK2 centrifuge tube. Centrifugation was carried out at 5000 rpm at 4° C. for 10 min and the plasma was collected.

Time points for plasma collection in G1 group: 0, 5 min, 15 min, 30 min, 1 h, 2 h, 4 h, 6 h, 8 h, and 24 h.

Time points for plasma collection in G2 group: 0, 15 min, 30 min, 1 h, 2 h, 4 h, 6 h, 8 h, and 24 h.

Before analysis and detection, all samples were stored at −80° C. The samples were analyzed quantitatively by LC-MS/MS. The results were shown in Table 8.

TABLE 8

The pharmacokinetic parameters of compounds in plasma of rats

| Test compounds | Mode of administration* | $AUC_{0-t}$ (ng/ml · h) | F (%) |
|---|---|---|---|
| P13I** | i.g. (20 mg/kg) | 0# | 0# |
| Compound 38 | i.g. (20 mg/kg) | 7257 ± 2863 | 13.3 ± 5.2 |
| Compound 39 | i.g. (20 mg/kg) | 2831 ± 474 | 9.1 ± 1.5 |
| Compound 40 | i.g. (20 mg/kg) | 5419 ± 1263 | 17.4 ± 4.0 |
| Compound 41 | i.g. (20 mg/kg) | 7906 ± 1099 | 10.8 ± 1.5 |
| Compound 42 | i.g. (20 mg/kg) | 1195 ± 327 | 9.14 ± 2.5 |
| Compound 43 | i.g. (20 mg/kg) | 4495 ± 886 | 11.0 ± 2.2 |
| Compound 44 | i.g. (20 mg/kg) | 877 ± 98 | 5.73 ± 0.64 |
| Compound 45 | i.g. (20 mg/kg) | 3437 ± 1491 | 19.7 ± 8.5 |

*Notes: i.g. (intragastrically) administration of the compounds;
**Notes: Free form;
Notes: The concentration at each detection point was lower than the lower limit of quantification by 0.5 ng/mL.

Conclusion: The compounds synthesized by using the technique of the present disclosure had a certain oral bioavailability in rats.

5. Detection of BTK Degradation in Mino Cells

Mino human mantle cell lymphoma cell line was purchased from ATCC and cultured under the following conditions: in RPMI-1640+15% FBS+1% double antibody, in an incubator at 37° C. under 5% $CO_2$. Cells were plated in a 6-well plate, with $5×10^5$ cells/well. After plating, the compounds at different concentrations were added and cultured in an incubator at 37° C. under 5% $CO_2$ for 48 hours. After culturing, the cells were collected, and RIPA lysis buffer (Beyotime, Cat. P0013B) was added. The cells were lysed on ice for 15 minutes, and centrifuged at 12000 rpm at 4° C. for 10 minutes. The protein sample of the supernatant was collected, and the protein was quantified by using the BCA kit (Beyotime, Cat. P0009), and then the protein was diluted to 0.25 mg/mL. The expressions of BTK (CST, Cat. 8547S) and the internal reference β-actin (CST, Cat. 3700S) were detected using a fully automated western blot quantitative analyzer (Proteinsimple) with a kit (Protein simple, Cat. SM-W004). The expression level of BTK relative to the internal reference was calculated using Compass software, and the $DC_{50}$ value was calculated using Origen9.2 software according to formula (3). Specifically, the BTK administration denoted the expression level of BTK in administration groups at different doses, and the BTK vehicle denoted the expression level of BTK in the vehicle control group. The results were shown in Table 9.

$$BTK\ \% = BTK\ administration/BTK\ vehicle \times 100 \quad \text{formula (3)}$$

TABLE 9

$DC_{50}$ value of BTK degradation in Mino cells

| Serial No. | Compound No. | $DC_{50}$ (nM) |
|---|---|---|
| 1 | Compound 8-1 | 22.9 |
| 2 | Compound 17 | 10.9 |

Conclusion: The compounds synthesized by using the technique of the present disclosure had a significant degrading effect on BTK in Mino cells.

6. Detection of BTK Protein Degradation in Spleen of Mice

Female ICR mice, 6-8 weeks old, were purchased from BEIJING VITAL RIVER LABORATORY ANIMAL TECHNOLOGY CO., LTD, and the experiment was started after 3 days of adaptation. After 3 consecutive days of intragastric administration of different doses of the compound, the spleen of mice was taken, the spleen cells were collected, and RIPA lysis buffer (Beyotime, Cat. P0013B) was added. The cells were lysed on ice for 15 minutes, and centrifuged at 12000 rpm at 4° C. for 10 minutes. The protein sample of the supernatant was collected, and the protein was quantified by using the BCA kit (Beyotime, Cat. P0009), and then the protein was diluted to 0.25 mg/mL. The expressions of BTK (CST, Cat. 8547S) and the internal reference β-actin (CST, Cat. 3700S) were detected using a fully automated western blot quantitative analyzer (Proteinsimple). The expression level of BTK relative to the internal reference was calculated using Compass software, and the $DD_{50}$ value was calculated using Origen9.2 software according to formula (4). Specifically, the $BTK_{administration}$ denoted the expression level of BTK in administration groups at different doses, and the $BTK_{vehicle}$ denoted the expression level of BTK in the vehicle control group. The results were shown in Table 10.

$$BTK\% = BTK_{administration}/BTK_{vehicle} \times 100 \qquad \text{formula (4)}$$

TABLE 10

$DD_{50}$ value of compounds on BTK protein degradation in spleen of mice

| Serial No. | Compound No. | $DD_{50}$ (mg/kg) |
|---|---|---|
| 1 | Compound 8-1 | 3.8 |
| 2 | Compound 17 | 3.8 |
| 3 | Compound 17-a | 19.8 |
| 4 | Compound 17-b | 2.2 |
| 5 | Compound 18-1 | 1.9 |
| 6 | Compound 40 | 2.1 |
| 7 | Compound 42 | 1.9 |
| 8 | Compound 45 | 1.4 |

Conclusion: The compounds synthesized by using the technique of the present disclosure had a significant degrading effect on BTK protein in spleen of mice.

7. In Vitro Kinase Detection

Kinases BTK wt (Carna, Cat. No 08-180) and BTK C481S (Carna, Cat. No 08-547) were prepared into a 2.5× kinase solution, and the substrates FAM-P2 (GL Biochem, Cat. No. 112394) and ATP ((Sigma, Cat. No. A7699-4G) were prepared into a 2.5× substrate solution, respectively. 5 μL of the compounds at different concentrations were added to a 384-well plate, and 10 μL of 2.5× kinase solution was added, the cultures were incubated at room temperature for 10 minutes. 10 μL of 2.5× substrate solution was added, and the mixture was incubated at 28° C. for an appropriate period of time. The reaction was stopped by adding 30 μL of stop solution, and the detection was carried out using Caliper EZ reader2 instrument. The $IC_{50}$ value was calculated using XLFit excel add-in version 5.4.0.8 software. The calculation formula of the inhibition rate was shown in formula (5), wherein max denoted the readout of the DMSO control, min denoted the readout of the negative control, and conversion denoted the readout of the compound $$\text{Inhibition rate \%} = (\text{max}-\text{conversion})/(\text{max}-\text{min})*100. \qquad \text{formula (5)}$$

The results were shown in Table 11:

TABLE 11

$IC_{50}$ value on BTK wt/C481S kinase inhibition

| Serial No. | Compound No. | BTK C481S $IC_{50}$ (nM) | BTK wt $IC_{50}$ (nM) |
|---|---|---|---|
| 1 | Compound 17 | 8 | 6.3 |

Conclusion: The compounds synthesized by using the technique of the present disclosure had a significant inhibitory effect on BTKwt/C481S kinase.

The invention claimed is:
1. A compound represented by formula (I):

B-L-K  (I)

or a pharmaceutically acceptable salt or stereoisomer thereof, wherein:
K is:

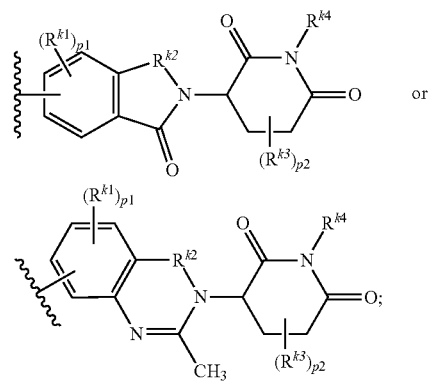

L is -Ak1-Cy1-Ak2-Cy2-Ak3-Cy3-Ak4-Cy4-Ak5-, wherein L is bonded to B on the left side and bonded to a carbon atom of the phenyl of the fused heterocyclylene on the right side;
Ak1 is a bond or —$CH_2$—;
Ak2 is a bond;
Ak3 is a bond or —O—;
Ak4 is a bond;
Ak5 is a bond;
Cy1 is a $C_{3-12}$ cycloalkylene or a 3- to 12-membered heterocyclylene, wherein the 3- to 12-membered heterocyclylene contains 1, 2, 3, or 4N heteroatoms, and further wherein the C3-12 cycloalkylene or 3- to 12-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;
Cy2 is a bond, a $C_{3-12}$ cycloalkylene, or a 3- to 12-membered heterocyclylene, wherein the 3- to 12-membered heterocyclylene contains 1, 2, 3, or 4N heteroatoms, and further wherein the C3-12 cycloalkylene or 3- to 12-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;
Cy3 is a bond or a 3- to 12-membered heterocyclylene, wherein the 3- to 12-membered heterocyclylene contains 1, 2, 3, or 4N heteroatoms, and further wherein the 3- to 12-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;
Cy4 is a bond or a 3- to 12-membered heterocyclylene, wherein the 3- to 12-membered heterocyclylene contains 1, 2, 3, or 4N heteroatoms, and further wherein the 3- to 12-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;
B is —B4-B3-B2-W1-B1;
B1 is phenyl or pyridinyl, wherein the phenyl or pyridinyl is optionally substituted with 1, 2, 3, or 4 independently selected $R^{b1}$ substituents;
B2 is phenylene, wherein the phenylene is optionally substituted with 1, 2, 3, or 4 independently selected $R^{b2}$ substituents;

B3 is a fused 8- to 10-membered heterocyclylene, wherein the fused 8- to 10-membered heterocyclylene contains 1, 2, 3, or 4 heteroatoms independently selected from the group consisting of N, O, and S, and further wherein the fused 8- to 10-membered heterocyclylene is optionally substituted with 1, 2, 3, or 4 independently selected $R^{b3}$ substituents;

B4 is a saturated 5- or 6-membered heterocyclylene, wherein the saturated 5- or 6-membered heterocyclylene contains 1N heteroatom, and further wherein the saturated 5- or 6-membered heterocyclylene is optionally substituted with 1, 2, 3, or 4 independently selected $R^{b4}$ substituents;

W1 is —C(O)NH—, —NH—, —NHC(O)—, —O—, or —S—;

each $R^{b1}$ is independently F, Cl, Br, I, CN, $C_{1-4}$ alkyl, $C(O)NH_2$, $NH_2$, OH, or $OC_{1-4}$ alkyl, wherein each $C_{1-4}$ alkyl and $OC_{1-4}$ alkyl is optionally and independently substituted with 1, 2, 3, or 4 substituents independently selected from the group consisting of F, Cl, Br, I, CN, $C_{1-4}$ alkyl, $C(O)NH_2$, $NH_2$, OH, and $OC_{1-4}$ alkyl;

each $R^{b2}$ is independently F, Cl, Br, I, CN, $C_{1-4}$ alkyl, $C(O)NH_2$, $NH_2$, OH, or $OC_{1-4}$ alkyl, wherein each $C_{1-4}$ alkyl and $OC_{1-4}$ alkyl is optionally and independently substituted with 1, 2, 3, or 4 substituents independently selected from the group consisting of F, Cl, Br, I, CN, $C_{1-4}$ alkyl, $C(O)NH_2$, $NH_2$, OH, and $OC_{1-4}$ alkyl;

each $R^{b3}$ is independently F, Cl, Br, I, CN, $C_{1-4}$ alkyl, $C(O)NH_2$, $NH_2$, OH, or $OC_{1-4}$ alkyl, wherein each $C_{1-4}$ alkyl and $OC_{1-4}$ alkyl is optionally and independently substituted with 1, 2, 3, or 4 substituents independently selected from the group consisting of F, Cl, Br, I, CN, $C_{1-4}$ alkyl, $C(O)NH_2$, $NH_2$, OH, and $OC_{1-4}$ alkyl;

each $R^{b4}$ is independently F, Cl, Br, I, CN, $C_{1-4}$ alkyl, $C(O)NH_2$, $NH_2$, OH, or $OC_{1-4}$ alkyl, wherein each $C_{1-4}$ alkyl and $OC_{1-4}$ alkyl is optionally and independently substituted with 1, 2, 3, or 4 substituents independently selected from the group consisting of F, Cl, Br, I, CN, $C_{1-4}$ alkyl, $C(O)NH_2$, $NH_2$, OH, and $OC_{1-4}$ alkyl;

$R^{k1}$ is H, F, Cl, Br, I, CN, $C_{1-4}$ alkyl, C(O)OH, $NH_2$, OH, or $OC_{1-4}$ alkyl;

$R^{k2}$ is —$CH_2$— or —C(O)—;

$R^{k3}$ is H, F, Cl, Br, I, CN, $C_{1-4}$ alkyl, C(O)OH, $NH_2$, OH, or $OC_{1-4}$ alkyl;

$R^{k4}$ is H, F, Cl, Br, I, CN, $C_{1-4}$ alkyl, C(O)OH, $NH_2$, OH, or $OC_{1-4}$ alkyl;

p1 is 0, 1, 2, 3, or 4; and p2 is 0, 1, 2, 3, or 4;

with the provisos that:

(1) if Ak1 is —$CH_2$— and Ak3 is —O—, then Ak1 and Ak3 are not directly bonded to one another;

(2) if Ak3 is —O—, then Ak3 is not directly bonded to B4;

(3) if Cy2 is a bond, Cy3 is a bond, and Cy4 is a bond, then Ak1 is —$CH_2$— bonded to B4; and (4) if at least four of Ak1, Ak3, Cy1, Cy2, Cy3, and Cy4 is not a bond, then at least one of Cy1, Cy2, Cy3, and Cy4 is not piperidinediyl, piperazinediyl, pyridinediyl, or pyrimidinediyl.

2. The compound according to claim 1, or a pharmaceutically acceptable salt or stereoisomer thereof, wherein the pharmaceutically acceptable salt is the trifluoracetate salt.

3. The compound according to claim 1, or a pharmaceutically acceptable salt or stereoisomer thereof, wherein:

Cy1 is a monocyclic $C_{4-7}$ cycloalkylene, fused $C_{5-10}$ cycloalkylene, spirocyclic $C_{6-12}$ cycloalkylene, bridged $C_{6-10}$ cycloalkylene, monocyclic 4- to 7-membered heterocyclylene, fused 5- to 10-membered heterocyclylene, spirocyclic 6- to 12-membered heterocyclylene, or bridged 7- to 10-membered heterocyclylene, wherein the monocyclic 4- to 7-membered heterocyclylene, fused 5- to 10-membered heterocyclylene, spirocyclic 6- to 12-membered heterocyclylene, or bridged 7- to 10-membered heterocyclylene contains 1, 2, 3, or 4N heteroatoms, and further wherein the monocyclic $C_{4-7}$ cycloalkylene, fused $C_{5-10}$ cycloalkylene, spirocyclic $C_{6-12}$ cycloalkylene, bridged $C_{6-10}$ cycloalkylene, monocyclic 4- to 7-membered heterocyclylene, fused 5- to 10-membered heterocyclylene, spirocyclic 6- to 12-membered heterocyclylene, or bridged 7- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy2 is a bond, a monocyclic $C_{4-7}$ cycloalkylene, fused $C_{5-10}$ cycloalkylene, spirocyclic $C_{6-12}$ cycloalkylene, bridged $C_{6-10}$ cycloalkylene, monocyclic 4- to 7-membered heterocyclylene, fused 5- to 10-membered heterocyclylene, spirocyclic 6- to 12-membered heterocyclylene, or bridged 7- to 10-membered heterocyclylene, wherein the monocyclic 4- to 7-membered heterocyclylene, fused 5- to 10-membered heterocyclylene, spirocyclic 6- to 12-membered heterocyclylene, or bridged 7- to 10-membered heterocyclylene contains 1, 2, 3, or 4N heteroatoms, and further wherein the monocyclic $C_{4-7}$ cycloalkylene, fused $C_{5-10}$ cycloalkylene, spirocyclic $C_{6-12}$ cycloalkylene, bridged $C_{6-10}$ cycloalkylene, monocyclic 4- to 7-membered heterocyclylene, fused 5- to 10-membered heterocyclylene, spirocyclic 6- to 12-membered heterocyclylene, or bridged 7- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy3 is a bond, monocyclic 4- to 7-membered heterocyclylene, fused 5- to 10-membered heterocyclylene, spirocyclic 6- to 12-membered heterocyclylene, or bridged 7- to 10-membered heterocyclylene, wherein the monocyclic 4- to 7-membered heterocyclylene, fused 5- to 10-membered heterocyclylene, spirocyclic 6- to 12-membered heterocyclylene, or bridged 7- to 10-membered heterocyclylene contains 1, 2, 3, or 4N heteroatoms, and further wherein the monocyclic 4- to 7-membered heterocyclylene, fused 5- to 10-membered heterocyclylene, spirocyclic 6- to 12-membered heterocyclylene, or bridged 7- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy4 is a bond, monocyclic 4- to 7-membered heterocyclylene, fused 5- to 10-membered heterocyclylene, spirocyclic 6- to 12-membered heterocyclylene, or bridged 7- to 10-membered heterocyclylene, wherein the monocyclic 4- to 7-membered heterocyclylene, fused 5- to 10-membered heterocyclylene, spirocyclic 6- to 12-membered heterocyclylene, or bridged 7- to 10-membered heterocyclylene contains 1, 2, 3, or 4N heteroatoms, and further wherein the monocyclic 4- to 7-membered heterocyclylene, fused 5- to 10-membered heterocyclylene, spirocyclic 6- to 12-membered heterocyclylene, or bridged 7- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

B3 is pyrazolotetrahydropyrimidinylene, imidazotetrahydropyrimidinylene, pyrazolopyrimidinylene, imidazopyrimidinylene, pyrazolopyrazinylene, or imidazopyrazinylene, wherein the pyrazolotetrahydropyrimidinylene, imidazotetrahydropyrimidinylene, pyrazolopyrimidinylene, imidazopyrimidinylene, pyrazolopyrazinylene, or imidazopyrazinylene is optionally substituted with 1, 2, 3, or 4 independently selected $R^{b3}$ substituents;

B4 is pyrrolidinylene or piperidinylene, wherein the pyrrolidinylene or piperidinylene is optionally substituted with 1, 2, 3, or 4 independently selected $R^{b4}$ substituents; and W1 is —C(O)NH—, —NHC(O)—, or —O—.

4. The compound according to claim 3, or a pharmaceutically acceptable salt or stereoisomer thereof, wherein:

Cy1 is cyclobutylene, cyclopentylene, cyclohexylene, fused cyclopentylene, fused cyclohexylene, spirocyclic cyclohexylene, azetidinylene, pyrrolidinylene, piperidinylene, piperazinylene, pyrrolylene, pyrazolylene, imidazolylene, triazolylene, tetrazolylene, pyridinylene, pyridazinylene, pyrimidinylene, pyrazinylene, fused pyrrolidinylene, fused piperidinylene, spirocyclic piperidinylene,

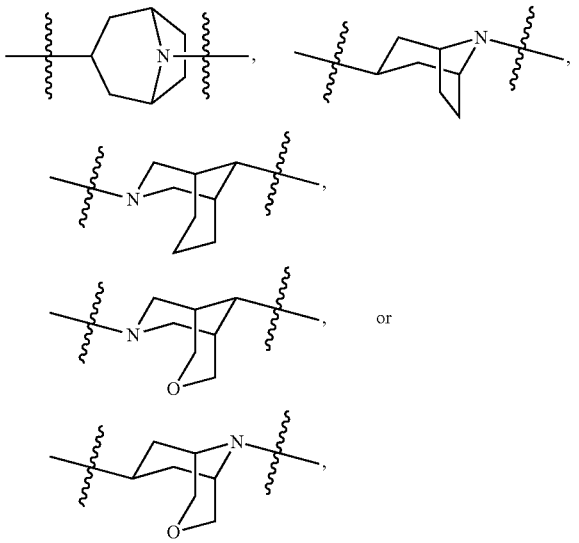

wherein Cy1 is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy2 is a bond, cyclobutylene, cyclopentylene, cyclohexylene, fused cyclopentylene, fused cyclohexylene, spirocyclic cyclohexylene, azetidinylene, pyrrolidinylene, piperidinylene, piperazinylene, pyrrolylene, pyrazolylene, imidazolylene, triazolylene, tetrazolylene, pyridinylene, pyridazinylene, pyrimidinylene, pyrazinylene, fused pyrrolidinylene, fused piperidinylene, spirocyclic piperidinylene,

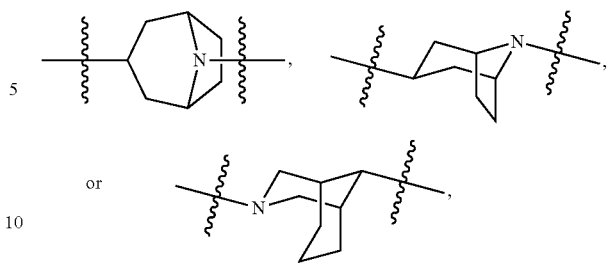

wherein Cy2 is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy3 is a bond, azetidinylene, pyrrolidinylene, piperidinylene, piperazinylene, pyrrolylene, pyrazolylene, imidazolylene, triazolylene, tetrazolylene, pyridinylene, pyridazinylene, pyrimidinylene, pyrazinylene, fused pyrrolidinylene, fused piperidinylene, spirocyclic piperidinylene,

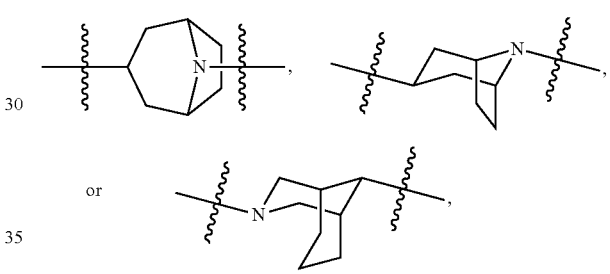

wherein Cy3 is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy4 is a bond, azetidinylene, pyrrolidinylene, piperidinylene, piperazinylene, pyrrolylene, pyrazolylene, imidazolylene, triazolylene, tetrazolylene, pyridinylene, pyridazinylene, pyrimidinylene, pyrazinylene, fused pyrrolidinylene, fused piperidinylene, spirocyclic piperidinylene,

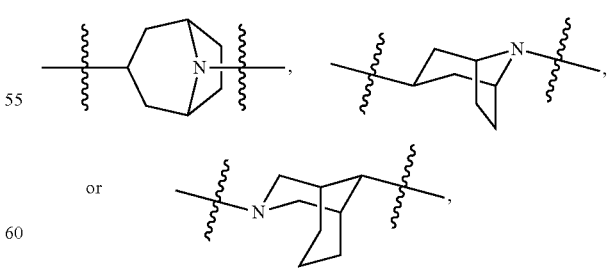

wherein Cy4 is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

B is:

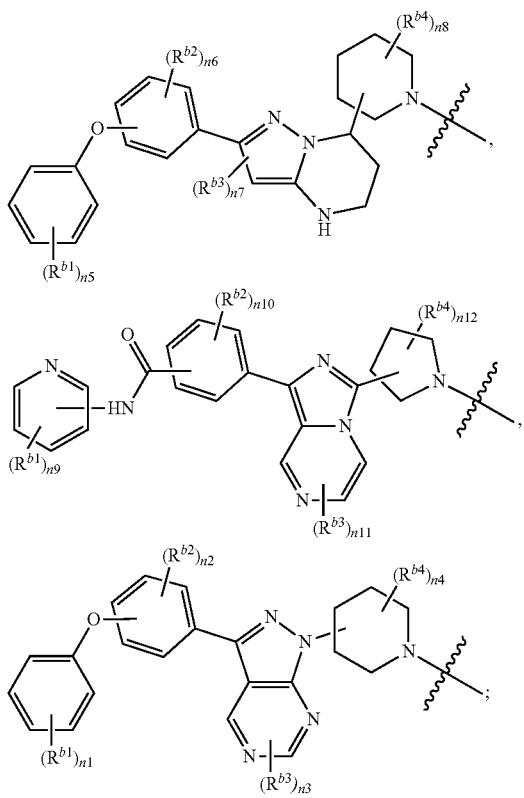

- each $R^{b1}$ is independently F, Cl, Br, I, CN, CH$_3$, C(O)NH$_2$, NH$_2$, OH, or OCH$_3$, wherein each CH$_3$ and OCH$_3$ is optionally and independently substituted with 1, 2, or 3 substituents independently selected from the group consisting of F, Cl, Br, and I;
- each $R^{b2}$ is independently F, Cl, Br, I, CN, CH$_3$, C(O)NH$_2$, NH$_2$, OH, or OCH$_3$, wherein each CH$_3$ and OCH$_3$ is optionally and independently substituted with 1, 2, or 3 substituents independently selected from the group consisting of F, Cl, Br, and I;
- each $R^{b3}$ is independently F, Cl, Br, I, CN, CH$_3$, C(O)NH$_2$, NH$_2$, OH, or OCH$_3$, wherein each CH$_3$ and OCH$_3$ is optionally and independently substituted with 1, 2, or 3 substituents independently selected from the group consisting of F, Cl, Br, and I;
- each $R^{b4}$ is independently F, Cl, Br, I, CN, CH$_3$, C(O)NH$_2$, NH$_2$, OH, or OCH$_3$, wherein each CH$_3$ and OCH$_3$ is optionally and independently substituted with 1, 2, or 3 substituents independently selected from the group consisting of F, Cl, Br, and I;
- n1 is 0, 1, 2, 3, or 4;
- n2 is 0, 1, 2, 3, or 4;
- n3 is 0, 1, 2, 3, or 4;
- n4 is 0, 1, 2, 3, or 4;
- n5 is 0, 1, 2, 3, or 4;
- n6 is 0, 1, 2, 3, or 4;
- n7 is 0, 1, 2, 3, or 4;
- n8 is 0, 1, 2, 3, or 4;
- n9 is 0, 1, 2, 3, or 4;
- n10 is 0, 1, 2, 3, or 4;
- n11 is 0, 1, 2, 3, or 4;
- n12 is 0, 1, 2, 3, or 4;
- $R^{k1}$ is H, F, Cl, Br, I, NH$_2$, or OH;
- $R^{k3}$ is H, F, Cl, Br, I, NH$_2$, or OH;
- $R^{k4}$ is H, F, Cl, Br, I, NH$_2$, or OH;
- p1 is 0, 1, or 2; and
- p2 is 0, 1, or 2.

5. The compound according to claim 4, or a pharmaceutically acceptable salt or stereoisomer thereof, wherein:

K is:

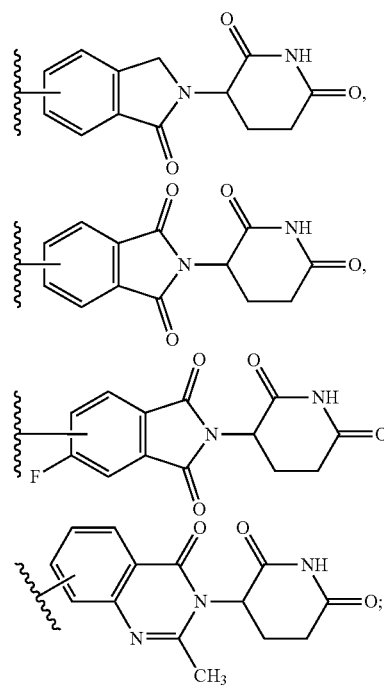

L is:

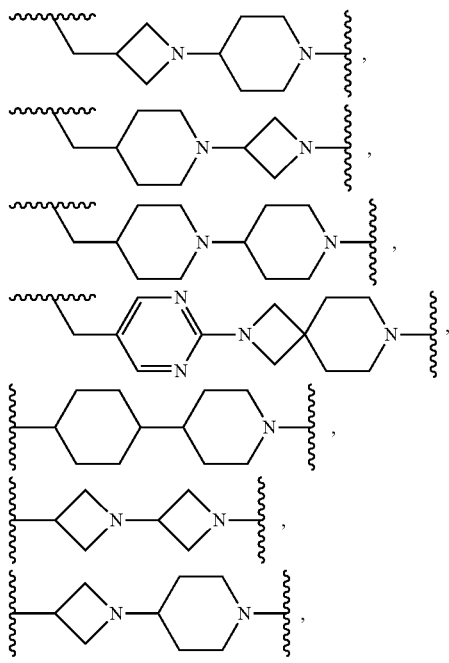

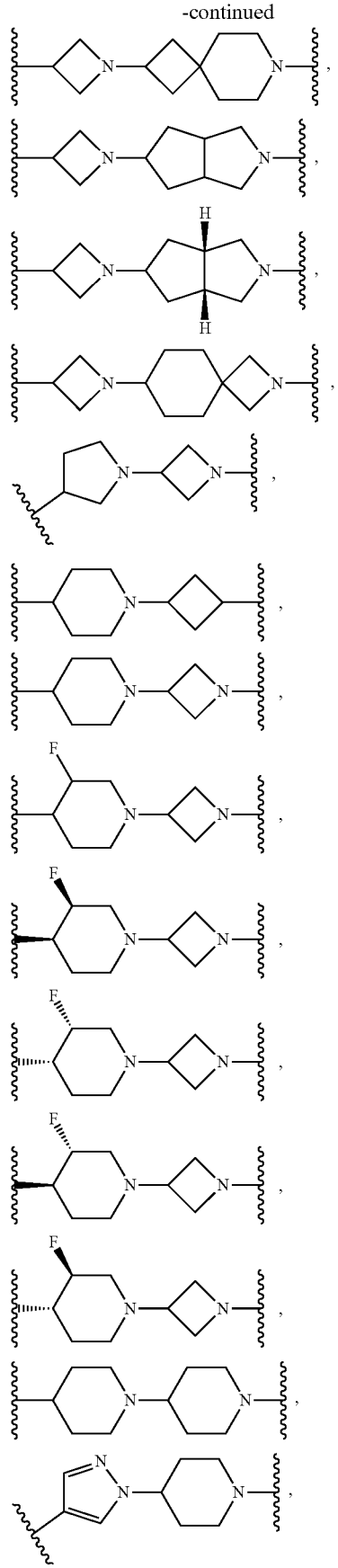
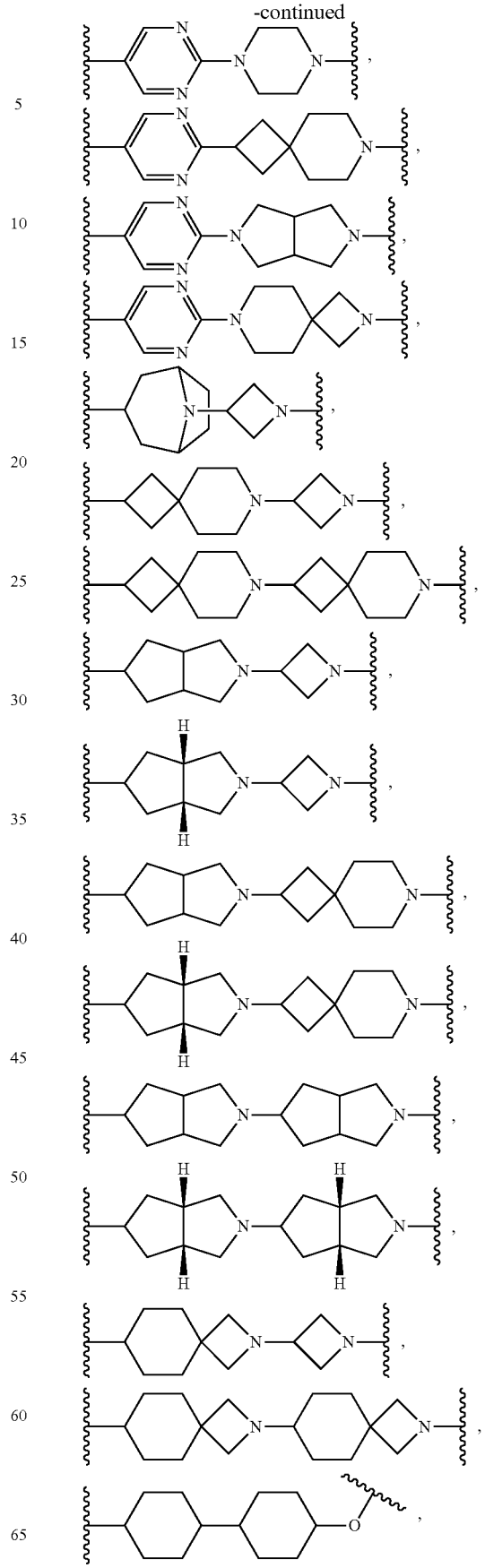

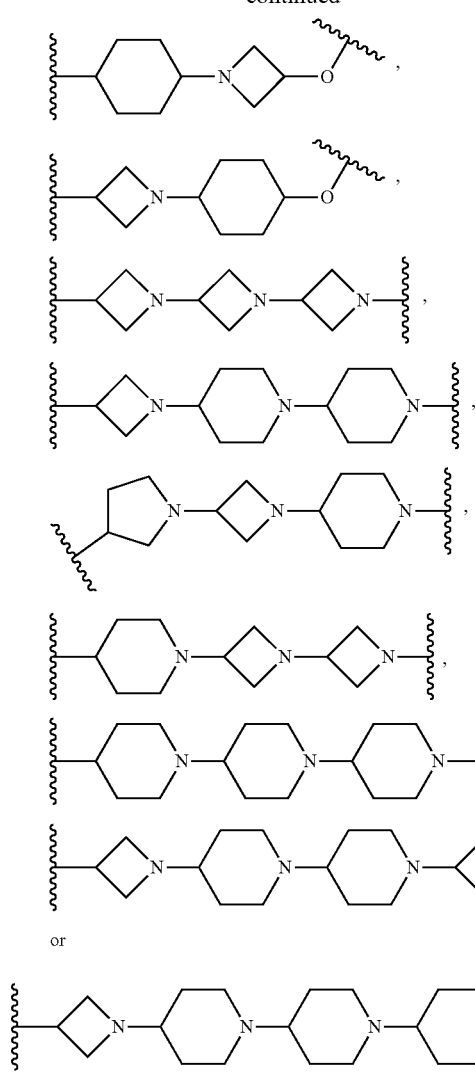
wherein L is bonded to B on the left side and bonded to a carbon atom of the phenyl of the fused heterocyclylene on the right side; and B is:
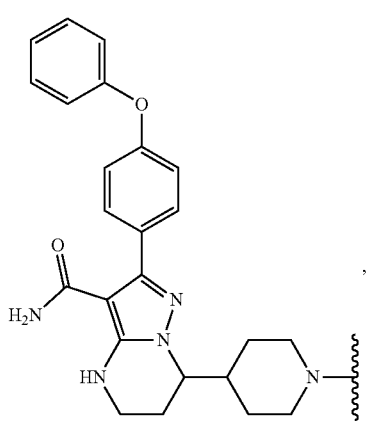
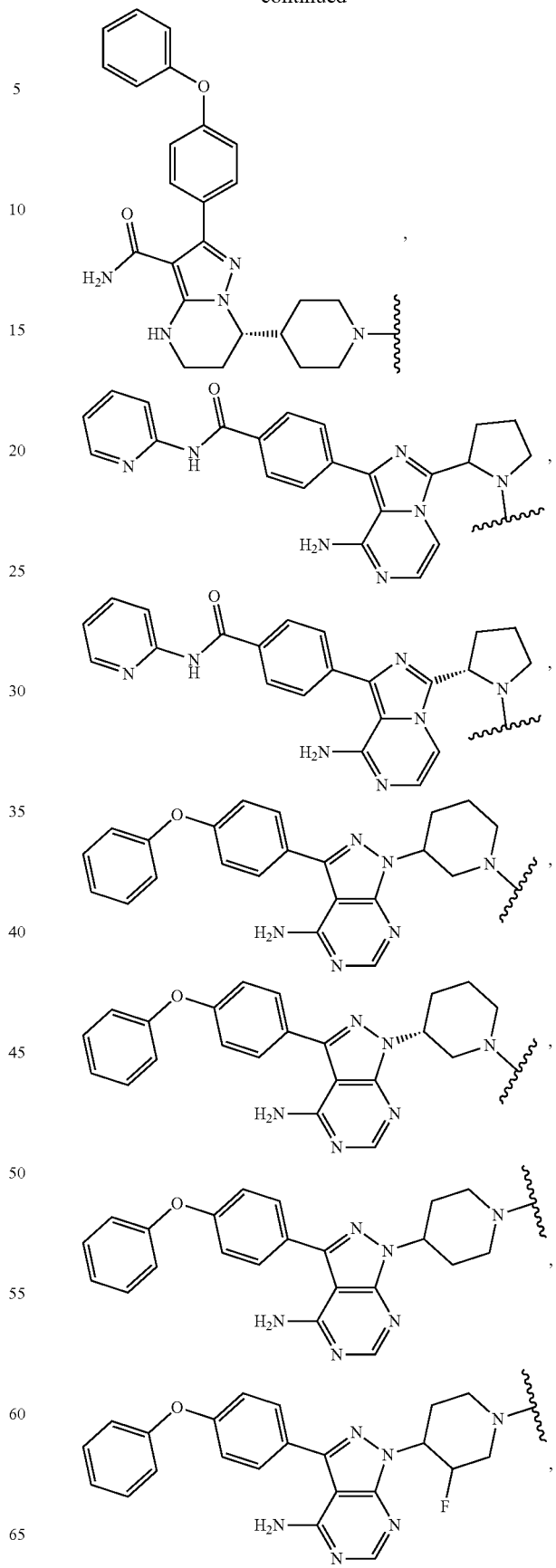

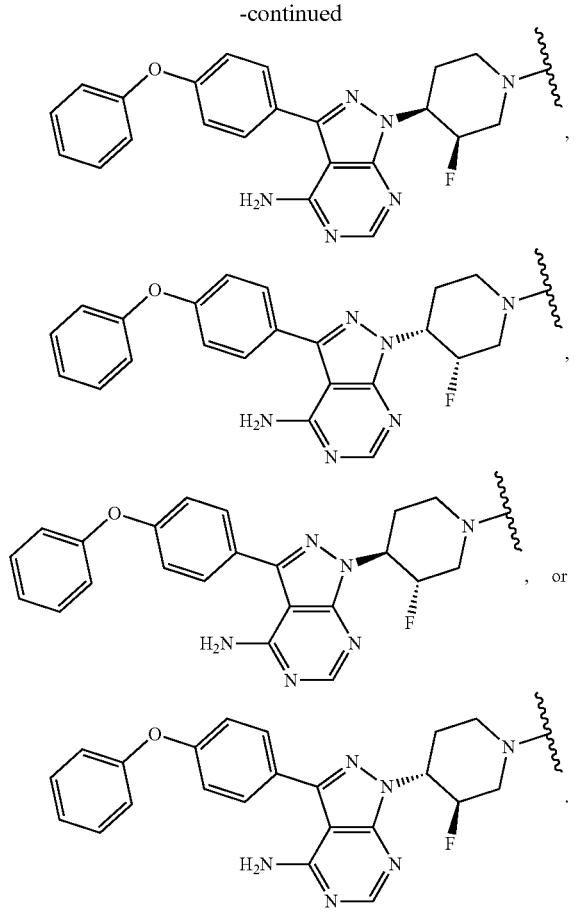
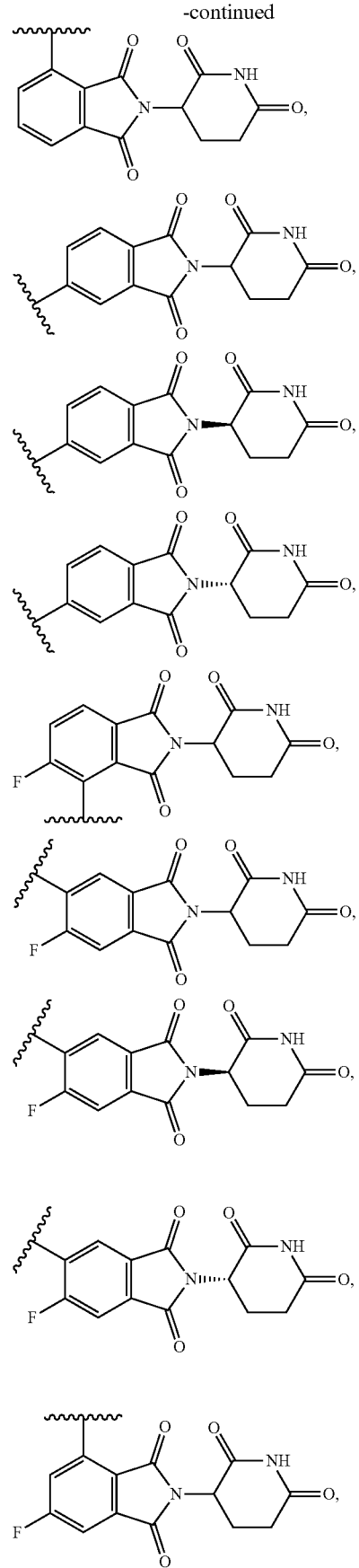
6. The compound according to claim 5, or a pharmaceutically acceptable salt or stereoisomer thereof, wherein K is:
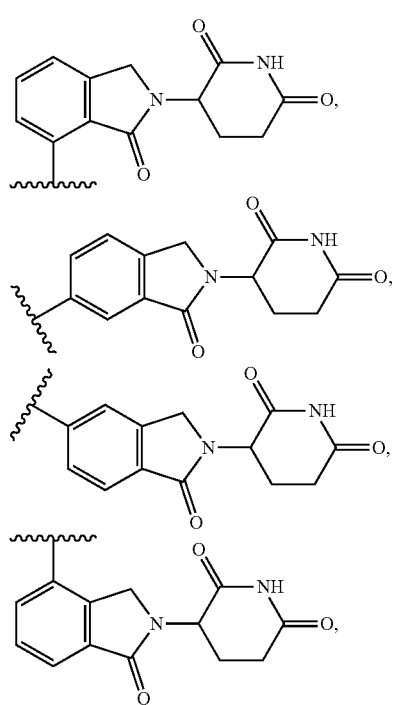

657
-continued
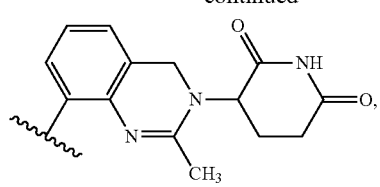
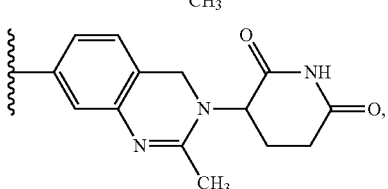
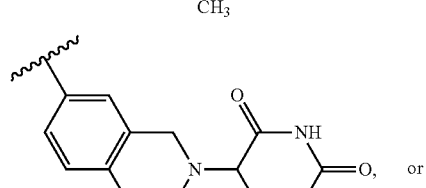
or
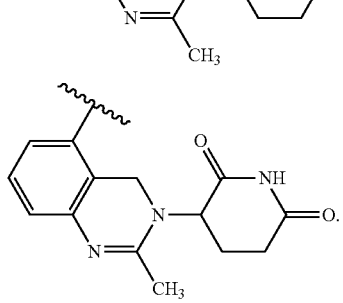
7. The compound according to claim 5, or a pharmaceutically acceptable salt or stereoisomer thereof, wherein K is:
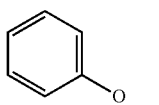
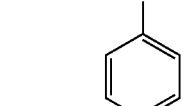
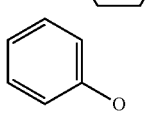
658
-continued
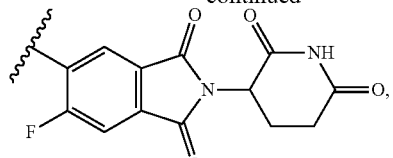
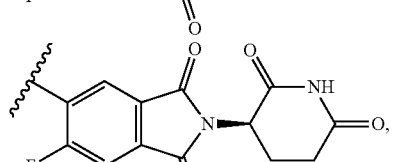
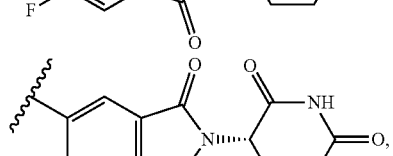
or
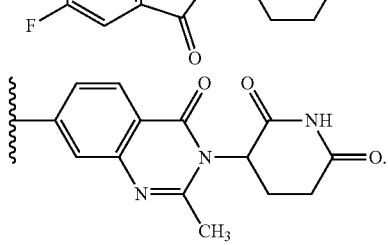
8. The compound according to claim 5, or a pharmaceutically acceptable salt or stereoisomer thereof, wherein B is:
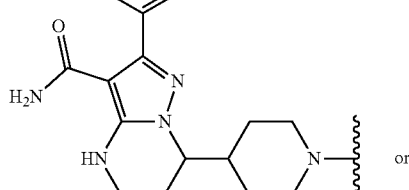
or
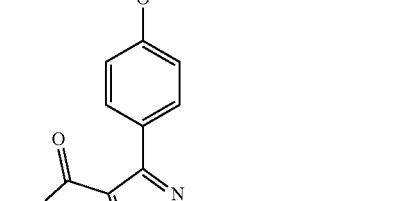
9. The compound according to claim 5, or a pharmaceutically acceptable salt or stereoisomer thereof, wherein B is:

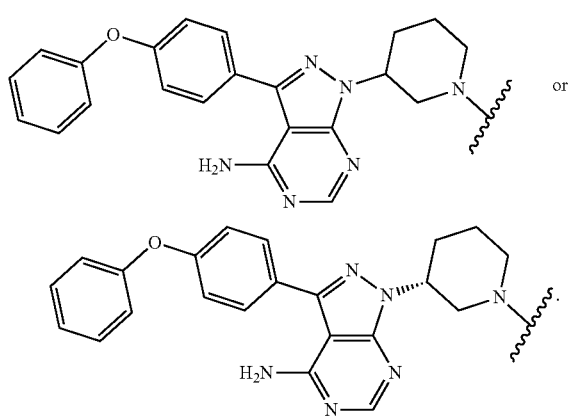

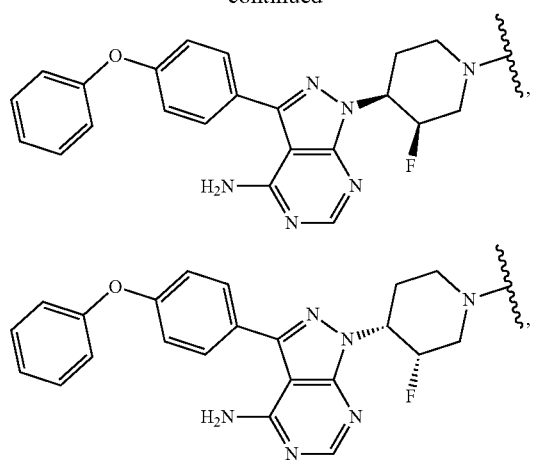

10. The compound according to claim 5, or a pharmaceutically acceptable salt or stereoisomer thereof, wherein B is:

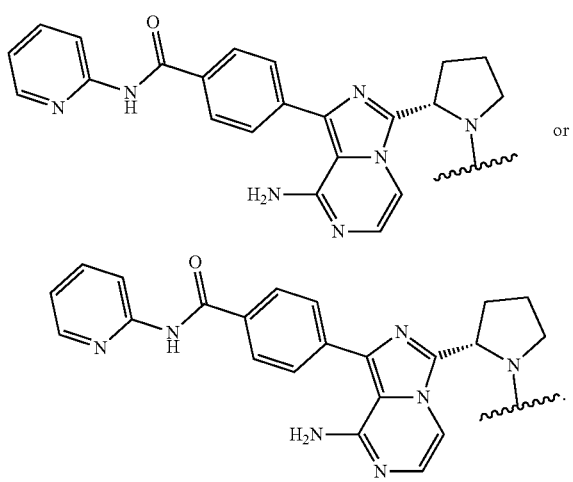

11. The compound according to claim 5, or a pharmaceutically acceptable salt or stereoisomer thereof, wherein B is:

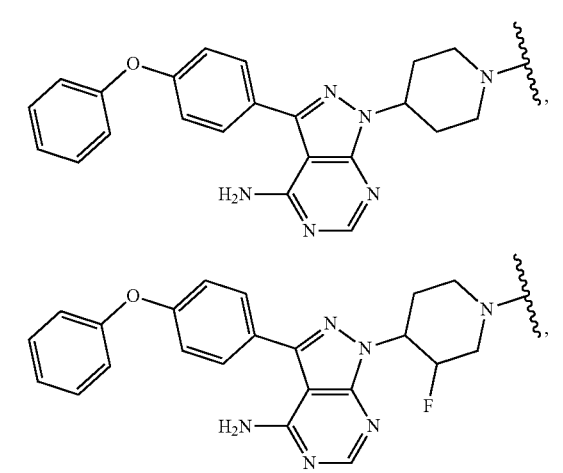

12. The compound according to claim 3, or a pharmaceutically acceptable salt or stereoisomer thereof, wherein the compound is represented by formula (Ia) or formula (Ib):

B-Cy1-Cy2-K     (Ia) or

B-Cy1-Cy2-Cy3-K     (Ib)

K is:

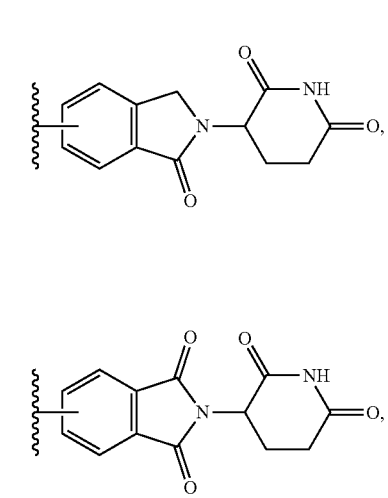

661

-continued

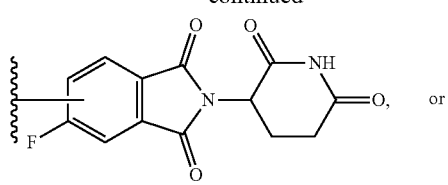, or

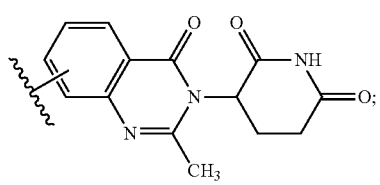;

Cy1 is a monocyclic $C_{4-6}$ cycloalkylene, monocyclic 4- to 6-membered heterocyclylene, fused 5- to 10-membered heterocyclylene, or spirocyclic 6- to 10-membered heterocyclylene, wherein the monocyclic 4- to 6-membered heterocyclylene, fused 5- to 10-membered heterocyclylene, or spirocyclic 6- to 10-membered heterocyclylene contains 1, 2, 3, or 4N heteroatoms, and further wherein the monocyclic $C_{4-6}$ cycloalkylene, monocyclic 4- to 6-membered heterocyclylene, fused 5- to 10-membered heterocyclylene, or spirocyclic 6- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy2 is a monocyclic $C_{4-6}$ cycloalkylene, monocyclic 4- to 6-membered heterocyclylene, fused 5- to 10-membered heterocyclylene, or spirocyclic 6- to 10-membered heterocyclylene, wherein the monocyclic 4- to 6-membered heterocyclylene, fused 5- to 10-membered heterocyclylene, or spirocyclic 6- to 10-membered heterocyclylene contains 1, 2, 3, or 4N heteroatoms, and further wherein the monocyclic $C_{4-6}$ cycloalkylene, monocyclic 4- to 6-membered heterocyclylene, fused 5- to 10-membered heterocyclylene, or spirocyclic 6- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O;

Cy3 is a monocyclic 4- to 6-membered heterocyclylene, fused 5- to 10-membered heterocyclylene, or spirocyclic 6- to 10-membered heterocyclylene, wherein the monocyclic 4- to 6-membered heterocyclylene, fused 5- to 10-membered heterocyclylene, or spirocyclic 6- to 10-membered heterocyclylene contains 1, 2, 3, or 4N heteroatoms, and further wherein the monocyclic 4- to 6-membered heterocyclylene, fused 5- to 10-membered heterocyclylene, or spirocyclic 6- to 10-membered heterocyclylene is optionally substituted with 1, 2, 3, or 4 substituents independently selected from the group consisting of F, Cl, Br, I, $C_{1-4}$ alkyl, $NH_2$, OH, $OC_{1-4}$ alkyl, and =O; and

662

B is:

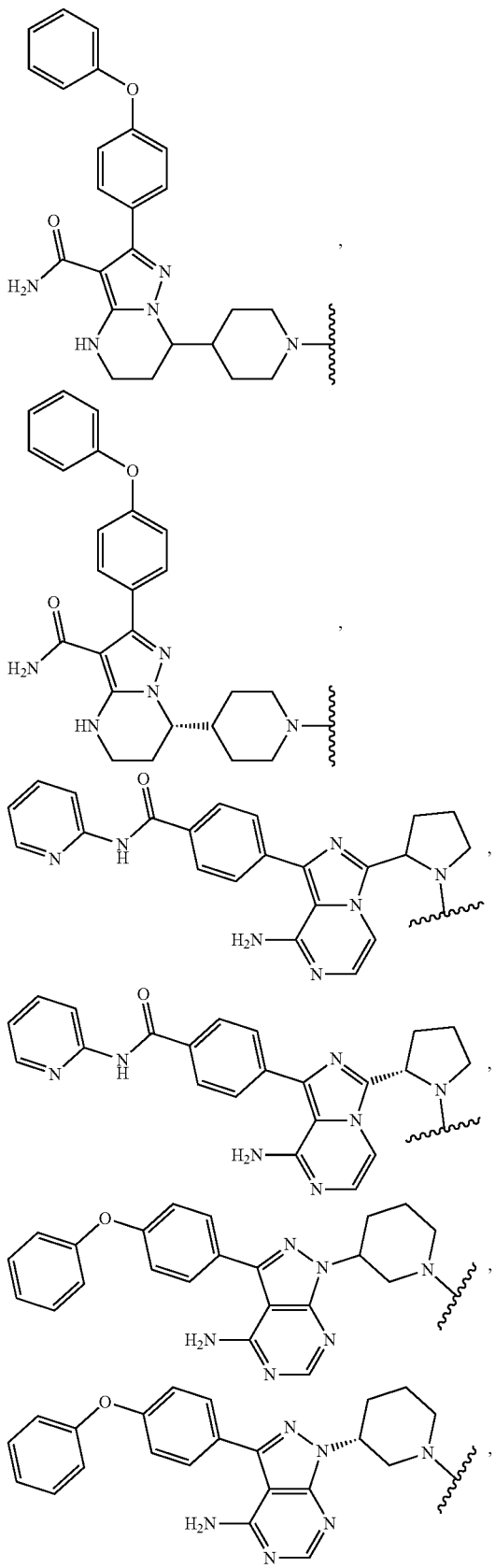

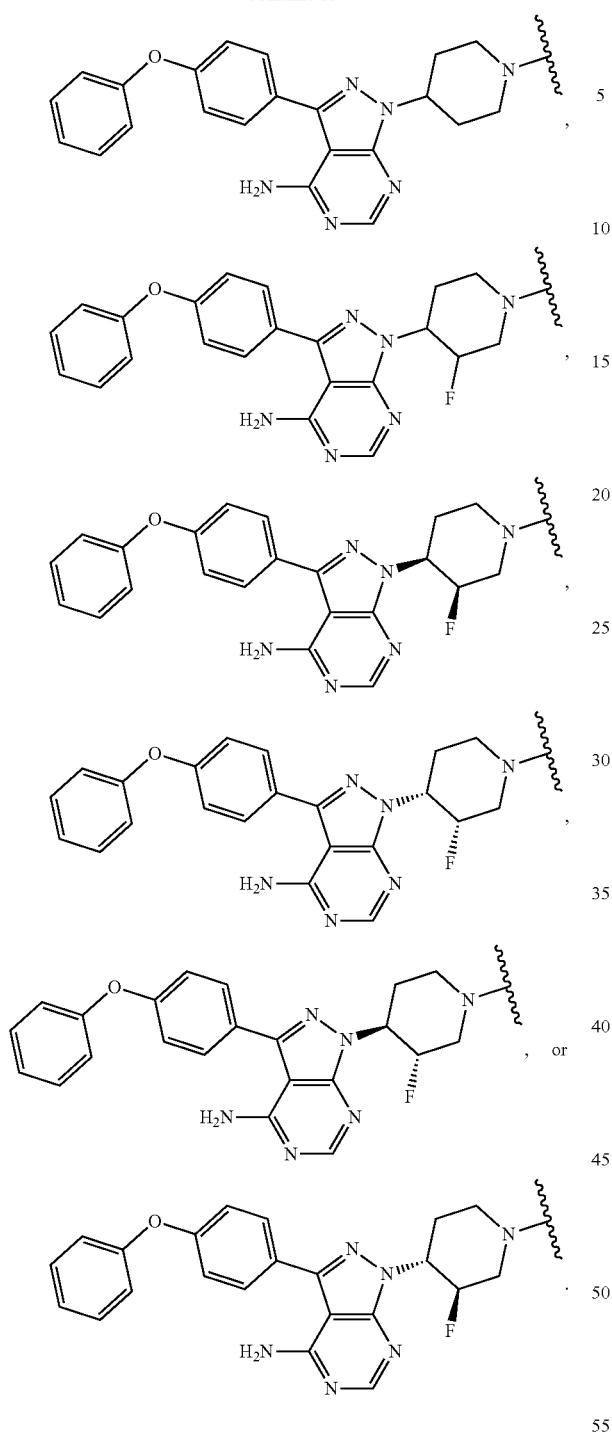
13. The compound according to claim 12, or a pharmaceutically acceptable salt or stereoisomer thereof, wherein:
K is:
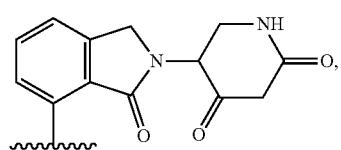
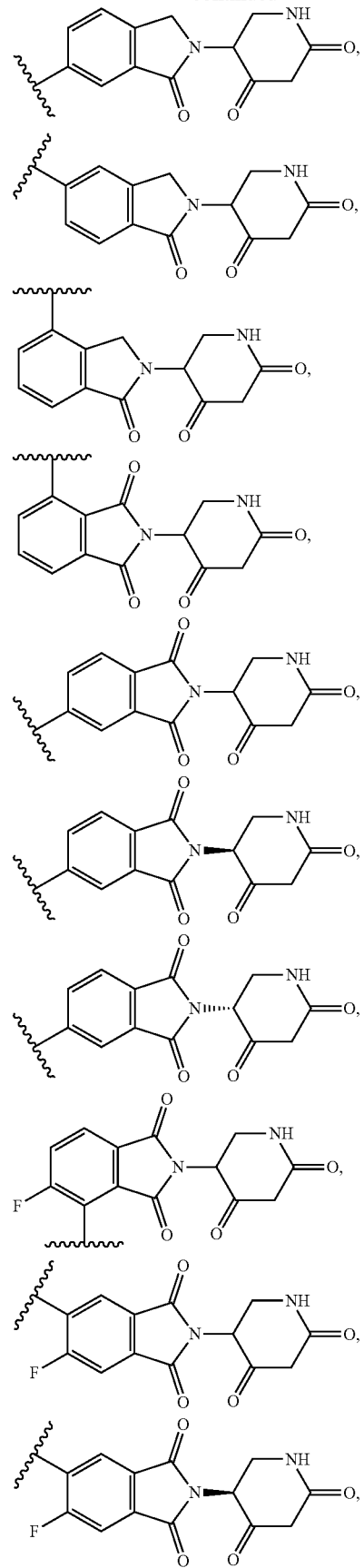

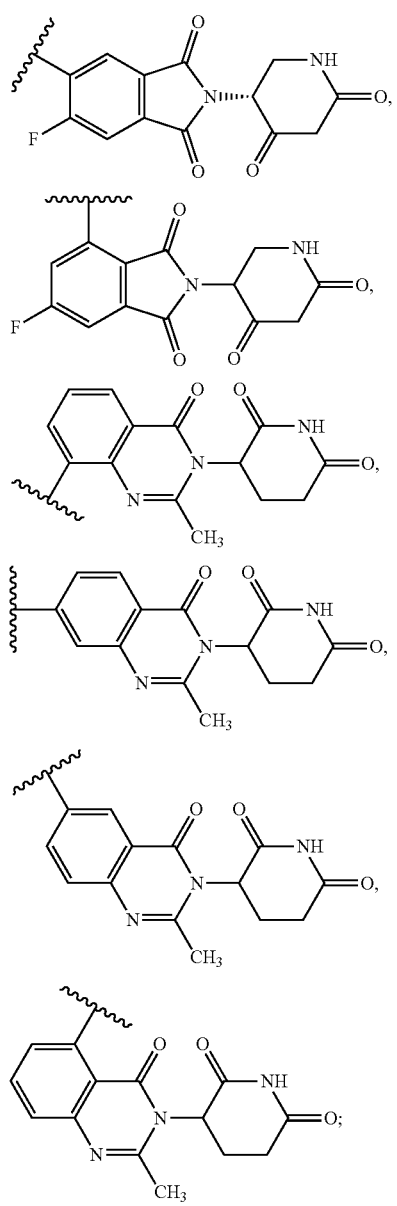
Cy1 is:
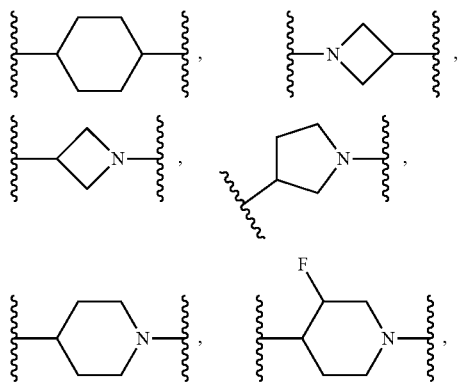
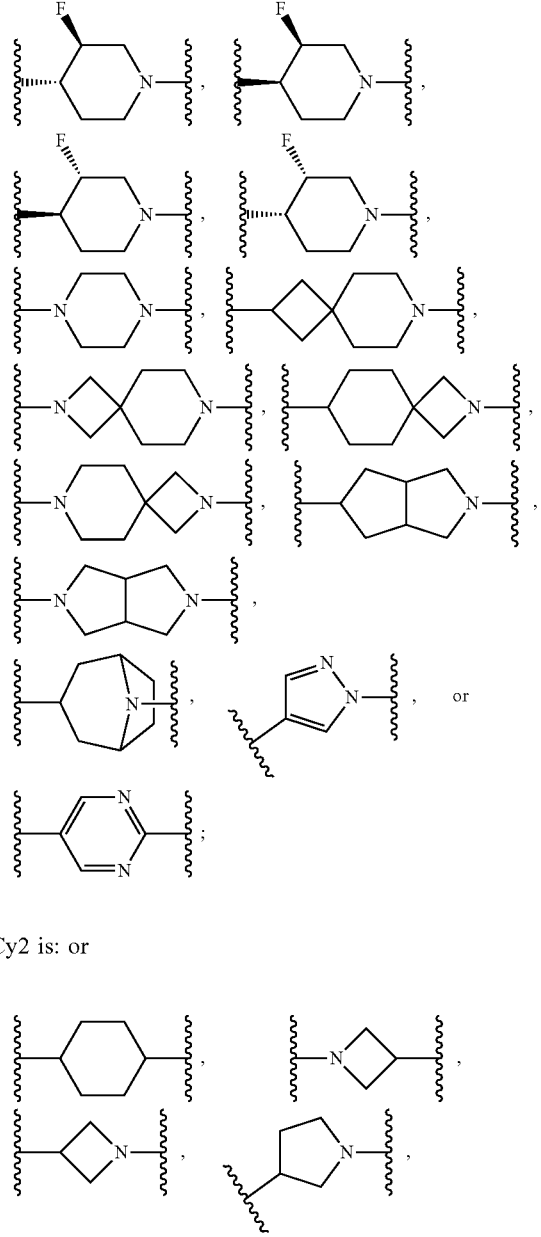
Cy2 is: or
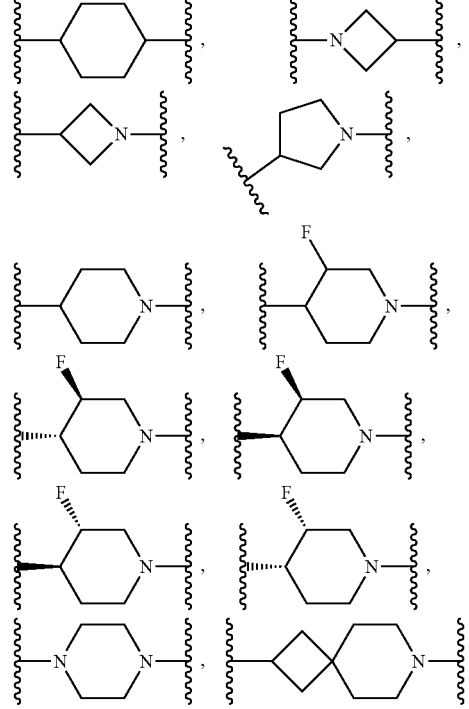

667
-continued
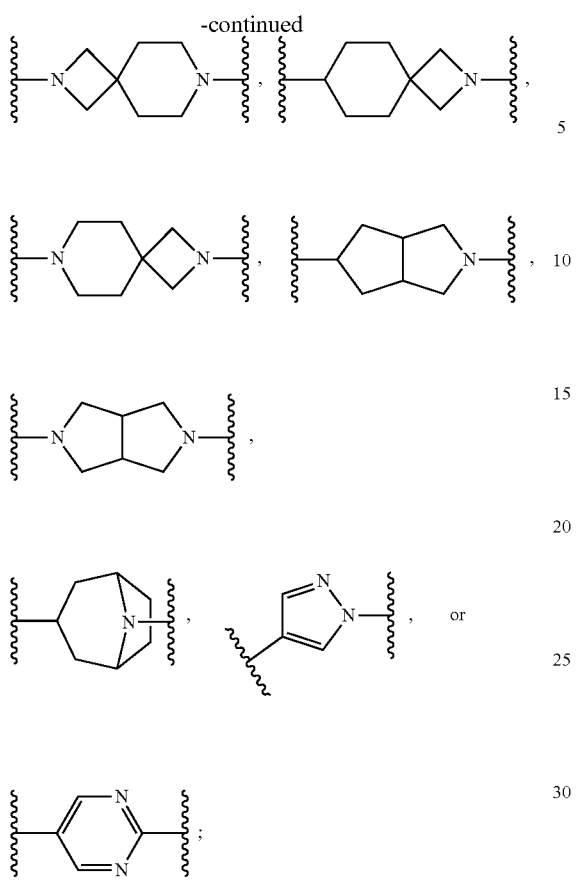
and
Cy3 is:
668
-continued
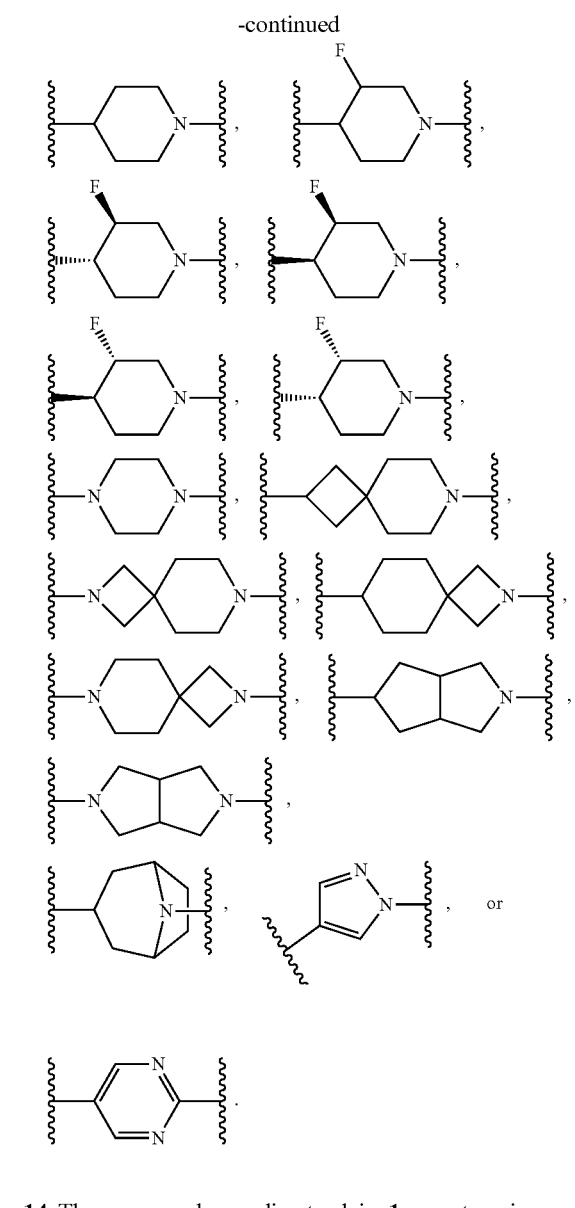
14. The compound according to claim 1, or a stereoisomer thereof, wherein the compound, or stereoisomer thereof, is selected from the group consisting of:
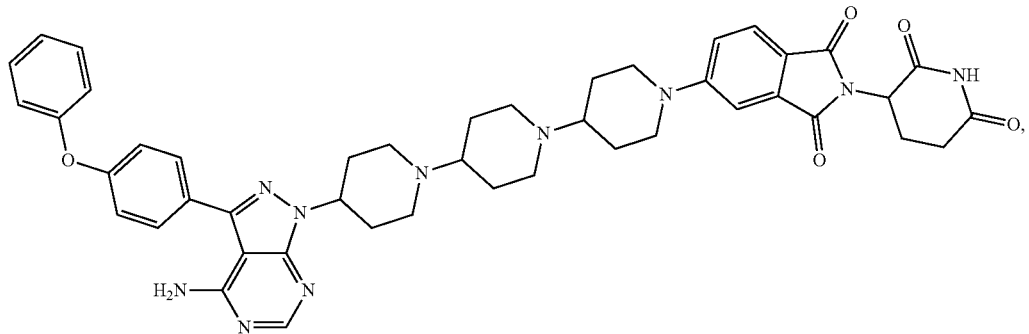

669 670
-continued
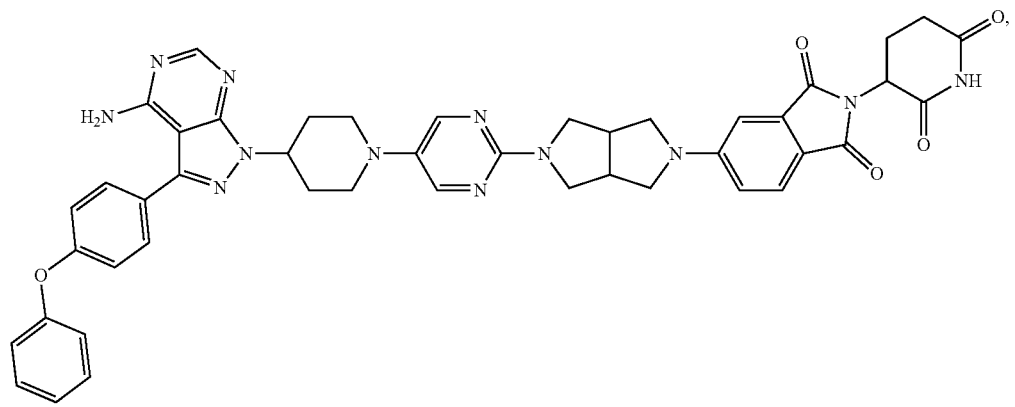
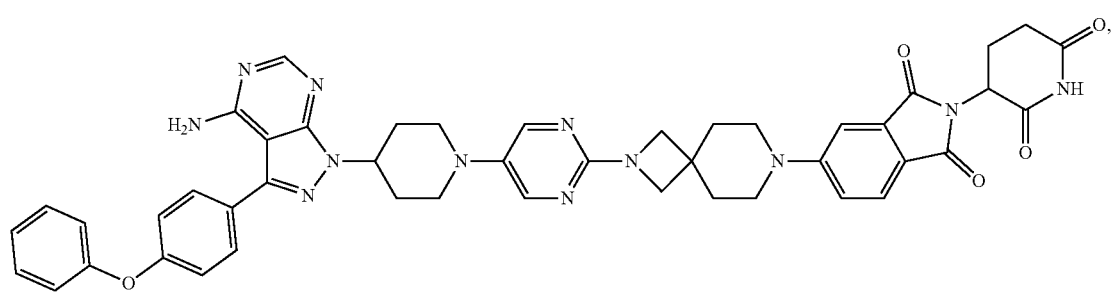
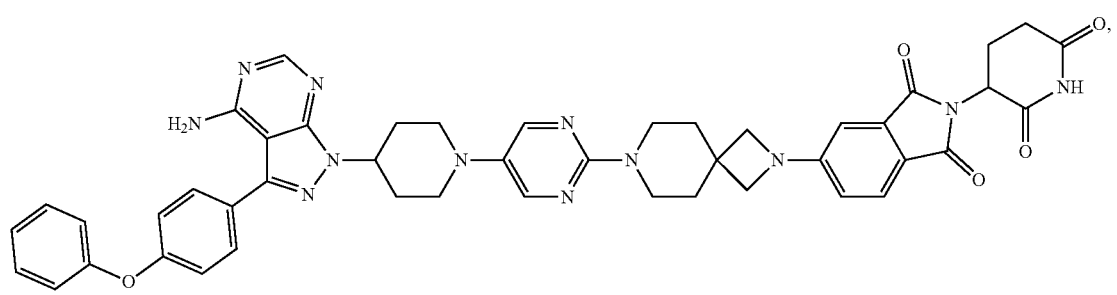
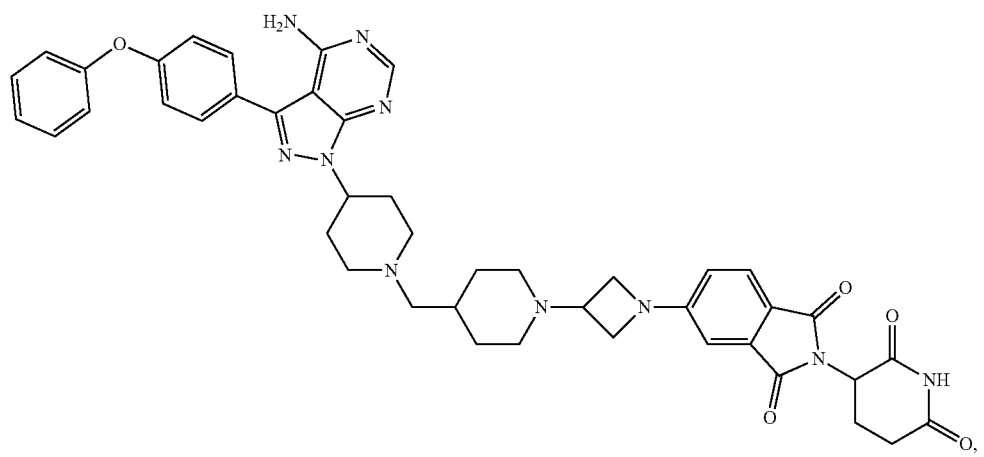

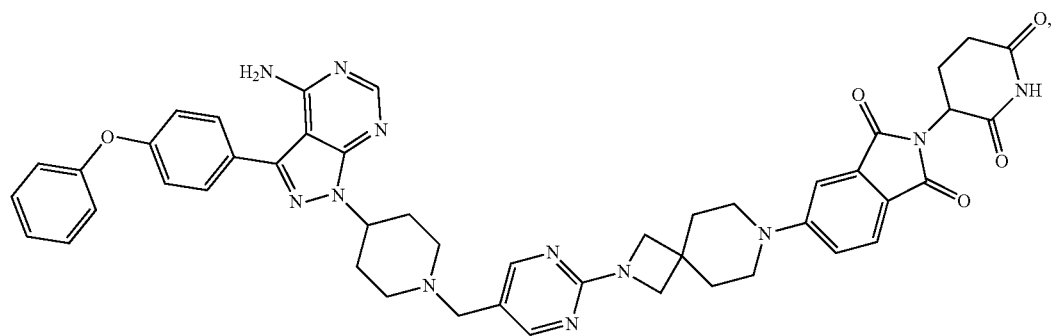
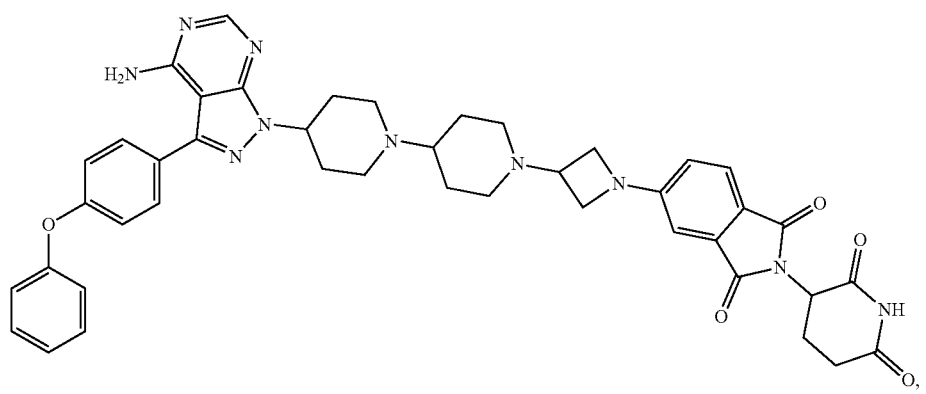
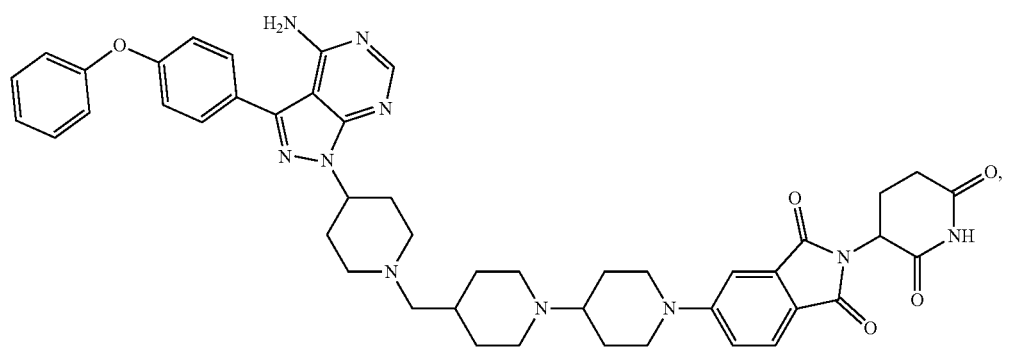
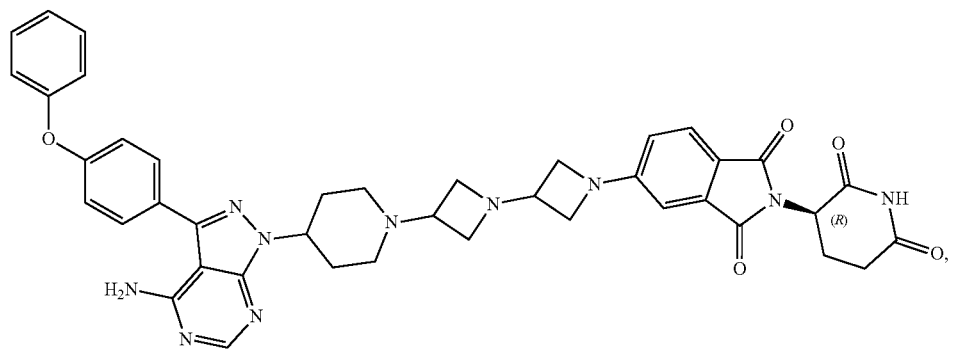

-continued
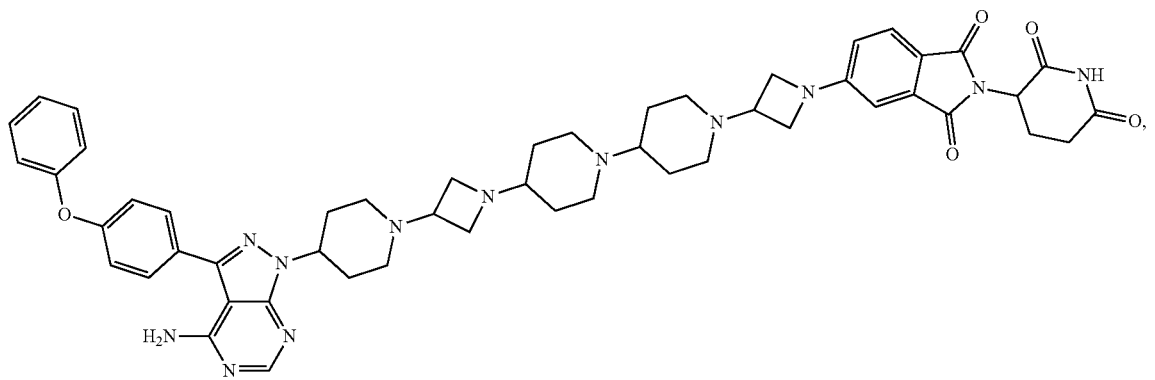
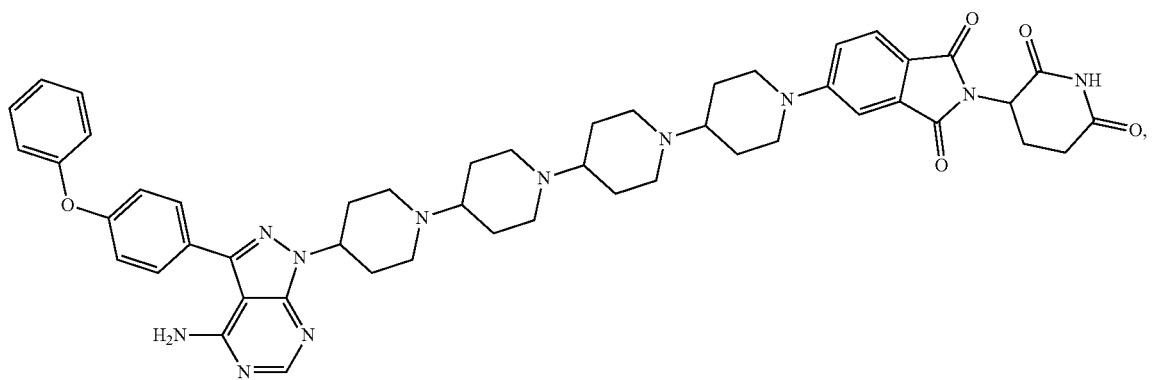
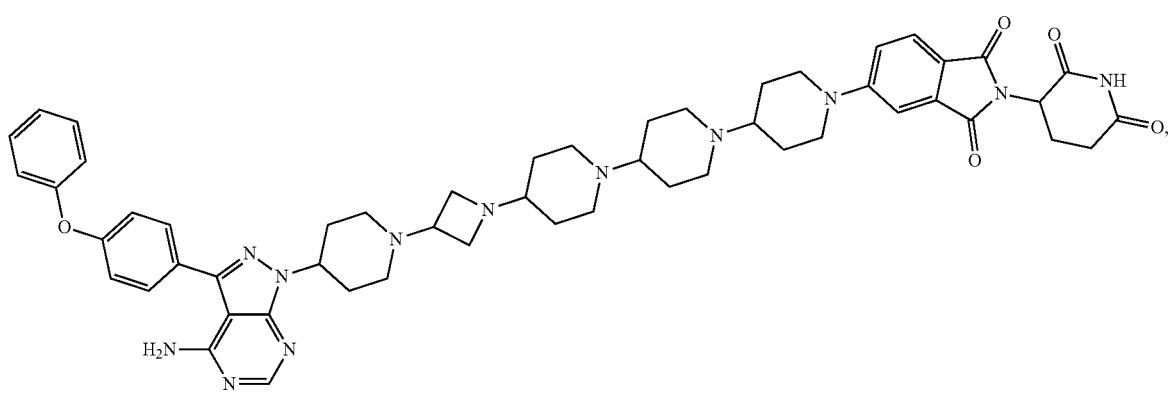
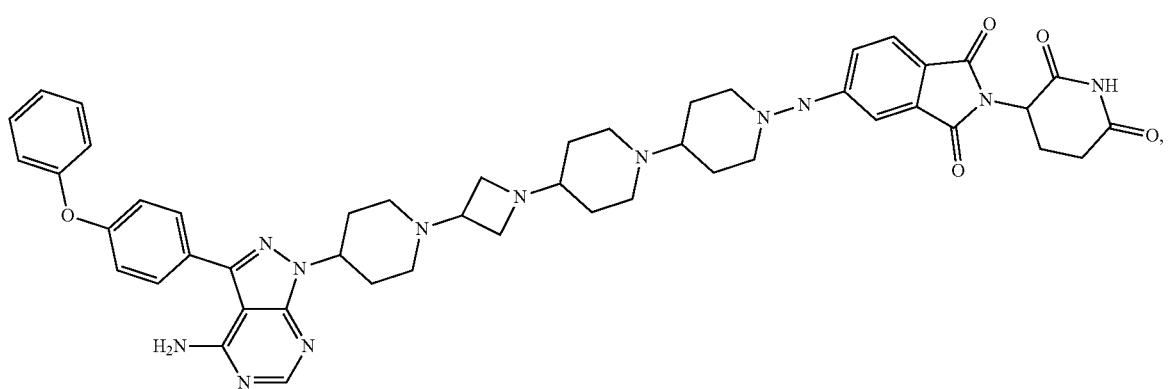

-continued
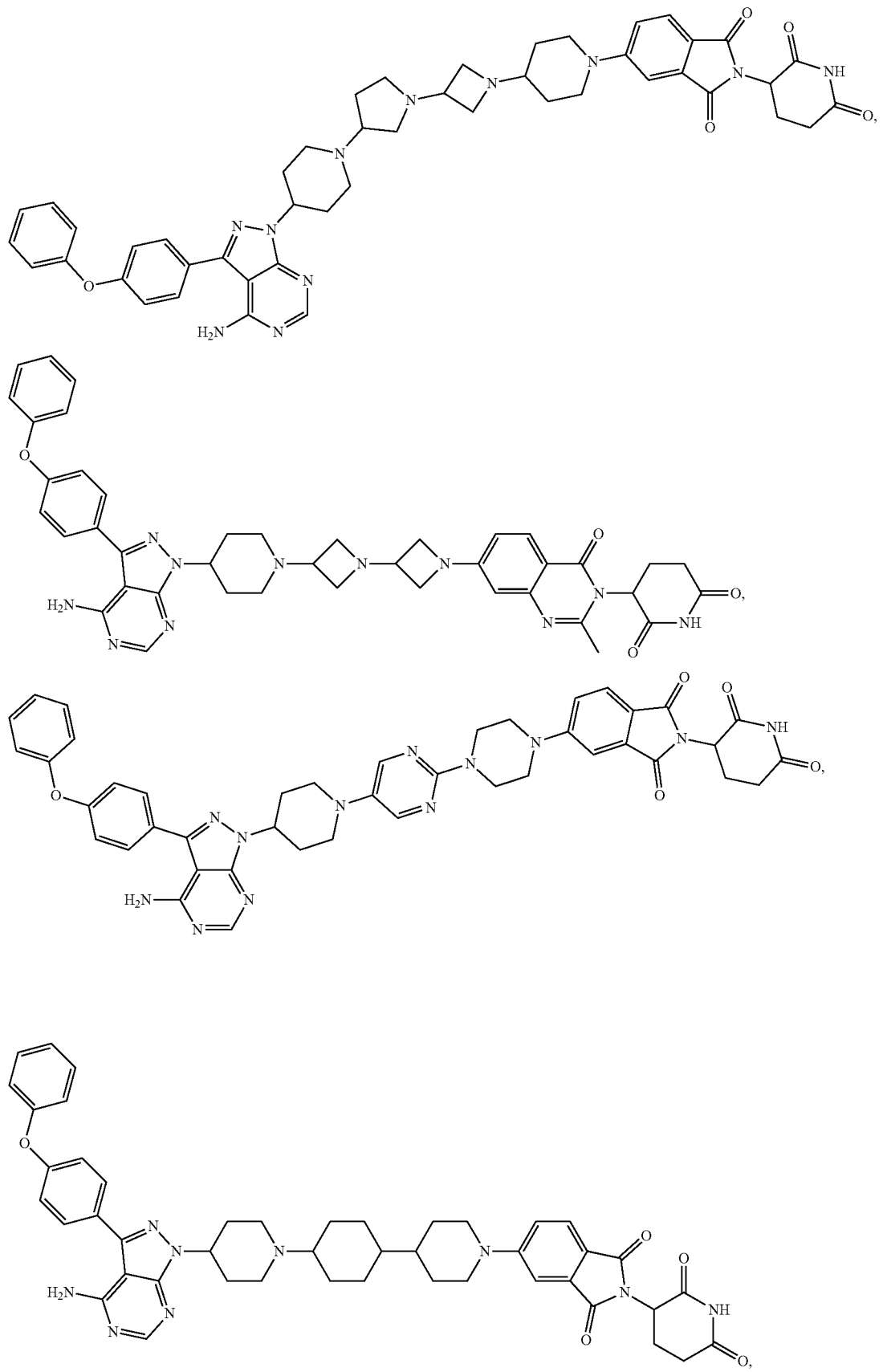

-continued
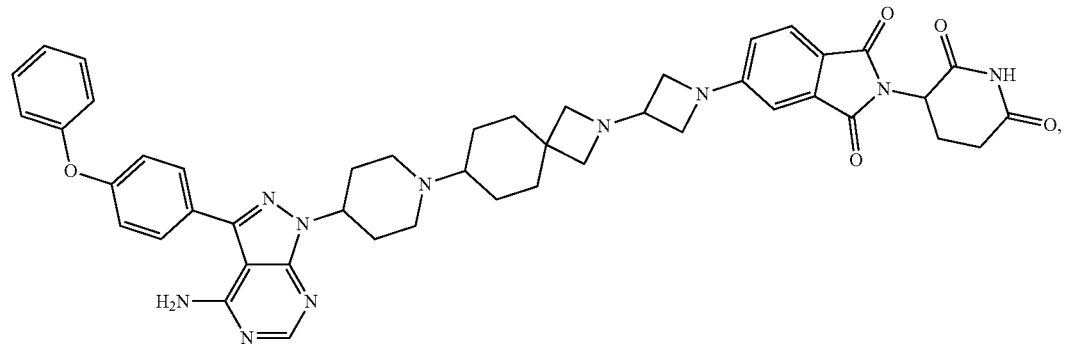
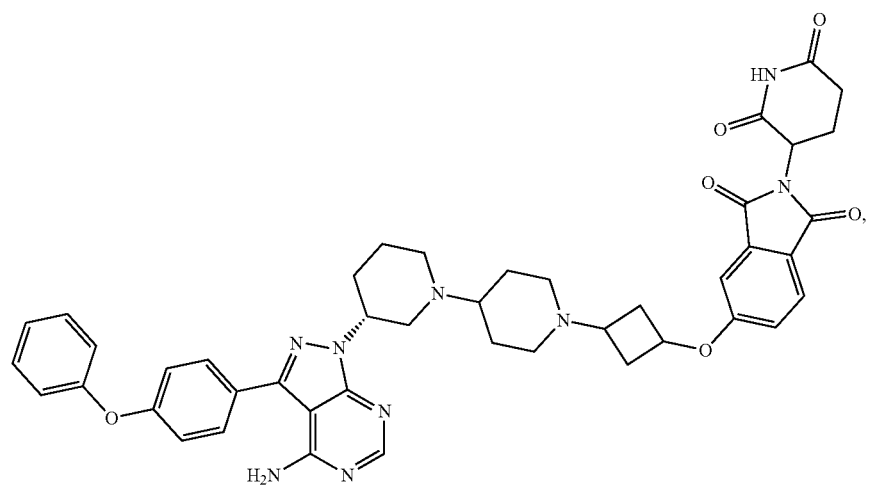
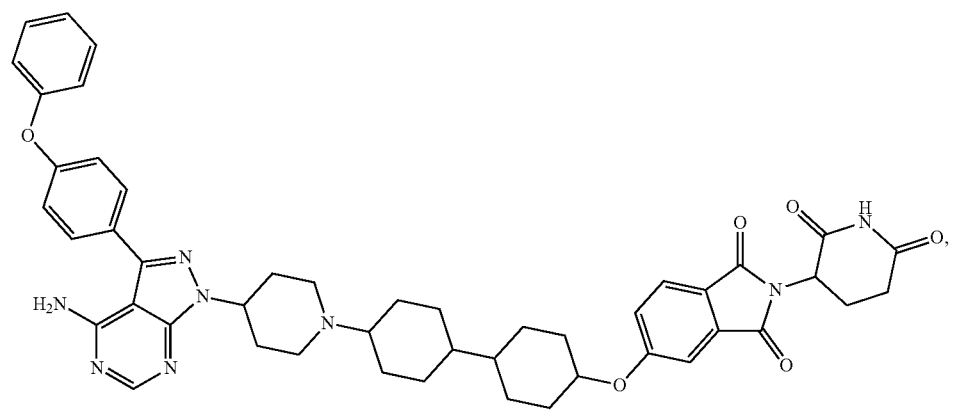
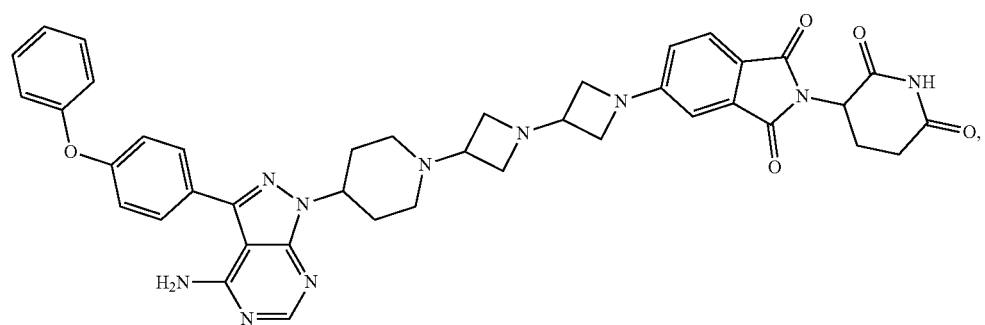

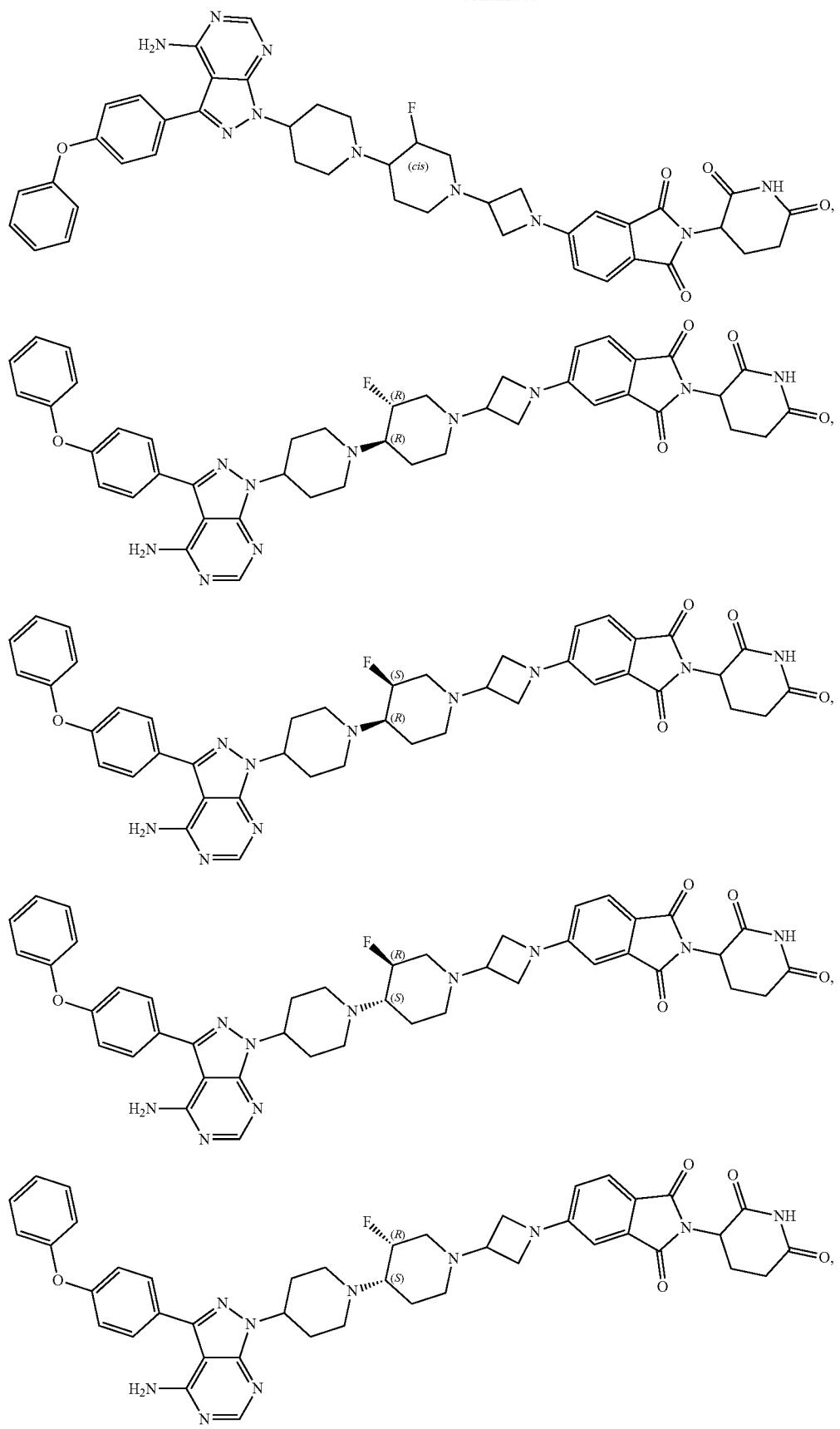

-continued
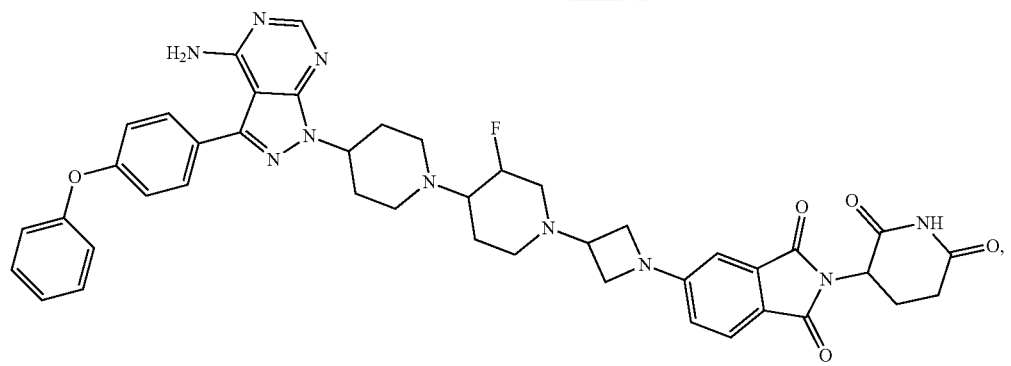
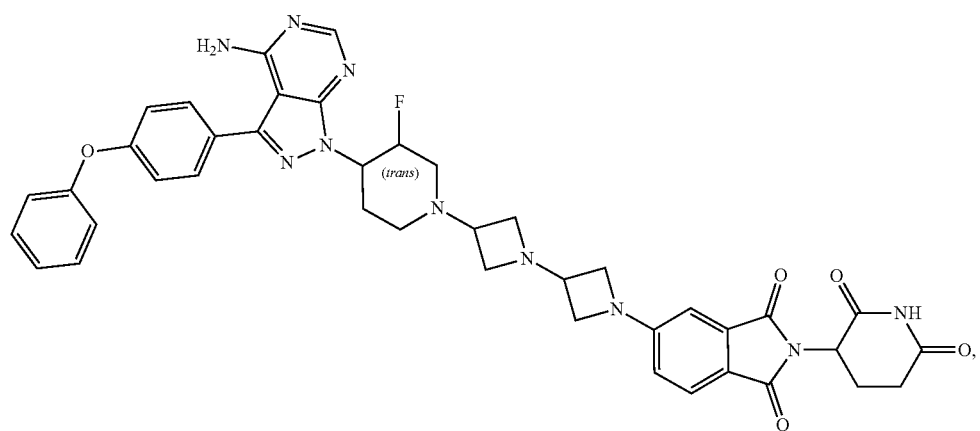
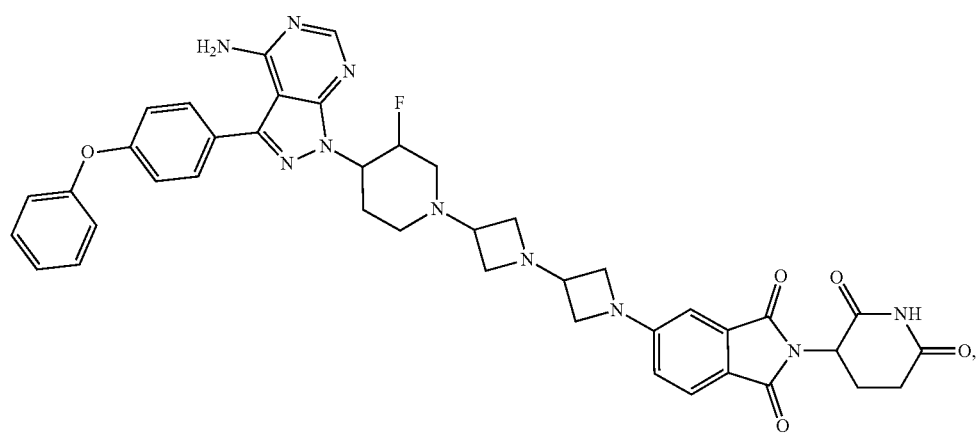
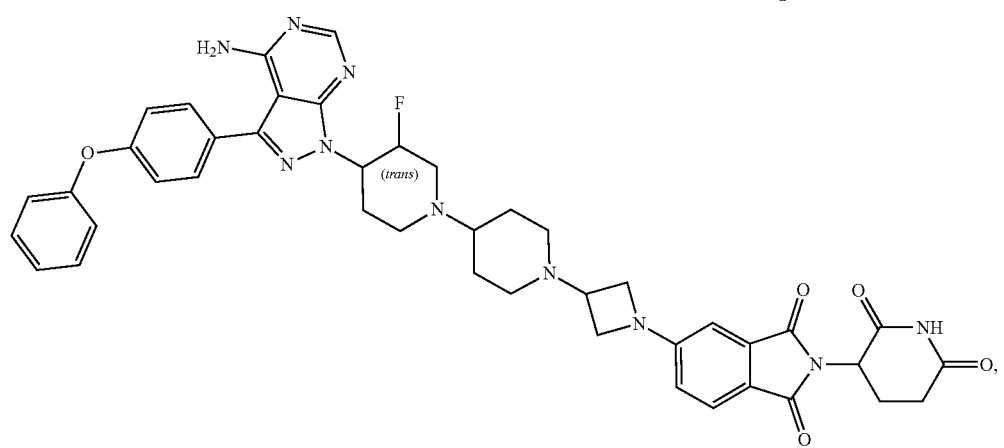

-continued
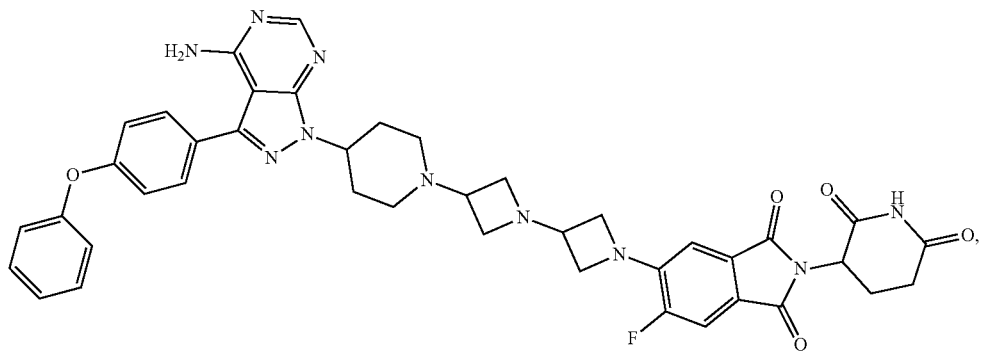
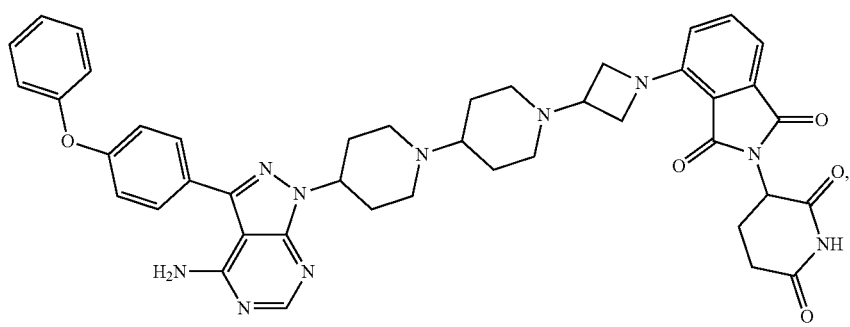
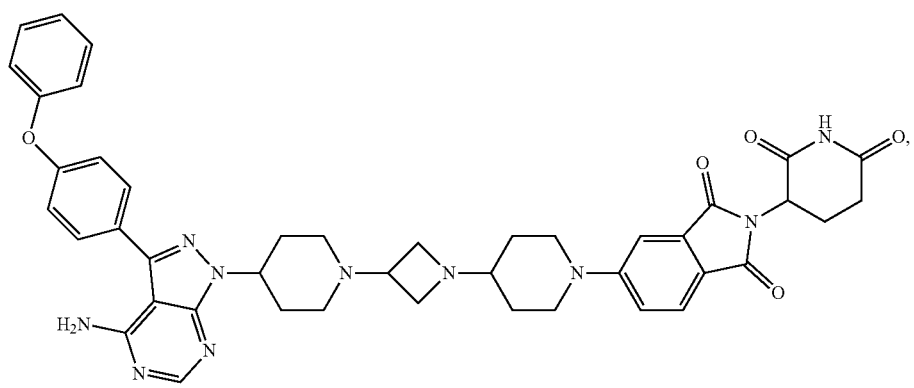
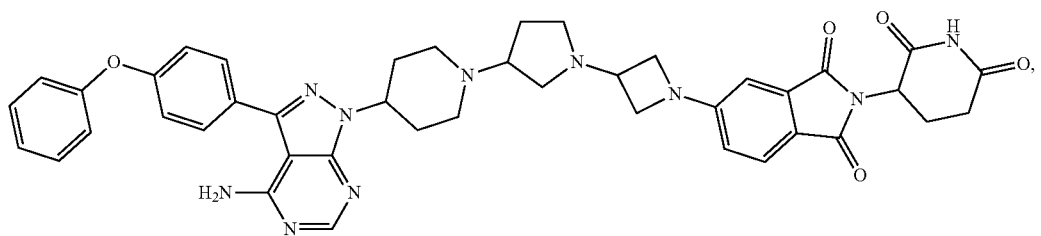
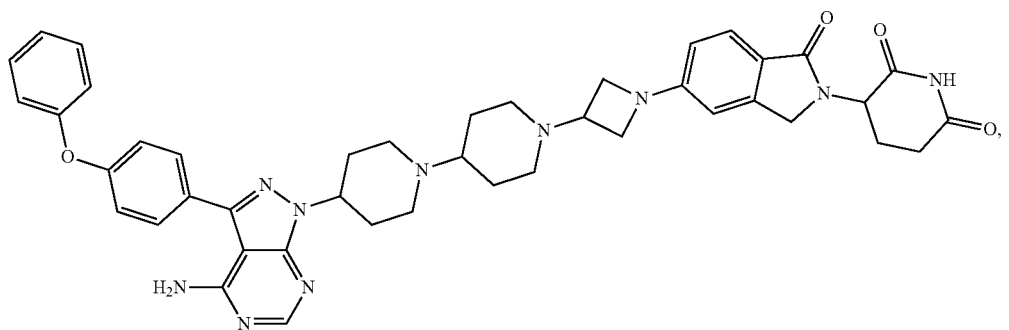

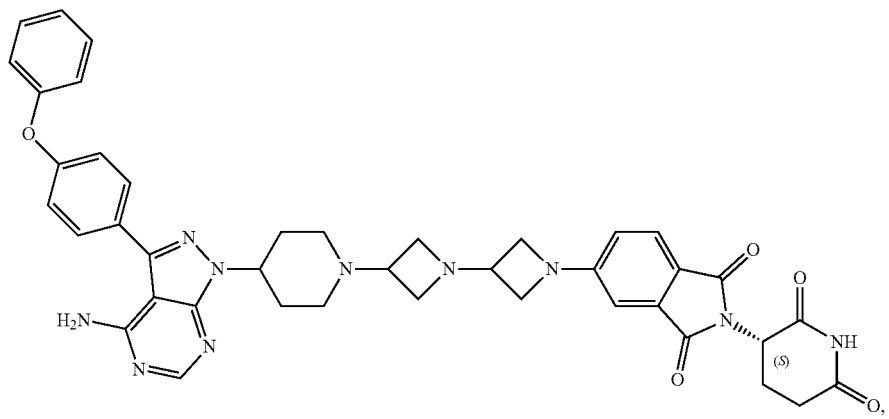
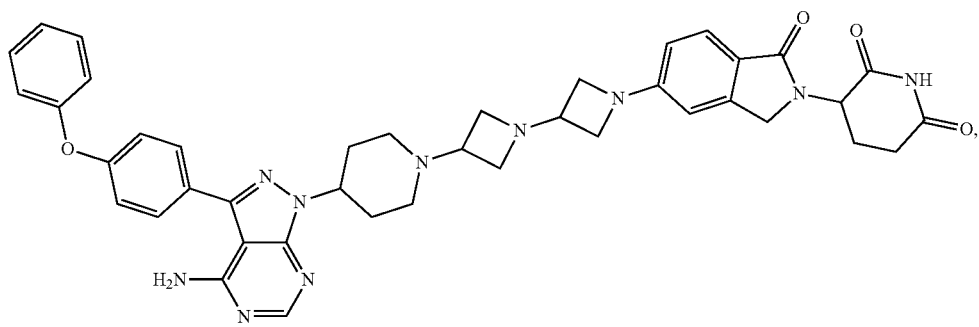
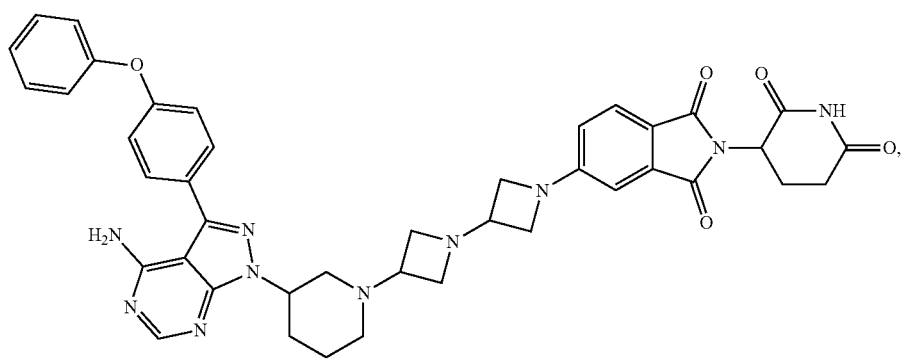
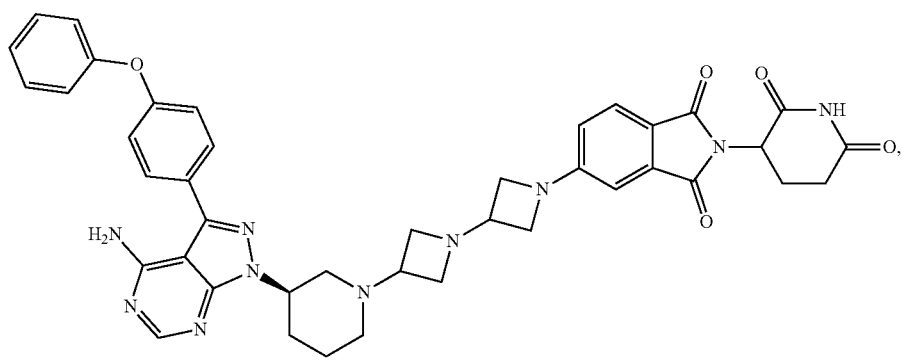

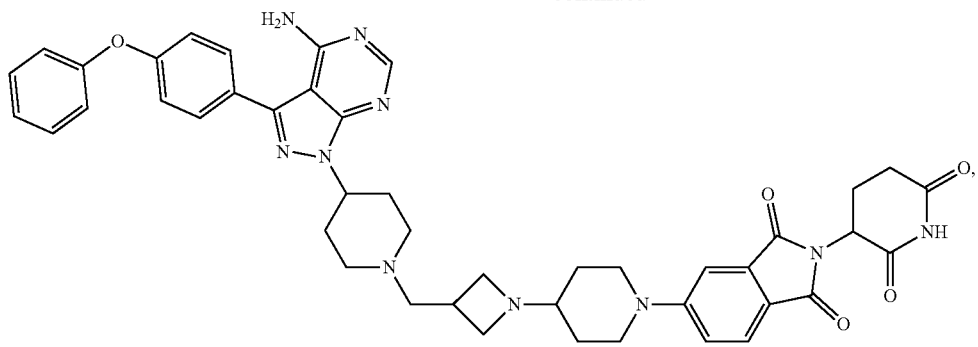
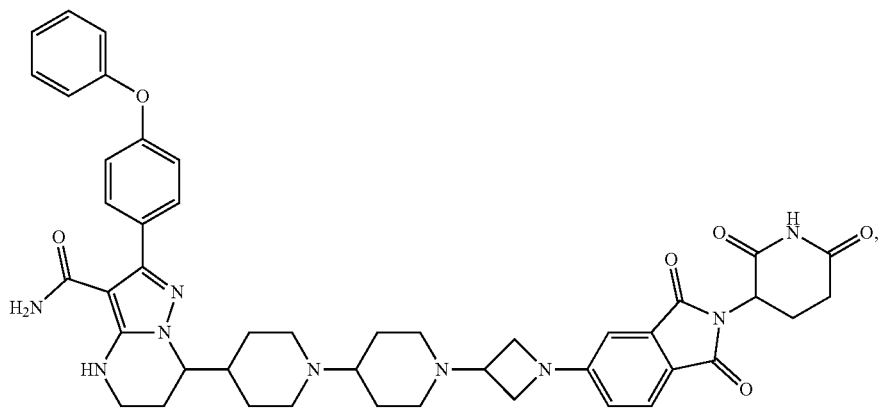
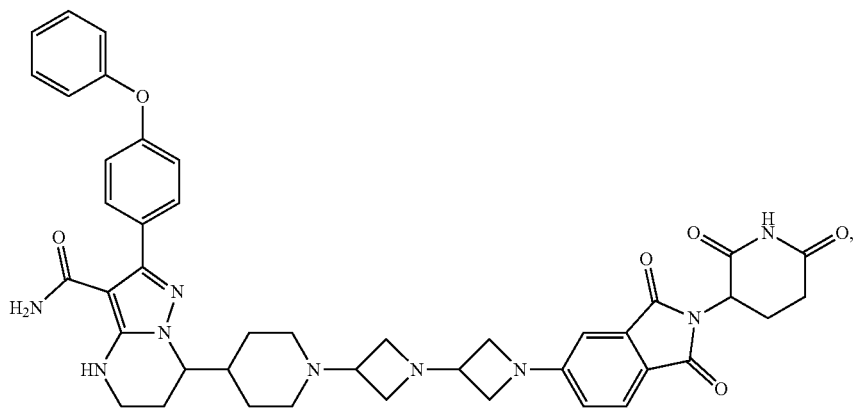

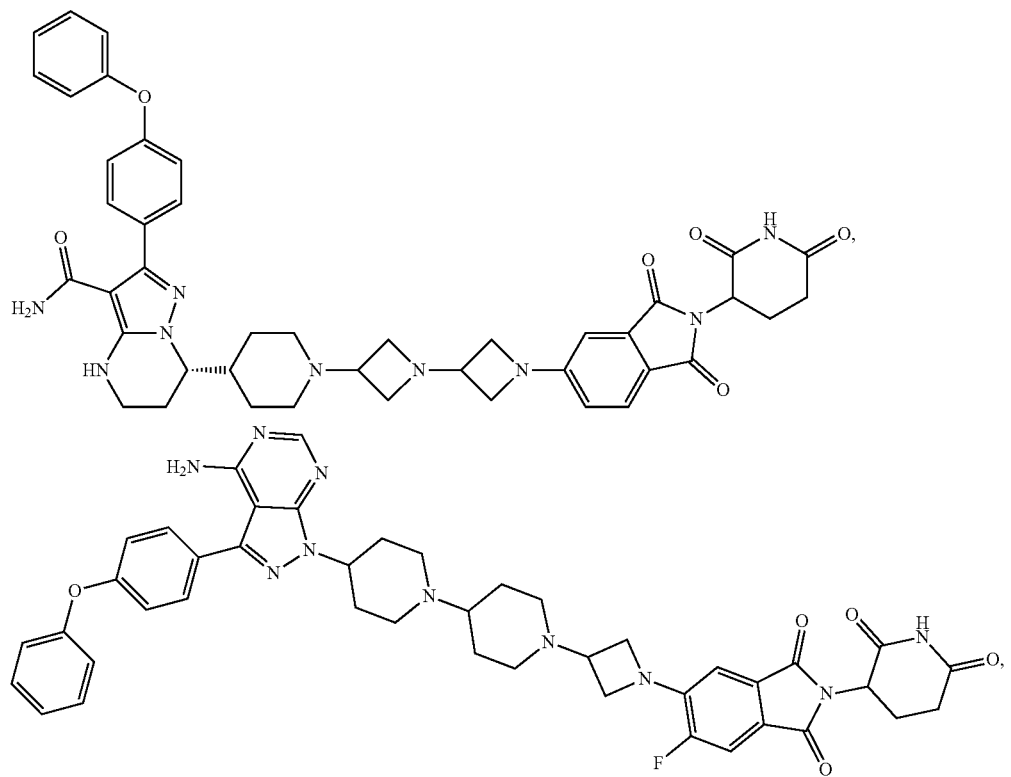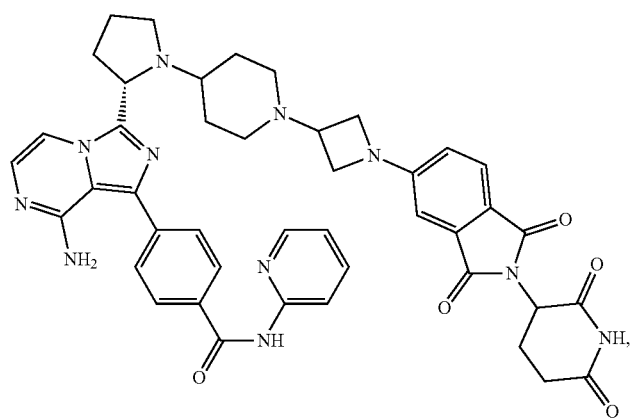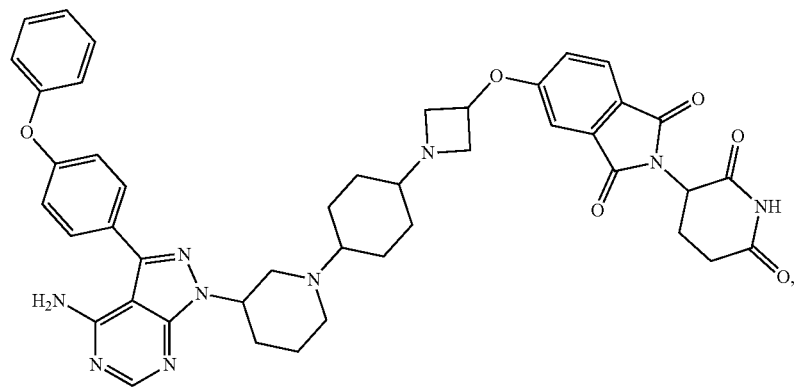

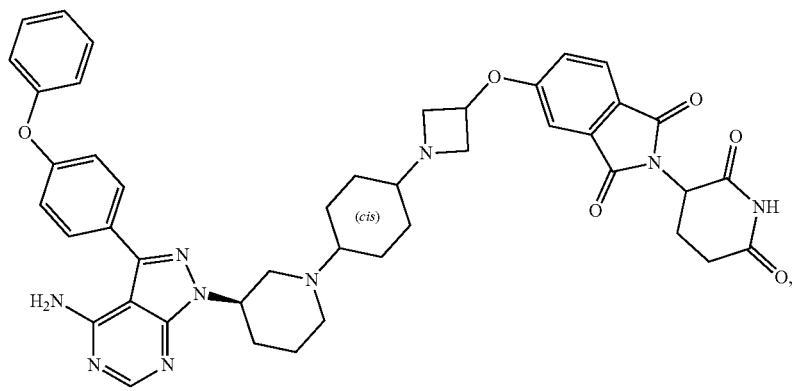
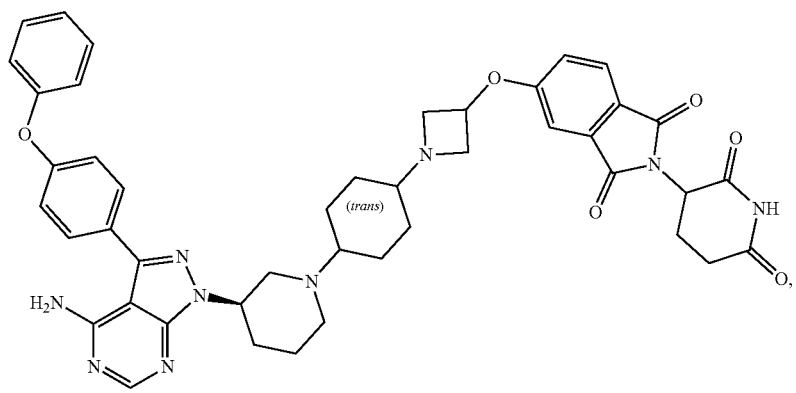
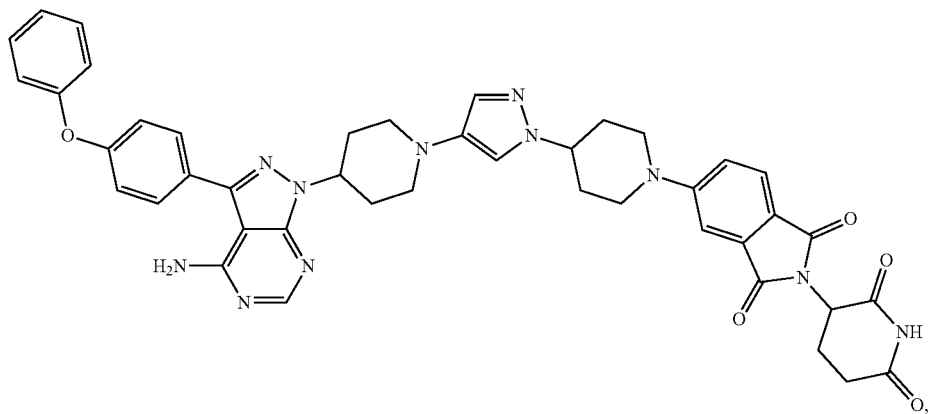
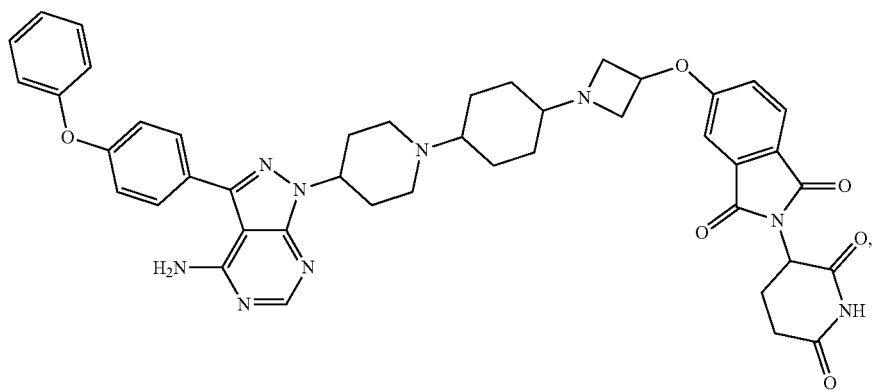

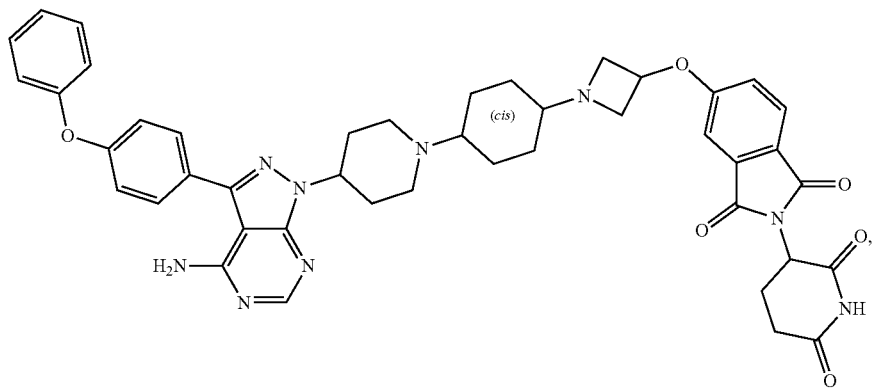
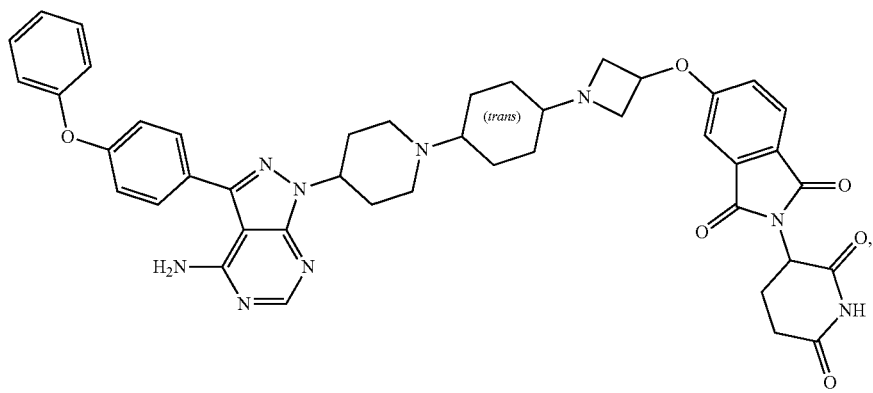
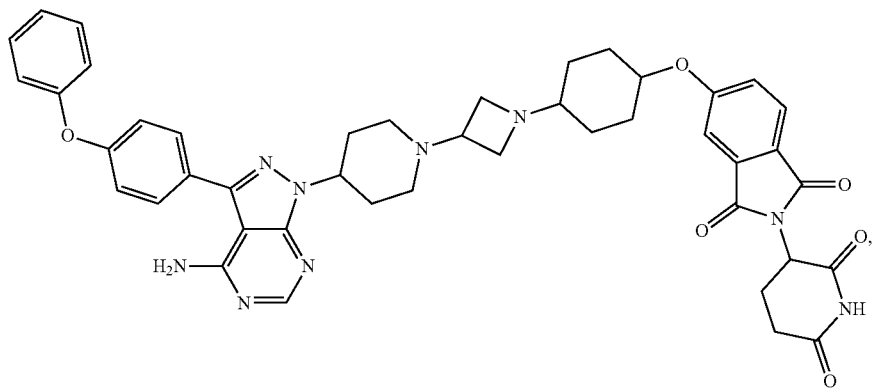
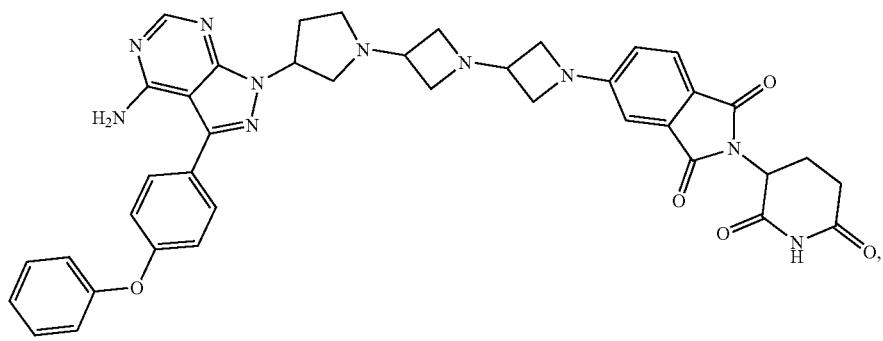

-continued
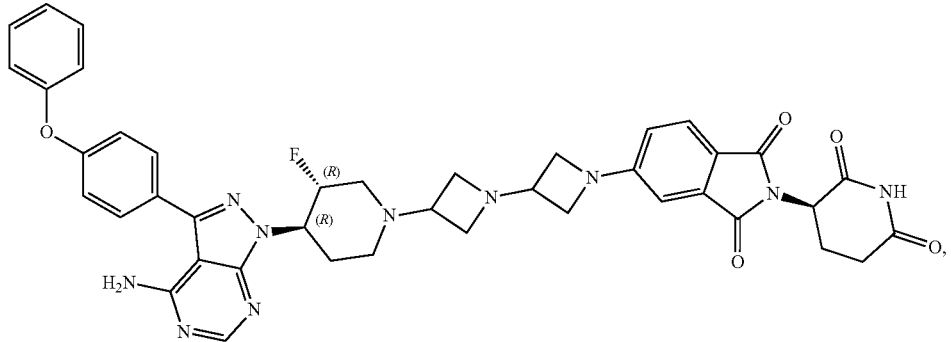
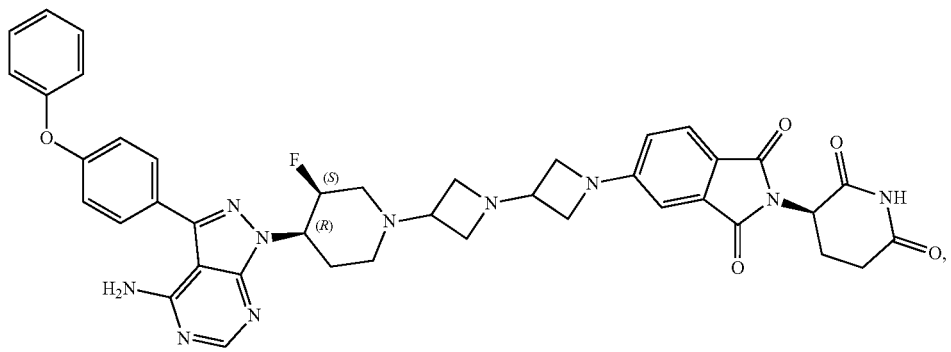
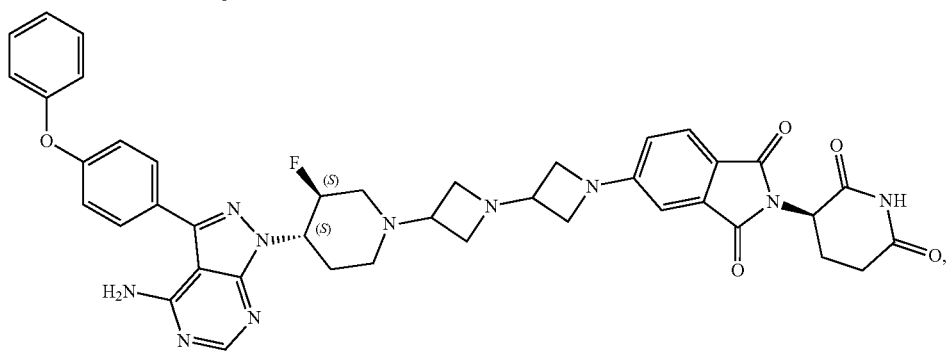
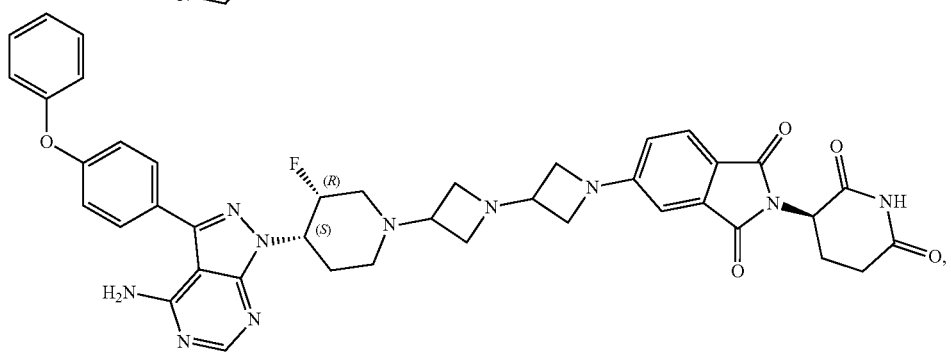
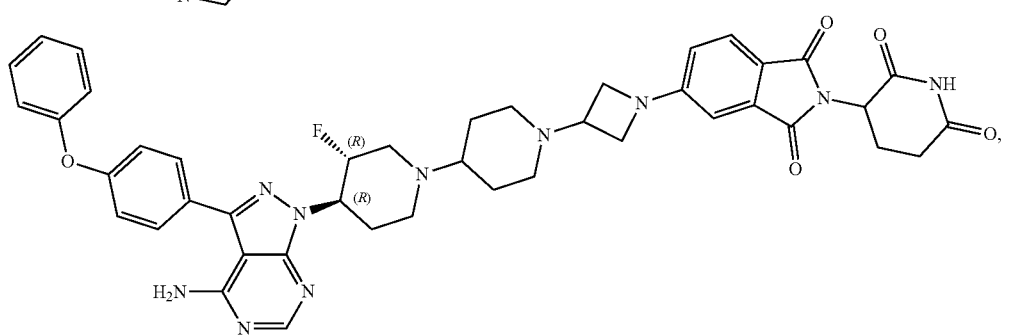

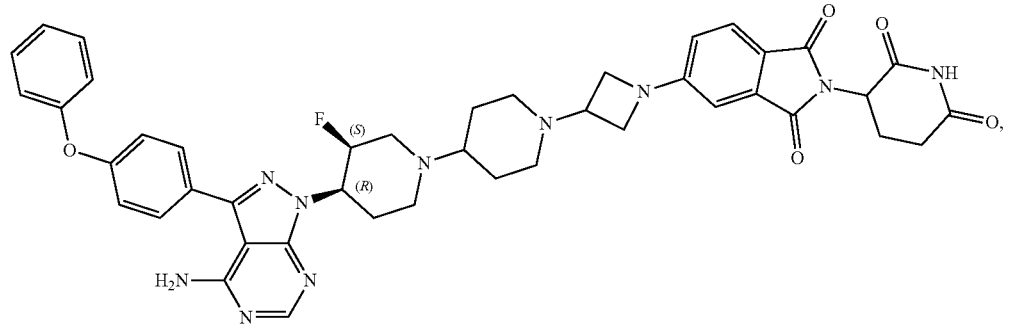
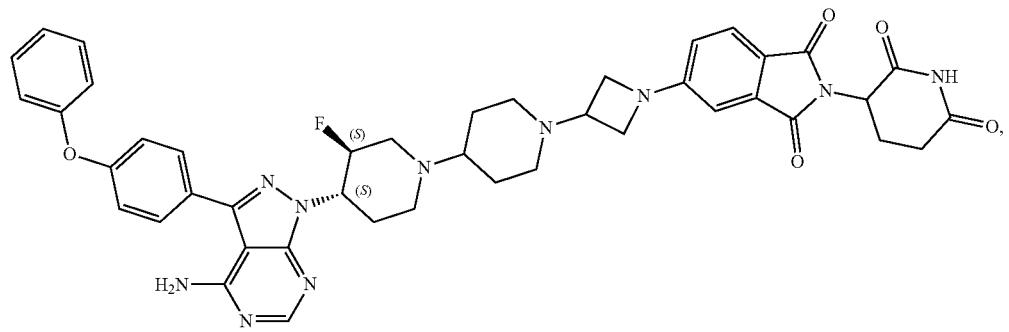
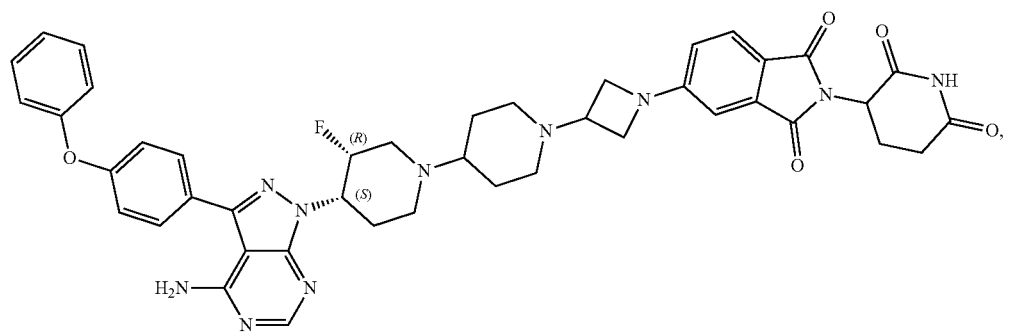
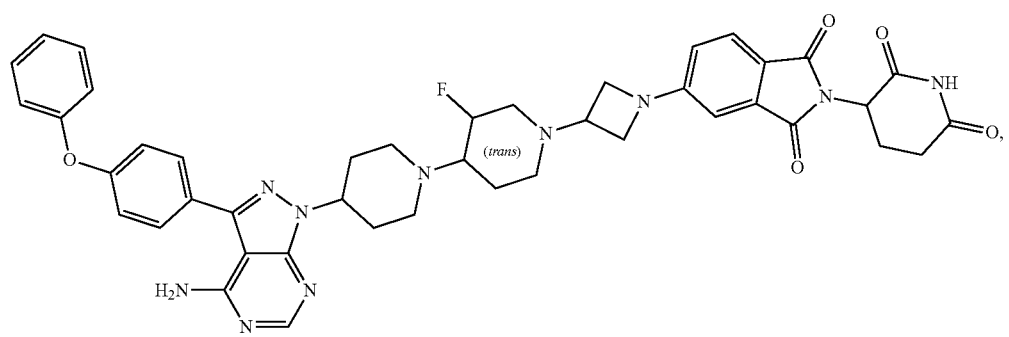

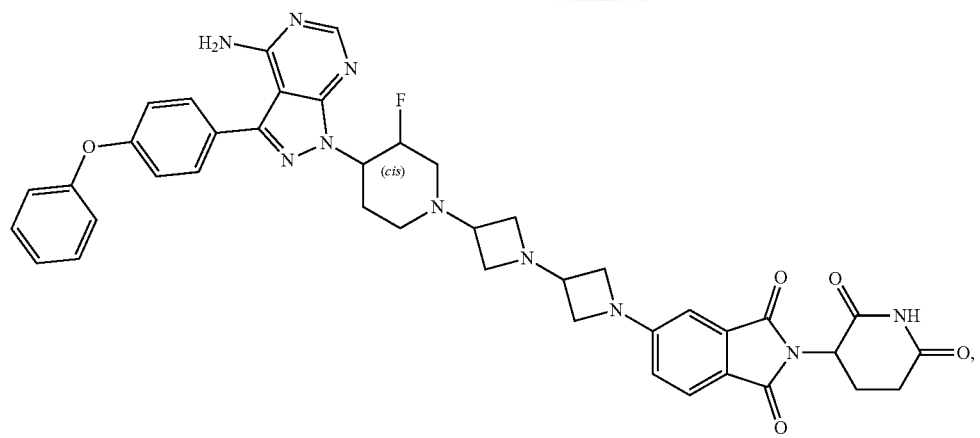
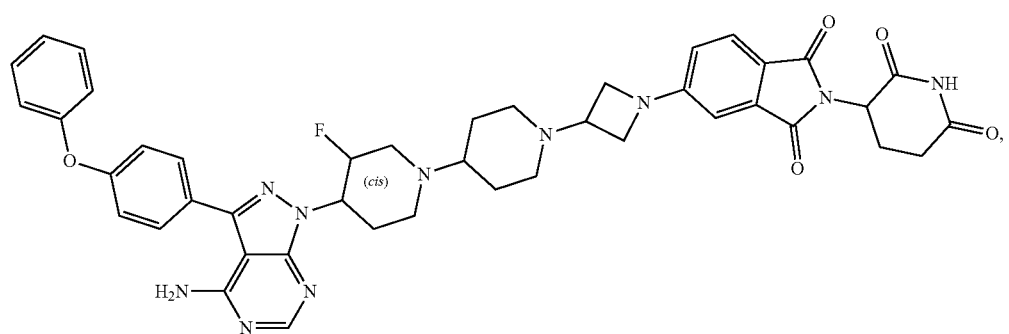
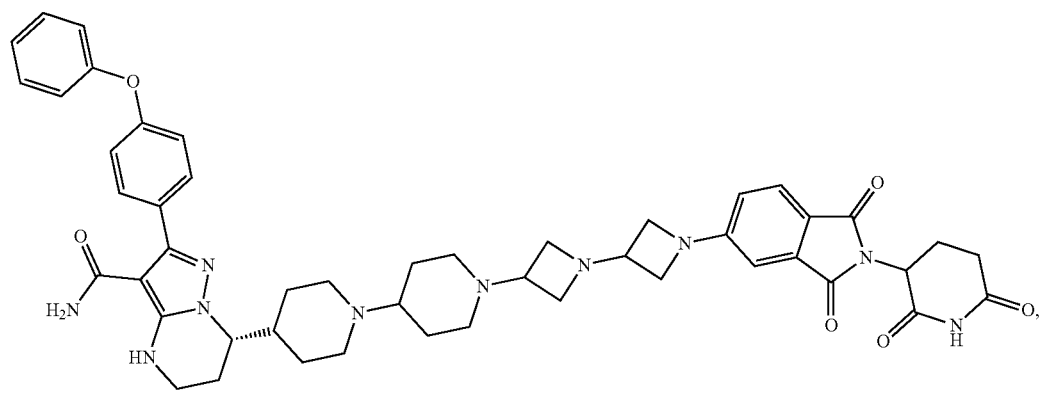
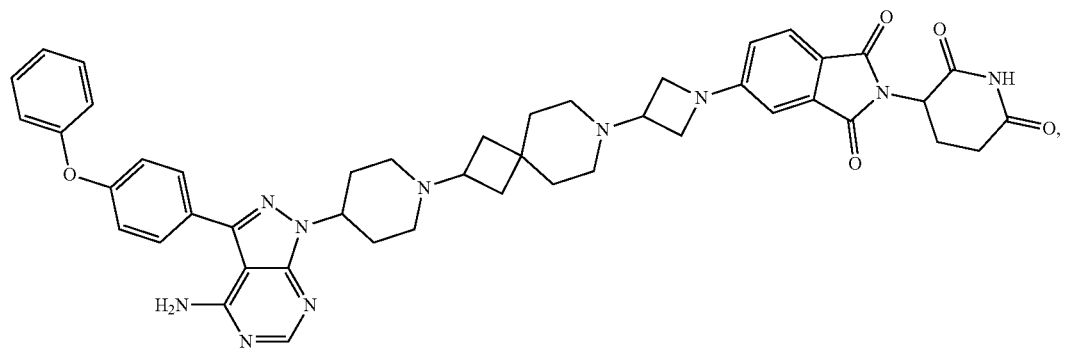

-continued
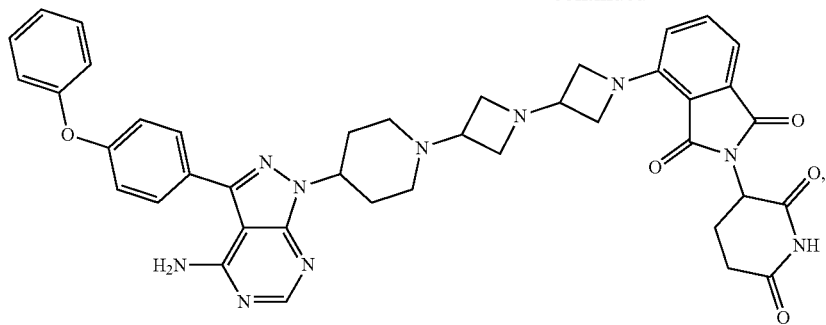
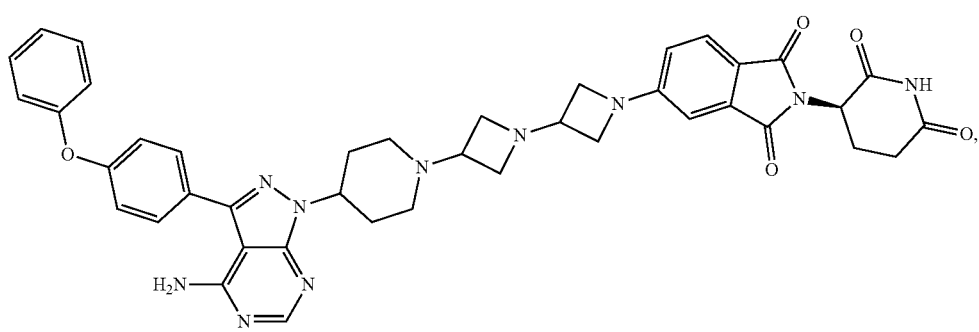
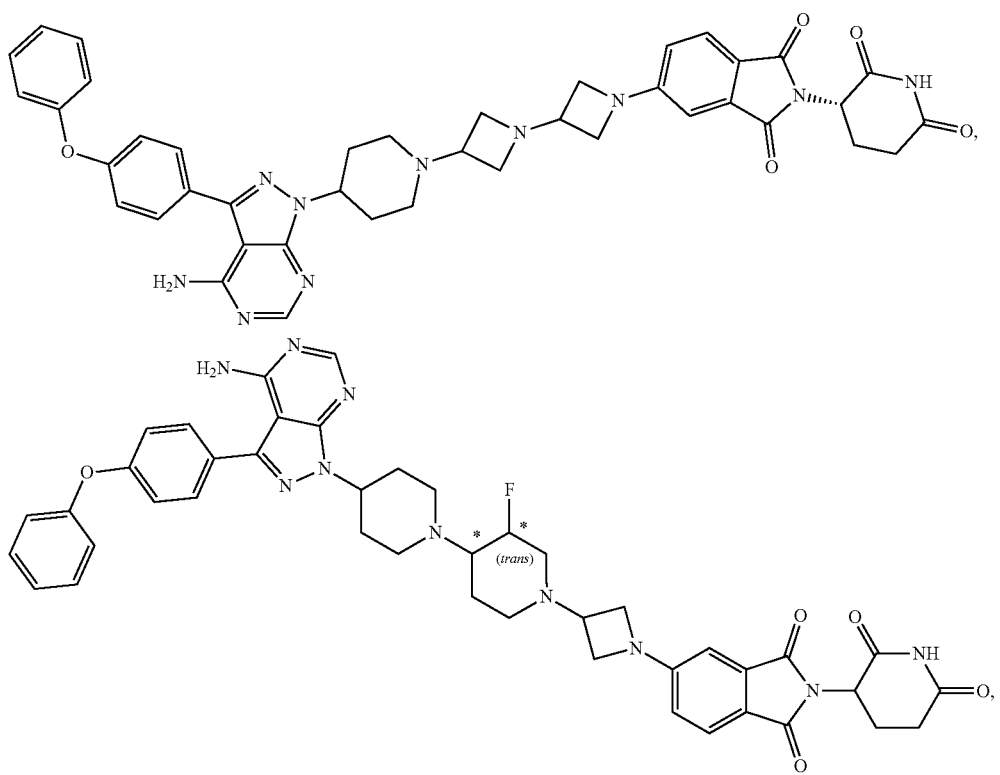

703
704
-continued
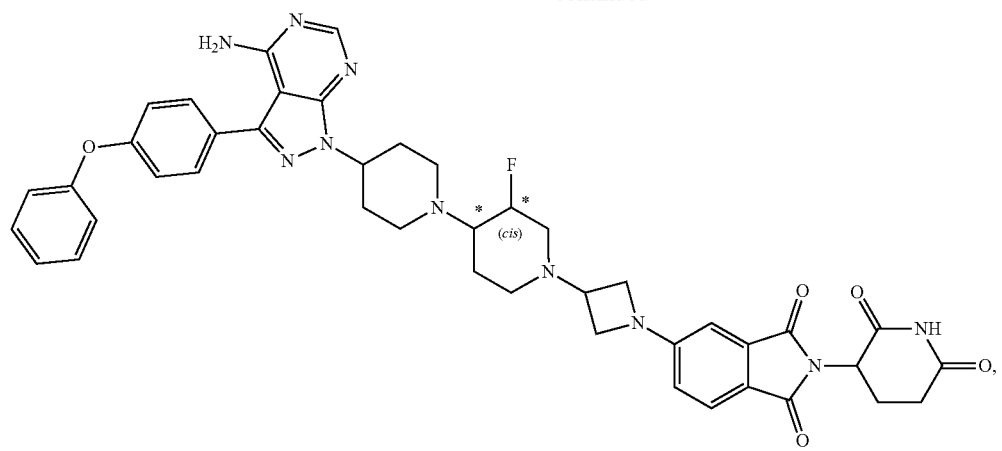
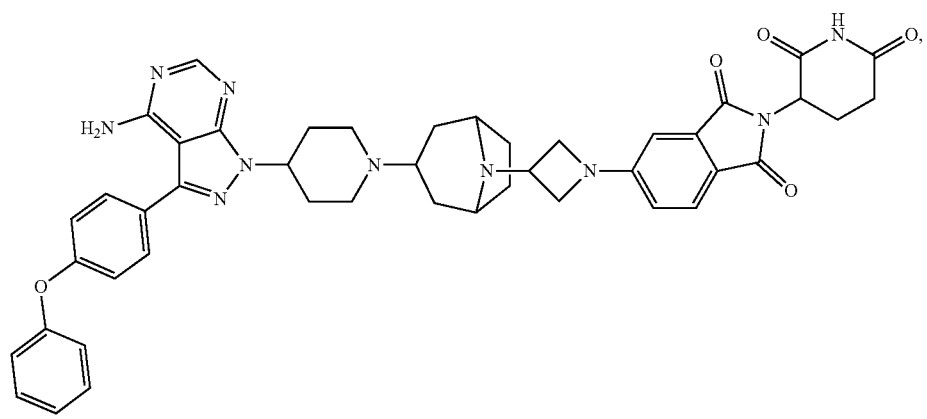
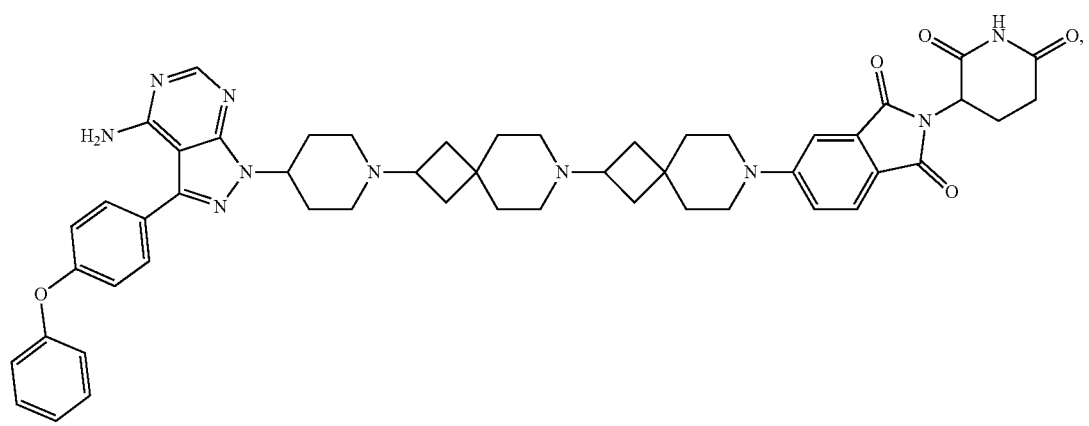
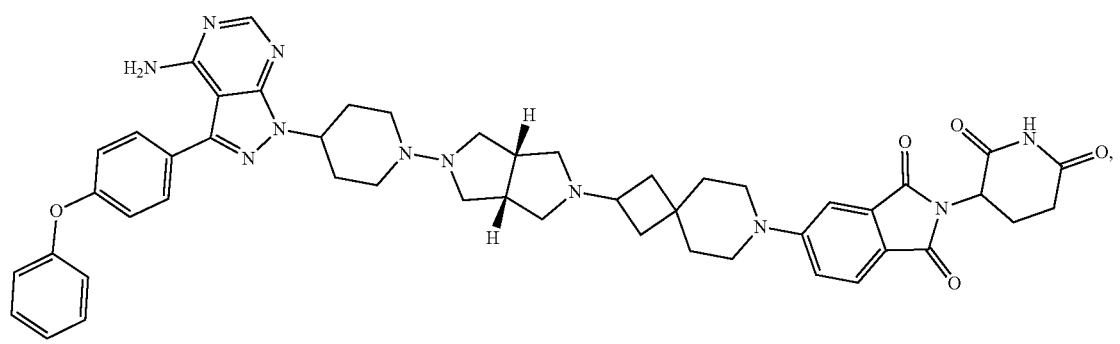

705
706
-continued
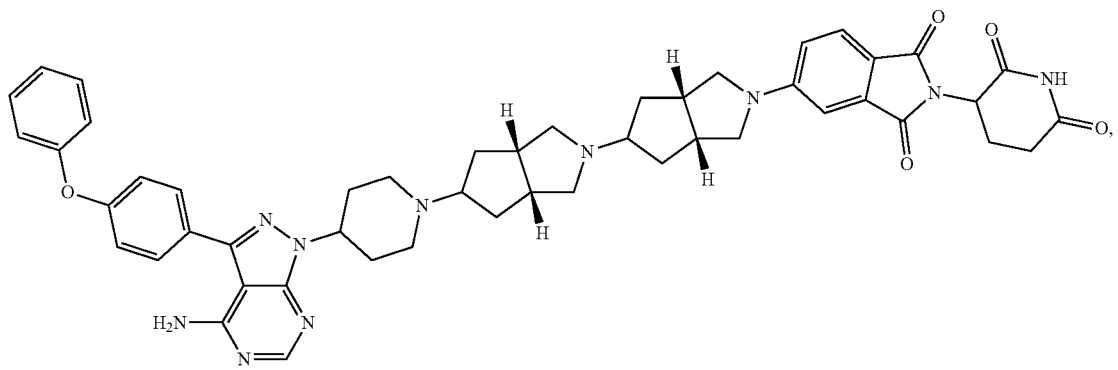
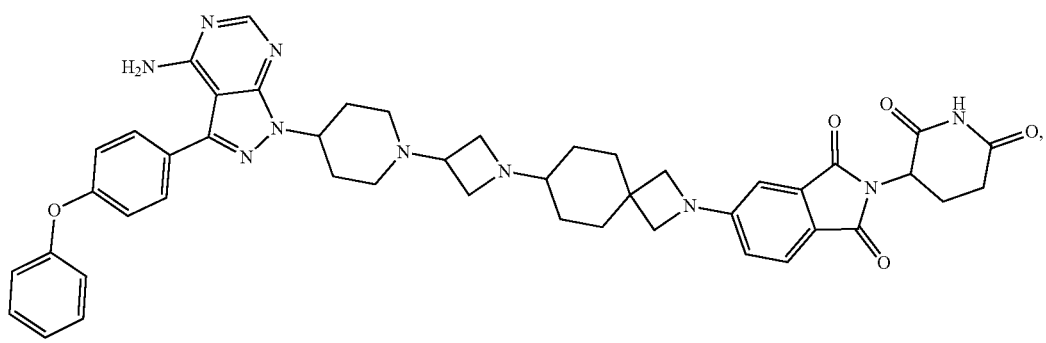
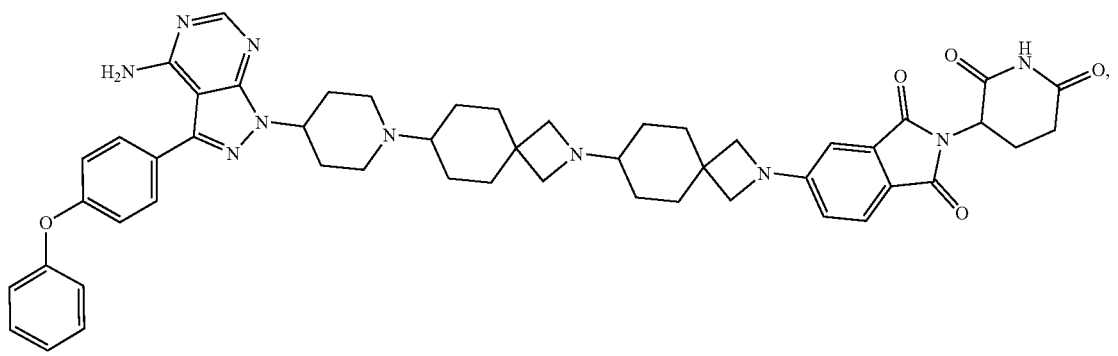
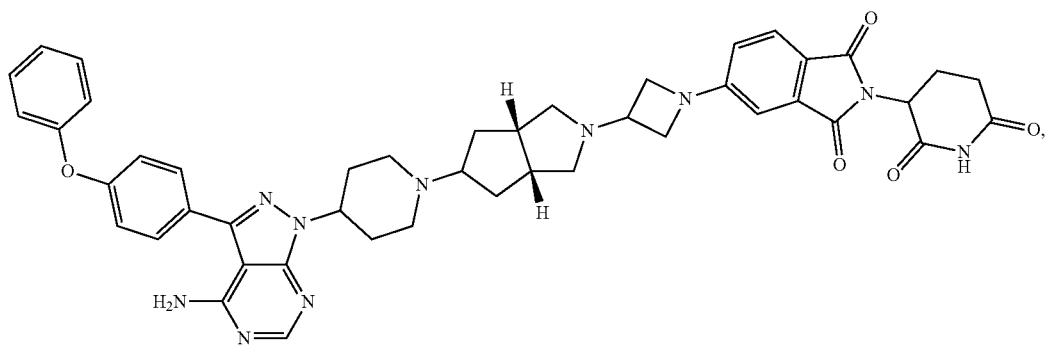

-continued
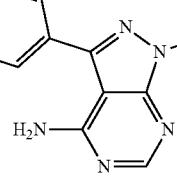
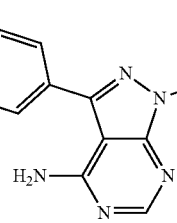
or a pharmaceutically acceptable salt thereof.
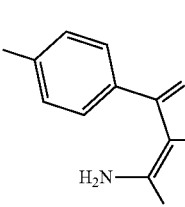
and

15. A pharmaceutical composition comprising a pharmaceutically acceptable carrier and the compound according to claim 1, or a pharmaceutically acceptable salt or stereoisomer thereof.

16. A method for inhibiting or degrading Bruton's tyrosine kinase activity in a subject, wherein the method comprises administering to the subject in need thereof a therapeutically effective amount of the compound according to claim 1, or a pharmaceutically acceptable salt or stereoisomer thereof.

17. The method according to claim 16, wherein the subject has a disease selected from the group consisting of an autoimmune disease and a tumor.

18. The method according to claim 17, wherein the autoimmune disease is selected from the group consisting of psoriasis and rheumatoid arthritis.

19. The method according to claim 17, wherein the tumor is selected from the group consisting of B cell lymphoma, chronic lymphocytic leukemia, mantle cell lymphoma, and non-Hodgkin's lymphoma.

\* \* \* \* \*